US009249070B2

(12) United States Patent
Calabria et al.

(10) Patent No.: US 9,249,070 B2
(45) Date of Patent: Feb. 2, 2016

(54) COMPOSITIONS AND METHODS FOR PRODUCING ISOPRENE FREE OF C5 HYDROCARBONS UNDER DECOUPLING CONDITIONS AND/OR SAFE OPERATING RANGES

(71) Applicants: Anthony R. Calabria, Wilmington, DE (US); Marguerite A. Cervin, Redwood City, CA (US); Gopal K. Chotani, Cupertino, CA (US); Richard La Duca, Pleasanton, CA (US); Joseph C. McAuliffe, Sunnyvale, CA (US); Michael C. Miller, San Francisco, CA (US); Timothy A. Sabo, Southington, OH (US); Karl J. Sanford, Cupertino, CA (US); Erin L. Spring, Akron, OH (US); Gregory M. Whited, Belmont, CA (US)

(72) Inventors: Anthony R. Calabria, Wilmington, DE (US); Marguerite A. Cervin, Redwood City, CA (US); Gopal K. Chotani, Cupertino, CA (US); Richard La Duca, Pleasanton, CA (US); Joseph C. McAuliffe, Sunnyvale, CA (US); Michael C. Miller, San Francisco, CA (US); Timothy A. Sabo, Southington, OH (US); Karl J. Sanford, Cupertino, CA (US); Erin L. Spring, Akron, OH (US); Gregory M. Whited, Belmont, CA (US)

(73) Assignees: DANISCO US INC., Palo Alto, CA (US); THE GOODYEAR TIRE & RUBBER COMPANY, Akron, OH (US)

( * ) Notice: Subject to any disclaimer, the term of this patent is extended or adjusted under 35 U.S.C. 154(b) by 0 days.

(21) Appl. No.: 13/898,320

(22) Filed: May 20, 2013

(65) Prior Publication Data

US 2014/0155660 A1 Jun. 5, 2014

Related U.S. Application Data

(62) Division of application No. 13/741,149, filed on Jan. 14, 2013, now Pat. No. 8,906,658, which is a division of application No. 12/496,573, filed on Jul. 1, 2009, now Pat. No. 8,420,360.

(Continued)

(51) Int. Cl.
*C07C 11/18* (2006.01)
*C12N 15/52* (2006.01)
(Continued)

(52) U.S. Cl.
CPC ................ *C07C 11/18* (2013.01); *C12N 15/52* (2013.01); *C12P 5/007* (2013.01); *C12P 5/02* (2013.01); *Y02E 50/343* (2013.01)

(58) Field of Classification Search
IPC .................... C07C 11/18,11/00, 33/00, 241/00, C07C 211/00
See application file for complete search history.

(56) References Cited

U.S. PATENT DOCUMENTS

| | | | |
|---|---|---|---|
| 1,344,713 | A | 6/1920 | Peters |
| 3,686,349 | A | 8/1972 | Schliebs et al. |

(Continued)

FOREIGN PATENT DOCUMENTS

| | | | |
|---|---|---|---|
| CN | 1970770 A | 5/2007 | |
| EP | 0 137 280 A1 | 4/1985 | |

(Continued)

OTHER PUBLICATIONS

Löfroth et al., "Characterization of environmental tobacco smoke," Environ Sci Technol 23(5):610-614, 1989.*

(Continued)

*Primary Examiner* — Rosanne Kosson

(74) *Attorney, Agent, or Firm* — Terri Shieh-Newton; Mintz, Levin, Cohn, Ferris, Glovsky and Popeo, P.C.

(57) ABSTRACT

The invention features methods for producing isoprene from cultured cells wherein the cells in the stationary phase. The invention also provides compositions that include these cultured cells and/or increased amount of isoprene. The invention also provides for systems that include a nonflammable concentration of isoprene in the gas phase. Additionally, the invention provides isoprene compositions, such as compositions with increased amount of isoprene or increased purity.

12 Claims, 189 Drawing Sheets

Related U.S. Application Data

(60) Provisional application No. 61/134,094, filed on Jul. 2, 2008, provisional application No. 61/133,947, filed on Jul. 2, 2008, provisional application No. 61/134,011, filed on Jul. 2, 2008.

(51) Int. Cl.
*C12P 5/00* (2006.01)
*C12P 5/02* (2006.01)

(56) References Cited

U.S. PATENT DOCUMENTS

| | | | | |
|---|---|---|---|---|
| 4,570,029 | A | 2/1986 | Kulprathipanja et al. | |
| 4,647,344 | A | 3/1987 | Linder et al. | |
| 4,683,202 | A | 7/1987 | Mullis | |
| 4,703,007 | A | 10/1987 | Mulholland et al. | |
| 5,849,970 | A | 12/1998 | Fall et al. | |
| 5,872,277 | A * | 2/1999 | Babler | 560/261 |
| 5,874,276 | A | 2/1999 | Fowler et al. | |
| 6,022,725 | A | 2/2000 | Fowler et al. | |
| 6,106,888 | A | 8/2000 | Dale et al. | |
| 6,176,176 | B1 | 1/2001 | Dale et al. | |
| 6,268,328 | B1 | 7/2001 | Mitchinson et al. | |
| 6,270,739 | B1 | 8/2001 | Barnicki et al. | |
| 6,553,689 | B2 | 4/2003 | Jain et al. | |
| 7,132,527 | B2 | 11/2006 | Payne et al. | |
| 7,157,533 | B2 | 1/2007 | Gandon-Pain | |
| 7,241,587 | B2 | 7/2007 | Dodge et al. | |
| 7,262,041 | B2 | 8/2007 | Baldwin et al. | |
| 7,479,565 | B2 | 1/2009 | Yeates et al. | |
| 8,420,360 | B2 | 4/2013 | Calabria et al. | |
| 8,906,658 | B2 | 12/2014 | Calabria et al. | |
| 2002/0095818 | A1 | 7/2002 | Jain et al. | |
| 2006/0079476 | A1 | 4/2006 | Keasling et al. | |
| 2007/0270607 | A1 * | 11/2007 | Shen et al. | 560/262 |
| 2008/0038805 | A1 | 2/2008 | Melis | |
| 2013/0196402 | A1 | 8/2013 | Calabria et al. | |
| 2014/0187839 | A1 | 7/2014 | Feher et al. | |

FOREIGN PATENT DOCUMENTS

| | | | |
|---|---|---|---|
| EP | 0 215 594 | A2 | 3/1987 |
| EP | 0 238 023 | A2 | 9/1987 |
| EP | 0 244 234 | A2 | 11/1987 |
| EP | 0 955 363 | A2 | 11/1999 |
| EP | 0 955 363 | A3 | 11/1999 |
| EP | 1 118 855 | A2 | 7/2001 |
| JP | 2010-525816 | A | 7/2010 |
| JP | 2011-505841 | A | 3/2011 |
| RU | 2027760 | C1 | 1/1995 |
| WO | WO-95/04134 | A1 | 2/1995 |
| WO | WO-96/35796 | A1 | 11/1996 |
| WO | WO-98/02550 | A2 | 1/1998 |
| WO | Wo-98/02550 | A3 | 1/1998 |
| WO | WO-01/58839 | A1 | 8/2001 |
| WO | WO-2004/033646 | A2 | 4/2004 |
| WO | WO-2005/001036 | A2 | 1/2005 |
| WO | WO-2007/140339 | A2 | 12/2007 |
| WO | WO-2008/003078 | A2 | 1/2008 |
| WO | WO-2008/137092 | A2 | 11/2008 |
| WO | WO-2008/137092 | A3 | 11/2008 |
| WO | WO-2009/076676 | A2 | 6/2009 |

OTHER PUBLICATIONS

Anderson, M.S. et al. "Isopentenyl diphosphate: dimethylallyl diphosphate isomerase. An improved purification of the enzyme and isolation of the gene from *Saccharomyces cerevisiae*," *Journal of Biological Chemistry* 264(32):19169-19175, 1989.

Boel, E. et al. "Two different types of intervening sequences in the glucoamylase gene from Aspergillus niger." *EMBO J.* 3(7):1581-1585, 1984.

Bouvier, F. et al. "Biogenesis, molecular regulation and function of plant isoprenoids." *Progress in Lipid Research* 44(6):357-429, 2005.

Brown, L. et al. "Enzymatic Saccharification of Lignocellulosic Biomass," Golden, CO: National Renewable Energy Laboratory, 1996.

Bunge, M. et al. "On-Line Monitoring of Microbial Volatile Metabolites by Proton Transfer Reaction-Mass Spectrometry." *Appl. Environ. Microbiol.* 74(7):2179-2186, 2008.

Campbell, E.I. et al. "Improved transformation efficiency of Aspergillus niger using the homologous niaD gene for nitrate reductase." *Current Genetics* 16(1):53-56, 1989.

Cao, Q.N. et al. "Penicillopepsin-JT2, a recombinant enzyme from Penicillium janthinellum and the contribution of a hydrogen bond in subsite S3 to k(cat)." *Protein Sci* 9(5):991-1001, 2000.

Davidson, S. "Light Factories." *ECOS* (117):10-12, 2003.

Dhe-Paganon, S. et al. "Mechanism of mevalonate pyrophosphate decarboxylase: evidence for a carbocationic transition state." *Biochemistry* 33(45):13355-13362, 1994.

Finkelstein, D.B. "Transformation." In *Biotechnology of Filamentous Fungi: Technology and Products*, eds. D.B. Finkelstein et al. Boston, MA: Butterworth-Heinemann, pp. 113-156, 1992.

Farzaneh, T. et al, "Optimization of the ammonia fiber explosion (AFEX) treatment parameters for enzymatic hydrolysis of corn stover." *Bioresource Technology* 96(18):2014-2018, 2005.

Goedegebuur, F. et al. "Cloning and relational analysis of 15 novel fungal endoglucanases from family 12 glycosyl hydrolase." *Current Genetics* 41(2):89-98, 2002.

Gräwert, T. et al. "IspH Protein of *Escherichia coli*: Studies on Iron—Sulfur Cluster Implementation and Catalysis." *Journal of the American Chemical Society* 126(40):12847-12855, 2004.

Greenberg, James P. et al. "Sub-parts per billion detection of isoprene using a reduction gas detector with a portable gas chromatograph." *Atmospheric Environment. Part A. General Topics* 27(16):2689-2692, 1993.

Harkki, A. et al. "Genetic engineering of Trichoderma to produce strains with novel cellulase profiles." *Enzyme Microb. Technol* 13(3):227-33, 1991.

Harkki, A. et al. "A Novel Fungal Expression System: Secretion of Active Calf Chymosin from the Filamentous Fungus *Trichoderma reesei*." *Bio/Technology* 7(6):596-603, 1989.

Hedl, M. et al. "Enterococcus faecalis Acetoacetyl-Coenzyme A Thiolase/3-Hydroxy-3-Methylglutaryl-Coenzyme a Reductase, a Dual-Function Protein of Isopentenyl Diphosphate Biosynthesis." *J. Bacteriol.* 184(8):2116-2122, 2002.

Hoeffler, J.-F. et al. "Isoprenoid biosynthesis via the methylerythritol phosphate pathway." *European Journal of Biochemistry* 269(18):4446-4457, 2002.

Hunter, B.K. et al. "Formaldehyde metabolism by *Escherichia coli*. Carbon and solvent deuterium incorporation into glycerol, 1,2-propanediol, and 1,3-propanediol." *Biochemistry* 24(15):4148-4155, 1985.

Ilmen, M. et al. "Regulation of cellulase gene expression in the filamentous fungus *Trichoderma reesei*." *Appl. Environ. Microbiol.* 63(4):1298-1306, 1997.

Innis, M. A. et al. "Expression, Glycosylation, and Secretion of an Aspergillus Glucoamylase by *Saccharomyces cerevisiae*." *Science* 228(4695):21-26, 1985.

Julsing, Mattijs et al. "Functional analysis of genes involved in the biosynthesis of isoprene in Bacillus subtilis." *Applied Microbiology and Biotechnology* 75(6):1377-1384, 2007.

Kelly, J.M. et al. "Transformation of Aspergillus niger by the amdS gene of Aspergillus nidulans." *The EMBO Journal* 4(2):475-479, 1985.

Law, C.K. "Heat and mass transfer in combustion: Fundamental concepts and analytical techniques." *Progress in Energy and Combustion Science* 10(3):295-318, 1984.

Lüttgen, H. et al. "Biosynthesis of terpenoids: YchB protein of *Escherichia coli* phosphorylates the 2-hydroxy group of 4-diphosphocytidyl-2C-methyl-d-erythritol." *Proceedings of the National Academy of Sciences of the United States of America* 97(3):1062-1067, 2000.

Martin, V.J.J. et al. "Engineering a mevalonate pathway in *Escherichia coli* for production of terpenoids." *Nat Biotech* 21(7):796-802, 2003.

(56) References Cited

OTHER PUBLICATIONS

Maury, J. et al. "Microbial isoprenoid production: an example of green chemistry through metabolic engineering." *Advances in Biochemical Engineering/Biotechnology* 100:19-51, 2005.
Miller, B. et al. "First isolation of an isoprene synthase gene from poplar and successful expression of the gene in *Escherichia coli*." *Planta* 213(3):483-487, 2001.
Neidhardt, F.C. et al. "Culture Medium for Enterobacteria." *J. Bacteriol.* 119(3):736-747, 1974.
Nevalainen, K.M.H. et al. (1991). "The Molecular Biology of *Trichoderma* and its Application to the Expression of Both Homologous and Heterologous Genes," in *Molecular Industrial Mycology*, Leong, S.A. et al., eds., Marcel Dekker, New York, pp. 129-148.
Nunberg, J.H. et al. "Molecular cloning and characterization of the glucoamylase gene of Aspergillus awamori." *Mol. Cell. Biol.* 4(11):2306-2315, 1984.
Oulmouden, A. et al. "Nucleotide sequence of the ERG12 gene of *Saccharomyces cerevisiae* encoding mevalonate kinase." *Current Genetics* 19(1):9-14, 1991.
Penttilä, M. et al. "A versatile transformation system for the cellulolytic filamentous fungus *Trichoderma reesei*." *Gene* 61(2):155-64, 1987.
Rohdich, F. et al. "Biosynthesis of terpenoids: 4-Diphosphocytidyl-2C-methyl-d-erythritol synthase of Arabidopsis thaliana." *Proceedings of the National Academy of Sciences of the United States of America* 97(12):6451-6456, 2000.
Rohdich, F. et al. "Cytidine 5'-triphosphate-dependent biosynthesis of isoprenoids: YgbP protein of *Escherichia coli* catalyzes the formation of 4-diphosphocytidyl-2-C-methylerythritol." *Proceedings of the National Academy of Sciences of the United States of America* 96(21):11758-11763, 1999.
Schnitzler, J.-P. et al. "Biochemical properties of isoprene synthase in poplar (Populus × canescens)." *Planta* 222(5):777-786, 2005.
Sharkey, T.D. et al. "Evolution of the Isoprene Biosynthetic Pathway in Kudzu." *Plant Physiol.* 137(2):700-712, Feb. 1, 2005.
Sheir-Neiss, G. et al. "Characterization of the secreted cellulases of Trichoderma reesei wild type and mutants during controlled fermentations." *Applied Microbiology and Biotechnology* 20(1):46-53, 1984.
Silver, G.M. et al. "Enzymatic Synthesis of Isoprene from Dimethylallyl Diphosphate in Aspen Leaf Extracts." *Plant Physiol.* 97(4):1588-1591, 1991.
Silver, G.M. et al. "Characterization of Aspen Isoprene Synthase, an Enzyme Responsible for Leaf Isoprene Emission to the Atmosphere." *Journal of Biological Chemistry* 270(22):13010-13016, 1995.
Sprenger, G.A. et al. "Identification of a thiamin-dependent synthase in *Escherichia coli* required for the formation of the 1-deoxy-d-xylulose 5-phosphate precursor to isoprenoids, thiamin, and pyridoxol." *Proceedings of the National Academy of Sciences of the United States of America* 94(24):12857-12862, 1997.
Sulter, G.J. et al. "Proliferation and metabolic significance of peroxisomes in Candida boidinii during growth on d-alanine or oleic acid as the sole carbon source." *Archives of Microbiology* 153(5):485-489, 1990.
Sutherlin, A. et al. "Enterococcus faecalis 3-Hydroxy-3-Methylglutaryl Coenzyme A Synthase, an Enzyme of Isopentenyl Diphosphate Biosynthesis." *J. Bacteriol.* 184(15):4065-4070, 2002.
Tsay, Y.H. et al. "Cloning and characterization of ERG8, an essential gene of *Saccharomyces cerevisiae* that encodes phosphomevalonate kinase.." *Mol. Cell. Biol.* 11(2):620-631, 1991.
Vidal, M. et al. "Evaluation of lower flammability limits of fuel-air-diluent mixtures using calculated adiabatic flame temperatures." *Journal of Hazardous Materials* 130(1-2):21-27, 2006.
Van den Hondel, C. et al, "Heterologous gene expression in filamentous fungi." In *More Gene Manipulations in Fungi*, eds. J.W. Bennett et al. San Diego, CA : Academic Press, pp. 396-428, 1991.
Ward, M. et al. "Use of Aspergillus overproducing mutants, cured for intergrated plasmid, to overproduce heterologous proteins." *Applied Microbiology and Biotechnology* 39(6):738-743, 1993.
Withers, S.T. et al. "Identification of Isopentenol Biosynthetic Genes from Bacillus subtilis by a Screening Method Based on Isoprenoid Precursor Toxicity." *Appl. Environ. Microbiol.* 73(19):6277-6283, 2007.
Yamada, K. et al. "Production of glycerol from methanol by a mutant strain of Candida boidinii No. 2201." *Agricultural and Biological Chemistry* 53(2):541-543, 1989.
Yelton, M.M. et al. "Transformation of Aspergillus nidulans by using a trpC plasmid." *Proc. Natl. Acad. Sci. U.S.A* 81(5):1470-4, 1984.
Zepeck, F. et al. "Biosynthesis of Isoprenoids. Purification and Properties of IspG Protein from *Escherichia coli." The Journal of Organic Chemistry* 70(23):9168-9174, 2005.
Singaporean Search Report mailed on Apr. 5, 2012, for Singaporean Patent Application No. 201009566-9, filed on Jul. 1, 2009, 5 pages.
International Search Report mailed on Mar. 9, 2010 for PCT Patent Application No. PCT/US2009/049429, filed on Jul. 1, 2009, 9 pages.
Kuzma, J. et al. (Feb. 1995). "Bacteria Produce the Volatile Hydrocarbon Isoprene," *Curr. Microbiol.* 30(2):97-103.
Sigma-Aldrich Product Specification (May 2, 2011). Product No. 464953, 1 page.

* cited by examiner

Figure 1

1-
*atg*tgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtacctttttccatcacccacctgaagaacaacctgaaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggattttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagacccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttactttttccgtatgccagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaccgcatcaaactgctgctgattgaccc
tttcccgattaaccagctgatgtatgtc
taactgcag
(SEQ ID NO:1)

Figure 3A

1- gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtcTAActgca
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

Figure 3B agggtggcggggcaggacgcccgccataaactgccaggcatcaaattaagcagaaggccatcctg
acggatggcctttttgcgtttctacaaactcttttgtttatttttctaaatacattcaaatat
gtatccgctcatgagacaataaccctgataaatgcttcaataatattgaaaaaggaagagtatg
agtattcaacatttccgtgtcgcccttattcccttttttgcggcattttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatgggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

Figure 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

Figure 5A 1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaacccctcaagacccgtttagaggccccaaggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatctttttccattcggcgtcgatcagtttacgcagttcttcgcgggcctgttc
ctcgctggtaccatcgtttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataattttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtcccagcgctctacagcatcggtgaacagttgcagttcgtccagagtgc
cataaacgtcatacacgtcatcgatgatcgtcaccagaccaaacatttttagtaacagctttgcg
acattcaccaaactgcgggtctggcgccatacccagtgcccagaaataaacttccatcaggcgg
tcgcgtacaaaatccagtttgctagccaggcccatctcggtccaccagcgggacagatcttgca
gctctttctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttctttttgttttcgtc
cagcagtacgatgttttccagggctttaatgatgtctttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacgggaatta
tgctcggtaatctgagtaaattgagaagaggtcgcacacatatgacgaccttcgatatggccgc
tgctgtgatgatgatgatgatgatgatgatgatggcccatggtatatctccttcttaaagttaa
acaaaattatttctagaggggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggccccgtggccgggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaacctttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

Figure 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctccccgcgcg
ttggccgattcattaatgcagctggcacgacaggtttcccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcattttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacgggttggcatggattgtaggcgccgccctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtgaatgcgcaaaccaacccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgatttttctct
ggtcccgccgcatccataccgccagttgtttaccctcacaacgttccagtaaccgggcatgttc
atcatcagtaacccgtatcgtgagcatcctctctcgtttcatcggtatcattacccccatgaac
agaaatcccccttacacggaggcatcagtgaccaaacaggaaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgtttttccataggctccgcccccctgacgagcatcacaaaaatcgacgctcaagtcaga

Figure 5C ggtggcgaaacccgacaggactataaagataccaggcgtttccccctggaagctccctcgtgcg
ctctcctgttccgaccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggtttttttgtttgcaagcagcagattacg
cgcagaaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatcccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatctttt
actttcaccagcgtttctgggtgagcaaaaacaggaaggcaaaatgccgcaaaaaagggaataa
gggcgacacggaaatgttgaatactcatactcttcctttttcaatattattgaagcatttatca
gggttattgtctcatgagcggatacatatttgaatgtatttagaaaaataaacaaataggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

Figure 7A 1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaaagaacaaa
tctgacctgcacgcaaccgctctgtctttccgtctgctgcgtcagcacggtttcgaggtttctc
aggatgtttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtacctttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtcccgctggt
ggaccgagatgggcctggctagcaaactggattttgtacgcgaccgcctgatggaagtttattt
ctgggcactgggtatggcgccagacccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttacttttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatccccctttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaagccagcc
tttcatgatatatctcccaatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

Figure 7B cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcacccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgaccccggatgaa
gtggttcgcatcctcggtttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgatttttccccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatctttttttacaccgttttcatctgtgca
tatggacagttttccctttgatatgtaacggtgaacagttgttctacttttgtttgttagtctt
gatgcttcactgatagatacaagagccataagaacctcagatccttccgtatttagccagtatg
ttctctagtgtggttcgttgttttgcgtgagccatgagaacgaaccattgagatcatacttac
tttgcatgtcactcaaaaattttgcctcaaaactggtgagctgaattttttgcagttaaagcatc
gtgtagtgtttttcttagtccgttatgtaggtaggaatctgatgtaatggttgttggtattttg
tcaccattcatttttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgtttc
aaaagacttaacatgttccagattatattttatgaatttttttaactggaaaagataaggcaat
atctcttcactaaaaactaattctaatttttcgcttgagaacttggcatagtttgtccactgga
aaatctcaaagcctttaaccaaaggattcctgatttccacagttctcgtcatcagctctctggt
tgctttagctaatacaccataagcattttccctactgatgttcatcatctgagcgtattggtta
taagtgaacgataccgtccgttctttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgattttaatcactatac
caattgagatgggctagtcaatgataattactagtcctttttcctttgagttgtgggtatctgta

Figure 7C

Aattctgctagacctttgctggaaaacttgtaaattctgctagaccctctgtaaattccgctag
acctttgtgtgttttttttgtttatattcaagtggttataatttatagaataaagaaagaataa
aaaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtctttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcacccagtaaggcagcggtatcatcaacaggctta
(SEQ ID NO:7)

Figure 9
A.
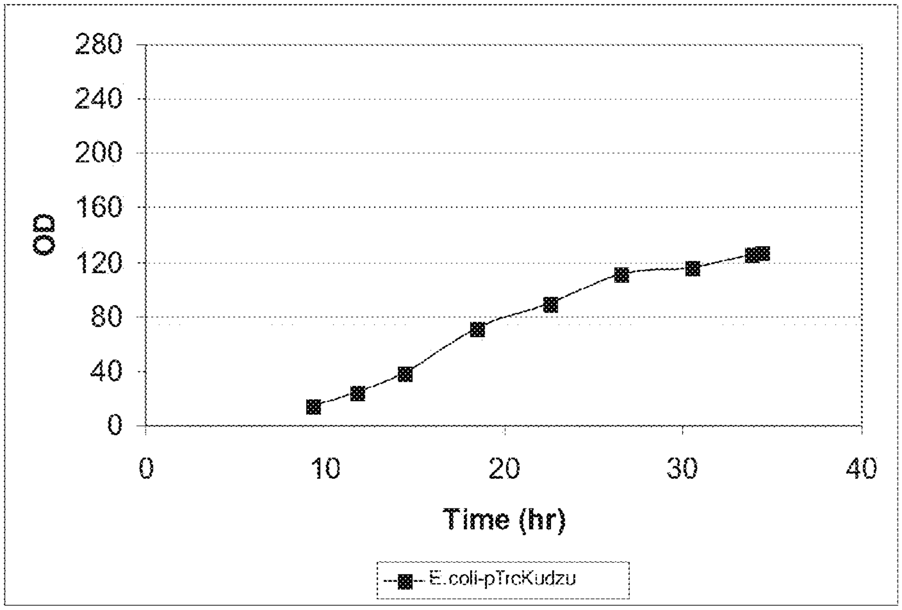
B.
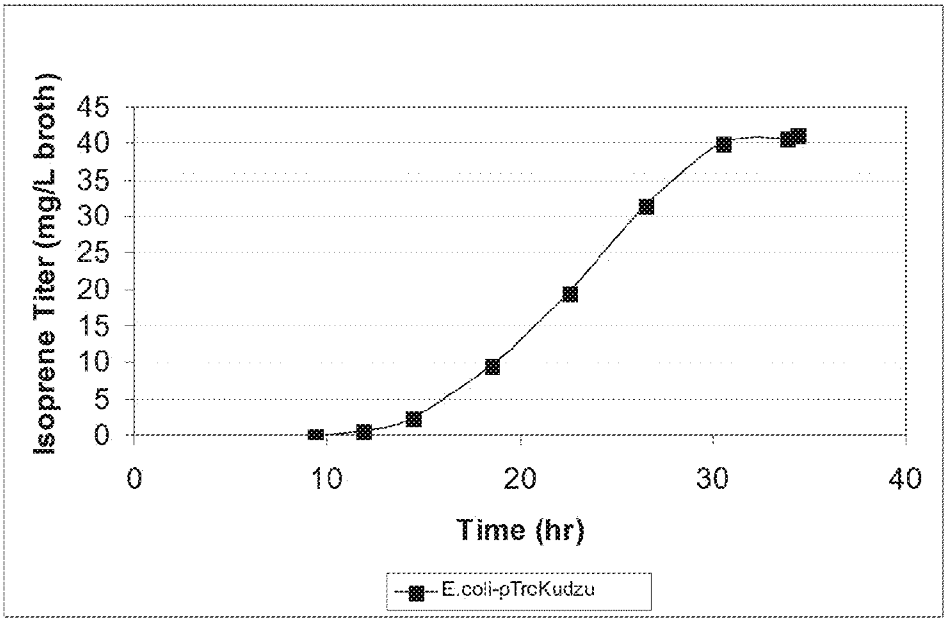

Figure 12A 1-
gaattgctccatttttcttctgctatcaaaataacagactcgtgattttccaaacgagctttcaa
aaaagcctctgccccttgcaaatcggatgcctgtctataaaattcccgatattggttaaacagc
ggcgcaatggcggccgcatctgatgtctttgcttggcgaatgttcatcttatttcttcctccct
ctcaataatttttttcattctatcccttttctgtaaagtttatttttcagaatacttttatcatc
atgctttgaaaaaatatcacgataatatccattgttctcacggaagcacacgcaggtcatttga
acgaatttttcgacaggaatttgccgggactcaggagcatttaacctaaaaaagcatgacatt
tcagcataatgaacatttactcatgtctattttcgttcttttctgtatgaaaatagttatttcg
agtctctacggaaatagcgagagatgatatacctaaatagagataaaatcatctcaaaaaaatg
ggtctactaaaatattattccatctattacaataaattcacagaatagtcttttaagtaagtct
actctgaatttttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaaagacatcattaaagccctggaaaacat
cgtactgctggacgaaaacaaaaagaacaaatctgacctgcacgcaaccgctctgtctttccgt
ctgctgcgtcagcacggtttcgaggtttctcaggatgtttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtacctttttccatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgaccctttcccgattaaccagctgatgtatgtctaa
aaaaaaccggccttggccccgccggtttttttattatttttcttcctccgcatgttcaatccgct
ccataatcgacggatggctccctctgaaaattttaacgagaaacggcgggttgacccggctcag
tcccgtaacggccaagtcctgaaacgtctcaatcgccgcttcccggtttccggtcagctcaatg
ccgtaacggtcggcggcgttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaaggatcgaagtcggttcagaaaaagaaggatatggatctggagctgtaata
taaaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattacctttattaatgaattttcctgctgtaataatgggtagaaggtaattacta
ttattattgatatttaagttaaacccagtaaatgaagtccatggaataatagaaagagaaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcacccttgtcactaagaaaataaa
tgcagggtaaatttatatccttcttgttttatgtttcggtataaaacactaatatcaatttct
gtggttatactaaaagtcgtttgttggttcaaataatgattaaatatctcttttctcttccaat
tgtctaaatcaattttattaaagttcatttgatatgcctcctaaatttttatctaaagtgaatt
taggaggcttacttgtctgctttcttcattagaatcaatcctttttttaaagtcaatattactgt
aacataaatatatattttaaaaatatcccactttatccaattttcgtttgttgaactaatgggt
gctttagttgaagaataaagaccacattaaaaaatgtggtctttttgtgtttttttaaaggattt
gagcgtacgcgaaaaatcctttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatccccat
atttatccaatattcgttccttaatttcatgaacaatcttcattctttcttctctagtcattat
tattggtccattcactattctcattcccttttcagataatttagatttgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataattttccgttcccaattccacattgcaataatagaaaatccatcttcatcggct
tttcgtcatcatctgtatgaatcaaatcgccttcttctgtgtcatcaaggtttaatttttat
gtatttcttttaacaaaccaccataggagattaacctttacggtgtaaaccttcctccaaatc
agacaaacgtttcaaattcttttcttcatcatcggtcataaaatccgtatcctttacaggatat
tttgcagtttcgtcaattgccgattgtatatccgatttatatttatttttcggtcgaatcattt
gaacttttacatttggatcatagtctaatttcattgcctttttccaaaattgaatccattgttt

Figure 12C ttgattcacgtagttttctgttattctaaaataagttggttccacacataccattacatgcatg
tgctgattataagaattatctttattatttattgtcacatccgttgcacgcataaaaccaacaa
gatttttattaatttttttatattgcatcattcggcgaaatccttgagccatatctgtcaaact
cttatttaattcttcgccatcataaacattttttaactgttaatgtgagaaacaaccaacgaact
gttggcttttgtttaataacttcagcaacaacctttttgtgactgaatgccatgtttcattgctc
tcctccagttgcacattggacaaagcctggatttgcaaaaccacactcgataccactttctttc
gcctgtttcacgattttgtttatactctaatatttcagcacaatcttttactctttcagcctttt
ttaaattcaagaatatgcagaagttcaaagtaatcaacattagcgatttttcttttctctccatg
gtctcacttttccactttttgtcttgtccactaaaacccttgatttttcatctgaataaatgct
actattaggacacataatattaaaagaaacccccatctatttagttatttgtttagtcacttat
aactttaacagatggggtttttctgtgcaaccaattttaagggttttcaatactttaaaacaca
tacataccaacacttcaacgcacctttcagcaactaaaataaaaatgacgttatttctatatgt
atcaagataagaaagaacaagttcaaaaccatcaaaaaaagacaccttttcaggtgctttttttt
attttataaactcattccctgatctcgacttcgttcttttttttacctctcggttatgagttagt
tcaaattcgttcttttttaggttctaaatcgtgtttttcttggaattgtgctgttttatcctttta
ccttgtctacaaacccccttaaaaacgtttttaaaggcttttaagccgtctgtacgttccttaag (SEQ ID NO:57)

Figure 13

ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
(SEQ ID NO:8)

Figure 15A

1 TCGACCGGTG AGAAGAACAG CATCGGGACA AGGGAAGGAA GAACAAAGAC AAAGAAAACA
61 AAAGAAAGCA ATTGAAAACA AAACAAAACA ATTTTCATTC CTTCTCTTAT CATTCCTTTT
121 CTTTTCTTTT CTCTCATTCA ACGCACTCCA TCGTATCCGT ATTCCTCTTA TTTTTTCTCT
181 TTCTCTATAT CCATTTCTTT CTCTCTAGGT GTGTCCTCTC TCTCTCTTCA ATTTCTCTAC
241 TCCGCATTCC AACGCATCCT TCCCCCAACC TCCCATTTCC TCCTTACGGC CCGATAGCGA
301 TCGTCTTTCC CTCGCTATCA CTCGCTACCG GCCCCTCCTC TGCACCGTAA CCTCCTACGT
361 ATTTACCATA TCATAAAGTT TTTTCCGACG CTTATCGCTG ACCCCCTGTC GCCCTCCTAT
421 TGGCTTCCGG ATTATCTTCT TGTCCATAAG GTGATCCATG CTTCCTGAAG ATTCCCGAAA
481 TGTGTCCACT TTGGCGGGGA ATCATTCCAT CCACTTCTTT CTCTCTCGCT TTCCTCATTC
541 GGCGCTCCCC TTCCGCGTCT CATTGGTCTT CCGCTCCGTT TTTGCTTTGC CGATGTTACT
601 TGGGGAGAGG TGCGATAATC CTTTCGCAAA AACTCGGTTT GACGCCTCCC ATGGTATAAA
661 TAGTGGGTGG TGGACAGGTG CCTTCGCTTT TCTTTAAGCA AGAGAATCCC ATTGTCTTGA
721 CTATCACGAA TTCACATACA TTATGAAGAT CACCGCTGTC ATTGCCCTTT TATTCTCACT
781 TGCTGCTGCC TCACCTATTC CAGTTGCCGA TCCTGGTGTG GTTTCAGTTA GCAAGTCATA
841 TGCTGATTTC CTTCGTGTTT ACCAAAGTTG GAACACTTTT GCTAATCCTG ATAGACCCAA
901 CCTTAAGAAG AGAAATGATA CACCTGCAAG TGGATATCAA GTTGAAAAAG TCGTAATTTT
961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```

(SEQ ID NO:13)

Figure 18A1
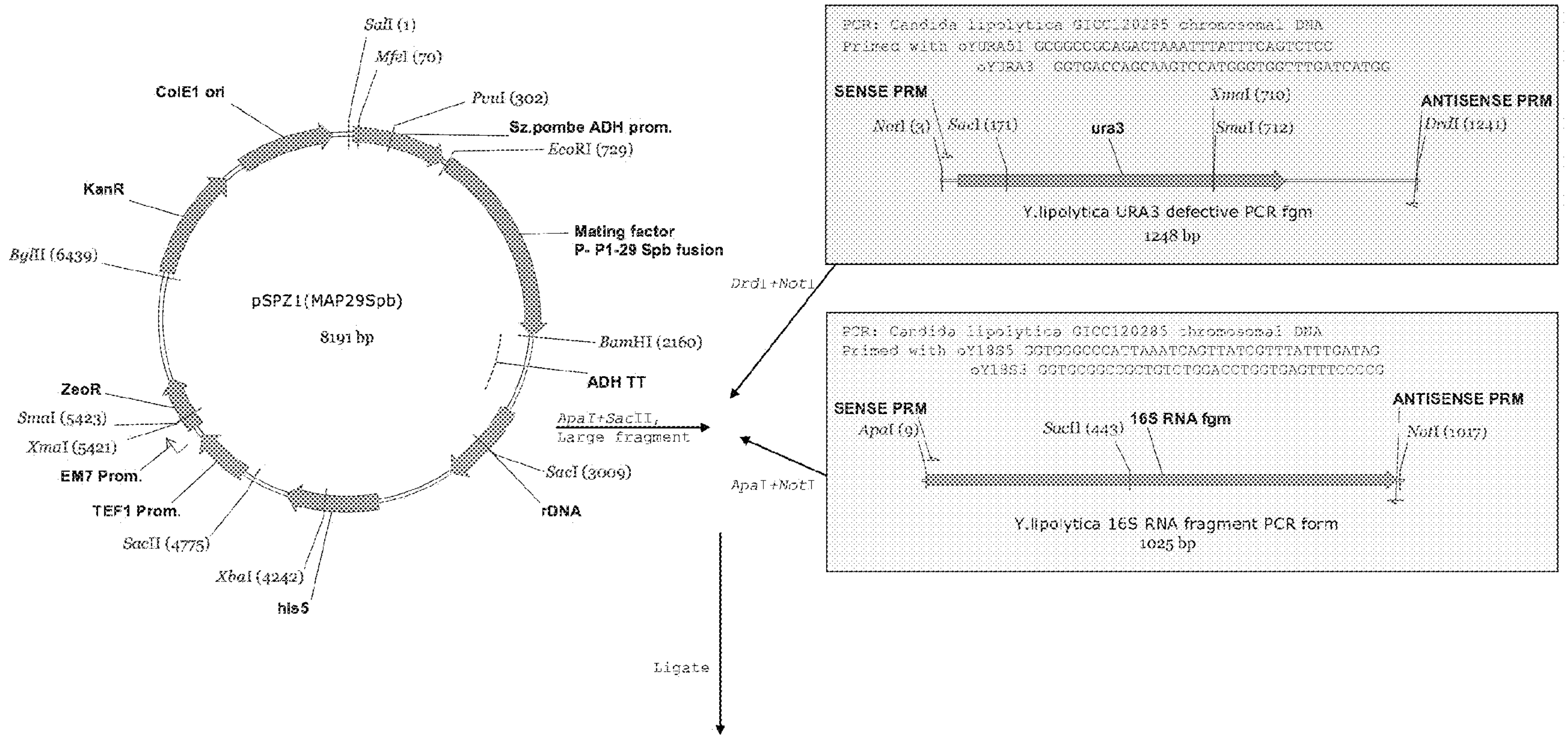

Figure 18A2
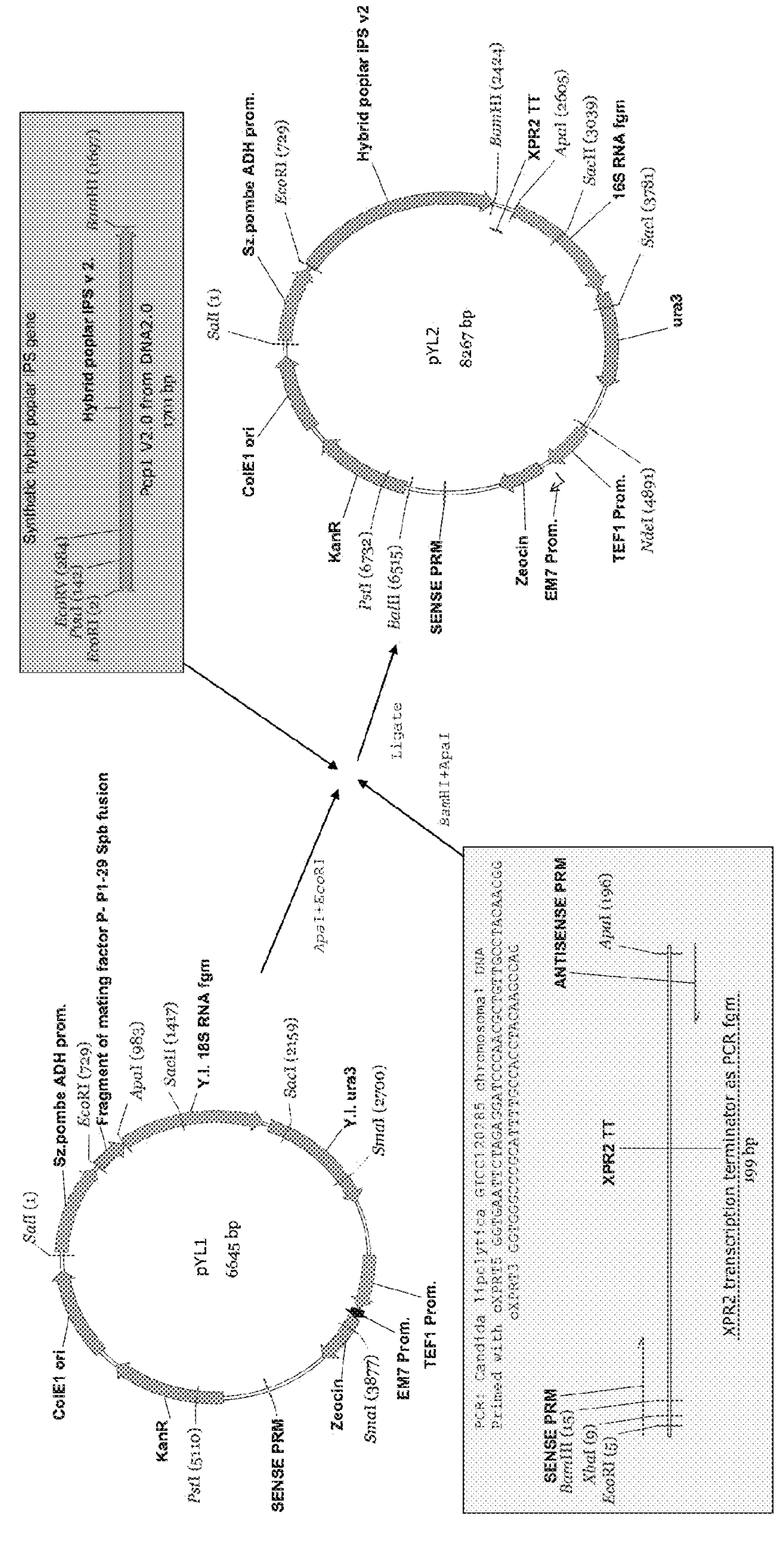

Figure 22A 1-
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggcctttttgcgtttctacaaactctttttgtttatttttctaaatacattcaaatat
gtatccgcttaaccggaattgccagctggggcgccctctggtaaggttgggaagccctgcaaag
taaactggatggctttctcgccgccaaggatctgatggcgcaggggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttctttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatcctttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccagggggaaacgcctggtatctttatagtcc
tgtcgggtttcgccacctctgacttgagcgtcgatttttgtgatgctcgtcaggggggcggagc
ctatggaaaaacgccagcaacgcggcctttttacggttcctggccttttgctggccttttgctc
acatgttctttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacacccatcaacagtattattttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccaccctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgttttttgcgccgacatcataacggttctggcaaatattctgaaatgagctgttgacaat
taatcatccggctcgtataatgtgtggaattgtgagcggataacaatttcacacaggaaacagc
gccgctgagaaaaagcgaagcggcactgctctttaacaatttatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaaagacatcattaaagccctggaaaacatcgtactgctggac
gaaaacaaaaagaacaaatctgacctgcacgcaaccgctctgtctttccgtctgctgcgtcagc
acggtttcgaggtttctcaggatgtttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtacctttttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagacccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta

Figure 22C tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgaccctttcccgattaaccagctgatgtatgtctaactgcatcgccctt
aggaggtaaaaaaaatgactgccgacaacaatagtatgccccatggtgcagtatctagttacg
ccaaattagtgcaaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaagggcgctattactgcggc
ggtgagaaaactagatcatgaattaggtattccagaagatgaaactaagacaaggggtaagttt
cactttttaaacagaatccattacatggcaccaagcaatgaaccatggggtgaacatgaaattg
attacatcctattttataagatcaacgctaaagaaaacttgactgtcaacccaaacgtcaatga
agttagagacttcaaatgggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgctttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg

Figure 22D cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
(SEQ ID NO:20)

Figure 25A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatggatccgagctcggatccactagtaacggccgcc
agtgtgctggaattcgcccttaggaggtaaaaaaacatgtcattaccgttcttaacttctgcac
cgggaaaggttattatttttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtcttttggatccgttgttagctcaactatccgaatccttccactaccatgcagcgttt
tgtttcctgtatatgtttgtttgcctatgcccccatgccaagaatattaagttttctttaaagt
ctactttacccatcggtgctgggttgggctcaagcgcctctatttctgtatcactggccttagc
tatggcctacttgggggggttaataggatctaatgacttggaaaagctgtcagaaaacgataag
catatagtgaatcaatgggccttcataggtgaaaagtgtattcacggtacccccttcaggaatag
ataacgctgtggccacttatggtaatgccctgctatttgaaaaagactcacataatggaacaat
aaacacaaacaattttaagttcttagatgatttcccagccattccaatgatcctaacctatact
agaattccaaggtctacaaaagatcttgttgctcgcgttcgtgtgttggtcaccgagaaattc
ctgaagttatgaagccaattctagatgccatgggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaaagaaattgcaagatgattttagttacgagacatttgaaacagacttgggtggga
ctggctgctgtttgttaagcgcaaaaaatttgaataaagatcttaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtgaaaagtaaacaatttaaag
atggggagtggctgtaccatataagtcctaaaagtggcttcattcctgtttcgataggcggatc
taagaaccctttcattgaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctgggctcctcggcaggtttagtcacagttttaactacagctttggcc
tcctttttttgtatcggacctggaaaataatgtagacaaatatagagaagttattcataatttag
cacaagttgctcattgtcaagctcagggtaaaattggaagcgggtttgatgtagcggcggcagc
atatggatctatcagatatagaagattcccacccgcattaatctctaatttgccagatattgga
agtgctacttacggcagtaaactggcgcatttggttgatgaagaagactggaatattacgatta
aaagtaaccatttaccttcgggattaactttatggatgggcgatattaagaatggttcagaaac
agtaaaactggtccagaaggtaaaaaattggtatgattcgcatatgccagaaagcttgaaata

Figure 25B tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaaataactaaagaatctggtgccgatatcgaacctcccgtacaaactagcttattggatgatt
gccagaccttaaaggagttcttacttgcttaatacctggtgctggtggttatgacgccattgc
agtgattactaagcaagatgttgatcttagggctcaaaccgctaatgacaaaagattttctaag
gttcaatggctggatgtaactcaggctgactggggtgttaggaaagaaaaagatccggaaactt
atcttgataaataacttaaggtagctgcatgcagaattcgcccttaaggaggaaaaaaaaatga
ccgtttacacagcatccgttaccgcacccgtcaacatcgcaacccttaagtattgggggaaaag
ggacacgaagttgaatctgcccaccaattcgtccatatcagtgactttatcgcaagatgacctc
agaacgttgacctctgcggctactgcacctgagtttgaacgcgacactttgtggttaaatggag
aaccacacagcatcgacaatgaaagaactcaaaattgtctgcgcgacctacgccaattaagaaa
ggaaatggaatcgaaggacgcctcattgcccacattatctcaatggaaactccacattgtctcc
gaaaataactttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaaggatgtgagttccactcagggtatgcaattgac
cgtggcaacctccgaactatttaaagaaagaattgaacatgtcgtaccaaagagatttgaagtc
atgcgtaaagccattgttgaaaaagatttcgccacctttgcaaaggaaacaatgatggattcca
actctttccatgccacatgtttggactctttccctccaatattctacatgaatgacacttccaa
gcgtatcatcagttggtgccacaccattaatcagttttacggagaaacaatcgttgcatacacg
tttgatgcaggtccaaatgctgtgttgtactacttagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgccagagtgattttaactcaagtcggttcaggcccacaagaaacaaacgaatctt
tgattgacgcaaagactggtctaccaaaggaataagatcaattcgctgcatcgcccttaggagg
taaaaaaaaatgactgccgacaacaatagtatgccccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgtttttctggt
catgatgaggagcaaattaagttaatgaatgaaaattgtattgttttggattgggacgataatg
ctattggtgccggtaccaagaaagtttgtcatttaatggaaaatattgaaaagggtttactaca
tcgtgcattctccgtctttattttcaatgaacaaggtgaattacttttacaacaaagagccact
gaaaaaataactttccctgatctttggactaacacatgctgctctcatccactatgtattgatg
acgaattaggtttgaagggtaagctagacgataagattaagggcgctattactgcggcggtgag
aaaactagatcatgaattaggtattccagaagatgaaactaagacaaggggtaagtttcacttt
ttaaacagaatccattacatggcaccaagcaatgaaccatggggtgaacatgaaattgattaca
tcctattttataagatcaacgctaaagaaaacttgactgtcaacccaaacgtcaatgaagttag
agacttcaaatgggtttcaccaaatgatttgaaaactatgtttgctgacccaagttacaagttt
acgccttggtttaagattatttgcgagaattacttattcaactggtgggagcaattagatgacc
tttctgaagtggaaaatgacaggcaaattcatagaatgctataacaacgcgtcctgcattcgcc
cttaggaggtaaaaaaacatgtgtgcgacctcttctcaatttactcagattaccgagcataatt
cccgtcgttccgcaaactatcagccaaacctgtggaatttcgaattcctgcaatccctggagaa
cgacctgaaagtggaaaagctggaggagaaagcgaccaaactggaggaagaagttcgctgcatg

Figure 25C atcaaccgtgtagacacccagccgctgtccctgctggagctgatcgacgatgtgcagcgcctgg
gtctgacctacaaatttgaaaaagacatcattaaagccctggaaaacatcgtactgctggacga
aaacaaaaagaacaaatctgacctgcacgcaaccgctctgtctttccgtctgctgcgtcagcac
ggtttcgaggtttctcaggatgtttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtaccttttccatcacccacctgaagaacaacctgaaagaa
ggcattaataccaaggttgcagaacaagtgagccacgccctggaactgccatatcaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgtttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtgcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgcccagactacgcgactgaaaaccgcatcaa
actgctgctgattgaccctttcccgattaaccagctgatgtatgtctaactgcagctggtacca
tatgggaattcgaagctttctagaacaaaaactcatctcagaagaggatctgaatagcgccgtc
gaccatcatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgaccccatgccgaactcagaagtgaaacgccgta
gcgccgatggtagtgtggggtctccccatgcgagagtagggaactgccaggcatcaaataaaac
gaaaggctcagtcgaaagactgggcctttcgttttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
tttttgcgtttctacaaactctttttgtttatttttctaaatacattcaaatatgtatccgctt
aaccggaattgccagctggggcgccctctggtaaggttgggaagccctgcaaagtaaactggat
ggctttctcgccgccaaggatctgatggcgcaggggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttctttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcaggggctcgcgcc
agccgaactgttcgccaggctcaaggcgagcatgcccgacggcgaggatctcgtcgtgaccat

Figure 25D ggcgatgcctgcttgccgaatatcatggtggaaaatggccgcttttctggattcatcgactgtg
gccggctgggtgtggcggaccgctatcaggacatagcgttggctacccgtgatattgctgaaga
gcttggcggcgaatgggctgaccgcttcctcgtgctttacggtatcgccgctcccgattcgcag
cgcatcgccttctatcgccttcttgacgagttcttctgacgcatgaccaaaatcccttaacgtg
agttttcgttccactgagcgtcagaccccgtagaaaagatcaaaggatcttcttgagatccttt
ttttctgcgcgtaatctgctgcttgcaaacaaaaaaaccaccgctaccagcggtggtttgtttg
ccggatcaagagctaccaactctttttccgaaggtaactggcttcagcagagcgcagataccaa
atactgtccttctagtgtagccgtagttaggccaccacttcaagaactctgtagcaccgcctac
atacctcgctctgctaatcctgttaccagtggctgctgccagtggcgataagtcgtgtcttacc
gggttggactcaagacgatagttaccggataaggcgcagcggtcgggctgaacggggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagcttccagggggaaacgcctggtatctttatagtcctgtcgggt
ttcgccacctctgacttgagcgtcgatttttgtgatgctcgtcaggggggcggagcctatggaa
aaacgccagcaacgcggcctttttacggttcctggccttttgctggccttttgctcacatgttc
tttcctgcgttatcccctgattctgtggataaccgtattaccgcctttgagtgagctgataccg
ctcgccgcagccgaacgaccgagcgcagcgagtcagtgagcgaggaagcggaagagcgcctgat
gcggtattttctccttacgcatctgtgcggtatttcacaccgcatatggtgcactctcagtaca
atctgctctgatgccgcatagttaagccagtatacactccgctatcgctacgtgactgggtcat
ggctgcgccccgacacccgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaat
tcagggtggtgaatgtgaaaccagtaacgttatacgatgtcgcagagtatgccggtgtctctta
tcagaccgtttcccgcgtggtgaaccaggccagccacgtttctgcgaaaacgcgggaaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtgggctgatca
ttaactatccgctggatgaccaggatgccattgctgtggaagctgcctgcactaatgttccggc
gttatttcttgatgtctctgaccagacacccatcaacagtattattttctcccatgaagacggt
acgcgactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggattttcgc
ctgctggggcaaaccagcgtggaccgcttgctgcaactctctcagggccaggcggtgaagggca
atcagctgttgcccgtctcactggtgaaaagaaaaaccaccctggcgcccaatacgcaaaccgc
ctctccccgcgcgttggccgattcattaatgcagctggcacgacaggtttcccgactggaaagc
gggcagtgagcgcaacgcaattaatgtgagttagcgcgaattgatctg
(SEQ ID NO:33)

Figure 27A

5′-
cccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaaatataaaggcagcttaagtcaagtaa
gtgccgtagacttaggaacacatgttacaacacaacttttaaaaagacattccactatttctga
agaaattgatcaagtaatctttggaaatgttttacaagctggaaatggccaaaatcccgcacga
caaatagcaataaacagcggtttgtctcatgaaattcccgcaatgacggttaatgaggtctgcg
gatcaggaatgaaggccgttattttggcgaaacaattgattcaattaggagaagcggaagtttt
aattgctggcgggattgagaatatgtcccaagcacctaaattacaacgttttaattacgaaaca
gaaagctacgatgcgcctttttctagtatgatgtatgatggattaacggatgcctttagtggtc
aggcaatgggcttaactgctgaaaatgtggccgaaaagtatcatgtaactagagaagagcaaga
tcaattttctgtacattcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagttttttaaagaagacggtactgtaacagcagg
gaatgcatcaaccattaatgatggggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtccaaagagaa
ctggctttaccagaggaaaaggtcaacatttatggtggcggtatttcattaggtcatgcgattg
gtgccacaggtgctcgtttattaacgagtttaagttatcaattaaatcaaaaagaaaagaaata
tggagtggcttctttatgtatcggcggtggcttaggactcgctatgctactagagagacctcag
caaaaaaaaaacagccgattttatcaaatgagtcctgaggaacgcctggcttctcttcttaatg
aaggccagatttctgctgatacaaaaaaagaatttgaaaatacggctttatcttcgcagattgc
caatcatatgattgaaaatcaaatcagtgaaacagaagtgccgatgggcgttggcttacattta
acagtggacgaaactgattatttggtaccaatggcgacagaagagccctcagttattgcggctt
tgagtaatggtgcaaaaatagcacaaggatttaaaacagtgaatcaacaacgcttaatgcgtgg
acaaatcgtttttttacgatgttgcagatcccgagtcattgattgataaactacaagtaagagaa
gcggaagtttttcaacaagcagagttaagttatccatctatcgttaaacggggcggcggcttaa
gagatttgcaatatcgtacttttgatgaatcatttgtatctgtcgactttttagtagatgttaa
ggatgcaatgggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaatttcagttccgcttgctttagccacggttggcggtgccaca
aaagtcttacctaaatctcaagcagctgctgatttgttagcagtgacggatgcaaaagaactaa
gtcgagtagtagcggctgttggtttggcacaaaatttagcggcgttacgggccttagtctctga
aggaattcaaaaaggacacatggctctacaagcacgttctttagcgatgacggtcggagctact
ggtaaagaagttgaggcagtcgctcaacaattaaaacgtcaaaaaacgatgaaccaagaccgag
ccatggctattttaaatgatttaagaaaacaataaaggaggtaaaaaaacatgacaattgggat

Figure 27B tgataaaattagtttttttgtgccccttattatattgatatgacggcactggctgaagccaga
aatgtagaccctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaacctttcgctcgctctttcgaaatcaaggaagcttgtt
acggagcaacagcaggcttacagttagctaagaatcacgtagccttacatccagataaaaagt
cttggtcgtagcggcagatattgcaaaatatggcttaaattctggcggtgagcctacacaagga
gctggggcggttgcaatgttagttgctagtgaaccgcgcattttggctttaaaagaggataatg
tgatgctgacgcaagatatctatgacttttggcgtccaacaggccacccgtatcctatggtcga
tggtcctttgtcaaacgaaacctacatccaatcttttgcccaagtctgggatgaacataaaaa
cgaaccggtcttgattttgcagattatgatgctttagcgttccatattccttacacaaaaatgg
gcaaaaaagccttattagcaaaaatctccgaccaaactgaagcagaacaggaacgaattttagc
ccgttatgaagaaagtatcgtctatagtcgtcgcgtaggaaacttgtatacgggttcacttttat
ctgggactcatttccctttagaaaatgcaacgactttaaccgcaggcaatcaaattggtttat
tcagttatggttctggtgctgtcgctgaatttttcactggtgaattagtagctggttatcaaaa
tcatttacaaaaagaaactcatttagcactgctggataatcggacagaactttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttgggcccgaacaaaaactcatctcagaagaggatctgaata
gcgccgtcgaccatcatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgaccccatgccgaactcagaagtgaa
acgccgtagcgccgatggtagtgtggggtctccccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggcctttttgcgtttctacaaactctttttgtttatttttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagattttaatgcggatgttgcgattacttcgccaactattgcgataacaagaaaaagc
cagcctttcatgatatatctcccaatttgtgtagggcttattatgcacgcttaaaaataataa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat

Figure 27C caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctacttttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaatttgcctcaaaactggtgagctgaatttttgcagttaaa
gcatcgtgtagtgtttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtcctttttcctttgagttgtgggtat
ctgtaaattctgctagacctttgctggaaaacttgtaaattctgctagaccctctgtaaattcc
gctagacctttgtgtgtttttttgtttatattcaagtggttataatttatagaataaagaaag
aataaaaaaagataaaagaatagatcccagccctgtgtataactcactactttagtcagttcc
gcagtattacaaaaggatgtcgcaaacgctgtttgctcctctacaaaacagaccttaaaccct
aaaggcttaagtagcaccctcgcaagctcgggcaaatcgctgaatattccttttgtctccgacc

Figure 27D

Atcaggcacctgagtcgctgtctttttcgtgacattcagttcgctgcgctcacggctctggcag
tgaatgggggtaaatggcactacaggcgcctttttatggattcatgcaaggaaactacccataat
acaagaaaagcccgtcacgggcttctcagggcgttttatggcgggtctgctatgtggtgctatc
tgactttttgctgttcagcagttcctgccctctgattttccagtctgaccacttcggattatcc
cgtgacaggtcattcagactggctaatgcacccagtaaggcagcggtatcatcaacaggctta
(SEQ ID NO:46)

Lower Pathway Bacillus Cassette 9371 bp

Figure 29A

5'-
tgtaacctttgctttcaaatgagtagaaataatgcacatccatgtttgtatcgtgcaaataaag
tgtttcatccgtaggaaaaaatgactttagtatctgttccgctttttctgatgaaatgtgctcc
ccgacaaaattgaatgaatcatggacatttgctggctttgatacagcgaaagcagccgttccta
tgttatatatcggatttaacagcaggacaaaaacaccatgacagccatcgtcacccacttatt
cacacgcacataaacctttcctgacttttggaacagatgatagctcatcaaaatcccgccatt
gccaaataaatcgtatatggcattactgcaccataatcttttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatcccatccgggtattccttccaatacgaaaagaaactaaaaa
tcatttgtacgatcggcaaactgacaacagcaaggtcgaacgtataaaacttaccctttccgcc
atgatcacgcggcatcagcatatagtgaaaagccgtcagcagcacatatccgtataacaaaaaa
tgcagcagcggcagcagttcttttccgtcctcttaagtaagcgctggtgaagtttgttgatt
gcacctggtgaataagttcaacagacactcccgccagcagcacaatccgcaatataacacccgc
caagaacattgtgcgctgccggtttattttgggatgatgcaccaaaagatataagcccgccaga
acaacaattgaccattgaatcagcagggtgctttgtctgcttaatataaaataacgttcgaaat
gcaatacataatgactgaataactccaacacgaacaacaactccatttcttctgctatcaaaa
taacagactcgtgattttccaaacgagctttcaaaaagcctctgccccttgcaaatcggatgc
ctgtctataaaattcccgatattggttaaacagcggcgcaatggcggccgcatctgatgtcttt
gcttggcgaatgttcatcttatttcttcctccctctcaataatttttcattctatccctttc
tgtaaagtttatttttcagaatactttatcatcatgctttgaaaaaatatcacgataatatcc
attgttctcacggaagcacacgcaggtcatttgaacgaatttttcgacaggaatttgccggga
ctcaggagcatttaacctaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaaaatgggtctactaaaatattattccatctattac
aataaattcacagaatagtcttttaagtaagtctactctgaatttttttaaaggagagggtaa
agagtgtcattaccgttcttaacttctgcaccgggaaaggttattattttggtgaacactctg
ctgtgtacaacaagcctgccgtcgctgctagtgtgtctgcgttgagaacctacctgctaataag
cgagtcatctgcaccagatactattgaattggacttcccggacattagctttaatcataagtgg
tccatcaatgatttcaatgccatcaccgaggatcaagtaaactcccaaaaattggccaaggctc
aacaagccaccgatggcttgtctcaggaactcgttagtcttttggatccgttgttagctcaact
atccgaatccttccactaccatgcagcgttttgtttcctgtatatgtttgtttgcctatgcccc
catgccaagaatattaagtttctttaaagtctactttacccatcggtgctgggttgggctcaa
gcgcctctatttctgtatcactggccttagctatggcctacttgggggggttaataggatctaa
tgacttggaaaagctgtcagaaaacgataagcatatagtgaatcaatgggccttcataggtgaa
aagtgtattcacggtaccccttcaggaatagataacgctgtggccacttatggtaatgccctgc
tatttgaaaaagactcacataatggaacaataaacacaaacaattttaagttcttagatgattt
cccagccattccaatgatcctaacctatactagaattccaaggtctacaaaagatcttgttgct
cgcgttcgtgtgttggtcaccgagaaatttcctgaagttatgaagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctctttgactttgtt
acgaagagacattactcaagagcaaattgacagcttcaaaaagaaattgcaagatgattttagt

Figure 29B tacgagacatttgaaacagacttgggtgggactggctgctgtttgttaagcgcaaaaaatttga
ataaagatcttaaaatcaaatccctagtattccaattatttgaaaataaaactaccacaaagca
acaaattgacgatctattattgccaggaaacacgaatttaccatggacttcataaaggagagg
gtgtcagagttgagagccttcagtgccccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaaccctttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
ctttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccacccgcattaatctctaatttgccagatattggaag
tgctacttacggcagtaaactggcgcatttggttgatgaagaagactggaatattacgattaaa
agtaaccatttaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagttagagatgcagttgccacaattagacgttcctttagaaa
aataactaaagaatctggtgccgatatcgaacctcccgtacaaactagcttattggatgattgc
cagaccttaaaggagttcttacttgcttaatacctggtgctggtggttatgacgccattgcag
tgattactaagcaagatgttgatcttagggctcaaaccgctaatgacaaaagatttctaaggt
tcaatggctggatgtaactcaggctgactggggtgttaggaaagaaaaagatccggaaacttat
cttgataaataaaggagagggtgaccgtttacacagcatccgttaccgcacccgtcaacatcg
caaccccttaagtattgggggaaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaaggggtctggttcagcttgtagatcgttgtttggcggata
cgtggcctgggaaatgggaaaagctgaagatggtcatgattccatggcagtacaaatcgcagac
agctctgactggcctcagatgaaagcttgtgtcctagttgtcagcgatattaaaaaggatgtga
gttccactcagggtatgcaattgaccgtggcaacctccgaactatttaaagaaagaattgaaca
tgtcgtaccaaagagatttgaagtcatgcgtaaagccattgttgaaaaagatttcgccaccttt
gcaaaggaaacaatgatggattccaactctttccatgccacatgtttggactctttccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctctgttcctggatgggaca
agaaatttactactgagcagcttgaggctttcaaccatcaatttgaatcatctaactttactgc
acgtgaattggatcttgagttgcaaaaggatgttgccagagtgattttaactcaagtcggttca
ggcccacaagaaacaaacgaatctttgattgacgcaaagactggtctaccaaaggaataaaagg
agagggtgactgccgacaacaatagtatgccccatggtgcagtatctagttacgccaaattagt

Figure 29C gcaaaaccaaacacctgaagacattttggaagagtttcctgaaattattgcattacaacaaaga
cctaatacccgatctagtgagacgtcaaatgacgaaagcggagaaacatgtttttctggtcatg
atgaggagcaaattaagttaatgaatgaaaattgtattgttttggattgggacgataatgctat
tggtgccggtaccaagaaagtttgtcatttaatggaaaatattgaaaagggtttactacatcgt
gcattctccgtctttattttcaatgaacaaggtgaattacttttacaacaaagagccactgaaa
aaataactttccctgatctttggactaacacatgctgctctcatccactatgtattgatgacga
attaggtttgaagggtaagctagacgataagattaagggcgctattactgcggcggtgagaaaa
ctagatcatgaattaggtattccagaagatgaaactaagacaaggggtaagtttcactttttaa
acagaatccattacatggcaccaagcaatgaaccatggggtgaacatgaaattgattacatcct
attttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaccggccttggccccgccg
gtttttttattatttttcttcctccgcatgttcaatccgctccataatcgacggatggctccctc
tgaaaattttaacgagaaacggcgggttgacccggctcagtcccgtaacggccaagtcctgaaa
cgtctcaatcgccgcttcccggtttccggtcagctcaatgccgtaacggtcggcggcgttttcc
tgataccgggagacggcattcgtaatttgaatacatacgaacaaattaataaagtgaaaaaaat
acttcggaaacatttaaaaaataaccttattggtacttacatgtttggatcaggagttgagagt
ggactaaaaccaaatagtgatcttgactttttagtcgtcgtatctgaaccattgacagatcaaa
gtaaagaaatacttatacaaaaaattagacctatttcaaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatatacgg
aaattatgacttagaggaattactacctgatattccattttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacatagggagagaattttgttagcagttcgtagttatcttgga
gagaatattgaatggactaatgaaaatgtaaatttaactataaactatttaaataacagattaa
aaaaattataatgtaacctttgctttcaaatgagtagaaataatgcacatccatgtttgtatcg
tgcaaataaagtgtttcatccgtaggaaaaaatgactttagtatctgttccgcttttttctgatg
aaatgtgctccccgacaaaattgaatgaatcatggacatttgctggctttgatacagcgaaagc
agccgttcctatgttatatatcggatttaacagcaggacaaaaaacaccatgacagccatcgtc
acccacttattcacacgcacataaacctttcctgacttttggaacagatgatagctcatcaaaa
atcccgccattgccaaataaatcgtatatggcattactgcaccataatctttttgagatttgatt
gggatatggcgcaagcagcaagacaagcagtccgataatcagcgtataaaataagcctagtaag
atcttatccgttctccaatacagcttgaaaaacactacattcaacgcaatgggaagagtgatga
tgaaaaacagaaacacgaatgcaatcggctccatcccatccgggtattccttccaatacgaaaa
gaaactaaaaatcatttgtacgatcggcaaactgacaacagcaaggtcgaacgtataaaactta
ccctttccgccatgatcacgcggcatcagcatatagtgaaaagccgtcagcagcacatatccgt
ataacaaaaaatgcagcagcggcagcagttcttttccgtcctctcttaagtaagcgctggtgaa
gtttgttgattgcacctggtgaataagttcaacagacactcccgccagcagcacaatccgcaat
ataacacccgccaagaacattgtgcgctgccggtttattttgggatgatgcaccaaaagatata
agcccgccagaacaacaattgaccattgaatcagcagggtgctttgtctgcttaatataaaata
acgttcgaaatgcaatacataatgactgaataactccaacacgaacaacaaaagtgcgcatttt

Figure 29D

Ataaaagctaatgattcagtccacataattgatagacgaattctgctacaggtcacgtggctat
gtgaaggatcgcgcgtccagttaagagcaaaaacattgacaaaaaatttatttatgctaaaat
ttactattaatatatttgtatgtataataagattctcctggccaggggaatcttatttttttgtg
gaggatcatttcatgaggaaaaatgagtccagcttaacgtctctaatttcagcttttgcccgtg
catatcacagccgatatgacacacctcttatttttgatgattttatcgcaaaagatctcattaa
cgaaaaagagtttatcgacatcagtaaaaatatgattcaagaaatatcgtttttcaacaaagag
atcgccgaacgtcttcaaaatgatcctgaaaaaatattaaaatgggttgcacaaatccagctgt
ctccaacgcccctagcacgtgcttcttattgtgaaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaaataagc
tgaaggatgcaaatctgacaattccgggtcatcttcattttgttcctatggatttcaccaaaac
gttttcgtatgatcctctcttagatgaaggatttaaaaacacaaaaacattcttcagccttctc
ggagtgtcttattatgtaacacgggaagaaaatgcaagcttgatcagcaatttattttctcatg
tcccgcctggaagctctattgtttttgattatgcggacgaaacactttttacagcaaaaggac
gtcgaatcgagttgaacatatggtgaagatggctgccgcaagcggggaaccgatgaaatcatgt
ttcacttatcaagagattgaacatctg
(SEQ ID NO:47)

Figure 31A

5'-
tagaaaaactcatcgagcatcaaatgaaactgcaatttattcatatcaggattatcaatacccat
atttttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaaggacaattacaaacaggaatcgagtgcaaccggcgcaggaacactgccagcg
catcaacaatattttcacctgaatcaggatattcttctaatacctggaacgctgtttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttcccgttgaatatggctcatattcttcctttttcaatattatt
gaagcatttatcagggttattgtctcatgagcggatacatatttgaatgtatttagaaaaataa
acaaataggggtcagtgttacaaccaattaaccaattctgaacattatcgcgagcccatttata
cctgaatatggctcataacaccccttgtttgcctggcggcagtagcgcggtggtcccacctgac
cccatgccgaactcagaagtgaaacgccgtagcgccgatggtagtgtggggactccccatgcga
gagtagggaactgccaggcatcaaataaaacgaaaggctcagtcgaaagactgggcctttcgcc
cgggctaattagggggtgtcgccctttagtcgctgaacatgtgctctgtttctaccgagaacgt
ttccttcactgagacggaaaccgaggcacgtcgtagcgcgaactacgagccgaatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctcccgttggtggcgccgtgtgggcctggc
gaccaaactgcacttcgctaaggaccgcctgattgagtctttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaaatggctgtataa
caaatccactccgacctttgacgattatttcggcaatgcctggaaatccagctctggcccgctg
caactgatcttcgcttattttgcggttgtccaaaacatcaaaaaggaggaaattgaaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

Figure 31B ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgctttttttctcatttataaggttaaataattctcatatatcaagcaaagt
gacaggcgcccttaaatattctgacaaatgctctttccctaaactccccccataaaaaaacccg
ccgaagcgggtttttacgttatttgcggattaacgattactcgttatcagaaccgcccagggggg
cccgagcttaagactggccgtcgttttacaacacagaaagagtttgtagaaacgcaaaaaggcc
atccgtcaggggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgtttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtggcctaactacggctacactagaagaacagtatttggtatctgcgctctgctga
agccagttaccttcggaaaaagagttggtagctcttgatccggcaaacaaaccaccgctggtag
cggtggtttttttgtttgcaagcagcagattacgcgcagaaaaaaaggatctcaagaagatcct
ttgatcttttctacggggtctgacgctcagtggaacgacgcgcgcgtaactcacgttaagggat
tttggtcatgagcttgcgccgtcccgtcaagtcagcgtaatgctctgcttt
(SEQ ID NO:48)

Figure 33A

5′-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctgggtctgggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtcttttactgggcagtcggcgttgcgttcgaacctc
agtattctgactgccgtaacagcgttgcgaaaatgttcagcttcgttactattatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaaggtgaaaacatcctgccgtacctgactaa
agcgtgggcggatctgtgtaacgcttttctgcaagaagcgaaatggctgtataacaaatccact
ccgacctttgacgattatttcggcaatgcctggaaatccagctctggcccgctgcaactgatct
tcgcttattttgcggttgtccaaaacatcaaaaaggaggaaattgaaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggcctttttt
gcgtttctacaaactctttttgtttatttttctaaatacattcaaatatgtatccgctcatgag
acaataaccctgataaatgcttcaataatattgaaaaaggaagagtatgagtattcaacatttc

Figure 33B cgtgtcgcccttattcccttttttgcggcattttgccttcctgtttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcactttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgcttttttgcacaacatgggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagaccccgtagaaaagatcaaaggatcttcttgagatcctt
tttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccagggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc

Figure 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:49)

Figure 35A

5′-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt

Figure 35B ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
tcgcccttaggaggtaaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgtttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttattttcaatgaacaaggtgaattacttttac
aacaaagagccactgaaaaataactttccctgatctttggactaacacatgctgctctcatcc
actatgtattgatgacgaattaggtttgaagggtaagctagacgataagattaagggcgctatt
actgcggcggtgagaaaactagatcatgaattaggtattccagaagatgaaactaagacaaggg
gtaagtttcactttttaaacagaatccattacatggcaccaagcaatgaaccatggggtgaaca
tgaaattgattacatcctatttttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtggggtctccccatgcgagagtagggaactg
ccaggcatcaaataaaacgaaaggctcagtcgaaagactgggcctttcgttttatctgttgttt
gtcggtgaacgctctcctgagtaggacaaatccgccgggagcggatttgaacgttgcgaagcaa
cggcccggagggtggcgggcaggacgcccgccataaactgccaggcatcaaattaagcagaagg
ccatcctgacggatggcctttttgcgtttctacaaactctttttgtttatttttctaaatacat
tcaaatatgtatccgcttaaccggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttgggtggagaggctattcggctatgactgggcacaacagacaatcggctgctctga
tgccgccgtgttccggctgtcagcgcaggggcgcccggttctttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat

Figure 35C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
(SEQ ID NO:50)

Figure 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

Figure 37B attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagtttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg

Figure 37C gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggcctttcgttttatctgttgtttgtcggtgaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggcctttttgcgtttctacaaa
ctctttttgtttatttttctaaatacattcaaatatgtatccgcttaaccggaattgccagctg
gggcgccctctggtaaggttgggaagccctgcaaagtaaactggatggctttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttctttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctcccgattcgcagcgcatcgccttctatcgc
cttcttgacgagttcttctgacgcatgaccaaaatcccttaacgtgagttttcgttccactgag
cgtcagaccccgtagaaaagatcaaaggatcttcttgagatcctttttttctgcgcgtaatctg
ctgcttgcaaacaaaaaaaccaccgctaccagcggtggtttgtttgccggatcaagagctacca
actctttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccagggggaaacgcctggtatctttatagtcctgtcgggtttcgccacctctgacttg
agcgtcgatttttgtgatgctcgtcaggggggcggagcctatggaaaaacgccagcaacgcggc
ctttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
(SEQ ID NO:51)

Figure 39A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctactttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaattttgcctcaaaactggt
gagctgaatttttgcagttaaagcatcgtgtagtgtttttcttagtccgttatgtaggtaggaa
tctgatgtaatggttgttggtattttgtcaccattcattttatctggttgttctcaagttcgg

Figure 39B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttaactggaaaagataaggcaatatctcttcactaaaaactaattctaatttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgtttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattcctttgtctccgaccatcaggcacctgagtcgctgtctttttcgtgacattcagttc
gctgcgctcacggctctggcagtgaatgggggtaaatggcactacaggcgcctttatggattc
atgcaaggaaactacccataatacaagaaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

Figure 39C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctccccatgcgaga
gtagggaactgccaggcatcaaataaaacgaaaggctcagtcgaaagactgggcctttcgtttt
atctgttgtttgtcggtgaacgctctcctgagtaggacaaatccgccgggagcggatttgaacg
ttgcgaagcaacggcccggagggtggcgggcaggacgcccgccataaactgccaggcatcaaat
taagcagaaggccatcctgacggatggcctttttgcgtttctacaaactctttttgtttatttt
tctaaatacattcaaatatgtatccgctcatgagacaataaccctgataaatgcttcaataat
(SEQ ID NO:52)

Figure 41A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatctttttccattcggcgtcgatcagtttacg
cagttcttcgcgggcctgttcctcgctggtaccatcgtttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgtttccaggtacttggagaaagccgggataatttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
cattttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctctttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttctttttgttttcgtccagcagtacgatgttttccagggctttaatgatgtctttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttatttaatcgatacattaatatatacctctttaatttttaataataaagtta
atcgataattccggtcgagtgcccacacagattgtctgataaattgttaaagagcagtgccgct
tcgctttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

Figure 41B tgatgccgcatagttaagccagccccgacacccgccaacacccgctgacgagcttagtaaagcc
ctcgctagatttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctacttttgtttgtta
gtcttgatgcttcactgatagatacaagagccataagaacctcagatccttccgtatttagcca
gtatgttctctagtgtggttcgttgttttgcgtgagccatgagaacgaaccattgagatcata
cttactttgcatgtcactcaaaaattttgcctcaaaactggtgagctgaatttttgcagttaaa
gcatcgtgtagtgtttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc

Figure 41C cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtcctttttcctttgagttgtgggtat
ctgtaaattctgctagacctttgctggaaaacttgtaaattctgctagaccctctgtaaattcc
gctagacctttgtgtgtttttttttgtttatattcaagtggttataatttatagaataaagaaag
aataaaaaaagataaaaagaatagatcccagccctgtgtataactcactactttagtcagttcc
gcagtattacaaaaggatgtcgcaaacgctgtttgctcctctacaaaacagaccttaaaccct
aaaggcttaagtagcaccctcgcaagctcgggcaaatcgctgaatattcctttttgtctccgacc
atcaggcacctgagtcgctgtctttttcgtgacattcagttcgctgcgctcacggctctggcag
tgaatgggggtaaatggcactacaggcgcctttttatggattcatgcaaggaaactacccataat
acaagaaaagcccgtcacgggcttctcagggcgttttatggcgggtctgctatgtggtgctatc
tgactttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)

Figure 43A

5’-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgattttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaatttgcctcaaaactggt
gagctgaattttgcagttaaagcatcgtgtagtgtttttcttagtccgttatgtaggtaggaa
tctgatgtaatggttgttggtattttgtcaccattcattttatctggttgttctcaagttcgg

Figure 43B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttaactggaaaagataaggcaatatctcttcactaaaactaattctaattttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaacttgtaaattc
tgctagaccctctgtaaattccgctagacctttgtgtgttttttttgtttatattcaagtggtt
ataatttatagaataaagaaagaataaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgcctttatggattc
atgcaaggaaactacccataatacaagaaaagcccgtcacgggcttctcagggcgttttatggc
gggtctgctatgtggtgctatctgacttttgctgttcagcagttcctgccctctgatttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

Figure 43C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaatacccgatctagtgagacgtca
aatgacgaaagcggagaaacatgttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttattttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcactttttaaacagaatccattacatggcaccaagca
atgaaccatggggtgaacatgaaattgattacatcctattttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaatttgcctggcggcagtagcgcggtggtccca
cctgaccccatgccgaactcagaagtgaaacgccgtagcgccgatggtagtgtggggtctcccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactctttttg
tttatttttctaaatacattcaaatatgtatccgctcatgagacaataaccctgataaatgctt
caataat
(SEQ ID NO:54)

Figure 45A

5′-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttatgccagccaggccttgattttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagtttttccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagattttgaatagctcggcaaaccgccgctacttttcg
gcaaacaaccgctggagggatcaaatttaggcacggcgtggaaagtgatcgggtctttttctgc
cggttcataaccacgaccttttttggtcatgatatgcaggaactgcgggcctttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctctttaattggcggcacgccagagaaaactttttcccgccttcgcgcagtgaagag
taaagcttaccggaaagcagctgtgccagatggttgttgagcgcgccgacattttcggaaatcg
acatttcattgtcgttgagaatcaccagcatatcaggacggatatcgcccgcgtgattcatcgc
ttcaaacgccatgcctgcggtaatcgcgccatcgccaatgacacagacggtgcggcgattttg
cctttcttttcggcagcaaccgcaataccaattccggcactgatggaggttgatgaatgcccga
cgcttaatacgtcatattcgctttcgccgcgccacgggaacgggtgcagaccgcctttctgacg
gatggtgccgattttgtcgcggcgtccggtcaaaattttatgcggataagcctgatgccccaca
tcccaaatcaattggtcaaacggggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgtttttttacctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcagggtggagtcgctaacgcgttcacg

Figure 45B attcatctttttccattcggcgtcgatcagtttacgcagttcttcgcgggcctgttcctcgctg
gtaccatcgttttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
aagccgggataatttgttgttggaccatttcgcctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtcccagcgctctacagcatcggtgaacagttgcagttcgtccagagtgccataaac
gtcatacacgtcatcgatgatcgtcaccagaccaaacatttagtaacagctttgcgacattca
ccaaactgcgggtctggcgccatacccagtgcccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttctttttgttttcgtccagcagt
acgatgttttccagggctttaatgatgtctttttcaaatttgtaggtcagacccaggcgctgca
catcgtcgatcagctccagcagggacagcggctgggtgtctacacggttgatcatgcagcgaac
ttcttcctccagtttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaatttttaataataaagttaatcgataattccggtcgagtgcccacac
agattgtctgataaattgttaaagagcagtgccgcttcgctttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacacccgctgacgagcttagtaaagccctcgctagatttaatgcggatgttgcg
attacttcgccaactattgcgataacaagaaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc

Figure 45C cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtaccccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgaccccggatgaagtggttcgcatcctcggttttct
ggaaggcgagcatcgtttgttcgcccagcttctgtatggaacgggcatgcggatcagtgagggt
ttgcaactgcgggtcaaggatctggatttcgatcacggcacgatcatcgtgcgggagggcaagg
gctccaaggatcgggccttgatgttacccgagagcttggcacccagcctgcgcgagcaggggaa
ttaattcccacgggttttgctgcccgcaaacgggctgttctggtgttgctagtttgttatcaga
atcgcagatccggcttcagccggtttgccggctgaaagcgctatttcttccagaattgccatga
tttttccccacgggaggcgtcactggctcccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaaagc
tctgatgtatctatctttttacaccgttttcatctgtgcatatggacagttttccctttgata
tgtaacggtgaacagttgttctacttttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaatttt
gcctcaaaactggtgagctgaattttgcagttaaagcatcgtgtagtgtttttcttagtccgt
tatgtaggtaggaatctgatgtaatggttgttggtattttgtcaccattcatttttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatattttatgaatttttttaactggaaaagataaggcaatatctcttcactaaaaactaattc
taatttttcgcttgagaacttggcatagtttgtccactggaaaatctcaaagcctttaaccaaa
ggattcctgatttccacagttctcgtcatcagctctctggttgctttagctaatacaccataag
cattttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtcctttttcctttgagttgtgggtatctgtaaattctgctagacctttgctgga
aaacttgtaaattctgctagaccctctgtaaattccgctagacctttgtgtgtttttttttgttt
atattcaagtggttataatttatagaataaagaaagaataaaaaaagataaaaagaatagatcc
cagccctgtgtataactcactactttagtcagttccgcagtattacaaaggatgtcgcaaacg
ctgtttgctcctctacaaaacagaccttaaaaccctaaaggcttaagtagcaccctcgcaagct
cgggcaaatcgctgaatattccttttgtctccgaccatcaggcacctgagtcgctgtctttttc

Figure 45D

Gtgacattcagttcgctgcgctcacggctctggcagtgaatgggggtaaatggcactacaggcg
ccttttatggattcatgcaaggaaactacccataatacaagaaaagcccgtcacgggcttctca
gggcgttttatggcgggtctgctatgtggtgctatctgacttttttgctgttcagcagttcctgc
cctctgattttccagtctgaccacttcggattatcccgtgacaggtcattcagactggctaatg
cacccagtaaggcagcggtatcatcaacaggctta
(SEQ ID NO:55)

5′ -
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccccgttcagcccgaccgctgcgcct
tatccggtaactatcgtcttgagtccaacccggtaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggtttttt
tgtttgcaagcagcagattacgcgcagaaaaaaaggatctcaagaagatcctttgatcttttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatcccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaaagggaataagggcgacacggaaatgttgaatactcatactcttcctttttc
aatattattgaagcatttatcagggttattgtctcatgagcggatacatatttgaatgtattta
gaaaaataaacaaataggggttccgcgcacatttccccgaaaagtgccacctgacgtctaagaa
accattattatcatgacattaacctataaaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaaagaga
aaaagcattttcaggtataggtgttttgggaaacaatttccccgaaccattatatttctctaca
tcagaaaggtataaatcataaaactctttgaagtcattctttacaggagtccaaataccagaga
atgttttagatacaccatcaaaattgtataaagtggctctaacttatcccaataacctaactc
tccgtcgctattgtaaccagttctaaaagctgtatttgagtttatcacccttgtcactaagaaa
ataaatgcagggtaaaatttatatccttcttgttttatgtttc

Figure 51B ggtataaaacactaatatcaatttctgtggttatactaaaagtcgtttgttggttcaaataatg
attaaatatctcttttctcttccaattgtctaaatcaattttattaaagttcatttgatatgcc
tcctaaatttttatctaaagtgaatttaggaggcttacttgtctgctttcttcattagaatcaa
tcctttttttaaaagtcaatattactgtaacataaatatatattttaaaaatatcccactttatc
caattttcgtttgttgaactaatgggtgctttagttgaagaataaaagacctatgcggtgtgaa
ataccgcacagatgcgtaaggagaaaataccgcatcaggcgccattcgccattcaggctgcgca
actgttgggaagggcgatcggtgcgggcctcttcgctattacgccagctggcgaaagggggatg
tgctgcaaggcgattaagttgggtaacgccagggttttcccagtcacgacgttgtaaaacgacg
gccagtgccaagcttgcatgcctgcactccatttcttctgctatcaaaataacagactcgtga
ttttccaaacgagctttcaaaaaagcctctgccccttgcaaatcggatgcctgtctataaatt
cccgatattggttaaacagcggcgcaatggcggccgcatctgatgtctttgcttggcgaatgtt
catcttatttcttcctccctctcaataatttttttcattctatccctttttctgtaaagtttattt
ttcagaatacttttatcatcatgctttgaaaaaatatcacgataatatccattgttctcacgga
agcacacgcaggtcatttgaacgaatttttttcgacaggaatttgccgggactcaggagcattta
acctaaaaaagcatgacatttcagcataatgaacatttactcatgtctattttcgttcttttct
gtatgaaaatagttatttcgagtctctacggaaatagcgagagatgatatacctaaatagagat
aaaatcatctcaaaaaaatgggtctactaaaatattattccatctattacaataaattcacaga
atagtcttttaagtaagtctactctgaatttttttaaaaggagagggtaaagagtgaaaacagt
agttattattgatgcattacgaacaccaattggaaaatataaaggcagcttaagtcaagtaagt
gccgtagacttaggaacacatgttacaacacaacttttaaaaagacattccactatttctgaag
aaattgatcaagtaatctttggaaatgttttacaagctggaaatggccaaaatcccgcacgaca
aatagcaataaacagcggtttgtctcatgaaattcccgcaatgacggttaatgaggtctgcgga
tcaggaatgaaggccgttattttggcgaaacaattgattcaattaggagaagcggaagttttaa
ttgctggcgggattgagaatatgtcccaagcacctaaattacaacgttttaattacgaaacaga
aagctacgatgcgcctttttctagtatgatgtatgatggattaacggatgcctttagtggtcag
gcaatgggcttaactgctgaaaatgtggccgaaaagtatcatgtaactagagaagagcaagatc
aattttctgtacattcacaattaaaagcagctcaagcacaagcagaagggatattcgctgacga
aatagccccattagaagtatcaggaacgcttgtggagaaagatgaagggattcgccctaattcg
agcgttgagaagctaggaacgcttaaaacagtttttaaagaagacggtactgtaacagcaggga
atgcatcaaccattaatgatggggcttctgctttgattattgcttcacaagaatatgccgaagc
acacggtcttccttatttagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaaagagaact
ggctttaccagaggaaaaggtcaacatttatggtggcggtatttcattaggtcatgcgattggt
gccacaggtgctcgtttattaacgagtttaagttatcaattaaatcaaaaagaaaagaaatatg
gagtggcttctttatgtatcggcggtggcttaggactcgctatgctactagagagacctcagca
aaaaaaaaacagccgattttatcaaatgagtcctgaggaacgcctggcttctcttcttaatgaa
ggccagatttctgctgatacaaaaaaagaatttgaaaatacggctttatcttcgcagattgcca
atcatatgattgaaaatcaaatcagtgaaacagaagtgccgatgggcgttggcttacatttaac
agtggacgaaactgattatttggtaccaatggcgacagaagagccctcagttattgcggctttg
agtaatggtgcaaaaatagcacaaggatttaaaacagtgaatcaacaacgcttaatgcgtggac
aaatcgtttttttacgatgttgcagatcccgagtcattgattgataaactacaagtaagagaagc
ggaagtttttcaacaagcagagttaagttatccatctatcgttaaacggggcggcggcttaaga
gatttgcaatatcgtacttttgatgaatcatttgtatctgtcgactttttagtagatgttaagg
atgcaatgggggcaaatatcgttaacgctatgttggaaggtgtg

Figure 51C gccgagttgttccgtgaatggtttgcggagcaaaagattttattcagtattttaagtaattatg
ccacggagtcggttgttacgatgaaaacggctattccagtttcacgtttaagtaaggggagcaa
tggccgggaaattgctgaaaaattgttttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaaggacacatggctctacaagcacgttctttagcg
atgacggtcggagctactggtaaagaagttgaggcagtcgctcaacaattaaaacgtcaaaaaa
cgatgaaccaagaccgagccatggctattttaaatgatttaagaaaacaataaaggagagggt
gacaattgggattgataaaattagtttttttgtgccccttattatattgatatgacggcactg
gctgaagccagaaatgtagaccctggaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctctttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcattttggctttaa
aagaggataatgtgatgctgacgcaagatatctatgacttttggcgtccaacaggccacccgta
tcctatggtcgatggtcctttgtcaaacgaaacctacatccaatcttttgcccaagtctgggat
gaacataaaaaacgaaccggtcttgattttgcagattatgatgctttagcgttccatattcctt
acacaaaaatgggcaaaaaagccttattagcaaaaatctccgaccaaactgaagcagaacagga
acgaattttagcccgttatgaagaaagtatcgtctatagtcgtcgcgtaggaaacttgtatacg
ggttcactttatctgggactcatttccctttagaaaatgcaacgactttaaccgcaggcaatc
aaattggtttattcagttatggttctggtgctgtcgctgaatttttcactggtgaattagtagc
tggttatcaaaatcatttacaaaaagaaactcatttagcactgctggataatcggacagaactt
tctatcgctgaatatgaagccatgtttgcagaaactttagacacagacattgatcaaacgttag
aagatgaattaaaatatagtatttctgctattaataataccgttcgttcttatcgaaactaaaa
aaaaccggccttggccccgccggtttttttattatttttcttcctccgcatgttcaatccgctcc
ataatcgacggatggctccctctgaaaattttaacgagaaacggcgggttgacccggctcagtc
ccgtaacggccaagtcctgaaacgtctcaatcgccgcttcccggtttccggtcagctcaatgcc
gtaacggtcggcggcgttttcctgataccgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
(SEQ ID NO:56)

Figure 61
A
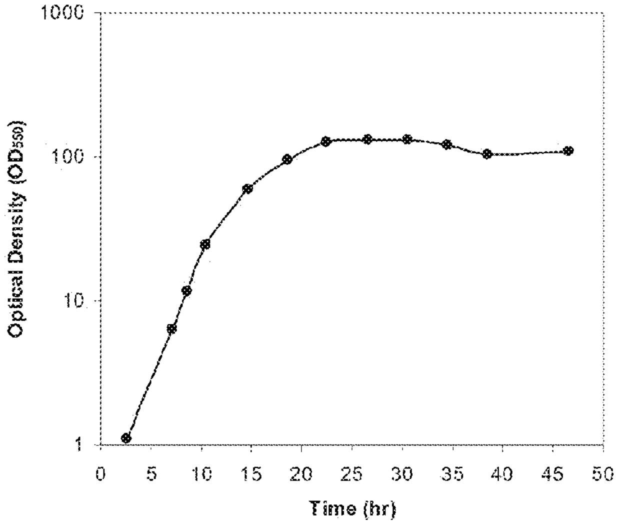
B
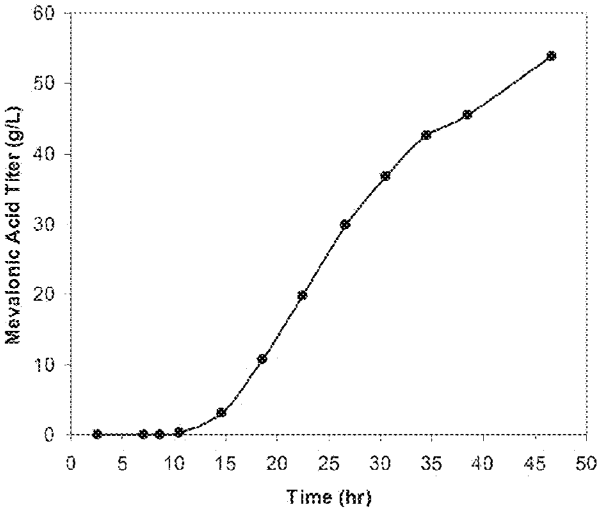
C
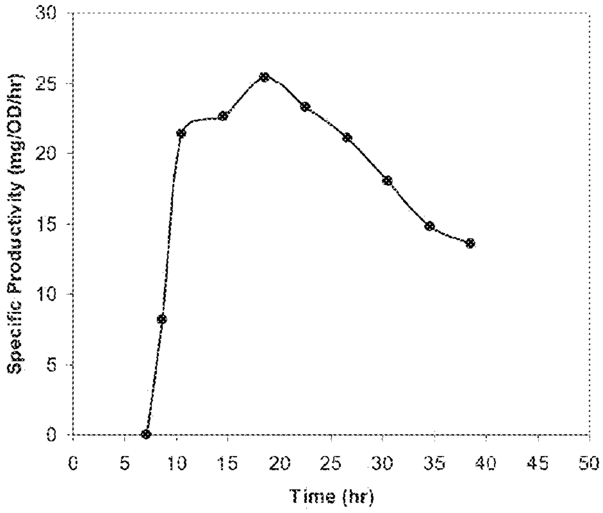

Figure 75A

| Concentration at Deflagration | | | | | | | | | | | | | | | | | | |
|---|---|---|---|---|---|---|---|---|---|---|---|---|---|---|---|---|---|---|
| | | Fuel Makeup | Oxidizer Makeup | | | Molar Concentration based on 100g of sample | | | | | Volumetric Concentrations based on ideal gas law | | | |
| Fuel Conc. (wt.%) | Oxidizer Conc. (wt.%) | Isoprene (wt. %) | $H_2O$ (wt. %) | $O_2$ (wt. %) | $N_2$ (wt. %) | Isoprene (mole) | $H_2O$ (mole) | $O_2$ (mole) | $N_2$ (mole) | Total (mole) | Isoprene (vol. %) | $O_2$ (vol. %) | $N_2$ (vol. %) | $H_2O$ (vol. %) |
| 3.10 | 96.90 | 100 | 0 | 12 | 88 | 4.56 | 0.00 | 36.34 | 304.54 | 345.44 | 1.32 | 10.52 | 88.16 | 0.00 |
| 3.10 | 96.90 | 100 | 0 | 13 | 87 | 4.56 | 0.00 | 39.37 | 301.08 | 345.01 | 1.32 | 11.41 | 87.27 | 0.00 |
| 3.10 | 96.90 | 100 | 0 | 14 | 86 | 4.56 | 0.00 | 42.39 | 297.62 | 344.57 | 1.32 | 12.30 | 86.37 | 0.00 |
| 3.10 | 96.90 | 100 | 0 | 15 | 85 | 4.56 | 0.00 | 45.42 | 294.16 | 344.14 | 1.32 | 13.20 | 85.48 | 0.00 |
| 3.10 | 96.90 | 100 | 0 | 16 | 84 | 4.56 | 0.00 | 48.45 | 290.70 | 343.71 | 1.33 | 14.10 | 84.58 | 0.00 |
| 3.10 | 96.90 | 100 | 0 | 17 | 83 | 4.56 | 0.00 | 51.48 | 287.24 | 343.28 | 1.33 | 15.00 | 83.68 | 0.00 |
| 3.10 | 96.90 | 100 | 0 | 21 | 79 | 4.56 | 0.00 | 63.59 | 273.40 | 341.55 | 1.33 | 18.62 | 80.05 | 0.00 |
| 3.50 | 96.50 | 100 | 0 | 11.1 | 88.9 | 5.15 | 0.00 | 33.47 | 306.39 | 345.01 | 1.49 | 9.70 | 88.81 | 0.00 |
| 4.40 | 95.60 | 100 | 0 | 12 | 88 | 6.47 | 0.00 | 35.85 | 300.46 | 342.78 | 1.89 | 10.46 | 87.65 | 0.00 |
| 5.50 | 94.50 | 100 | 0 | 13 | 87 | 8.09 | 0.00 | 38.39 | 293.63 | 340.10 | 2.38 | 11.29 | 86.33 | 0.00 |
| 6.60 | 93.40 | 100 | 0 | 14 | 86 | 9.71 | 0.00 | 40.86 | 286.87 | 337.44 | 2.88 | 12.11 | 85.01 | 0.00 |
| 7.60 | 92.40 | 100 | 0 | 15 | 85 | 11.18 | 0.00 | 43.31 | 280.50 | 334.99 | 3.34 | 12.93 | 83.73 | 0.00 |
| 8.50 | 91.50 | 100 | 0 | 16 | 84 | 12.50 | 0.00 | 45.75 | 274.50 | 332.75 | 3.76 | 13.75 | 82.49 | 0.00 |
| 9.60 | 90.40 | 100 | 0 | 17 | 83 | 14.12 | 0.00 | 48.03 | 267.97 | 330.11 | 4.28 | 14.55 | 81.18 | 0.00 |
| 13.50 | 86.50 | 100 | 0 | 21 | 79 | 19.85 | 0.00 | 56.77 | 244.05 | 320.67 | 6.19 | 17.70 | 76.11 | 0.00 |

Figure 76A

| Concentration at Deflagration | | | | | | | | | | | | | | | |
|---|---|---|---|---|---|---|---|---|---|---|---|---|---|---|---|
| | | Fuel Makeup | Oxidizer Makeup | | | Molar Concentration based on 100g of sample | | | | | Volumetric Concentrations based on ideal gas law | | | | |
| Fuel Conc. (wt.%) | Oxidizer Conc. (wt.%) | Isoprene (wt. %) | $H_2O$ (wt. %) | $O_2$ (wt. %) | $N_2$ (wt. %) | Isoprene (mole) | $H_2O$ (mole) | $O_2$ (mole) | $N_2$ (mole) | Total (mole) | Isoprene (vol. %) | $O_2$ (vol. %) | $N_2$ (vol. %) | $H_2O$ (vol. %) |
| 3.252 | 96.748 | 100 | 4 | 12 | 84 | 4.78 | 21.50 | 36.28 | 290.24 | 352.81 | 1.36 | 10.28 | 82.27 | 6.09 |
| 3.274 | 96.726 | 100 | 4 | 13 | 83 | 4.81 | 21.49 | 39.29 | 286.72 | 352.33 | 1.37 | 11.15 | 81.38 | 6.10 |
| 3.290 | 96.710 | 100 | 4 | 14 | 82 | 4.84 | 21.49 | 42.31 | 283.22 | 351.86 | 1.38 | 12.02 | 80.49 | 6.11 |
| 3.288 | 96.712 | 100 | 4 | 15 | 81 | 4.84 | 21.49 | 45.33 | 279.77 | 351.43 | 1.38 | 12.90 | 79.61 | 6.12 |
| 3.286 | 96.714 | 100 | 4 | 16 | 80 | 4.83 | 21.49 | 48.36 | 276.33 | 351.01 | 1.38 | 13.78 | 78.72 | 6.12 |
| 3.284 | 96.716 | 100 | 4 | 17 | 79 | 4.83 | 21.49 | 51.38 | 272.88 | 350.58 | 1.38 | 14.66 | 77.84 | 6.13 |
| 3.276 | 96.724 | 100 | 4 | 21 | 75 | 4.82 | 21.49 | 63.48 | 259.08 | 348.87 | 1.38 | 18.19 | 74.26 | 6.16 |
| 3.500 | 96.500 | 100 | 4 | 11.5 | 84.5 | 5.15 | 21.44 | 34.68 | 291.22 | 352.49 | 1.46 | 9.84 | 82.62 | 6.08 |
| 4.200 | 95.800 | 100 | 4 | 12 | 84 | 6.18 | 21.29 | 35.93 | 287.40 | 350.79 | 1.76 | 10.24 | 81.93 | 6.07 |
| 5.300 | 94.700 | 100 | 4 | 13 | 83 | 7.79 | 21.04 | 38.47 | 280.72 | 348.03 | 2.24 | 11.05 | 80.66 | 6.05 |
| 6.400 | 93.600 | 100 | 4 | 14 | 82 | 9.41 | 20.80 | 40.95 | 274.11 | 345.28 | 2.73 | 11.86 | 79.39 | 6.02 |
| 7.400 | 92.600 | 100 | 4 | 15 | 81 | 10.88 | 20.58 | 43.41 | 267.88 | 342.74 | 3.18 | 12.66 | 78.16 | 6.00 |
| 8.500 | 91.500 | 100 | 4 | 16 | 80 | 12.50 | 20.33 | 45.75 | 261.43 | 340.01 | 3.68 | 13.46 | 76.89 | 5.98 |
| 9.400 | 90.600 | 100 | 4 | 17 | 79 | 13.82 | 20.13 | 48.13 | 255.62 | 337.71 | 4.09 | 14.25 | 75.69 | 5.96 |
| 13.300 | 86.700 | 100 | 4 | 21 | 75 | 19.56 | 19.27 | 56.90 | 232.23 | 327.95 | 5.96 | 17.35 | 70.81 | 5.87 |

Figure 78B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 1.5 | 21.0 | 1.4 |
| 13.0 | 1.5 | 13.0 | 1.4 |
| 11.0 | 1.6 | 11.0 | 1.5 |
| 10.4 | 1.8 | 10.4 | 1.7 |
| 10.0 | 1.9 | 10.0 | 1.8 |
| 9.8 | 2 | 9.7 | 2 |
| 10.0 | 2.2 | 10.0 | 2.3 |
| 10.4 | 2.5 | 10.4 | 2.6 |
| 11.0 | 2.9 | 11.0 | 3.0 |
| 13.0 | 4.0 | 13.0 | 4.1 |
| 17.7 | 8.0 | 17.6 | 8.0 |
| 21.0 | 11.8 | 21.0 | 11.9 |

Figure 79B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 11.7 | 21.0 | 11.9 |
| 21.0 | 11.8 | 21.0 | 11.9 |
| 21.0 | 11.8 | 21.0 | 11.9 |
| 21.0 | 1.5 | 21.0 | 1.4 |
| 21.0 | 1.5 | 21.0 | 1.4 |
| 10.2 | 2.0 | 21.0 | 1.4 |
| 10.1 | 2.0 | 9.8 | 2.0 |
| 10.0 | 2.0 | 9.8 | 2.0 |
| 9.9 | 2.0 | 9.8 | 2.0 |

Figure 80A

TEST SERIES 1

| Test | Data File Name | Temp | Initial Pressure | Partial Pressures | | | Concentrations | | | Result | Pax |
|---|---|---|---|---|---|---|---|---|---|---|---|
| | | | | $C_3H_8$ | $N_2$ | $O_2$ | $C_3H_8$ | $N_2$ | $O_2$ | | |
| | | °C | bara | mbar | mbar | mbar | vol. % | vol. % | vol. % | | bara |
| 1 | T11120700 | 40 | 1.012 | 12 | 787 | 213 | 1.2 | 77.8 | 21.0 | Non-Explosion | 1.05 |
| 2 | T11120701 | 40 | 1.016 | 16 | 787 | 213 | 1.6 | 77.5 | 21.0 | Explosion | 5.5 |
| 3 | T11120702 | 40 | 1.015 | 14 | 788 | 213 | 1.4 | 77.6 | 21.0 | Non-Explosion | <1.02 |
| 4 | T11120703 | 40 | 1.014 | 15 | 786 | 213 | 1.5 | 77.5 | 21.0 | Non-Explosion | <1.02 |
| 5 | T11120704 | 40 | 1.014 | 15 | 786 | 213 | 1.5 | 77.5 | 21.0 | Explosion | 4.31 |
| 6 | T11120705 | 40 | 1.017 | 18 | 785 | 214 | 1.8 | 77.2 | 21.0 | Explosion | 5.47 |
| 7 | T11120706 | 40 | 1.014 | 15 | 786 | 213 | 1.5 | 77.5 | 21.0 | Explosion | 4.51 |
| 8 | T11120707 | 40 | 1.014 | 14 | 787 | 213 | 1.4 | 77.6 | 21.0 | Non-Explosion | <1.02 |
| 9 | T11120708 | 40 | 1.014 | 14 | 787 | 213 | 1.4 | 77.6 | 21.0 | Non-Explosion | 1.05 |
| 10 | T11120709 | 40 | 1.015 | 102 | 700 | 213 | 10.0 | 69.0 | 21.0 | Explosion | 1.45 |
| 11 | T11120710 | 40 | 1.014 | 102 | 699 | 213 | 10.1 | 68.9 | 21.0 | Explosion | 1.39 |
| 12 | T11120711 | 40 | 1.014 | 106 | 695 | 213 | 10.5 | 68.5 | 21.0 | Explosion | 1.34 |
| 13 | T11120712 | 40 | 1.014 | 113 | 688 | 213 | 11.1 | 67.9 | 21.0 | Explosion | 1.29 |
| 14 | T11120713 | 40 | 1.014 | 122 | 679 | 213 | 12.0 | 67.0 | 21.0 | Non-Explosion | <1.02 |
| 15 | T11120714 | 40 | 1.014 | 117 | 684 | 213 | 11.5 | 67.5 | 21.0 | Explosion | 1.32 |
| 16 | T11120715 | 40 | 1.014 | 120 | 681 | 213 | 11.8 | 67.2 | 21.0 | Non-Explosion | 1.08 |
| 17 | T11130700 | 40 | 1.014 | 120 | 681 | 213 | 11.8 | 67.2 | 21.0 | Explosion | 1.09 |
| 18 | T11130701 | 40 | 1.014 | 121 | 680 | 213 | 11.9 | 67.1 | 21.0 | Non-Explosion | 1.07 |
| 19 | T11130702 | 40 | 1.015 | 121 | 681 | 213 | 11.9 | 67.1 | 21.0 | Non-Explosion | 1.06 |
| 20 | T11130703 | 40 | 1.015 | 121 | 681 | 213 | 11.9 | 67.1 | 21.0 | Non-Explosion | 1.07 |
| 21 | T11130704 | 40 | 1.015 | 30 | 853 | 132 | 3.0 | 84.0 | 13.0 | Explosion | 1.61 |
| 22 | T11130705 | 40 | 1.014 | 36 | 846 | 132 | 3.6 | 83.4 | 13.0 | Explosion | 1.28 |
| 23 | T11130706 | 40 | 1.014 | 39 | 843 | 132 | 3.8 | 83.1 | 13.0 | Explosion | 1.12 |
| 24 | T11130707 | 40 | 1.015 | 41 | 842 | 132 | 4.0 | 83.0 | 13.0 | Explosion | 1.09 |
| 25 | T11130708 | 40 | 1.014 | 42 | 840 | 132 | 4.1 | 82.8 | 13.0 | Non-Explosion | 1.06 |
| 26 | T11130709 | 40 | 1.015 | 42 | 841 | 132 | 4.1 | 82.9 | 13.0 | Non-Explosion | 1.06 |
| 27 | T11130710 | 40 | 1.014 | 42 | 840 | 132 | 4.1 | 82.8 | 13.0 | Non-Explosion | 1.05 |
| 28 | T11130711 | 40 | 1.014 | 15 | 867 | 132 | 1.5 | 85.5 | 13.0 | Non-Explosion | 1.03 |
| 29 | T11130712 | 40 | 1.014 | 16 | 866 | 132 | 1.6 | 85.4 | 13.0 | Explosion | 4.61 |
| 30 | T11130713 | 40 | 1.014 | 15 | 867 | 132 | 1.5 | 85.5 | 13.0 | Explosion | 4 |
| 31 | T11130714 | 40 | 1.014 | 14 | 868 | 132 | 1.4 | 85.6 | 13.0 | Non-Explosion | 1.03 |
| 32 | T11130715 | 40 | 1.014 | 14 | 868 | 132 | 1.4 | 85.6 | 13.0 | Non-Explosion | <1.02 |
| 33 | T11130716 | 40 | 1.014 | 14 | 868 | 132 | 1.4 | 85.6 | 13.0 | Non-Explosion | 1.03 |
| 34 | T11130717 | 40 | 1.015 | 20 | 883 | 112 | 2.0 | 87.0 | 11.0 | Explosion | 1.7 |
| 35 | T11130718 | 40 | 1.014 | 28 | 874 | 112 | 2.8 | 86.2 | 11.0 | Non-Explosion | 1.08 |
| 36 | T11130719 | 40 | 1.014 | 28 | 874 | 112 | 2.8 | 86.2 | 11.0 | Non-Explosion | 1.08 |
| 37 | T11130720 | 40 | 1.014 | 28 | 874 | 112 | 2.8 | 86.2 | 11.0 | Explosion | 1.13 |
| 38 | T11130721 | 40 | 1.015 | 29 | 874 | 112 | 2.9 | 86.1 | 11.0 | Non-Explosion | 1.06 |
| 39 | T11130722 | 40 | 1.014 | 29 | 873 | 112 | 2.9 | 86.1 | 11.0 | Explosion | 1.1 |

Figure 80B

| Test | Data File Name | Temp | Initial Pressure | Partial Pressures | | | Concentrations | | | Result | Pex |
|---|---|---|---|---|---|---|---|---|---|---|---|
| | | | | $C_3H_8$ | $N_2$ | $O_2$ | $C_3H_8$ | $N_2$ | $O_2$ | | |
| | | °C | bara | mbar | mbar | mbar | vol. % | vol. % | vol. % | | bara |
| 40 | T11130723 | 40 | 1.014 | 30 | 872 | 112 | 3.0 | 86.0 | 11.0 | Non-Explosion | 1.08 |
| 41 | T11130724 | 40 | 1.014 | 30 | 872 | 112 | 3.0 | 86.0 | 11.0 | Non-Explosion | 1.05 |
| 42 | T11130725 | 40 | 1.014 | 30 | 872 | 112 | 3.0 | 86.0 | 11.0 | Non-Explosion | 1.05 |
| 43 | T11130726 | 40 | 1.014 | 15 | 887 | 112 | 1.5 | 87.5 | 11.0 | Non-Explosion | <1.02 |
| 44 | T11130727 | 40 | 1.014 | 15 | 887 | 112 | 1.5 | 87.5 | 11.0 | Non-Explosion | <1.02 |
| 45 | T11140700 | 40 | 1.014 | 16 | 886 | 112 | 1.6 | 87.4 | 11.0 | Non-Explosion | <1.02 |
| 46 | T11140701 | 40 | 1.014 | 17 | 885 | 112 | 1.7 | 87.3 | 11.0 | Explosion | 1.81 |
| 47 | T11140702 | 40 | 1.014 | 16 | 886 | 112 | 1.6 | 87.4 | 11.0 | Explosion | 1.54 |
| 48 | T11140703 | 40 | 1.014 | 15 | 887 | 112 | 1.5 | 87.5 | 11.0 | Non-Explosion | <1.02 |
| 49 | T11140704 | 40 | 1.015 | 20 | 899 | 96 | 2.0 | 88.6 | 9.5 | Non-Explosion | 1.05 |
| 50 | T11140705 | 40 | 1.014 | 20 | 898 | 96 | 2.0 | 88.6 | 9.5 | Non-Explosion | 1.05 |
| 51 | T11140706 | 40 | 1.014 | 23 | 890 | 101 | 2.3 | 87.8 | 10.0 | Non-Explosion | 1.05 |
| 52 | T11140707 | 40 | 1.015 | 23 | 886 | 106 | 2.3 | 87.3 | 10.4 | Explosion | 1.19 |
| 53 | T11140708 | 40 | 1.014 | 25 | 884 | 105 | 2.5 | 87.2 | 10.4 | Explosion | 1.09 |
| 54 | T11140709 | 40 | 1.014 | 26 | 883 | 105 | 2.6 | 87.1 | 10.4 | Non-Explosion | 1.05 |
| 55 | T11140710 | 40 | 1.014 | 26 | 883 | 105 | 2.6 | 87.1 | 10.4 | Non-Explosion | 1.06 |
| 56 | T11140711 | 40 | 1.014 | 26 | 883 | 105 | 2.6 | 87.1 | 10.4 | Non-Explosion | 1.07 |
| 57 | T11140712 | 40 | 1.014 | 20 | 889 | 105 | 2.0 | 87.7 | 10.4 | Explosion | 1.21 |
| 58 | T11140713 | 40 | 1.014 | 17 | 892 | 105 | 1.7 | 88.0 | 10.4 | Non-Explosion | 1.04 |
| 59 | T11140714 | 40 | 1.014 | 18 | 891 | 105 | 1.8 | 87.9 | 10.4 | Explosion | 1.21 |
| 60 | T11140715 | 40 | 1.014 | 17 | 892 | 105 | 1.7 | 88.0 | 10.4 | Non-Explosion | 1.03 |
| 61 | T11140716 | 40 | 1.014 | 17 | 892 | 105 | 1.7 | 88.0 | 10.4 | Non-Explosion | 1.03 |
| 62 | T11140717 | 40 | 1.014 | 21 | 890 | 103 | 2.1 | 87.8 | 10.2 | Explosion | 1.1 |
| 63 | T11140718 | 40 | 1.014 | 21 | 891 | 102 | 2.1 | 87.9 | 10.1 | Explosion | 1.09 |
| 64 | T11140719 | 40 | 1.014 | 21 | 892 | 101 | 2.1 | 88.0 | 10.0 | Explosion | 1.09 |
| 65 | T11140720 | 40 | 1.014 | 22 | 891 | 101 | 2.2 | 87.9 | 10.0 | Explosion | 1.1 |
| 66 | T11140721 | 40 | 1.014 | 23 | 890 | 101 | 2.3 | 87.8 | 10.0 | Non-Explosion | 1.06 |
| 67 | T11140722 | 40 | 1.014 | 23 | 890 | 101 | 2.3 | 87.8 | 10.0 | Non-Explosion | 1.08 |
| 68 | T11140723 | 40 | 1.014 | 19 | 894 | 101 | 1.9 | 88.2 | 10.0 | Explosion | 1.12 |
| 69 | T11140724 | 40 | 1.014 | 18 | 895 | 101 | 1.8 | 88.3 | 10.0 | Non-Explosion | 1.06 |
| 70 | T11140725 | 40 | 1.014 | 18 | 895 | 101 | 1.8 | 88.3 | 10.0 | Non-Explosion | 1.03 |
| 71 | T11140726 | 40 | 1.014 | 18 | 895 | 101 | 1.8 | 88.3 | 10.0 | Non-Explosion | 1.04 |
| 72 | T11140727 | 40 | 1.014 | 20 | 895 | 99 | 2.0 | 88.3 | 9.8 | Non-Explosion | 1.08 |
| 73 | T11140728 | 40 | 1.014 | 20 | 895 | 99 | 2.0 | 88.3 | 9.8 | Explosion | 1.1 |
| 74 | T11140729 | 40 | 1.014 | 20 | 896 | 98 | 2.0 | 88.4 | 9.7 | Non-Explosion | 1.06 |
| 75 | T11140730 | 40 | 1.014 | 20 | 896 | 98 | 2.0 | 88.4 | 9.7 | Non-Explosion | 1.08 |
| 76 | T11140731 | 40 | 1.014 | 20 | 896 | 98 | 2.0 | 88.4 | 9.7 | Non-Explosion | 1.07 |
| 77 | T11140732 | 40 | 1.014 | 81 | 761 | 172 | 8.0 | 75.0 | 17.0 | Non-Explosion | 1.04 |
| 78 | T11140733 | 40 | 1.014 | 81 | 750 | 183 | 8.0 | 74.0 | 18.0 | Explosion | 1.3 |
| 79 | T11140734 | 40 | 1.014 | 81 | 754 | 179 | 8.0 | 74.4 | 17.7 | Explosion | 1.24 |
| 80 | T11140735 | 40 | 1.014 | 81 | 757 | 176 | 8.0 | 74.7 | 17.4 | Non-Explosion | 1.03 |
| 81 | T11140736 | 40 | 1.014 | 81 | 755 | 178 | 8.0 | 74.5 | 17.6 | Non-Explosion | 1.05 |
| 82 | T11140737 | 40 | 1.014 | 81 | 755 | 178 | 8.0 | 74.5 | 17.6 | Non-Explosion | 1.03 |
| 83 | T11140738 | 40 | 1.014 | 81 | 755 | 178 | 8.0 | 74.5 | 17.6 | Non-Explosion | 1.03 |

Figure 81

TEST SERIES 2

| Test | Data File Name | Temp | Initial Pressure | Partial Pressures | | | | Concentrations | | | | Result | Pex |
|---|---|---|---|---|---|---|---|---|---|---|---|---|---|
| | | | | $H_2O$ | $C_3H_8$ | $N_2$ | $O_2$ | $H_2O$ | $C_3H_8$ | $N_2$ | $O_2$ | | |
| | | °C | bara | mbar | mbar | mbar | mbar | vol. % | vol. % | vol. % | vol. % | | bara |
| 1 | T11150700 | 40 | 1.014 | 41 | 119 | 641 | 213 | 4.0 | 11.7 | 63.2 | 21.0 | Explosion | 1.33 |
| 2 | T11150701 | 40 | 1.014 | 40 | 121 | 640 | 213 | 3.9 | 11.9 | 63.1 | 21.0 | Non explosion | 1.07 |
| 3 | T11150702 | 40 | 1.014 | 41 | 120 | 640 | 213 | 4.0 | 11.8 | 63.1 | 21.0 | Explosion | 1.09 |
| 4 | T11150703 | 40 | 1.014 | 40 | 121 | 640 | 213 | 3.9 | 11.9 | 63.1 | 21.0 | Non-explosion | 1.09 |
| 5 | T11150704 | 40 | 1.014 | 40 | 120 | 641 | 213 | 3.9 | 11.8 | 63.2 | 21.0 | Explosion | 1.09 |
| 6 | T11150705 | 40 | 1.014 | 40 | 121 | 640 | 213 | 3.9 | 11.9 | 63.1 | 21.0 | Non-explosion | 1.08 |
| 7 | T11150706 | 40 | 1.014 | 40 | 15 | 746 | 213 | 3.9 | 1.5 | 73.6 | 21.0 | Explosion | 4.88 |
| 8 | T11150707 | 40 | 1.014 | 41 | 15 | 745 | 213 | 4.0 | 1.5 | 73.5 | 21.0 | Explosion | 5.27 |
| 9 | T11150708 | 40 | 1.014 | 41 | 14 | 746 | 213 | 4.0 | 1.4 | 73.6 | 21.0 | Non-explosion | 1.03 |
| 10 | T11150709 | 40 | 1.014 | 42 | 14 | 745 | 213 | 4.1 | 1.4 | 73.5 | 21.0 | Non-explosion | 1.03 |
| 11 | T11160700 | 40 | 1.014 | 41 | 14 | 746 | 213 | 4.0 | 1.4 | 73.6 | 21.0 | Non-explosion | 1.03 |
| 12 | T11160701 | 40 | 1.014 | 41 | 20 | 850 | 103 | 4.0 | 2.0 | 83.8 | 10.2 | Explosion | 1.11 |
| 13 | T11160702 | 40 | 1.014 | 41 | 20 | 851 | 102 | 4.0 | 2.0 | 83.9 | 10.1 | Explosion | 1.11 |
| 14 | T11160703 | 40 | 1.014 | 41 | 20 | 852 | 101 | 4.0 | 2.0 | 84.0 | 10.0 | Explosion | 1.09 |
| 15 | T11160704 | 40 | 1.014 | 41 | 20 | 853 | 100 | 4.0 | 2.0 | 84.1 | 9.9 | Explosion | 1.09 |
| 16 | T11160705 | 40 | 1.014 | 41 | 20 | 854 | 99 | 4.0 | 2.0 | 84.2 | 9.8 | Non-explosion | 1.07 |
| 17 | T11160706 | 40 | 1.014 | 40 | 20 | 855 | 99 | 3.9 | 2.0 | 84.3 | 9.6 | Non-explosion | 1.06 |
| 18 | T11160707 | 40 | 1.014 | 41 | 20 | 854 | 99 | 4.0 | 2.0 | 84.2 | 9.8 | Non-explosion | 1.08 |

2-methyl-1,3-butadiene standard.

2-methyl-1,3-butadiene from recombinant *E. coli*

Figure 90
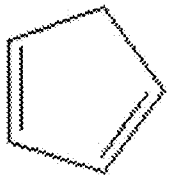
cyclopentadiene
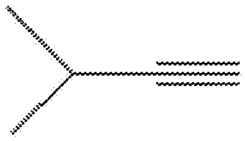
"isopryne" = 3-Me-1-butyne
trans-piperylene
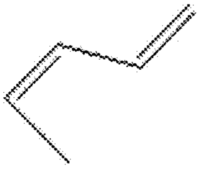
cis-piperylene
1-pentyne
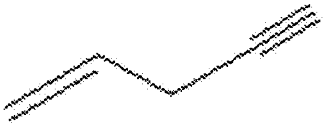
pent-4-ene-1-yne
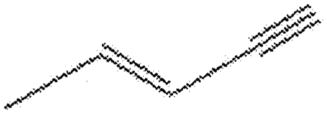
trans-pent-3-ene-1-yne
cis-pent-3-ene-1-yne

Figure 92A

1- gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatggatccgagctcaggaggtaaaaaaacatgaaaacagtagttattattgatgcattac
gaacaccaattggaaaatataaaggcagcttaagtcaagtaagtgccgtagacttaggaacacatgttacaacacaactttaaaaagacatt
ccactatttctgaagaaattgatcaagtaatctttggaaatgttttacaagctggaaatggccaaaatcccgcacgacaaatagcaataaacag
cggtttgtctcatgaaattcccgcaatgacggttaatgaggtctgcggatcaggaatgaaggccgttatttggcgaaacaattgattcaattag
gagaagcggaagttttaattgctggcgggattgagaatatgtcccaagcacctaaattacaacgttttaattacgaaacagaaagctacgatg
cgcctttttctagtatgatgtatgatggattaacggatgcctttagtggtcaggcaatgggcttaactgctgaaaatgtggccgaaaagtatcat
gtaactagagaagagcaagatcaattttctgtacattcacaattaaaagcagctcaagcacaagcagaagggatattcgctgacgaaatagc
cccattagaagtatcaggaacgcttgtggagaaagatgaagggattcgccctaattcgagcgttgagaagctaggaacgcttaaaacagttt
ttaaagaagacggtactgtaacagcagggaatgcatcaaccattaatgatggggcttctgctttgattattgcttcacaagaatatgccgaagc
acacggtcttccttatttagctattattcgagacagtgtggaagtcggtattgatccagcctatatgggaatttcgccgattaaagccattcaaaa
actgttagcgcgcaatcaacttactacggaagaaattgatctgtatgaaatcaacgaagcatttgcagcaacttcaatcgtggtccaaagaga
actggctttaccagaggaaaaggtcaacatttatggtggcggtatttcattaggtcatgcgattggtgccacaggtgctcgtttattaacgagttt
aagttatcaattaaatcaaaaagaaaagaaatatggagtggcttctttatgtatcggcggtggcttaggactcgctatgctactagagagacct
cagcaaaaaaaaaacagccgattttatcaaatgagtcctgaggaacgcctggcttctcttcttaatgaaggccagatttctgctgatacaaaaa
aagaatttgaaaatacggctttatcttcgcagattgccaatcatatgattgaaaatcaaatcagtgaaacagaagtgccgatgggcgttggctt
acatttaacagtggacgaaactgattatttggtaccaatggcgacagaagagccctcagttattgcggctttgagtaatggtgcaaaaatagc
acaaggatttaaaacagtgaatcaacaacgcttaatgcgtggacaaatcgtttttacgatgttgcagatcccgagtcattgattgataaactac
aagtaagagaagcggaagtttttcaacaagcagagttaagttatccatctatcgttaaacggggcggcggcttaagagatttgcaatatcgta
ctttgatgaatcatttgtatctgtcgacttttagtagatgttaaggatgcaatgggggcaaatatcgttaacgctatgttggaaggtgtggccga
gttgttccgtgaatggtttgcggagcaaaagattttattcagtattttaagtaattatgccacggagtcggttgttacgatgaaaacggctattcca
gtttcacgtttaagtaaggggagcaatggccgggaaattgctgaaaaaattgttttagcttcacgctatgcttcattagatccttatcgggcagtc
acgcataacaaaggaatcatgaatggcattgaagctgtagttttagctacaggaaatgatacacgcgctgttagcgcttcttgtcatgcttttgc
ggtgaaggaaggtcgctaccaaggcttgactagttggacgctggatggcgaacaactaattggtgaaatttcagttccgcttgctttagccac
ggttggcggtgccacaaaagtcttacctaaatctcaagcagctgctgatttgttagcagtgacggatgcaaaagaactaagtcgagtagtag
cggctgttggtttggcacaaaatttagcggcgttacgggccttagtctctgaaggaattcaaaaaggacacatggctctacaagcacgttcttt
agcgatgacggtcggagctactggtaaagaagttgaggcagtcgctcaacaattaaaacgtcaaaaaacgatgaaccaagaccgagccat
ggctattttaaatgatttaagaaaacaataaaggaggtaaaaaaacatgacaattgggattgataaaattagtttttttgtgcccccttattatattg
atatgacggcactggctgaagccagaaatgtagaccctggaaaatttcatattggtattgggcaagaccaaatggcggtgaacccaatcag
ccaagatattgtgacatttgcagccaatgccgcagaagcgatcttgaccaaagaagataaagaggccattgatatggtgattgtcgggactg
agtccagtatcgatgagtcaaaagcggccgcagttgtcttacatcgtttaatggggattcaacctttcgctcgctctttcgaaatcaaggaagct
tgttacggagcaacagcaggcttacagttagctaagaatcacgtagccttacatccagataaaaaagtcttggtcgtagcggcagatattgca
aaatatggcttaaattctggcggtgagcctacacaaggagctggggcggttgcaatgttagttgctagtgaaccgcgcattttggctttaaaag
aggataatgtgatgctgacgcaagatatctatgacttttggcgtccaacaggccacccgtatcctatggtcgatggtcctttgtcaaacgaaac
ctacatccaatcttttgcccaagtctgggatgaacataaaaaacgaaccggtcttgattttgcagattatgatgctttagcgttccatattccttac
acaaaaatgggcaaaaaagccttattagcaaaaatctccgaccaaactgaagcagaacaggaacgaatttagcccgttatgaagaaagtat
cgtctatagtcgtcgcgtaggaaacttgtatacgggttcactttatctgggactcatttccctttagaaaatgcaacgactttaaccgcaggcaa
tcaaattggtttattcagttatggttctggtgctgtcgctgaatttttcactggtgaattag

Figure 92B tagctggttatcaaaatcatttacaaaaagaaactcatttagcactgctggataatcggacagaactttctatcgctgaatatgaagccatgtttg
cagaaactttagacacagacattgatcaaacgttagaagatgaattaaaatatagtatttctgctattaataataccgttcgttcttatcgaaacta
agagatctgcagctggtaccatatgggaattcgaagcttgggcccgaacaaaaactcatctcagaagaggatctgaatagcgccgtcgacc
atcatcatcatcatcattgagtttaaacggtctccagcttggctgttttggcggatgagagaagattttcagcctgatacagattaaatcagaacg
cagaagcggtctgataaaacagaatttgcctggcggcagtagcgcggtggtcccacctgaccccatgccgaactcagaagtgaaacgcc
gtagcgccgatggtagtgtggggtctccccatgcgagagtagggaactgccaggcatcaaataaaacgaaaggctcagtcgaaagactg
ggcctttcgttttatctgttgtttgtcggtgaacgctctcctgagtaggacaaatccgccgggagcggatttgaacgttgcgaagcaacggccc
ggagggtggcgggcaggacgcccgccataaactgccaggcatcaaattaagcagaaggccatcctgacggatggcctttttgcgtttctac
aaactctttttgtttatttttctaaatacattcaaatatgtatccgctcatgagacaataaccctgataaatgcttcaataatattgaaaaaggaagag
tatgagtattcaacatttccgtgtcgcccttattcccttttttgcggcattttgccttcctgtttttgctcacccagaaacgctggtgaaagtaaaaga
tgctgaagatcagttgggtgcacgagtgggttacatcgaactggatctcaacagcggtaagatccttgagagttttcgccccgaagaacgttt
tccaatgatgagcacttttaaagttctgctatgtggcgcggtattatcccgtgttgacgccgggcaagagcaactcggtcgccgcatacactat
tctcagaatgacttggttgagtactcaccagtcacagaaaagcatcttacggatggcatgacagtaagagaattatgcagtgctgccataacc
atgagtgataacactgcggccaacttacttctgacaacgatcggaggaccgaaggagctaaccgcttttttgcacaacatgggggatcatgt
aactcgccttgatcgttgggaaccggagctgaatgaagccataccaaacgacgagcgtgacaccacgatgcctgtagcaatggcaacaac
gttgcgcaaactattaactggcgaactacttactctagcttcccggcaacaattaatagactggatggaggcggataaagttgcaggaccact
tctgcgctcggcccttccggctggctggtttattgctgataaatctggagccggtgagcgtgggtctcgcggtatcattgcagcactggggcc
agatggtaagccctcccgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcatttttaatttaaaaggatctaggtg
aagatcctttttgataatctcatgaccaaaatcccttaacgtgagttttcgttccactgagcgtcagaccccgtagaaaagatcaaaggatcttct
tgagatcctttttttctgcgcgtaatctgctgcttgcaaacaaaaaaaccaccgctaccagcggtggtttgtttgccggatcaagagctaccaac
tctttttccgaaggtaactggcttcagcagagcgcagataccaaatactgtccttctagtgtagccgtagttaggccaccacttcaagaactctg
tagcaccgcctacatacctcgctctgctaatcctgttaccagtggctgctgccagtggcgataagtcgtgtcttaccgggttggactcaagac
gatagttaccggataaggcgcagcggtcgggctgaacggggggttcgtgcacacagcccagcttggagcgaacgacctacaccgaact
gagatacctacagcgtgagctatgagaaagcgccacgcttcccgaagggagaaaggcggacaggtatccggtaagcggcagggtcgg
aacaggagagcgcacgagggagcttccagggggaaacgcctggtatctttatagtcctgtcgggtttcgccacctctgacttgagcgtcgat
ttttgtgatgctcgtcaggggggcggagcctatggaaaaacgccagcaacgcggcctttttacggttcctggccttttgctggccttttgctca
catgttctttcctgcgttatcccctgattctgtggataaccgtattaccgcctttgagtgagctgataccgctcgccgcagccgaacgaccgag
cgcagcgagtcagtgagcgaggaagcggaagagcgcctgatgcggtattttctccttacgcatctgtgcggtatttcacaccgcatatggtg
cactctcagtacaatctgctctgatgccgcatagttaagccagtatacactccgctatcgctacgtgactgggtcatggctgcgccccgacac
ccgccaacacccgctgacgcgccctgacgggcttgtctgctcccggcatccgcttacagacaagctgtgaccgtctccgggagctgcatgt
gtcagaggttttcaccgtcatcaccgaaacgcgcgaggcagcagatcaattcgcgcgcgaaggcgaagcggcatgcatttacgttgacac
catcgaatggtgcaaaacctttcgcggtatggcatgatagcgcccggaagagagtcaattcagggtggtgaatgtgaaaccagtaacgttat
acgatgtcgcagagtatgccggtgtctcttatcagaccgtttcccgcgtggtgaaccaggccagccacgtttctgcgaaaacgcgggaaaa
agtggaagcggcgatggcggagctgaattacattcccaaccgcgtggcacaacaactggcgggcaaacagtcgttgctgattggcgttgc
cacctccagtctggccctgcacgcgccgtcgcaaattgtcgcggcgattaaatctcgcgccgatcaactgggtgccagcgtggtggtgtcg
atggtagaacgaagcggcgtcgaagcctgtaaagcggcggtgcacaatcttctcgcgcaacgcgtcagtgggctgatcattaactatccgc
tggatgaccaggatgccattgctgtggaagctgcctgcactaatgttccggcgttatttcttgatgtctctgaccagacacccatcaacagtatt
attttctcccatgaagacggtacgcgactgggcgtggagcatctggtcgcattgggtcaccagcaaatcgcgctgttagcgggcccattaag
ttctgtctcggcgcgtctgcgtctggctggctggcataaatatctcactcgcaatcaaattcagccgatagcggaacgggaaggcgactgga
gtgccatgtccggttttcaacaaaccatgcaaatgctgaatgagggcatcg

Figure 92C ttcccactgcgatgctggttgccaacgatcagatggcgctgggcgcaatgcgcgccattaccgagtccgggctgcgcgttggtgcggatat
ctcggtagtgggatacgacgataccgaagacagctcatgttatatcccgccgtcaaccaccatcaaacaggattttcgcctgctggggcaaa
ccagcgtggaccgcttgctgcaactctctcagggccaggcggtgaagggcaatcagctgttgcccgtctcactggtgaaaagaaaaacca
ccctggcgcccaatacgcaaaccgcctctccccgcgcgttggccgattcattaatgcagctggcacgacaggtttcccgactggaaagcg
ggcagtgagcgcaacgcaattaatgtgagttagcgcgaattgatctg (SEQ ID NO:86)

Figure 103A cccgtcttactgtcgggaattcgcgttggccgattcattaatgcagattctgaaatgagctgttgacaattaatcatccggctcgtataatgtgtg
gaattgtgagcggataacaatttcacacaggaaacagcgccgctgagaaaagcgaagcggcactgctctttaacaatttatcagacaatct
gtgtgggcactcgaccggaattatcgattaactttattattaaaaattaaagaggtatatattaatgtatcgattaaataaggaggaataaaccat
ggatccgagctcaggaggtaaaaaaacatgaaaacagtagttattattgatgcattacgaacaccaattggaaaatataaaggcagcttaagt
caagtaagtgccgtagacttaggaacacatgttacaacacaactttaaaaagacattccactatttctgaagaaattgatcaagtaatctttgga
aatgttttacaagctggaaatggccaaaatcccgcacgacaaatagcaataaacagcggtttgtctcatgaaattcccgcaatgacggttaat
gaggtctgcggatcaggaatgaaggccgttatttggcgaaacaattgattcaattaggagaagcggaagttttaattgctggcgggattgag
aatatgtcccaagcacctaaattacaacgttttaattacgaaacagaaagctacgatgcgcctttttctagtatgatgtatgatggattaacggat
gcctttagtggtcaggcaatgggcttaactgctgaaaatgtggccgaaaagtatcatgtaactagagaagagcaagatcaatttctgtacatt
cacaattaaaagcagctcaagcacaagcagaagggatattcgctgacgaaatagccccattagaagtatcaggaacgcttgtggagaaag
atgaagggattcgccctaattcgagcgttgagaagctaggaacgcttaaaacagttttaaagaagacggtactgtaacagcagggaatgca
tcaaccattaatgatggggcttctgctttgattattgcttcacaagaatatgccgaagcacacggtcttccttatttagctattattcgagacagtgt
ggaagtcggtattgatccagcctatatgggaatttcgccgattaaagccattcaaaaactgttagcgcgcaatcaacttactacggaagaaatt
gatctgtatgaaatcaacgaagcatttgcagcaacttcaatcgtggtccaaagagaactggctttaccagaggaaaaggtcaacatttatggt
ggcggtatttcattaggtcatgcgattggtgccacaggtgctcgtttattaacgagtttaagttatcaattaaatcaaaaagaaaagaaatatgg
agtggcttctttatgtatcggcggtggcttaggactcgctatgctactagagagacctcagcaaaaaaaaaacagccgattttatcaaatgagt
cctgaggaacgcctggcttctcttcttaatgaaggccagatttctgctgatacaaaaaaagaatttgaaaatacggctttatcttcgcagattgc
caatcatatgattgaaaatcaaatcagtgaaacagaagtgccgatgggcgttggcttacatttaacagtggacgaaactgattatttggtacca
atggcgacagaagagccctcagttattgcggctttgagtaatggtgcaaaaatagcacaaggatttaaaacagtgaatcaacaacgcttaat
gcgtggacaaatcgtttttacgatgttgcagatcccgagtcattgattgataaactacaagtaagagaagcggaagtttttcaacaagcagag
ttaagttatccatctatcgttaaacggggcggcggcttaagagatttgcaatatcgtacttttgatgaatcatttgtatctgtcgactttttagtagat
gttaaggatgcaatgggggcaaatatcgttaacgctatgttggaaggtgtggccgagttgttccgtgaatggtttgcggagcaaaagattttat
tcagtattttaagtaattatgccacggagtcggttgttacgatgaaaacggctattccagtttcacgtttaagtaagggggagcaatggccggga
aattgctgaaaaaattgttttagcttcacgctatgcttcattagatccttatcgggcagtcacgcataacaaaggaatcatgaatggcattgaag
ctgtagttttagctacaggaaatgatacacgcgctgttagcgcttcttgtcatgctttgcggtgaaggaaggtcgctaccaaggcttgactagt
tggacgctggatggcgaacaactaattggtgaaatttcagttccgcttgctttagccacggttggcggtgccacaaaagtcttacctaaatctc
aagcagctgctgatttgttagcagtgacggatgcaaaagaactaagtcgagtagtagcggctgttggtttggcacaaaatttagcggcgttac
gggccttagtctctgaaggaattcaaaaaggacacatggctctacaagcacgttctttagcgatgacggtcggagctactggtaaagaagtt
gaggcagtcgctcaacaattaaaacgtcaaaaaacgatgaaccaagaccgagccatggctattttaaatgatttaagaaaacaataaagga
ggtaaaaaaacatgacaattgggattgataaaattagtttttttgtgcccccttattatattgatatgacggcactggctgaagccagaaatgtag
accctggaaaatttcatattggtattgggcaagaccaaatggcggtgaacccaatcagccaagatattgtgacatttgcagccaatgccgca
gaagcgatcttgaccaaagaagataaagaggccattgatatggtgattgtcgggactgagtccagtatcgatgagtcaaaagcggccgcag
ttgtcttacatcgtttaatggggattcaacctttcgctcgctctttcgaaatcaaggaagcttgttacggagcaacagcaggcttacagttagcta
agaatcacgtagccttacatccagataaaaagtcttggtcgtagcggcagatattgcaaaatatggcttaaattctggcggtgagcctacac
aaggagctggggcggttgcaatgttagttgctagtgaaccgcgcattttggctttaaaagaggataatgtgatgctgacgcaagatatctatg
actttggcgtccaacaggccacccgtatcctatggtcgatggtcctttgtcaaacgaaacctacatccaatctttgcccaagtctgggatgaa
cataaaaaacgaaccggtcttgatttgcagattatgatgctttagcgttccatattccttacacaaaaatgggcaaaaaagccttattagcaaaa
atctccgaccaaactgaagcagaacaggaacgaatttagcccgttatgaagaaagtatcgtctatagtcgtcgcgtaggaaacttgtatacg
ggttcactttatctgggactcatttcccttttagaaaatgcaacgactttaaccgcaggcaatcaaattggtttattcagttatggttctggtgctgt
cgctgaatttttcactggtgaattagtagctggttatcaaaatcatttacaaaaagaaactcatttagcactgctggataatcggacagaactttct
atcgctgaatatgaagccatgtttgcagaaactttagacacagacattgatcaaacgtta

Figure 103B gaagatgaattaaaatatagtatttctgctattaataataccgttcgttcttatcgaaactaaagatctgcatcctgcattcgcccttaggaggtaa
aaaaacatgtgtgcgacctcttctcaatttactcagattaccgagcataattcccgtcgttccgcaaactatcagccaaacctgtggaatttcga
attcctgcaatccctggagaacgacctgaaagtggaaaagctggaggagaaagcgaccaaactggaggaagaagttcgctgcatgatca
accgtgtagacacccagccgctgtccctgctggagctgatcgacgatgtgcagcgcctgggtctgacctacaaatttgaaaaagacatcatt
aaagccctggaaaacatcgtactgctggacgaaaacaaaaagaacaaatctgacctgcacgcaaccgctctgtctttccgtctgctgcgtca
gcacggtttcgaggtttctcaggatgtttttgagcgtttcaaggataaagaaggtggtttcagcggtgaactgaaaggtgacgtccaaggcct
gctgagcctgtatgaagcgtcttacctgggtttcgagggtgagaacctgctggaggaggcgcgtacctttccatcacccacctgaagaaca
acctgaaagaaggcattaataccaaggttgcagaacaagtgagccacgccctggaactgccatatcaccagcgtctgcaccgtctggagg
cacgttggttcctggataaatacgaaccgaaagaaccgcatcaccagctgctgctggagctggcgaagctggattttaacatggtacagac
cctgcaccagaaagagctgcaagatctgtcccgctggtggaccgagatgggcctggctagcaaactggattttgtacgcgaccgcctgatg
gaagtttatttctgggcactgggtatggcgccagacccgcagtttggtgaatgtcgcaaagctgttactaaaatgtttggtctggtgacgatcat
cgatgacgtgtatgacgtttatggcactctggacgaactgcaactgttcaccgatgctgtagagcgctgggacgttaacgctattaacaccct
gccggactatatgaaactgtgtttcctggcactgtacaacaccgttaacgacacgtcctattctattctgaaagagaaaggtcataacaacctg
tcctatctgacgaaaagctggcgtgaactgtgcaaagcctttctgcaagaggcgaaatggtccaacaacaaaattatcccggctttctccaag
tacctggaaaacgccagcgtttcctcctccggtgtagcgctgctggcgccgtcttactttccgtatgccagcagcaggaagacatctccgac
cacgcgctgcgttccctgaccgacttccatggtctggtgcgttctagctgcgttatcttccgcctgtgcaacgatctggccacctctgcggcg
gagctggaacgtggcgagactaccaattctatcattagctacatgcacgaaaacgatggtaccagcgaggaacaggcccgcgaagaact
gcgtaaactgatcgacgccgaatggaaaaagatgaatcgtgaacgcgttagcgactccaccctgctgcctaaagcgttcatggaaatcgca
gttaacatggcacgtgtttcccactgcacctaccagtatggcgatggtctgggtcgcccagactacgcgactgaaaaccgcatcaaactgct
gctgattgaccctttcccgattaaccagctgatgtatgtctaactgcagctggtaccatatgggaattcgaagcttgggcccgaacaaaaactc
atctcagaagaggatctgaatagcgccgtcgaccatcatcatcatcatcattgagtttaaacggtctccagcttggctgttttggcggatgaga
gaagattttcagcctgatacagattaaatcagaacgcagaagcggtctgataaaacagaatttgcctggcggcagtagcgcggtggtccca
cctgaccccatgccgaactcagaagtgaaacgccgtagcgccgatggtagtgtggggtctccccatgcgagagtagggaactgccaggc
atcaaataaaacgaaaggctcagtcgaaagactgggcctttcgttttatctgttgtttgtcggtgaacgctctcctgagtaggacaaatccgcc
gggagcggatttgaacgttgcgaagcaacggcccggagggtggcgggcaggacgcccgccataaactgccaggcatcaaattaagca
gaaggccatcctgacggatggcctttttgcgtttctacaaactctttttgtttatttttctaaatacattcaaatatgtatccgctcatgagacaataa
ccctgataaatgcttcaataatctggcgtaatagcgaagaggcccgcaccgatcgcccttcccaacagttgcgcagcctgaatggcgaatg
gcgcctgatgcggtattttctccttacgcatctgtgcggtatttcacaccgcatatggtgcactctcagtacaatctgctctgatgccgcatagtt
aagccagccccgacacccgccaacacccgctgacgagcttagtaaagccctcgctagattttaatgcggatgttgcgattacttcgccaact
attgcgataacaagaaaaagccagcctttcatgatatatctcccaatttgtgtagggcttattatgcacgcttaaaaataataaaagcagacttg
acctgatagtttggctgtgagcaattatgtgcttagtgcatctaacgcttgagttaagccgcgccgcgaagcggcgtcggcttgaacgaattgt
tagacattatttgccgactaccttggtgatctcgcctttcacgtagtggacaaattcttccaactgatctgcgcgcgaggccaagcgatcttcttc
ttgtccaagataagcctgtctagcttcaagtatgacgggctgatactgggccggcaggcgctccattgcccagtcggcagcgacatccttcg
gcgcgattttgccggttactgcgctgtaccaaatgcgggacaacgtaagcactacatttcgctcatcgccagcccagtcgggcggcgagttc
catagcgttaaggtttcatttagcgcctcaaatagatcctgttcaggaaccggatcaaagagttcctccgccgctggacctaccaaggcaacg
ctatgttctcttgcttttgtcagcaagatagccagatcaatgtcgatcgtggctggctcgaagatacctgcaagaatgtcattgcgctgccattct
ccaaattgcagttcgcgcttagctggataacgccacggaatgatgtcgtcgtgcacaacaatggtgacttctacagcgcggagaatctcgct
ctctccaggggaagccgaagtttccaaaaggtcgttgatcaaagctcgccgcgttgtttcatcaagccttacggtcaccgtaaccagcaaatc
aatatcactgtgtggcttcaggccgccatccactgcggagccgtacaaatgtacggccagcaacgtcggttcgagatggcgctcgatgacg
ccaactacctctgatagttgagtcgatacttcggcgatcaccgcttccctcatgatgtttaactttgttttagggcgactgccctgctgcgtaaca
tcgttgctgctccataacatcaaacatcgacccacggcgtaacgcgcttgctgcttggat

Figure 103C gcccgaggcatagactgtaccccaaaaaaacagtcataacaagccatgaaaaccgccactgcgccgttaccaccgctgcgttcggtcaag
gttctggaccagttgcgtgagcgcatacgctacttgcattacagcttacgaaccgaacaggcttatgtccactgggttcgtgccttcatccgttt
ccacggtgtgcgtcacccggcaaccttgggcagcagcgaagtcgaggcatttctgtcctggctggcgaacgagcgcaaggtttcggtctc
cacgcatcgtcaggcattggcggccttgctgttcttctacggcaaggtgctgtgcacggatctgccctggcttcaggagatcggaagacctc
ggccgtcgcggcgcttgccggtggtgctgaccccggatgaagtggttcgcatcctcggtttctggaaggcgagcatcgtttgttcgcccag
cttctgtatggaacgggcatgcggatcagtgagggtttgcaactgcgggtcaaggatctggatttcgatcacggcacgatcatcgtgcggga
gggcaagggctccaaggatcgggccttgatgttacccgagagcttggcacccagcctgcgcgagcaggggaattaattcccacgggttt
gctgcccgcaaacgggctgttctggtgttgctagtttgttatcagaatcgcagatccggcttcagccggtttgccggctgaaagcgctatttctt
ccagaattgccatgatttttccccacgggaggcgtcactggctcccgtgttgtcggcagctttgattcgataagcagcatcgcctgtttcagg
ctgtctatgtgtgactgttgagctgtaacaagttgtctcaggtgttcaatttcatgttctagttgctttgttttactggtttcacctgttctattaggtgtt
acatgctgttcatctgttacattgtcgatctgttcatggtgaacagctttgaatgcaccaaaaactcgtaaaagctctgatgtatctatctttttaca
ccgtttcatctgtgcatatggacagttttccctttgatatgtaacggtgaacagttgttctactttgtttgttagtcttgatgcttcactgatagatac
aagagccataagaacctcagatccttccgtatttagccagtatgttctctagtgtggttcgttgtttttgcgtgagccatgagaacgaaccattga
gatcatacttactttgcatgtcactcaaaaattttgcctcaaaactggtgagctgaatttttgcagttaaagcatcgtgtagtgtttttcttagtccgtt
atgtaggtaggaatctgatgtaatggttgttggtattttgtcaccattcatttttatctggttgttctcaagttcggttacgagatccatttgtctatcta
gttcaacttggaaaatcaacgtatcagtcgggcggcctcgcttatcaaccaccaatttcatattgctgtaagtgtttaaatctttacttattggtttc
aaaacccattggttaagccttttaaactcatggtagttattttcaagcattaacatgaacttaaattcatcaaggctaatctctatatttgccttgtga
gttttcttttgtgttagttcttttaataaccactcataaatcctcatagagtatttgttttcaaaagacttaacatgttccagattatattttatgaattttttt
aactggaaaagataaggcaatatctcttcactaaaaactaattctaatttttcgcttgagaacttggcatagtttgtccactggaaaatctcaaag
cctttaaccaaaggattcctgatttccacagttctcgtcatcagctctctggttgctttagctaatacaccataagcattttccctactgatgttcatc
atctgagcgtattggttataagtgaacgataccgtccgttctttccttgtagggttttcaatcgtggggttgagtagtgccacacagcataaaatt
agcttggtttcatgctccgttaagtcatagcgactaatcgctagttcatttgctttgaaaacaactaattcagacatacatctcaattggtctaggt
gattttaatcactataccaattgagatgggctagtcaatgataattactagtcctttttcctttgagttgtgggtatctgtaaattctgctagacctttgc
tggaaaacttgtaaattctgctagaccctctgtaaattccgctagacctttgtgtgttttttttgtttatattcaagtggttataatttatagaataaaga
aagaataaaaaaagataaaaagaatagatcccagccctgtgtataactcactactttagtcagttccgcagtattacaaaggatgtcgcaaa
cgctgtttgctcctctacaaaacagaccttaaaaccctaaaggcttaagtagcaccctcgcaagctcgggcaaatcgctgaatattcctttgtc
tccgaccatcaggcacctgagtcgctgtctttttcgtgacattcagttcgctgcgctcacggctctggcagtgaatgggggtaaatggcacta
caggcgccttttatggattcatgcaaggaaactacccataatacaagaaaagcccgtcacgggcttctcagggcgttttatggcgggtctgct
atgtggtgctatctgactttttgctgttcagcagttcctgccctctgattttccagtctgaccacttcggattatcccgtgacaggtcattcagactg
gctaatgcacccagtaaggcagcggtatcatcaacaggctta (SEQ ID NO:87)

MCM330 - FRT-cm-FRT-gi1.2-KKDyI at attTn7

Figure 108A

I- caagaaaaatgccccgcttacgcagggcatccatttattactcaaccgtaaccgattttgccaggttacgcggctggtcaacgtcggtgcctttgatcagcgcgacatggtaagccagcagctgcagcggaacggtgtagaagatcggtgcaatcacctcttccacatgcggcatctcgatgatgtgcatgttatcgctacttacaaaacccgcatcctgatcggcgaagacatacaactgaccgccacgcgcgcgaacttcttcaatgttggatttcagtttttccagcaattcgttgttcggtgcaacaacaataaccggcatatcggcatcaattagcgccagcggaccgtgtttcagttcgccagcagcgtaggcttcagcgtgaatgtaagagatctctttcaacttcaatgcgccttccagcgcgattgggtactgatcgccacggcccaggaacagcgcgtgatgtttgtcagagaaatcttctgccagcgcttcaatgcgtttgtcctgagacagcatctgctcaatacggctcggcagcgcctgcagaccatgcacgatgtcatgttcaatggaggcatccagacctttcaggcgagacagcttcgccaccagcatcaacagcacagttaactgagtggtgaatgctttagtggatgccacgccgatttctgtacccgcgttggtcattagcgccagatcggattcgcgcaccagagaagaacccggaacgttacagattgccagtgaaccaaggtaacccagctctttcgacagacgcaggccagccagggtatccgcggtttcgccagactgtgacacgatcgcccttcccaacagttgcgcagcctatacgtacggcagtttaaggtttacacctataaaagagagagccgttatcgtctgtttgtggatgtacagagtgatattattgacacgccggggcgacggatggtgatcccctggccagtgcacgtctgctgtcagataaagtctcccgtgaactttacccggtggtgcatatcggggatgaaagctggcgcatgatgaccaccgatatggccagtgtgccggtctccgttatcggggaagaagtggctgatctcagccaccgcgaaaatgacatcaaaaacgccattaacctgatgttctggggaatataaatgtcaggcatgagattatcaaaaaggatcttcacctagatccttttcacgtagaaagccagtccgcagaaacggtgctgaccccggatgaatgtcagctactgggctatctggacaagggaaaacgcaagcgcaaagagaaagcaggtagcttgcagtgggcttacatggcgatagctagactgggcggttttatggacagcaagcgaaccggaattgccagctggggcgccctctggtaaggttgggaagccctgcaaagtaaactggatggctttctcgccgccaaggatctgatggcgcaggggatcaagctctgatcaagagacaggatgaggatcgtttcgcatgattgaacaagatggattgcacgcaggttctccggccgcttgggtggagaggctattcggctatgactgggcacaacagacaatcggctgctctgatgccgccgtgttccggctgtcagcgcaggggcgcccggttctttttgtcaagaccgacctgtccggtgccctgaatgaactgcaagacgaggcagcgcggctatcgtggctggccacgacgggcgttccttgcgcagctgtgctcgacgttgtcactgaagcgggaagggactggctgctattgggcgaagtgccggggcaggatctcctgtcatctcaccttgctcctgccgagaaagtatccatcatggctgatgcaatgcggcggctgcatacgcttgatccggctacctgcccattcgaccaccaagcgaaacatcgcatcgagcgagcacgtactcggatggaagccggtcttgtcgatcaggatgatctggacgaagagcatcaggggctcgcgccagccgaactgttcgccaggctcaaggcgagcatgcccgacggcgaggatctcgtcgtgacccatggcgatgcctgcttgccgaatatcatggtggaaaatggccgcttttctggattcatcgactgtggccggctgggtgtggcggaccgctatcaggacatagcgttggctacccgtgatattgctgaagagcttggcggcgaatgggctgaccgcttcctcgtgctttacggtatcgccgctcccgattcgcagcgcatcgccttctatcgccttcttgacgagttcttctgaattattaacgcttacaatttcctgatgcggtattttctccttacgcatctgtgcggtatttcacaccgcatacaggtggcacttttcggggaaatgtgcgcggaacccctatttgtttatttttctaaatacattcaaatatgtatccgctcatgagacaataaccctgataaatgcttcaataatagcacgtgaggagggccaccatggccaagttgaccagtgccgttccggtgctcaccgcgcgcgacgtcgccggagcggtcgagttctggaccgaccggctcgggttctcccctagtaacggccgccagtgtgctggaattcaggcagttcaacctgttgatagtacgtactaagctctcatgtttcacgtactaagctctcatgtttaacgtactaagctctcatgtttaacgaactaaaccctcatggctaacgtactaagctctcatggctaacgtactaagctctcatgtttcacgtactaagctctcatgtttgaacaataaaattaatataaatcagcaacttaaatagcctctaaggttttaagttttataagaaaaaaaagaatatataaggcttttaaagcttttaaggtttaacggttgtggacaacaagccagggatgtaacgcactgagaagcccttagagcctctcaaagcaattttcagtgacacaggaacacttaacggctgacagcctgaattctgcagatatctgtttttccactcttcgttcactttcgccaggtagctggtgaagacgaaggaagtcccggagccatctgcgcggcgtactacagcaatgttttgtgaaggcagtttcagacccggattcagtttggcgatggcttcatcatcccacttcttgattttgcccaggtagatgtcgccgagggttttaccatccagcaccagttcgccagacttcagccctggaatgttaaccgccagcaccacgccgccaatcacggtcgggaactggaacagaccttcctgagccagtttttcgtcagacagcggcgcgtcagaggcaccaaaatcaacggtattagcgataatctgttttacgccaccggaagaaccgatacctggtagttaactttattaccggtttctttctggtaagtgtcagcccatttggcatacaccggcgcagggaaggttgcacctgcacctgtcaggcttgcttctgcaaacacagagaaagcactcatcgataaggtcgcggcgacaacagttgcgacggtggtacgcataactttcataatgtctcctgggaggattcataaagcattgtttgttggctacgagaagcaaaataggacaaacaggtgacagttatatgtaaggaatatgacagttttatgacagagagataaagtcttcagtctgatttaaataagcgttgatattcagtcaattacaaacattaataacg

Figure 108B aagagatgacagaaaatttcattctgtgacagagaaaaagtagccgaagatgacggtttgtcacatggagttggcaggatgtttgattaaa
agcaattaaccctcactaaagggcggccgcgaagttcctattctctagaaagtataggaacttcattctaccgggtaggggaggcgcttttcc
caaggcagtctggagcatgcgctttagcagccccgctgggcacttggcgctacacaagtggcctctggcctcgcacacattccacatccac
cggtaggcgccaaccggctccgttctttggtggccccttcgcgccaccttccactcctcccctagtcaggaagttcccccccgccccgcag
ctcgcgtcgtgcaggacgtgacaaatggaagtagcacgtctcactagtctcgtgcagatggacagcaccgctgagcaatggaagcgggta
ggcctttggggcagcggccaatagcagctttgctccttcgctttctgggctcagaggctgggaaggggtgggtccgggggcgggctcagg
ggcgggctcaggggcggggcgggcgcccgaaggtcctccggaggcccggcattctgcacgcttcaaaagcgcacgtctgccgcgctg
ttctcctcttcctcatctccgggcctttcgacctgcagcagcacgtgttgacaattaatcatcggcatagtatatcggcatagtataatacgacaa
ggtgaggaactaaaccatggagaaaaaaatcactggatataccaccgttgatatatcccaatggcatcgtaaagaacattttgaggcatttca
gtcagttgctcaatgtacctataaccagaccgttcagctggatattacggcctttttaaagaccgtaaagaaaaataagcacaagttttatccgg
cctttattcacattcttgcccgcctgatgaatgctcatccggaattccgtatggcaatgaaagacggtgagctggtgatatgggatagtgttcac
ccttgttacaccgttttccatgagcaaactgaaacgttttcatcgctctggagtgaataccacgacgatttccggcagtttctacacatatattcg
caagatgtggcgtgttacggtgaaaacctggcctatttccctaaagggtttattgagaatatgtttttcgtctcagccaatccctgggtgagtttc
accagttttgatttaaacgtggccaatatggacaacttcttcgcccccgttttcaccatgggcaaatattatacgcaaggcgacaaggtgctgat
gccgctggcgattcaggttcatcatgccgtttgtgatggcttccatgtcggcagaatgcttaatgaattacaacagtactgcgatgagtggcag
ggcggggcgtaagcgggactctggggttcgaataaagaccgaccaagcgacgtctgagagctccctggcgaattcggtaccaataaaag
agctttatttcatgatctgtgtgttggtttttgtgtgcggcgcggaagttcctattctctagaaagtataggaacttcctcgagccctatagtgagt
cgtattagcccttgacgatgccacatcctgagcaaataattcaaccactaattgtgagcggataacacaaggaggaaacagctatgtcattac
cgttcttaacttctgcaccgggaaaggttattatttttggtgaacactctgctgtgtacaacaagcctgccgtcgctgctagtgtgtctgcgttga
gaacctacctgctaataagcgagtcatctgcaccagatactattgaattggacttcccggacattagctttaatcataagtggtccatcaatgatt
tcaatgccatcaccgaggatcaagtaaactcccaaaaattggccaaggctcaacaagccaccgatggcttgtctcaggaactcgttagtcttt
tggatccgttgttagctcaactatccgaatccttccactaccatgcagcgtttgtttcctgtatatgtttgtttgcctatgcccccatgccaagaat
attaagttttctttaaagtctactttacccatcggtgctgggttgggctcaagcgcctctatttctgtatcactggccttagctatggcctacttggg
ggggttaataggatctaatgacttggaaaagctgtcagaaaacgataagcatatagtgaatcaatgggccttcataggtgaaaagtgtattca
cggtacccccttcaggaatagataacgctgtggccacttatggtaatgccctgctatttgaaaaagactcacataatggaacaataaacacaaa
caatttaagttcttagatgatttcccagccattccaatgatcctaacctatactagaattccaaggtctacaaaagatcttgttgctcgcgttcgtg
tgttggtcaccgagaaatttcctgaagttatgaagccaattctagatgccatgggtgaatgtgccctacaaggcttagagatcatgactaagtta
agtaaatgtaaaggcaccgatgacgaggctgtagaaactaataatgaactgtatgaacaactattggaattgataagaataaatcatggactg
cttgtctcaatcggtgtttctcatcctggattagaacttattaaaaatctgagcgatgatttgagaattggctccacaaaacttaccggtgctggtg
gcggcggttgctctttgactttgttacgaagagacattactcaagagcaaattgacagcttcaaaaagaaattgcaagatgattttagttacgag
acatttgaaacagacttgggtgggactggctgctgtttgttaagcgcaaaaaatttgaataaagatcttaaaatcaaatccctagtattccaatta
tttgaaaataaaactaccacaaagcaacaaattgacgatctattattgccaggaaacacgaatttaccatggacttcataagctaatttgcgata
ggcctgcacccttaaggaggaaaaaacatgtcagagttgagagccttcagtgccccagggaaagcgttactagctggtggatatttagtttt
agatacaaaatatgaagcatttgtagtcggattatcggcaagaatgcatgctgtagcccatccttacggttcattgcaagggtctgataagtttg
aagtgcgtgtgaaaagtaaacaatttaaagatggggagtggctgtaccatataagtcctaaaagtggcttcattcctgtttcgataggcggatc
taagaacccttttcattgaaaaagttatcgctaacgtatttagctactttaaacctaacatggacgactactgcaatagaaacttgttcgttattgata
ttttctctgatgatgcctaccattctcaggaggatagcgttaccgaacatcgtggcaacagaagattgagttttcattcgcacagaattgaagaa
gttcccaaaacagggctgggctcctcggcaggtttagtcacagttttaactacagctttggcctccttttttgtatcggacctggaaaataatgta
gacaaatatagagaagttattcataatttagcacaagttgctcattgtcaagctcagggtaaaattggaagcgggtttgatgtagcggcggca
gcatatggatctatcagatatagaagattcccacccgcattaatctctaatttgccagatattggaagtgctacttacggcagtaaactggcgca
tttggttgatgaagaagactggaatattacgattaaaagtaaccatttaccttc

Figure 108C gggattaactttatggatgggcgatattaagaatggttcagaaacagtaaaactggtccagaaggtaaaaaattggtatgattcgcatatgcca
gaaagcttgaaaatatatacagaactcgatcatgcaaattctagatttatggatggactatctaaactagatcgcttacacgagactcatgacga
ttacagcgatcagatatttgagtctcttgagaggaatgactgtacctgtcaaaagtatcctgaaatcacagaagttagagatgcagttgccaca
attagacgttcctttagaaaaataactaaagaatctggtgccgatatcgaacctcccgtacaaactagcttatggatgattgccagaccttaaa
aggagttcttacttgcttaatacctggtgctggtggttatgacgccattgcagtgattactaagcaagatgttgatcttagggctcaaaccgctaa
tgacaaaagatttctaaggttcaatggctggatgtaactcaggctgactggggtgttaggaaagaaaaagatccggaaacttatcttgataaa
taacttaaggtagctgcatgcagaattcgcccttaaggaggaaaaaaaaatgaccgtttacacagcatccgttaccgcacccgtcaacatcg
caaccccttaagtattgggggaaaagggacacgaagttgaatctgcccaccaattcgtccatatcagtgactttatcgcaagatgacctcagaa
cgttgacctctgcggctactgcacctgagtttgaacgcgacactttgtggttaaatggagaaccacacagcatcgacaatgaaagaactcaa
aattgtctgcgcgacctacgccaattaagaaaggaaatggaatcgaaggacgcctcattgcccacattatctcaatggaaactccacattgtc
tccgaaaataactttcctacagcagctggtttagcttcctccgctgctggctttgctgcattggtctctgcaattgctaagttataccaattaccac
agtcaacttcagaaatatctagaatagcaagaaaggggtctggttcagcttgtagatcgttgtttggcggatacgtggcctgggaaatgggaa
aagctgaagatggtcatgattccatggcagtacaaatcgcagacagctctgactggcctcagatgaaagcttgtgtcctagttgtcagcgata
ttaaaaaggatgtgagttccactcagggtatgcaattgaccgtggcaacctccgaactatttaaagaaagaattgaacatgtcgtaccaaaga
gatttgaagtcatgcgtaaagccattgttgaaaaagatttcgccacctttgcaaaggaaacaatgatggattccaactctttccatgccacatgtt
tggactctttccctccaatattctacatgaatgacacttccaagcgtatcatcagttggtgccacaccattaatcagtttacggagaaacaatcg
ttgcatacacgtttgatgcaggtccaaatgctgtgttgtactacttagctgaaaatgagtcgaaactctttgcatttatctataaattgtttggctctg
ttcctggatgggacaagaaatttactactgagcagcttgaggctttcaaccatcaatttgaatcatctaactttactgcacgtgaattggatcttga
gttgcaaaaggatgttgccagagtgattttaactcaagtcggttcaggcccacaagaaacaaacgaatctttgattgacgcaaagactggtct
accaaaggaataagatcaattcgctgcatcgcccttaggaggtaaaaaaaaatgactgccgacaacaatagtatgccccatggtgcagtatc
tagttacgccaaattagtgcaaaaccaaacacctgaagacattttggaagagtttcctgaaattattccattacaacaaagacctaatacccgat
ctagtgagacgtcaaatgacgaaagcggagaaacatgtttttctggtcatgatgaggagcaaattaagttaatgaatgaaaattgtattgtttg
gattgggacgataatgctattggtgccggtaccaagaaagtttgtcatttaatggaaaatattgaaaagggtttactacatcgtgcattctccgtc
tttattttcaatgaacaaggtgaattactttacaacaaagagccactgaaaaaataactttccctgatctttggactaacacatgctgctctcatc
cactatgtattgatgacgaattaggtttgaagggtaagctagacgataagattaagggcgctattactgcggcggtgagaaaactagatcatg
aattaggtattccagaagatgaaactaagacaaggggtaagtttcactttttaaacagaatccattacatggcaccaagcaatgaaccatggg
gtgaacatgaaattgattacatcctattttataagatcaacgctaaagaaaacttgactgtcaacccaaacgtcaatgaagttagagacttcaaa
tgggtttcaccaaatgatttgaaaactatgtttgctgacccaagttacaagtttacgccttggtttaagattatttgcgagaattactattcaactg
gtgggagcaattagatgacctttctgaagtggaaaatgacaggcaaattcatagaatgctataacaacgcgtctacaaataaaaaaggcacg
tcagatgacgtgcctttttcttggggcc (SEQ ID NO:90)

Figure 110A 1-
gtgcggccgcaagcttgtcgacggagctcgaattcggatccctgcagttagacatacatcagctggttaatcgggaaagggtcaatcagca
gcagtttgatgcggttttcagtcgcgtagtctgggcgacccagaccatcgccatactggtaggtgcagtgggaaacacgtgccatgttaact
gcgatttccatgaacgctttaggcagcagggtggagtcgctaacgcgttcacgattcatctttttccattcggcgtcgatcagtttacgcagttct
tcgcgggcctgttcctcgctggtaccatcgttttcgtgcatgtagctaatgatagaattggtagtctcgccacgttccagctccgccgcagagg
tggccagatcgttgcacaggcggaagataacgcagctagaacgcaccagaccatggaagtcggtcagggaacgcagcgcgtggtcgga
gatgtcttcctgctgctggcatacggaaaagtaagacggcgccagcagcgctacaccggaggaggaaacgctggcgttttccaggtactt
ggagaaagccgggataatttgttgttggaccattcgcctcttgcagaaaggctttgcacagttcacgccagctttcgtcagataggacagg
ttgttatgacctttctctttcagaatagaataggacgtgtcgttaacggtgttgtacagtgccaggaaacacagtttcatatagtccggcagggt
gttaatagcgttaacgtcccagcgctctacagcatcggtgaacagttgcagttcgtccagagtgccataaacgtcatacacgtcatcgatgat
cgtcaccagaccaaacatttagtaacagctttgcgacattcaccaaactgcgggtctggcgccatacccagtgcccagaaataaacttccat
caggcggtcgcgtacaaaatccagtttgctagccaggcccatctcggtccaccagcgggacagatcttgcagctctttctggtgcagggtct
gtaccatgttaaaatccagcttcgccagctccagcagcagctggtgatgcggttctttcggttcgtatttatccaggaaccaacgtgcctccag
acggtgcagacgctggtgatatggcagttccagggcgtggctcacttgttctgcaaccttggtattaatgccttctttcaggttgttcttcaggtg
ggtgatggaaaaggtacgcgcctcctccagcaggttctcaccctcgaaacccaggtaagacgcttcatacaggctcagcaggccttggac
gtcacctttcagttcaccgctgaaaccaccttctttatccttgaaacgctcaaaaacatcctgagaaacctcgaaaccgtgctgacgcagcag
acggaaagacagagcggttgcgtgcaggtcagatttgttctttttgttttcgtccagcagtacgatgttttccagggctttaatgatgtctttttcaa
atttgtaggtcagacccaggcgctgcacatcgtcgatcagctccagcagggacagcggctgggtgtctacacggttgatcatgcagcgaac
ttcttcctccagtttggtcgctttctcctccagctttccactttcaggtcgttctccagggattgcaggaattcgaaattccacaggtttggctgat
agtttgcggaacgacgggaattatgctcggtaatctgagtaaattgagaagaggtcgcacacatggtatatctccttcttaaagttaaacaaaa
ttatttctagaggggaattgttatccgctcacaattcccctatagtgagtcgtattaatttcgcgggatcgagatctcgatcctctacgccggacg
catcgtggccggcatcaccggcgccacaggtgcggttgctggcgcctatatcgccgacatcaccgatggggaagatcgggctcgccactt
cgggctcatgagcgcttgtttcggcgtgggtatggtggcaggccccgtggccgggggactgttgggcgccatctccttgcatgcaccattc
cttgcggcggcggtgctcaacggcctcaacctactactgggctgcttcctaatgcaggagtcgcataagggagagcgtcgagatcccgga
caccatcgaatggcgcaaaacctttcgcggtatggcatgatagcgcccggaagagagtcaattcagggtggtgaatgtgaaaccagtaac
gttatacgatgtcgcagagtatgccggtgtctcttatcagaccgtttcccgcgtggtgaaccaggccagccacgtttctgcgaaaacgcggg
aaaaagtggaagcggcgatggcggagctgaattacattcccaaccgcgtggcacaacaactggcgggcaaacagtcgttgctgattggc
gttgccacctccagtctggccctgcacgcgccgtcgcaaattgtcgcggcgattaaatctcgcgccgatcaactgggtgccagcgtggtgg
tgtcgatggtagaacgaagcggcgtcgaagcctgtaaagcggcggtgcacaatcttctcgcgcaacgcgtcagtgggctgatcattaacta
tccgctggatgaccaggatgccattgctgtggaagctgcctgcactaatgttccggcgttatttcttgatgtctctgaccagacacccatcaac
agtattattttctcccatgaagacggtacgcgactgggcgtggagcatctggtcgcattgggtcaccagcaaatcgcgctgttagcgggccc
attaagttctgtctcggcgcgtctgcgtctggctggctggcataaatatctcactcgcaatcaaattcagccgatagcggaacgggaaggcg
actggagtgccatgtccggttttcaacaaaccatgcaaatgctgaatgagggcatcgttcccactgcgatgctggttgccaacgatcagatg
gcgctgggcgcaatgcgcgccattaccgagtccgggctgcgcgttggtgcggatatctcggtagtgggatacgacgataccgaagacag
ctcatgttatatcccgccgttaaccaccatcaaacaggattttcgcctgctggggcaaaccagcgtggaccgcttgctgcaactctctcaggg
ccaggcggtgaagggcaatcagctgttgcccgtctcactggtgaaaagaaaaaccaccctggcgcccaatacgcaaaccgcctctcccc
gcgcgttggccgattcattaatgcagctggcacgacaggtttcccgactggaaagcgggcagtgagcgcaacgcaattaatgtaagttagc
tcactcattaggcaccgggatctcgaccgatgcccttgagagccttcaacccagtcagctccttccggtgggcgcggggcatgactatcgtc
gccgcacttatgactgtcttctttatcatgcaactcgtaggacaggtgccggcagcgctctgggtcattttcggcgaggaccgctttcgctgga
gcgcgacgatgatcggcctgtcgcttgcggtattcggaatcttgcacgccctcgctcaagccttcgtcactggtcccgccaccaaacgtttcg
gcgagaagcaggccattatcgccggcatggcggccccacgggtgcgcatgatcgtgctcctg

Figure 110B tcgttgaggacccggctaggctggcggggttgccttactggttagcagaatgaatcaccgatacgcgagcgaacgtgaagcgactgctgct
gcaaaacgtctgcgacctgagcaacaacatgaatggtcttcggtttccgtgtttcgtaaagtctggaaacgcggaagtcagcgccctgcacc
attatgttccggatctgcatcgcaggatgctgctggctaccctgtggaacacctacatctgtattaacgaagcgctggcattgaccctgagtga
tttttctctggtcccgccgcatccataccgccagttgtttaccctcacaacgttccagtaaccgggcatgttcatcatcagtaacccgtatcgtga
gcatcctctctcgtttcatcggtatcattacccccatgaacagaaatcccccttacacggaggcatcagtgaccaaacaggaaaaaaccgcc
cttaacatggcccgctttatcagaagccagacattaacgcttctggagaaactcaacgagctggacgcggatgaacaggcagacatctgtg
aatcgcttcacgaccacgctgatgagctttaccgcagctgcctcgcgcgtttcggtgatgacggtgaaaacctctgacacatgcagctcccg
gagacggtcacagcttgtctgtaagcggatgccgggagcagacaagcccgtcagggcgcgtcagcgggtgttggcgggtgtcggggcg
cagccatgacccagtcacgtagcgatagcggagtgtatactggcttaactatgcggcatcagagcagattgtactgagagtgcaccatatat
gcggtgtgaaataccgcacagatgcgtaaggagaaaataccgcatcaggcgctcttccgcttcctcgctcactgactcgctgcgctcggtc
gttcggctgcggcgagcggtatcagctcactcaaaggcggtaatacggttatccacagaatcaggggataacgcaggaaagaacatgtga
gcaaaaggccagcaaaaggccaggaaccgtaaaaaggccgcgttgctggcgtttttccataggctccgcccccctgacgagcatcacaa
aaatcgacgctcaagtcagaggtggcgaaacccgacaggactataaagataccaggcgtttccccctggaagctccctcgtgcgctctcct
gttccgaccctgccgcttaccggatacctgtccgcctttctcccttcgggaagcgtggcgctttctcatagctcacgctgtaggtatctcagttc
ggtgtaggtcgttcgctccaagctgggctgtgtgcacgaaccccccgttcagcccgaccgctgcgccttatccggtaactatcgtcttgagtc
caacccggtaagacacgacttatcgccactggcagcagccactggtaacaggattagcagagcgaggtatgtaggcggtgctacagagtt
cttgaagtggtggcctaactacggctacactagaaggacagtatttggtatctgcgctctgctgaagccagttaccttcggaaaaagagttgg
tagctcttgatccggcaaacaaaccaccgctggtagcggtggtttttttgtttgcaagcagcagattacgcgcagaaaaaaaggatctcaaga
agatcctttgatcttttctacggggtctgacgctcagtggaacgaaaactcacgttaagggattttggtcatgaacaataaaactgtctgcttaca
taaacagtaatacaaggggtgttatgagccatattcaacgggaaacgtcttgctctaggccgcgattaaattccaacatggatgctgatttatat
gggtataaatgggctcgcgataatgtcgggcaatcaggtgcgacaatctatcgattgtatgggaagcccgatgcgccagagttgtttctgaa
acatggcaaaggtagcgttgccaatgatgttacagatgagatggtcagactaaactggctgacggaatttatgcctcttccgaccatcaagca
ttttatccgtactcctgatgatgcatggttactcaccactgcgatccccgggaaaacagcattccaggtattagaagaatatcctgattcaggtg
aaaatattgttgatgcgctggcagtgttcctgcgccggttgcattcgattcctgtttgtaattgtccttttaacagcgatcgcgtatttcgtctcgct
caggcgcaatcacgaatgaataacggtttggttgatgcgagtgattttgatgacgagcgtaatggctggcctgttgaacaagtctggaaaga
aatgcataaacttttgccattctcaccggattcagtcgtcactcatggtgatttctcacttgataaccttatttttgacgaggggaaattaataggtt
gtattgatgttggacgagtcggaatcgcagaccgataccaggatcttgccatcctatggaactgcctcggtgagttttctccttcattacagaaa
cggctttttcaaaaatatggtattgataatcctgatatgaataaattgcagtttcatttgatgctcgatgagtttttctaagaattaattcatgagcgg
atacatatttgaatgtatttagaaaaataaacaaataggggttccgcgcacatttccccgaaaagtgccacctgaaattgtaaacgttaatattt
gttaaaattcgcgttaaatttttgttaaatcagctcattttttaaccaataggccgaaatcggcaaaatcccttataaatcaaaagaatagaccga
gatagggttgagtgttgttccagtttggaacaagagtccactattaaagaacgtggactccaacgtcaaagggcgaaaaaccgtctatcagg
gcgatggcccactacgtgaaccatcaccctaatcaagttttttggggtcgaggtgccgtaaagcactaaatcggaaccctaaagggagccc
ccgatttagagcttgacggggaaagccggcgaacgtggcgagaaaggaagggaagaaagcgaaaggagcgggcgctagggcgctgg
caagtgtagcggtcacgctgcgcgtaaccaccacacccgccgcgcttaatgcgccgctacagggcgcgtcccattcgccaatccggatat
agttcctcctttcagcaaaaaacccctcaagacccgtttagaggccccaaggggttatgctagttattgctcagcggtggcagcagccaactc
agcttcctttcgggctttgttagcagccggatctcagtggtggtggtggtggtgctcga

SEQUENCE LISTING

```
<160> NUMBER OF SEQ ID NOS: 104

<210> SEQ ID NO 1
<211> LENGTH: 1701
<212> TYPE: DNA
<213> ORGANISM: Escherichia coli

<400> SEQUENCE: 1

atgtgtgcga cctcttctca atttactcag attaccgagc ataattcccg tcgttccgca      60

aactatcagc caaacctgtg gaatttcgaa ttcctgcaat ccctggagaa cgacctgaaa     120

gtggaaaagc tggaggagaa agcgaccaaa ctggaggaag aagttcgctg catgatcaac     180

cgtgtagaca cccagccgct gtccctgctg gagctgatcg acgatgtgca gcgcctgggt     240

ctgacctaca aatttgaaaa agacatcatt aaagccctgg aaaacatcgt actgctggac     300

gaaaacaaaa agaacaaatc tgacctgcac gcaaccgctc tgtctttccg tctgctgcgt     360

cagcacggtt tcgaggtttc tcaggatgtt tttgagcgtt tcaaggataa agaaggtggt     420

ttcagcggtg aactgaaagg tgacgtccaa ggcctgctga gcctgtatga agcgtcttac     480

ctgggtttcg agggtgagaa cctgctggag gaggcgcgta ccttttccat cacccacctg     540

aagaacaacc tgaaagaagg cattaatacc aaggttgcag aacaagtgag ccacgccctg     600

gaactgccat atcaccagcg tctgcaccgt ctggaggcac gttggttcct ggataaatac     660

gaaccgaaag aaccgcatca ccagctgctg ctggagctgg cgaagctgga ttttaacatg     720

gtacagaccc tgcaccagaa agagctgcaa gatctgtccc gctggtggac cgagatgggc     780

ctggctagca aactggattt tgtacgcgac cgcctgatgg aagtttattt ctgggcactg     840

ggtatggcgc cagacccgca gtttggtgaa tgtcgcaaag ctgttactaa aatgtttggt     900

ctggtgacga tcatcgatga cgtgtatgac gtttatggca ctctggacga actgcaactg     960
```

ttcaccgatg ctgtagagcg ctgggacgtt aacgctatta acaccctgcc ggactatatg 1020
aaactgtgtt tcctggcact gtacaacacc gttaacgaca cgtcctattc tattctgaaa 1080
gagaaaggtc ataacaacct gtcctatctg acgaaaagct ggcgtgaact gtgcaaagcc 1140
tttctgcaag aggcgaaatg gtccaacaac aaaattatcc cggctttctc caagtacctg 1200
gaaaacgcca gcgtttcctc ctccggtgta gcgctgctgg cgccgtctta cttttccgta 1260
tgccagcagc aggaagacat ctccgaccac gcgctgcgtt ccctgaccga cttccatggt 1320
ctggtgcgtt ctagctgcgt tatcttccgc ctgtgcaacg atctggccac ctctgcggcg 1380
gagctggaac gtggcgagac taccaattct atcattagct acatgcacga aaacgatggt 1440
accagcgagg aacaggcccg cgaagaactg cgtaaactga tcgacgccga atggaaaaag 1500
atgaatcgtg aacgcgttag cgactccacc ctgctgccta aagcgttcat ggaaatcgca 1560
gttaacatgg cacgtgtttc ccactgcacc taccagtatg gcgatggtct gggtcgccca 1620
gactacgcga ctgaaaaccg catcaaactg ctgctgattg accctttccc gattaaccag 1680
ctgatgtatg tctaactgca g 1701

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgtgtgc 420
gacctcttct caatttactc agattaccga gcataattcc cgtcgttccg caaactatca 480
gccaaacctg tggaatttcg aattcctgca atccctggag aacgacctga aagtggaaaa 540
gctggaggag aaagcgacca aactggagga agaagttcgc tgcatgatca accgtgtaga 600
cacccagccg ctgtccctgc tggagctgat cgacgatgtg cagcgcctgg gtctgaccta 660
caaatttgaa aaagacatca ttaaagccct ggaaaacatc gtactgctgg acgaaaacaa 720
aaagaacaaa tctgacctgc acgcaaccgc tctgtctttc cgtctgctgc gtcagcacgg 780
tttcgaggtt tctcaggatg tttttgagcg tttcaaggat aaagaaggtg gtttcagcgg 840
tgaactgaaa ggtgacgtcc aaggcctgct gagcctgtat gaagcgtctt acctgggttt 900
cgagggtgag aacctgctgg aggaggcgcg taccttttcc atcacccacc tgaagaacaa 960
cctgaaagaa ggcattaata ccaaggttgc agaacaagtg agccacgccc tggaactgcc 1020
atatcaccag cgtctgcacc gtctggaggc acgttggttc ctggataaat acgaaccgaa 1080
agaaccgcat caccagctgc tgctggagct ggcgaagctg gattttaaca tggtacagac 1140
cctgcaccag aaagagctgc aagatctgtc ccgctggtgg accgagatgg gcctggctag 1200
caaactggat tttgtacgcg accgcctgat ggaagtttat ttctgggcac tgggtatggc 1260

-continued gccagacccg cagtttggtg aatgtcgcaa agctgttact aaaatgtttg gtctggtgac 1320
gatcatcgat gacgtgtatg acgtttatgg cactctggac gaactgcaac tgttcaccga 1380
tgctgtagag cgctgggacg ttaacgctat taacaccctg ccggactata tgaaactgtg 1440
tttcctggca ctgtacaaca ccgttaacga cacgtcctat tctattctga aagagaaagg 1500
tcataacaac ctgtcctatc tgacgaaaag ctggcgtgaa ctgtgcaaag cctttctgca 1560
agaggcgaaa tggtccaaca acaaaattat cccggctttc tccaagtacc tggaaaacgc 1620
cagcgtttcc tcctccggtg tagcgctgct ggcgccgtct tacttttccg tatgccagca 1680
gcaggaagac atctccgacc acgcgctgcg ttccctgacc gacttccatg gtctggtgcg 1740
ttctagctgc gttatcttcc gcctgtgcaa cgatctggcc acctctgcgg cggagctgga 1800
acgtggcgag actaccaatt ctatcattag ctacatgcac gaaaacgatg gtaccagcga 1860
ggaacaggcc cgcgaagaac tgcgtaaact gatcgacgcc gaatggaaaa agatgaatcg 1920
tgaacgcgtt agcgactcca ccctgctgcc taaagcgttc atggaaatcg cagttaacat 1980
ggcacgtgtt tcccactgca cctaccagta tggcgatggt ctgggtcgcc cagactacgc 2040
gactgaaaac cgcatcaaac tgctgctgat tgaccctttc ccgattaacc agctgatgta 2100
tgtctaactg cagctggtac catatgggaa ttcgaagctt tctagaacaa aaactcatct 2160
cagaagagga tctgaatagc gccgtcgacc atcatcatca tcatcattga gtttaaacgg 2220
tctccagctt ggctgttttg gcggatgaga gaagattttc agcctgatac agattaaatc 2280
agaacgcaga agcggtctga taaaacagaa tttgcctggc ggcagtagcg cggtggtccc 2340
acctgacccc atgccgaact cagaagtgaa acgccgtagc gccgatggta gtgtggggtc 2400
tccccatgcg agagtaggga actgccaggc atcaaataaa acgaaaggct cagtcgaaag 2460
actgggcctt tcgttttatc tgttgtttgt cggtgaacgc tctcctgagt aggacaaatc 2520
cgccgggagc ggatttgaac gttgcgaagc aacggcccgg agggtggcgg gcaggacgcc 2580
cgccataaac tgccaggcat caaattaagc agaaggccat cctgacggat ggcctttttg 2640
cgtttctaca aactcttttt gtttattttt ctaaatacat tcaaatatgt atccgctcat 2700
gagacaataa ccctgataaa tgcttcaata atattgaaaa aggaagagta tgagtattca 2760
acatttccgt gtcgccctta ttcccttttt tgcggcattt tgccttcctg tttttgctca 2820
cccagaaacg ctggtgaaag taaaagatgc tgaagatcag ttgggtgcac gagtgggtta 2880
catcgaactg gatctcaaca gcggtaagat ccttgagagt tttcgccccg aagaacgttt 2940
tccaatgatg agcactttta aagttctgct atgtggcgcg gtattatccc gtgttgacgc 3000
cgggcaagag caactcggtc gccgcataca ctattctcag aatgacttgg ttgagtactc 3060
accagtcaca gaaaagcatc ttacggatgg catgacagta agagaattat gcagtgctgc 3120
cataaccatg agtgataaca ctgcggccaa cttacttctg acaacgatcg gaggaccgaa 3180
ggagctaacc gcttttttgc acaacatggg ggatcatgta actcgccttg atcgttggga 3240
accggagctg aatgaagcca taccaaacga cgagcgtgac accacgatgc ctgtagcaat 3300
ggcaacaacg ttgcgcaaac tattaactgg cgaactactt actctagctt cccggcaaca 3360
attaatagac tggatggagg cggataaagt tgcaggacca cttctgcgct cggcccttcc 3420
ggctggctgg tttattgctg ataaatctgg agccggtgag cgtgggtctc gcggtatcat 3480
tgcagcactg gggccagatg gtaagccctc ccgtatcgta gttatctaca cgacggggag 3540
tcaggcaact atggatgaac gaaatagaca gatcgctgag ataggtgcct cactgattaa 3600
gcattggtaa ctgtcagacc aagtttactc atatatactt tagattgatt taaaacttca 3660

```
tttttaattt aaaaggatct aggtgaagat cctttttgat aatctcatga ccaaaatccc   3720
ttaacgtgag ttttcgttcc actgagcgtc agaccccgta gaaaagatca aaggatcttc   3780
ttgagatcct ttttttctgc gcgtaatctg ctgcttgcaa acaaaaaaac caccgctacc   3840
agcggtggtt tgtttgccgg atcaagagct accaactctt tttccgaagg taactggctt   3900
cagcagagcg cagataccaa atactgtcct tctagtgtag ccgtagttag gccaccactt   3960
caagaactct gtagcaccgc ctacatacct cgctctgcta atcctgttac cagtggctgc   4020
tgccagtggc gataagtcgt gtcttaccgg gttggactca agacgatagt taccggataa   4080
ggcgcagcgg tcgggctgaa cggggggttc gtgcacacag cccagcttgg agcgaacgac   4140
ctacaccgaa ctgagatacc tacagcgtga gctatgagaa agcgccacgc ttcccgaagg   4200
gagaaaggcg gacaggtatc cggtaagcgg cagggtcgga acaggagagc gcacgaggga   4260
gcttccaggg ggaaacgcct ggtatcttta tagtcctgtc gggtttcgcc acctctgact   4320
tgagcgtcga tttttgtgat gctcgtcagg ggggcggagc ctatggaaaa acgccagcaa   4380
cgcggccttt ttacggttcc tggccttttg ctggcctttt gctcacatgt tctttcctgc   4440
gttatcccct gattctgtgg ataaccgtat taccgccttt gagtgagctg ataccgctcg   4500
ccgcagccga acgaccgagc gcagcgagtc agtgagcgag gaagcggaag agcgcctgat   4560
gcggtatttt ctccttacgc atctgtgcgg tatttcacac cgcatatggt gcactctcag   4620
tacaatctgc tctgatgccg catagttaag ccagtataca ctccgctatc gctacgtgac   4680
tgggtcatgg ctgcgccccg acacccgcca acacccgctg acgcgccctg acgggcttgt   4740
ctgctcccgg catccgctta cagacaagct gtgaccgtct ccgggagctg catgtgtcag   4800
aggttttcac cgtcatcacc gaaacgcgcg aggcagcaga tcaattcgcg cgcgaaggcg   4860
aagcggcatg catttacgtt gacaccatcg aatggtgcaa aacctttcgc ggtatggcat   4920
gatagcgccc ggaagagagt caattcaggg tggtgaatgt gaaaccagta acgttatacg   4980
atgtcgcaga gtatgccggt gtctcttatc agaccgtttc ccgcgtggtg aaccaggcca   5040
gccacgtttc tgcgaaaacg cgggaaaaag tggaagcggc gatggcggag ctgaattaca   5100
ttcccaaccg cgtggcacaa caactggcgg gcaaacagtc gttgctgatt ggcgttgcca   5160
cctccagtct ggccctgcac gcgccgtcgc aaattgtcgc ggcgattaaa tctcgcgccg   5220
atcaactggg tgccagcgtg gtggtgtcga tggtagaacg aagcggcgtc gaagcctgta   5280
aagcggcggt gcacaatctt ctcgcgcaac gcgtcagtgg gctgatcatt aactatccgc   5340
tggatgacca ggatgccatt gctgtggaag ctgcctgcac taatgttccg gcgttatttc   5400
ttgatgtctc tgaccagaca cccatcaaca gtattatttt ctcccatgaa gacggtacgc   5460
gactgggcgt ggagcatctg gtcgcattgg gtcaccagca aatcgcgctg ttagcgggcc   5520
cattaagttc tgtctcggcg cgtctgcgtc tggctggctg gcataaatat ctcactcgca   5580
atcaaattca gccgatagcg gaacgggaag gcgactggag tgccatgtcc ggttttcaac   5640
aaaccatgca aatgctgaat gagggcatcg ttcccactgc gatgctggtt gccaacgatc   5700
agatggcgct gggcgcaatg cgcgccatta ccgagtccgg gctgcgcgtt ggtgcggata   5760
tctcggtagt gggatacgac gataccgaag acagctcatg ttatatcccg ccgtcaacca   5820
ccatcaaaca ggattttcgc ctgctggggc aaaccagcgt ggaccgcttg ctgcaactct   5880
ctcagggcca ggcggtgaag ggcaatcagc tgttgcccgt ctcactggtg aaaagaaaaa   5940
ccaccctggc gcccaatacg caaaccgcct ctccccgcgc gttggccgat tcattaatgc   6000
```

agctggcacg acaggtttcc cgactggaaa gcgggcagtg agcgcaacgc aattaatgtg 6060
agttagcgcg aattgatctg 6080

<210> SEQ ID NO 3
<211> LENGTH: 37
<212> TYPE: DNA
<213> ORGANISM: Artificial Sequence
<220> FEATURE:
<223> OTHER INFORMATION: PCR Primer

<400> SEQUENCE: 3
cgtgagatca tatgtgtgcg acctcttctc aatttac 37

<210> SEQ ID NO 4
<211> LENGTH: 38
<212> TYPE: DNA
<213> ORGANISM: Artificial Sequence
<220> FEATURE:
<223> OTHER INFORMATION: PCR Primer

<400> SEQUENCE: 4
cggtcgacgg atccctgcag ttagacatac atcagctg 38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180
gcgggatatc cggatatagt tcctcctttc agcaaaaaac ccctcaagac ccgtttagag 240
gccccaaggg gttatgctag ttattgctca gcggtggcag cagccaactc agcttccttt 300
cgggctttgt tagcagccgg atccctgcag ttagacatac atcagctggt taatcgggaa 360
agggtcaatc agcagcagtt tgatgcggtt ttcagtcgcg tagtctgggc gacccagacc 420
atcgccatac tggtaggtgc agtgggaaac acgtgccatg ttaactgcga tttccatgaa 480
cgctttaggc agcagggtgg agtcgctaac gcgttcacga ttcatctttt tccattcggc 540
gtcgatcagt ttacgcagtt cttcgcgggc ctgttcctcg ctggtaccat cgttttcgtg 600
catgtagcta atgatagaat tggtagtctc gccacgttcc agctccgccg cagaggtggc 660
cagatcgttg cacaggcgga agataacgca gctagaacgc accagaccat ggaagtcggt 720
cagggaacgc agcgcgtggt cggagatgtc ttcctgctgc tggcatacgg aaaagtaaga 780
cggcgccagc agcgctacac cggaggagga aacgctggcg ttttccaggt acttggagaa 840
agccgggata attttgttgt tggaccattt cgcctcttgc agaaaggctt tgcacagttc 900
acgccagctt ttcgtcagat aggacaggtt gttatgacct ttctctttca gaatagaata 960
ggacgtgtcg ttaacggtgt tgtacagtgc caggaaacac agtttcatat agtccggcag 1020
ggtgttaata gcgttaacgt cccagcgctc tacagcatcg gtgaacagtt gcagttcgtc 1080
cagagtgcca taaacgtcat acacgtcatc gatgatcgtc accagaccaa acattttagt 1140
aacagctttg cgacattcac caaactgcgg gtctggcgcc atacccagtg cccagaaata 1200
aacttccatc aggcggtcgc gtacaaaatc cagtttgcta gccaggccca tctcggtcca 1260

-continued

```
ccagcgggac agatcttgca gctctttctg gtgcagggtc tgtaccatgt taaaatccag   1320
cttcgccagc tccagcagca gctggtgatg cggttctttc ggttcgtatt tatccaggaa   1380
ccaacgtgcc tccagacggt gcagacgctg gtgatatggc agttccaggg cgtggctcac   1440
ttgttctgca accttggtat taatgccttc tttcaggttg ttcttcaggt gggtgatgga   1500
aaaggtacgc gcctcctcca gcaggttctc accctcgaaa cccaggtaag acgcttcata   1560
caggctcagc aggccttgga cgtcaccttt cagttcaccg ctgaaaccac cttctttatc   1620
cttgaaacgc tcaaaaacat cctgagaaac ctcgaaaccg tgctgacgca gcagacggaa   1680
agacagagcg gttgcgtgca ggtcagattt gttctttttg ttttcgtcca gcagtacgat   1740
gttttccagg gctttaatga tgtctttttc aaatttgtag gtcagaccca ggcgctgcac   1800
atcgtcgatc agctccagca gggacagcgg ctgggtgtct acacggttga tcatgcagcg   1860
aacttcttcc tccagtttgg tcgctttctc ctccagcttt tccactttca ggtcgttctc   1920
cagggattgc aggaattcga aattccacag gtttggctga tagtttgcgg aacgacggga   1980
attatgctcg gtaatctgag taaattgaga agaggtcgca cacatatgac gaccttcgat   2040
atggccgctg ctgtgatgat gatgatgatg atgatgatga tggcccatgg tatatctcct   2100
tcttaaagtt aaacaaaatt atttctagag gggaattgtt atccgctcac aattccccta   2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280
tggggaagat cgggctcgcc acttcgggct catgagcgct tgtttcggcg tgggtatggt   2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
acgatgtcgc agagtatgcc ggtgtctctt atcagaccgt ttcccgcgtg gtgaaccagg   2640
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
ccacctccag tctggccctg cacgcgccgt cgcaaattgt cgcggcgatt aaatctcgcg   2820
ccgatcaact gggtgccagc gtggtggtgt cgatggtaga acgaagcggc gtcgaagcct   2880
gtaaagcggc ggtgcacaat cttctcgcgc aacgcgtcag tgggctgatc attaactatc   2940
cgctggatga ccaggatgcc attgctgtgg aagctgcctg cactaatgtt ccggcgttat   3000
ttcttgatgt ctctgaccag acacccatca acagtattat tttctcccat gaagacggta   3060
cgcgactggg cgtggagcat ctggtcgcat tgggtcacca gcaaatcgcg ctgttagcgg   3120
gcccattaag ttctgtctcg gcgcgtctgc gtctggctgg ctggcataaa tatctcactc   3180
gcaatcaaat tcagccgata gcggaacggg aaggcgactg gagtgccatg tccggttttc   3240
aacaaaccat gcaaatgctg aatgagggca tcgttcccac tgcgatgctg gttgccaacg   3300
atcagatggc gctgggcgca atgcgcgcca ttaccgagtc cgggctgcgc gttggtgcgg   3360
atatctcggt agtgggatac gacgataccg aagacagctc atgttatatc ccgccgttaa   3420
ccaccatcaa acaggatttt cgcctgctgg ggcaaaccag cgtggaccgc ttgctgcaac   3480
tctctcaggg ccaggcggtg aagggcaatc agctgttgcc cgtctcactg gtgaaaagaa   3540
aaaccaccct ggcgcccaat acgcaaaccg cctctccccg cgcgttggcc gattcattaa   3600
```

-continued

```
tgcagctggc acgacaggtt tcccgactgg aaagcgggca gtgagcgcaa cgcaattaat   3660
gtaagttagc tcactcatta ggcaccggga tctcgaccga tgcccttgag agccttcaac   3720
ccagtcagct ccttccggtg ggcgcggggc atgactatcg tcgccgcact tatgactgtc   3780
ttctttatca tgcaactcgt aggacaggtg ccggcagcgc tctgggtcat tttcggcgag   3840
gaccgctttc gctggagcgc gacgatgatc ggcctgtcgc ttgcggtatt cggaatcttg   3900
cacgccctcg ctcaagcctt cgtcactggt cccgccacca aacgtttcgg cgagaagcag   3960
gccattatcg ccggcatggc ggccgacgcg ctgggctacg tcttgctggc gttcgcgacg   4020
cgaggctgga tggccttccc cattatgatt cttctcgctt ccggcggcat cgggatgccc   4080
gcgttgcagg ccatgctgtc caggcaggta gatgacgacc atcagggaca gcttcaagga   4140
tcgctcgcgg ctcttaccag cctaacttcg atcactggac cgctgatcgt cacggcgatt   4200
tatgccgcct cggcgagcac atggaacggg ttggcatgga ttgtaggcgc cgccctatac   4260
cttgtctgcc tccccgcgtt gcgtcgcggt gcatggagcc gggccacctc gacctgaatg   4320
gaagccggcg gcacctcgct aacggattca ccactccaag aattggagcc aatcaattct   4380
tgcggagaac tgtgaatgcg caaaccaacc cttggcagaa catatccatc gcgtccgcca   4440
tctccagcag ccgcacgcgg cgcatctcgg gcagcgttgg gtcctggcca cgggtgcgca   4500
tgatcgtgct cctgtcgttg aggacccggc taggctggcg gggttgcctt actggttagc   4560
agaatgaatc accgatacgc gagcgaacgt gaagcgactg ctgctgcaaa acgtctgcga   4620
cctgagcaac aacatgaatg gtcttcggtt tccgtgtttc gtaaagtctg gaaacgcgga   4680
agtcagcgcc ctgcaccatt atgttccgga tctgcatcgc aggatgctgc tggctaccct   4740
gtggaacacc tacatctgta ttaacgaagc gctggcattg accctgagtg atttttctct   4800
ggtcccgccg catccatacc gccagttgtt taccctcaca acgttccagt aaccgggcat   4860
gttcatcatc agtaacccgt atcgtgagca tcctctctcg tttcatcggt atcattaccc   4920
ccatgaacag aaatccccct tacacggagg catcagtgac caaacaggaa aaaaccgccc   4980
ttaacatggc ccgctttatc agaagccaga cattaacgct tctggagaaa ctcaacgagc   5040
tggacgcgga tgaacaggca gacatctgtg aatcgcttca cgaccacgct gatgagcttt   5100
accgcagctg cctcgcgcgt ttcggtgatg acggtgaaaa cctctgacac atgcagctcc   5160
cggagacggt cacagcttgt ctgtaagcgg atgccgggag cagacaagcc cgtcagggcg   5220
cgtcagcggg tgttggcggg tgtcggggcg cagccatgac ccagtcacgt agcgatagcg   5280
gagtgtatac tggcttaact atgcggcatc agagcagatt gtactgagag tgcaccatat   5340
atgcggtgtg aaataccgca cagatgcgta aggagaaaat accgcatcag gcgctcttcc   5400
gcttcctcgc tcactgactc gctgcgctcg gtcgttcggc tgcggcgagc ggtatcagct   5460
cactcaaagg cggtaatacg gttatccaca gaatcagggg ataacgcagg aaagaacatg   5520
tgagcaaaag gccagcaaaa ggccaggaac cgtaaaaagg ccgcgttgct ggcgtttttc   5580
cataggctcc gcccccctga cgagcatcac aaaaatcgac gctcaagtca gaggtggcga   5640
aacccgacag gactataaag ataccaggcg tttccccctg gaagctccct cgtgcgctct   5700
cctgttccga ccctgccgct taccggatac ctgtccgcct ttctcccttc gggaagcgtg   5760
gcgctttctc atagctcacg ctgtaggtat ctcagttcgg tgtaggtcgt tcgctccaag   5820
ctgggctgtg tgcacgaacc ccccgttcag cccgaccgct gcgccttatc cggtaactat   5880
cgtcttgagt ccaacccggt aagacacgac ttatcgccac tggcagcagc cactggtaac   5940
aggattagca gagcgaggta tgtaggcggt gctacagagt tcttgaagtg gtggcctaac   6000
```

tacggctaca ctagaaggac agtatttggt atctgcgctc tgctgaagcc agttaccttc 6060
ggaaaaagag ttggtagctc ttgatccggc aaacaaacca ccgctggtag cggtggtttt 6120
tttgtttgca agcagcagat tacgcgcaga aaaaaaggat ctcaagaaga tcctttgatc 6180
ttttctacgg ggtctgacgc tcagtggaac gaaaactcac gttaagggat tttggtcatg 6240
agattatcaa aaaggatctt cacctagatc cttttaaatt aaaaatgaag ttttaaatca 6300
atctaaagta tatatgagta aacttggtct gacagttacc aatgcttaat cagtgaggca 6360
cctatctcag cgatctgtct atttcgttca tccatagttg cctgactccc cgtcgtgtag 6420
ataactacga tacgggaggg cttaccatct ggccccagtg ctgcaatgat accgcgagac 6480
ccacgctcac cggctccaga tttatcagca ataaaccagc cagccggaag ggccgagcgc 6540
agaagtggtc ctgcaacttt atccgcctcc atccagtcta ttaattgttg ccgggaagct 6600
agagtaagta gttcgccagt taatagtttg cgcaacgttg ttgccattgc tgcaggcatc 6660
gtggtgtcac gctcgtcgtt tggtatggct tcattcagct ccggttccca acgatcaagg 6720
cgagttacat gatcccccat gttgtgcaaa aaagcggtta gctccttcgg tcctccgatc 6780
gttgtcagaa gtaagttggc cgcagtgtta tcactcatgg ttatggcagc actgcataat 6840
tctcttactg tcatgccatc cgtaagatgc ttttctgtga ctggtgagta ctcaaccaag 6900
tcattctgag aatagtgtat gcggcgaccg agttgctctt gcccggcgtc aacacgggat 6960
aataccgcgc cacatagcag aactttaaaa gtgctcatca ttggaaaacg ttcttcgggg 7020
cgaaaactct caaggatctt accgctgttg agatccagtt cgatgtaacc cactcgtgca 7080
cccaactgat cttcagcatc ttttactttc accagcgttt ctgggtgagc aaaaacagga 7140
aggcaaaatg ccgcaaaaaa gggaataagg gcgacacgga aatgttgaat actcatactc 7200
ttcctttttc aatattattg aagcatttat cagggttatt gtctcatgag cggatacata 7260
tttgaatgta tttagaaaaa taaacaaata ggggttccgc gcacatttcc ccgaaaagtg 7320
ccacctgacg tctaagaaac cattattatc atgacattaa cctataaaaa taggcgtatc 7380
acgaggccct ttcgtcttca agaa 7404

<210> SEQ ID NO 6
<211> LENGTH: 41
<212> TYPE: DNA
<213> ORGANISM: Artificial Sequence
<220> FEATURE:
<223> OTHER INFORMATION: PCR Primer

<400> SEQUENCE: 6
catatgaaag cttgtatcga ttaaataagg aggaataaac c 41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt 60
ttcccgactg gaaagcgggc agtgagcgca acgcaattaa tgtgagttag ctcactcatt 120
aggcacccca ggctttacac tttatgcttc cggctcgtat gttgtgtgga attgtgagcg 180
gataacaatt tcacacagga aacagctatg accatgatta cgccaagctt gtatcgatta 240

-continued

```
aataaggagg aataaaccat gtgtgcgacc tcttctcaat ttactcagat taccgagcat    300
aattcccgtc gttccgcaaa ctatcagcca aacctgtgga atttcgaatt cctgcaatcc    360
ctggagaacg acctgaaagt ggaaaagctg gaggagaaag cgaccaaact ggaggaagaa    420
gttcgctgca tgatcaaccg tgtagacacc cagccgctgt ccctgctgga gctgatcgac    480
gatgtgcagc gcctgggtct gacctacaaa tttgaaaaag acatcattaa agccctggaa    540
aacatcgtac tgctggacga aaacaaaaag aacaaatctg acctgcacgc aaccgctctg    600
tctttccgtc tgctgcgtca gcacggtttc gaggtttctc aggatgtttt tgagcgtttc    660
aaggataaag aaggtggttt cagcggtgaa ctgaaaggtg acgtccaagg cctgctgagc    720
ctgtatgaag cgtcttacct gggtttcgag ggtgagaacc tgctggagga ggcgcgtacc    780
ttttccatca cccacctgaa gaacaacctg aaagaaggca ttaataccaa ggttgcagaa    840
caagtgagcc acgccctgga actgccatat caccagcgtc tgcaccgtct ggaggcacgt    900
tggttcctgg ataaatacga accgaaagaa ccgcatcacc agctgctgct ggagctggcg    960
aagctggatt ttaacatggt acagaccctg caccagaaag agctgcaaga tctgtcccgc   1020
tggtggaccg agatgggcct ggctagcaaa ctggattttg tacgcgaccg cctgatggaa   1080
gtttatttct gggcactggg tatggcgcca gacccgcagt ttggtgaatg tcgcaaagct   1140
gttactaaaa tgtttggtct ggtgacgatc atcgatgacg tgtatgacgt ttatggcact   1200
ctggacgaac tgcaactgtt caccgatgct gtagagcgct gggacgttaa cgctattaac   1260
accctgccgg actatatgaa actgtgtttc ctggcactgt acaacaccgt taacgacacg   1320
tcctattcta ttctgaaaga gaaaggtcat aacaacctgt cctatctgac gaaaagctgg   1380
cgtgaactgt gcaaagcctt tctgcaagag gcgaaatggt ccaacaacaa aattatcccg   1440
gctttctcca agtacctgga aaacgccagc gtttcctcct ccggtgtagc gctgctggcg   1500
ccgtcttact tttccgtatg ccagcagcag gaagacatct ccgaccacgc gctgcgttcc   1560
ctgaccgact tccatggtct ggtgcgttct agctgcgtta tcttccgcct gtgcaacgat   1620
ctggccacct ctgcggcgga gctggaacgt ggcgagacta ccaattctat cattagctac   1680
atgcacgaaa acgatggtac cagcgaggaa caggcccgcg aagaactgcg taaactgatc   1740
gacgccgaat ggaaaaagat gaatcgtgaa cgcgttagcg actccaccct gctgcctaaa   1800
gcgttcatgg aaatcgcagt taacatggca cgtgtttccc actgcaccta ccagtatggc   1860
gatggtctgg gtcgcccaga ctacgcgact gaaaaccgca tcaaactgct gctgattgac   1920
cctttcccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg gcgtcggctt   2520
gaacgaattg ttagacatta tttgccgact accttggtga tctcgccttt cacgtagtgg   2580
acaaattctt ccaactgatc tgcgcgcgag gccaagcgat cttcttcttg tccaagataa   2640
```

-continued gcctgtctag cttcaagtat gacgggctga tactgggccg gcaggcgctc cattgcccag 2700
tcggcagcga catccttcgg cgcgattttg ccggttactg cgctgtacca aatgcgggac 2760
aacgtaagca ctacatttcg ctcatcgcca gcccagtcgg gcggcgagtt ccatagcgtt 2820
aaggtttcat ttagcgcctc aaatagatcc tgttcaggaa ccggatcaaa gagttcctcc 2880
gccgctggac ctaccaaggc aacgctatgt tctcttgctt ttgtcagcaa gatagccaga 2940
tcaatgtcga tcgtggctgg ctcgaagata cctgcaagaa tgtcattgcg ctgccattct 3000
ccaaattgca gttcgcgctt agctggataa cgccacggaa tgatgtcgtc gtgcacaaca 3060
atggtgactt ctacagcgcg gagaatctcg ctctctccag gggaagccga agtttccaaa 3120
aggtcgttga tcaaagctcg ccgcgttgtt tcatcaagcc ttacggtcac cgtaaccagc 3180
aaatcaatat cactgtgtgg cttcaggccg ccatccactg cggagccgta caaatgtacg 3240
gccagcaacg tcggttcgag atggcgctcg atgacgccaa ctacctctga tagttgagtc 3300
gatacttcgg cgatcaccgc ttccctcatg atgtttaact ttgttttagg gcgactgccc 3360
tgctgcgtaa catcgttgct gctccataac atcaaacatc gacccacggc gtaacgcgct 3420
tgctgcttgg atgcccgagg catagactgt accccaaaaa aacagtcata acaagccatg 3480
aaaaccgcca ctgcgccgtt accaccgctg cgttcggtca aggttctgga ccagttgcgt 3540
gagcgcatac gctacttgca ttacagctta cgaaccgaac aggcttatgt ccactgggtt 3600
cgtgccttca tccgtttcca cggtgtgcgt cacccggcaa ccttgggcag cagcgaagtc 3660
gaggcatttc tgtcctggct ggcgaacgag cgcaaggttt cggtctccac gcatcgtcag 3720
gcattggcgg ccttgctgtt cttctacggc aaggtgctgt gcacggatct gccctggctt 3780
caggagatcg gaagacctcg gccgtcgcgg cgcttgccgg tggtgctgac cccggatgaa 3840
gtggttcgca tcctcggttt tctggaaggc gagcatcgtt tgttcgccca gcttctgtat 3900
ggaacgggca tgcggatcag tgagggtttg caactgcggg tcaaggatct ggatttcgat 3960
cacggcacga tcatcgtgcg ggagggcaag ggctccaagg atcgggcctt gatgttaccc 4020
gagagcttgg cacccagcct gcgcgagcag gggaattaat tcccacgggt tttgctgccc 4080
gcaaacgggc tgttctggtg ttgctagttt gttatcagaa tcgcagatcc ggcttcagcc 4140
ggtttgccgg ctgaaagcgc tatttcttcc agaattgcca tgattttttc cccacgggag 4200
gcgtcactgg ctcccgtgtt gtcggcagct ttgattcgat aagcagcatc gcctgtttca 4260
ggctgtctat gtgtgactgt tgagctgtaa caagttgtct caggtgttca atttcatgtt 4320
ctagttgctt tgttttactg gtttcacctg ttctattagg tgttacatgc tgttcatctg 4380
ttacattgtc gatctgttca tggtgaacag ctttgaatgc accaaaaact cgtaaaagct 4440
ctgatgtatc tatctttttt acaccgtttt catctgtgca tatggacagt tttccctttg 4500
atatgtaacg gtgaacagtt gttctacttt tgtttgttag tcttgatgct tcactgatag 4560
atacaagagc cataagaacc tcagatcctt ccgtatttag ccagtatgtt ctctagtgtg 4620
gttcgttgtt tttgcgtgag ccatgagaac gaaccattga gatcatactt actttgcatg 4680
tcactcaaaa attttgcctc aaaactggtg agctgaattt ttgcagttaa agcatcgtgt 4740
agtgtttttc ttagtccgtt atgtaggtag gaatctgatg taatggttgt tggtattttg 4800
tcaccattca tttttatctg gttgttctca agttcggtta cgagatccat ttgtctatct 4860
agttcaactt ggaaaatcaa cgtatcagtc gggcggcctc gcttatcaac caccaatttc 4920
atattgctgt aagtgtttaa atctttactt attggtttca aaacccattg gttaagcctt 4980
ttaaactcat ggtagttatt ttcaagcatt aacatgaact taaattcatc aaggctaatc 5040
tctatatttg ccttgtgagt tttcttttgt gttagttctt ttaataacca ctcataaatc 5100
ctcatagagt atttgttttc aaaagactta acatgttcca gattatattt tatgaatttt 5160
tttaactgga aaagataagg caatatctct tcactaaaaa ctaattctaa tttttcgctt 5220
gagaacttgg catagtttgt ccactggaaa atctcaaagc ctttaaccaa aggattcctg 5280
atttccacag ttctcgtcat cagctctctg gttgctttag ctaatacacc ataagcattt 5340
tccctactga tgttcatcat ctgagcgtat tggttataag tgaacgatac cgtccgttct 5400
ttccttgtag ggttttcaat cgtggggttg agtagtgcca cacagcataa aattagcttg 5460
gtttcatgct ccgttaagtc atagcgacta atcgctagtt catttgcttt gaaaacaact 5520
aattcagaca tacatctcaa ttggtctagg tgattttaat cactatacca attgagatgg 5580
gctagtcaat gataattact agtccttttc ctttgagttg tgggtatctg taaattctgc 5640
tagacctttg ctggaaaact tgtaaattct gctagaccct ctgtaaattc cgctagacct 5700
ttgtgtgttt tttttgttta tattcaagtg gttataattt atagaataaa gaaagaataa 5760
aaaaagataa aaagaataga tcccagccct gtgtataact cactacttta gtcagttccg 5820
cagtattaca aaaggatgtc gcaaacgctg tttgctcctc tacaaaacag accttaaaac 5880
cctaaaggct taagtagcac cctcgcaagc tcgggcaaat cgctgaatat tccttttgtc 5940
tccgaccatc aggcacctga gtcgctgtct ttttcgtgac attcagttcg ctgcgctcac 6000
ggctctggca gtgaatgggg gtaaatggca ctacaggcgc cttttatgga ttcatgcaag 6060
gaaactaccc ataatacaag aaaagcccgt cacgggcttc tcagggcgtt ttatggcggg 6120
tctgctatgt ggtgctatct gactttttgc tgttcagcag ttcctgccct ctgattttcc 6180
agtctgacca cttcggatta tcccgtgaca ggtcattcag actggctaat gcacccagta 6240
aggcagcggt atcatcaaca ggctta 6266

<210> SEQ ID NO 8
<211> LENGTH: 1695
<212> TYPE: DNA
<213> ORGANISM: Yarrowia lipolytica

<400> SEQUENCE: 8
atgtgtgcaa cctcctccca gtttactcag attaccgagc ataattctcg acgatctgct 60
aactaccagc cgaacctttg gaactttgag tttctccagt ctctcgaaaa tgacctgaag 120
gtggaaaagc tcgaggagaa ggcgaccaaa ctcgaggagg aggtgcgatg tatgatcaac 180
agagttgaca cccaacccct gtctttgctg gagctgatcg acgatgtgca gcggttgggt 240
ttgacttata aattcgagaa ggacattatc aaggcactgg agaacattgt gctcctcgac 300
gagaacaaga agaacaagtc tgatcttcac gctaccgctc tctctttccg acttcttcga 360
caacacggct tcgaggtgtc gcaggacgtc ttcgagagat ttaaggacaa ggagggagga 420
tttagcggcg agctgaaggg agacgttcag ggtcttctct ccttgtacga ggcgtcctac 480
ctgggattcg agggagagaa cctcctggag gaagctcgta cattttccat cactcacctt 540
aagaataacc ttaaggaggg aattaacacc aaggtggccg agcaggtttc tcacgccctg 600
gagctcccct accaccaacg gctccataga ctggaggctc gttggttcct ggacaaatat 660
gagccaaagg agcctcatca tcagttgctg ttggagttgg ccaagctgga cttcaatatg 720
gttcagacgc tgcaccaaaa ggagttgcag gacctgtctc gatggtggac cgagatggga 780
ttggcctcga agctggattt tgtccgtgac cgacttatgg aggtctattt ttgggccctt 840
ggaatggcgc ctgaccccca gttcggagag tgccggaagg cggtgacgaa gatgttcggt 900
cttgtgacta tcatcgacga cgtctacgat gtctacggca cactcgacga gttgcagctg 960
ttcactgacg ccgtcgagcg atgggatgtg aacgccatta atactctccc tgactatatg 1020
aagctgtgct tcctggctct gtacaacact gtcaacgata cctcgtactc tatcctcaag 1080
gagaagggac acaacaatct ctcctacttg accaaatcct ggcgagaact gtgcaaggct 1140
tttctgcagg aggctaaatg gtccaataac aagatcattc ctgctttttc taaatacctg 1200
gaaaatgcct cggtgtcgag ctctggcgtc gcccttctgg ccccttccta cttctccgtc 1260
tgccagcagc aggaggatat ttccgatcat gctcttagat cgctgaccga ttttcacggc 1320
ctcgtgcgat cttcctgcgt gatttttcgg ttgtgtaatg accttgcgac ctctgctgct 1380
gagctggaac gaggcgagac tacaaattcc attatttctt acatgcacga aaacgatgga 1440
acatctgaag aacaggctag agaggaactg cgaaagttga tcgacgccga gtggaagaag 1500
atgaacagag agcgggtgtc cgactctacc ctgcttccca aggccttcat ggagatcgcc 1560
gtgaacatgg ctcgagtttc ccattgtact taccagtacg gtgacggcct gggtcgtccg 1620
gactacgcta cagagaaccg aatcaagctg ctgctcatcg accccttccc tatcaaccaa 1680
ttgatgtacg tgtaa 1695

<210> SEQ ID NO 9
<211> LENGTH: 40
<212> TYPE: DNA
<213> ORGANISM: Artificial Sequence
<220> FEATURE:
<223> OTHER INFORMATION: PCR Primer

<400> SEQUENCE: 9
gcttatggat cctctagact attacacgta catcaattgg 40

<210> SEQ ID NO 10
<211> LENGTH: 30
<212> TYPE: DNA
<213> ORGANISM: Artificial Sequence
<220> FEATURE:
<223> OTHER INFORMATION: PCR Primer

<400> SEQUENCE: 10
caccatgtgt gcaacctcct cccagtttac 30

<210> SEQ ID NO 11
<211> LENGTH: 8190
<212> TYPE: DNA
<213> ORGANISM: Artificial Sequence
<220> FEATURE:
<223> OTHER INFORMATION: Synthetic Construct

<400> SEQUENCE: 11
tcgaccggtg agaagaacag catcgggaca agggaaggaa gaacaaagac aaagaaaaca 60
aaagaaagca attgaaaaca aaacaaaaca attttcattc cttctcttat cattcctttt 120
cttttctttt ctctcattca acgcactcca tcgtatccgt attcctctta ttttttctct 180
ttctctatat ccatttcttt ctctctaggt gtgtcctctc tctctcttca atttctctac 240
tccgcattcc aacgcatcct tcccccaacc tcccatttcc tccttacggc ccgatagcga 300
tcgtctttcc ctcgctatca ctcgctaccg gcccctcctc tgcaccgtaa cctcctacgt 360
atttaccata tcataaagtt ttttccgacg cttatcgctg accccctgtc gccctcctat 420

-continued

```
tggcttccgg attatcttct tgtccataag gtgatccatg cttcctgaag attcccgaaa    480
tgtgtccact ttggcgggga atcattccat ccacttcttt ctctctcgct ttcctcattc    540
ggcgctcccc ttccgcgtct cattggtctt ccgctccgtt tttgctttgc cgatgttact    600
tggggagagg tgcgataatc ctttcgcaaa aactcggttt gacgcctccc atggtataaa    660
tagtgggtgg tggacaggtg ccttcgcttt tctttaagca agagaatccc attgtcttga    720
ctatcacgaa ttcacataca ttatgaagat caccgctgtc attgcccttt tattctcact    780
tgctgctgcc tcacctattc cagttgccga tcctggtgtg gtttcagtta gcaagtcata    840
tgctgatttc cttcgtgttt accaaagttg gaacactttt gctaatcctg atagacccaa    900
ccttaagaag agaaatgata cacctgcaag tggatatcaa gttgaaaaag tcgtaatttt    960
gtcacgtcac ggtgttaggg cccctacaaa aatgactcaa accatgcgtg atgtcactcc   1020
taatacatgg ccagaatggc ccgttaaatt aggatatatt acaccaagag gtgaacactt   1080
gatatcactt atgggcggtt tttaccgtca aaaattccag caacaaggaa tcctttctca   1140
gggctcctgt cctactccta actccatata tgtctgggct gacgtcgatc agcgtacttt   1200
aaaaactggt gaagcattcc ttgctggttt ggcaccacaa tgtggcttga caattcatca   1260
ccaacaaaat cttgagaaag ctgatcctct ttttcatccc gttaaagctg gaacctgctc   1320
tatggataaa actcaagttc aacaagctgt tgagaaggag gcacaaactc ctatagataa   1380
tttgaatcaa cattacatcc cctttttagc tttaatgaat acaacattaa attttagtac   1440
ttctgcctgg tgccaaaaac actctgctga taaatcctgt gacctaggtt tatccatgcc   1500
ttctaaattg tccataaaag ataatggtaa caaggtcgca ttggatggag ctattggtct   1560
atcctctact ttggccgaga tttttcttct tgaatatgct caaggcatgc ctcaagctgc   1620
ttggggtaac atccactcag agcaagagtg ggcttccttg ctaaagttgc ataatgttca   1680
attcgatttg atggcccgaa caccttatat tgctcgacat aacggtactc ctttattgca   1740
agctatatca aatgccctta atcccaacgc cactgaatca aaacttccag atatttcacc   1800
tgataacaaa atattgttca ttgcaggtca tgacacaaat attgctaata tagccggcat   1860
gttaaatatg cgttggacat taccaggtca accagataat actcctccag gtggtgccct   1920
agtatttgaa cgtcttgctg ataaaagtgg aaaacaatat gtttctgtat ctatggttta   1980
tcaaacacta gaacaacttc gatcacagac tccccttttct ctaaatcagc ctgccggatc  2040
tgttcaactt aaaattccag gttgcaatga tcaaacagcc gagggttact gtcctctttc   2100
cacttttaca agagttgttt cccaatctgt tgaacctgga tgccaacttc aataatgagg   2160
atccaagtaa gggaatgaga atgtgatcca cttttaattc ctaatgaata catgcctata   2220
gttcttttct tttgttcttt atgtcgtttt tcgatggtac ggccgttgtc aatctcagtt   2280
tgtgtgcttg gttgcagctt ggtttcaaat ctgttcatct catgaatctt ttaccatttc   2340
accacacgtt tataccattc tctcatagaa tcttcatcaa accatctcgg ggttagagtg   2400
gaaagaaagt cttgttcttt tatttccttt tttccatctt caaggctttt cttttcttcc   2460
tcctcctcgt tcatcttgag gtttgacgtg tctgtttaga attttgagct gttgcagcat   2520
cttatttttt gttttgcgaa aacgaagcgc tttactctct tcatcagttg gacgattgta   2580
cctttgaaaa ccaactactt ttgcatgttt tgtatagaaa tcaatgatat tagaatccca   2640
tcctttaatt tctttcaaag tagttgagct atagttaagt gtaagggccc tactgcgaaa   2700
gcatttgcca aggatgtttt cattaatcaa gaacgaaagt taggggatcg aagacgatca   2760
gataccgtcg tagtcttaac cataaactat gccgactagg gatcgggcaa tgtttcattt   2820
```

-continued

```
atcgacttgc tcggcacctt acgagaaatc aaagtctttg ggttccgggg ggagtatggt   2880
cgcaaggctg aaacttaaag gaattgacgg aagggcacca caatggagtg gagcctgcgg   2940
cttaatttga ctcaacacgg ggaaactcac caggtccaga catagtaagg attgacagat   3000
tgagagctct ttcttgattc tatgggtggt ggtgcatggc cgttcttagt tggtggagtg   3060
atttgtctgc ttaattgcga taacgaacga gaccttaacc tgctaaatag ctggatcagc   3120
cattttggct gatcattagc ttcttagagg gactattggc ataaagccaa tggaagtttg   3180
aggcaataac aggtctgtga tgcccttaga tgttctgggc cgcacgcgcg ctacactgac   3240
ggagccaacg agttgaaaaa aatcttttga tttttttatcc ttggccggaa ggtctgggta   3300
atcttgttaa actccgtcgt gctggggata gagcattgca attattgcgg ccgctcctca   3360
attcgatgtt gcagatttta caagttttta aaatgtattt cattattact ttttatatgc   3420
ctaataaaaa agccatagtt taatctatag ataacttttt ttccagtgca ctaacggacg   3480
ttacattccc atacaaaact gcgtagttaa agctaaggaa aagttaatat catgttaatt   3540
aaatacgcta tttacaataa gacattgaac tcatttatat cgttgaatat gaataaccaa   3600
tttcagcgaa tttttaacaa acatcgttca cctcgtttaa ggatatcttg tgtatggggt   3660
gttgacttgc tttatcgaat aattaccgta cctgtaattg gcttgctgga tatagcggta   3720
gtctaatatc tagcaaaaat cttttgggtg aaaaggcttg caatttcacg acaccgaact   3780
atttgtcatt ttttaataag gaagttttcc ataaattcct gtaattctcg gttgatctaa   3840
ttgaaaagag tagttttgca tcacgatgag gagggctttt gtagaaagaa atacgaacga   3900
aacgaaaatc agcgttgcca tcgctttgga caaagctccc ttacctgaag agtcgaattt   3960
tattgatgaa cttataactt ccaagcatgc aaaccaaaag ggagaacaag taatccaagt   4020
agacacggga attggattct tggatcacat gtatcatgca ctggctaaac atgcaggctg   4080
gagcttacga ctttactcaa gaggtgattt aatcatcgat gatcatcaca ctgcagaaga   4140
tactgctatt gcacttggta ttgcattcaa gcaggctatg ggtaactttg ccggcgttaa   4200
aagatttgga catgcttatt gtccacttga cgaagctctt tctagaagcg tagttgactt   4260
gtcgggacgg ccctatgctg ttatcgattt gggattaaag cgtgaaaagg ttggggaatt   4320
gtcctgtgaa atgatccctc acttactata ttcctttcg gtagcagctg gaattacttt   4380
gcatgttacc tgcttatatg gtagtaatga ccatcatcgt gctgaaagcg cttttaaatc   4440
tctggctgtt gccatgcgcg cggctactag tcttactgga agttctgaag tcccaagcac   4500
gaagggagtg ttgtaaagat gaattggatt atgtcaggaa aagaacgaca attttgcatc   4560
caaattgtct aaattttaga gttgcttgaa aacaatagaa ccttacttgc tttataatta   4620
cgttaattag aagcgttatc tcgtgaagga atatagtacg tagccgtata aattgaattg   4680
aatgttcagc ttatagaata gagacacttt gctgttcaat gcgtcgtcac ttaccatact   4740
cactttatta tacgacttta agtataaact ccgcggttat ggtaaaatta atgatgcaca   4800
aacgtccgat tccatatggg tacactacaa ttaaatactt ttaagctgat cccccacaca   4860
ccatagcttc aaaatgtttc tactcctttt ttactcttcc agattttctc ggactccgcg   4920
catcgccgta ccacttcaaa acacccaagc acagcatact aaattttccc tctttcttcc   4980
tctagggtgt cgttaattac ccgtactaaa ggtttggaaa agaaaaaaga gaccgcctcg   5040
tttcttttc ttcgtcgaaa aaggcaataa aaatttttat cacgtttctt tttcttgaaa   5100
ttttttttt tagtttttt ctctttcagt gacctccatt gatatttaag ttaataaacg   5160
```

-continued

```
gtcttcaatt tctcaagttt cagtttcatt tttcttgttc tattacaact ttttttactt   5220
cttgttcatt agaaagaaag catagcaatc taatctaagg gcggtgttga caattaatca   5280
tcggcatagt atatcggcat agtataatac gacaaggtga ggaactaaac catggccaag   5340
ttgaccagtg ccgttccggt gctcaccgcg cgcgacgtcg ccggagcggt cgagttctgg   5400
accgaccggc tcgggttctc ccgggacttc gtggaggacg acttcgccgg tgtggtccgg   5460
gacgacgtga ccctgttcat cagcgcggtc caggaccagg tggtgccgga caacaccctg   5520
gcctgggtgt gggtgcgcgg cctggacgag ctgtacgccg agtggtcgga ggtcgtgtcc   5580
acgaacttcc gggacgcctc cgggccggcc atgaccgaga tcggcgagca gccgtggggg   5640
cgggagttcg ccctgcgcga cccggccggc aactgcgtgc acttcgtggc cgaggagcag   5700
gactgacacg tccgacggcg gcccacgggt cccaggcctc ggagatccgt ccccctttc    5760
ctttgtcgat atcatgtaat tagttatgtc acgcttacat tcacgccctc cccccacatc   5820
cgctctaacc gaaaaggaag gagttagaca acctgaagtc taggtcccta tttatttttt   5880
tatagttatg ttagtattaa gaacgttatt tatatttcaa atttttcttt tttttctgta   5940
cagacgcgag cttcccagta aatgtgccat ctcgtaggca gaaaacggtt cccccgtagg   6000
gtctctctct tggcctcctt tctaggtcgg gctgattgct cttgaagctc tctagggggg   6060
ctcacaccat aggcagataa cgttccccac cggctcgcct cgtaagcgca caaggactgc   6120
tcccaaagat cctaggcggg attttgccga tttcggccta aaggaaccgg aacacgtaga   6180
aagccagtcc gcagaaacgg tgctgacccc ggatgaatgt cagctactgg gctatctgga   6240
caagggaaaa cgcaagcgca aagagaaagc aggtagcttg cagtgggctt acatggcgat   6300
agctagactg ggcggtttta tggacagcaa gcgaaccgga attgccagct ggggcgccct   6360
ctggtaaggt tgggaagccc tgcaaagtaa actggatggc tttcttgccg ccaaggatct   6420
gatggcgcag gggatcaaga tctgatcaag agacaggatg aggatcgttt cgcatgattg   6480
aacaagatgg attgcacgca ggttctccgg ccgcttgggt ggagaggcta ttcggctatg   6540
actgggcaca acagacaatc ggctgctctg atgccgccgt gttccggctg tcagcgcagg   6600
ggcgcccggt tctttttgtc aagaccgacc tgtccggtgc cctgaatgaa ctgcaggacg   6660
aggcagcgcg gctatcgtgg ctggccacga cgggcgttcc ttgcgcagct gtgctcgacg   6720
ttgtcactga agcgggaagg gactggctgc tattgggcga agtgccgggg caggatctcc   6780
tgtcatctcg ccttgctcct gccgagaaag tatccatcat ggctgatgca atgcggcggc   6840
tgcatacgct tgatccggct acctgcccat tcgaccacca agcgaaacat cgcatcgagc   6900
gagcacgtac tcggatggaa gccggtcttg tcgatcagga tgatctggac gaagagcatc   6960
aggggctcgc gccagccgaa ctgttcgcca ggctcaaggc gcgcatgccc gacggcgagg   7020
atctcgtcgt gatccatggc gatgcctgct tgccgaatat catggtggaa aatggccgct   7080
tttctggatt caacgactgt ggccggctgg gtgtggcgga ccgctatcag gacatagcgt   7140
tggatacccg tgatattgct gaagagcttg gcggcgaatg ggctgaccgc ttcctcgtgc   7200
tttacggtat cgccgctccc gattcgcagc gcatcgcctt ctatcgcctt cttgacgagt   7260
tcttctgaat tgaaaaaggt accaagttta ctcatatata ctttagattg atttaaaact   7320
tcatttttaa tttaaaagga tctaggtgaa gatccttttt gataatctca tgaccaaaat   7380
cccttaacgt gagttttcgt tccactgagc gtcagacccc gtagaaaaga tcaaaggatc   7440
ttcttgagat cctttttttc tgcgcgtaat ctgctgcttg caaacaaaaa aaccaccgct   7500
accagcggtg gtttgtttgc cggatcaaga gctaccaact ctttttccga aggtaactgg   7560
```

```
cttcagcaga gcgcagatac caaatactgt ccttctagtg tagccgtagt taggccacca   7620

cttcaagaac tctgtagcac cgcctacata cctcgctctg ctaatcctgt taccagtggc   7680

tgctgccagt ggcgataagt cgtgtcttac cgggttggac tcaagacgat agttaccgga   7740

taaggcgcag cggtcgggct gaacgggggg ttcgtgcaca cagcccagct tggagcgaac   7800

gacctacacc gaactgagat acctacagcg tgagcattga gaaagcgcca cgcttcccga   7860

agggagaaag gcggacaggt atccggtaag cggcagggtc ggaacaggag agcgcacgag   7920

ggagcttcca gggggaaacg cctggtatct ttatagtcct gtcgggtttc gccacctctg   7980

acttgagcgt cgatttttgt gatgctcgtc aggggggcgg agcctatgga aaaacgccag   8040

caacgcggcc tttttacggt tcctggcctt ttgctggcct tttgctcaca tgttctttcc   8100

tgcgttatcc cctgattctg tggataaccg tattaccgcc tttgagtgag ctgataccgc   8160

tcgccgcagc cgaacgaccg agcgcagcga                                    8190
```

<210> SEQ ID NO 12
<211> LENGTH: 1724
<212> TYPE: DNA
<213> ORGANISM: Yarrowia lipolytica

<400> SEQUENCE: 12

```
gaattcaaaa caaaatgtgt gcaacctcct cccagtttac tcagattacc gagcataatt     60

ctcgacgatc tgctaactac cagccgaacc tttggaactt tgagtttctc cagtctctcg    120

aaaatgacct gaaggtggaa aagctcgagg agaaggcgac caaactcgag gaggaggtgc    180

gatgtatgat caacagagtt gacacccaac ccctgtcttt gctggagctg atcgacgatg    240

tgcagcggtt gggtttgact tataaattcg agaaggacat tatcaaggca ctggagaaca    300

ttgtgctcct cgacgagaac aagaagaaca agtctgatct tcacgctacc gctctctctt    360

tccgacttct tcgacaacac ggcttcgagg tgtcgcagga cgtcttcgag agatttaagg    420

acaaggaggg aggatttagc ggcgagctga agggagacgt tcagggtctt ctctccttgt    480

acgaggcgtc ctacctggga ttcgagggag agaacctcct ggaggaagct cgtacatttt    540

ccatcactca ccttaagaat aaccttaagg agggaattaa caccaaggtg gccgagcagg    600

tttctcacgc cctggagctc ccctaccacc aacggctcca tagactggag gctcgttggt    660

tcctggacaa atatgagcca aaggagcctc atcatcagtt gctgttggag ttggccaagc    720

tggacttcaa tatggttcag acgctgcacc aaaaggagtt gcaggacctg tctcgatggt    780

ggaccgagat gggattggcc tcgaagctgg attttgtccg tgaccgactt atggaggtct    840

atttttgggc ccttggaatg gcgcctgacc cccagttcgg agagtgccgg aaggcggtga    900

cgaagatgtt cggtcttgtg actatcatcg acgacgtcta cgatgtctac ggcacactcg    960

acgagttgca gctgttcact gacgccgtcg agcgatggga tgtgaacgcc attaatactc   1020

tccctgacta tatgaagctg tgcttcctgg ctctgtacaa cactgtcaac gatacctcgt   1080

actctatcct caaggagaag ggacacaaca atctctccta cttgaccaaa tcctggcgag   1140

aactgtgcaa ggcttttctg caggaggcta aatggtccaa taacaagatc attcctgctt   1200

tttctaaata cctggaaaat gcctcggtgt cgagctctgg cgtcgccctt ctggcccctt   1260

cctacttctc cgtctgccag cagcaggagg atatttccga tcatgctctt agatcgctga   1320

ccgattttca cggcctcgtg cgatcttcct gcgtgatttt tcggttgtgt aatgaccttg   1380

cgacctctgc tgctgagctg gaacgaggcg agactacaaa ttccattatt tcttacatgc   1440
```

```
acgaaaacga tggaacatct gaagaacagg ctagagagga actgcgaaag ttgatcgacg   1500

ccgagtggaa gaagatgaac agagagcggg tgtccgactc taccctgctt cccaaggcct   1560

tcatggagat cgccgtgaac atggctcgag tttcccattg tacttaccag tacggtgacg   1620

gcctgggtcg tccggactac gctacagaga accgaatcaa gctgctgctc atcgacccct   1680

tccctatcaa ccaattgatg tacgtgtaat agtctagagg atcc                    1724


<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

gaattcaaca aaaatgtgct ctgtttccac tgagaacgtg tcctttactg agactgagac     60

tgaagcacgt agaagcgcca actacgaacc caactcctgg gattatgact ttctgctgtc    120

ttctgacacc gacgagtcga tcgaggttta taaggataag gccaagaaac ttgaggccga    180

ggtcagacga gagattaaca acgagaaggc cgagttcctg acccttcttg agctgatcga    240

caacgttcaa cgacttggtc ttggttaccg tttcgaatcc gatatccgac gtgcattgga    300

tcgatttgtc tcgtccggag gtttcgatgg tgtgactaag acgtcgctgc acgccacagc    360

tctttccttc agactgttgc ggcagcatgg atttgaggtt tcccaggaag ccttttctgg    420

tttcaaggat cagaacggaa actttttgga gaatctcaag gaggacacca aggccatcct    480

gtcgttgtat gaggcctcgt tcctggctct tgagggcgag aatattctgg atgaggctcg    540

ggttttcgct atttcgcacc tgaaggagtt gtcggaggaa aagatcggaa aggaactggc    600

cgagcaggtc aaccatgcac ttgaacttcc cctgcatcga cgtacccagc gactggaggc    660

cgtgtggagc atcgaggcgt acagaaaaaa ggaggatgct aatcaggttc tgctcgaact    720

cgctatcctc gactataaca tgattcagag cgtgtaccag cgtgacttgc gagagacaag    780

ccggtggtgg cgacgggtgg gactggccac gaagctccac tttgctaaag atcgattgat    840

tgagtcgttc tactgggcag tgggtgtggc ctttgagcct cagtactccg actgccgaaa    900

ctccgttgca aagatgtttt cttttgtcac tatcatcgac gacatctacg atgtttacgg    960

cactctcgat gaactcgaac tcttcacgga cgctgtcgag cgatgggatg tgaatgccat   1020

taatgatctg ccagattata tgaagttgtg tttcttggcg ctctacaaca caattaatga   1080

aattgcctac gacaacctca aggacaaggg agagaacatt ctgccctacc ttactaaagc   1140

ctgggccgac ctgtgtaacg cctttttgca ggaagccaag tggctctata acaaatctac   1200

tcctacattt gatgactact tcggcaacgc ttggaagtct tccagcggcc ctctccagtt   1260

gatcttcgct tactttgcag tggtccagaa catcaagaaa gaggagattg agaacctcca   1320

gaagtatcac gacatcatct cccgaccttc gcacatcttt cgactgtgca atgaccttgc   1380

ctccgcatcc gctgagattg cccgaggaga aacagccaat tctgtgtcgt gttacatgcg   1440

tacaaagggc atctccgagg agctggctac cgagtctgtg atgaacctga tcgatgaaac   1500

ctgtaagaag atgaacaaag agaaactggg cggttctctg ttcgccaaac catttgttga   1560

aaccgcgatc aatctggctc gtcagtctca ttgtacttac cataacggtg acgcgcacac   1620

ttcgccggac gaattgaccc gtaagcgtgt gctttcggtg attaccgagc cgatcctgcc   1680

gttcgaaaga taataggatc c                                             1701
```

<210> SEQ ID NO 14
<211> LENGTH: 28
<212> TYPE: DNA
<213> ORGANISM: Artificial Sequence
<220> FEATURE:
<223> OTHER INFORMATION: PCR Primer

<400> SEQUENCE: 14
gatcaagctt aaccggaatt gccagctg 28

<210> SEQ ID NO 15
<211> LENGTH: 33
<212> TYPE: DNA
<213> ORGANISM: Artificial Sequence
<220> FEATURE:
<223> OTHER INFORMATION: PCR Primer

<400> SEQUENCE: 15
gatccgatcg tcagaagaac tcgtcaagaa ggc 33

<210> SEQ ID NO 16
<211> LENGTH: 38
<212> TYPE: DNA
<213> ORGANISM: Artificial Sequence
<220> FEATURE:
<223> OTHER INFORMATION: PCR Primer

<400> SEQUENCE: 16
catcaatgca tcgcccttag gaggtaaaaa aaaatgac 38

<210> SEQ ID NO 17
<211> LENGTH: 26
<212> TYPE: DNA
<213> ORGANISM: Artificial Sequence
<220> FEATURE:
<223> OTHER INFORMATION: PCR Primer

<400> SEQUENCE: 17
ccttctgcag gacgcgttgt tatagc 26

<210> SEQ ID NO 18
<211> LENGTH: 60
<212> TYPE: DNA
<213> ORGANISM: Artificial Sequence
<220> FEATURE:
<223> OTHER INFORMATION: PCR Primer

<400> SEQUENCE: 18
gatcatgcat tcgcccttag gaggtaaaaa aacatgagtt ttgatattgc caaatacccg 60

<210> SEQ ID NO 19
<211> LENGTH: 31
<212> TYPE: DNA
<213> ORGANISM: Artificial Sequence
<220> FEATURE:
<223> OTHER INFORMATION: PCR Primer

<400> SEQUENCE: 19
catgctgcag ttatgccagc caggccttga t 31

<210> SEQ ID NO 20
<211> LENGTH: 8803
<212> TYPE: DNA
<213> ORGANISM: Artificial Sequence
<220> FEATURE:
<223> OTHER INFORMATION: Synthetic Construct

<400> SEQUENCE: 20

```
gctggtacca tatgggaatt cgaagctttc tagaacaaaa actcatctca gaagaggatc     60
tgaatagcgc cgtcgaccat catcatcatc atcattgagt ttaaacggtc tccagcttgg    120
ctgttttggc ggatgagaga agattttcag cctgatacag attaaatcag aacgcagaag    180
cggtctgata aaacagaatt tgcctggcgg cagtagcgcg gtggtcccac ctgaccccat    240
gccgaactca gaagtgaaac gccgtagcgc cgatggtagt gtggggtctc cccatgcgag    300
agtagggaac tgccaggcat caaataaaac gaaaggctca gtcgaaagac tgggcctttc    360
gttttatctg ttgtttgtcg gtgaacgctc tcctgagtag gacaaatccg ccgggagcgg    420
atttgaacgt tgcgaagcaa cggcccggag ggtggcgggc aggacgcccg ccataaactg    480
ccaggcatca aattaagcag aaggccatcc tgacggatgg cctttttgcg tttctacaaa    540
ctctttttgt ttatttttct aaatacattc aaatatgtat ccgcttaacc ggaattgcca    600
gctggggcgc cctctggtaa ggttgggaag ccctgcaaag taaactggat ggctttctcg    660
ccgccaagga tctgatggcg caggggatca agctctgatc aagagacagg atgaggatcg    720
tttcgcatga ttgaacaaga tggattgcac gcaggttctc cggccgcttg ggtggagagg    780
ctattcggct atgactgggc acaacagaca atcggctgct ctgatgccgc cgtgttccgg    840
ctgtcagcgc aggggcgccc ggttcttttt gtcaagaccg acctgtccgg tgccctgaat    900
gaactgcaag acgaggcagc gcggctatcg tggctggcca cgacgggcgt tccttgcgca    960
gctgtgctcg acgttgtcac tgaagcggga agggactggc tgctattggg cgaagtgccg   1020
gggcaggatc tcctgtcatc tcaccttgct cctgccgaga aagtatccat catggctgat   1080
gcaatgcggc ggctgcatac gcttgatccg gctacctgcc cattcgacca ccaagcgaaa   1140
catcgcatcg agcgagcacg tactcggatg gaagccggtc ttgtcgatca ggatgatctg   1200
gacgaagagc atcaggggct cgcgccagcc gaactgttcg ccaggctcaa ggcgagcatg   1260
cccgacggcg aggatctcgt cgtgacccat ggcgatgcct gcttgccgaa tatcatggtg   1320
gaaaatggcc gcttttctgg attcatcgac tgtggccggc tgggtgtggc ggaccgctat   1380
caggacatag cgttggctac ccgtgatatt gctgaagagc ttggcggcga atgggctgac   1440
cgcttcctcg tgctttacgg tatcgccgct cccgattcgc agcgcatcgc cttctatcgc   1500
cttcttgacg agttcttctg acatgaccaa aatcccttaa cgtgagtttt cgttccactg   1560
agcgtcagac cccgtagaaa agatcaaagg atcttcttga gatccttttt ttctgcgcgt   1620
aatctgctgc ttgcaaacaa aaaaaccacc gctaccagcg gtggtttgtt tgccggatca   1680
agagctacca actctttttc cgaaggtaac tggcttcagc agagcgcaga taccaaatac   1740
tgtccttcta gtgtagccgt agttaggcca ccacttcaag aactctgtag caccgcctac   1800
atacctcgct ctgctaatcc tgttaccagt ggctgctgcc agtggcgata agtcgtgtct   1860
taccgggttg gactcaagac gatagttacc ggataaggcg cagcggtcgg gctgaacggg   1920
gggttcgtgc acacagccca gcttggagcg aacgacctac accgaactga gatacctaca   1980
gcgtgagcta tgagaaagcg ccacgcttcc cgaagggaga aaggcggaca ggtatccggt   2040
aagcggcagg gtcggaacag gagagcgcac gagggagctt ccagggggaa acgcctggta   2100
tctttatagt cctgtcgggt ttcgccacct ctgacttgag cgtcgatttt tgtgatgctc   2160
gtcagggggg cggagcctat ggaaaaacgc cagcaacgcg gcctttttac ggttcctggc   2220
cttttgctgg ccttttgctc acatgttctt tcctgcgtta tcccctgatt ctgtggataa   2280
ccgtattacc gcctttgagt gagctgatac cgctcgccgc agccgaacga ccgagcgcag   2340
```

```
cgagtcagtg agcgaggaag cggaagagcg cctgatgcgg tattttctcc ttacgcatct   2400
gtgcggtatt tcacaccgca tatggtgcac tctcagtaca atctgctctg atgccgcata   2460
gttaagccag tatacactcc gctatcgcta cgtgactggg tcatggctgc gccccgacac   2520
ccgccaacac ccgctgacgc gccctgacgg gcttgtctgc tcccggcatc cgcttacaga   2580
caagctgtga ccgtctccgg gagctgcatg tgtcagaggt tttcaccgtc atcaccgaaa   2640
cgcgcgaggc agcagatcaa ttcgcgcgcg aaggcgaagc ggcatgcatt tacgttgaca   2700
ccatcgaatg gtgcaaaacc tttcgcggta tggcatgata gcgcccggaa gagagtcaat   2760
tcagggtggt gaatgtgaaa ccagtaacgt tatacgatgt cgcagagtat gccggtgtct   2820
cttatcagac cgtttcccgc gtggtgaacc aggccagcca cgtttctgcg aaaacgcggg   2880
aaaaagtgga agcggcgatg gcggagctga attacattcc caaccgcgtg gcacaacaac   2940
tggcgggcaa acagtcgttg ctgattggcg ttgccacctc cagtctggcc ctgcacgcgc   3000
cgtcgcaaat tgtcgcggcg attaaatctc gcgccgatca actgggtgcc agcgtggtgg   3060
tgtcgatggt agaacgaagc ggcgtcgaag cctgtaaagc ggcggtgcac aatcttctcg   3120
cgcaacgcgt cagtgggctg atcattaact atccgctgga tgaccaggat gccattgctg   3180
tggaagctgc ctgcactaat gttccggcgt tatttcttga tgtctctgac cagacaccca   3240
tcaacagtat tattttctcc catgaagacg gtacgcgact gggcgtggag catctggtcg   3300
cattgggtca ccagcaaatc gcgctgttag cgggcccatt aagttctgtc tcggcgcgtc   3360
tgcgtctggc tggctggcat aaatatctca ctcgcaatca aattcagccg atagcggaac   3420
gggaaggcga ctggagtgcc atgtccggtt ttcaacaaac catgcaaatg ctgaatgagg   3480
gcatcgttcc cactgcgatg ctggttgcca acgatcagat ggcgctgggc gcaatgcgcg   3540
ccattaccga gtccgggctg cgcgttggtg cggatatctc ggtagtggga tacgacgata   3600
ccgaagacag ctcatgttat atcccgccgt caaccaccat caaacaggat tttcgcctgc   3660
tggggcaaac cagcgtggac cgcttgctgc aactctctca gggccaggcg gtgaagggca   3720
atcagctgtt gcccgtctca ctggtgaaaa gaaaaaccac cctggcgccc aatacgcaaa   3780
ccgcctctcc ccgcgcgttg gccgattcat taatgcagct ggcacgacag gtttcccgac   3840
tggaaagcgg gcagtgagcg caacgcaatt aatgtgagtt agcgcgaatt gatctggttt   3900
gacagcttat catcgactgc acggtgcacc aatgcttctg gcgtcaggca gccatcggaa   3960
gctgtggtat ggctgtgcag gtcgtaaatc actgcataat tcgtgtcgct caaggcgcac   4020
tcccgttctg gataatgttt tttgcgccga catcataacg gttctggcaa atattctgaa   4080
atgagctgtt gacaattaat catccggctc gtataatgtg tggaattgtg agcggataac   4140
aatttcacac aggaaacagc gccgctgaga aaaagcgaag cggcactgct ctttaacaat   4200
ttatcagaca atctgtgtgg gcactcgacc ggaattatcg attaacttta ttattaaaaa   4260
ttaaagaggt atatattaat gtatcgatta aataaggagg aataaaccat gtgtgcgacc   4320
tcttctcaat ttactcagat taccgagcat aattcccgtc gttccgcaaa ctatcagcca   4380
aacctgtgga atttcgaatt cctgcaatcc ctggagaacg acctgaaagt ggaaaagctg   4440
gaggagaaag cgaccaaact ggaggaagaa gttcgctgca tgatcaaccg tgtagacacc   4500
cagccgctgt ccctgctgga gctgatcgac gatgtgcagc gcctgggtct gacctacaaa   4560
tttgaaaaag acatcattaa agccctggaa aacatcgtac tgctggacga aaacaaaaag   4620
aacaaatctg acctgcacgc aaccgctctg tctttccgtc tgctgcgtca gcacggtttc   4680
```

-continued

```
gaggtttctc aggatgtttt tgagcgtttc aaggataaag aaggtggttt cagcggtgaa   4740
ctgaaaggtg acgtccaagg cctgctgagc ctgtatgaag cgtcttacct gggtttcgag   4800
ggtgagaacc tgctggagga ggcgcgtacc ttttccatca cccacctgaa gaacaacctg   4860
aaagaaggca ttaataccaa ggttgcagaa caagtgagcc acgccctgga actgccatat   4920
caccagcgtc tgcaccgtct ggaggcacgt tggttcctgg ataaatacga accgaaagaa   4980
ccgcatcacc agctgctgct ggagctggcg aagctggatt ttaacatggt acagaccctg   5040
caccagaaag agctgcaaga tctgtcccgc tggtggaccg agatgggcct ggctagcaaa   5100
ctggattttg tacgcgaccg cctgatggaa gtttatttct gggcactggg tatggcgcca   5160
gacccgcagt ttggtgaatg tcgcaaagct gttactaaaa tgtttggtct ggtgacgatc   5220
atcgatgacg tgtatgacgt ttatggcact ctggacgaac tgcaactgtt caccgatgct   5280
gtagagcgct gggacgttaa cgctattaac accctgccgg actatatgaa actgtgtttc   5340
ctggcactgt acaacaccgt taacgacacg tcctattcta ttctgaaaga gaaaggtcat   5400
aacaacctgt cctatctgac gaaaagctgg cgtgaactgt gcaaagcctt tctgcaagag   5460
gcgaaatggt ccaacaacaa aattatcccg gctttctcca agtacctgga aaacgccagc   5520
gtttcctcct ccggtgtagc gctgctggcg ccgtcttact tttccgtatg ccagcagcag   5580
gaagacatct ccgaccacgc gctgcgttcc ctgaccgact tccatggtct ggtgcgttct   5640
agctgcgtta tcttccgcct gtgcaacgat ctggccacct ctgcggcgga gctggaacgt   5700
ggcgagacta ccaattctat cattagctac atgcacgaaa acgatggtac cagcgaggaa   5760
caggcccgcg aagaactgcg taaactgatc gacgccgaat ggaaaaagat gaatcgtgaa   5820
cgcgttagcg actccaccct gctgcctaaa gcgttcatgg aaatcgcagt taacatggca   5880
cgtgtttccc actgcaccta ccagtatggc gatggtctgg gtcgcccaga ctacgcgact   5940
gaaaaccgca tcaaactgct gctgattgac cctttcccga ttaaccagct gatgtatgtc   6000
taactgcatc gcccttagga ggtaaaaaaa aatgactgcc gacaacaata gtatgcccca   6060
tggtgcagta tctagttacg ccaaattagt gcaaaaccaa acacctgaag acattttgga   6120
agagtttcct gaaattattc cattacaaca aagacctaat acccgatcta gtgagacgtc   6180
aaatgacgaa agcggagaaa catgtttttc tggtcatgat gaggagcaaa ttaagttaat   6240
gaatgaaaat tgtattgttt tggattggga cgataatgct attggtgccg gtaccaagaa   6300
agtttgtcat ttaatggaaa atattgaaaa gggtttacta catcgtgcat tctccgtctt   6360
tattttcaat gaacaaggtg aattactttt acaacaaaga gccactgaaa aaataacttt   6420
ccctgatctt tggactaaca catgctgctc tcatccacta tgtattgatg acgaattagg   6480
tttgaagggt aagctagacg ataagattaa gggcgctatt actgcggcgg tgagaaaact   6540
agatcatgaa ttaggtattc cagaagatga aactaagaca aggggtaagt ttcacttttt   6600
aaacagaatc cattacatgg caccaagcaa tgaaccatgg ggtgaacatg aaattgatta   6660
catcctattt tataagatca acgctaaaga aaacttgact gtcaacccaa acgtcaatga   6720
agttagagac ttcaaatggg tttcaccaaa tgatttgaaa actatgtttg ctgacccaag   6780
ttacaagttt acgccttggt ttaagattat ttgcgagaat tacttattca actggtggga   6840
gcaattagat gacctttctg aagtggaaaa tgacaggcaa attcatagaa tgctataaca   6900
acgcgtcctg cattcgccct taggaggtaa aaaaacatga gttttgatat tgccaaatac   6960
ccgaccctgg cactggtcga ctccacccag gagttacgac tgttgccgaa agagagttta   7020
ccgaaactct gcgacgaact gcgccgctat ttactcgaca gcgtgagccg ttccagcggg   7080
```

```
cacttcgcct ccgggctggg cacggtcgaa ctgaccgtgg cgctgcacta tgtctacaac   7140
accccgtttg accaattgat ttgggatgtg gggcatcagg cttatccgca taaaattttg   7200
accggacgcc gcgacaaaat cggcaccatc cgtcagaaag gcggtctgca cccgttcccg   7260
tggcgcggcg aaagcgaata tgacgtatta agcgtcgggc attcatcaac ctccatcagt   7320
gccggaattg gtattgcggt tgctgccgaa aaagaaggca aaaatcgccg caccgtctgt   7380
gtcattggcg atggcgcgat taccgcaggc atggcgtttg aagcgatgaa tcacgcgggc   7440
gatatccgtc ctgatatgct ggtgattctc aacgacaatg aaatgtcgat ttccgaaaat   7500
gtcggcgcgc tcaacaacca tctggcacag ctgctttccg gtaagcttta ctcttcactg   7560
cgcgaaggcg ggaaaaaagt ttctctggc gtgccgccaa ttaaagagct gctcaaacgc   7620
accgaagaac atattaaagg catggtagtg cctggcacgt tgtttgaaga gctgggcttt   7680
aactacatcg gcccggtgga cggtcacgat gtgctggggc ttatcaccac gctaaagaac   7740
atgcgcgacc tgaaaggccc gcagttcctg catatcatga ccaaaaaagg tcgtggttat   7800
gaaccggcag aaaaagaccc gatcactttc cacgccgtgc ctaaatttga tccctccagc   7860
ggttgtttgc cgaaaagtag cggcggtttg ccgagctatt caaaaatctt tggcgactgg   7920
ttgtgcgaaa cggcagcgaa agacaacaag ctgatggcga ttactccggc gatgcgtgaa   7980
ggttccggca tggtcgagtt ttcacgtaaa ttcccggatc gctacttcga cgtggcaatt   8040
gccgagcaac acgcggtgac ctttgctgcg ggtctggcga ttggtgggta caaacccatt   8100
gtcgcgattt actccacttt cctgcaacgc gcctatgatc aggtgctgca tgacgtggcg   8160
attcaaaagc ttccggtcct gttcgccatc gaccgcgcgg gcattgttgg tgctgacggt   8220
caaacccatc agggtgcttt tgatctctct tacctgcgct gcataccgga aatggtcatt   8280
atgaccccga gcgatgaaaa cgaatgtcgc cagatgctct ataccggcta tcactataac   8340
gatggcccgt cagcggtgcg ctacccgcgt ggcaacgcgg tcgggtggaa ctgacgccgc   8400
tggaaaaact accaattggc aaaggcattg tgaagcgtcg tggcgagaaa ctggcgatcc   8460
ttaactttgg tacgctgatg ccagaagcgg cgaaagtcgc cgaatcgctg aacgccacgc   8520
tggtcgatat gcgttttgtg aaaccgcttg atgaagcgtt aattctggaa atggccgcca   8580
gccatgaagc gctggtcacc gtagaagaaa acgccattat gggcggcgca ggcagcggcg   8640
tgaacgaagt gctgatggcc catcgtaaac cagtacccgt gctgaacatt ggcctgccgg   8700
acttctttat tccgcaagga actcaggaag aaatgcgcgc cgaactcggc ctcgatgccg   8760
ctggtatgga agccaaaatc aaggcctggc tggcataact gca                     8803
```

<210> SEQ ID NO 21
<211> LENGTH: 41
<212> TYPE: DNA
<213> ORGANISM: Artificial Sequence
<220> FEATURE:
<223> OTHER INFORMATION: PCR Primer

<400> SEQUENCE: 21

```
aggaggtaaa aaaacatgtc attaccgttc ttaacttctg c                         41
```

<210> SEQ ID NO 22
<211> LENGTH: 52
<212> TYPE: DNA
<213> ORGANISM: Artificial Sequence
<220> FEATURE:
<223> OTHER INFORMATION: PCR Primer -continued

<400> SEQUENCE: 22
atggctgcag gcctatcgca aattagctta tgaagtccat ggtaaattcg tg 52

<210> SEQ ID NO 23
<211> LENGTH: 23
<212> TYPE: DNA
<213> ORGANISM: Artificial Sequence
<220> FEATURE:
<223> OTHER INFORMATION: PCR Primer

<400> SEQUENCE: 23
gaattcgccc ttctgcagct acc 23

<210> SEQ ID NO 24
<211> LENGTH: 38
<212> TYPE: DNA
<213> ORGANISM: Artificial Sequence
<220> FEATURE:
<223> OTHER INFORMATION: PCR Primer

<400> SEQUENCE: 24
cgactggtgc acccttaagg aggaaaaaaa catgtcag 38

<210> SEQ ID NO 25
<211> LENGTH: 25
<212> TYPE: DNA
<213> ORGANISM: Artificial Sequence
<220> FEATURE:
<223> OTHER INFORMATION: PCR Primer

<400> SEQUENCE: 25
gtgctggaat tcgcccttct gcagc 25

<210> SEQ ID NO 26
<211> LENGTH: 32
<212> TYPE: DNA
<213> ORGANISM: Artificial Sequence
<220> FEATURE:
<223> OTHER INFORMATION: PCR Primer

<400> SEQUENCE: 26
gtagatgcat gcagaattcg cccttaagga gg 32

<210> SEQ ID NO 27
<211> LENGTH: 26
<212> TYPE: DNA
<213> ORGANISM: Artificial Sequence
<220> FEATURE:
<223> OTHER INFORMATION: PCR Primer

<400> SEQUENCE: 27
ccttctgcag gacgcgttgt tatagc 26

<210> SEQ ID NO 28
<211> LENGTH: 38
<212> TYPE: DNA
<213> ORGANISM: Artificial Sequence
<220> FEATURE:
<223> OTHER INFORMATION: PCR Primer

<400> SEQUENCE: 28
catcaatgca tcgcccttag gaggtaaaaa aaaatgac 38

<210> SEQ ID NO 29
<211> LENGTH: 25

<212> TYPE: DNA
<213> ORGANISM: Artificial Sequence
<220> FEATURE:
<223> OTHER INFORMATION: PCR Primer

<400> SEQUENCE: 29
gtgtgatgga tatctgcaga attcg 25

<210> SEQ ID NO 30
<211> LENGTH: 36
<212> TYPE: DNA
<213> ORGANISM: Artificial Sequence
<220> FEATURE:
<223> OTHER INFORMATION: PCR Primer

<400> SEQUENCE: 30
catcaatgca tcgcccttag gaggtaaaaa aacatg 36

<210> SEQ ID NO 31
<211> LENGTH: 60
<212> TYPE: DNA
<213> ORGANISM: Artificial Sequence
<220> FEATURE:
<223> OTHER INFORMATION: PCR Primer

<400> SEQUENCE: 31
gatcatgcat tcgcccttag gaggtaaaaa aacatgtgtg cgacctcttc tcaatttact 60

<210> SEQ ID NO 32
<211> LENGTH: 38
<212> TYPE: DNA
<213> ORGANISM: Artificial Sequence
<220> FEATURE:
<223> OTHER INFORMATION: PCR Primer

<400> SEQUENCE: 32
cggtcgacgg atccctgcag ttagacatac atcagctg 38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatggatcc 420
gagctcggat ccactagtaa cggccgccag tgtgctggaa ttcgccctta ggaggtaaaa 480
aaacatgtca ttaccgttct taacttctgc accgggaaag gttattattt ttggtgaaca 540
ctctgctgtg tacaacaagc ctgccgtcgc tgctagtgtg tctgcgttga gaacctacct 600
gctaataagc gagtcatctg caccagatac tattgaattg gacttcccgg acattagctt 660
taatcataag tggtccatca atgatttcaa tgccatcacc gaggatcaag taaactccca 720

-continued

```
aaaattggcc aaggctcaac aagccaccga tggcttgtct caggaactcg ttagtctttt    780
ggatccgttg ttagctcaac tatccgaatc cttccactac catgcagcgt tttgtttcct    840
gtatatgttt gtttgcctat gcccccatgc caagaatatt aagttttctt taaagtctac    900
tttacccatc ggtgctgggt tgggctcaag cgcctctatt tctgtatcac tggccttagc    960
tatggcctac ttggggggt taataggatc taatgacttg gaaaagctgt cagaaaacga   1020
taagcatata gtgaatcaat gggccttcat aggtgaaaag tgtattcacg gtaccccttc   1080
aggaatagat aacgctgtgg ccacttatgg taatgccctg ctatttgaaa aagactcaca   1140
taatggaaca ataaacacaa acaattttaa gttcttagat gatttcccag ccattccaat   1200
gatcctaacc tatactagaa ttccaaggtc tacaaaagat cttgttgctc gcgttcgtgt   1260
gttggtcacc gagaaatttc ctgaagttat gaagccaatt ctagatgcca tgggtgaatg   1320
tgccctacaa ggcttagaga tcatgactaa gttaagtaaa tgtaaaggca ccgatgacga   1380
ggctgtagaa actaataatg aactgtatga acaactattg gaattgataa gaataaatca   1440
tggactgctt gtctcaatcg gtgtttctca tcctggatta gaacttatta aaaatctgag   1500
cgatgatttg agaattggct ccacaaaact taccggtgct ggtggcggcg gttgctcttt   1560
gactttgtta cgaagagaca ttactcaaga gcaaattgac agcttcaaaa agaaattgca   1620
agatgatttt agttacgaga catttgaaac agacttgggt gggactggct gctgtttgtt   1680
aagcgcaaaa aatttgaata aagatcttaa aatcaaatcc ctagtattcc aattatttga   1740
aaataaaact accacaaagc aacaaattga cgatctatta ttgccaggaa acacgaattt   1800
accatggact tcataagcta atttgcgata ggcctgcacc cttaaggagg aaaaaaacat   1860
gtcagagttg agagccttca gtgccccagg gaaagcgtta ctagctggtg gatatttagt   1920
tttagataca aaatatgaag catttgtagt cggattatcg gcaagaatgc atgctgtagc   1980
ccatccttac ggttcattgc aagggtctga taagtttgaa gtgcgtgtga aaagtaaaca   2040
atttaaagat ggggagtggc tgtaccatat aagtcctaaa agtggcttca ttcctgtttc   2100
gataggcgga tctaagaacc ctttcattga aaaagttatc gctaacgtat ttagctactt   2160
taaacctaac atggacgact actgcaatag aaacttgttc gttattgata ttttctctga   2220
tgatgcctac cattctcagg aggatagcgt taccgaacat cgtggcaaca gaagattgag   2280
ttttcattcg cacagaattg aagaagttcc caaaacaggg ctgggctcct cggcaggttt   2340
agtcacagtt ttaactacag ctttggcctc ctttttgta tcggacctgg aaaataatgt   2400
agacaaatat agagaagtta ttcataattt agcacaagtt gctcattgtc aagctcaggg   2460
taaaattgga agcgggtttg atgtagcggc ggcagcatat ggatctatca gatatagaag   2520
attcccaccc gcattaatct ctaatttgcc agatattgga agtgctactt acggcagtaa   2580
actggcgcat ttggttgatg aagaagactg gaatattacg attaaaagta accatttacc   2640
ttcgggatta actttatgga tgggcgatat taagaatggt tcagaaacag taaaactggt   2700
ccagaaggta aaaaattggt atgattcgca tatgccagaa agcttgaaaa tatatacaga   2760
actcgatcat gcaaattcta gatttatgga tggactatct aaactagatc gcttacacga   2820
gactcatgac gattacagcg atcagatatt tgagtctctt gagaggaatg actgtacctg   2880
tcaaaagtat cctgaaatca cagaagttag agatgcagtt gccacaatta gacgttcctt   2940
tagaaaaata actaaagaat ctggtgccga tatcgaacct cccgtacaaa ctagcttatt   3000
ggatgattgc cagaccttaa aaggagttct tacttgctta atacctggtg ctggtggtta   3060
tgacgccatt gcagtgatta ctaagcaaga tgttgatctt agggctcaaa ccgctaatga   3120
```

caaaagattt tctaaggttc aatggctgga tgtaactcag gctgactggg gtgttaggaa 3180
agaaaaagat ccggaaactt atcttgataa ataacttaag gtagctgcat gcagaattcg 3240
cccttaagga ggaaaaaaaa atgaccgttt acacagcatc cgttaccgca cccgtcaaca 3300
tcgcaaccct taagtattgg gggaaaaggg acacgaagtt gaatctgccc accaattcgt 3360
ccatatcagt gactttatcg caagatgacc tcagaacgtt gacctctgcg gctactgcac 3420
ctgagtttga acgcgacact ttgtggttaa atggagaacc acacagcatc gacaatgaaa 3480
gaactcaaaa ttgtctgcgc gacctacgcc aattaagaaa ggaaatggaa tcgaaggacg 3540
cctcattgcc cacattatct caatggaaac tccacattgt ctccgaaaat aactttccta 3600
cagcagctgg tttagcttcc tccgctgctg gctttgctgc attggtctct gcaattgcta 3660
agttatacca attaccacag tcaacttcag aaatatctag aatagcaaga aaggggtctg 3720
gttcagcttg tagatcgttg tttggcggat acgtggcctg ggaaatggga aaagctgaag 3780
atggtcatga ttccatggca gtacaaatcg cagacagctc tgactggcct cagatgaaag 3840
cttgtgtcct agttgtcagc gatattaaaa aggatgtgag ttccactcag ggtatgcaat 3900
tgaccgtggc aacctccgaa ctatttaaag aaagaattga acatgtcgta ccaaagagat 3960
ttgaagtcat gcgtaaagcc attgttgaaa aagatttcgc cacctttgca aaggaaacaa 4020
tgatggattc caactctttc catgccacat gtttggactc tttccctcca atattctaca 4080
tgaatgacac ttccaagcgt atcatcagtt ggtgccacac cattaatcag ttttacggag 4140
aaacaatcgt tgcatacacg tttgatgcag gtccaaatgc tgtgttgtac tacttagctg 4200
aaaatgagtc gaaactcttt gcatttatct ataaattgtt tggctctgtt cctggatggg 4260
acaagaaatt tactactgag cagcttgagg ctttcaacca tcaatttgaa tcatctaact 4320
ttactgcacg tgaattggat cttgagttgc aaaaggatgt tgccagagtg attttaactc 4380
aagtcggttc aggcccacaa gaaacaaacg aatctttgat tgacgcaaag actggtctac 4440
caaaggaata agatcaattc gctgcatcgc ccttaggagg taaaaaaaaa tgactgccga 4500
caacaatagt atgccccatg gtgcagtatc tagttacgcc aaattagtgc aaaaccaaac 4560
acctgaagac attttggaag agtttcctga aattattcca ttacaacaaa gacctaatac 4620
ccgatctagt gagacgtcaa atgacgaaag cggagaaaca tgtttttctg gtcatgatga 4680
ggagcaaatt aagttaatga atgaaaattg tattgttttg gattgggacg ataatgctat 4740
tggtgccggt accaagaaag tttgtcattt aatggaaaat attgaaaagg gtttactaca 4800
tcgtgcattc tccgtcttta ttttcaatga acaaggtgaa ttacttttac aacaaagagc 4860
cactgaaaaa ataactttcc ctgatctttg gactaacaca tgctgctctc atccactatg 4920
tattgatgac gaattaggtt tgaagggtaa gctagacgat aagattaagg gcgctattac 4980
tgcggcggtg agaaaactag atcatgaatt aggtattcca gaagatgaaa ctaagacaag 5040
ggtaagttt cactttttaa acagaatcca ttacatggca ccaagcaatg aaccatgggg 5100
tgaacatgaa attgattaca tcctatttta taagatcaac gctaaagaaa acttgactgt 5160
caacccaaac gtcaatgaag ttagagactt caaatgggtt tcaccaaatg atttgaaaac 5220
tatgtttgct gacccaagtt acaagtttac gccttggttt aagattattt gcgagaatta 5280
cttattcaac tggtgggagc aattagatga cctttctgaa gtggaaaatg acaggcaaat 5340
tcatagaatg ctataacaac gcgtcctgca ttcgccctta ggaggtaaaa aaacatgtgt 5400
gcgacctctt ctcaatttac tcagattacc gagcataatt cccgtcgttc cgcaaactat 5460

-continued

```
cagccaaacc tgtggaattt cgaattcctg caatccctgg agaacgacct gaaagtggaa   5520
aagctggagg agaaagcgac caaactggag gaagaagttc gctgcatgat caaccgtgta   5580
gacacccagc cgctgtccct gctggagctg atcgacgatg tgcagcgcct gggtctgacc   5640
tacaaatttg aaaaagacat cattaaagcc ctggaaaaca tcgtactgct ggacgaaaac   5700
aaaaagaaca aatctgacct gcacgcaacc gctctgtctt tccgtctgct gcgtcagcac   5760
ggtttcgagg tttctcagga tgtttttgag cgtttcaagg ataaagaagg tggtttcagc   5820
ggtgaactga aggtgacgt ccaaggcctg ctgagcctgt atgaagcgtc ttacctgggt   5880
ttcgagggtg agaacctgct ggaggaggcg cgtacctttt ccatcaccca cctgaagaac   5940
aacctgaaag aaggcattaa taccaaggtt gcagaacaag tgagccacgc cctggaactg   6000
ccatatcacc agcgtctgca ccgtctggag gcacgttggt tcctggataa atacgaaccg   6060
aaagaaccgc atcaccagct gctgctggag ctggcgaagc tggattttaa catggtacag   6120
accctgcacc agaaagagct gcaagatctg tcccgctggt ggaccgagat gggcctggct   6180
agcaaactgg attttgtacg cgaccgcctg atggaagttt atttctgggc actgggtatg   6240
gcgccagacc cgcagtttgg tgaatgtcgc aaagctgtta ctaaaatgtt tggtctggtg   6300
acgatcatcg atgacgtgta tgacgtttat ggcactctgg acgaactgca actgttcacc   6360
gatgctgtag agcgctggga cgttaacgct attaacaccc tgccggacta tatgaaactg   6420
tgtttcctgg cactgtacaa caccgttaac gacacgtcct attctattct gaaagagaaa   6480
ggtcataaca acctgtccta tctgacgaaa agctggcgtg aactgtgcaa agcctttctg   6540
caagaggcga aatggtccaa caacaaaatt atcccggctt tctccaagta cctggaaaac   6600
gccagcgttt cctcctccgg tgtagcgctg ctggcgccgt cttacttttc cgtatgccag   6660
cagcaggaag acatctccga ccacgcgctg cgttccctga ccgacttcca tggtctggtg   6720
cgttctagct gcgttatctt ccgcctgtgc aacgatctgg ccacctctgc ggcggagctg   6780
gaacgtggcg agactaccaa ttctatcatt agctacatgc acgaaaacga tggtaccagc   6840
gaggaacagg cccgcgaaga actgcgtaaa ctgatcgacg ccgaatggaa aaagatgaat   6900
cgtgaacgcg ttagcgactc caccctgctg cctaaagcgt tcatggaaat cgcagttaac   6960
atggcacgtg tttcccactg cacctaccag tatggcgatg gtctgggtcg cccagactac   7020
gcgactgaaa accgcatcaa actgctgctg attgaccctt tcccgattaa ccagctgatg   7080
tatgtctaac tgcagctggt accatatggg aattcgaagc tttctagaac aaaaactcat   7140
ctcagaagag gatctgaata gcgccgtcga ccatcatcat catcatcatt gagtttaaac   7200
ggtctccagc ttggctgttt tggcggatga gagaagattt tcagcctgat acagattaaa   7260
tcagaacgca gaagcggtct gataaaacag aatttgcctg gcggcagtag cgcggtggtc   7320
ccacctgacc ccatgccgaa ctcagaagtg aaacgccgta gcgccgatgg tagtgtgggg   7380
tctccccatg cgagagtagg gaactgccag gcatcaaata aaacgaaagg ctcagtcgaa   7440
agactgggcc tttcgtttta tctgttgttt gtcggtgaac gctctcctga gtaggacaaa   7500
tccgccggga gcggatttga acgttgcgaa gcaacggccc ggagggtggc gggcaggacg   7560
cccgccataa actgccaggc atcaaattaa gcagaaggcc atcctgacgg atggcctttt   7620
tgcgtttcta caaactcttt ttgtttattt ttctaaatac attcaaatat gtatccgctt   7680
aaccggaatt gccagctggg gcgccctctg gtaaggttgg gaagccctgc aaagtaaact   7740
ggatggcttt ctcgccgcca aggatctgat ggcgcagggg atcaagctct gatcaagaga   7800
caggatgagg atcgtttcgc atgattgaac aagatggatt gcacgcaggt tctccggccg   7860
```

-continued

```
cttgggtgga gaggctattc ggctatgact gggcacaaca gacaatcggc tgctctgatg   7920
ccgccgtgtt ccggctgtca gcgcaggggc gcccggttct ttttgtcaag accgacctgt   7980
ccggtgccct gaatgaactg caagacgagg cagcgcggct atcgtggctg gccacgacgg   8040
gcgttccttg cgcagctgtg ctcgacgttg tcactgaagc gggaagggac tggctgctat   8100
tgggcgaagt gccggggcag gatctcctgt catctcacct tgctcctgcc gagaaagtat   8160
ccatcatggc tgatgcaatg cggcggctgc atacgcttga tccggctacc tgcccattcg   8220
accaccaagc gaaacatcgc atcgagcgag cacgtactcg gatggaagcc ggtcttgtcg   8280
atcaggatga tctggacgaa gagcatcagg ggctcgcgcc agccgaactg ttcgccaggc   8340
tcaaggcgag catgcccgac ggcgaggatc tcgtcgtgac ccatggcgat gcctgcttgc   8400
cgaatatcat ggtggaaaat ggccgctttt ctggattcat cgactgtggc cggctgggtg   8460
tggcggaccg ctatcaggac atagcgttgg ctacccgtga tattgctgaa gagcttggcg   8520
gcgaatgggc tgaccgcttc ctcgtgcttt acggtatcgc cgctcccgat tcgcagcgca   8580
tcgccttcta tcgccttctt gacgagttct tctgacgcat gaccaaaatc ccttaacgtg   8640
agttttcgtt ccactgagcg tcagaccccg tagaaaagat caaaggatct tcttgagatc   8700
ctttttttct gcgcgtaatc tgctgcttgc aaacaaaaaa accaccgcta ccagcggtgg   8760
tttgtttgcc ggatcaagag ctaccaactc tttttccgaa ggtaactggc ttcagcagag   8820
cgcagatacc aaatactgtc cttctagtgt agccgtagtt aggccaccac ttcaagaact   8880
ctgtagcacc gcctacatac ctcgctctgc taatcctgtt accagtggct gctgccagtg   8940
gcgataagtc gtgtcttacc gggttggact caagacgata gttaccggat aaggcgcagc   9000
ggtcgggctg aacggggggt tcgtgcacac agcccagctt ggagcgaacg acctacaccg   9060
aactgagata cctacagcgt gagctatgag aaagcgccac gcttcccgaa gggagaaagg   9120
cggacaggta tccggtaagc ggcagggtcg gaacaggaga gcgcacgagg gagcttccag   9180
ggggaaacgc ctggtatctt tatagtcctg tcgggtttcg ccacctctga cttgagcgtc   9240
gatttttgtg atgctcgtca ggggggcgga gcctatggaa aaacgccagc aacgcggcct   9300
ttttacggtt cctggccttt tgctggcctt ttgctcacat gttctttcct gcgttatccc   9360
ctgattctgt ggataaccgt attaccgcct ttgagtgagc tgataccgct cgccgcagcc   9420
gaacgaccga gcgcagcgag tcagtgagcg aggaagcgga agagcgcctg atgcggtatt   9480
ttctccttac gcatctgtgc ggtatttcac accgcatatg gtgcactctc agtacaatct   9540
gctctgatgc cgcatagtta agccagtata cactccgcta tcgctacgtg actgggtcat   9600
ggctgcgccc cgacacccgc caacacccgc tgacgcgccc tgacgggctt gtctgctccc   9660
ggcatccgct tacagacaag ctgtgaccgt ctccgggagc tgcatgtgtc agaggttttc   9720
accgtcatca ccgaaacgcg cgaggcagca gatcaattcg cgcgcgaagg cgaagcggca   9780
tgcatttacg ttgacaccat cgaatggtgc aaaacctttc gcggtatggc atgatagcgc   9840
ccggaagaga gtcaattcag ggtggtgaat gtgaaaccag taacgttata cgatgtcgca   9900
gagtatgccg gtgtctctta tcagaccgtt tcccgcgtgg tgaaccaggc cagccacgtt   9960
tctgcgaaaa cgcgggaaaa agtggaagcg gcgatggcgg agctgaatta cattcccaac  10020
cgcgtggcac aacaactggc gggcaaacag tcgttgctga ttggcgttgc cacctccagt  10080
ctggccctgc acgcgccgtc gcaaattgtc gcggcgatta aatctcgcgc cgatcaactg  10140
ggtgccagcg tggtggtgtc gatggtagaa cgaagcggcg tcgaagcctg taaagcggcg  10200
```

```
gtgcacaatc ttctcgcgca acgcgtcagt gggctgatca ttaactatcc gctggatgac  10260

caggatgcca ttgctgtgga agctgcctgc actaatgttc cggcgttatt tcttgatgtc  10320

tctgaccaga cacccatcaa cagtattatt ttctcccatg aagacggtac gcgactgggc  10380

gtggagcatc tggtcgcatt gggtcaccag caaatcgcgc tgttagcggg cccattaagt  10440

tctgtctcgg cgcgtctgcg tctggctggc tggcataaat atctcactcg caatcaaatt  10500

cagccgatag cggaacggga aggcgactgg agtgccatgt ccggttttca acaaaccatg  10560

caaatgctga atgagggcat cgttcccact gcgatgctgg ttgccaacga tcagatggcg  10620

ctgggcgcaa tgcgcgccat taccgagtcc gggctgcgcg ttggtgcgga tatctcggta  10680

gtgggatacg acgataccga agacagctca tgttatatcc cgccgtcaac caccatcaaa  10740

caggattttc gcctgctggg gcaaaccagc gtggaccgct tgctgcaact ctctcagggc  10800

caggcggtga agggcaatca gctgttgccc gtctcactgg tgaaaagaaa aaccaccctg  10860

gcgcccaata cgcaaaccgc ctctccccgc gcgttggccg attcattaat gcagctggca  10920

cgacaggttt cccgactgga aagcgggcag tgagcgcaac gcaattaatg tgagttagcg  10980

cgaattgatc tg                                                      10992
```

<210> SEQ ID NO 34
<211> LENGTH: 50
<212> TYPE: DNA
<213> ORGANISM: Artificial Sequence
<220> FEATURE:
<223> OTHER INFORMATION: PCR Primer

<400> SEQUENCE: 34

```
gagacatgag ctcaggaggt aaaaaaacat gaaaacagta gttattattg             50
```

<210> SEQ ID NO 35
<211> LENGTH: 54
<212> TYPE: DNA
<213> ORGANISM: Artificial Sequence
<220> FEATURE:
<223> OTHER INFORMATION: PCR Primer

<400> SEQUENCE: 35

```
tttatcaatc ccaattgtca tgttttttta cctcctttat tgttttctta aatc        54
```

<210> SEQ ID NO 36
<211> LENGTH: 54
<212> TYPE: DNA
<213> ORGANISM: Artificial Sequence
<220> FEATURE:
<223> OTHER INFORMATION: PCR Primer

<400> SEQUENCE: 36

```
gatttaagaa aacaataaag gaggtaaaaa aacatgacaa ttgggattga taaa        54
```

<210> SEQ ID NO 37
<211> LENGTH: 40
<212> TYPE: DNA
<213> ORGANISM: Artificial Sequence
<220> FEATURE:
<223> OTHER INFORMATION: PCR Primer

<400> SEQUENCE: 37

```
gacatgacat agatctttag tttcgataag aacgaacggt                        40
```

<210> SEQ ID NO 38
<211> LENGTH: 26

<212> TYPE: DNA
<213> ORGANISM: Artificial Sequence
<220> FEATURE:
<223> OTHER INFORMATION: PCR Primer

<400> SEQUENCE: 38
atgaaaacag tagttattat tgatgc 26

<210> SEQ ID NO 39
<211> LENGTH: 33
<212> TYPE: DNA
<213> ORGANISM: Artificial Sequence
<220> FEATURE:
<223> OTHER INFORMATION: PCR Primer

<400> SEQUENCE: 39
atgttattgt tttcttaaat catttaaaat agc 33

<210> SEQ ID NO 40
<211> LENGTH: 26
<212> TYPE: DNA
<213> ORGANISM: Artificial Sequence
<220> FEATURE:
<223> OTHER INFORMATION: PCR Primer

<400> SEQUENCE: 40
atgacaattg ggattgataa aattag 26

<210> SEQ ID NO 41
<211> LENGTH: 24
<212> TYPE: DNA
<213> ORGANISM: Artificial Sequence
<220> FEATURE:
<223> OTHER INFORMATION: PCR Primer

<400> SEQUENCE: 41
ttagtttcga taagaacgaa cggt 24

<210> SEQ ID NO 42
<211> LENGTH: 23
<212> TYPE: DNA
<213> ORGANISM: Artificial Sequence
<220> FEATURE:
<223> OTHER INFORMATION: PCR Primer

<400> SEQUENCE: 42
gaaatagccc cattagaagt atc 23

<210> SEQ ID NO 43
<211> LENGTH: 24
<212> TYPE: DNA
<213> ORGANISM: Artificial Sequence
<220> FEATURE:
<223> OTHER INFORMATION: PCR Primer

<400> SEQUENCE: 43
ttgccaatca tatgattgaa aatc 24

<210> SEQ ID NO 44
<211> LENGTH: 25
<212> TYPE: DNA
<213> ORGANISM: Artificial Sequence
<220> FEATURE:
<223> OTHER INFORMATION: PCR Primer

<400> SEQUENCE: 44
gctatgcttc attagatcct tatcg 25

<210> SEQ ID NO 45
<211> LENGTH: 25
<212> TYPE: DNA
<213> ORGANISM: Artificial Sequence
<220> FEATURE:
<223> OTHER INFORMATION: PCR Primer

<400> SEQUENCE: 45
gaaacctaca tccaatcttt tgccc 25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46
cccgtcttac tgtcgggaat tcgcgttggc cgattcatta atgcagattc tgaaatgagc 60
tgttgacaat taatcatccg gctcgtataa tgtgtggaat tgtgagcgga taacaatttc 120
acacaggaaa cagcgccgct gagaaaaagc gaagcggcac tgctctttaa caatttatca 180
gacaatctgt gtgggcactc gaccggaatt atcgattaac tttattatta aaaattaaag 240
aggtatatat taatgtatcg attaaataag gaggaataaa ccatggatcc gagctcagga 300
ggtaaaaaaa catgaaaaca gtagttatta ttgatgcatt acgaacacca attggaaaat 360
ataaaggcag cttaagtcaa gtaagtgccg tagacttagg aacacatgtt acaacacaac 420
ttttaaaaag acattccact atttctgaag aaattgatca agtaatcttt ggaaatgttt 480
tacaagctgg aaatggccaa aatcccgcac gacaaatagc aataaacagc ggtttgtctc 540
atgaaattcc cgcaatgacg gttaatgagg tctgcggatc aggaatgaag gccgttattt 600
tggcgaaaca attgattcaa ttaggagaag cggaagtttt aattgctggc gggattgaga 660
atatgtccca agcacctaaa ttacaacgtt ttaattacga aacagaaagc tacgatgcgc 720
ctttttctag tatgatgtat gatggattaa cggatgcctt tagtggtcag gcaatgggct 780
taactgctga aaatgtggcc gaaaagtatc atgtaactag agaagagcaa gatcaatttt 840
ctgtacattc acaattaaaa gcagctcaag cacaagcaga agggatattc gctgacgaaa 900
tagccccatt agaagtatca ggaacgcttg tggagaaaga tgaagggatt cgccctaatt 960
cgagcgttga gaagctagga acgcttaaaa cagtttttaa agaagacggt actgtaacag 1020
cagggaatgc atcaaccatt aatgatgggg cttctgcttt gattattgct tcacaagaat 1080
atgccgaagc acacggtctt ccttatttag ctattattcg agacagtgtg gaagtcggta 1140
ttgatccagc ctatatggga atttcgccga ttaaagccat tcaaaaactg ttagcgcgca 1200
atcaacttac tacggaagaa attgatctgt atgaaatcaa cgaagcattt gcagcaactt 1260
caatcgtggt ccaaagagaa ctggctttac cagaggaaaa ggtcaacatt tatggtggcg 1320
gtatttcatt aggtcatgcg attggtgcca caggtgctcg tttattaacg agtttaagtt 1380
atcaattaaa tcaaaaagaa aagaaatatg gagtggcttc tttatgtatc ggcggtggct 1440
taggactcgc tatgctacta gagagacctc agcaaaaaaa aaacagccga ttttatcaaa 1500
tgagtcctga ggaacgcctg gcttctcttc ttaatgaagg ccagatttct gctgatacaa 1560
aaaaagaatt tgaaaatacg gctttatctt cgcagattgc caatcatatg attgaaaatc 1620
aaatcagtga aacagaagtg ccgatgggcg ttggcttaca tttaacagtg gacgaaactg 1680

-continued attatttggt accaatggcg acagaagagc cctcagttat tgcggctttg agtaatggtg 1740
caaaaatagc acaaggattt aaaacagtga atcaacaacg cttaatgcgt ggacaaatcg 1800
ttttttacga tgttgcagat cccgagtcat tgattgataa actacaagta agagaagcgg 1860
aagtttttca acaagcagag ttaagttatc catctatcgt taaacggggc ggcggcttaa 1920
gagatttgca atatcgtact tttgatgaat catttgtatc tgtcgacttt ttagtagatg 1980
ttaaggatgc aatgggggca aatatcgtta acgctatgtt ggaaggtgtg gccgagttgt 2040
tccgtgaatg gtttgcggag caaaagattt tattcagtat tttaagtaat tatgccacgg 2100
agtcggttgt tacgatgaaa acggctattc cagtttcacg tttaagtaag gggagcaatg 2160
gccgggaaat tgctgaaaaa attgttttag cttcacgcta tgcttcatta gatccttatc 2220
gggcagtcac gcataacaaa ggaatcatga atggcattga agctgtagtt ttagctacag 2280
gaaatgatac acgcgctgtt agcgcttctt gtcatgcttt tgcggtgaag gaaggtcgct 2340
accaaggctt gactagttgg acgctggatg gcgaacaact aattggtgaa atttcagttc 2400
cgcttgcttt agccacggtt ggcggtgcca caaaagtctt acctaaatct caagcagctg 2460
ctgatttgtt agcagtgacg gatgcaaaag aactaagtcg agtagtagcg gctgttggtt 2520
tggcacaaaa tttagcggcg ttacgggcct tagtctctga aggaattcaa aaaggacaca 2580
tggctctaca agcacgttct ttagcgatga cggtcggagc tactggtaaa gaagttgagg 2640
cagtcgctca acaattaaaa cgtcaaaaaa cgatgaacca agaccgagcc atggctattt 2700
taaatgattt aagaaaacaa taaaggaggt aaaaaaacat gacaattggg attgataaaa 2760
ttagtttttt tgtgccccct tattatattg atatgacggc actggctgaa gccagaaatg 2820
tagaccctgg aaaatttcat attggtattg ggcaagacca aatggcggtg aacccaatca 2880
gccaagatat tgtgacattt gcagccaatg ccgcagaagc gatcttgacc aaagaagata 2940
aagaggccat tgatatggtg attgtcggga ctgagtccag tatcgatgag tcaaaagcgg 3000
ccgcagttgt cttacatcgt ttaatgggga ttcaaccttt cgctcgctct ttcgaaatca 3060
aggaagcttg ttacggagca acagcaggct tacagttagc taagaatcac gtagccttac 3120
atccagataa aaaagtcttg gtcgtagcgg cagatattgc aaaatatggc ttaaattctg 3180
gcggtgagcc tacacaagga gctggggcgg ttgcaatgtt agttgctagt gaaccgcgca 3240
ttttggcttt aaaagaggat aatgtgatgc tgacgcaaga tatctatgac ttttggcgtc 3300
caacaggcca cccgtatcct atggtcgatg gtcctttgtc aaacgaaacc tacatccaat 3360
cttttgccca agtctgggat gaacataaaa aacgaaccgg tcttgatttt gcagattatg 3420
atgctttagc gttccatatt ccttacacaa aaatgggcaa aaaagcctta ttagcaaaaa 3480
tctccgacca aactgaagca gaacaggaac gaattttagc ccgttatgaa gaaagtatcg 3540
tctatagtcg tcgcgtagga aacttgtata cgggttcact ttatctggga ctcatttccc 3600
ttttagaaaa tgcaacgact ttaaccgcag gcaatcaaat tggtttattc agttatggtt 3660
ctggtgctgt cgctgaattt ttcactggtg aattagtagc tggttatcaa aatcatttac 3720
aaaaagaaac tcatttagca ctgctggata atcggacaga actttctatc gctgaatatg 3780
aagccatgtt tgcagaaact ttagacacag acattgatca aacgttagaa gatgaattaa 3840
aatatagtat ttctgctatt aataataccg ttcgttctta tcgaaactaa gagatctgca 3900
gctggtacca tatgggaatt cgaagcttgg gcccgaacaa aaactcatct cagaagagga 3960
tctgaatagc gccgtcgacc atcatcatca tcatcattga gtttaaacgg tctccagctt 4020

-continued ggctgttttg gcggatgaga gaagattttc agcctgatac agattaaatc agaacgcaga 4080
agcggtctga taaaacagaa tttgcctggc ggcagtagcg cggtggtccc acctgacccc 4140
atgccgaact cagaagtgaa acgccgtagc gccgatggta gtgtggggtc tccccatgcg 4200
agagtaggga actgccaggc atcaaataaa acgaaaggct cagtcgaaag actgggcctt 4260
tcgttttatc tgttgtttgt cggtgaacgc tctcctgagt aggacaaatc cgccgggagc 4320
ggatttgaac gttgcgaagc aacggcccgg agggtggcgg gcaggacgcc cgccataaac 4380
tgccaggcat caaattaagc agaaggccat cctgacggat ggcctttttg cgtttctaca 4440
aactcttttt gtttattttt ctaaatacat tcaaatatgt atccgctcat gagacaataa 4500
ccctgataaa tgcttcaata atctggcgta atagcgaaga ggcccgcacc gatcgccctt 4560
cccaacagtt gcgcagcctg aatggcgaat ggcgcctgat gcggtatttt ctccttacgc 4620
atctgtgcgg tatttcacac cgcatatggt gcactctcag tacaatctgc tctgatgccg 4680
catagttaag ccagccccga cacccgccaa cacccgctga cgagcttagt aaagccctcg 4740
ctagatttta atgcggatgt tgcgattact tcgccaacta ttgcgataac aagaaaaagc 4800
cagcctttca tgatatatct cccaatttgt gtagggctta ttatgcacgc ttaaaaataa 4860
taaaagcaga cttgacctga tagtttggct gtgagcaatt atgtgcttag tgcatctaac 4920
gcttgagtta agccgcgccg cgaagcggcg tcggcttgaa cgaattgtta gacattattt 4980
gccgactacc ttggtgatct cgcctttcac gtagtggaca aattcttcca actgatctgc 5040
gcgcgaggcc aagcgatctt cttcttgtcc aagataagcc tgtctagctt caagtatgac 5100
gggctgatac tgggccggca ggcgctccat tgcccagtcg gcagcgacat ccttcggcgc 5160
gattttgccg gttactgcgc tgtaccaaat gcgggacaac gtaagcacta catttcgctc 5220
atcgccagcc cagtcgggcg gcgagttcca tagcgttaag gtttcattta gcgcctcaaa 5280
tagatcctgt tcaggaaccg gatcaaagag ttcctccgcc gctggaccta ccaaggcaac 5340
gctatgttct cttgcttttg tcagcaagat agccagatca atgtcgatcg tggctggctc 5400
gaagatacct gcaagaatgt cattgcgctg ccattctcca aattgcagtt cgcgcttagc 5460
tggataacgc cacggaatga tgtcgtcgtg cacaacaatg gtgacttcta cagcgcggag 5520
aatctcgctc tctccagggg aagccgaagt ttccaaaagg tcgttgatca aagctcgccg 5580
cgttgtttca tcaagcctta cggtcaccgt aaccagcaaa tcaatatcac tgtgtggctt 5640
caggccgcca tccactgcgg agccgtacaa atgtacggcc agcaacgtcg gttcgagatg 5700
gcgctcgatg acgccaacta cctctgatag ttgagtcgat acttcggcga tcaccgcttc 5760
cctcatgatg tttaactttg ttttagggcg actgccctgc tgcgtaacat cgttgctgct 5820
ccataacatc aaacatcgac ccacggcgta acgcgcttgc tgcttggatg cccgaggcat 5880
agactgtacc ccaaaaaaac agtcataaca agccatgaaa accgccactg cgccgttacc 5940
accgctgcgt tcggtcaagg ttctggacca gttgcgtgag cgcatacgct acttgcatta 6000
cagcttacga accgaacagg cttatgtcca ctgggttcgt gccttcatcc gtttccacgg 6060
tgtgcgtcac ccggcaacct tgggcagcag cgaagtcgag gcatttctgt cctggctggc 6120
gaacgagcgc aaggtttcgg tctccacgca tcgtcaggca ttggcggcct tgctgttctt 6180
ctacggcaag gtgctgtgca cggatctgcc ctggcttcag gagatcggaa gacctcggcc 6240
gtcgcggcgc ttgccggtgg tgctgacccc ggatgaagtg gttcgcatcc tcggttttct 6300
ggaaggcgag catcgtttgt tcgcccagct tctgtatgga acgggcatgc ggatcagtga 6360
gggtttgcaa ctgcgggtca aggatctgga tttcgatcac ggcacgatca tcgtgcggga 6420

```
gggcaagggc tccaaggatc gggccttgat gttacccgag agcttggcac ccagcctgcg   6480
cgagcagggg aattaattcc cacgggtttt gctgcccgca aacgggctgt tctggtgttg   6540
ctagtttgtt atcagaatcg cagatccggc ttcagccggt ttgccggctg aaagcgctat   6600
ttcttccaga attgccatga tttttcccc acgggaggcg tcactggctc ccgtgttgtc   6660
ggcagctttg attcgataag cagcatcgcc tgtttcaggc tgtctatgtg tgactgttga   6720
gctgtaacaa gttgtctcag gtgttcaatt tcatgttcta gttgctttgt tttactggtt   6780
tcacctgttc tattaggtgt tacatgctgt tcatctgtta cattgtcgat ctgttcatgg   6840
tgaacagctt tgaatgcacc aaaaactcgt aaaagctctg atgtatctat ctttttaca   6900
ccgttttcat ctgtgcatat ggacagtttt ccctttgata tgtaacggtg aacagttgtt   6960
ctacttttgt ttgttagtct tgatgcttca ctgatagata caagagccat aagaacctca   7020
gatccttccg tatttagcca gtatgttctc tagtgtggtt cgttgttttt gcgtgagcca   7080
tgagaacgaa ccattgagat catacttact ttgcatgtca ctcaaaaatt ttgcctcaaa   7140
actggtgagc tgaatttttg cagttaaagc atcgtgtagt gtttttctta gtccgttatg   7200
taggtaggaa tctgatgtaa tggttgttgg tattttgtca ccattcattt ttatctggtt   7260
gttctcaagt tcggttacga gatccatttg tctatctagt tcaacttgga aaatcaacgt   7320
atcagtcggg cggcctcgct tatcaaccac caatttcata ttgctgtaag tgtttaaatc   7380
tttacttatt ggtttcaaaa cccattggtt aagcctttta aactcatggt agttattttc   7440
aagcattaac atgaacttaa attcatcaag gctaatctct atatttgcct tgtgagtttt   7500
cttttgtgtt agttctttta ataaccactc ataaatcctc atagagtatt tgttttcaaa   7560
agacttaaca tgttccagat tatattttat gaattttttt aactggaaaa gataaggcaa   7620
tatctcttca ctaaaaacta attctaattt ttcgcttgag aacttggcat agtttgtcca   7680
ctggaaaatc tcaaagcctt taaccaaagg attcctgatt tccacagttc tcgtcatcag   7740
ctctctggtt gctttagcta atacaccata agcattttcc ctactgatgt tcatcatctg   7800
agcgtattgg ttataagtga acgataccgt ccgttctttc cttgtagggt tttcaatcgt   7860
ggggttgagt agtgccacac agcataaaat tagcttggtt tcatgctccg ttaagtcata   7920
gcgactaatc gctagttcat ttgctttgaa aacaactaat tcagacatac atctcaattg   7980
gtctaggtga ttttaatcac tataccaatt gagatgggct agtcaatgat aattactagt   8040
ccttttcctt tgagttgtgg gtatctgtaa attctgctag acctttgctg gaaaacttgt   8100
aaattctgct agaccctctg taaattccgc tagacctttg tgtgtttttt ttgtttatat   8160
tcaagtggtt ataatttata gaataaagaa agaataaaaa aagataaaaa gaatagatcc   8220
cagccctgtg tataactcac tactttagtc agttccgcag tattacaaaa ggatgtcgca   8280
aacgctgttt gctcctctac aaaacagacc ttaaaaccct aaaggcttaa gtagcaccct   8340
cgcaagctcg ggcaaatcgc tgaatattcc ttttgtctcc gaccatcagg cacctgagtc   8400
gctgtctttt tcgtgacatt cagttcgctg cgctcacggc tctggcagtg aatgggggta   8460
aatggcacta caggcgcctt ttatggattc atgcaaggaa actacccata atacaagaaa   8520
agcccgtcac gggcttctca gggcgtttta tggcgggtct gctatgtggt gctatctgac   8580
tttttgctgt tcagcagttc ctgccctctg attttccagt ctgaccactt cggattatcc   8640
cgtgacaggt cattcagact ggctaatgca cccagtaagg cagcggtatc atcaacaggc   8700
tta                                                                 8703
```

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47
tgtaaccttt gctttcaaat gagtagaaat aatgcacatc catgtttgta tcgtgcaaat 60
aaagtgtttc atccgtagga aaaaatgact ttagtatctg ttccgctttt tctgatgaaa 120
tgtgctcccc gacaaaattg aatgaatcat ggacatttgc tggctttgat acagcgaaag 180
cagccgttcc tatgttatat atcggattta acagcaggac aaaaaacacc atgacagcca 240
tcgtcaccca cttattcaca cgcacataaa cctttcctga cttttggaac agatgatagc 300
tcatcaaaaa tcccgccatt gccaaataaa tcgtatatgg cattactgca ccataatctt 360
ttgagatttg attgggatat ggcgcaagca gcaagacaag cagtccgata atcagcgtat 420
aaaataagcc tagtaagatc ttatccgttc tccaatacag cttgaaaaac actacattca 480
acgcaatggg aagagtgatg atgaaaaaca gaaacacgaa tgcaatcggc tccatcccat 540
ccgggtattc cttccaatac gaaaagaaac taaaaatcat ttgtacgatc ggcaaactga 600
caacagcaag gtcgaacgta taaaacttac cctttccgcc atgatcacgc ggcatcagca 660
tatagtgaaa agccgtcagc agcacatatc cgtataacaa aaatgcagc agcggcagca 720 gttcttttcc gtcctctctt aagtaagcgc tggtgaagtt tgttgattgc acctggtgaa 780
taagttcaac agacactccc gccagcagca caatccgcaa tataacaccc gccaagaaca 840
ttgtgcgctg ccggtttatt ttgggatgat gcaccaaaag atataagccc gccagaacaa 900
caattgacca ttgaatcagc agggtgcttt gtctgcttaa tataaaataa cgttcgaaat 960
gcaatacata atgactgaat aactccaaca cgaacaacaa ctccattttc ttctgctatc 1020
aaaataacag actcgtgatt ttccaaacga gctttcaaaa aagcctctgc cccttgcaaa 1080
tcggatgcct gtctataaaa ttcccgatat tggttaaaca gcggcgcaat ggcggccgca 1140
tctgatgtct ttgcttggcg aatgttcatc ttatttcttc ctccctctca ataatttttt 1200
cattctatcc cttttctgta aagtttattt ttcagaatac ttttatcatc atgctttgaa 1260
aaaatatcac gataatatcc attgttctca cggaagcaca cgcaggtcat ttgaacgaat 1320
tttttcgaca ggaatttgcc gggactcagg agcatttaac ctaaaaaagc atgacatttc 1380
agcataatga acatttactc atgtctattt tcgttctttt ctgtatgaaa atagttattt 1440
cgagtctcta cggaaatagc gagagatgat atacctaaat agagataaaa tcatctcaaa 1500
aaaatgggtc tactaaaata ttattccatc tattacaata aattcacaga atagtctttt 1560
aagtaagtct actctgaatt tttttaaaag gagagggtaa agagtgtcat taccgttctt 1620
aacttctgca ccgggaaagg ttattatttt tggtgaacac tctgctgtgt acaacaagcc 1680
tgccgtcgct gctagtgtgt ctgcgttgag aacctacctg ctaataagcg agtcatctgc 1740
accagatact attgaattgg acttcccgga cattagcttt aatcataagt ggtccatcaa 1800
tgatttcaat gccatcaccg aggatcaagt aaactcccaa aaattggcca aggctcaaca 1860
agccaccgat ggcttgtctc aggaactcgt tagtcttttg gatccgttgt tagctcaact 1920
atccgaatcc ttccactacc atgcagcgtt ttgtttcctg tatatgtttg tttgcctatg 1980
cccccatgcc aagaatatta agttttcttt aaagtctact ttacccatcg gtgctgggtt 2040
gggctcaagc gcctctattt ctgtatcact ggccttagct atggcctact tggggggggtt 2100 aataggatct aatgacttgg aaaagctgtc agaaaacgat aagcatatag tgaatcaatg 2160
ggccttcata ggtgaaaagt gtattcacgg taccccttca ggaatagata acgctgtggc 2220
cacttatggt aatgccctgc tatttgaaaa agactcacat aatggaacaa taaacacaaa 2280
caattttaag ttcttagatg atttcccagc cattccaatg atcctaacct atactagaat 2340
tccaaggtct acaaaagatc ttgttgctcg cgttcgtgtg ttggtcaccg agaaatttcc 2400
tgaagttatg aagccaattc tagatgccat gggtgaatgt gccctacaag gcttagagat 2460
catgactaag ttaagtaaat gtaaaggcac cgatgacgag gctgtagaaa ctaataatga 2520
actgtatgaa caactattgg aattgataag aataaatcat ggactgcttg tctcaatcgg 2580
tgtttctcat cctggattag aacttattaa aaatctgagc gatgatttga gaattggctc 2640
cacaaaactt accggtgctg gtggcggcgg ttgctctttg actttgttac gaagagacat 2700
tactcaagag caaattgaca gcttcaaaaa gaaattgcaa gatgatttta gttacgagac 2760
atttgaaaca gacttgggtg ggactggctg ctgtttgtta agcgcaaaaa atttgaataa 2820
agatcttaaa atcaaatccc tagtattcca attatttgaa aataaaacta ccacaaagca 2880
acaaattgac gatctattat tgccaggaaa cacgaattta ccatggactt cataaaagga 2940
gagggtgtca gagttgagag ccttcagtgc cccagggaaa gcgttactag ctggtggata 3000
tttagtttta gatacaaaat atgaagcatt tgtagtcgga ttatcggcaa gaatgcatgc 3060
tgtagcccat ccttacggtt cattgcaagg gtctgataag tttgaagtgc gtgtgaaaag 3120
taaacaattt aaagatgggg agtggctgta ccatataagt cctaaaagtg gcttcattcc 3180
tgtttcgata ggcggatcta agaacccttt cattgaaaaa gttatcgcta acgtatttag 3240
ctactttaaa cctaacatgg acgactactg caatagaaac ttgttcgtta ttgatatttt 3300
ctctgatgat gcctaccatt ctcaggagga tagcgttacc gaacatcgtg gcaacagaag 3360
attgagtttt cattcgcaca gaattgaaga agttcccaaa acagggctgg gctcctcggc 3420
aggtttagtc acagttttaa ctacagcttt ggcctccttt tttgtatcgg acctggaaaa 3480
taatgtagac aaatatagag aagttattca taatttagca caagttgctc attgtcaagc 3540
tcagggtaaa attggaagcg ggtttgatgt agcggcggca gcatatggat ctatcagata 3600
tagaagattc ccacccgcat taatctctaa tttgccagat attggaagtg ctacttacgg 3660
cagtaaactg gcgcatttgg ttgatgaaga agactggaat attacgatta aaagtaacca 3720
tttaccttcg ggattaactt tatggatggg cgatattaag aatggttcag aaacagtaaa 3780
actggtccag aaggtaaaaa attggtatga ttcgcatatg ccagaaagct tgaaaatata 3840
tacagaactc gatcatgcaa attctagatt tatggatgga ctatctaaac tagatcgctt 3900
acacgagact catgacgatt acagcgatca gatatttgag tctcttgaga ggaatgactg 3960
tacctgtcaa aagtatcctg aaatcacaga agttagagat gcagttgcca caattagacg 4020
ttcctttaga aaaataacta aagaatctgg tgccgatatc gaacctcccg tacaaactag 4080
cttattggat gattgccaga ccttaaaagg agttcttact tgcttaatac ctggtgctgg 4140
tggttatgac gccattgcag tgattactaa gcaagatgtt gatcttaggg ctcaaaccgc 4200
taatgacaaa agattttcta aggttcaatg gctggatgta actcaggctg actggggtgt 4260
taggaaagaa aaagatccgg aaacttatct tgataaataa aaggagaggg tgaccgttta 4320
cacagcatcc gttaccgcac ccgtcaacat cgcaaccctt aagtattggg ggaaaaggga 4380
cacgaagttg aatctgccca ccaattcgtc catatcagtg actttatcgc aagatgacct 4440

-continued

```
cagaacgttg acctctgcgg ctactgcacc tgagtttgaa cgcgacactt tgtggttaaa   4500
tggagaacca cacagcatcg acaatgaaag aactcaaaat tgtctgcgcg acctacgcca   4560
attaagaaag gaaatggaat cgaaggacgc ctcattgccc acattatctc aatggaaact   4620
ccacattgtc tccgaaaata actttcctac agcagctggt ttagcttcct ccgctgctgg   4680
ctttgctgca ttggtctctg caattgctaa gttataccaa ttaccacagt caacttcaga   4740
aatatctaga atagcaagaa aggggtctgg ttcagcttgt agatcgttgt ttggcggata   4800
cgtggcctgg gaaatgggaa aagctgaaga tggtcatgat tccatggcag tacaaatcgc   4860
agacagctct gactggcctc agatgaaagc ttgtgtccta gttgtcagcg atattaaaaa   4920
ggatgtgagt tccactcagg gtatgcaatt gaccgtggca acctccgaac tatttaaaga   4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga aacaatcgtt gcatacacgt ttgatgcagg   5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
caacaatagt atgccccatg gtgcagtatc tagttacgcc aaattagtgc aaaaccaaac   5580
acctgaagac attttggaag agtttcctga aattattcca ttacaacaaa gacctaatac   5640
ccgatctagt gagacgtcaa atgacgaaag cggagaaaca tgtttttctg gtcatgatga   5700
ggagcaaatt aagttaatga atgaaaattg tattgttttg gattgggacg ataatgctat   5760
tggtgccggt accaagaaag tttgtcattt aatggaaaat attgaaaagg gtttactaca   5820
tcgtgcattc tccgtcttta ttttcaatga acaaggtgaa ttacttttac aacaaagagc   5880
cactgaaaaa ataactttcc ctgatctttg gactaacaca tgctgctctc atccactatg   5940
tattgatgac gaattaggtt tgaagggtaa gctagacgat aagattaagg gcgctattac   6000
tgcggcggtg agaaaactag atcatgaatt aggtattcca gaagatgaaa ctaagacaag   6060
gggtaagttt cactttttaa acagaatcca ttacatggca ccaagcaatg aaccatgggg   6120
tgaacatgaa attgattaca tcctatttta taagatcaac gctaaagaaa acttgactgt   6180
caacccaaac gtcaatgaag ttagagactt caaatgggtt tcaccaaatg atttgaaaac   6240
tatgtttgct gacccaagtt acaagtttac gccttggttt aagattattt gcgagaatta   6300
cttattcaac tggtgggagc aattagatga cctttctgaa gtggaaaatg acaggcaaat   6360
tcatagaatg ctataaaaaa aaccggcctt ggccccgccg gttttttatt atttttcttc   6420
ctccgcatgt tcaatccgct ccataatcga cggatggctc cctctgaaaa ttttaacgag   6480
aaacggcggg ttgacccggc tcagtcccgt aacggccaag tcctgaaacg tctcaatcgc   6540
cgcttcccgg tttccggtca gctcaatgcc gtaacggtcg gcggcgtttt cctgataccg   6600
ggagacggca ttcgtaattt gaatacatac gaacaaatta ataaagtgaa aaaaatactt   6660
cggaaacatt taaaaaataa ccttattggt acttacatgt ttggatcagg agttgagagt   6720
ggactaaaac caaatagtga tcttgacttt ttagtcgtcg tatctgaacc attgacagat   6780
caaagtaaag aaatacttat acaaaaaatt agacctattt caaaaaaaat aggagataaa   6840
```

```
agcaacttac gatatattga attaacaatt attattcagc aagaaatggt accgtggaat   6900
catcctccca aacaagaatt tatttatgga gaatggttac aagagcttta tgaacaagga   6960
tacattcctc agaaggaatt aaattcagat ttaaccataa tgctttacca agcaaaacga   7020
aaaaataaaa gaatatacgg aaattatgac ttagaggaat tactacctga tattccattt   7080
tctgatgtga gaagagccat tatggattcg tcagaggaat taatagataa ttatcaggat   7140
gatgaaacca actctatatt aactttatgc cgtatgattt taactatgga cacgggtaaa   7200
atcataccaa aagatattgc gggaaatgca gtggctgaat cttctccatt agaacatagg   7260
gagagaattt tgttagcagt tcgtagttat cttggagaga atattgaatg gactaatgaa   7320
aatgtaaatt taactataaa ctatttaaat aacagattaa aaaaattata atgtaacctt   7380
tgctttcaaa tgagtagaaa taatgcacat ccatgtttgt atcgtgcaaa taaagtgttt   7440
catccgtagg aaaaaatgac tttagtatct gttccgcttt ttctgatgaa atgtgctccc   7500
cgacaaaatt gaatgaatca tggacatttg ctggctttga tacagcgaaa gcagccgttc   7560
ctatgttata tatcggattt aacagcagga caaaaaacac catgacagcc atcgtcaccc   7620
acttattcac acgcacataa acctttcctg acttttggaa cagatgatag ctcatcaaaa   7680
atcccgccat tgccaaataa atcgtatatg gcattactgc accataatct tttgagattt   7740
gattgggata tggcgcaagc agcaagacaa gcagtccgat aatcagcgta taaaataagc   7800
ctagtaagat cttatccgtt ctccaataca gcttgaaaaa cactacattc aacgcaatgg   7860
gaagagtgat gatgaaaaac agaaacacga atgcaatcgg ctccatccca tccgggtatt   7920
ccttccaata cgaaaagaaa ctaaaaatca tttgtacgat cggcaaactg acaacagcaa   7980
ggtcgaacgt ataaaactta ccctttccgc catgatcacg cggcatcagc atatagtgaa   8040
aagccgtcag cagcacatat ccgtataaca aaaaatgcag cagcggcagc agttcttttc   8100
cgtcctctct taagtaagcg ctggtgaagt ttgttgattg cacctggtga ataagttcaa   8160
cagacactcc cgccagcagc acaatccgca atataacacc cgccaagaac attgtgcgct   8220
gccggtttat tttgggatga tgcaccaaaa gatataagcc cgccagaaca acaattgacc   8280
attgaatcag cagggtgctt tgtctgctta atataaaata acgttcgaaa tgcaatacat   8340
aatgactgaa taactccaac acgaacaaca aaagtgcgca ttttataaaa gctaatgatt   8400
cagtccacat aattgataga cgaattctgc tacaggtcac gtggctatgt gaaggatcgc   8460
gcgtccagtt aagagcaaaa acattgacaa aaaaatttat ttatgctaaa atttactatt   8520
aatatatttg tatgtataat aagattctcc tggccagggg aatcttattt tttgtggagg   8580
atcatttcat gaggaaaaat gagtccagct taacgtctct aatttcagct tttgcccgtg   8640
catatcacag ccgatatgac acacctctta tttttgatga ttttatcgca aaagatctca   8700
ttaacgaaaa agagtttatc gacatcagta aaaatatgat tcaagaaata tcgtttttca   8760
acaaagagat cgccgaacgt cttcaaaatg atcctgaaaa aatattaaaa tgggttgcac   8820
aaatccagct gtctccaacg cccctagcac gtgcttctta ttgtgaaaaa gtcttgcaca   8880
acgaattaat cctgggggca aaacagtatg tcattcttgg agcgggactg gatactttct   8940
gctttcggca tccagaatta gaaaacagct tacaggtttt cgaggttgat catccggcca   9000
cacagcaatt gaaaaaaaat aagctgaagg atgcaaatct gacaattccg ggtcatcttc   9060
attttgttcc tatggatttc accaaaacgt tttcgtatga tcctctctta gatgaaggat   9120
ttaaaaacac aaaaacattc ttcagccttc tcggagtgtc ttattatgta acacgggaag   9180
```

aaaatgcaag cttgatcagc aatttatttt ctcatgtccc gcctggaagc tctattgttt 9240
ttgattatgc ggacgaaaca ctttttacag caaaagggac gtcgaatcga gttgaacata 9300
tggtgaagat ggctgccgca agcggggaac cgatgaaatc atgtttcact tatcaagaga 9360
ttgaacatct g 9371

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttta gtcgctgaac atgtgctctg 1200
tttctaccga gaacgtttcc ttcactgaga cggaaaccga ggcacgtcgt agcgcgaact 1260
acgagccgaa tagctgggac tacgatttcc tgctgtcttc cgatactgac gaatctattg 1320
aggtgtacaa agacaaagca aagaaactgg aggctgaagt gcgccgcgaa attaacaacg 1380
agaaagctga attcctgact ctgctggagc tgatcgataa cgtacagcgc ctgggtctgg 1440
gttaccgctt cgaatctgat atccgtcgcg cactggatcg tttcgtaagc agcggcggtt 1500
tcgatggcgt gaccaaaacg agcctgcacg ctaccgcgct gtccttccgt ctgctgcgtc 1560
agcacggctt cgaagtttct caggaagcat tctccggttt caaagatcaa aacggtaact 1620
tcctggaaaa cctgaaagaa gacactaagg cgatcctgag cctgtatgag gcaagctttc 1680
tggccctgga gggtgagaac atcctggatg aggcgcgcgt attcgccatc tcccatctga 1740
aagagctgtc tgaagagaaa atcggtaagg aactggcaga gcaggttaat cacgcactgg 1800
aactgccgct gcatcgtcgt acccagcgtc tggaggcggt ttggtccatc gaagcgtacc 1860

```
gcaaaaagga ggatgctaac caggttctgc tggaactggc catcctggac tacaacatga   1920
tccagtccgt ttaccagcgt gatctgcgtg aaacctcccg ttggtggcgc cgtgtgggcc   1980
tggcgaccaa actgcacttc gctaaggacc gcctgattga gtctttttac tgggcagtcg   2040
gcgttgcgtt cgaacctcag tattctgact gccgtaacag cgttgcgaaa atgttcagct   2100
tcgttactat tatcgacgac atctacgacg tttacggtac tctggacgag ctggaactgt   2160
ttaccgacgc tgtcgaacgt tgggatgtta acgccatcaa cgatctgcct gactacatga   2220
aactgtgctt cctggcactg tataacacga tcaacgaaat tgcatacgac aacctgaaag   2280
acaaaggtga aaacatcctg ccgtacctga ctaaagcgtg ggcggatctg tgtaacgctt   2340
ttctgcaaga agcgaaatgg ctgtataaca aatccactcc gacctttgac gattatttcg   2400
gcaatgcctg gaaatccagc tctggcccgc tgcaactgat cttcgcttat tttgcggttg   2460
tccaaaacat caaaaaggag gaaattgaaa acctgcaaaa ataccacgat atcattagcc   2520
gtccttctca tatctttcgc ctgtgcaacg acctggcaag cgcgtccgca gagatcgcac   2580
gtggcgaaac cgctaactct gtttcctgct acatgcgcac caagggcatt tccgaagagc   2640
tggcaaccga gagcgtaatg aatctgatcg acgaaacctg taagaaaatg aacaaagaaa   2700
aactgggtgg ctccctgttc gctaaaccgt tcgtagagac tgctattaac ctggcacgtc   2760
agagccactg cacctaccac aatggtgacg cacatactag cccggatgaa ctgactcgta   2820
aacgtgtact gtctgttatc accgaaccga ttctgccgtt cgaacgttaa ctgcagcgtc   2880
aatcgaaagg gcgacacaaa atttattcta aatgcataat aaatactgat aacatcttat   2940
agtttgtatt atattttgta ttatcgttga catgtataat tttgatatca aaaactgatt   3000
ttccctttat tattttcgag atttattttc ttaattctct ttaacaaact agaaatattg   3060
tatatacaaa aaatcataaa taatagatga atagtttaat tataggtgtt catcaatcga   3120
aaaagcaacg tatcttattt aaagtgcgtt gcttttttct catttataag gttaaataat   3180
tctcatatat caagcaaagt gacaggcgcc cttaaatatt ctgacaaatg ctctttccct   3240
aaactccccc cataaaaaaa cccgccgaag cgggttttta cgttatttgc ggattaacga   3300
ttactcgtta tcagaaccgc ccagggggcc cgagcttaag actggccgtc gttttacaac   3360
acagaaagag tttgtagaaa cgcaaaaagg ccatccgtca ggggccttct gcttagtttg   3420
atgcctggca gttccctact ctcgccttcc gcttcctcgc tcactgactc gctgcgctcg   3480
gtcgttcggc tgcggcgagc ggtatcagct cactcaaagg cggtaatacg gttatccaca   3540
gaatcagggg ataacgcagg aaagaacatg tgagcaaaag gccagcaaaa ggccaggaac   3600
cgtaaaaagg ccgcgttgct ggcgtttttc cataggctcc gcccccctga cgagcatcac   3660
aaaaatcgac gctcaagtca gaggtggcga aacccgacag gactataaag ataccaggcg   3720
tttccccctg gaagctccct cgtgcgctct cctgttccga ccctgccgct taccggatac   3780
ctgtccgcct ttctcccttc gggaagcgtg gcgctttctc atagctcacg ctgtaggtat   3840
ctcagttcgg tgtaggtcgt tcgctccaag ctgggctgtg tgcacgaacc ccccgttcag   3900
cccgaccgct gcgccttatc cggtaactat cgtcttgagt ccaacccggt aagacacgac   3960
ttatcgccac tggcagcagc cactggtaac aggattagca gagcgaggta tgtaggcggt   4020
gctacagagt tcttgaagtg gtgggctaac tacggctaca ctagaagaac agtatttggt   4080
atctgcgctc tgctgaagcc agttaccttc ggaaaaagag ttggtagctc ttgatccggc   4140
aaacaaacca ccgctggtag cggtggtttt tttgtttgca agcagcagat tacgcgcaga   4200
```

aaaaaaggat ctcaagaaga tcctttgatc ttttctacgg ggtctgacgc tcagtggaac 4260
gacgcgcgcg taactcacgt taagggattt tggtcatgag cttgcgccgt cccgtcaagt 4320
cagcgtaatg ctctgcttt 4339

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgtgctc 420
tgtttctacc gagaacgttt ccttcactga gacggaaacc gaggcacgtc gtagcgcgaa 480
ctacgagccg aatagctggg actacgattt cctgctgtct tccgatactg acgaatctat 540
tgaggtgtac aaagacaaag caaagaaact ggaggctgaa gtgcgccgcg aaattaacaa 600
cgagaaagct gaattcctga ctctgctgga gctgatcgat aacgtacagc gcctgggtct 660
gggttaccgc ttcgaatctg atatccgtcg cgcactggat cgtttcgtaa gcagcggcgg 720
tttcgatggc gtgaccaaaa cgagcctgca cgctaccgcg ctgtccttcc gtctgctgcg 780
tcagcacggc ttcgaagttt ctcaggaagc attctccggt ttcaaagatc aaaacggtaa 840
cttcctggaa aacctgaaag aagacactaa ggcgatcctg agcctgtatg aggcaagctt 900
tctggccctg gagggtgaga acatcctgga tgaggcgcgc gtattcgcca tctcccatct 960
gaaagagctg tctgaagaga aaatcggtaa ggaactggca gagcaggtta atcacgcact 1020
ggaactgccg ctgcatcgtc gtacccagcg tctggaggcg gtttggtcca tcgaagcgta 1080
ccgcaaaaag gaggatgcta accaggttct gctggaactg gccatcctgg actacaacat 1140
gatccagtcc gtttaccagc gtgatctgcg tgaaacctcc cgttggtggc gccgtgtggg 1200
cctggcgacc aaactgcact tcgctaagga ccgcctgatt gagtcttttt actgggcagt 1260
cggcgttgcg ttcgaacctc agtattctga ctgccgtaac agcgttgcga aaatgttcag 1320
cttcgttact attatcgacg acatctacga cgtttacggt actctggacg agctggaact 1380
gtttaccgac gctgtcgaac gttgggatgt taacgccatc aacgatctgc ctgactacat 1440
gaaactgtgc ttcctggcac tgtataacac gatcaacgaa attgcatacg acaacctgaa 1500
agacaaaggt gaaaacatcc tgccgtacct gactaaagcg tgggcggatc tgtgtaacgc 1560
ttttctgcaa gaagcgaaat ggctgtataa caaatccact ccgacctttg acgattattt 1620
cggcaatgcc tggaaatcca gctctggccc gctgcaactg atcttcgctt attttgcggt 1680
tgtccaaaac atcaaaaagg aggaaattga aaacctgcaa aaataccacg atatcattag 1740
ccgtccttct catatctttc gcctgtgcaa cgacctggca agcgcgtccg cagagatcgc 1800
acgtggcgaa accgctaact ctgtttcctg ctacatgcgc accaagggca tttccgaaga 1860
gctggcaacc gagagcgtaa tgaatctgat cgacgaaacc tgtaagaaaa tgaacaaaga 1920

-continued

```
aaaactgggt ggctccctgt tcgctaaacc gttcgtagag actgctatta acctggcacg   1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agctttctag aacaaaaact catctcagaa gaggatctga   2160
atagcgccgt cgaccatcat catcatcatc attgagttta aacggtctcc agcttggctg   2220
ttttggcgga tgagagaaga ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
agggaactgc caggcatcaa ataaaacgaa aggctcagtc gaaagactgg gcctttcgtt   2460
ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag gccatcctga cggatggcct ttttgcgttt ctacaaactc   2640
tttttgttta tttttctaaa tacattcaaa tatgtatccg ctcatgagac aataaccctg   2700
ataaatgctt caataatatt gaaaaaggaa gagtatgagt attcaacatt tccgtgtcgc   2760
ccttattccc ttttttgcgg cattttgcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atcccgtgtt gacgccgggc aagagcaact   3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
taacactgcg gccaacttac ttctgacaac gatcggagga ccgaaggagc taaccgcttt   3180
tttgcacaac atgggggatc atgtaactcg ccttgatcgt tgggaaccgg agctgaatga   3240
agccatacca aacgacgagc gtgacaccac gatgcctgta gcaatggcaa caacgttgcg   3300
caaactatta actggcgaac tacttactct agcttcccgg caacaattaa tagactggat   3360
ggaggcggat aaagttgcag gaccacttct gcgctcggcc cttccggctg gctggtttat   3420
tgctgataaa tctggagccg gtgagcgtgg gtctcgcggt atcattgcag cactggggcc   3480
agatggtaag ccctcccgta tcgtagttat ctacacgacg gggagtcagg caactatgga   3540
tgaacgaaat agacagatcg ctgagatagg tgcctcactg attaagcatt ggtaactgtc   3600
agaccaagtt tactcatata tactttagat tgatttaaaa cttcattttt aatttaaaag   3660
gatctaggtg aagatccttt ttgataatct catgaccaaa atcccttaac gtgagttttc   3720
gttccactga gcgtcagacc ccgtagaaaa gatcaaagga tcttcttgag atcctttttt   3780
tctgcgcgta atctgctgct tgcaaacaaa aaaaccaccg ctaccagcgg tggtttgttt   3840
gccggatcaa gagctaccaa ctctttttcc gaaggtaact ggcttcagca gagcgcagat   3900
accaaatact gtccttctag tgtagccgta gttaggccac cacttcaaga actctgtagc   3960
accgcctaca tacctcgctc tgctaatcct gttaccagtg gctgctgcca gtggcgataa   4020
gtcgtgtctt accgggttgg actcaagacg atagttaccg gataaggcgc agcggtcggg   4080
ctgaacgggg ggttcgtgca cacagcccag cttggagcga acgacctaca ccgaactgag   4140
atacctacag cgtgagctat gagaaagcgc cacgcttccc gaagggagaa aggcggacag   4200
gtatccggta agcggcaggg tcggaacagg agagcgcacg agggagcttc caggggggaaa   4260
```

cgcctggtat ctttatagtc ctgtcgggtt tcgccacctc tgacttgagc gtcgattttt 4320
gtgatgctcg tcaggggggc ggagcctatg gaaaaacgcc agcaacgcgg cctttttacg 4380
gttcctggcc ttttgctggc cttttgctca catgttcttt cctgcgttat cccctgattc 4440
tgtggataac cgtattaccg cctttgagtg agctgatacc gctcgccgca gccgaacgac 4500
cgagcgcagc gagtcagtga gcgaggaagc ggaagagcgc ctgatgcggt attttctcct 4560
tacgcatctg tgcggtattt cacaccgcat atggtgcact ctcagtacaa tctgctctga 4620
tgccgcatag ttaagccagt atacactccg ctatcgctac gtgactgggt catggctgcg 4680
ccccgacacc cgccaacacc cgctgacgcg ccctgacggg cttgtctgct cccggcatcc 4740
gcttacagac aagctgtgac cgtctccggg agctgcatgt gtcagaggtt ttcaccgtca 4800
tcaccgaaac gcgcgaggca gcagatcaat tcgcgcgcga aggcgaagcg gcatgcattt 4860
acgttgacac catcgaatgg tgcaaaacct ttcgcggtat ggcatgatag cgcccggaag 4920
agagtcaatt cagggtggtg aatgtgaaac cagtaacgtt atacgatgtc gcagagtatg 4980
ccggtgtctc ttatcagacc gtttcccgcg tggtgaacca ggccagccac gtttctgcga 5040
aaacgcggga aaaagtggaa gcggcgatgg cggagctgaa ttacattccc aaccgcgtgg 5100
cacaacaact ggcgggcaaa cagtcgttgc tgattggcgt tgccacctcc agtctggccc 5160
tgcacgcgcc gtcgcaaatt gtcgcggcga ttaaatctcg cgccgatcaa ctgggtgcca 5220
gcgtggtggt gtcgatggta gaacgaagcg gcgtcgaagc ctgtaaagcg gcggtgcaca 5280
atcttctcgc gcaacgcgtc agtgggctga tcattaacta tccgctggat gaccaggatg 5340
ccattgctgt ggaagctgcc tgcactaatg ttccggcgtt atttcttgat gtctctgacc 5400
agacacccat caacagtatt attttctccc atgaagacgg tacgcgactg ggcgtggagc 5460
atctggtcgc attgggtcac cagcaaatcg cgctgttagc gggcccatta agttctgtct 5520
cggcgcgtct gcgtctggct ggctggcata aatatctcac tcgcaatcaa attcagccga 5580
tagcggaacg ggaaggcgac tggagtgcca tgtccggttt tcaacaaacc atgcaaatgc 5640
tgaatgaggg catcgttccc actgcgatgc tggttgccaa cgatcagatg gcgctgggcg 5700
caatgcgcgc cattaccgag tccgggctgc gcgttggtgc ggatatctcg gtagtgggat 5760
acgacgatac cgaagacagc tcatgttata tcccgccgtc aaccaccatc aaacaggatt 5820
ttcgcctgct ggggcaaacc agcgtggacc gcttgctgca actctctcag ggccaggcgg 5880
tgaagggcaa tcagctgttg cccgtctcac tggtgaaaag aaaaaccacc ctggcgccca 5940
atacgcaaac cgcctctccc cgcgcgttgg ccgattcatt aatgcagctg gcacgacagg 6000
tttcccgact ggaaagcggg cagtgagcgc aacgcaatta atgtgagtta gcgcgaattg 6060
atctg 6065

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50
ttgtctgctc ccggcatccg cttacagaca agctgtgacc gtctccggga gctgcatgtg 60
tcagaggttt tcaccgtcat caccgaaacg cgcgaggcag cagatcaatt cgcgcgcgaa 120
ggcgaagcgg catgcattta cgttgacacc atcgaatggt gcaaaacctt tcgcggtatg 180
gcatgatagc gcccggaaga gagtcaattc agggtggtga atgtgaaacc agtaacgtta 240

-continued

```
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca aacaggattt tcgcctgctg gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
```

```
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcatcgc ccttaggagg taaaaaaaaa   3480
tgactgccga caacaatagt atgccccatg gtgcagtatc tagttacgcc aaattagtgc   3540
aaaaccaaac acctgaagac attttggaag agtttcctga aattattcca ttacaacaaa   3600
gacctaatac ccgatctagt gagacgtcaa atgacgaaag cggagaaaca tgtttttctg   3660
gtcatgatga ggagcaaatt aagttaatga atgaaaattg tattgttttg gattgggacg   3720
ataatgctat tggtgccggt accaagaaag tttgtcattt aatggaaaat attgaaaagg   3780
gtttactaca tcgtgcattc tccgtcttta ttttcaatga acaaggtgaa ttacttttac   3840
aacaaagagc cactgaaaaa ataactttcc ctgatctttg gactaacaca tgctgctctc   3900
atccactatg tattgatgac gaattaggtt tgaagggtaa gctagacgat aagattaagg   3960
gcgctattac tgcggcggtg agaaaactag atcatgaatt aggtattcca gaagatgaaa   4020
ctaagacaag ggtaagtttt cactttttaa acagaatcca ttacatggca ccaagcaatg   4080
aaccatgggg tgaacatgaa attgattaca tcctatttta taagatcaac gctaaagaaa   4140
acttgactgt caacccaaac gtcaatgaag ttagagactt caaatgggtt tcaccaaatg   4200
atttgaaaac tatgtttgct gacccaagtt acaagtttac gccttggttt aagattattt   4260
gcgagaatta cttattcaac tggtgggagc aattagatga cctttctgaa gtggaaaatg   4320
acaggcaaat tcatagaatg ctataacaac gcgtcctgca gctggtacca tatgggaatt   4380
cgaagctttc tagaacaaaa actcatctca gaagaggatc tgaatagcgc cgtcgaccat   4440
catcatcatc atcattgagt ttaaacggtc tccagcttgg ctgttttggc ggatgagaga   4500
agattttcag cctgatacag attaaatcag aacgcagaag cggtctgata aaacagaatt   4560
tgcctggcgg cagtagcgcg gtggtcccac ctgaccccat gccgaactca gaagtgaaac   4620
gccgtagcgc cgatggtagt gtggggtctc cccatgcgag agtagggaac tgccaggcat   4680
caaataaaac gaaaggctca gtcgaaagac tgggcctttc gttttatctg ttgtttgtcg   4740
gtgaacgctc tcctgagtag gacaaatccg ccgggagcgg atttgaacgt tgcgaagcaa   4800
cggcccggag ggtggcgggc aggacgcccg ccataaactg ccaggcatca aattaagcag   4860
aaggccatcc tgacggatgg cctttttgcg tttctacaaa ctctttttgt ttatttttct   4920
aaatacattc aaatatgtat ccgcttaacc ggaattgcca gctggggcgc cctctggtaa   4980
```

ggttgggaag ccctgcaaag taaactggat ggctttctcg ccgccaagga tctgatggcg 5040
caggggatca agctctgatc aagagacagg atgaggatcg tttcgcatga ttgaacaaga 5100
tggattgcac gcaggttctc cggccgcttg ggtggagagg ctattcggct atgactgggc 5160
acaacagaca atcggctgct ctgatgccgc cgtgttccgg ctgtcagcgc aggggcgccc 5220
ggttcttttt gtcaagaccg acctgtccgg tgccctgaat gaactgcaag acgaggcagc 5280
gcggctatcg tggctggcca cgacgggcgt tccttgcgca gctgtgctcg acgttgtcac 5340
tgaagcggga agggactggc tgctattggg cgaagtgccg gggcaggatc tcctgtcatc 5400
tcaccttgct cctgccgaga aagtatccat catggctgat gcaatgcggc ggctgcatac 5460
gcttgatccg gctacctgcc cattcgacca ccaagcgaaa catcgcatcg agcgagcacg 5520
tactcggatg gaagccggtc ttgtcgatca ggatgatctg gacgaagagc atcaggggct 5580
cgcgccagcc gaactgttcg ccaggctcaa ggcgagcatg cccgacggcg aggatctcgt 5640
cgtgacccat ggcgatgcct gcttgccgaa tatcatggtg gaaaatggcc gcttttctgg 5700
attcatcgac tgtggccggc tgggtgtggc ggaccgctat caggacatag cgttggctac 5760
ccgtgatatt gctgaagagc ttggcggcga atgggctgac cgcttcctcg tgctttacgg 5820
tatcgccgct cccgattcgc agcgcatcgc cttctatcgc cttcttgacg agttcttctg 5880
acatgaccaa aatcccttaa cgtgagtttt cgttccactg agcgtcagac cccgtagaaa 5940
agatcaaagg atcttcttga gatccttttt ttctgcgcgt aatctgctgc ttgcaaacaa 6000
aaaaaccacc gctaccagcg gtggtttgtt tgccggatca agagctacca actctttttc 6060
cgaaggtaac tggcttcagc agagcgcaga taccaaatac tgtccttcta gtgtagccgt 6120
agttaggcca ccacttcaag aactctgtag caccgcctac atacctcgct ctgctaatcc 6180
tgttaccagt ggctgctgcc agtggcgata agtcgtgtct taccgggttg gactcaagac 6240
gatagttacc ggataaggcg cagcggtcgg gctgaacggg gggttcgtgc acacagccca 6300
gcttggagcg aacgacctac accgaactga gatacctaca gcgtgagcta tgagaaagcg 6360
ccacgcttcc cgaagggaga aaggcggaca ggtatccggt aagcggcagg gtcggaacag 6420
gagagcgcac gagggagctt ccagggggaa acgcctggta tctttatagt cctgtcgggt 6480
ttcgccacct ctgacttgag cgtcgatttt tgtgatgctc gtcagggggg cggagcctat 6540
ggaaaaacgc cagcaacgcg gcctttttac ggttcctggc cttttgctgg ccttttgctc 6600
acatgttctt tcctgcgtta tcccctgatt ctgtggataa ccgtattacc gcctttgagt 6660
gagctgatac cgctcgccgc agccgaacga ccgagcgcag cgagtcagtg agcgaggaag 6720
cggaagagcg cctgatgcgg tattttctcc ttacgcatct gtgcggtatt tcacaccgca 6780
tatggtgcac tctcagtaca atctgctctg atgccgcata gttaagccag tatacactcc 6840
gctatcgcta cgtgactggg tcatggctgc gccccgacac ccgccaacac ccgctgacgc 6900
gccctgacgg gc 6912

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51
ttgtctgctc ccggcatccg cttacagaca agctgtgacc gtctccggga gctgcatgtg 60

-continued

```
tcagaggttt tcaccgtcat caccgaaacg cgcgaggcag cagatcaatt cgcgcgcgaa    120
ggcgaagcgg catgcattta cgttgacacc atcgaatggt gcaaaacctt tcgcggtatg    180
gcatgatagc gcccggaaga gagtcaattc agggtggtga atgtgaaacc agtaacgtta    240
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca aacaggattt tcgcctgctg gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
```

-continued

```
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcattcg cccttaggag gtaaaaaaac   3480
atgagttttg atattgccaa atacccgacc ctggcactgg tcgactccac ccaggagtta   3540
cgactgttgc cgaaagagag tttaccgaaa ctctgcgacg aactgcgccg ctatttactc   3600
gacagcgtga gccgttccag cgggcacttc gcctccgggc tgggcacggt cgaactgacc   3660
gtggcgctgc actatgtcta caacaccccg tttgaccaat tgatttggga tgtggggcat   3720
caggcttatc cgcataaaat tttgaccgga cgccgcgaca aaatcggcac catccgtcag   3780
aaaggcggtc tgcacccgtt cccgtggcgc ggcgaaagcg aatatgacgt attaagcgtc   3840
gggcattcat caacctccat cagtgccgga attggtattg cggttgctgc cgaaaaagaa   3900
ggcaaaaatc gccgcaccgt ctgtgtcatt ggcgatggcg cgattaccgc aggcatggcg   3960
tttgaagcga tgaatcacgc gggcgatatc cgtcctgata tgctggtgat tctcaacgac   4020
aatgaaatgt cgatttccga aaatgtcggc gcgctcaaca accatctggc acagctgctt   4080
tccggtaagc tttactcttc actgcgcgaa ggcgggaaaa aagttttctc tggcgtgccg   4140
ccaattaaag agctgctcaa acgcaccgaa gaacatatta aaggcatggt agtgcctggc   4200
acgttgtttg aagagctggg ctttaactac atcggcccgg tggacggtca cgatgtgctg   4260
gggcttatca ccacgctaaa gaacatgcgc gacctgaaag gcccgcagtt cctgcatatc   4320
atgaccaaaa aaggtcgtgg ttatgaaccg gcagaaaaag acccgatcac tttccacgcc   4380
gtgcctaaat ttgatccctc cagcggttgt ttgccgaaaa gtagcggcgg tttgccgagc   4440
tattcaaaaa tctttggcga ctggttgtgc gaaacggcag cgaaagacaa caagctgatg   4500
gcgattactc cggcgatgcg tgaaggttcc ggcatggtcg agttttcacg taaattcccg   4560
gatcgctact tcgacgtggc aattgccgag caacacgcgg tgacctttgc tgcgggtctg   4620
gcgattggtg ggtacaaacc cattgtcgcg atttactcca ctttcctgca acgcgcctat   4680
gatcaggtgc tgcatgacgt ggcgattcaa aagcttccgg tcctgttcgc catcgaccgc   4740
gcgggcattg ttggtgctga cggtcaaacc catcagggtg cttttgatct ctcttacctg   4800
```

-continued

```
cgctgcatac cggaaatggt cattatgacc ccgagcgatg aaaacgaatg tcgccagatg   4860
ctctataccg gctatcacta taacgatggc ccgtcagcgg tgcgctaccc gcgtggcaac   4920
gcggtcggcg tggaactgac gccgctggaa aaactaccaa ttggcaaagg cattgtgaag   4980
cgtcgtggcg agaaactggc gatccttaac tttggtacgc tgatgccaga agcggcgaaa   5040
gtcgccgaat cgctgaacgc cacgctggtc gatatgcgtt ttgtgaaacc gcttgatgaa   5100
gcgttaattc tggaaatggc cgccagccat gaagcgctgg tcaccgtaga agaaaacgcc   5160
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcggcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
cgcagaagcg gtctgataaa acagaatttg cctggcggca gtagcgcggt ggtcccacct   5580
gaccccatgc cgaactcaga agtgaaacgc cgtagcgccg atggtagtgt ggggtctccc   5640
catgcgagag tagggaactg ccaggcatca aataaaacga aaggctcagt cgaaagactg   5700
ggcctttcgt tttatctgtt gtttgtcggt gaacgctctc ctgagtagga caaatccgcc   5760
gggagcggat ttgaacgttg cgaagcaacg gcccggaggg tggcgggcag gacgcccgcc   5820
ataaactgcc aggcatcaaa ttaagcagaa ggccatcctg acggatggcc tttttgcgtt   5880
tctacaaact ctttttgttt atttttctaa atacattcaa atatgtatcc gcttaaccgg   5940
aattgccagc tggggcgccc tctggtaagg ttgggaagcc ctgcaaagta aactggatgg   6000
ctttctcgcc gccaaggatc tgatggcgca ggggatcaag ctctgatcaa gagacaggat   6060
gaggatcgtt tcgcatgatt gaacaagatg gattgcacgc aggttctccg gccgcttggg   6120
tggagaggct attcggctat gactgggcac aacagacaat cggctgctct gatgccgccg   6180
tgttccggct gtcagcgcag gggcgcccgg ttctttttgt caagaccgac ctgtccggtg   6240
ccctgaatga actgcaagac gaggcagcgc ggctatcgtg gctggccacg acgggcgttc   6300
cttgcgcagc tgtgctcgac gttgtcactg aagcgggaag ggactggctg ctattgggcg   6360
aagtgccggg gcaggatctc ctgtcatctc accttgctcc tgccgagaaa gtatccatca   6420
tggctgatgc aatgcggcgg ctgcatacgc ttgatccggc tacctgccca ttcgaccacc   6480
aagcgaaaca tcgcatcgag cgagcacgta ctcggatgga agccggtctt gtcgatcagg   6540
atgatctgga cgaagagcat caggggctcg cgccagccga actgttcgcc aggctcaagg   6600
cgagcatgcc cgacggcgag gatctcgtcg tgacccatgg cgatgcctgc ttgccgaata   6660
tcatggtgga aaatggccgc ttttctggat tcatcgactg tggccggctg ggtgtggcgg   6720
accgctatca ggacatagcg ttggctaccc gtgatattgc tgaagagctt ggcggcgaat   6780
gggctgaccg cttcctcgtg ctttacggta tcgccgctcc cgattcgcag cgcatcgcct   6840
tctatcgcct tcttgacgag ttcttctgac gcatgaccaa aatcccttaa cgtgagtttt   6900
cgttccactg agcgtcagac cccgtagaaa agatcaaagg atcttcttga gatccttttt   6960
ttctgcgcgt aatctgctgc ttgcaaacaa aaaaaccacc gctaccagcg gtggtttgtt   7020
tgccggatca agagctacca actctttttc cgaaggtaac tggcttcagc agagcgcaga   7080
taccaaatac tgtccttcta gtgtagccgt agttaggcca ccacttcaag aactctgtag   7140
caccgcctac atacctcgct ctgctaatcc tgttaccagt ggctgctgcc agtggcgata   7200
```

agtcgtgtct taccgggttg gactcaagac gatagttacc ggataaggcg cagcggtcgg 7260
gctgaacggg gggttcgtgc acacagccca gcttggagcg aacgacctac accgaactga 7320
gatacctaca gcgtgagcta tgagaaagcg ccacgcttcc cgaagggaga aaggcggaca 7380
ggtatccggt aagcggcagg gtcggaacag gagagcgcac gagggagctt ccagggggaa 7440
acgcctggta tctttatagt cctgtcgggt ttcgccacct ctgacttgag cgtcgatttt 7500
tgtgatgctc gtcagggggg cggagcctat ggaaaaacgc cagcaacgcg gcctttttac 7560
ggttcctggc cttttgctgg ccttttgctc acatgttctt tcctgcgtta tcccctgatt 7620
ctgtggataa ccgtattacc gcctttgagt gagctgatac cgctcgccgc agccgaacga 7680
ccgagcgcag cgagtcagtg agcgaggaag cggaagagcg cctgatgcgg tattttctcc 7740
ttacgcatct gtgcggtatt tcacaccgca tatggtgcac tctcagtaca atctgctctg 7800
atgccgcata gttaagccag tatacactcc gctatcgcta cgtgactggg tcatggctgc 7860
gccccgacac ccgccaacac ccgctgacgc gccctgacgg gc 7902

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52
ctggcgtaat agcgaagagg cccgcaccga tcgcccttcc caacagttgc gcagcctgaa 60
tggcgaatgg cgcctgatgc ggtattttct ccttacgcat ctgtgcggta tttcacaccg 120
catatggtgc actctcagta caatctgctc tgatgccgca tagttaagcc agccccgaca 180
cccgccaaca cccgctgacg agcttagtaa agccctcgct agattttaat gcggatgttg 240
cgattacttc gccaactatt gcgataacaa gaaaaagcca gcctttcatg atatatctcc 300
caatttgtgt agggcttatt atgcacgctt aaaaataata aaagcagact tgacctgata 360
gtttggctgt gagcaattat gtgcttagtg catctaacgc ttgagttaag ccgcgccgcg 420
aagcggcgtc ggcttgaacg aattgttaga cattatttgc cgactacctt ggtgatctcg 480
cctttcacgt agtggacaaa ttcttccaac tgatctgcgc gcgaggccaa gcgatcttct 540
tcttgtccaa gataagcctg tctagcttca agtatgacgg gctgatactg ggccggcagg 600
cgctccattg cccagtcggc agcgacatcc ttcggcgcga ttttgccggt tactgcgctg 660
taccaaatgc gggacaacgt aagcactaca tttcgctcat cgccagccca gtcgggcggc 720
gagttccata gcgttaaggt ttcatttagc gcctcaaata gatcctgttc aggaaccgga 780
tcaaagagtt cctccgccgc tggacctacc aaggcaacgc tatgttctct tgcttttgtc 840
agcaagatag ccagatcaat gtcgatcgtg gctggctcga agatacctgc aagaatgtca 900
ttgcgctgcc attctccaaa ttgcagttcg cgcttagctg gataacgcca cggaatgatg 960
tcgtcgtgca caacaatggt gacttctaca gcgcggagaa tctcgctctc tccaggggaa 1020
gccgaagttt ccaaaaggtc gttgatcaaa gctcgccgcg ttgtttcatc aagccttacg 1080
gtcaccgtaa ccagcaaatc aatatcactg tgtggcttca ggccgccatc cactgcggag 1140
ccgtacaaat gtacggccag caacgtcggt tcgagatggc gctcgatgac gccaactacc 1200
tctgatagtt gagtcgatac ttcggcgatc accgcttccc tcatgatgtt taactttgtt 1260
ttagggcgac tgccctgctg cgtaacatcg ttgctgctcc ataacatcaa acatcgaccc 1320

-continued acggcgtaac gcgcttgctg cttggatgcc cgaggcatag actgtacccc aaaaaaacag 1380
tcataacaag ccatgaaaac cgccactgcg ccgttaccac cgctgcgttc ggtcaaggtt 1440
ctggaccagt tgcgtgagcg catacgctac ttgcattaca gcttacgaac cgaacaggct 1500
tatgtccact gggttcgtgc cttcatccgt ttccacggtg tgcgtcaccc ggcaaccttg 1560
ggcagcagcg aagtcgaggc atttctgtcc tggctggcga acgagcgcaa ggtttcggtc 1620
tccacgcatc gtcaggcatt ggcggccttg ctgttcttct acggcaaggt gctgtgcacg 1680
gatctgccct ggcttcagga gatcggaaga cctcggccgt cgcggcgctt gccggtggtg 1740
ctgaccccgg atgaagtggt tcgcatcctc ggttttctgg aaggcgagca tcgtttgttc 1800
gcccagcttc tgtatggaac gggcatgcgg atcagtgagg gtttgcaact gcgggtcaag 1860
gatctggatt tcgatcacgg cacgatcatc gtgcgggagg gcaagggctc caaggatcgg 1920
gccttgatgt tacccgagag cttggcaccc agcctgcgcg agcaggggaa ttaattccca 1980
cgggttttgc tgcccgcaaa cgggctgttc tggtgttgct agtttgttat cagaatcgca 2040
gatccggctt cagccggttt gccggctgaa agcgctattt cttccagaat tgccatgatt 2100
ttttccccac gggaggcgtc actggctccc gtgttgtcgg cagctttgat tcgataagca 2160
gcatcgcctg tttcaggctg tctatgtgtg actgttgagc tgtaacaagt tgtctcaggt 2220
gttcaatttc atgttctagt tgctttgttt tactggtttc acctgttcta ttaggtgtta 2280
catgctgttc atctgttaca ttgtcgatct gttcatggtg aacagctttg aatgcaccaa 2340
aaactcgtaa aagctctgat gtatctatct tttttacacc gttttcatct gtgcatatgg 2400
acagttttcc ctttgatatg taacggtgaa cagttgttct acttttgttt gttagtcttg 2460
atgcttcact gatagataca agagccataa gaacctcaga tccttccgta tttagccagt 2520
atgttctcta gtgtggttcg ttgtttttgc gtgagccatg agaacgaacc attgagatca 2580
tacttacttt gcatgtcact caaaaatttt gcctcaaaac tggtgagctg aatttttgca 2640
gttaaagcat cgtgtagtgt ttttcttagt ccgttatgta ggtaggaatc tgatgtaatg 2700
gttgttggta ttttgtcacc attcattttt atctggttgt tctcaagttc ggttacgaga 2760
tccatttgtc tatctagttc aacttggaaa atcaacgtat cagtcgggcg gcctcgctta 2820
tcaaccacca atttcatatt gctgtaagtg tttaaatctt tacttattgg tttcaaaacc 2880
cattggttaa gccttttaaa ctcatggtag ttattttcaa gcattaacat gaacttaaat 2940
tcatcaaggc taatctctat atttgccttg tgagttttct tttgtgttag ttcttttaat 3000
aaccactcat aaatcctcat agagtatttg ttttcaaaag acttaacatg ttccagatta 3060
tattttatga atttttttaa ctggaaaaga taaggcaata tctcttcact aaaaactaat 3120
tctaattttt cgcttgagaa cttggcatag tttgtccact ggaaaatctc aaagccttta 3180
accaaaggat tcctgatttc cacagttctc gtcatcagct ctctggttgc tttagctaat 3240
acaccataag cattttccct actgatgttc atcatctgag cgtattggtt ataagtgaac 3300
gataccgtcc gttctttcct tgtagggttt tcaatcgtgg ggttgagtag tgccacacag 3360
cataaaatta gcttggtttc atgctccgtt aagtcatagc gactaatcgc tagttcattt 3420
gctttgaaaa caactaattc agacatacat ctcaattggt ctaggtgatt ttaatcacta 3480
taccaattga gatgggctag tcaatgataa ttactagtcc ttttcctttg agttgtgggt 3540
atctgtaaat tctgctagac ctttgctgga aaacttgtaa attctgctag accctctgta 3600
aattccgcta gacctttgtg tgtttttttt gtttatattc aagtggttat aatttataga 3660
ataaagaaag aataaaaaaa gataaaaaga atagatccca gccctgtgta taactcacta 3720
ctttagtcag ttccgcagta ttacaaaagg atgtcgcaaa cgctgtttgc tcctctacaa 3780
aacagacctt aaaaccctaa aggcttaagt agcaccctcg caagctcggg caaatcgctg 3840
aatattcctt ttgtctccga ccatcaggca cctgagtcgc tgtctttttc gtgacattca 3900
gttcgctgcg ctcacggctc tggcagtgaa tgggggtaaa tggcactaca ggcgcctttt 3960
atggattcat gcaaggaaac tacccataat acaagaaaag cccgtcacgg gcttctcagg 4020
gcgttttatg gcgggtctgc tatgtggtgc tatctgactt tttgctgttc agcagttcct 4080
gccctctgat tttccagtct gaccacttcg gattatcccg tgacaggtca ttcagactgg 4140
ctaatgcacc cagtaaggca gcggtatcat caacaggctt acccgtctta ctgtcgggaa 4200
ttcgcgttgg ccgattcatt aatgcagatt ctgaaatgag ctgttgacaa ttaatcatcc 4260
ggctcgtata atgtgtggaa ttgtgagcgg ataacaattt cacacaggaa acagcgccgc 4320
tgagaaaaag cgaagcggca ctgctcttta acaatttatc agacaatctg tgtgggcact 4380
cgaccggaat tatcgattaa ctttattatt aaaaattaaa gaggtatata ttaatgtatc 4440
gattaaataa ggaggaataa accatgtgtg cgacctcttc tcaatttact cagattaccg 4500
agcataattc ccgtcgttcc gcaaactatc agccaaacct gtggaatttc gaattcctgc 4560
aatccctgga gaacgacctg aaagtggaaa agctggagga gaaagcgacc aaactggagg 4620
aagaagttcg ctgcatgatc aaccgtgtag acacccagcc gctgtccctg ctggagctga 4680
tcgacgatgt gcagcgcctg ggtctgacct acaaatttga aaaagacatc attaaagccc 4740
tggaaaacat cgtactgctg gacgaaaaca aaaagaacaa atctgacctg cacgcaaccg 4800
ctctgtcttt ccgtctgctg cgtcagcacg gtttcgaggt ttctcaggat gtttttgagc 4860
gtttcaagga taaagaaggt ggtttcagcg gtgaactgaa aggtgacgtc caaggcctgc 4920
tgagcctgta tgaagcgtct tacctgggtt tcgagggtga gaacctgctg gaggaggcgc 4980
gtacctttc catcacccac ctgaagaaca acctgaaaga aggcattaat accaaggttg 5040
cagaacaagt gagccacgcc ctggaactgc catatcacca gcgtctgcac cgtctggagg 5100
cacgttggtt cctggataaa tacgaaccga aagaaccgca tcaccagctg ctgctggagc 5160
tggcgaagct ggattttaac atggtacaga ccctgcacca gaaagagctg caagatctgt 5220
cccgctggtg gaccgagatg ggcctggcta gcaaactgga ttttgtacgc gaccgcctga 5280
tggaagttta tttctgggca ctgggtatgg cgccagaccc gcagtttggt gaatgtcgca 5340
aagctgttac taaaatgttt ggtctggtga cgatcatcga tgacgtgtat gacgtttatg 5400
gcactctgga cgaactgcaa ctgttcaccg atgctgtaga gcgctgggac gttaacgcta 5460
ttaacaccct gccggactat atgaaactgt gtttcctggc actgtacaac accgttaacg 5520
acacgtccta ttctattctg aaagagaaag gtcataacaa cctgtcctat ctgacgaaaa 5580
gctggcgtga actgtgcaaa gcctttctgc aagaggcgaa atggtccaac aacaaaatta 5640
tcccggcttt ctccaagtac ctggaaaacg ccagcgtttc ctcctccggt gtagcgctgc 5700
tggcgccgtc ttacttttcc gtatgccagc agcaggaaga catctccgac cacgcgctgc 5760
gttccctgac cgacttccat ggtctggtgc gttctagctg cgttatcttc cgcctgtgca 5820
acgatctggc cacctctgcg gcggagctgg aacgtggcga gactaccaat tctatcatta 5880
gctacatgca cgaaaacgat ggtaccagcg aggaacaggc ccgcgaagaa ctgcgtaaac 5940
tgatcgacgc cgaatggaaa aagatgaatc gtgaacgcgt tagcgactcc accctgctgc 6000
ctaaagcgtt catggaaatc gcagttaaca tggcacgtgt ttcccactgc acctaccagt 6060
atggcgatgg tctgggtcgc ccagactacg cgactgaaaa ccgcatcaaa ctgctgctga 6120
ttgacccttt cccgattaac cagctgatgt atgtctaact gcagctggta ccatatggga 6180
attcgaagct ttctagaaca aaaactcatc tcagaagagg atctgaatag cgccgtcgac 6240
catcatcatc atcatcattg agtttaaacg gtctccagct tggctgtttt ggcggatgag 6300
agaagatttt cagcctgata cagattaaat cagaacgcag aagcggtctg ataaaacaga 6360
atttgcctgg cggcagtagc gcggtggtcc cacctgaccc catgccgaac tcagaagtga 6420
aacgccgtag cgccgatggt agtgtggggt ctccccatgc gagagtaggg aactgccagg 6480
catcaaataa aacgaaaggc tcagtcgaaa gactgggcct ttcgttttat ctgttgtttg 6540
tcggtgaacg ctctcctgag taggacaaat ccgccgggag cggatttgaa cgttgcgaag 6600
caacggcccg gagggtggcg ggcaggacgc ccgccataaa ctgccaggca tcaaattaag 6660
cagaaggcca tcctgacgga tggccttttt gcgtttctac aaactctttt tgtttatttt 6720
tctaaataca ttcaaatatg tatccgctca tgagacaata accctgataa atgcttcaat 6780
aat 6783

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53
cccgtcttac tgtcgggaat tcgcgttggc cgattcatta atgcagatta ttgaagcatt 60
tatcagggtt attgtctcat gagcggatac atatttgaat gtatttagaa aaataaacaa 120
aaagagtttg tagaaacgca aaaaggccat ccgtcaggat ggccttctgc ttaatttgat 180
gcctggcagt ttatggcggg cgtcctgccc gccaccctcc gggccgttgc ttcgcaacgt 240
tcaaatccgc tcccggcgga tttgtcctac tcaggagagc gttcaccgac aaacaacaga 300
taaaacgaaa ggcccagtct ttcgactgag cctttcgttt tatttgatgc ctggcagttc 360
cctactctcg catggggaga ccccacacta ccatcggcgc tacggcgttt cacttctgag 420
ttcggcatgg ggtcaggtgg gaccaccgcg ctactgccgc caggcaaatt ctgttttatc 480
agaccgcttc tgcgttctga tttaatctgt atcaggctga aaatcttctc tcatccgcca 540
aaacagccaa gctggagacc gtttaaactc aatgatgatg atgatgatgg tcgacggcgc 600
tattcagatc ctcttctgag atgagttttt gttctagaaa gcttcgaatt cccatatggt 660
accagctgca gttagacata catcagctgg ttaatcggga aagggtcaat cagcagcagt 720
ttgatgcggt tttcagtcgc gtagtctggg cgacccagac catcgccata ctggtaggtg 780
cagtgggaaa cacgtgccat gttaactgcg atttccatga acgctttagg cagcagggtg 840
gagtcgctaa cgcgttcacg attcatcttt ttccattcgg cgtcgatcag tttacgcagt 900
tcttcgcggg cctgttcctc gctggtacca tcgttttcgt gcatgtagct aatgatagaa 960
ttggtagtct cgccacgttc cagctccgcc gcagaggtgg ccagatcgtt gcacaggcgg 1020
aagataacgc agctagaacg caccagacca tggaagtcgg tcagggaacg cagcgcgtgg 1080
tcggagatgt cttcctgctg ctggcatacg gaaaagtaag acggcgccag cagcgctaca 1140
ccggaggagg aaacgctggc gttttccagg tacttggaga aagccgggat aattttgttg 1200
ttggaccatt tcgcctcttg cagaaaggct ttgcacagtt cacgccagct tttcgtcaga 1260
taggacaggt tgttatgacc tttctctttc agaatagaat aggacgtgtc gttaacggtg 1320

-continued ttgtacagtg ccaggaaaca cagtttcata tagtccggca gggtgttaat agcgttaacg 1380
tcccagcgct ctacagcatc ggtgaacagt tgcagttcgt ccagagtgcc ataaacgtca 1440
tacacgtcat cgatgatcgt caccagacca aacattttag taacagcttt gcgacattca 1500
ccaaactgcg ggtctggcgc catacccagt gcccagaaat aaacttccat caggcggtcg 1560
cgtacaaaat ccagtttgct agccaggccc atctcggtcc accagcggga cagatcttgc 1620
agctctttct ggtgcagggt ctgtaccatg ttaaaatcca gcttcgccag ctccagcagc 1680
agctggtgat gcggttcttt cggttcgtat ttatccagga accaacgtgc ctccagacgg 1740
tgcagacgct ggtgatatgg cagttccagg gcgtggctca cttgttctgc aaccttggta 1800
ttaatgcctt ctttcaggtt gttcttcagg tgggtgatgg aaaaggtacg cgcctcctcc 1860
agcaggttct caccctcgaa acccaggtaa gacgcttcat acaggctcag caggccttgg 1920
acgtcacctt tcagttcacc gctgaaacca ccttctttat ccttgaaacg ctcaaaaaca 1980
tcctgagaaa cctcgaaacc gtgctgacgc agcagacgga aagacagagc ggttgcgtgc 2040
aggtcagatt tgttcttttt gttttcgtcc agcagtacga tgttttccag ggctttaatg 2100
atgtcttttt caaatttgta ggtcagaccc aggcgctgca catcgtcgat cagctccagc 2160
agggacagcg gctgggtgtc tacacggttg atcatgcagc gaacttcttc ctccagtttg 2220
gtcgctttct cctccagctt ttccactttc aggtcgttct ccagggattg caggaattcg 2280
aaattccaca ggtttggctg atagtttgcg gaacgacggg aattatgctc ggtaatctga 2340
gtaaattgag aagaggtcgc acacatggtt tattcctcct tatttaatcg atacattaat 2400
atatacctct ttaattttta ataataaagt taatcgataa ttccggtcga gtgcccacac 2460
agattgtctg ataaattgtt aaagagcagt gccgcttcgc tttttctcag cggcgctgtt 2520
tcctgtgtga aattgttatc cgctcacaat tccacacatt atacgagccg gatgattaat 2580
tgtcaacagc tcatttcaga atctggcgta atagcgaaga ggcccgcacc gatcgccctt 2640
cccaacagtt gcgcagcctg aatggcgaat ggcgcctgat gcggtatttt ctccttacgc 2700
atctgtgcgg tatttcacac cgcatatggt gcactctcag tacaatctgc tctgatgccg 2760
catagttaag ccagccccga cacccgccaa cacccgctga cgagcttagt aaagccctcg 2820
ctagatttta atgcggatgt tgcgattact tcgccaacta ttgcgataac aagaaaaagc 2880
cagcctttca tgatatatct cccaatttgt gtagggctta ttatgcacgc ttaaaaataa 2940
taaaagcaga cttgacctga tagtttggct gtgagcaatt atgtgcttag tgcatctaac 3000
gcttgagtta agccgcgccg cgaagcggcg tcggcttgaa cgaattgtta gacattattt 3060
gccgactacc ttggtgatct cgcctttcac gtagtggaca aattcttcca actgatctgc 3120
gcgcgaggcc aagcgatctt cttcttgtcc aagataagcc tgtctagctt caagtatgac 3180
gggctgatac tgggccggca ggcgctccat tgcccagtcg gcagcgacat ccttcggcgc 3240
gattttgccg gttactgcgc tgtaccaaat gcgggacaac gtaagcacta catttcgctc 3300
atcgccagcc cagtcgggcg gcgagttcca tagcgttaag gtttcattta gcgcctcaaa 3360
tagatcctgt tcaggaaccg gatcaaagag ttcctccgcc gctggaccta ccaaggcaac 3420
gctatgttct cttgcttttg tcagcaagat agccagatca atgtcgatcg tggctggctc 3480
gaagatacct gcaagaatgt cattgcgctg ccattctcca aattgcagtt cgcgcttagc 3540
tggataacgc cacggaatga tgtcgtcgtg cacaacaatg gtgacttcta cagcgcggag 3600
aatctcgctc tctccagggg aagccgaagt ttccaaaagg tcgttgatca aagctcgccg 3660

-continued cgttgtttca tcaagcctta cggtcaccgt aaccagcaaa tcaatatcac tgtgtggctt 3720
caggccgcca tccactgcgg agccgtacaa atgtacggcc agcaacgtcg gttcgagatg 3780
gcgctcgatg acgccaacta cctctgatag ttgagtcgat acttcggcga tcaccgcttc 3840
cctcatgatg tttaactttg ttttagggcg actgccctgc tgcgtaacat cgttgctgct 3900
ccataacatc aaacatcgac ccacggcgta acgcgcttgc tgcttggatg cccgaggcat 3960
agactgtacc ccaaaaaaac agtcataaca agccatgaaa accgccactg cgccgttacc 4020
accgctgcgt tcggtcaagg ttctggacca gttgcgtgag cgcatacgct acttgcatta 4080
cagcttacga accgaacagg cttatgtcca ctgggttcgt gccttcatcc gtttccacgg 4140
tgtgcgtcac ccggcaacct tgggcagcag cgaagtcgag gcatttctgt cctggctggc 4200
gaacgagcgc aaggtttcgg tctccacgca tcgtcaggca ttggcggcct tgctgttctt 4260
ctacggcaag gtgctgtgca cggatctgcc ctggcttcag gagatcggaa gacctcggcc 4320
gtcgcggcgc ttgccggtgg tgctgacccc ggatgaagtg gttcgcatcc tcggttttct 4380
ggaaggcgag catcgtttgt tcgcccagct tctgtatgga acgggcatgc ggatcagtga 4440
gggtttgcaa ctgcgggtca aggatctgga tttcgatcac ggcacgatca tcgtgcggga 4500
gggcaagggc tccaaggatc gggccttgat gttacccgag agcttggcac ccagcctgcg 4560
cgagcagggg aattaattcc cacgggtttt gctgcccgca aacgggctgt tctggtgttg 4620
ctagtttgtt atcagaatcg cagatccggc ttcagccggt ttgccggctg aaagcgctat 4680
ttcttccaga attgccatga tttttcccc acgggaggcg tcactggctc ccgtgttgtc 4740
ggcagctttg attcgataag cagcatcgcc tgtttcaggc tgtctatgtg tgactgttga 4800
gctgtaacaa gttgtctcag gtgttcaatt tcatgttcta gttgctttgt tttactggtt 4860
tcacctgttc tattaggtgt tacatgctgt tcatctgtta cattgtcgat ctgttcatgg 4920
tgaacagctt tgaatgcacc aaaaactcgt aaaagctctg atgtatctat cttttttaca 4980
ccgttttcat ctgtgcatat ggacagtttt ccctttgata tgtaacggtg aacagttgtt 5040
ctacttttgt ttgttagtct tgatgcttca ctgatagata caagagccat aagaacctca 5100
gatccttccg tatttagcca gtatgttctc tagtgtggtt cgttgttttt gcgtgagcca 5160
tgagaacgaa ccattgagat catacttact ttgcatgtca ctcaaaaatt ttgcctcaaa 5220
actggtgagc tgaatttttg cagttaaagc atcgtgtagt gtttttctta gtccgttatg 5280
taggtaggaa tctgatgtaa tggttgttgg tattttgtca ccattcattt ttatctggtt 5340
gttctcaagt tcggttacga gatccatttg tctatctagt tcaacttgga aaatcaacgt 5400
atcagtcggg cggcctcgct tatcaaccac caatttcata ttgctgtaag tgtttaaatc 5460
tttacttatt ggtttcaaaa cccattggtt aagcctttta aactcatggt agttattttc 5520
aagcattaac atgaacttaa attcatcaag gctaatctct atatttgcct tgtgagtttt 5580
cttttgtgtt agttctttta ataaccactc ataaatcctc atagagtatt tgttttcaaa 5640
agacttaaca tgttccagat tatattttat gaattttttt aactggaaaa gataaggcaa 5700
tatctcttca ctaaaaacta attctaattt ttcgcttgag aacttggcat agtttgtcca 5760
ctggaaaatc tcaaagcctt taaccaaagg attcctgatt tccacagttc tcgtcatcag 5820
ctctctggtt gctttagcta atacaccata agcattttcc ctactgatgt tcatcatctg 5880
agcgtattgg ttataagtga acgataccgt ccgttctttc cttgtagggt tttcaatcgt 5940
ggggttgagt agtgccacac agcataaaat tagcttggtt tcatgctccg ttaagtcata 6000
gcgactaatc gctagttcat ttgctttgaa aacaactaat tcagacatac atctcaattg 6060
gtctaggtga ttttaatcac tataccaatt gagatgggct agtcaatgat aattactagt 6120
ccttttcctt tgagttgtgg gtatctgtaa attctgctag acctttgctg gaaaacttgt 6180
aaattctgct agaccctctg taaattccgc tagacctttg tgtgtttttt ttgtttatat 6240
tcaagtggtt ataatttata gaataaagaa agaataaaaa aagataaaaa gaatagatcc 6300
cagccctgtg tataactcac tactttagtc agttccgcag tattacaaaa ggatgtcgca 6360
aacgctgttt gctcctctac aaaacagacc ttaaaaccct aaaggcttaa gtagcaccct 6420
cgcaagctcg ggcaaatcgc tgaatattcc ttttgtctcc gaccatcagg cacctgagtc 6480
gctgtctttt tcgtgacatt cagttcgctg cgctcacggc tctggcagtg aatgggggta 6540
aatggcacta caggcgcctt ttatggattc atgcaaggaa actacccata atacaagaaa 6600
agcccgtcac gggcttctca gggcgtttta tggcgggtct gctatgtggt gctatctgac 6660
tttttgctgt tcagcagttc ctgccctctg attttccagt ctgaccactt cggattatcc 6720
cgtgacaggt cattcagact ggctaatgca cccagtaagg cagcggtatc atcaacaggc 6780
tta 6783

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54
ctggcgtaat agcgaagagg cccgcaccga tcgcccttcc caacagttgc gcagcctgaa 60
tggcgaatgg cgcctgatgc ggtattttct ccttacgcat ctgtgcggta tttcacaccg 120
catatggtgc actctcagta caatctgctc tgatgccgca tagttaagcc agccccgaca 180
cccgccaaca cccgctgacg agcttagtaa agccctcgct agattttaat gcggatgttg 240
cgattacttc gccaactatt gcgataacaa gaaaaagcca gcctttcatg atatatctcc 300
caatttgtgt agggcttatt atgcacgctt aaaaataata aaagcagact tgacctgata 360
gtttggctgt gagcaattat gtgcttagtg catctaacgc ttgagttaag ccgcgccgcg 420
aagcggcgtc ggcttgaacg aattgttaga cattatttgc cgactacctt ggtgatctcg 480
cctttcacgt agtggacaaa ttcttccaac tgatctgcgc gcgaggccaa gcgatcttct 540
tcttgtccaa gataagcctg tctagcttca agtatgacgg gctgatactg ggccggcagg 600
cgctccattg cccagtcggc agcgacatcc ttcggcgcga ttttgccggt tactgcgctg 660
taccaaatgc gggacaacgt aagcactaca tttcgctcat cgccagccca gtcgggcggc 720
gagttccata gcgttaaggt ttcatttagc gcctcaaata gatcctgttc aggaaccgga 780
tcaaagagtt cctccgccgc tggacctacc aaggcaacgc tatgttctct tgcttttgtc 840
agcaagatag ccagatcaat gtcgatcgtg gctggctcga agatacctgc aagaatgtca 900
ttgcgctgcc attctccaaa ttgcagttcg cgcttagctg gataacgcca cggaatgatg 960
tcgtcgtgca caacaatggt gacttctaca gcgcggagaa tctcgctctc tccaggggaa 1020
gccgaagttt ccaaaaggtc gttgatcaaa gctcgccgcg ttgtttcatc aagccttacg 1080
gtcaccgtaa ccagcaaatc aatatcactg tgtggcttca ggccgccatc cactgcggag 1140
ccgtacaaat gtacggccag caacgtcggt tcgagatggc gctcgatgac gccaactacc 1200
tctgatagtt gagtcgatac ttcggcgatc accgcttccc tcatgatgtt taactttgtt 1260
ttagggcgac tgccctgctg cgtaacatcg ttgctgctcc ataacatcaa acatcgaccc 1320
acggcgtaac gcgcttgctg cttggatgcc cgaggcatag actgtacccc aaaaaaacag 1380
tcataacaag ccatgaaaac cgccactgcg ccgttaccac cgctgcgttc ggtcaaggtt 1440
ctggaccagt tgcgtgagcg catacgctac ttgcattaca gcttacgaac cgaacaggct 1500
tatgtccact gggttcgtgc cttcatccgt ttccacggtg tgcgtcaccc ggcaaccttg 1560
ggcagcagcg aagtcgaggc atttctgtcc tggctggcga acgagcgcaa ggtttcggtc 1620
tccacgcatc gtcaggcatt ggcggccttg ctgttcttct acggcaaggt gctgtgcacg 1680
gatctgccct ggcttcagga gatcggaaga cctcggccgt cgcggcgctt gccggtggtg 1740
ctgaccccgg atgaagtggt tcgcatcctc ggttttctgg aaggcgagca tcgtttgttc 1800
gcccagcttc tgtatggaac gggcatgcgg atcagtgagg gtttgcaact gcgggtcaag 1860
gatctggatt tcgatcacgg cacgatcatc gtgcgggagg gcaagggctc caaggatcgg 1920
gccttgatgt tacccgagag cttggcaccc agcctgcgcg agcaggggaa ttaattccca 1980
cgggttttgc tgcccgcaaa cgggctgttc tggtgttgct agtttgttat cagaatcgca 2040
gatccggctt cagccggttt gccggctgaa agcgctattt cttccagaat tgccatgatt 2100
ttttccccac gggaggcgtc actggctccc gtgttgtcgg cagctttgat tcgataagca 2160
gcatcgcctg tttcaggctg tctatgtgtg actgttgagc tgtaacaagt tgtctcaggt 2220
gttcaatttc atgttctagt tgctttgttt tactggtttc acctgttcta ttaggtgtta 2280
catgctgttc atctgttaca ttgtcgatct gttcatggtg aacagctttg aatgcaccaa 2340
aaactcgtaa aagctctgat gtatctatct tttttacacc gttttcatct gtgcatatgg 2400
acagttttcc ctttgatatg taacggtgaa cagttgttct acttttgttt gttagtcttg 2460
atgcttcact gatagataca agagccataa gaacctcaga tccttccgta tttagccagt 2520
atgttctcta gtgtggttcg ttgtttttgc gtgagccatg agaacgaacc attgagatca 2580
tacttacttt gcatgtcact caaaaatttt gcctcaaaac tggtgagctg aatttttgca 2640
gttaaagcat cgtgtagtgt ttttcttagt ccgttatgta ggtaggaatc tgatgtaatg 2700
gttgttggta ttttgtcacc attcattttt atctggttgt tctcaagttc ggttacgaga 2760
tccatttgtc tatctagttc aacttggaaa atcaacgtat cagtcgggcg gcctcgctta 2820
tcaaccacca atttcatatt gctgtaagtg tttaaatctt tacttattgg tttcaaaacc 2880
cattggttaa gccttttaaa ctcatggtag ttattttcaa gcattaacat gaacttaaat 2940
tcatcaaggc taatctctat atttgccttg tgagttttct tttgtgttag ttcttttaat 3000
aaccactcat aaatcctcat agagtatttg ttttcaaaag acttaacatg ttccagatta 3060
tattttatga atttttttaa ctggaaaaga taaggcaata tctcttcact aaaaactaat 3120
tctaattttt cgcttgagaa cttggcatag tttgtccact ggaaaatctc aaagccttta 3180
accaaaggat tcctgatttc cacagttctc gtcatcagct ctctggttgc tttagctaat 3240
acaccataag cattttccct actgatgttc atcatctgag cgtattggtt ataagtgaac 3300
gataccgtcc gttctttcct tgtagggttt tcaatcgtgg ggttgagtag tgccacacag 3360
cataaaatta gcttggtttc atgctccgtt aagtcatagc gactaatcgc tagttcattt 3420
gctttgaaaa caactaattc agacatacat ctcaattggt ctaggtgatt ttaatcacta 3480
taccaattga gatgggctag tcaatgataa ttactagtcc ttttcctttg agttgtgggt 3540
atctgtaaat tctgctagac ctttgctgga aaacttgtaa attctgctag accctctgta 3600
aattccgcta gacctttgtg tgtttttttt gtttatattc aagtggttat aatttataga 3660

```
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtctttttc gtgacattca   3900
gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat ttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gtttttgagc   4860
gtttcaagga taaagaaggt ggtttcagcg gtgaactgaa aggtgacgtc caaggcctgc   4920
tgagcctgta tgaagcgtct tacctgggtt tcgagggtga gaacctgctg gaggaggcgc   4980
gtaccttttc catcacccac ctgaagaaca acctgaaaga aggcattaat accaaggttg   5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
aagctgttac taaaatgttt ggtctggtga cgatcatcga tgacgtgtat gacgtttatg   5400
gcactctgga cgaactgcaa ctgttcaccg atgctgtaga gcgctgggac gttaacgcta   5460
ttaacaccct gccggactat atgaaactgt gtttcctggc actgtacaac accgttaacg   5520
acacgtccta ttctattctg aaagagaaag gtcataacaa cctgtcctat ctgacgaaaa   5580
gctggcgtga actgtgcaaa gcctttctgc aagaggcgaa atggtccaac aacaaaatta   5640
tcccggcttt ctccaagtac ctggaaaacg ccagcgtttc ctcctccggt gtagcgctgc   5700
tggcgccgtc ttacttttcc gtatgccagc agcaggaaga catctccgac cacgcgctgc   5760
gttccctgac cgacttccat ggtctggtgc gttctagctg cgttatcttc cgcctgtgca   5820
acgatctggc cacctctgcg gcggagctgg aacgtggcga gactaccaat tctatcatta   5880
gctacatgca cgaaaacgat ggtaccagcg aggaacaggc ccgcgaagaa ctgcgtaaac   5940
tgatcgacgc cgaatggaaa aagatgaatc gtgaacgcgt tagcgactcc accctgctgc   6000
```

ctaaagcgtt catggaaatc gcagttaaca tggcacgtgt ttcccactgc acctaccagt 6060
atggcgatgg tctgggtcgc ccagactacg cgactgaaaa ccgcatcaaa ctgctgctga 6120
ttgacccttt cccgattaac cagctgatgt atgtctaact gcatcgccct taggaggtaa 6180
aaaaaaatga ctgccgacaa caatagtatg ccccatggtg cagtatctag ttacgccaaa 6240
ttagtgcaaa accaaacacc tgaagacatt ttggaagagt ttcctgaaat tattccatta 6300
caacaaagac ctaatacccg atctagtgag acgtcaaatg acgaaagcgg agaaacatgt 6360
ttttctggtc atgatgagga gcaaattaag ttaatgaatg aaaattgtat tgttttggat 6420
tgggacgata atgctattgg tgccggtacc aagaaagttt gtcatttaat ggaaaatatt 6480
gaaaagggtt tactacatcg tgcattctcc gtctttattt tcaatgaaca aggtgaatta 6540
cttttacaac aaagagccac tgaaaaaata actttccctg atctttggac taacacatgc 6600
tgctctcatc cactatgtat tgatgacgaa ttaggtttga agggtaagct agacgataag 6660
attaagggcg ctattactgc ggcggtgaga aaactagatc atgaattagg tattccagaa 6720
gatgaaacta agacaagggg taagtttcac tttttaaaca gaatccatta catggcacca 6780
agcaatgaac catggggtga acatgaaatt gattacatcc tattttataa gatcaacgct 6840
aaagaaaact tgactgtcaa cccaaacgtc aatgaagtta gagacttcaa atgggtttca 6900
ccaaatgatt tgaaaactat gtttgctgac ccaagttaca agtttacgcc ttggtttaag 6960
attatttgcg agaattactt attcaactgg tgggagcaat tagatgacct ttctgaagtg 7020
gaaaatgaca ggcaaattca tagaatgcta taacgacgcg tcctgcagct ggtaccatat 7080
gggaattcga agctttctag aacgaaaact catctcagaa gaggatctga atagcgccgt 7140
cgaccatcat catcatcatc attgagttta aacggtctcc agcttggctg ttttggcgga 7200
tgagagaaga ttttcagcct gatacagatt aaatcagaac gcagaagcgg tctgataaaa 7260
cagaatttgc ctggcggcag tagcgcggtg gtcccacctg accccatgcc gaactcagaa 7320
gtgaaacgcc gtagcgccga tggtagtgtg gggtctcccc atgcgagagt agggaactgc 7380
caggcatcaa ataaaacgaa aggctcagtc gaaagactgg gcctttcgtt ttatctgttg 7440
tttgtcggtg aacgctctcc tgagtaggac aaatccgccg ggagcggatt tgaacgttgc 7500
gaagcaacgg cccggagggt ggcgggcagg acgcccgcca taaactgcca ggcatcaaat 7560
taagcagaag gccatcctga cggatggcct ttttgcgttt ctacaaactc tttttgttta 7620
tttttctaaa tacattcaaa tatgtatccg ctcatgagac aataaccctg ataaatgctt 7680
caataat 7687

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55
cccgtcttac tgtcgggaat tcgcgttggc cgattcatta atgcagatta ttgaagcatt 60
tatcagggtt attgtctcat gagcggatac atatttgaat gtatttagaa aaataaacaa 120
aaagagtttg tagaaacgca aaaaggccat ccgtcaggat ggccttctgc ttaatttgat 180
gcctggcagt ttatggcggg cgtcctgccc gccaccctcc gggccgttgc ttcgcaacgt 240
tcaaatccgc tcccggcgga tttgtcctac tcaggagagc gttcaccgac aaacaacaga 300
taaaacgaaa ggcccagtct ttcgactgag cctttcgttt tatttgatgc ctggcagttc 360

-continued cctactctcg catggggaga ccccacacta ccatcggcgc tacggcgttt cacttctgag 420
ttcggcatgg ggtcaggtgg gaccaccgcg ctactgccgc caggcaaatt ctgttttatc 480
agaccgcttc tgcgttctga tttaatctgt atcaggctga aaatcttctc tcatccgcca 540
aaacagccaa gctggagacc gtttaaactc aatgatgatg atgatgatgg tcgacggcgc 600
tattcagatc ctcttctgag atgagttttt gttctagaaa gcttcgaatt cccatatggt 660
accagctgca gttatgccag ccaggccttg attttggctt ccataccagc ggcatcgagg 720
ccgagttcgg cgcgcatttc ttcctgagtt ccttgcggaa taaagaagtc cggcaggcca 780
atgttcagca cgggtactgg tttacgatgg gccatcagca cttcgttcac gccgctgcct 840
gcgccgccca taatggcgtt ttcttctacg gtgaccagcg cttcatggct ggcggccatt 900
tccagaatta acgcttcatc aagcggtttc acaaaacgca tatcgaccag cgtggcgttc 960
agcgattcgg cgactttcgc cgcttctggc atcagcgtac caaagttaag gatcgccagt 1020
ttctcgccac gacgcttcac aatgcctttg ccaattggta gtttttccag cggcgtcagt 1080
tccacgccga ccgcgttgcc acgcgggtag cgcaccgctg acgggccatc gttatagtga 1140
tagccggtat agagcatctg gcgacattcg ttttcatcgc tcggggtcat aatgaccatt 1200
tccggtatgc agcgcaggta agagagatca aaagcaccct gatgggtttg accgtcagca 1260
ccaacaatgc ccgcgcggtc gatggcgaac aggaccggaa gcttttgaat cgccacgtca 1320
tgcagcacct gatcataggc gcgttgcagg aaagtggagt aaatcgcgac aatgggtttg 1380
tacccaccaa tcgccagacc cgcagcaaag gtcaccgcgt gttgctcggc aattgccacg 1440
tcgaagtagc gatccgggaa tttacgtgaa aactcgacca tgccggaacc ttcacgcatc 1500
gccggagtaa tcgccatcag cttgttgtct ttcgctgccg tttcgcacaa ccagtcgcca 1560
aagatttttg aatagctcgg caaaccgccg ctacttttcg gcaaacaacc gctggaggga 1620
tcaaatttag gcacggcgtg gaaagtgatc gggtcttttt ctgccggttc ataaccacga 1680
ccttttttgg tcatgatatg caggaactgc gggcctttca ggtcgcgcat gttctttagc 1740
gtggtgataa gccccagcac atcgtgaccg tccaccgggc cgatgtagtt aaagcccagc 1800
tcttcaaaca acgtgccagg cactaccatg cctttaatat gttcttcggt gcgtttgagc 1860
agctctttaa ttggcggcac gccagagaaa acttttttcc cgccttcgcg cagtgaagag 1920
taaagcttac cggaaagcag ctgtgccaga tggttgttga gcgcgccgac attttcggaa 1980
atcgacattt cattgtcgtt gagaatcacc agcatatcag gacggatatc gcccgcgtga 2040
ttcatcgctt caaacgccat gcctgcggta atcgcgccat cgccaatgac acagacggtg 2100
cggcgatttt tgccttcttt ttcggcagca accgcaatac caattccggc actgatggag 2160
gttgatgaat gcccgacgct taatacgtca tattcgcttt cgccgcgcca cgggaacggg 2220
tgcagaccgc ctttctgacg gatggtgccg attttgtcgc ggcgtccggt caaaatttta 2280
tgcggataag cctgatgccc cacatcccaa atcaattggt caaacggggt gttgtagaca 2340
tagtgcagcg ccacggtcag ttcgaccgtg cccagcccgg aggcgaagtg cccgctggaa 2400
cggctcacgc tgtcgagtaa atagcggcgc agttcgtcgc agagtttcgg taaactctct 2460
ttcggcaaca gtcgtaactc ctgggtggag tcgaccagtg ccagggtcgg gtatttggca 2520
atatcaaaac tcatgttttt ttacctccta agggcgaatg cagttagaca tacatcagct 2580
ggttaatcgg gaaagggtca atcagcagca gtttgatgcg gttttcagtc gcgtagtctg 2640
ggcgacccag accatcgcca tactggtagg tgcagtggga aacacgtgcc atgttaactg 2700

-continued

```
cgatttccat gaacgcttta ggcagcaggg tggagtcgct aacgcgttca cgattcatct   2760
ttttccattc ggcgtcgatc agtttacgca gttcttcgcg ggcctgttcc tcgctggtac   2820
catcgttttc gtgcatgtag ctaatgatag aattggtagt ctcgccacgt tccagctccg   2880
ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
cggaaaagta agacggcgcc agcagcgcta caccggagga ggaaacgctg gcgttttcca   3060
ggtacttgga gaaagccggg ataattttgt tgttggacca tttcgcctct tgcagaaagg   3120
ctttgcacag ttcacgccag cttttcgtca gataggacag gttgttatga cctttctctt   3180
tcagaataga ataggacgtg tcgttaacgg tgttgtacag tgccaggaaa cacagtttca   3240
tatagtccgg cagggtgtta atagcgttaa cgtcccagcg ctctacagca tcggtgaaca   3300
gttgcagttc gtccagagtg ccataaacgt catacacgtc atcgatgatc gtcaccagac   3360
caaacatttt agtaacagct ttgcgacatt caccaaactg cgggtctggc gccataccca   3420
gtgcccagaa ataaacttcc atcaggcggt cgcgtacaaa atccagtttg ctagccaggc   3480
ccatctcggt ccaccagcgg gacagatctt gcagctcttt ctggtgcagg gtctgtacca   3540
tgttaaaatc cagcttcgcc agctccagca gcagctggtg atgcggttct ttcggttcgt   3600
atttatccag gaaccaacgt gcctccagac ggtgcagacg ctggtgatat ggcagttcca   3660
gggcgtggct cacttgttct gcaaccttgg tattaatgcc ttctttcagg ttgttcttca   3720
ggtgggtgat ggaaaaggta cgcgcctcct ccagcaggtt ctcaccctcg aaacccaggt   3780
aagacgcttc atacaggctc agcaggcctt ggacgtcacc tttcagttca ccgctgaaac   3840
caccttcttt atccttgaaa cgctcaaaaa catcctgaga aacctcgaaa ccgtgctgac   3900
gcagcagacg gaaagacaga gcggttgcgt gcaggtcaga tttgttcttt ttgttttcgt   3960
ccagcagtac gatgttttcc agggctttaa tgatgtcttt ttcaaatttg taggtcagac   4020
ccaggcgctg cacatcgtcg atcagctcca gcagggacag cggctgggtg tctacacggt   4080
tgatcatgca gcgaacttct tcctccagtt tggtcgcttt ctcctccagc ttttccactt   4140
tcaggtcgtt ctccagggat tgcaggaatt cgaaattcca caggtttggc tgatagtttg   4200
cggaacgacg ggaattatgc tcggtaatct gagtaaattg agaagaggtc gcacacatgg   4260
tttattcctc cttatttaat cgatacatta atatatacct ctttaatttt taataataaa   4320
gttaatcgat aattccggtc gagtgcccac acagattgtc tgataaattg ttaaagagca   4380
gtgccgcttc gctttttctc agcggcgctg tttcctgtgt gaaattgtta tccgctcaca   4440
attccacaca ttatacgagc cggatgatta attgtcaaca gctcatttca gaatctggcg   4500
taatagcgaa gaggcccgca ccgatcgccc ttcccaacag ttgcgcagcc tgaatggcga   4560
atggcgcctg atgcggtatt ttctccttac gcatctgtgc ggtatttcac accgcatatg   4620
gtgcactctc agtacaatct gctctgatgc cgcatagtta agccagcccc gacacccgcc   4680
aacacccgct gacgagctta gtaaagccct cgctagattt taatgcggat gttgcgatta   4740
cttcgccaac tattgcgata acaagaaaaa gccagccttt catgatatat ctcccaattt   4800
gtgtagggct tattatgcac gcttaaaaat aataaaagca gacttgacct gatagtttgg   4860
ctgtgagcaa ttatgtgctt agtgcatcta acgcttgagt taagccgcgc cgcgaagcgg   4920
cgtcggcttg aacgaattgt tagacattat ttgccgacta ccttggtgat ctcgcctttc   4980
acgtagtgga caaattcttc caactgatct gcgcgcgagg ccaagcgatc ttcttcttgt   5040
ccaagataag cctgtctagc ttcaagtatg acgggctgat actgggccgg caggcgctcc   5100
```

attgcccagt cggcagcgac atccttcggc gcgattttgc cggttactgc gctgtaccaa 5160
atgcgggaca acgtaagcac tacatttcgc tcatcgccag cccagtcggg cggcgagttc 5220
catagcgtta aggtttcatt tagcgcctca aatagatcct gttcaggaac cggatcaaag 5280
agttcctccg ccgctggacc taccaaggca acgctatgtt ctcttgcttt tgtcagcaag 5340
atagccagat caatgtcgat cgtggctggc tcgaagatac ctgcaagaat gtcattgcgc 5400
tgccattctc caaattgcag ttcgcgctta gctggataac gccacggaat gatgtcgtcg 5460
tgcacaacaa tggtgacttc tacagcgcgg agaatctcgc tctctccagg ggaagccgaa 5520
gtttccaaaa ggtcgttgat caaagctcgc cgcgttgttt catcaagcct tacggtcacc 5580
gtaaccagca aatcaatatc actgtgtggc ttcaggccgc catccactgc ggagccgtac 5640
aaatgtacgg ccagcaacgt cggttcgaga tggcgctcga tgacgccaac tacctctgat 5700
agttgagtcg atacttcggc gatcaccgct tccctcatga tgtttaactt tgttttaggg 5760
cgactgccct gctgcgtaac atcgttgctg ctccataaca tcaaacatcg acccacggcg 5820
taacgcgctt gctgcttgga tgcccgaggc atagactgta ccccaaaaaa acagtcataa 5880
caagccatga aaaccgccac tgcgccgtta ccaccgctgc gttcggtcaa ggttctggac 5940
cagttgcgtg agcgcatacg ctacttgcat tacagcttac gaaccgaaca ggcttatgtc 6000
cactgggttc gtgccttcat ccgtttccac ggtgtgcgtc acccggcaac cttgggcagc 6060
agcgaagtcg aggcatttct gtcctggctg gcgaacgagc gcaaggtttc ggtctccacg 6120
catcgtcagg cattggcggc cttgctgttc ttctacggca aggtgctgtg cacggatctg 6180
ccctggcttc aggagatcgg aagacctcgg ccgtcgcggc gcttgccggt ggtgctgacc 6240
ccggatgaag tggttcgcat cctcggtttt ctggaaggcg agcatcgttt gttcgcccag 6300
cttctgtatg gaacgggcat gcggatcagt gagggtttgc aactgcgggt caaggatctg 6360
gatttcgatc acggcacgat catcgtgcgg gagggcaagg gctccaagga tcgggccttg 6420
atgttacccg agagcttggc acccagcctg cgcgagcagg ggaattaatt cccacgggtt 6480
ttgctgcccg caaacgggct gttctggtgt tgctagtttg ttatcagaat cgcagatccg 6540
gcttcagccg gtttgccggc tgaaagcgct atttcttcca gaattgccat gatttttttcc 6600 ccacgggagg cgtcactggc tcccgtgttg tcggcagctt tgattcgata agcagcatcg 6660
cctgtttcag gctgtctatg tgtgactgtt gagctgtaac aagttgtctc aggtgttcaa 6720
tttcatgttc tagttgcttt gttttactgg tttcacctgt tctattaggt gttacatgct 6780
gttcatctgt tacattgtcg atctgttcat ggtgaacagc tttgaatgca ccaaaaactc 6840
gtaaaagctc tgatgtatct atctttttta caccgttttc atctgtgcat atggacagtt 6900
ttccctttga tatgtaacgg tgaacagttg ttctactttt gtttgttagt cttgatgctt 6960
cactgataga tacaagagcc ataagaacct cagatccttc cgtatttagc cagtatgttc 7020
tctagtgtgg ttcgttgttt ttgcgtgagc catgagaacg aaccattgag atcatactta 7080
ctttgcatgt cactcaaaaa ttttgcctca aaactggtga gctgaatttt tgcagttaaa 7140
gcatcgtgta gtgtttttct tagtccgtta tgtaggtagg aatctgatgt aatggttgtt 7200
ggtattttgt caccattcat ttttatctgg ttgttctcaa gttcggttac gagatccatt 7260
tgtctatcta gttcaacttg gaaaatcaac gtatcagtcg ggcggcctcg cttatcaacc 7320
accaatttca tattgctgta agtgtttaaa tctttactta ttggtttcaa aacccattgg 7380
ttaagccttt taaactcatg gtagttattt tcaagcatta acatgaactt aaattcatca 7440
aggctaatct ctatatttgc cttgtgagtt ttcttttgtg ttagttcttt taataaccac 7500
tcataaatcc tcatagagta tttgttttca aaagacttaa catgttccag attatatttt 7560
atgaattttt ttaactggaa aagataaggc aatatctctt cactaaaaac taattctaat 7620
ttttcgcttg agaacttggc atagtttgtc cactggaaaa tctcaaagcc tttaaccaaa 7680
ggattcctga tttccacagt tctcgtcatc agctctctgg ttgctttagc taatacacca 7740
taagcatttt ccctactgat gttcatcatc tgagcgtatt ggttataagt gaacgatacc 7800
gtccgttctt tccttgtagg gttttcaatc gtggggttga gtagtgccac acagcataaa 7860
attagcttgg tttcatgctc cgttaagtca tagcgactaa tcgctagttc atttgctttg 7920
aaaacaacta attcagacat acatctcaat tggtctaggt gattttaatc actataccaa 7980
ttgagatggg ctagtcaatg ataattacta gtccttttcc tttgagttgt gggtatctgt 8040
aaattctgct agacctttgc tggaaaactt gtaaattctg ctagaccctc tgtaaattcc 8100
gctagacctt tgtgtgtttt ttttgtttat attcaagtgg ttataattta tagaataaag 8160
aaagaataaa aaaagataaa aagaatagat cccagccctg tgtataactc actactttag 8220
tcagttccgc agtattacaa aaggatgtcg caaacgctgt ttgctcctct acaaaacaga 8280
ccttaaaacc ctaaaggctt aagtagcacc ctcgcaagct cgggcaaatc gctgaatatt 8340
ccttttgtct ccgaccatca ggcacctgag tcgctgtctt tttcgtgaca ttcagttcgc 8400
tgcgctcacg gctctggcag tgaatggggg taaatggcac tacaggcgcc ttttatggat 8460
tcatgcaagg aaactaccca taatacaaga aaagcccgtc acgggcttct cagggcgttt 8520
tatggcgggt ctgctatgtg gtgctatctg actttttgct gttcagcagt tcctgccctc 8580
tgattttcca gtctgaccac ttcggattat cccgtgacag gtcattcaga ctggctaatg 8640
cacccagtaa ggcagcggta tcatcaacag gctta 8675

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56
tcgctgcgct cggtcgttcg gctgcggcga gcggtatcag ctcactcaaa ggcggtaata 60
cggttatcca cagaatcagg ggataacgca ggaaagaaca tgtgagcaaa aggccagcaa 120
aaggccagga accgtaaaaa ggccgcgttg ctggcgtttt tccataggct ccgcccccct 180
gacgagcatc acaaaaatcg acgctcaagt cagaggtggc gaaacccgac aggactataa 240
agataccagg cgtttccccc tggaagctcc ctcgtgcgct ctcctgttcc gaccctgccg 300
cttaccggat acctgtccgc ctttctccct tcgggaagcg tggcgctttc tcatagctca 360
cgctgtaggt atctcagttc ggtgtaggtc gttcgctcca agctgggctg tgtgcacgaa 420
ccccccgttc agcccgaccg ctgcgcctta tccggtaact atcgtcttga gtccaacccg 480
gtaagacacg acttatcgcc actggcagca gccactggta acaggattag cagagcgagg 540
tatgtaggcg gtgctacaga gttcttgaag tggtggccta actacggcta cactagaaga 600
acagtatttg gtatctgcgc tctgctgaag ccagttacct tcggaaaaag agttggtagc 660
tcttgatccg gcaaacaaac caccgctggt agcggtggtt tttttgtttg caagcagcag 720
attacgcgca gaaaaaaagg atctcaagaa gatcctttga tcttttctac ggggtctgac 780
gctcagtgga acgaaaactc acgttaaggg attttggtca tgagattatc aaaaaggatc 840

```
ttcacctaga tccttttaaa ttaaaaatga agttttaaat caatctaaag tatatatgag    900
taaacttggt ctgacagtta ccaatgctta atcagtgagg cacctatctc agcgatctgt    960
ctatttcgtt catccatagt tgcctgactc cccgtcgtgt agataactac gatacgggag   1020
ggcttaccat ctggccccag tgctgcaatg ataccgcgag acccacgctc accggctcca   1080
gatttatcag caataaacca gccagccgga agggccgagc gcagaagtgg tcctgcaact   1140
ttatccgcct ccatccagtc tattaattgt tgccgggaag ctagagtaag tagttcgcca   1200
gttaatagtt tgcgcaacgt tgttgccatt gctacaggca tcgtggtgtc acgctcgtcg   1260
tttggtatgg cttcattcag ctccggttcc caacgatcaa ggcgagttac atgatccccc   1320
atgttgtgca aaaaagcggt tagctccttc ggtcctccga tcgttgtcag aagtaagttg   1380
gccgcagtgt tatcactcat ggttatggca gcactgcata attctcttac tgtcatgcca   1440
tccgtaagat gcttttctgt gactggtgag tactcaacca agtcattctg agaatagtgt   1500
atgcggcgac cgagttgctc ttgcccggcg tcaatacggg ataataccgc gccacatagc   1560
agaactttaa aagtgctcat cattggaaaa cgttcttcgg ggcgaaaact ctcaaggatc   1620
ttaccgctgt tgagatccag ttcgatgtaa cccactcgtg cacccaactg atcttcagca   1680
tcttttactt tcaccagcgt ttctgggtga gcaaaaacag gaaggcaaaa tgccgcaaaa   1740
aagggaataa gggcgacacg gaaatgttga atactcatac tcttcctttt tcaatattat   1800
tgaagcattt atcagggtta ttgtctcatg agcggataca tatttgaatg tatttagaaa   1860
aataaacaaa taggggttcc gcgcacattt ccccgaaaag tgccacctga cgtctaagaa   1920
accattatta tcatgacatt aacctataaa aataggcgta tcacgaggcc ctttcgtctc   1980
gcgcgtttcg gtgatgacgg tgaaaacctc tgacacatgc agctcccgga gacggtcaca   2040
gcttgtctgt aagcggatgc cgggagcaga caagcccgtc agggcgcgtc agcgggtgtt   2100
ggcgggtgtc ggggctggct taactatgcg gcatcagagc agattgtact gagagtgcac   2160
catagatctg gagctgtaat ataaaaacct tcttcaacta acggggcagg ttagtgacat   2220
tagaaaaccg actgtaaaaa gtacagtcgg cattatctca tattataaaa gccagtcatt   2280
aggcctatct gacaattcct gaatagagtt cataaacaat cctgcatgat aaccatcaca   2340
aacagaatga tgtacctgta aagatagcgg taaatatatt gaattacctt tattaatgaa   2400
ttttcctgct gtaataatgg gtagaaggta attactatta ttattgatat ttaagttaaa   2460
cccagtaaat gaagtccatg gaataataga aagagaaaaa gcattttcag gtataggtgt   2520
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataaagtg gctctaactt atcccaataa cctaactctc cgtcgctatt   2700
gtaaccagtt ctaaaagctg tatttgagtt tatcaccctt gtcactaaga aaataaatgc   2760
agggtaaaat ttatatcctt cttgttttat gtttcggtat aaaacactaa tatcaatttc   2820
tgtggttata ctaaaagtcg tttgttggtt caaataatga ttaaatatct cttttctctt   2880
ccaattgtct aaatcaattt tattaaagtt catttgatat gcctcctaaa tttttatcta   2940
aagtgaattt aggaggctta cttgtctgct ttcttcatta gaatcaatcc tttttttaaaa  3000
gtcaatatta ctgtaacata aatatatatt ttaaaaatat cccactttat ccaattttcg   3060
tttgttgaac taatgggtgc tttagttgaa gaataaaaga cctatgcggt gtgaaatacc   3120
gcacagatgc gtaaggagaa aataccgcat caggcgccat tcgccattca ggctgcgcaa   3180
```

-continued ctgttgggaa gggcgatcgg tgcgggcctc ttcgctatta cgccagctgg cgaaaggggg 3240
atgtgctgca aggcgattaa gttgggtaac gccagggttt tcccagtcac gacgttgtaa 3300
aacgacggcc agtgccaagc ttgcatgcct gcactccatt ttcttctgct atcaaaataa 3360
cagactcgtg attttccaaa cgagctttca aaaaagcctc tgccccttgc aaatcggatg 3420
cctgtctata aaattcccga tattggttaa acagcggcgc aatggcggcc gcatctgatg 3480
tctttgcttg gcgaatgttc atcttatttc ttcctccctc tcaataattt tttcattcta 3540
tcccttttct gtaaagttta tttttcagaa tacttttatc atcatgcttt gaaaaaatat 3600
cacgataata tccattgttc tcacggaagc acacgcaggt catttgaacg aatttttcg 3660 acaggaattt gccgggactc aggagcattt aacctaaaaa agcatgacat ttcagcataa 3720
tgaacattta ctcatgtcta ttttcgttct tttctgtatg aaaatagtta tttcgagtct 3780
ctacggaaat agcgagagat gatataccta aatagagata aaatcatctc aaaaaaatgg 3840
gtctactaaa atattattcc atctattaca ataaattcac agaatagtct tttaagtaag 3900
tctactctga atttttttaa aaggagaggg taaagagtga aaacagtagt tattattgat 3960
gcattacgaa caccaattgg aaaatataaa ggcagcttaa gtcaagtaag tgccgtagac 4020
ttaggaacac atgttacaac acaactttta aaaagacatt ccactatttc tgaagaaatt 4080
gatcaagtaa tctttggaaa tgttttacaa gctggaaatg gccaaaatcc cgcacgacaa 4140
atagcaataa acagcggttt gtctcatgaa attcccgcaa tgacggttaa tgaggtctgc 4200
ggatcaggaa tgaaggccgt tattttggcg aaacaattga ttcaattagg agaagcggaa 4260
gttttaattg ctggcgggat tgagaatatg tcccaagcac ctaaattaca acgttttaat 4320
tacgaaacag aaagctacga tgcgcctttt tctagtatga tgtatgatgg attaacggat 4380
gcctttagtg gtcaggcaat gggcttaact gctgaaaatg tggccgaaaa gtatcatgta 4440
actagagaag agcaagatca attttctgta cattcacaat taaaagcagc tcaagcacaa 4500
gcagaaggga tattcgctga cgaaatagcc ccattagaag tatcaggaac gcttgtggag 4560
aaagatgaag ggattcgccc taattcgagc gttgagaagc taggaacgct taaaacagtt 4620
tttaaagaag acggtactgt aacagcaggg aatgcatcaa ccattaatga tggggcttct 4680
gctttgatta ttgcttcaca agaatatgcc gaagcacacg gtcttcctta tttagctatt 4740
attcgagaca gtgtggaagt cggtattgat ccagcctata tgggaatttc gccgattaaa 4800
gccattcaaa aactgttagc gcgcaatcaa cttactacgg aagaaattga tctgtatgaa 4860
atcaacgaag catttgcagc aacttcaatc gtggtccaaa gagaactggc tttaccagag 4920
gaaaaggtca acatttatgg tggcggtatt tcattaggtc atgcgattgg tgccacaggt 4980
gctcgtttat taacgagttt aagttatcaa ttaaatcaaa aagaaaagaa atatggagtg 5040
gcttctttat gtatcggcgg tggcttagga ctcgctatgc tactagagag acctcagcaa 5100
aaaaaaaaca gccgatttta tcaaatgagt cctgaggaac gcctggcttc tcttcttaat 5160
gaaggccaga tttctgctga tacaaaaaaa gaatttgaaa atacggcttt atcttcgcag 5220
attgccaatc atatgattga aaatcaaatc agtgaaacag aagtgccgat gggcgttggc 5280
ttacatttaa cagtggacga aactgattat ttggtaccaa tggcgacaga agagccctca 5340
gttattgcgg ctttgagtaa tggtgcaaaa atagcacaag gatttaaaac agtgaatcaa 5400
caacgcttaa tgcgtggaca aatcgttttt tacgatgttg cagatcccga gtcattgatt 5460
gataaactac aagtaagaga agcggaagtt tttcaacaag cagagttaag ttatccatct 5520
atcgttaaac ggggcggcgg cttaagagat ttgcaatatc gtacttttga tgaatcattt 5580

```
gtatctgtcg actttttagt agatgttaag gatgcaatgg gggcaaatat cgttaacgct   5640
atgttggaag gtgtggccga gttgttccgt gaatggtttg cggagcaaaa gattttattc   5700
agtattttaa gtaattatgc cacggagtcg gttgttacga tgaaaacggc tattccagtt   5760
tcacgtttaa gtaaggggag caatggccgg gaaattgctg aaaaaattgt tttagcttca   5820
cgctatgctt cattagatcc ttatcgggca gtcacgcata acaaaggaat catgaatggc   5880
attgaagctg tagttttagc tacaggaaat gatacacgcg ctgttagcgc ttcttgtcat   5940
gcttttgcgg tgaaggaagg tcgctaccaa ggcttgacta gttggacgct ggatggcgaa   6000
caactaattg gtgaaatttc agttccgctt gctttagcca cggttggcgg tgccacaaaa   6060
gtcttaccta aatctcaagc agctgctgat ttgttagcag tgacggatgc aaaagaacta   6120
agtcgagtag tagcggctgt tggtttggca caaaatttag cggcgttacg ggccttagtc   6180
tctgaaggaa ttcaaaaagg acacatggct ctacaagcac gttctttagc gatgacggtc   6240
ggagctactg gtaaagaagt tgaggcagtc gctcaacaat taaaacgtca aaaaacgatg   6300
aaccaagacc gagccatggc tattttaaat gatttaagaa aacaataaaa ggagagggtg   6360
acaattggga ttgataaaat tagttttttt gtgccccctt attatattga tatgacggca   6420
ctggctgaag ccagaaatgt agaccctgga aaatttcata ttggtattgg gcaagaccaa   6480
atggcggtga acccaatcag ccaagatatt gtgacatttg cagccaatgc cgcagaagcg   6540
atcttgacca aagaagataa agaggccatt gatatggtga ttgtcgggac tgagtccagt   6600
atcgatgagt caaaagcggc cgcagttgtc ttacatcgtt taatggggat tcaacctttc   6660
gctcgctctt tcgaaatcaa ggaagcttgt tacggagcaa cagcaggctt acagttagct   6720
aagaatcacg tagccttaca tccagataaa aaagtcttgg tcgtagcggc agatattgca   6780
aaatatggct taaattctgg cggtgagcct acacaaggag ctggggcggt tgcaatgtta   6840
gttgctagtg aaccgcgcat tttggcttta aaagaggata atgtgatgct gacgcaagat   6900
atctatgact tttggcgtcc aacaggccac ccgtatccta tggtcgatgg tcctttgtca   6960
aacgaaacct acatccaatc ttttgcccaa gtctgggatg aacataaaaa acgaaccggt   7020
cttgattttg cagattatga tgctttagcg ttccatattc cttacacaaa aatgggcaaa   7080
aaagccttat tagcaaaaat ctccgaccaa actgaagcag aacaggaacg aattttagcc   7140
cgttatgaag aaagtatcgt ctatagtcgt cgcgtaggaa acttgtatac gggttcactt   7200
tatctgggac tcatttccct tttagaaaat gcaacgactt taaccgcagg caatcaaatt   7260
ggtttattca gttatggttc tggtgctgtc gctgaatttt tcactggtga attagtagct   7320
ggttatcaaa atcatttaca aaaagaaact catttagcac tgctggataa tcggacagaa   7380
ctttctatcg ctgaatatga agccatgttt gcagaaactt tagacacaga cattgatcaa   7440
acgttagaag atgaattaaa atatagtatt tctgctatta ataataccgt tcgttcttat   7500
cgaaactaaa aaaaaccggc cttggccccg ccggtttttt attatttttc ttcctccgca   7560
tgttcaatcc gctccataat cgacggatgg ctccctctga aaattttaac gagaaacggc   7620
gggttgaccc ggctcagtcc cgtaacggcc aagtcctgaa acgtctcaat cgccgcttcc   7680
cggtttccgg tcagctcaat gccgtaacgg tcggcggcgt tttcctgata ccgggagacg   7740
gcattcgtaa tcgggatccc cgggtaccga gctcgaattc gtaatcatgt catagctgtt   7800
tcctgtgtga aattgttatc cgctcacaat tccacacaac atacgagccg gaagcataaa   7860
gtgtaaagcc tggggtgcct aatgagtgag ctaactcaca ttaattgcgt tgcgctcact   7920
```

-continued gcccgctttc cagtcgggaa acctgtcgtg ccagctgcat taatgaatcg gccaacgcgc 7980
ggggagaggc ggtttgcgta ttgggcgctc ttccgcttcc tcgctcactg ac 8032

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57
gaattgctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa tttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaaagag tgtgtgcgac ctcttctcaa tttactcaga ttaccgagca taattcccgt 660
cgttccgcaa actatcagcc aaacctgtgg aatttcgaat tcctgcaatc cctggagaac 720
gacctgaaag tggaaaagct ggaggagaaa gcgaccaaac tggaggaaga agttcgctgc 780
atgatcaacc gtgtagacac ccagccgctg tccctgctgg agctgatcga cgatgtgcag 840
cgcctgggtc tgacctacaa atttgaaaaa gacatcatta aagccctgga aaacatcgta 900
ctgctggacg aaaacaaaaa gaacaaatct gacctgcacg caaccgctct gtctttccgt 960
ctgctgcgtc agcacggttt cgaggtttct caggatgttt ttgagcgttt caaggataaa 1020
gaaggtggtt tcagcggtga actgaaaggt gacgtccaag gcctgctgag cctgtatgaa 1080
gcgtcttacc tgggtttcga gggtgagaac ctgctggagg aggcgcgtac cttttccatc 1140
acccacctga agaacaacct gaaagaaggc attaatacca aggttgcaga acaagtgagc 1200
cacgccctgg aactgccata tcaccagcgt ctgcaccgtc tggaggcacg ttggttcctg 1260
gataaatacg aaccgaaaga accgcatcac cagctgctgc tggagctggc gaagctggat 1320
tttaacatgg tacagaccct gcaccagaaa gagctgcaag atctgtcccg ctggtggacc 1380
gagatgggcc tggctagcaa actggatttt gtacgcgacc gcctgatgga agtttatttc 1440
tgggcactgg gtatggcgcc agacccgcag tttggtgaat gtcgcaaagc tgttactaaa 1500
atgtttggtc tggtgacgat catcgatgac gtgtatgacg tttatggcac tctggacgaa 1560
ctgcaactgt tcaccgatgc tgtagagcgc tgggacgtta acgctattaa caccctgccg 1620
gactatatga aactgtgttt cctggcactg tacaacaccg ttaacgacac gtcctattct 1680
attctgaaag agaaaggtca taacaacctg tcctatctga cgaaaagctg gcgtgaactg 1740
tgcaaagcct ttctgcaaga ggcgaaatgg tccaacaaca aaattatccc ggctttctcc 1800
aagtacctgg aaaacgccag cgtttcctcc tccggtgtag cgctgctggc gccgtcttac 1860
ttttccgtat gccagcagca ggaagacatc tccgaccacg cgctgcgttc cctgaccgac 1920
ttccatggtc tggtgcgttc tagctgcgtt atcttccgcc tgtgcaacga tctggccacc 1980

```
tctgcggcgg agctggaacg tggcgagact accaattcta tcattagcta catgcacgaa   2040
aacgatggta ccagcgagga acaggcccgc gaagaactgc gtaaactgat cgacgccgaa   2100
tggaaaaaga tgaatcgtga acgcgttagc gactccaccc tgctgcctaa agcgttcatg   2160
gaaatcgcag ttaacatggc acgtgtttcc cactgcacct accagtatgg cgatggtctg   2220
ggtcgcccag actacgcgac tgaaaaccgc atcaaactgc tgctgattga ccctttcccg   2280
attaaccagc tgatgtatgt ctaaaaaaaa ccggccttgg ccccgccggt tttttattat   2340
ttttcttcct ccgcatgttc aatccgctcc ataatcgacg gatggctccc tctgaaaatt   2400
ttaacgagaa acggcgggtt gacccggctc agtcccgtaa cggccaagtc ctgaaacgtc   2460
tcaatcgccg cttcccggtt tccggtcagc tcaatgccgt aacggtcggc ggcgttttcc   2520
tgataccggg agacggcatt cgtaatcgga tcctctagag tcgacctgca ggcatgcaag   2580
ctttgcctcg cgcgtttcgg tgatgacggt gaaaacctct gacacatgca gctcccggag   2640
acggtcacag cttgtctgta agcggatgcc gggagcagac aagcccgtca gggcgcgtca   2700
gcgggtgttg gcgggtgtcg gggcgcagcc atgacccagt cacgtagcga tagcggagtg   2760
tatactggct taactatgcg gcatcagagc agattgtact gagagtgcac catatgcggt   2820
gtgaaatacc gcacagatgc gtaaggagaa aataccgcat caggcgctct tccgcttcct   2880
cgctcactga ctcgctgcgc tcggtcgttc ggctgcggcg agcggtatca gctcactcaa   2940
aggcggtaat acggttatcc acagaatcag gggataacgc aggaaagaac atgtgagcaa   3000
aaggccagca aaaggccagg aaccgtaaaa aggccgcgtt gctggcgttt ttccataggc   3060
tccgcccccc tgacgagcat cacaaaaatc gacgctcaag tcagaggtgg cgaaacccga   3120
caggactata aagataccag gcgtttcccc ctggaagctc cctcgtgcgc tctcctgttc   3180
cgaccctgcc gcttaccgga tacctgtccg cctttctccc ttcgggaagc gtggcgcttt   3240
ctcaatgctc acgctgtagg tatctcagtt cggtgtaggt cgttcgctcc aagctgggct   3300
gtgtgcacga accccccgtt cagcccgacc gctgcgcctt atccggtaac tatcgtcttg   3360
agtccaaccc ggtaagacac gacttatcgc cactggcagc agccactggt aacaggatta   3420
gcagagcgag gtatgtaggc ggtgctacag agttcttgaa gtggtggcct aactacggct   3480
acactagaag gacagtattt ggtatctgcg ctctgctgaa gccagttacc ttcggaaaaa   3540
gagttggtag ctcttgatcc ggcaaacaaa ccaccgctgg tagcggtggt ttttttgttt   3600
gcaagcagca gattacgcgc agaaaaaaag gatctcaaga agatcctttg atcttttcta   3660
cggggtctga cgctcagtgg aacgaaaact cacgttaagg gattttggtc atgagattat   3720
caaaaaggat cgaagtcggt tcagaaaaag aaggatatgg atctggagct gtaatataaa   3780
aaccttcttc aactaacggg gcaggttagt gacattagaa aaccgactgt aaaaagtaca   3840
gtcggcatta tctcatatta taaaagccag tcattaggcc tatctgacaa ttcctgaata   3900
gagttcataa acaatcctgc atgataacca tcacaaacag aatgatgtac ctgtaaagat   3960
agcggtaaat atattgaatt acctttatta atgaattttc ctgctgtaat aatgggtaga   4020
aggtaattac tattattatt gatatttaag ttaaacccag taaatgaagt ccatggaata   4080
atagaaagag aaaaagcatt ttcaggtata ggtgttttgg gaaacaattt aaaagaacca   4140
ttatatttct ctacatcaga aaggtataaa tcataaaact ctttgaagtc attctttaca   4200
ggagtccaaa taccagagaa tgttttagat acaccatcaa aaattgtata aagtggctct   4260
aacttatccc aataacctaa ctctccgtcg ctattgtaac cagttctaaa agctgtattt   4320
```

-continued

```
gagtttatca cccttgtcac taagaaaata aatgcagggt aaaatttata tccttcttgt   4380
tttatgtttc ggtataaaac actaatatca atttctgtgg ttatactaaa agtcgtttgt   4440
tggttcaaat aatgattaaa tatctctttt ctcttccaat tgtctaaatc aattttatta   4500
aagttcattt gatatgcctc ctaaattttt atctaaagtg aatttaggag gcttacttgt   4560
ctgctttctt cattagaatc aatccttttt taaagtcaat attactgtaa cataaatata   4620
tattttaaaa atatcccact ttatccaatt ttcgtttgtt gaactaatgg gtgctttagt   4680
tgaagaataa agaccacatt aaaaaatgtg gtcttttgtg ttttttaaa ggatttgagc    4740
gtacgcgaaa aatccttttc tttctttctt atcttgataa taagggtaac tattgccggt   4800
tgtccattca tggctgaact ctgcttcctc tgttgacatg acacacatca tctcaatatc   4860
cgaatagggc ccatcagtct gacgaccaag agagccataa acaccaatag ccttaacatc   4920
atccccatat ttatccaata ttcgttcctt aatttcatga acaatcttca ttctttcttc   4980
tctagtcatt attattggtc cattcactat tctcattccc ttttcagata attttagatt   5040
tgcttttcta aataagaata tttggagagc accgttctta ttcagctatt aataactcgt   5100
cttcctaagc atccttcaat ccttttaata acaattatag catctaatct tcaacaaact   5160
ggcccgtttg ttgaactact ctttaataaa ataattttc cgttcccaat tccacattgc    5220
aataatagaa aatccatctt catcggcttt ttcgtcatca tctgtatgaa tcaaatcgcc   5280
ttcttctgtg tcatcaaggt ttaatttttt atgtatttct tttaacaaac caccatagga   5340
gattaacctt ttacggtgta aaccttcctc caaatcagac aaacgtttca aattcttttc   5400
ttcatcatcg gtcataaaat ccgtatcctt tacaggatat tttgcagttt cgtcaattgc   5460
cgattgtata tccgatttat atttattttt cggtcgaatc atttgaactt ttacatttgg   5520
atcatagtct aatttcattg ccttttttcca aaattgaatc cattgttttt gattcacgta  5580
gtttctgtt attctaaaat aagttggttc cacacatacc attacatgca tgtgctgatt    5640
ataagaatta tctttattat ttattgtcac atccgttgca cgcataaaac caacaagatt   5700
tttattaatt tttttatatt gcatcattcg gcgaaatcct tgagccatat ctgtcaaact   5760
cttatttaat tcttcgccat cataaacatt tttaactgtt aatgtgagaa acaaccaacg   5820
aactgttggc ttttgtttaa taacttcagc aacaaccttt tgtgactgaa tgccatgttt   5880
cattgctctc ctccagttgc acattggaca aagcctggat ttgcaaaacc acactcgata   5940
ccactttctt tcgcctgttt cacgattttg tttatactct aatatttcag cacaatcttt   6000
tactctttca gccttttttaa attcaagaat atgcagaagt tcaaagtaat caacattagc  6060
gattttcttt tctctccatg gtctcacttt tccacttttt gtcttgtcca ctaaaaccct   6120
tgattttttca tctgaataaa tgctactatt aggacacata atattaaaag aaaccccccat 6180
ctatttagtt atttgtttag tcacttataa ctttaacaga tggggttttt ctgtgcaacc   6240
aattttaagg gttttcaata ctttaaaaca catacatacc aacacttcaa cgcacctttc   6300
agcaactaaa ataaaaatga cgttatttct atatgtatca agataagaaa gaacaagttc   6360
aaaaccatca aaaaaagaca ccttttcagg tgcttttttt attttataaa ctcattccct   6420
gatctcgact tcgttctttt tttacctctc ggttatgagt tagttcaaat tcgttctttt   6480
taggttctaa atcgtgtttt tcttggaatt gtgctgtttt atcctttacc ttgtctacaa   6540
accccttaaa aacgttttta aaggctttta agccgtctgt acgttcctta ag           6592
```

<210> SEQ ID NO 58
<211> LENGTH: 31

<212> TYPE: DNA
<213> ORGANISM: Artificial Sequence
<220> FEATURE:
<223> OTHER INFORMATION: PCR Primer

<400> SEQUENCE: 58
gacatcaatt gctccatttt cttctgctat c                          31

<210> SEQ ID NO 59
<211> LENGTH: 41
<212> TYPE: DNA
<213> ORGANISM: Artificial Sequence
<220> FEATURE:
<223> OTHER INFORMATION: PCR Primer

<400> SEQUENCE: 59
attgagaaga ggtcgcacac actctttacc ctctcctttt a               41

<210> SEQ ID NO 60
<211> LENGTH: 41
<212> TYPE: DNA
<213> ORGANISM: Artificial Sequence
<220> FEATURE:
<223> OTHER INFORMATION: PCR Primer

<400> SEQUENCE: 60
taaaaggaga gggtaaagag tgtgtgcgac ctcttctcaa t               41

<210> SEQ ID NO 61
<211> LENGTH: 41
<212> TYPE: DNA
<213> ORGANISM: Artificial Sequence
<220> FEATURE:
<223> OTHER INFORMATION: PCR Primer

<400> SEQUENCE: 61
ccaaggccgg ttttttttag acatacatca gctggttaat c               41

<210> SEQ ID NO 62
<211> LENGTH: 41
<212> TYPE: DNA
<213> ORGANISM: Artificial Sequence
<220> FEATURE:
<223> OTHER INFORMATION: PCR Primer

<400> SEQUENCE: 62
gattaaccag ctgatgtatg tctaaaaaaa accggccttg g               41

<210> SEQ ID NO 63
<211> LENGTH: 32
<212> TYPE: DNA
<213> ORGANISM: Artificial Sequence
<220> FEATURE:
<223> OTHER INFORMATION: PCR Primer

<400> SEQUENCE: 63
gacatgacgg atccgattac gaatgccgtc tc                         32

<210> SEQ ID NO 64
<211> LENGTH: 31
<212> TYPE: DNA
<213> ORGANISM: Artificial Sequence
<220> FEATURE:
<223> OTHER INFORMATION: PCR Primer

<400> SEQUENCE: 64
gacatcaatt gctccatttt cttctgctat c 31

<210> SEQ ID NO 65
<211> LENGTH: 27
<212> TYPE: DNA
<213> ORGANISM: Artificial Sequence
<220> FEATURE:
<223> OTHER INFORMATION: PCR Primer

<400> SEQUENCE: 65
gacatgaatt cctccatttt cttctgc 27

<210> SEQ ID NO 66
<211> LENGTH: 20
<212> TYPE: DNA
<213> ORGANISM: Artificial Sequence
<220> FEATURE:
<223> OTHER INFORMATION: PCR Primer

<400> SEQUENCE: 66
aggagagggt aaagagtgag 20

<210> SEQ ID NO 67
<211> LENGTH: 22
<212> TYPE: DNA
<213> ORGANISM: Artificial Sequence
<220> FEATURE:
<223> OTHER INFORMATION: PCR Primer

<400> SEQUENCE: 67
cttttccatc acccacctga ag 22

<210> SEQ ID NO 68
<211> LENGTH: 28
<212> TYPE: DNA
<213> ORGANISM: Artificial Sequence
<220> FEATURE:
<223> OTHER INFORMATION: PCR Primer

<400> SEQUENCE: 68
ggcgaaatgg tccaacaaca aaattatc 28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c 51

<210> SEQ ID NO 70
<211> LENGTH: 23
<212> TYPE: DNA
<213> ORGANISM: Artificial Sequence
<220> FEATURE:
<223> OTHER INFORMATION: PCR Primer

<400> SEQUENCE: 70
gcaggtggga aactatgcac tcc 23

<210> SEQ ID NO 71
<211> LENGTH: 36
<212> TYPE: DNA
<213> ORGANISM: Artificial Sequence
<220> FEATURE:
<223> OTHER INFORMATION: PCR Primer

<400> SEQUENCE: 71
cctgaattct gttggattgg aggattggat agtggg 36

<210> SEQ ID NO 72
<211> LENGTH: 30
<212> TYPE: DNA
<213> ORGANISM: Artificial Sequence
<220> FEATURE:
<223> OTHER INFORMATION: PCR Primer

<400> SEQUENCE: 72
ggtgtcgacg tacggtcgag cttattgacc 30

<210> SEQ ID NO 73
<211> LENGTH: 32
<212> TYPE: DNA
<213> ORGANISM: Artificial Sequence
<220> FEATURE:
<223> OTHER INFORMATION: PCR Primer

<400> SEQUENCE: 73
ggtgggcccg cattttgcca cctacaagcc ag 32

<210> SEQ ID NO 74
<211> LENGTH: 40
<212> TYPE: DNA
<213> ORGANISM: Artificial Sequence
<220> FEATURE:
<223> OTHER INFORMATION: PCR Primer

<400> SEQUENCE: 74
ggtgaattct agaggatccc aacgctgttg cctacaacgg 40

<210> SEQ ID NO 75
<211> LENGTH: 36
<212> TYPE: DNA
<213> ORGANISM: Artificial Sequence
<220> FEATURE:
<223> OTHER INFORMATION: PCR Primer

<400> SEQUENCE: 75
ggtgcggccg ctgtctggac ctggtgagtt tccccg 36

<210> SEQ ID NO 76
<211> LENGTH: 37
<212> TYPE: DNA
<213> ORGANISM: Artificial Sequence
<220> FEATURE:
<223> OTHER INFORMATION: PCR Primer

<400> SEQUENCE: 76
ggtgggccca ttaaatcagt tatcgtttat ttgatag 37

<210> SEQ ID NO 77
<211> LENGTH: 35
<212> TYPE: DNA
<213> ORGANISM: Artificial Sequence
<220> FEATURE:
<223> OTHER INFORMATION: PCR Primer

<400> SEQUENCE: 77
ggtgaccagc aagtccatgg gtggtttgat catgg 35

<210> SEQ ID NO 78
<211> LENGTH: 35
<212> TYPE: DNA
<213> ORGANISM: Artificial Sequence
<220> FEATURE:
<223> OTHER INFORMATION: PCR Primer

<400> SEQUENCE: 78
ggtgcggccg cctttggagt acgactccaa ctatg 35

<210> SEQ ID NO 79
<211> LENGTH: 31
<212> TYPE: DNA
<213> ORGANISM: Artificial Sequence
<220> FEATURE:
<223> OTHER INFORMATION: PCR Primer

<400> SEQUENCE: 79
gcggccgcag actaaattta tttcagtctc c 31

<210> SEQ ID NO 80
<211> LENGTH: 7
<212> TYPE: DNA
<213> ORGANISM: Escherichia coli

<400> SEQUENCE: 80 aggaggt 7

<210> SEQ ID NO 81
<211> LENGTH: 7
<212> TYPE: DNA
<213> ORGANISM: Escherichial coli

<400> SEQUENCE: 81 aaggagg 7

<210> SEQ ID NO 82
<211> LENGTH: 27
<212> TYPE: DNA
<213> ORGANISM: Artificial Sequence
<220> FEATURE:
<223> OTHER INFORMATION: PCR Primer

<400> SEQUENCE: 82
gacatctgca gctccatttt cttctgc 27

<210> SEQ ID NO 83
<211> LENGTH: 42
<212> TYPE: DNA
<213> ORGANISM: Artificial Sequence
<220> FEATURE:
<223> OTHER INFORMATION: PCR Primer

<400> SEQUENCE: 83
caataataac tactgttttc actctttacc ctctcctttt aa 42

<210> SEQ ID NO 84
<211> LENGTH: 42
<212> TYPE: DNA
<213> ORGANISM: Artificial Sequence
<220> FEATURE:
<223> OTHER INFORMATION: PCR Primer

<400> SEQUENCE: 84
ttaaaaggag agggtaaaga gtgaaaacag tagttattat tg 42

<210> SEQ ID NO 85
<211> LENGTH: 45
<212> TYPE: DNA
<213> ORGANISM: Artificial Sequence
<220> FEATURE:
<223> OTHER INFORMATION: PCR Primer

<400> SEQUENCE: 85
cggggccaag gccggttttt tttagtttcg ataagaacga acggt 45

<210> SEQ ID NO 86
<211> LENGTH: 7999
<212> TYPE: DNA
<213> ORGANISM: Artificial Sequence
<220> FEATURE:
<223> OTHER INFORMATION: Synthetic Construct

<400> SEQUENCE: 86
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatggatcc 420
gagctcagga ggtaaaaaaa catgaaaaca gtagttatta ttgatgcatt acgaacacca 480
attggaaaat ataaaggcag cttaagtcaa gtaagtgccg tagacttagg aacacatgtt 540
acaacacaac ttttaaaaag acattccact atttctgaag aaattgatca agtaatcttt 600
ggaaatgttt tacaagctgg aaatggccaa aatcccgcac gacaaatagc aataaacagc 660
ggtttgtctc atgaaattcc cgcaatgacg gttaatgagg tctgcggatc aggaatgaag 720
gccgttattt tggcgaaaca attgattcaa ttaggagaag cggaagtttt aattgctggc 780
gggattgaga atatgtccca agcacctaaa ttacaacgtt ttaattacga aacagaaagc 840
tacgatgcgc ctttttctag tatgatgtat gatggattaa cggatgcctt tagtggtcag 900
gcaatgggct taactgctga aaatgtggcc gaaaagtatc atgtaactag agaagagcaa 960
gatcaatttt ctgtacattc acaattaaaa gcagctcaag cacaagcaga agggatattc 1020
gctgacgaaa tagccccatt agaagtatca ggaacgcttg tggagaaaga tgaagggatt 1080
cgccctaatt cgagcgttga gaagctagga acgcttaaaa cagtttttaa agaagacggt 1140
actgtaacag cagggaatgc atcaaccatt aatgatgggg cttctgcttt gattattgct 1200
tcacaagaat atgccgaagc acacggtctt ccttatttag ctattattcg agacagtgtg 1260
gaagtcggta ttgatccagc ctatatggga atttcgccga ttaaagccat tcaaaaactg 1320
ttagcgcgca atcaacttac tacggaagaa attgatctgt atgaaatcaa cgaagcattt 1380
gcagcaactt caatcgtggt ccaaagagaa ctggctttac cagaggaaaa ggtcaacatt 1440
tatggtggcg gtatttcatt aggtcatgcg attggtgcca caggtgctcg tttattaacg 1500
agtttaagtt atcaattaaa tcaaaaagaa aagaaatatg gagtggcttc tttatgtatc 1560
ggcggtggct taggactcgc tatgctacta gagagacctc agcaaaaaaa aaacagccga 1620
ttttatcaaa tgagtcctga ggaacgcctg gcttctcttc ttaatgaagg ccagatttct 1680

-continued

```
gctgatacaa aaaaagaatt tgaaaatacg gctttatctt cgcagattgc caatcatatg   1740
attgaaaatc aaatcagtga aacagaagtg ccgatgggcg ttggcttaca tttaacagtg   1800
gacgaaactg attatttggt accaatggcg acagaagagc cctcagttat tgcggctttg   1860
agtaatggtg caaaaatagc acaaggattt aaaacagtga atcaacaacg cttaatgcgt   1920
ggacaaatcg tttttacga tgttgcagat cccgagtcat tgattgataa actacaagta   1980
agagaagcgg aagtttttca acaagcagag ttaagttatc catctatcgt taaacggggc   2040
ggcggcttaa gagatttgca atatcgtact tttgatgaat catttgtatc tgtcgacttt   2100
ttagtagatg ttaaggatgc aatgggggca aatatcgtta acgctatgtt ggaaggtgtg   2160
gccgagttgt tccgtgaatg gtttgcggag caaaagattt tattcagtat tttaagtaat   2220
tatgccacgg agtcggttgt tacgatgaaa acggctattc cagtttcacg tttaagtaag   2280
gggagcaatg gccgggaaat tgctgaaaaa attgttttag cttcacgcta tgcttcatta   2340
gatccttatc gggcagtcac gcataacaaa ggaatcatga atggcattga agctgtagtt   2400
ttagctacag gaaatgatac acgcgctgtt agcgcttctt gtcatgcttt tgcggtgaag   2460
gaaggtcgct accaaggctt gactagttgg acgctggatg gcgaacaact aattggtgaa   2520
atttcagttc cgcttgcttt agccacggtt ggcggtgcca caaaagtctt acctaaatct   2580
caagcagctg ctgatttgtt agcagtgacg gatgcaaaag aactaagtcg agtagtagcg   2640
gctgttggtt tggcacaaaa tttagcggcg ttacgggcct tagtctctga aggaattcaa   2700
aaaggacaca tggctctaca agcacgttct ttagcgatga cggtcggagc tactggtaaa   2760
gaagttgagg cagtcgctca acaattaaaa cgtcaaaaaa cgatgaacca agaccgagcc   2820
atggctattt taaatgattt aagaaaacaa taaaggaggt aaaaaaacat gacaattggg   2880
attgataaaa ttagtttttt tgtgccccct tattatattg atatgacggc actggctgaa   2940
gccagaaatg tagaccctgg aaaatttcat attggtattg ggcaagacca aatggcggtg   3000
aacccaatca gccaagatat tgtgacattt gcagccaatg ccgcagaagc gatcttgacc   3060
aaagaagata aagaggccat tgatatggtg attgtcggga ctgagtccag tatcgatgag   3120
tcaaaagcgg ccgcagttgt cttacatcgt ttaatgggga ttcaaccttt cgctcgctct   3180
ttcgaaatca aggaagcttg ttacggagca acagcaggct tacagttagc taagaatcac   3240
gtagccttac atccagataa aaaagtcttg gtcgtagcgg cagatattgc aaaatatggc   3300
ttaaattctg gcggtgagcc tacacaagga gctggggcgg ttgcaatgtt agttgctagt   3360
gaaccgcgca ttttggcttt aaaagaggat aatgtgatgc tgacgcaaga tatctatgac   3420
ttttggcgtc caacaggcca cccgtatcct atggtcgatg gtcctttgtc aaacgaaacc   3480
tacatccaat cttttgccca agtctgggat gaacataaaa aacgaaccgg tcttgatttt   3540
gcagattatg atgctttagc gttccatatt ccttacacaa aaatgggcaa aaaagcctta   3600
ttagcaaaaa tctccgacca aactgaagca gaacaggaac gaattttagc ccgttatgaa   3660
gaaagtatcg tctatagtcg tcgcgtagga aacttgtata cgggttcact ttatctggga   3720
ctcatttccc ttttagaaaa tgcaacgact ttaaccgcag gcaatcaaat tggtttattc   3780
agttatggtt ctggtgctgt cgctgaattt ttcactggtg aattagtagc tggttatcaa   3840
aatcatttac aaaaagaaac tcatttagca ctgctggata atcggacaga actttctatc   3900
gctgaatatg aagccatgtt tgcagaaact ttagacacag acattgatca aacgttagaa   3960
gatgaattaa aatatagtat ttctgctatt aataataccg ttcgttctta tcgaaactaa   4020
gagatctgca gctggtacca tatgggaatt cgaagcttgg gcccgaacaa aaactcatct   4080
```

-continued cagaagagga tctgaatagc gccgtcgacc atcatcatca tcatcattga gtttaaacgg 4140
tctccagctt ggctgttttg gcggatgaga gaagattttc agcctgatac agattaaatc 4200
agaacgcaga agcggtctga taaaacagaa tttgcctggc ggcagtagcg cggtggtccc 4260
acctgacccc atgccgaact cagaagtgaa acgccgtagc gccgatggta gtgtggggtc 4320
tccccatgcg agagtaggga actgccaggc atcaaataaa acgaaaggct cagtcgaaag 4380
actgggcctt tcgttttatc tgttgtttgt cggtgaacgc tctcctgagt aggacaaatc 4440
cgccgggagc ggatttgaac gttgcgaagc aacggcccgg agggtggcgg gcaggacgcc 4500
cgccataaac tgccaggcat caaattaagc agaaggccat cctgacggat ggcctttttg 4560
cgtttctaca aactcttttt gtttattttt ctaaatacat tcaaatatgt atccgctcat 4620
gagacaataa ccctgataaa tgcttcaata atattgaaaa aggaagagta tgagtattca 4680
acatttccgt gtcgccctta ttcccttttt tgcggcattt tgccttcctg tttttgctca 4740
cccagaaacg ctggtgaaag taaaagatgc tgaagatcag ttgggtgcac gagtgggtta 4800
catcgaactg gatctcaaca gcggtaagat ccttgagagt tttcgccccg aagaacgttt 4860
tccaatgatg agcactttta aagttctgct atgtggcgcg gtattatccc gtgttgacgc 4920
cgggcaagag caactcggtc gccgcataca ctattctcag aatgacttgg ttgagtactc 4980
accagtcaca gaaaagcatc ttacggatgg catgacagta agagaattat gcagtgctgc 5040
cataaccatg agtgataaca ctgcggccaa cttacttctg acaacgatcg gaggaccgaa 5100
ggagctaacc gcttttttgc acaacatggg ggatcatgta actcgccttg atcgttggga 5160
accggagctg aatgaagcca taccaaacga cgagcgtgac accacgatgc ctgtagcaat 5220
ggcaacaacg ttgcgcaaac tattaactgg cgaactactt actctagctt cccggcaaca 5280
attaatagac tggatggagg cggataaagt tgcaggacca cttctgcgct cggcccttcc 5340
ggctggctgg tttattgctg ataaatctgg agccggtgag cgtgggtctc gcggtatcat 5400
tgcagcactg gggccagatg gtaagccctc ccgtatcgta gttatctaca cgacggggag 5460
tcaggcaact atggatgaac gaaatagaca gatcgctgag ataggtgcct cactgattaa 5520
gcattggtaa ctgtcagacc aagtttactc atatatactt tagattgatt taaaacttca 5580
tttttaattt aaaaggatct aggtgaagat cctttttgat aatctcatga ccaaaatccc 5640
ttaacgtgag ttttcgttcc actgagcgtc agaccccgta gaaaagatca aaggatcttc 5700
ttgagatcct ttttttctgc gcgtaatctg ctgcttgcaa acaaaaaaac caccgctacc 5760
agcggtggtt tgtttgccgg atcaagagct accaactctt tttccgaagg taactggctt 5820
cagcagagcg cagataccaa atactgtcct tctagtgtag ccgtagttag gccaccactt 5880
caagaactct gtagcaccgc ctacatacct cgctctgcta atcctgttac cagtggctgc 5940
tgccagtggc gataagtcgt gtcttaccgg gttggactca agacgatagt taccggataa 6000
ggcgcagcgg tcgggctgaa cggggggttc gtgcacacag cccagcttgg agcgaacgac 6060
ctacaccgaa ctgagatacc tacagcgtga gctatgagaa agcgccacgc ttcccgaagg 6120
gagaaaggcg gacaggtatc cggtaagcgg cagggtcgga acaggagagc gcacgaggga 6180
gcttccaggg ggaaacgcct ggtatcttta tagtcctgtc gggtttcgcc acctctgact 6240
tgagcgtcga tttttgtgat gctcgtcagg ggggcggagc ctatggaaaa acgccagcaa 6300
cgcggccttt ttacggttcc tggccttttg ctggcctttt gctcacatgt tctttcctgc 6360
gttatcccct gattctgtgg ataaccgtat taccgccttt gagtgagctg ataccgctcg 6420

-continued

```
ccgcagccga acgaccgagc gcagcgagtc agtgagcgag gaagcggaag agcgcctgat   6480

gcggtatttt ctccttacgc atctgtgcgg tatttcacac cgcatatggt gcactctcag   6540

tacaatctgc tctgatgccg catagttaag ccagtataca ctccgctatc gctacgtgac   6600

tgggtcatgg ctgcgccccg acacccgcca acacccgctg acgcgccctg acgggcttgt   6660

ctgctcccgg catccgctta cagacaagct gtgaccgtct ccgggagctg catgtgtcag   6720

aggttttcac cgtcatcacc gaaacgcgcg aggcagcaga tcaattcgcg cgcgaaggcg   6780

aagcggcatg catttacgtt gacaccatcg aatggtgcaa aacctttcgc ggtatggcat   6840

gatagcgccc ggaagagagt caattcaggg tggtgaatgt gaaaccagta acgttatacg   6900

atgtcgcaga gtatgccggt gtctcttatc agaccgtttc ccgcgtggtg aaccaggcca   6960

gccacgtttc tgcgaaaacg cgggaaaaag tggaagcggc gatggcggag ctgaattaca   7020

ttcccaaccg cgtggcacaa caactggcgg gcaaacagtc gttgctgatt ggcgttgcca   7080

cctccagtct ggccctgcac gcgccgtcgc aaattgtcgc ggcgattaaa tctcgcgccg   7140

atcaactggg tgccagcgtg gtggtgtcga tggtagaacg aagcggcgtc gaagcctgta   7200

aagcggcggt gcacaatctt ctcgcgcaac gcgtcagtgg gctgatcatt aactatccgc   7260

tggatgacca ggatgccatt gctgtggaag ctgcctgcac taatgttccg gcgttatttc   7320

ttgatgtctc tgaccagaca cccatcaaca gtattatttt ctcccatgaa gacggtacgc   7380

gactgggcgt ggagcatctg gtcgcattgg gtcaccagca aatcgcgctg ttagcgggcc   7440

cattaagttc tgtctcggcg cgtctgcgtc tggctggctg gcataaatat ctcactcgca   7500

atcaaattca gccgatagcg gaacgggaag gcgactggag tgccatgtcc ggttttcaac   7560

aaaccatgca aatgctgaat gagggcatcg tcccactgcg atgctggttg ccaacgatca   7620

gatggcgctg ggcgcaatgc gcgccattac cgagtccggg ctgcgcgttg gtgcggatat   7680

ctcggtagtg ggatacgacg ataccgaaga cagctcatgt tatatcccgc cgtcaaccac   7740

catcaaacag gattttcgcc tgctggggca aaccagcgtg gaccgcttgc tgcaactctc   7800

tcagggccag gcggtgaagg gcaatcagct gttgcccgtc tcactggtga aaagaaaaac   7860

caccctggcg cccaatacgc aaaccgcctc tccccgcgcg ttggccgatt cattaatgca   7920

gctggcacga caggtttccc gactggaaag cgggcagtga gcgcaacgca attaatgtga   7980

gttagcgcga attgatctg                                                 7999
```

<210> SEQ ID NO 87
<211> LENGTH: 10433
<212> TYPE: DNA
<213> ORGANISM: Artificial Sequence
<220> FEATURE:
<223> OTHER INFORMATION: Synthetic Construct

<400> SEQUENCE: 87

```
cccgtcttac tgtcgggaat tcgcgttggc cgattcatta atgcagattc tgaaatgagc     60

tgttgacaat taatcatccg gctcgtataa tgtgtggaat tgtgagcgga taacaatttc    120

acacaggaaa cagcgccgct gagaaaaagc gaagcggcac tgctctttaa caatttatca    180

gacaatctgt gtgggcactc gaccggaatt atcgattaac tttattatta aaaattaaag    240

aggtatatat taatgtatcg attaaataag gaggaataaa ccatggatcc gagctcagga    300

ggtaaaaaaa catgaaaaca gtagttatta ttgatgcatt acgaacacca attggaaaat    360

ataaaggcag cttaagtcaa gtaagtgccg tagacttagg aacacatgtt acaacacaac    420

ttttaaaaag acattccact atttctgaag aaattgatca agtaatcttt ggaaatgttt    480
```

```
tacaagctgg aaatggccaa aatcccgcac gacaaatagc aataaacagc ggtttgtctc    540
atgaaattcc cgcaatgacg gttaatgagg tctgcggatc aggaatgaag gccgttattt    600
tggcgaaaca attgattcaa ttaggagaag cggaagtttt aattgctggc gggattgaga    660
atatgtccca agcacctaaa ttacaacgtt ttaattacga aacagaaagc tacgatgcgc    720
ctttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga gaagctagga acgcttaaaa cagtttttaa agaagacggt actgtaacag   1020
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga aacagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
tttttacga tgttgcagat cccgagtcat tgattgataa actacaagta agagaagcgg   1860
aagtttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaaagtctt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
cagtcgctca acaattaaaa cgtcaaaaaa cgatgaacca agaccgagcc atggctattt   2700
taaatgattt aagaaaacaa taaaggaggt aaaaaaacat gacaattggg attgataaaa   2760
ttagtttttt tgtgcccccct tattatattg atatgacggc actggctgaa gccagaaatg   2820
```

-continued

```
tagaccctgg aaaatttcat attggtattg ggcaagacca aatggcggtg aacccaatca   2880
gccaagatat tgtgacattt gcagccaatg ccgcagaagc gatcttgacc aaagaagata   2940
aagaggccat tgatatggtg attgtcggga ctgagtccag tatcgatgag tcaaaagcgg   3000
ccgcagttgt cttacatcgt ttaatgggga ttcaaccttt cgctcgctct ttcgaaatca   3060
aggaagcttg ttacggagca acagcaggct tacagttagc taagaatcac gtagccttac   3120
atccagataa aaaagtcttg gtcgtagcgg cagatattgc aaaatatggc ttaaattctg   3180
gcggtgagcc tacacaagga gctggggcgg ttgcaatgtt agttgctagt gaaccgcgca   3240
ttttggcttt aaaagaggat aatgtgatgc tgacgcaaga tatctatgac ttttggcgtc   3300
caacaggcca cccgtatcct atggtcgatg gtcctttgtc aaacgaaacc tacatccaat   3360
cttttgccca agtctgggat gaacataaaa aacgaaccgg tcttgatttt gcagattatg   3420
atgctttagc gttccatatt ccttacacaa aaatgggcaa aaaagcctta ttagcaaaaa   3480
tctccgacca aactgaagca gaacaggaac gaattttagc ccgttatgaa gaaagtatcg   3540
tctatagtcg tcgcgtagga aacttgtata cgggttcact ttatctggga ctcatttccc   3600
ttttagaaaa tgcaacgact ttaaccgcag gcaatcaaat tggtttattc agttatggtt   3660
ctggtgctgt cgctgaattt ttcactggtg aattagtagc tggttatcaa aatcatttac   3720
aaaaagaaac tcatttagca ctgctggata atcggacaga actttctatc gctgaatatg   3780
aagccatgtt tgcagaaact ttagacacag acattgatca aacgttagaa gatgaattaa   3840
aatatagtat ttctgctatt aataataccg ttcgttctta tcgaaactaa agatctgcat   3900
cctgcattcg cccttaggag gtaaaaaaac atgtgtgcga cctcttctca atttactcag   3960
attaccgagc ataattcccg tcgttccgca aactatcagc caaacctgtg gaatttcgaa   4020
ttcctgcaat ccctggagaa cgacctgaaa gtggaaaagc tggaggagaa agcgaccaaa   4080
ctggaggaag aagttcgctg catgatcaac cgtgtagaca cccagccgct gtccctgctg   4140
gagctgatcg acgatgtgca gcgcctgggt ctgacctaca aatttgaaaa agacatcatt   4200
aaagccctgg aaaacatcgt actgctggac gaaaacaaaa agaacaaatc tgacctgcac   4260
gcaaccgctc tgtctttccg tctgctgcgt cagcacggtt tcgaggtttc tcaggatgtt   4320
tttgagcgtt tcaaggataa agaaggtggt ttcagcggtg aactgaaagg tgacgtccaa   4380
ggcctgctga gcctgtatga agcgtcttac ctgggtttcg agggtgagaa cctgctggag   4440
gaggcgcgta ccttttccat cacccacctg aagaacaacc tgaaagaagg cattaatacc   4500
aaggttgcag aacaagtgag ccacgccctg gaactgccat atcaccagcg tctgcaccgt   4560
ctggaggcac gttggttcct ggataaatac gaaccgaaag aaccgcatca ccagctgctg   4620
ctggagctgg cgaagctgga ttttaacatg gtacagaccc tgcaccagaa agagctgcaa   4680
gatctgtccc gctggtggac cgagatgggc ctggctagca aactggattt tgtacgcgac   4740
cgcctgatgg aagtttattt ctgggcactg ggtatggcgc cagacccgca gtttggtgaa   4800
tgtcgcaaag ctgttactaa aatgtttggt ctggtgacga tcatcgatga cgtgtatgac   4860
gtttatggca ctctggacga actgcaactg ttcaccgatg ctgtagagcg ctgggacgtt   4920
aacgctatta acaccctgcc ggactatatg aaactgtgtt tcctggcact gtacaacacc   4980
gttaacgaca cgtcctattc tattctgaaa gagaaaggtc ataacaacct gtcctatctg   5040
acgaaaagct ggcgtgaact gtgcaaagcc tttctgcaag aggcgaaatg gtccaacaac   5100
aaaattatcc cggctttctc caagtacctg gaaaacgcca gcgtttcctc ctccggtgta   5160
gcgctgctgg cgccgtctta cttttccgta tgccagcagc aggaagacat ctccgaccac   5220
```

gcgctgcgtt ccctgaccga cttccatggt ctggtgcgtt ctagctgcgt tatcttccgc 5280
ctgtgcaacg atctggccac ctctgcggcg gagctggaac gtggcgagac taccaattct 5340
atcattagct acatgcacga aaacgatggt accagcgagg aacaggcccg cgaagaactg 5400
cgtaaactga tcgacgccga atggaaaaag atgaatcgtg aacgcgttag cgactccacc 5460
ctgctgccta aagcgttcat ggaaatcgca gttaacatgg cacgtgtttc ccactgcacc 5520
taccagtatg gcgatggtct gggtcgccca gactacgcga ctgaaaaccg catcaaactg 5580
ctgctgattg accctttccc gattaaccag ctgatgtatg tctaactgca gctggtacca 5640
tatgggaatt cgaagcttgg gcccgaacaa aaactcatct cagaagagga tctgaatagc 5700
gccgtcgacc atcatcatca tcatcattga gtttaaacgg tctccagctt ggctgttttg 5760
gcggatgaga gaagattttc agcctgatac agattaaatc agaacgcaga agcggtctga 5820
taaaacagaa tttgcctggc ggcagtagcg cggtggtccc acctgacccc atgccgaact 5880
cagaagtgaa acgccgtagc gccgatggta gtgtggggtc tccccatgcg agagtaggga 5940
actgccaggc atcaaataaa acgaaaggct cagtcgaaag actgggcctt tcgttttatc 6000
tgttgtttgt cggtgaacgc tctcctgagt aggacaaatc cgccgggagc ggatttgaac 6060
gttgcgaagc aacggcccgg agggtggcgg gcaggacgcc cgccataaac tgccaggcat 6120
caaattaagc agaaggccat cctgacggat ggcctttttg cgtttctaca aactcttttt 6180
gtttattttt ctaaatacat tcaaatatgt atccgctcat gagacaataa ccctgataaa 6240
tgcttcaata atctggcgta atagcgaaga ggcccgcacc gatcgccctt cccaacagtt 6300
gcgcagcctg aatggcgaat ggcgcctgat gcggtatttt ctccttacgc atctgtgcgg 6360
tatttcacac cgcatatggt gcactctcag tacaatctgc tctgatgccg catagttaag 6420
ccagccccga cacccgccaa cacccgctga cgagcttagt aaagccctcg ctagatttta 6480
atgcggatgt tgcgattact tcgccaacta ttgcgataac aagaaaaagc cagcctttca 6540
tgatatatct cccaatttgt gtagggctta ttatgcacgc ttaaaaataa taaaagcaga 6600
cttgacctga tagtttggct gtgagcaatt atgtgcttag tgcatctaac gcttgagtta 6660
agccgcgccg cgaagcggcg tcggcttgaa cgaattgtta gacattattt gccgactacc 6720
ttggtgatct cgcctttcac gtagtggaca aattcttcca actgatctgc gcgcgaggcc 6780
aagcgatctt cttcttgtcc aagataagcc tgtctagctt caagtatgac gggctgatac 6840
tgggccggca ggcgctccat tgcccagtcg gcagcgacat ccttcggcgc gattttgccg 6900
gttactgcgc tgtaccaaat gcgggacaac gtaagcacta catttcgctc atcgccagcc 6960
cagtcgggcg gcgagttcca tagcgttaag gtttcattta gcgcctcaaa tagatcctgt 7020
tcaggaaccg gatcaaagag ttcctccgcc gctggaccta ccaaggcaac gctatgttct 7080
cttgcttttg tcagcaagat agccagatca atgtcgatcg tggctggctc gaagatacct 7140
gcaagaatgt cattgcgctg ccattctcca aattgcagtt cgcgcttagc tggataacgc 7200
cacggaatga tgtcgtcgtg cacaacaatg gtgacttcta cagcgcggag aatctcgctc 7260
tctccagggg aagccgaagt ttccaaaagg tcgttgatca aagctcgccg cgttgtttca 7320
tcaagcctta cggtcaccgt aaccagcaaa tcaatatcac tgtgtggctt caggccgcca 7380
tccactgcgg agccgtacaa atgtacggcc agcaacgtcg gttcgagatg gcgctcgatg 7440
acgccaacta cctctgatag ttgagtcgat acttcggcga tcaccgcttc cctcatgatg 7500
tttaactttg ttttagggcg actgccctgc tgcgtaacat cgttgctgct ccataacatc 7560

```
aaacatcgac ccacggcgta acgcgcttgc tgcttggatg cccgaggcat agactgtacc   7620
ccaaaaaaac agtcataaca agccatgaaa accgccactg cgccgttacc accgctgcgt   7680
tcggtcaagg ttctggacca gttgcgtgag cgcatacgct acttgcatta cagcttacga   7740
accgaacagg cttatgtcca ctgggttcgt gccttcatcc gtttccacgg tgtgcgtcac   7800
ccggcaacct tgggcagcag cgaagtcgag gcatttctgt cctggctggc gaacgagcgc   7860
aaggtttcgg tctccacgca tcgtcaggca ttggcggcct tgctgttctt ctacggcaag   7920
gtgctgtgca cggatctgcc ctggcttcag gagatcggaa gacctcggcc gtcgcggcgc   7980
ttgccggtgg tgctgacccc ggatgaagtg gttcgcatcc tcggttttct ggaaggcgag   8040
catcgtttgt tcgcccagct tctgtatgga acgggcatgc ggatcagtga gggtttgcaa   8100
ctgcgggtca aggatctgga tttcgatcac ggcacgatca tcgtgcggga gggcaagggc   8160
tccaaggatc gggccttgat gttacccgag agcttggcac ccagcctgcg cgagcagggg   8220
aattaattcc cacgggtttt gctgcccgca aacgggctgt tctggtgttg ctagtttgtt   8280
atcagaatcg cagatccggc ttcagccggt ttgccggctg aaagcgctat ttcttccaga   8340
attgccatga tttttcccc acgggaggcg tcactggctc ccgtgttgtc ggcagctttg   8400
attcgataag cagcatcgcc tgtttcaggc tgtctatgtg tgactgttga gctgtaacaa   8460
gttgtctcag gtgttcaatt tcatgttcta gttgctttgt tttactggtt tcacctgttc   8520
tattaggtgt tacatgctgt tcatctgtta cattgtcgat ctgttcatgg tgaacagctt   8580
tgaatgcacc aaaaactcgt aaaagctctg atgtatctat cttttttaca ccgttttcat   8640
ctgtgcatat ggacagtttt ccctttgata tgtaacggtg aacagttgtt ctacttttgt   8700
ttgttagtct tgatgcttca ctgatagata caagagccat aagaacctca gatccttccg   8760
tatttagcca gtatgttctc tagtgtggtt cgttgttttt gcgtgagcca tgagaacgaa   8820
ccattgagat catacttact ttgcatgtca ctcaaaaatt ttgcctcaaa actggtgagc   8880
tgaatttttg cagttaaagc atcgtgtagt gtttttctta gtccgttatg taggtaggaa   8940
tctgatgtaa tggttgttgg tattttgtca ccattcattt ttatctggtt gttctcaagt   9000
tcggttacga gatccatttg tctatctagt tcaacttgga aaatcaacgt atcagtcggg   9060
cggcctcgct tatcaaccac caatttcata ttgctgtaag tgtttaaatc tttacttatt   9120
ggtttcaaaa cccattggtt aagcctttta aactcatggt agttattttc aagcattaac   9180
atgaacttaa attcatcaag gctaatctct atatttgcct tgtgagtttt cttttgtgtt   9240
agttctttta ataaccactc ataaatcctc atagagtatt tgttttcaaa agacttaaca   9300
tgttccagat tatattttat gaattttttt aactggaaaa gataaggcaa tatctcttca   9360
ctaaaaacta attctaattt ttcgcttgag aacttggcat agtttgtcca ctggaaaatc   9420
tcaaagcctt taaccaaagg attcctgatt tccacagttc tcgtcatcag ctctctggtt   9480
gctttagcta atacaccata agcattttcc ctactgatgt tcatcatctg agcgtattgg   9540
ttataagtga acgataccgt ccgttctttc cttgtagggt tttcaatcgt ggggttgagt   9600
agtgccacac agcataaaat tagcttggtt tcatgctccg ttaagtcata gcgactaatc   9660
gctagttcat ttgctttgaa aacaactaat tcagacatac atctcaattg gtctaggtga   9720
ttttaatcac tataccaatt gagatgggct agtcaatgat aattactagt ccttttcctt   9780
tgagttgtgg gtatctgtaa attctgctag acctttgctg gaaaacttgt aaattctgct   9840
agaccctctg taaattccgc tagacctttg tgtgtttttt ttgtttatat tcaagtggtt   9900
ataatttata gaataaagaa agaataaaaa aagataaaaa gaatagatcc cagccctgtg   9960
```

```
tataactcac tactttagtc agttccgcag tattacaaaa ggatgtcgca aacgctgttt  10020

gctcctctac aaaacagacc ttaaaaccct aaaggcttaa gtagcaccct cgcaagctcg  10080

ggcaaatcgc tgaatattcc ttttgtctcc gaccatcagg cacctgagtc gctgtctttt  10140

tcgtgacatt cagttcgctg cgctcacggc tctggcagtg aatgggggta aatggcacta  10200

caggcgcctt ttatggattc atgcaaggaa actacccata atacaagaaa agcccgtcac  10260

gggcttctca gggcgtttta tggcgggtct gctatgtggt gctatctgac tttttgctgt  10320

tcagcagttc ctgccctctg attttccagt ctgaccactt cggattatcc cgtgacaggt  10380

cattcagact ggctaatgca cccagtaagg cagcggtatc atcaacaggc tta         10433
```

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct

<400> SEQUENCE: 88

```
cttgatgcat cctgcattcg cccttaggag g                                    31
```

<210> SEQ ID NO 89
<211> LENGTH: 23
<212> TYPE: DNA
<213> ORGANISM: Artificial Sequence
<220> FEATURE:
<223> OTHER INFORMATION: PCR Primer

<400> SEQUENCE: 89

```
ccaggcaaat tctgttttat cag                                             23
```

<210> SEQ ID NO 90
<211> LENGTH: 10356
<212> TYPE: DNA
<213> ORGANISM: Artificial Sequence
<220> FEATURE:
<223> OTHER INFORMATION: Synthetic Construct

<400> SEQUENCE: 90

```
caagaaaaat gccccgctta cgcagggcat ccatttatta ctcaaccgta accgattttg     60

ccaggttacg cggctggtca acgtcggtgc ctttgatcag cgcgacatgg taagccagca    120

gctgcagcgg aacggtgtag aagatcggtg caatcacctc ttccacatgc ggcatctcga    180

tgatgtgcat gttatcgcta cttacaaaac ccgcatcctg atcggcgaag acatacaact    240

gaccgccacg cgcgcgaact tcttcaatgt tggatttcag tttttccagc aattcgttgt    300

tcggtgcaac aacaataacc ggcatatcgg catcaattag cgccagcgga ccgtgtttca    360

gttcgccagc agcgtaggct tcagcgtgaa tgtaagagat ctctttcaac ttcaatgcgc    420

cttccagcgc gattgggtac tgatcgccac ggcccaggaa cagcgcgtga tgtttgtcag    480

agaaatcttc tgccagcgct tcaatgcgtt tgtcctgaga cagcatctgc tcaatacggc    540

tcggcagcgc ctgcagacca tgcacgatgt catgttcaat ggaggcatcc agacctttca    600

ggcgagacag cttcgccacc agcatcaaca gcacagttaa ctgagtggtg aatgctttag    660

tggatgccac gccgatttct gtacccgcgt tggtcattag cgccagatcg gattcgcgca    720

ccagagaaga acccggaacg ttacagattg ccagtgaacc aaggtaaccc agctctttcg    780

acagacgcag gccagccagg gtatccgcgg tttcgccaga ctgtgacacg atcgcccttc    840
```

-continued

```
ccaacagttg cgcagcctat acgtacggca gtttaaggtt tacacctata aaagagagag    900
ccgttatcgt ctgtttgtgg atgtacagag tgatattatt gacacgccgg ggcgacggat    960
ggtgatcccc ctggccagtg cacgtctgct gtcagataaa gtctcccgtg aactttaccc   1020
ggtggtgcat atcggggatg aaagctggcg catgatgacc accgatatgg ccagtgtgcc   1080
ggtctccgtt atcggggaag aagtggctga tctcagccac cgcgaaaatg acatcaaaaa   1140
cgccattaac ctgatgttct ggggaatata aatgtcaggc atgagattat caaaaaggat   1200
cttcacctag atccttttca cgtagaaagc cagtccgcag aaacggtgct gaccccggat   1260
gaatgtcagc tactgggcta tctggacaag ggaaaacgca agcgcaaaga gaaagcaggt   1320
agcttgcagt gggcttacat ggcgatagct agactgggcg gttttatgga cagcaagcga   1380
accggaattg ccagctgggg cgccctctgg taaggttggg aagccctgca aagtaaactg   1440
gatggctttc tcgccgccaa ggatctgatg gcgcagggga tcaagctctg atcaagagac   1500
aggatgagga tcgtttcgca tgattgaaca agatggattg cacgcaggtt ctccggccgc   1560
ttgggtggag aggctattcg gctatgactg ggcacaacag acaatcggct gctctgatgc   1620
cgccgtgttc cggctgtcag cgcaggggcg cccggttctt tttgtcaaga ccgacctgtc   1680
cggtgccctg aatgaactgc aagacgaggc agcgcggcta tcgtggctgg ccacgacggg   1740
cgttccttgc gcagctgtgc tcgacgttgt cactgaagcg ggaagggact ggctgctatt   1800
gggcgaagtg ccggggcagg atctcctgtc atctcacctt gctcctgccg agaaagtatc   1860
catcatggct gatgcaatgc ggcggctgca tacgcttgat ccggctacct gcccattcga   1920
ccaccaagcg aaacatcgca tcgagcgagc acgtactcgg atggaagccg gtcttgtcga   1980
tcaggatgat ctggacgaag agcatcaggg gctcgcgcca gccgaactgt tcgccaggct   2040
caaggcgagc atgcccgacg gcgaggatct cgtcgtgacc catggcgatg cctgcttgcc   2100
gaatatcatg gtggaaaatg gccgcttttc tggattcatc gactgtggcc ggctgggtgt   2160
ggcggaccgc tatcaggaca tagcgttggc tacccgtgat attgctgaag agcttggcgg   2220
cgaatgggct gaccgcttcc tcgtgcttta cggtatcgcc gctcccgatt cgcagcgcat   2280
cgccttctat cgccttcttg acgagttctt ctgaattatt aacgcttaca atttcctgat   2340
gcggtatttt ctccttacgc atctgtgcgg tatttcacac cgcatacagg tggcactttt   2400
cggggaaatg tgcgcggaac ccctatttgt ttatttttct aaatacattc aaatatgtat   2460
ccgctcatga gacaataacc ctgataaatg cttcaataat agcacgtgag gagggccacc   2520
atggccaagt tgaccagtgc cgttccggtg ctcaccgcgc gcgacgtcgc cggagcggtc   2580
gagttctgga ccgaccggct cgggttctcc cctagtaacg gccgccagtg tgctggaatt   2640
caggcagttc aacctgttga tagtacgtac taagctctca tgtttcacgt actaagctct   2700
catgtttaac gtactaagct ctcatgttta acgaactaaa ccctcatggc taacgtacta   2760
agctctcatg gctaacgtac taagctctca tgtttcacgt actaagctct catgtttgaa   2820
caataaaatt aatataaatc agcaacttaa atagcctcta aggttttaag ttttataaga   2880
aaaaaaagaa tatataaggc ttttaaagct tttaaggttt aacggttgtg gacaacaagc   2940
cagggatgta acgcactgag aagcccttag agcctctcaa agcaattttc agtgacacag   3000
gaacacttaa cggctgacag cctgaattct gcagatatct gtttttccac tcttcgttca   3060
ctttcgccag gtagctggtg aagacgaagg aagtcccgga gccatctgcg cggcgtacta   3120
cagcaatgtt ttgtgaaggc agtttcagac ccggattcag tttggcgatg gcttcatcat   3180
cccacttctt gattttgccc aggtagatgt cgccgagggt tttaccatcc agcaccagtt   3240
```

cgccagactt cagccctgga atgttaaccg ccagcaccac gccgccaatc acggtcggga 3300
actggaacag accttcctga gccagttttt cgtcagacag cggcgcgtca gaggcaccaa 3360
aatcaacggt attagcgata atctgtttta cgccaccgga agaaccgata ccctggtagt 3420
taactttatt accggtttct ttctggtaag tgtcagccca tttggcatac accggcgcag 3480
ggaaggttgc acctgcacct gtcaggcttg cttctgcaaa cacagagaaa gcactcatcg 3540
ataaggtcgc ggcgacaaca gttgcgacgg tggtacgcat aactttcata atgtctcctg 3600
ggaggattca taaagcattg tttgttggct acgagaagca aaataggaca aacaggtgac 3660
agttatatgt aaggaatatg acagttttat gacagagaga taaagtcttc agtctgattt 3720
aaataagcgt tgatattcag tcaattacaa acattaataa cgaagagatg acagaaaaat 3780
tttcattctg tgacagagaa aaagtagccg aagatgacgg tttgtcacat ggagttggca 3840
ggatgtttga ttaaaagcaa ttaaccctca ctaaagggcg gccgcgaagt tcctattctc 3900
tagaaagtat aggaacttca ttctaccggg taggggaggc gcttttccca aggcagtctg 3960
gagcatgcgc tttagcagcc ccgctgggca cttggcgcta cacaagtggc ctctggcctc 4020
gcacacattc cacatccacc ggtaggcgcc aaccggctcc gttctttggt ggccccttcg 4080
cgccaccttc cactcctccc ctagtcagga agttcccccc cgccccgcag ctcgcgtcgt 4140
gcaggacgtg acaaatggaa gtagcacgtc tcactagtct cgtgcagatg gacagcaccg 4200
ctgagcaatg gaagcgggta ggcctttggg gcagcggcca atagcagctt tgctccttcg 4260
ctttctgggc tcagaggctg ggaaggggtg ggtccggggg cgggctcagg ggcgggctca 4320
ggggcggggc gggcgcccga aggtcctccg gaggcccggc attctgcacg cttcaaaagc 4380
gcacgtctgc cgcgctgttc tcctcttcct catctccggg cctttcgacc tgcagcagca 4440
cgtgttgaca attaatcatc ggcatagtat atcggcatag tataatacga caaggtgagg 4500
aactaaacca tggagaaaaa aatcactgga tataccaccg ttgatatatc ccaatggcat 4560
cgtaaagaac attttgaggc atttcagtca gttgctcaat gtacctataa ccagaccgtt 4620
cagctggata ttacggcctt tttaaagacc gtaaagaaaa ataagcacaa gttttatccg 4680
gcctttattc acattcttgc ccgcctgatg aatgctcatc cggaattccg tatggcaatg 4740
aaagacggtg agctggtgat atgggatagt gttcaccctt gttacaccgt tttccatgag 4800
caaactgaaa cgttttcatc gctctggagt gaataccacg acgatttccg gcagtttcta 4860
cacatatatt cgcaagatgt ggcgtgttac ggtgaaaacc tggcctattt ccctaaaggg 4920
tttattgaga atatgttttt cgtctcagcc aatccctggg tgagtttcac cagttttgat 4980
ttaaacgtgg ccaatatgga caacttcttc gcccccgttt tcaccatggg caaatattat 5040
acgcaaggcg acaaggtgct gatgccgctg gcgattcagg ttcatcatgc cgtttgtgat 5100
ggcttccatg tcggcagaat gcttaatgaa ttacaacagt actgcgatga gtggcagggc 5160
ggggcgtaag cgggactctg gggttcgaat aaagaccgac caagcgacgt ctgagagctc 5220
cctggcgaat tcggtaccaa taaaagagct ttattttcat gatctgtgtg ttggtttttg 5280
tgtgcggcgc ggaagttcct attctctaga aagtatagga acttcctcga gccctatagt 5340
gagtcgtatt agcccttgac gatgccacat cctgagcaaa taattcaacc actaattgtg 5400
agcggataac acaaggagga aacagctatg tcattaccgt tcttaacttc tgcaccggga 5460
aaggttatta tttttggtga acactctgct gtgtacaaca agcctgccgt cgctgctagt 5520
gtgtctgcgt tgagaaccta cctgctaata agcgagtcat ctgcaccaga tactattgaa 5580

-continued

```
ttggacttcc cggacattag ctttaatcat aagtggtcca tcaatgattt caatgccatc   5640
accgaggatc aagtaaactc ccaaaaattg gccaaggctc aacaagccac cgatggcttg   5700
tctcaggaac tcgttagtct tttggatccg ttgttagctc aactatccga atccttccac   5760
taccatgcag cgttttgttt cctgtatatg tttgtttgcc tatgcccccca tgccaagaat   5820
attaagtttt ctttaaagtc tactttaccc atcggtgctg ggttgggctc aagcgcctct   5880
atttctgtat cactggcctt agctatggcc tacttggggg ggttaatagg atctaatgac   5940
ttggaaaagc tgtcagaaaa cgataagcat atagtgaatc aatgggcctt cataggtgaa   6000
aagtgtattc acggtacccc ttcaggaata gataacgctg tggccactta tggtaatgcc   6060
ctgctatttg aaaaagactc acataatgga acaataaaca caaacaattt taagttctta   6120
gatgatttcc cagccattcc aatgatccta acctatacta gaattccaag gtctacaaaa   6180
gatcttgttg ctcgcgttcg tgtgttggtc accgagaaat ttcctgaagt tatgaagcca   6240
attctagatg ccatgggtga atgtgcccta caaggcttag agatcatgac taagttaagt   6300
aaatgtaaag gcaccgatga cgaggctgta gaaactaata atgaactgta tgaacaacta   6360
ttggaattga taagaataaa tcatggactg cttgtctcaa tcggtgtttc tcatcctgga   6420
ttagaactta ttaaaaatct gagcgatgat ttgagaattg gctccacaaa acttaccggt   6480
gctggtggcg gcggttgctc tttgactttg ttacgaagag acattactca agagcaaatt   6540
gacagcttca aaaagaaatt gcaagatgat tttagttacg agacatttga aacagacttg   6600
ggtgggactg gctgctgttt gttaagcgca aaaaatttga ataaagatct taaaatcaaa   6660
tccctagtat tccaattatt tgaaaataaa actaccacaa agcaacaaat tgacgatcta   6720
ttattgccag gaaacacgaa tttaccatgg acttcataag ctaatttgcg ataggcctgc   6780
acccttaagg aggaaaaaaa catgtcagag ttgagagcct tcagtgcccc agggaaagcg   6840
ttactagctg gtggatattt agttttagat acaaaatatg aagcatttgt agtcggatta   6900
tcggcaagaa tgcatgctgt agcccatcct tacggttcat tgcaagggtc tgataagttt   6960
gaagtgcgtg tgaaaagtaa acaatttaaa gatggggagt ggctgtacca tataagtcct   7020
aaaagtggct tcattcctgt ttcgataggc ggatctaaga accctttcat tgaaaaagtt   7080
atcgctaacg tatttagcta ctttaaacct aacatggacg actactgcaa tagaaacttg   7140
ttcgttattg atattttctc tgatgatgcc taccattctc aggaggatag cgttaccgaa   7200
catcgtggca acagaagatt gagttttcat tcgcacagaa ttgaagaagt tcccaaaaca   7260
gggctgggct cctcggcagg tttagtcaca gttttaacta cagctttggc ctcctttttt   7320
gtatcggacc tggaaaataa tgtagacaaa tatagagaag ttattcataa tttagcacaa   7380
gttgctcatt gtcaagctca gggtaaaatt ggaagcgggt ttgatgtagc ggcggcagca   7440
tatggatcta tcagatatag aagattccca cccgcattaa tctctaattt gccagatatt   7500
ggaagtgcta cttacggcag taaactggcg catttggttg atgaagaaga ctggaatatt   7560
acgattaaaa gtaaccattt accttcggga ttaactttat ggatgggcga tattaagaat   7620
ggttcagaaa cagtaaaact ggtccagaag gtaaaaaatt ggtatgattc gcatatgcca   7680
gaaagcttga aaatatatac agaactcgat catgcaaatt ctagatttat ggatggacta   7740
tctaaactag atcgcttaca cgagactcat gacgattaca gcgatcagat atttgagtct   7800
cttgagagga atgactgtac ctgtcaaaag tatcctgaaa tcacagaagt tagagatgca   7860
gttgccacaa ttagacgttc ctttagaaaa ataactaaag aatctggtgc cgatatcgaa   7920
cctcccgtac aaactagctt attggatgat tgccagacct taaaaggagt tcttacttgc   7980
```

```
ttaatacctg gtgctggtgg ttatgacgcc attgcagtga ttactaagca agatgttgat   8040
cttagggctc aaaccgctaa tgacaaaaga ttttctaagg ttcaatggct ggatgtaact   8100
caggctgact ggggtgttag gaaagaaaaa gatccggaaa cttatcttga taaataactt   8160
aaggtagctg catgcagaat tcgcccttaa ggaggaaaaa aaaatgaccg tttacacagc   8220
atccgttacc gcacccgtca acatcgcaac ccttaagtat tgggggaaaa gggacacgaa   8280
gttgaatctg cccaccaatt cgtccatatc agtgacttta tcgcaagatg acctcagaac   8340
gttgacctct gcggctactg cacctgagtt tgaacgcgac actttgtggt taaatggaga   8400
accacacagc atcgacaatg aaagaactca aaattgtctg cgcgacctac gccaattaag   8460
aaaggaaatg gaatcgaagg acgcctcatt gcccacatta tctcaatgga aactccacat   8520
tgtctccgaa aataactttc ctacagcagc tggtttagct tcctccgctg ctggctttgc   8580
tgcattggtc tctgcaattg ctaagttata ccaattacca cagtcaactt cagaaatatc   8640
tagaatagca agaaaggggt ctggttcagc ttgtagatcg ttgtttggcg gatacgtggc   8700
ctgggaaatg ggaaaagctg aagatggtca tgattccatg gcagtacaaa tcgcagacag   8760
ctctgactgg cctcagatga aagcttgtgt cctagttgtc agcgatatta aaaaggatgt   8820
gagttccact cagggtatgc aattgaccgt ggcaacctcc gaactattta aagaaagaat   8880
tgaacatgtc gtaccaaaga gatttgaagt catgcgtaaa gccattgttg aaaaagattt   8940
cgccaccttt gcaaaggaaa caatgatgga ttccaactct ttccatgcca catgtttgga   9000
ctctttccct ccaatattct acatgaatga cacttccaag cgtatcatca gttggtgcca   9060
caccattaat cagttttacg gagaaacaat cgttgcatac acgtttgatg caggtccaaa   9120
tgctgtgttg tactacttag ctgaaaatga gtcgaaactc tttgcattta tctataaatt   9180
gtttggctct gttcctggat gggacaagaa atttactact gagcagcttg aggctttcaa   9240
ccatcaattt gaatcatcta actttactgc acgtgaattg gatcttgagt tgcaaaagga   9300
tgttgccaga gtgattttaa ctcaagtcgg ttcaggccca caagaaacaa acgaatcttt   9360
gattgacgca aagactggtc taccaaagga ataagatcaa ttcgctgcat cgcccttagg   9420
aggtaaaaaa aaatgactgc cgacaacaat agtatgcccc atggtgcagt atctagttac   9480
gccaaattag tgcaaaacca aacacctgaa gacattttgg aagagtttcc tgaaattatt   9540
ccattacaac aaagacctaa tacccgatct agtgagacgt caaatgacga aagcggagaa   9600
acatgttttt ctggtcatga tgaggagcaa attaagttaa tgaatgaaaa ttgtattgtt   9660
ttggattggg acgataatgc tattggtgcc ggtaccaaga aagtttgtca tttaatggaa   9720
aatattgaaa agggtttact acatcgtgca ttctccgtct ttattttcaa tgaacaaggt   9780
gaattacttt tacaacaaag agccactgaa aaaataactt tccctgatct ttggactaac   9840
acatgctgct ctcatccact atgtattgat gacgaattag gtttgaaggg taagctagac   9900
gataagatta agggcgctat tactgcggcg gtgagaaaac tagatcatga attaggtatt   9960
ccagaagatg aaactaagac aaggggtaag tttcactttt taaacagaat ccattacatg  10020
gcaccaagca atgaaccatg gggtgaacat gaaattgatt acatcctatt ttataagatc  10080
aacgctaaag aaaacttgac tgtcaaccca aacgtcaatg aagttagaga cttcaaatgg  10140
gtttcaccaa atgatttgaa aactatgttt gctgacccaa gttacaagtt tacgccttgg  10200
tttaagatta tttgcgagaa ttacttattc aactggtggg agcaattaga tgacctttct  10260
gaagtggaaa atgacaggca aattcataga atgctataac aacgcgtcta caaataaaaa  10320
```

aggcacgtca gatgacgtgc ctttttttctt ggggcc 10356

<210> SEQ ID NO 91
<211> LENGTH: 43
<212> TYPE: DNA
<213> ORGANISM: Artificial Sequence
<220> FEATURE:
<223> OTHER INFORMATION: PCR Primer

<400> SEQUENCE: 91
gcatgctcga gcggccgctt ttaatcaaac atcctgccaa ctc 43

<210> SEQ ID NO 92
<211> LENGTH: 37
<212> TYPE: DNA
<213> ORGANISM: Artificial Sequence
<220> FEATURE:
<223> OTHER INFORMATION: PCR Primer

<400> SEQUENCE: 92
gatcgaaggg cgatcgtgtc acagtctggc gaaaccg 37

<210> SEQ ID NO 93
<211> LENGTH: 43
<212> TYPE: DNA
<213> ORGANISM: Artificial Sequence
<220> FEATURE:
<223> OTHER INFORMATION: PCR Primer

<400> SEQUENCE: 93
ctgaattctg cagatatctg tttttccact cttcgttcac ttt 43

<210> SEQ ID NO 94
<211> LENGTH: 33
<212> TYPE: DNA
<213> ORGANISM: Artificial Sequence
<220> FEATURE:
<223> OTHER INFORMATION: PCR Primer

<400> SEQUENCE: 94
tctagagggc ccaagaaaaa tgccccgctt acg 33

<210> SEQ ID NO 95
<211> LENGTH: 111
<212> TYPE: DNA
<213> ORGANISM: Artificial Sequence
<220> FEATURE:
<223> OTHER INFORMATION: PCR Primer

<400> SEQUENCE: 95
gatcgcggcc gcgcccttga cgatgccaca tcctgagcaa ataattcaac cactaattgt 60
gagcggataa cacaaggagg aaacagctat gtcattaccg ttcttaactt c 111

<210> SEQ ID NO 96
<211> LENGTH: 75
<212> TYPE: DNA
<213> ORGANISM: Artificial Sequence
<220> FEATURE:
<223> OTHER INFORMATION: PCR Primer

<400> SEQUENCE: 96
gatcgggccc caagaaaaaa ggcacgtcat ctgacgtgcc ttttttattt gtagacgcgt 60
tgttatagca ttcta 75

<210> SEQ ID NO 97
<211> LENGTH: 81
<212> TYPE: DNA
<213> ORGANISM: Artificial Sequence
<220> FEATURE:
<223> OTHER INFORMATION: PCR Primer

<400> SEQUENCE: 97
aaagtagccg aagatgacgg tttgtcacat ggagttggca ggatgtttga ttaaaagcaa 60
ttaaccctca ctaaagggcg g 81

<210> SEQ ID NO 98
<211> LENGTH: 160
<212> TYPE: DNA
<213> ORGANISM: Artificial Sequence
<220> FEATURE:
<223> OTHER INFORMATION: PCR Primer

<400> SEQUENCE: 98
agagtgttca ccaaaaataa taacctttcc cggtgcagaa gttaagaacg gtaatgacat 60
agctgtttcc tccttgtgtt atccgctcac aattagtggt tgaattattt gctcaggatg 120
tggcatcgtc aagggctaat acgactcact atagggctcg 160

<210> SEQ ID NO 99
<211> LENGTH: 60
<212> TYPE: DNA
<213> ORGANISM: Artificial Sequence
<220> FEATURE:
<223> OTHER INFORMATION: PCR Primer

<400> SEQUENCE: 99
gatcatgcat tcgcccttag gaggtaaaaa aacatgtgtg cgacctcttc tcaatttact 60

<210> SEQ ID NO 100
<211> LENGTH: 38
<212> TYPE: DNA
<213> ORGANISM: Artificial Sequence
<220> FEATURE:
<223> OTHER INFORMATION: PCR Primer

<400> SEQUENCE: 100
cggtcgacgg atccctgcag ttagacatac atcagctg 38

<210> SEQ ID NO 101
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 101
gtgcggccgc aagcttgtcg acggagctcg aattcggatc cctgcagtta gacatacatc 60
agctggttaa tcgggaaagg gtcaatcagc agcagtttga tgcggttttc agtcgcgtag 120
tctgggcgac ccagaccatc gccatactgg taggtgcagt gggaaacacg tgccatgtta 180
actgcgattt ccatgaacgc tttaggcagc agggtggagt cgctaacgcg ttcacgattc 240
atctttttcc attcggcgtc gatcagttta cgcagttctt cgcgggcctg ttcctcgctg 300
gtaccatcgt tttcgtgcat gtagctaatg atagaattgg tagtctcgcc acgttccagc 360
tccgccgcag aggtggccag atcgttgcac aggcggaaga taacgcagct agaacgcacc 420
agaccatgga agtcggtcag ggaacgcagc gcgtggtcgg agatgtcttc ctgctgctgg 480

-continued

```
catacggaaa agtaagacgg cgccagcagc gctacaccgg aggaggaaac gctggcgttt    540
tccaggtact tggagaaagc cgggataatt ttgttgttgg accatttcgc ctcttgcaga    600
aaggctttgc acagttcacg ccagcttttc gtcagatagg acaggttgtt atgacctttc    660
tctttcagaa tagaatagga cgtgtcgtta acggtgttgt acagtgccag gaaacacagt    720
ttcatatagt ccggcagggt gttaatagcg ttaacgtccc agcgctctac agcatcggtg    780
aacagttgca gttcgtccag agtgccataa acgtcataca cgtcatcgat gatcgtcacc    840
agaccaaaca ttttagtaac agctttgcga cattcaccaa actgcgggtc tggcgccata    900
cccagtgccc agaaataaac ttccatcagg cggtcgcgta caaaatccag tttgctagcc    960
aggcccatct cggtccacca gcgggacaga tcttgcagct ctttctggtg cagggtctgt   1020
accatgttaa aatccagctt cgccagctcc agcagcagct ggtgatgcgg ttctttcggt   1080
tcgtatttat ccaggaacca acgtgcctcc agacggtgca gacgctggtg atatggcagt   1140
tccagggcgt ggctcacttg ttctgcaacc ttggtattaa tgccttcttt caggttgttc   1200
ttcaggtggg tgatggaaaa ggtacgcgcc tcctccagca ggttctcacc ctcgaaaccc   1260
aggtaagacg cttcatacag gctcagcagg ccttggacgt cacctttcag ttcaccgctg   1320
aaaccacctt ctttatcctt gaaacgctca aaaacatcct gagaaacctc gaaaccgtgc   1380
tgacgcagca gacggaaaga cagagcggtt gcgtgcaggt cagatttgtt ctttttgttt   1440
tcgtccagca gtacgatgtt ttccagggct ttaatgatgt ctttttcaaa tttgtaggtc   1500
agacccaggc gctgcacatc gtcgatcagc tccagcaggg acagcggctg ggtgtctaca   1560
cggttgatca tgcagcgaac ttcttcctcc agtttggtcg ctttctcctc cagcttttcc   1620
actttcaggt cgttctccag ggattgcagg aattcgaaat tccacaggtt tggctgatag   1680
tttgcggaac gacgggaatt atgctcggta atctgagtaa attgagaaga ggtcgcacac   1740
atggtatatc tccttcttaa agttaaacaa aattatttct agaggggaat tgttatccgc   1800
tcacaattcc cctatagtga gtcgtattaa tttcgcggga tcgagatctc gatcctctac   1860
gccggacgca tcgtggccgg catcaccggc gccacaggtg cggttgctgg cgcctatatc   1920
gccgacatca ccgatgggga agatcgggct cgccacttcg ggctcatgag cgcttgtttc   1980
ggcgtgggta tggtggcagg ccccgtggcc gggggactgt tgggcgccat ctccttgcat   2040
gcaccattcc ttgcggcggc ggtgctcaac ggcctcaacc tactactggg ctgcttccta   2100
atgcaggagt cgcataaggg agagcgtcga gatcccggac accatcgaat ggcgcaaaac   2160
ctttcgcggt atggcatgat agcgcccgga agagagtcaa ttcagggtgg tgaatgtgaa   2220
accagtaacg ttatacgatg tcgcagagta tgccggtgtc tcttatcaga ccgtttcccg   2280
cgtggtgaac caggccagcc acgtttctgc gaaaacgcgg gaaaaagtgg aagcggcgat   2340
ggcggagctg aattacattc ccaaccgcgt ggcacaacaa ctggcgggca aacagtcgtt   2400
gctgattggc gttgccacct ccagtctggc cctgcacgcg ccgtcgcaaa ttgtcgcggc   2460
gattaaatct cgcgccgatc aactgggtgc cagcgtggtg gtgtcgatgg tagaacgaag   2520
cggcgtcgaa gcctgtaaag cggcggtgca caatcttctc gcgcaacgcg tcagtgggct   2580
gatcattaac tatccgctgg atgaccagga tgccattgct gtggaagctg cctgcactaa   2640
tgttccggcg ttatttcttg atgtctctga ccagacaccc atcaacagta ttattttctc   2700
ccatgaagac ggtacgcgac tgggcgtgga gcatctggtc gcattgggtc accagcaaat   2760
cgcgctgtta gcgggcccat taagttctgt ctcggcgcgt ctgcgtctgg ctggctggca   2820
taaatatctc actcgcaatc aaattcagcc gatagcggaa cgggaaggcg actggagtgc   2880
```

-continued

```
catgtccggt tttcaacaaa ccatgcaaat gctgaatgag ggcatcgttc ccactgcgat   2940
gctggttgcc aacgatcaga tggcgctggg cgcaatgcgc gccattaccg agtccgggct   3000
gcgcgttggt gcggatatct cggtagtggg atacgacgat accgaagaca gctcatgtta   3060
tatcccgccg ttaaccacca tcaaacagga ttttcgcctg ctggggcaaa ccagcgtgga   3120
ccgcttgctg caactctctc agggccaggc ggtgaagggc aatcagctgt tgcccgtctc   3180
actggtgaaa agaaaaacca ccctggcgcc caatacgcaa accgcctctc cccgcgcgtt   3240
ggccgattca ttaatgcagc tggcacgaca ggtttcccga ctggaaagcg ggcagtgagc   3300
gcaacgcaat taatgtaagt tagctcactc attaggcacc gggatctcga ccgatgccct   3360
tgagagcctt caacccagtc agctccttcc ggtgggcgcg gggcatgact atcgtcgccg   3420
cacttatgac tgtcttcttt atcatgcaac tcgtaggaca ggtgccggca gcgctctggg   3480
tcattttcgg cgaggaccgc tttcgctgga gcgcgacgat gatcggcctg tcgcttgcgg   3540
tattcggaat cttgcacgcc ctcgctcaag ccttcgtcac tggtcccgcc accaaacgtt   3600
tcggcgagaa gcaggccatt atcgccggca tggcggcccc acgggtgcgc atgatcgtgc   3660
tcctgtcgtt gaggacccgg ctaggctggc ggggttgcct tactggttag cagaatgaat   3720
caccgatacg cgagcgaacg tgaagcgact gctgctgcaa aacgtctgcg acctgagcaa   3780
caacatgaat ggtcttcggt ttccgtgttt cgtaaagtct ggaaacgcgg aagtcagcgc   3840
cctgcaccat tatgttccgg atctgcatcg caggatgctg ctggctaccc tgtggaacac   3900
ctacatctgt attaacgaag cgctggcatt gaccctgagt gatttttctc tggtcccgcc   3960
gcatccatac cgccagttgt ttaccctcac aacgttccag taaccgggca tgttcatcat   4020
cagtaacccg tatcgtgagc atcctctctc gtttcatcgg tatcattacc cccatgaaca   4080
gaaatccccc ttacacggag gcatcagtga ccaaacagga aaaaaccgcc cttaacatgg   4140
cccgctttat cagaagccag acattaacgc ttctggagaa actcaacgag ctggacgcgg   4200
atgaacaggc agacatctgt gaatcgcttc acgaccacgc tgatgagctt taccgcagct   4260
gcctcgcgcg tttcggtgat gacggtgaaa acctctgaca catgcagctc ccggagacgg   4320
tcacagcttg tctgtaagcg gatgccggga gcagacaagc ccgtcagggc gcgtcagcgg   4380
gtgttggcgg gtgtcggggc gcagccatga cccagtcacg tagcgatagc ggagtgtata   4440
ctggcttaac tatgcggcat cagagcagat tgtactgaga gtgcaccata tatgcggtgt   4500
gaaataccgc acagatgcgt aaggagaaaa taccgcatca ggcgctcttc cgcttcctcg   4560
ctcactgact cgctgcgctc ggtcgttcgg ctgcggcgag cggtatcagc tcactcaaag   4620
gcggtaatac ggttatccac agaatcaggg gataacgcag gaaagaacat gtgagcaaaa   4680
ggccagcaaa aggccaggaa ccgtaaaaag gccgcgttgc tggcgttttt ccataggctc   4740
cgcccccctg acgagcatca caaaaatcga cgctcaagtc agaggtggcg aaacccgaca   4800
ggactataaa gataccaggc gtttccccct ggaagctccc tcgtgcgctc tcctgttccg   4860
accctgccgc ttaccggata cctgtccgcc tttctccctt cgggaagcgt ggcgctttct   4920
catagctcac gctgtaggta tctcagttcg gtgtaggtcg ttcgctccaa gctgggctgt   4980
gtgcacgaac cccccgttca gcccgaccgc tgcgccttat ccggtaacta tcgtcttgag   5040
tccaacccgg taagacacga cttatcgcca ctggcagcag ccactggtaa caggattagc   5100
agagcgaggt atgtaggcgg tgctacagag ttcttgaagt ggtggcctaa ctacggctac   5160
actagaagga cagtatttgg tatctgcgct ctgctgaagc cagttacctt cggaaaaaga   5220
```

-continued

```
gttggtagct cttgatccgg caaacaaacc accgctggta gcggtggttt ttttgtttgc   5280

aagcagcaga ttacgcgcag aaaaaaagga tctcaagaag atcctttgat cttttctacg   5340

gggtctgacg ctcagtggaa cgaaaactca cgttaaggga ttttggtcat gaacaataaa   5400

actgtctgct tacataaaca gtaatacaag gggtgttatg agccatattc aacgggaaac   5460

gtcttgctct aggccgcgat taaattccaa catggatgct gatttatatg ggtataaatg   5520

ggctcgcgat aatgtcgggc aatcaggtgc gacaatctat cgattgtatg ggaagcccga   5580

tgcgccagag ttgtttctga aacatggcaa aggtagcgtt gccaatgatg ttacagatga   5640

gatggtcaga ctaaactggc tgacggaatt tatgcctctt ccgaccatca agcattttat   5700

ccgtactcct gatgatgcat ggttactcac cactgcgatc cccgggaaaa cagcattcca   5760

ggtattagaa gaatatcctg attcaggtga aaatattgtt gatgcgctgg cagtgttcct   5820

gcgccggttg cattcgattc ctgtttgtaa ttgtcctttt aacagcgatc gcgtatttcg   5880

tctcgctcag gcgcaatcac gaatgaataa cggtttggtt gatgcgagtg attttgatga   5940

cgagcgtaat ggctggcctg ttgaacaagt ctggaaagaa atgcataaac ttttgccatt   6000

ctcaccggat tcagtcgtca ctcatggtga tttctcactt gataacctta tttttgacga   6060

ggggaaatta ataggttgta ttgatgttgg acgagtcgga atcgcagacc gataccagga   6120

tcttgccatc ctatggaact gcctcggtga gttttctcct tcattacaga aacggctttt   6180

tcaaaaatat ggtattgata atcctgatat gaataaattg cagtttcatt tgatgctcga   6240

tgagtttttc taagaattaa ttcatgagcg gatacatatt tgaatgtatt tagaaaaata   6300

aacaaatagg ggttccgcgc acatttcccc gaaaagtgcc acctgaaatt gtaaacgtta   6360

atattttgtt aaaattcgcg ttaaattttt gttaaatcag ctcatttttt aaccaatagg   6420

ccgaaatcgg caaaatccct tataaatcaa aagaatagac cgagataggg ttgagtgttg   6480

ttccagtttg gaacaagagt ccactattaa agaacgtgga ctccaacgtc aaagggcgaa   6540

aaaccgtcta tcagggcgat ggcccactac gtgaaccatc accctaatca agttttttgg   6600

ggtcgaggtg ccgtaaagca ctaaatcgga accctaaagg gagcccccga tttagagctt   6660

gacggggaaa gccggcgaac gtggcgagaa aggaagggaa gaaagcgaaa ggagcgggcg   6720

ctagggcgct ggcaagtgta gcggtcacgc tgcgcgtaac caccacaccc gccgcgctta   6780

atgcgccgct acagggcgcg tcccattcgc caatccggat atagttcctc ctttcagcaa   6840

aaaacccctc aagacccgtt tagaggcccc aaggggttat gctagttatt gctcagcggt   6900

ggcagcagcc aactcagctt cctttcgggc tttgttagca gccggatctc agtggtggtg   6960

gtggtggtgc tcga                                                     6974
```

<210> SEQ ID NO 102
<211> LENGTH: 45
<212> TYPE: DNA
<213> ORGANISM: Artificial Sequence
<220> FEATURE:
<223> OTHER INFORMATION: PCR Primer

<400> SEQUENCE: 102

```
accgttcgtt cttatcgaaa ctaaaaaaaa ccggccttgg ccccg                     45
```

<210> SEQ ID NO 103
<211> LENGTH: 23
<212> TYPE: DNA
<213> ORGANISM: Artificial Sequence
<220> FEATURE:
<223> OTHER INFORMATION: PCR Primer -continued

```
<400> SEQUENCE: 103

gcaggtggga aactatgcac tcc                                              23


<210> SEQ ID NO 104
<211> LENGTH: 36
<212> TYPE: DNA
<213> ORGANISM: Artificial Sequence
<220> FEATURE:
<223> OTHER INFORMATION: PCR Primer

<400> SEQUENCE: 104

cctgaattct gttggattgg aggattggat agtggg                                36
```

COMPOSITIONS AND METHODS FOR PRODUCING ISOPRENE FREE OF C5 HYDROCARBONS UNDER DECOUPLING CONDITIONS AND/OR SAFE OPERATING RANGES

CROSS-REFERENCE TO RELATED APPLICATIONS

This application is a divisional of U.S. patent application Ser. No. 13/741,149, filed Jan. 14, 2013, which is a divisional of U.S. patent application Ser. No. 12/496,573 (now U.S. Pat. No. 8,420,360), filed Jul. 1, 2009, which claims the priority benefit of U.S. Provisional Application No. 61/134,094, filed Jul. 2, 2008, U.S. Provisional Application No. 61/133,947, filed Jul. 2, 2008, and U.S. Provisional Application No. 61/134,011, filed Jul. 2, 2008, the contents of each are hereby incorporated by reference in its entirety.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIG. 19). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

In one aspect, the invention features cells in culture that produce isoprene. In some embodiments, the invention provides cells in culture that produce greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, the method includes culturing cells under conditions sufficient to convert more than about 0.002% of the carbon (mol/mol) in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In one aspect, the invention features compositions and systems that comprise isoprene. In some embodiments, the composition comprises greater than or about 2, 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene (w/w) of the volatile organic fraction of the composition is isoprene.

In some embodiments, the composition comprises greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition.

In some embodiments, the composition has less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In particular embodiments, the composition also has greater than about 2 mg of isoprene.

In some embodiments, the composition has one or more compounds selected from the group consisting of ethanol, acetone, C5 prenyl alcohols, and isoprenoid compounds with 10 or more carbon atoms. In some embodiments, the composition has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the composition has greater than about 2 mg of isoprene and has one or more compounds selected from the group consisting of ethanol, acetone, C5 prenyl alcohols, and isoprenoid compounds with 10 or more carbon atoms.

In some embodiments, the composition includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-but-1-enyl acetate, 3-methyl-2-but-1-enyl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to the amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w).

In some embodiments, the composition comprises (i) a gas phase that comprises isoprene and (ii) cells in culture that produce greater than about 400 nmole/$g_{wcm}$/hr of isoprene. In some embodiments, the composition comprises a closed system, and the gas phase comprises greater than or about 5, 10, 20, 30, 40, 50, 60, 70, 80, 90, 100 ug/L of isoprene when normalized to 1 mL of 1 $OD_{600}$ cultured for 1 hour. In some embodiments, the composition comprises an open system, and the gas phase comprises greater than or about 5, 10, 20, 30, 40, 50, 60, 70, 80, 90, 100 ug/L of isoprene when sparged at a rate of 1 vvm. In some embodiments, the volatile organic fraction of the gas phase comprises greater than or about 99.90, 99.92, 99.94, 99.96, 99.98, or 100% isoprene by weight compared to the total weight of all C5 hydrocarbons in the volatile organic fraction. In some embodiments, the volatile organic fraction of the gas phase comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the volatile organic fraction. In some embodiments, the volatile organic fraction of the gas phase has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne by weight compared to the total weight of all C5 hydrocarbons in the volatile organic fraction. In particular embodiments, the volatile organic fraction of the gas phase has greater than about 2 mg of isoprene and has greater than or about 99.90, 99.92, 99.94, 99.96, 99.98, or 100% isoprene by weight compared to the total weight of all C5 hydrocarbons in the volatile organic fraction.

In some embodiments, the volatile organic fraction of the gas phase has less than or about 50, 40, 30, 20, 10, 5, 1, 0.5, 0.1, 0.05, 0.01, or 0.005 ug/L of a compound that inhibits the polymerization of isoprene for any compound in the volatile organic fraction of the gas phase that inhibits the polymerization of isoprene. In particular embodiments, the volatile organic fraction of the gas phase also has greater than about 2 mg of isoprene.

In some embodiments, the volatile organic fraction of the gas phase has one or more compounds selected from the group consisting of ethanol, acetone, C5 prenyl alcohols, and isoprenoid compounds with 10 or more carbon atoms. In some embodiments, the volatile organic fraction of the gas phase has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the volatile organic fraction of the gas phase has greater than about 2 mg of isoprene and has one or more compounds selected from the group consisting of ethanol, acetone, C5 prenyl alcohols, and isoprenoid compounds with 10 or more carbon atoms.

In some embodiments, the volatile organic fraction of the gas phase has includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-but-1-enyl acetate, 3-methyl-2-but-1-enyl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w) in the volatile organic fraction of the gas phase.

In some embodiments of any of the compositions of the invention, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a naturally-occurring polypeptide from a plant such as *Pueraria* (e.g., *Pueraria montana* or *Pueraria lobata*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIGS. 3A-3C is the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIGS. 5A-5C is the nucleotide sequence of pETNHisKudzu (SEQ ID NO:5).

FIGS. 7A-7C is the nucleotide sequence of pCL-lac-Kudzu (SEQ ID NO:7).

FIG. 9A is a graph showing OD over time of fermentation of *E. coli* BL21/pTrcKudzu in a 14 liter fed batch fermentation.

FIG. 9B is a graph showing isoprene production over time of fermentation of *E. coli* BL21/pTrcKudzu in a 14 liter fed batch fermentation.

BG3594comK is a *B. subtilis* strain without plasmid (native isoprene production). CF443-BG3594comK is a *B. subtilis* strain with pBSKudzu (recombinant isoprene production). IS on the y-axis indicates isoprene.

FIGS. 12A-12C is the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

Figure 14:
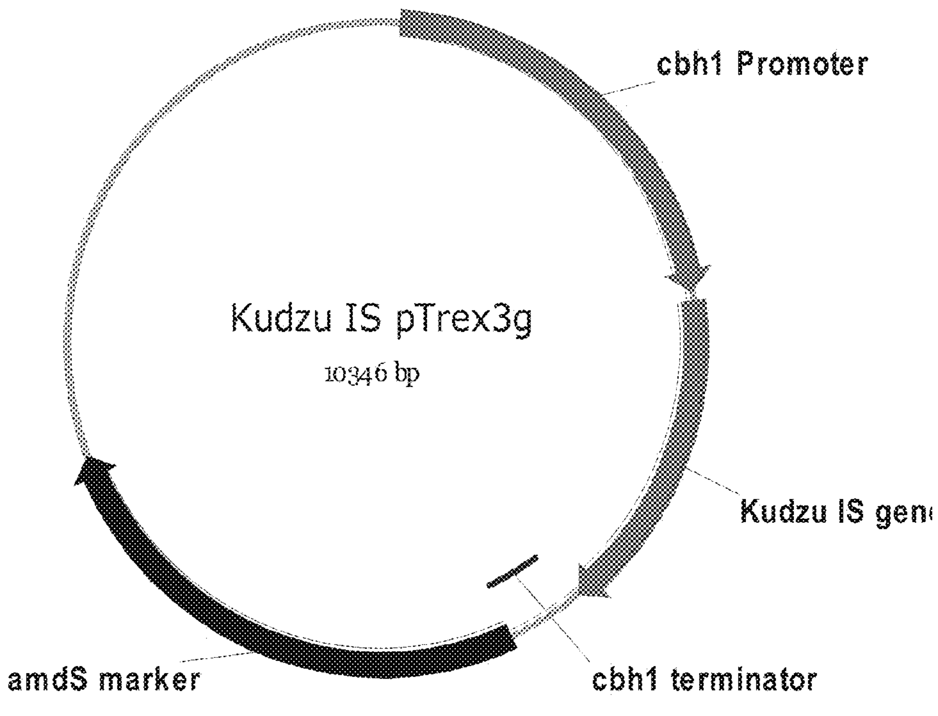

FIG. 14 is a map of pTrex3g comprising a kudzu isoprene synthase gene codon-optimized for expression in *Yarrowia.*

FIGS. 15A-15C is the nucleotide sequence of vector pSPZ1 (MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba×Populus tremula*) isoprene synthase gene (SEQ ID NO:13). The ATG start codon is in bold and the stop codon is underlined.

Figure 2:
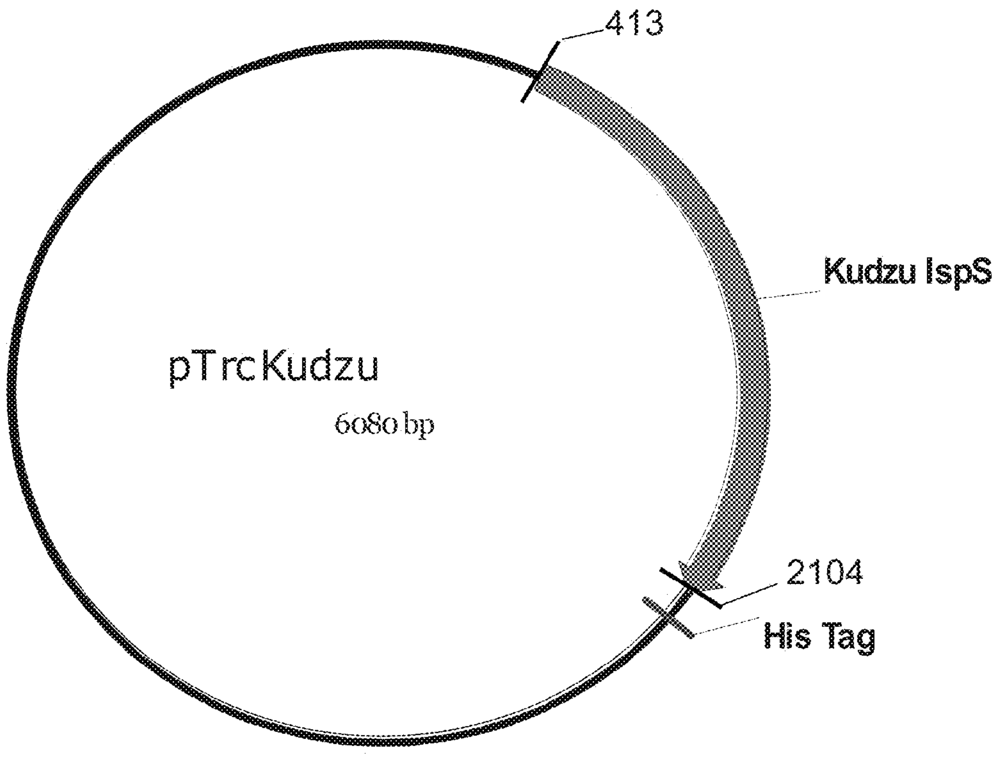
FIG. 2 is a map of pTrcKudzu.

FIGS. 18A1 and 18A2 shows a schematic outlining construction of vectors pYLA 1, pYL1 and pYL2 (SEQ ID NO:79, SEQ ID NO:73-77).

Figure 18B:
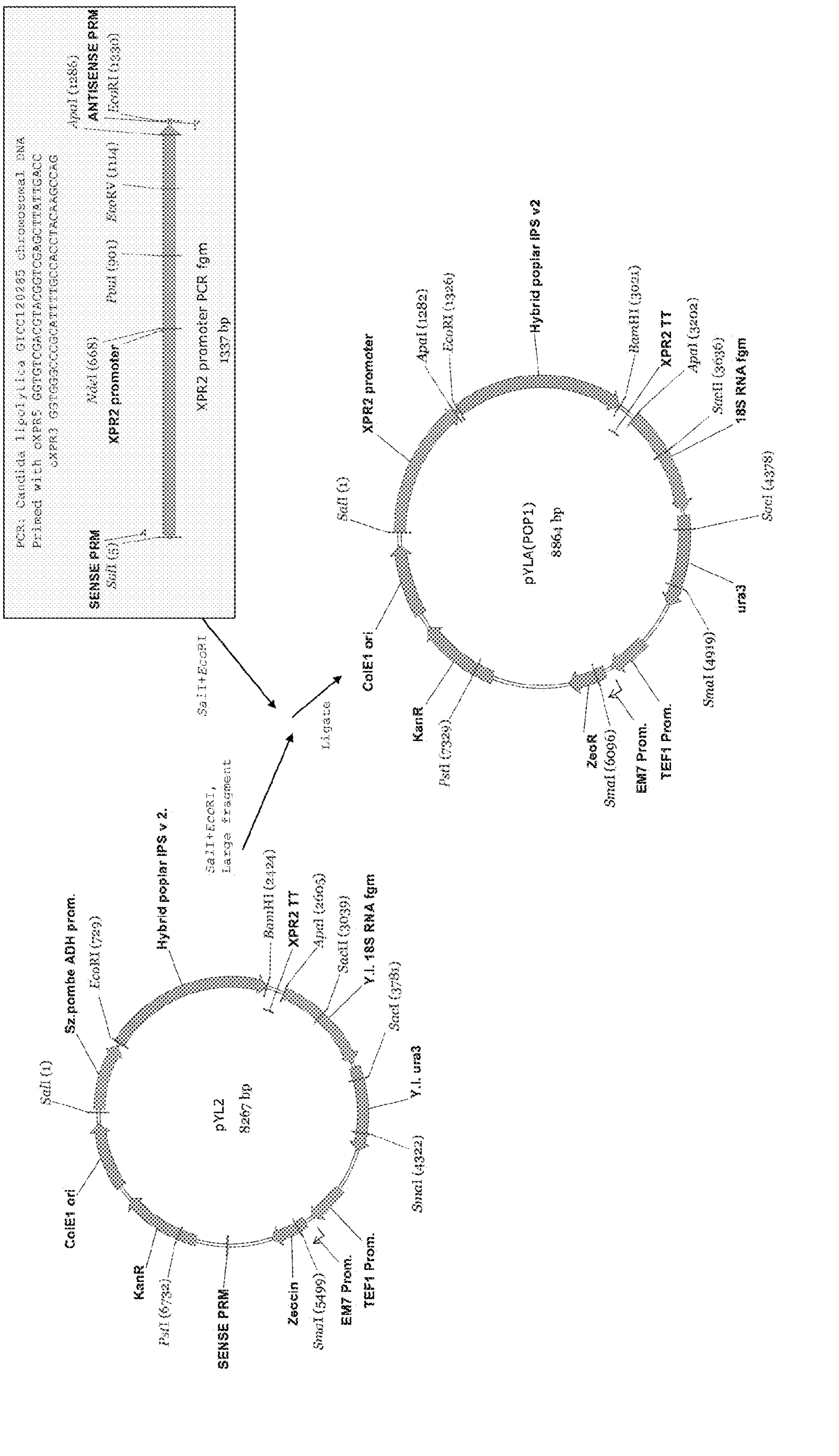

FIG. 18B shows a schematic outlining construction of the vector pYLA(POP1) (SEQ ID NO:70-73).

Figure 18C:
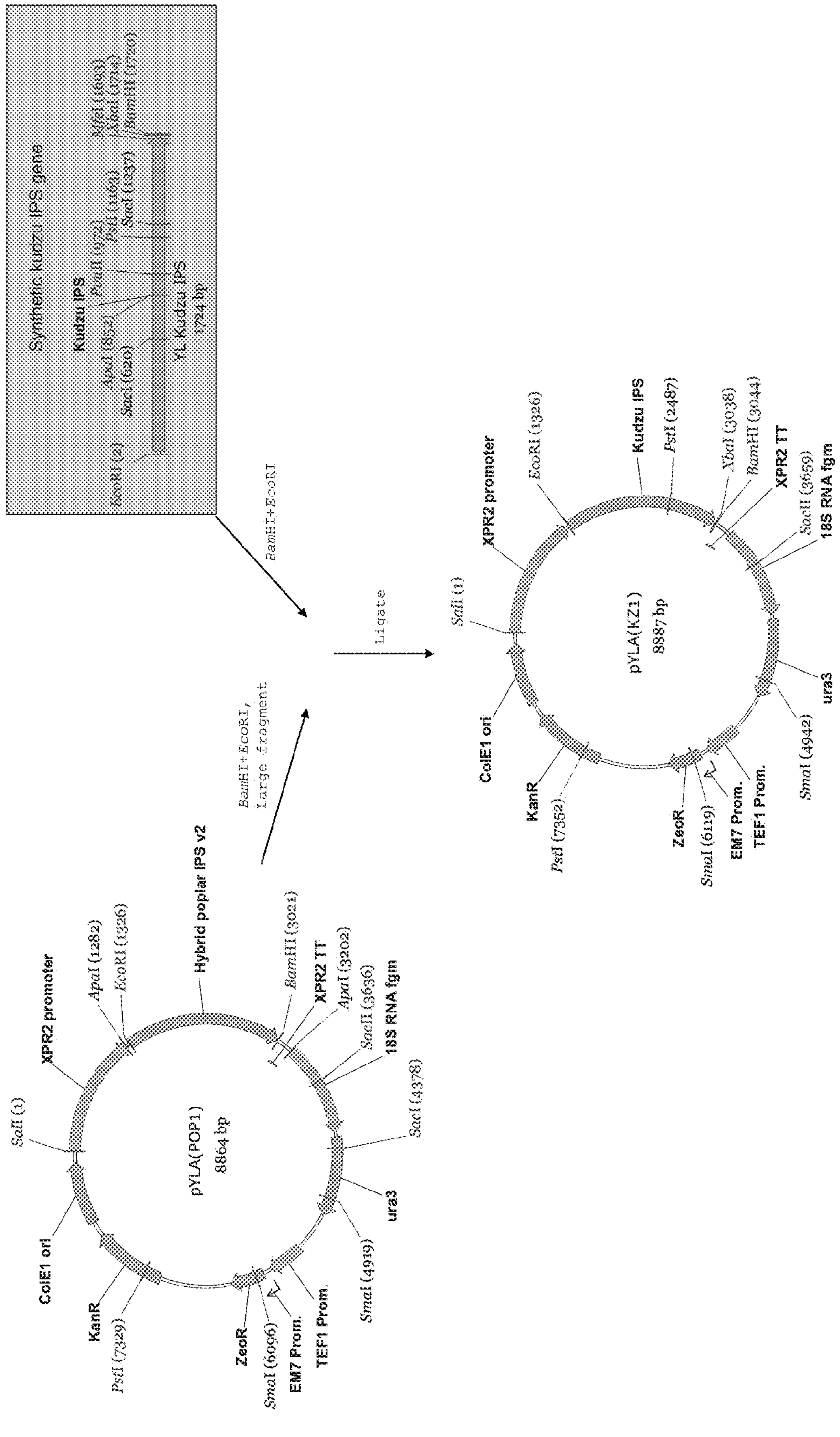

FIG. 18C shows a schematic outlining construction of the vector pYLA(KZ1)

Figure 18D:
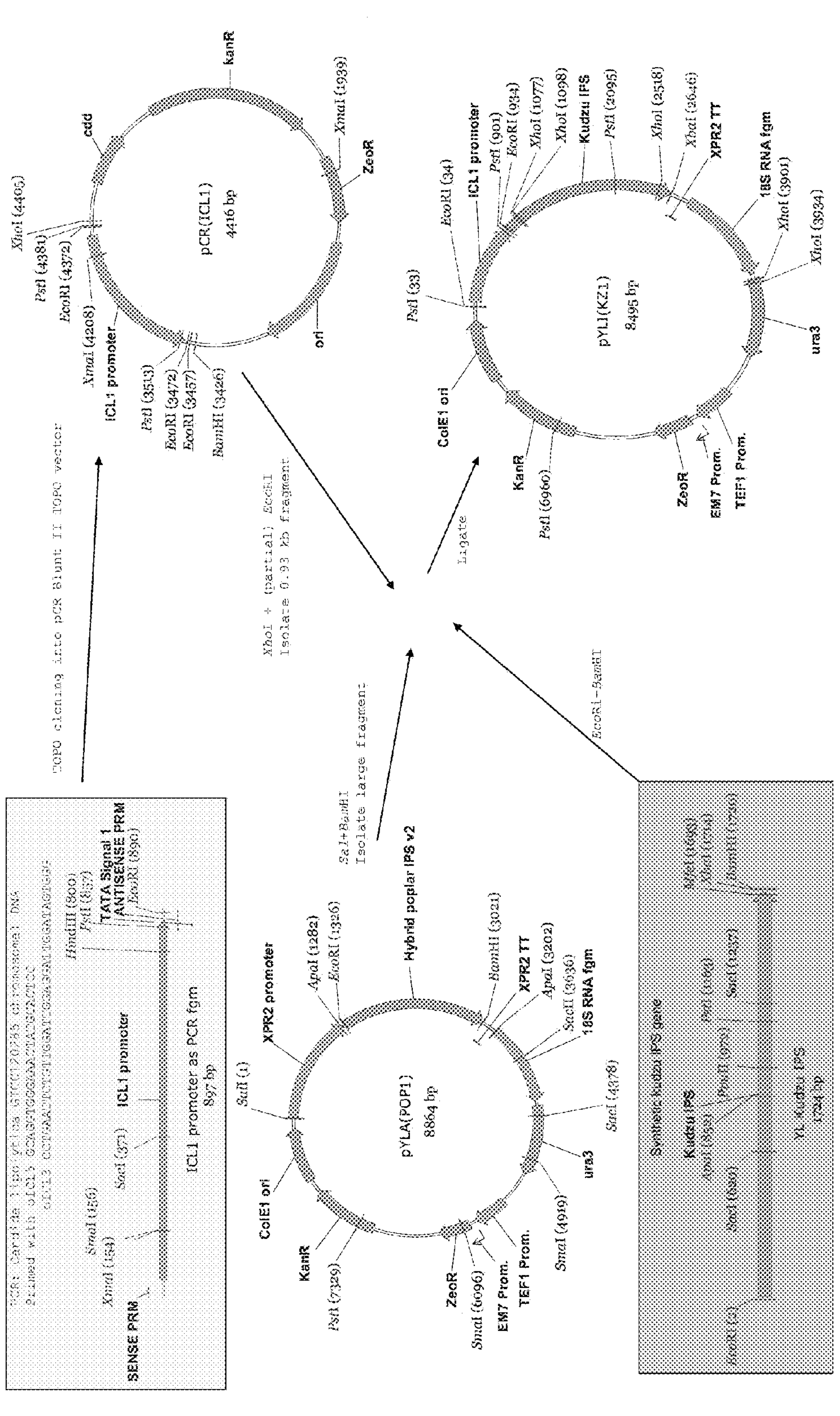

FIG. 18D shows a schematic outlining construction of the vector pYLI(KZ1) (SEQ IDS NOs:103-104).

Figure 18E:
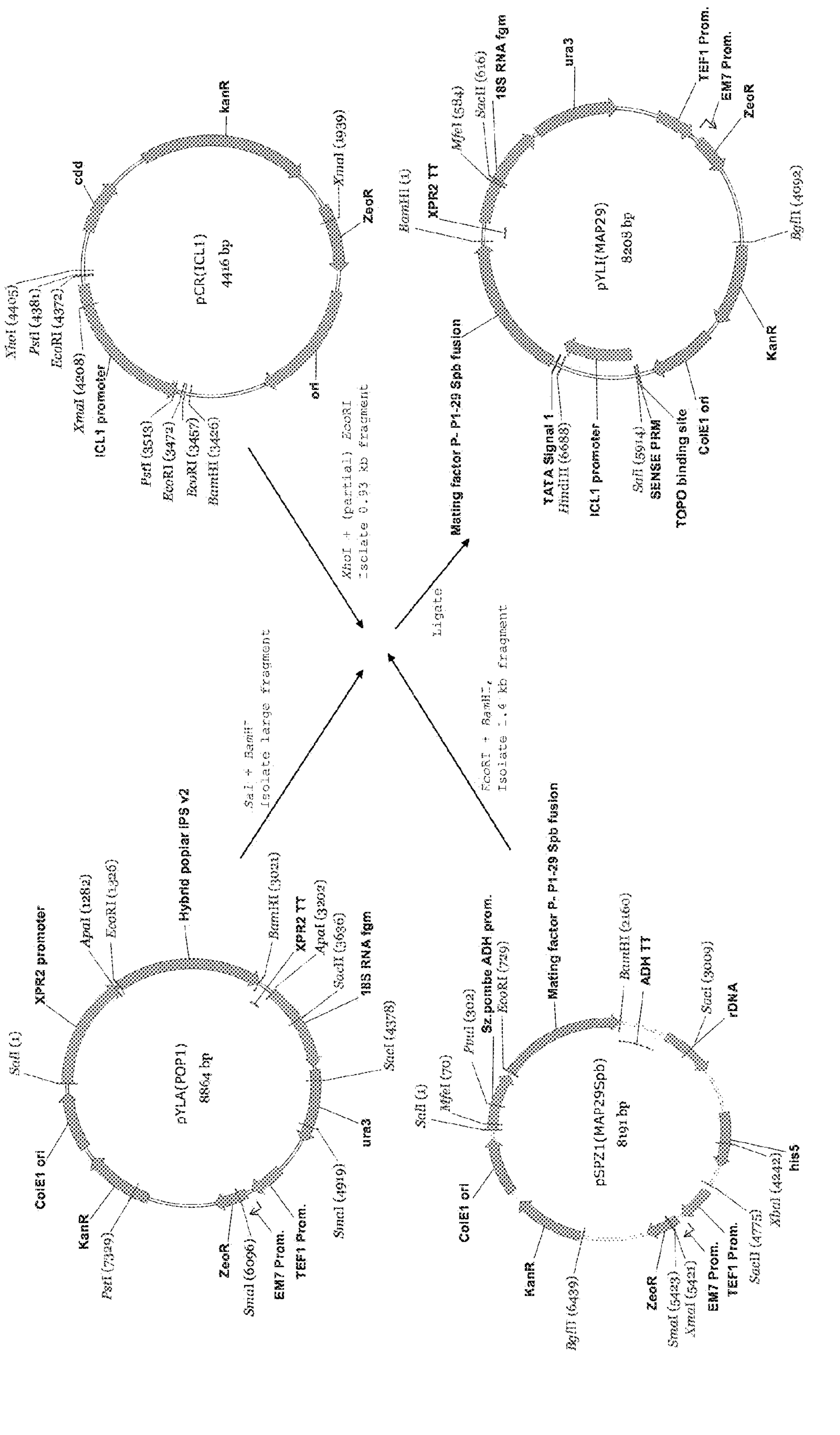

FIG. 18E shows a schematic outlining construction of the vector pYLI(MAP29)

Figure 18F:
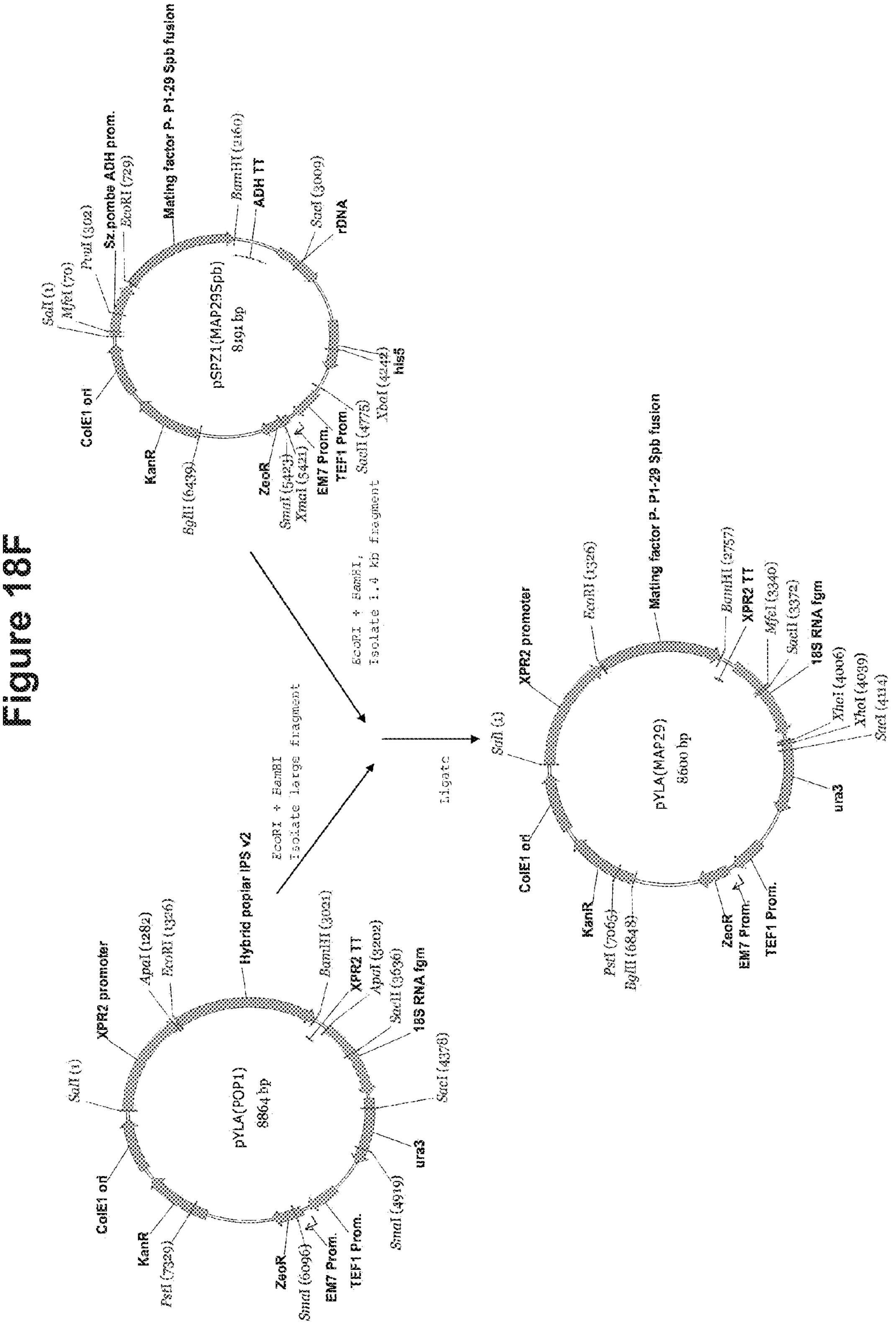

FIG. 18F shows a schematic outlining construction of the vector pYLA(MAP29)

Figure 19A:
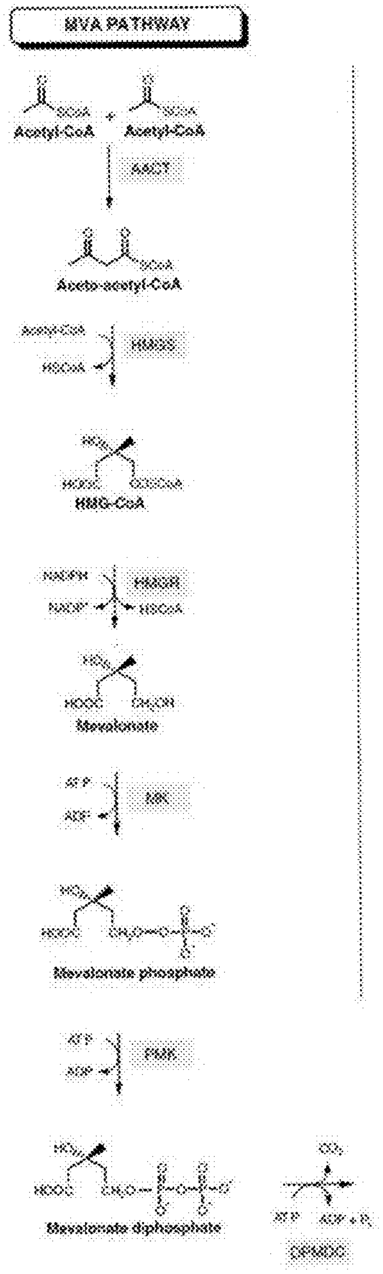
Figure 19B:
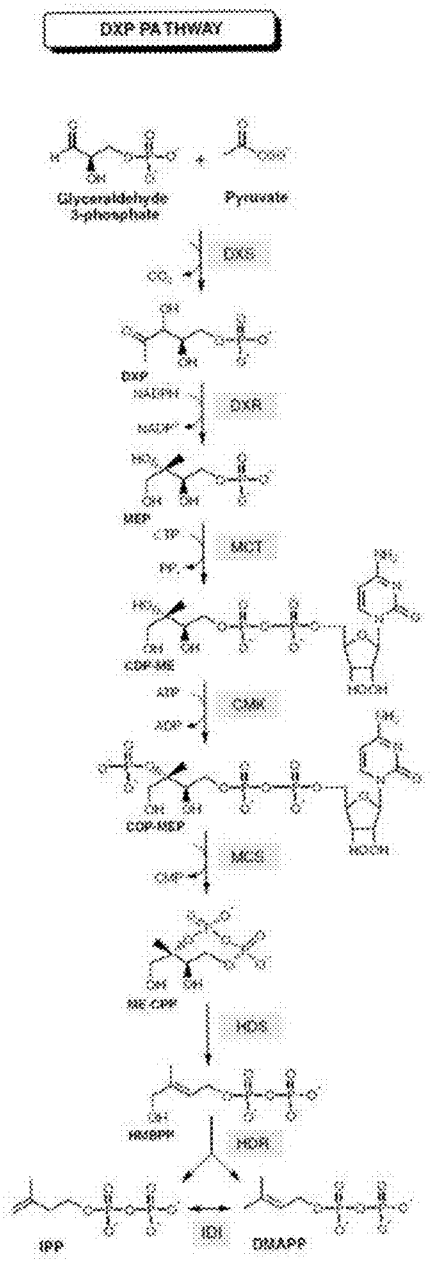

FIGS. 19A-19B shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERGS, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

Figure 20:
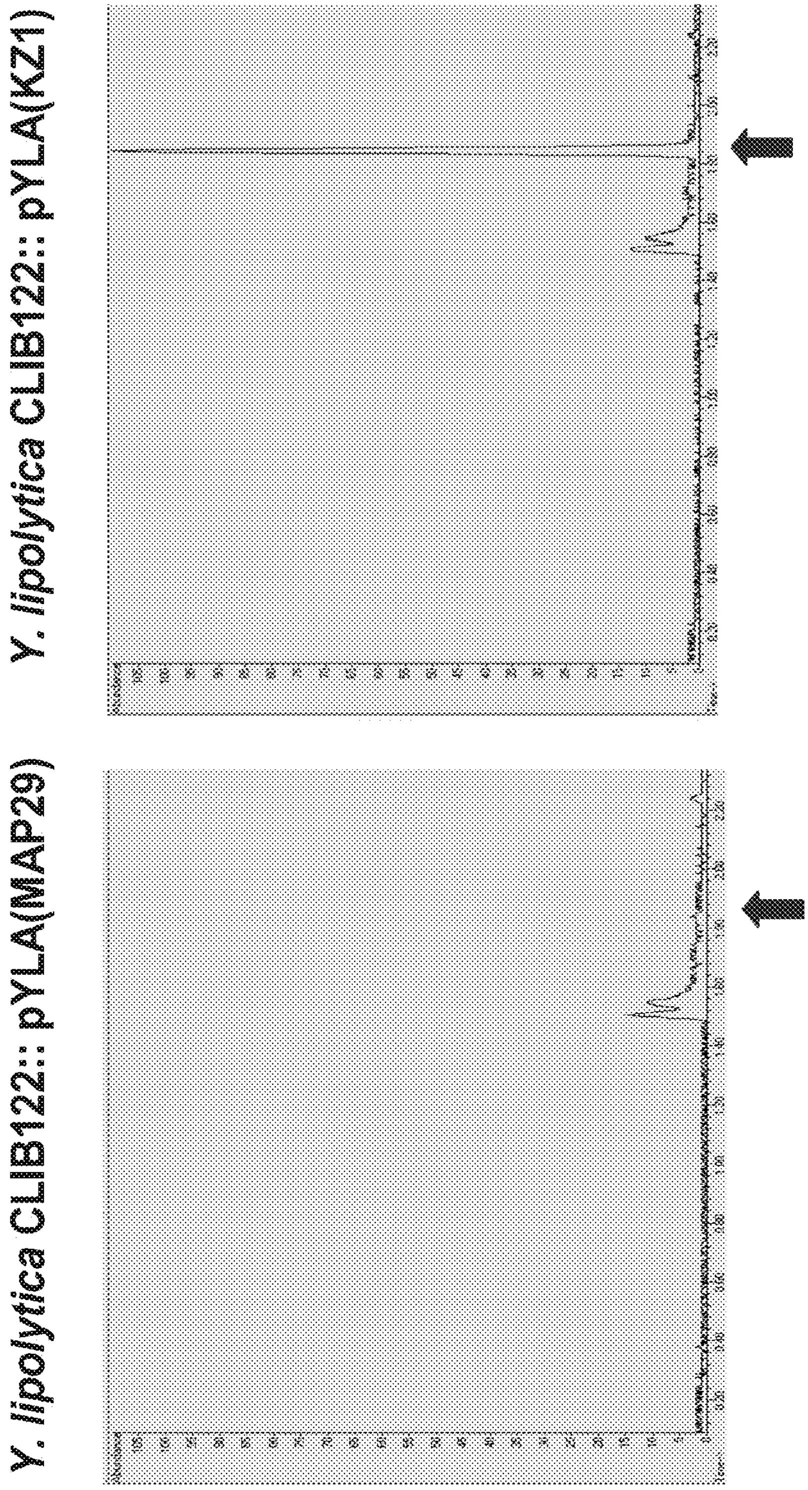

FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.

Figure 21:
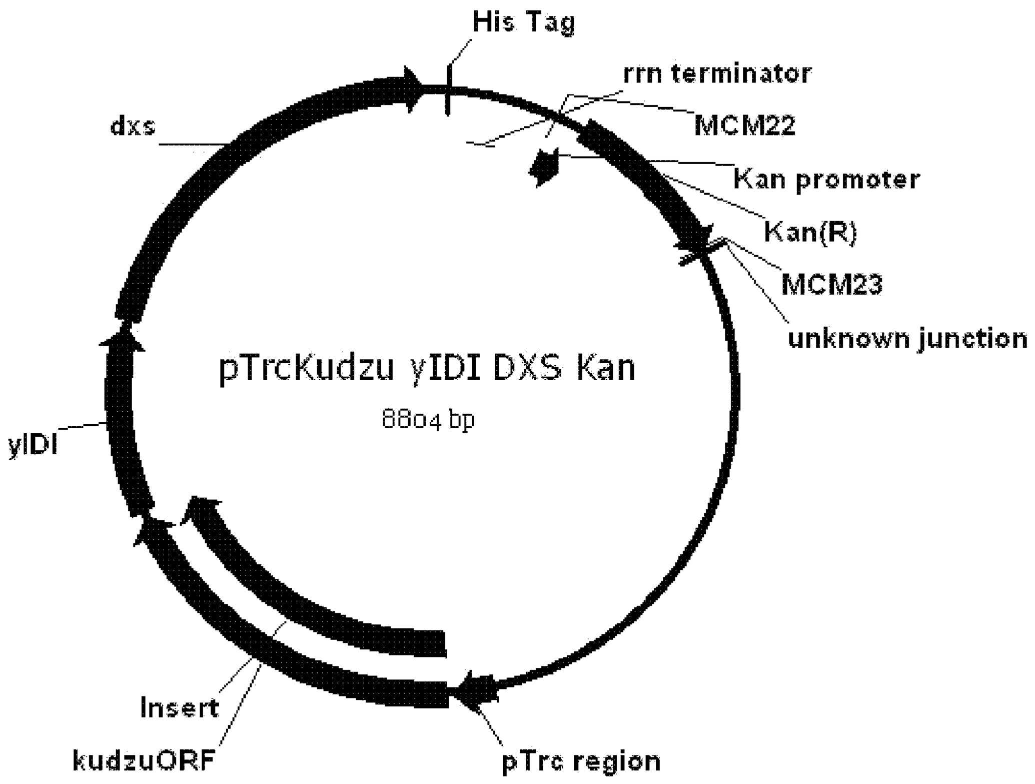

FIG. 21 is a map of pTrcKudzu yIDI DXS Kan.

FIGS. 22A-22D is the nucleotide sequence of pTrcKudzu yIDI DXS Kan (SEQ ID NO:20).

Figure 23A:
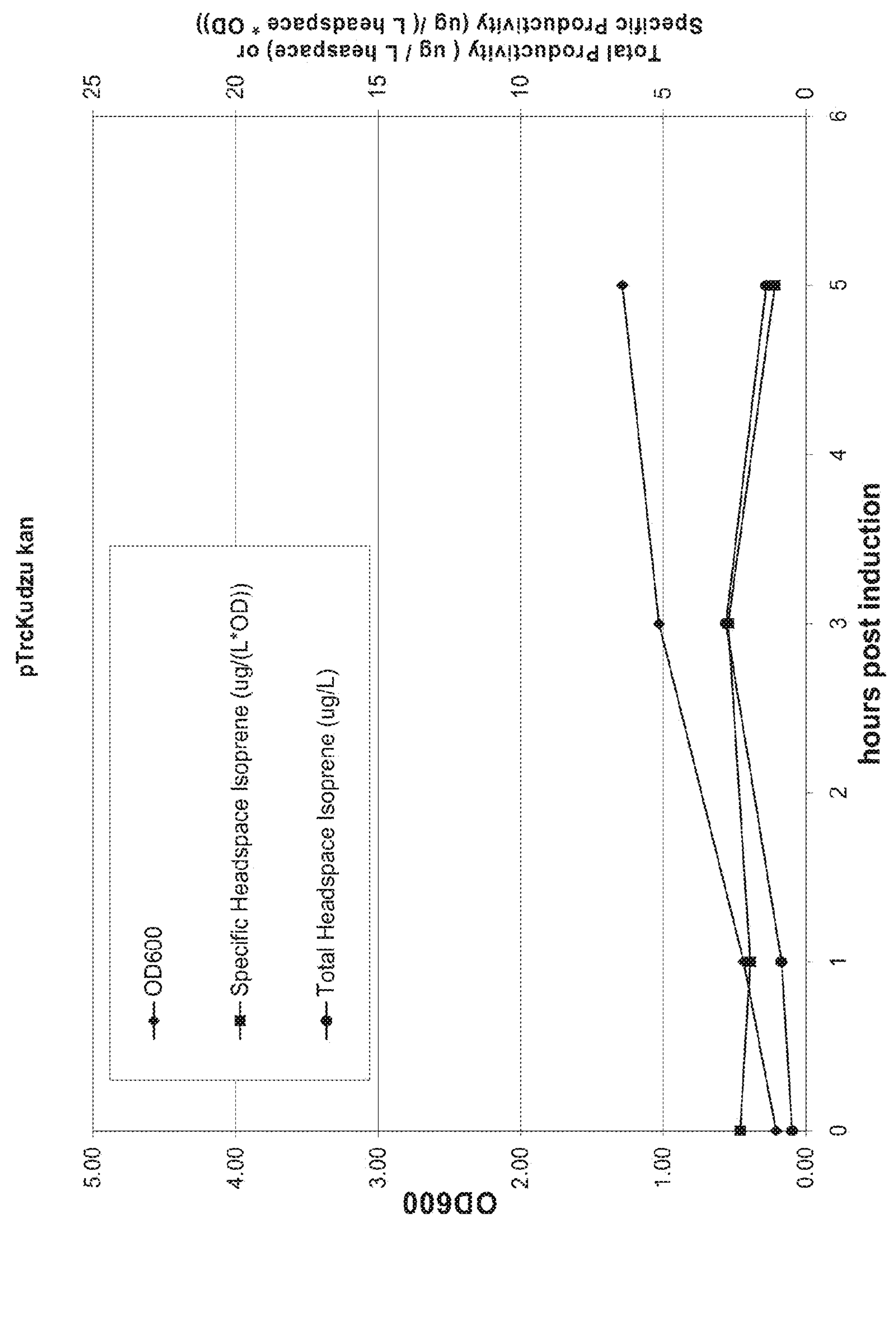

FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23B:
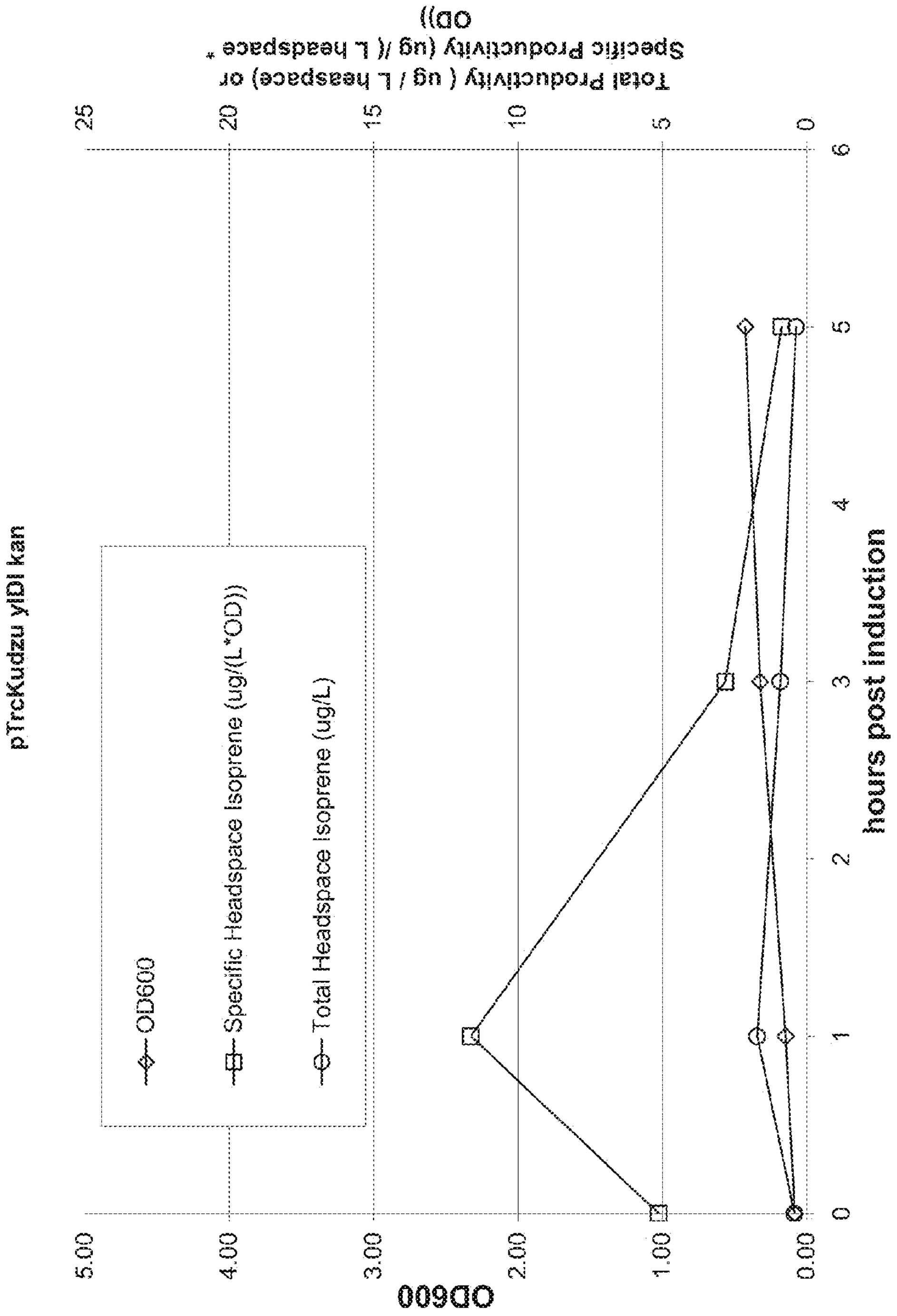

FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23C:
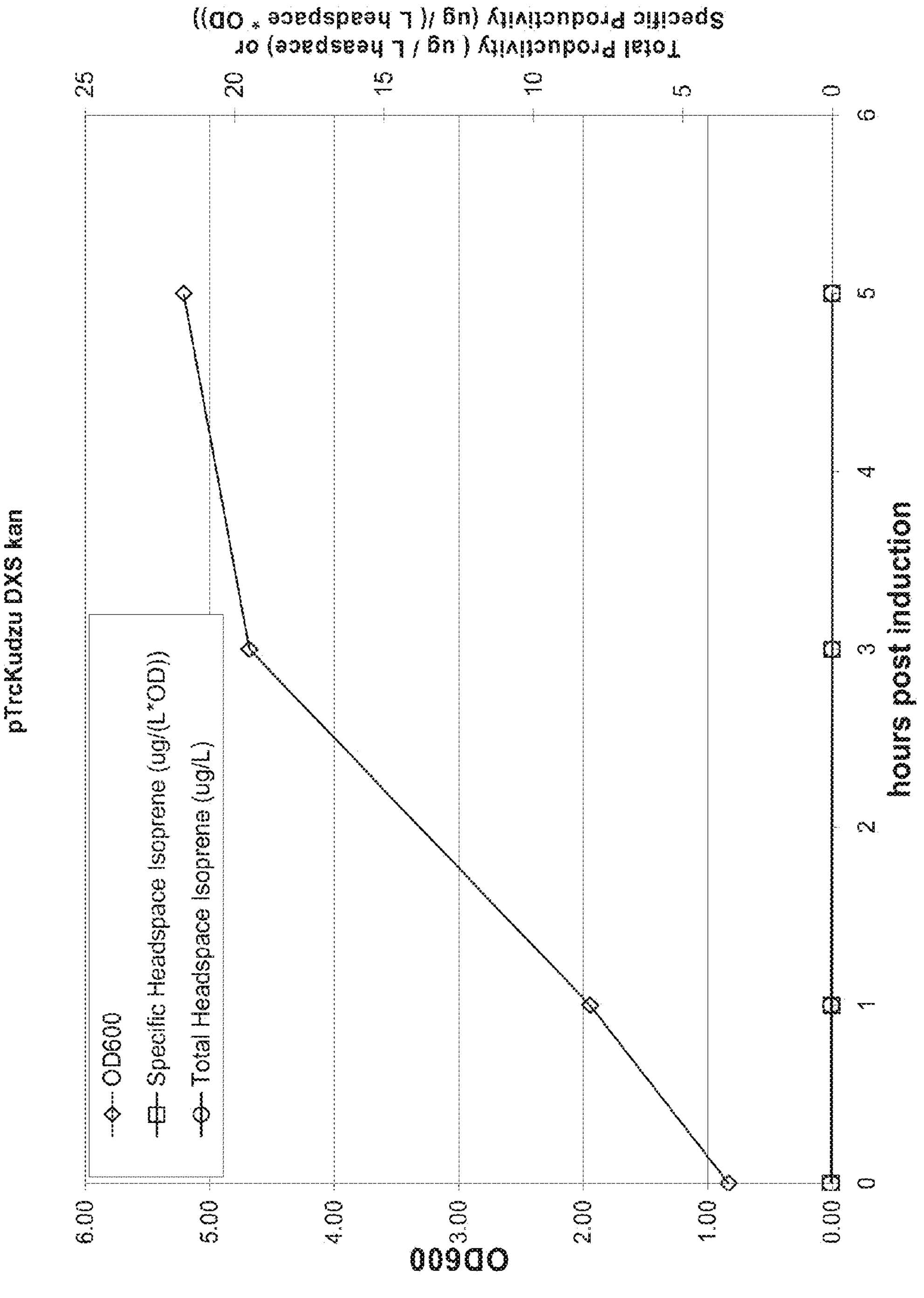

FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23D:
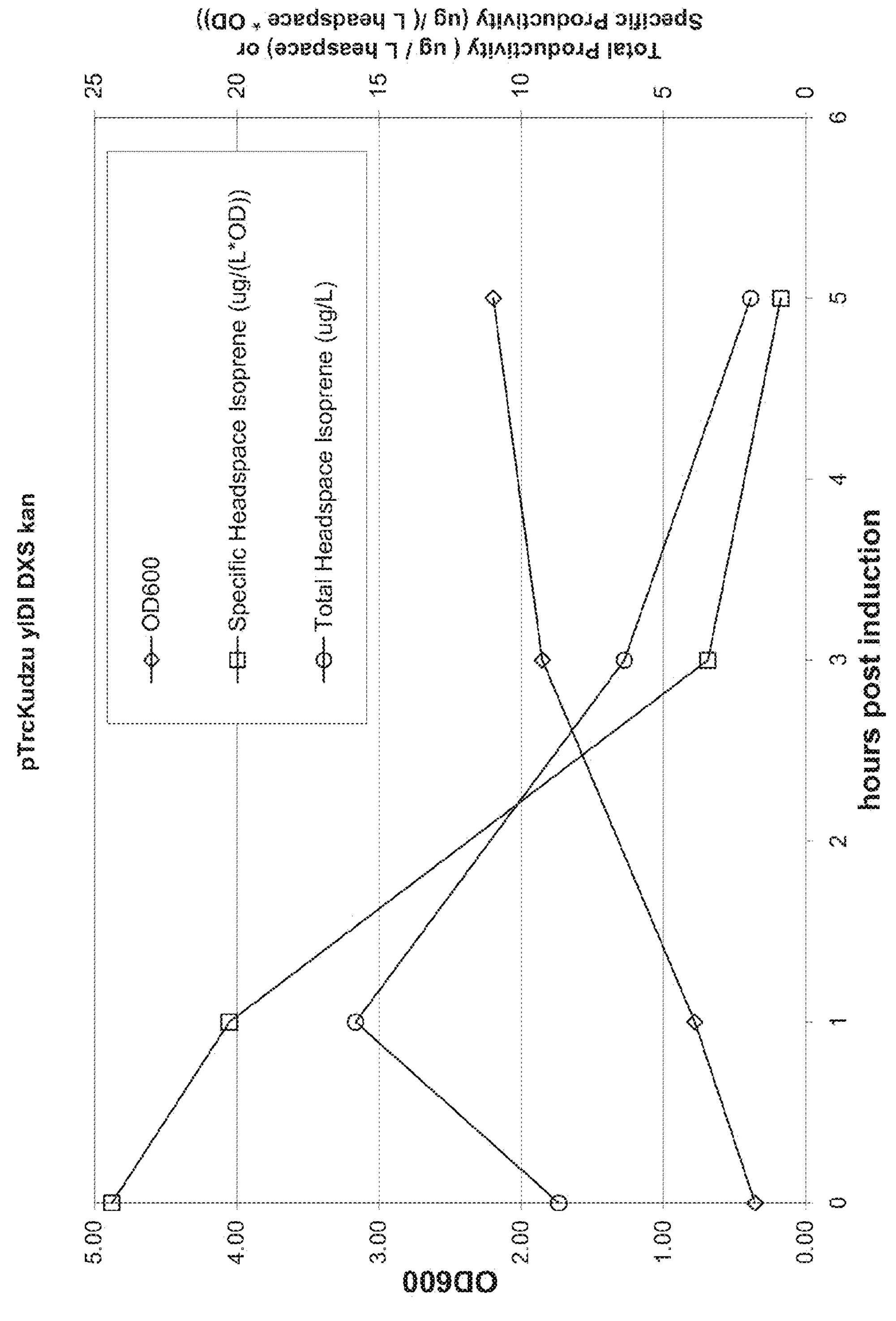

FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23E:
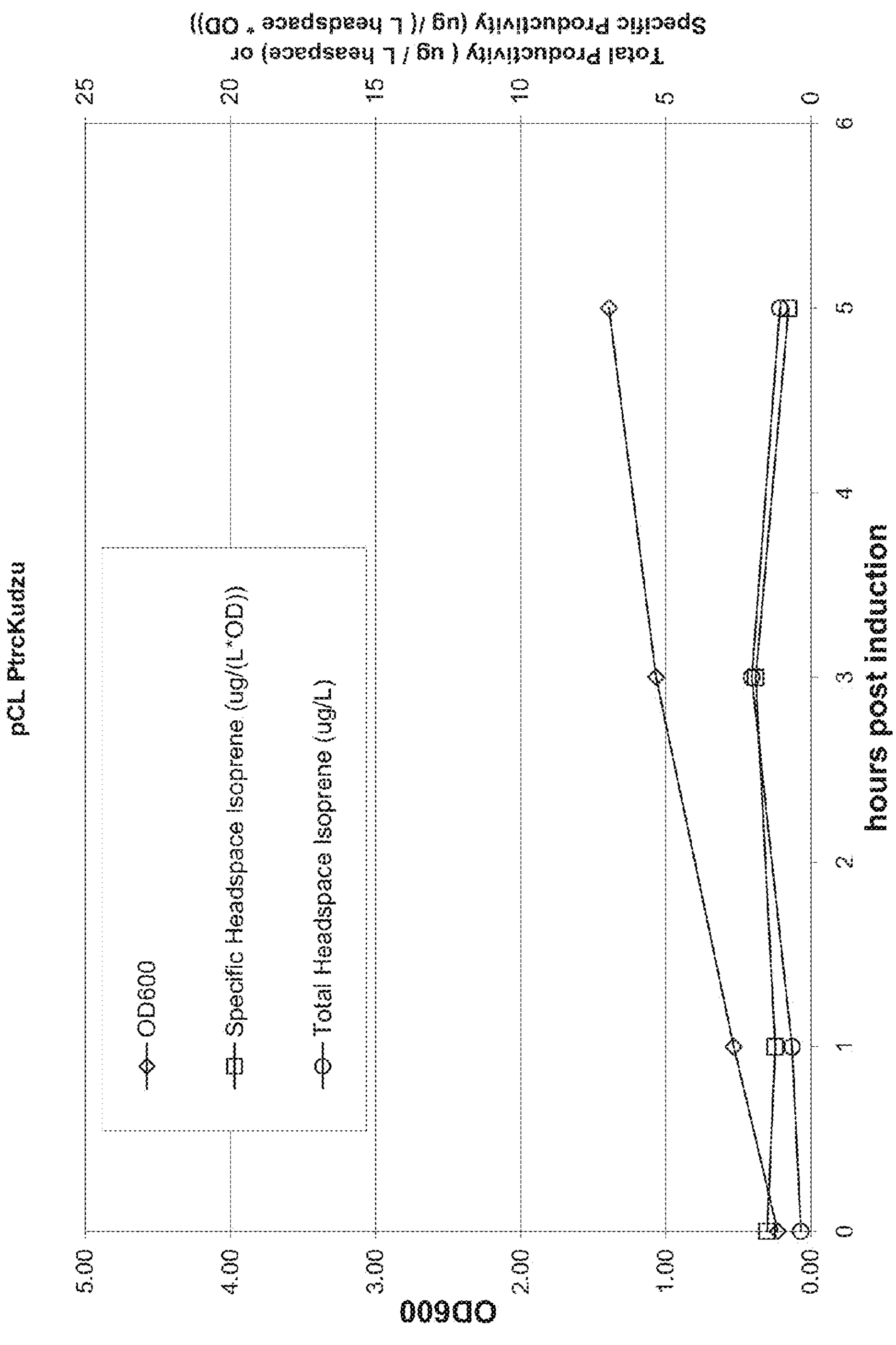

FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23F:
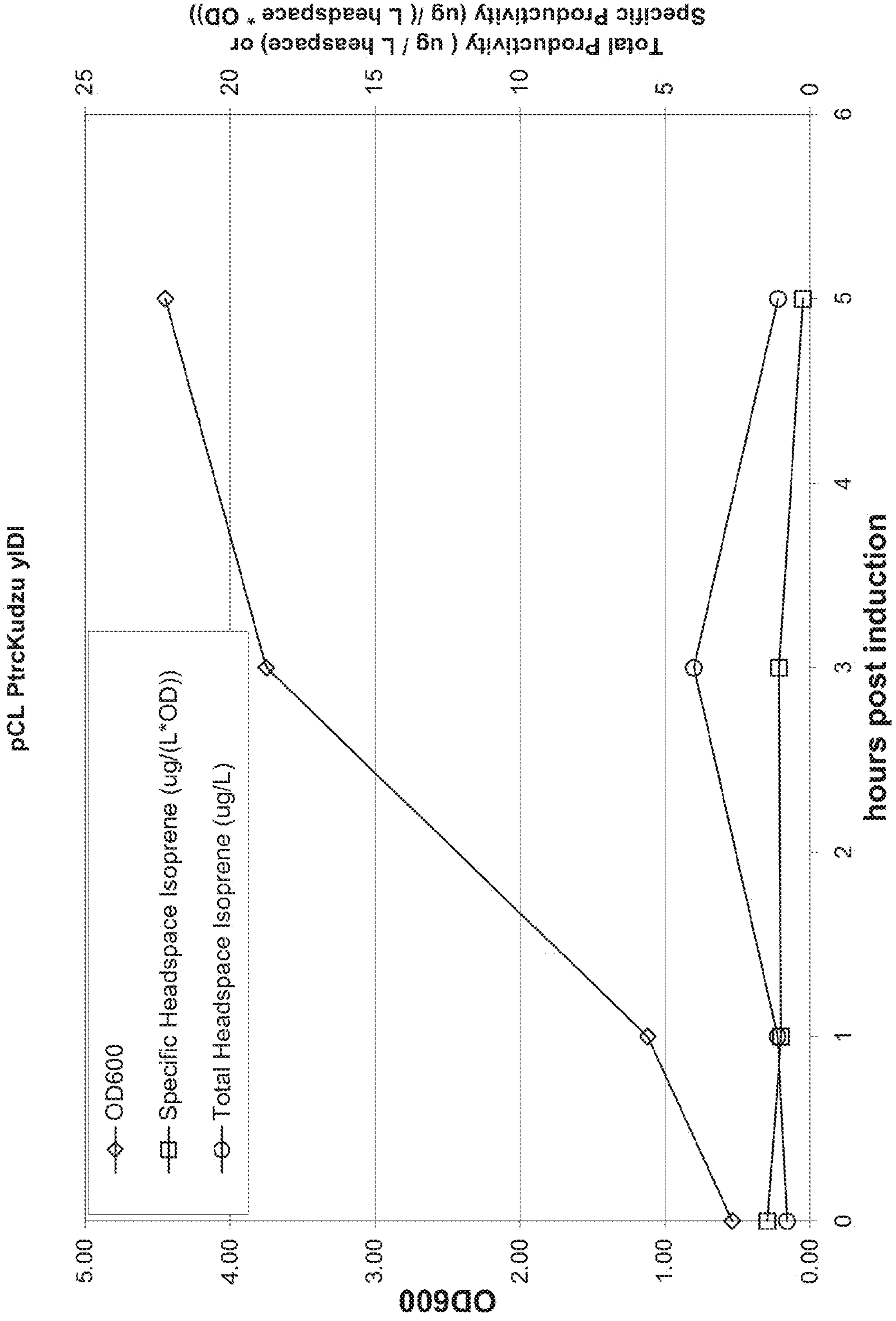

FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23G:
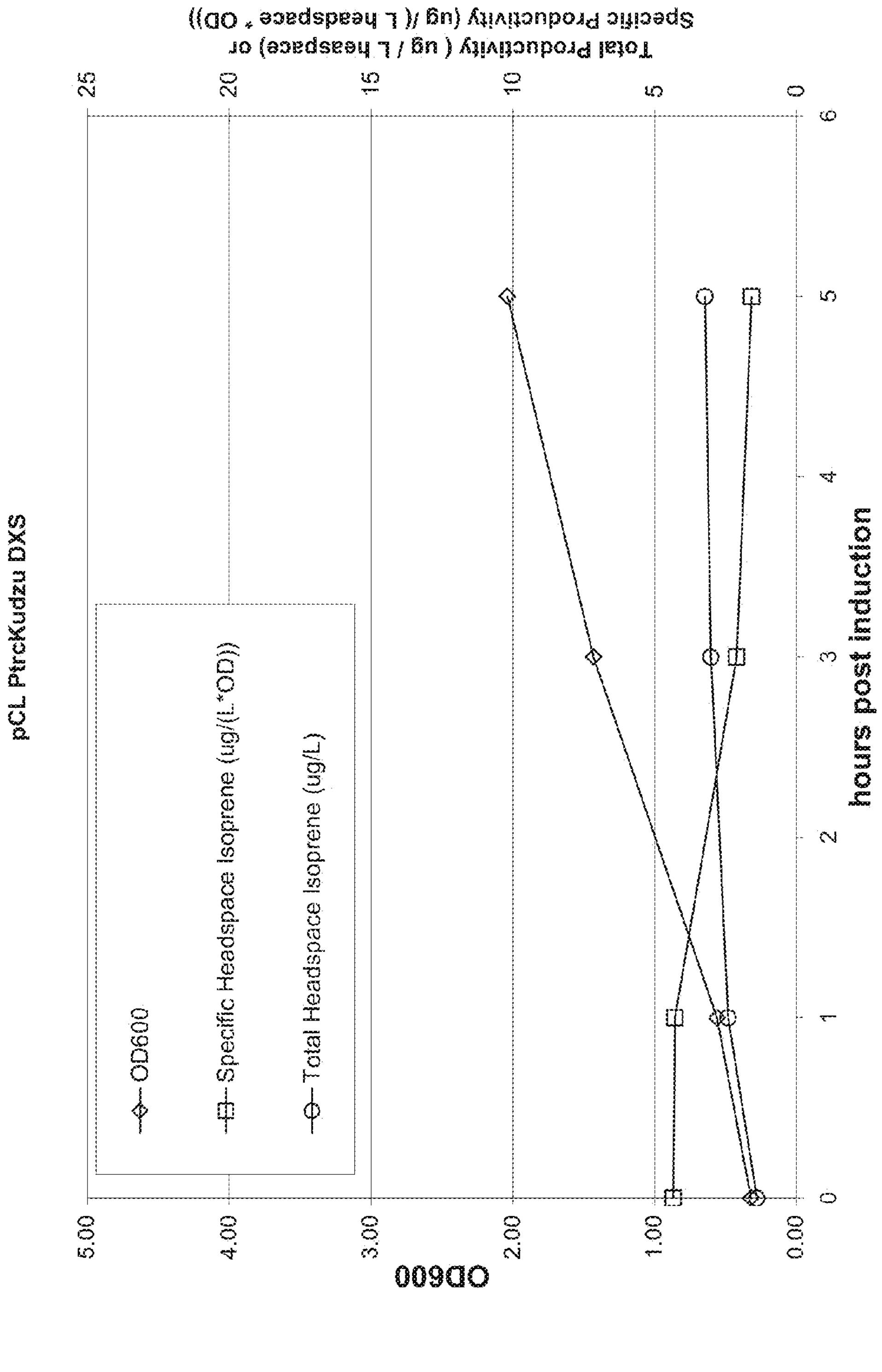

FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23H:
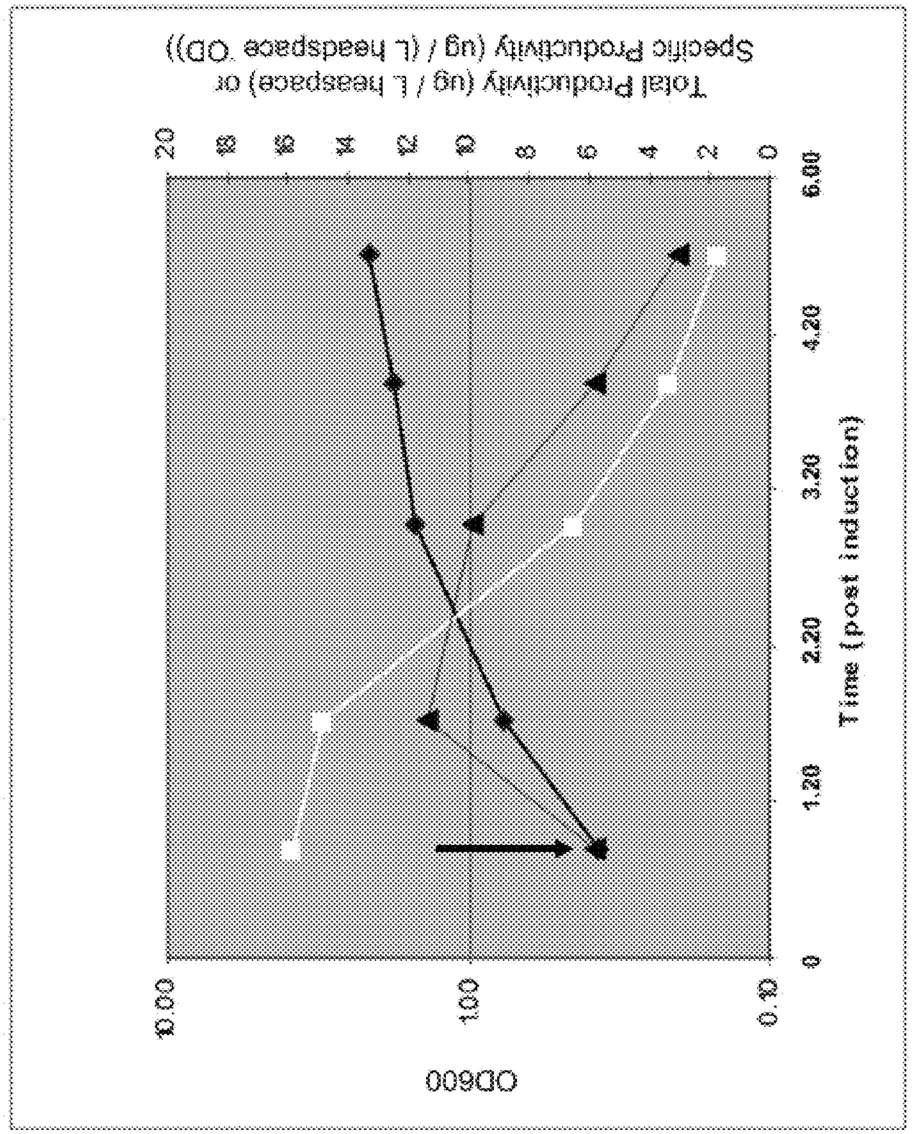

FIG. 23H is a graph showing production of isoprene from glucose in BL21/pTrcKudzuIDIDXSkan. The arrow indicates the time of induction with IPTG (400 μmol). The x-axis is time after induction; the y-axis is $OD_{600}$ and the y2-axis is total productivity of isoprene (μg/L headspace or specific productivity (μg/L headspace/OD). Black diamonds represent $OD_{600}$, black triangles represent isoprene productivity (μg/L) and white squares represent specific productivity of isoprene (μg/L/OD).

Figure 24:
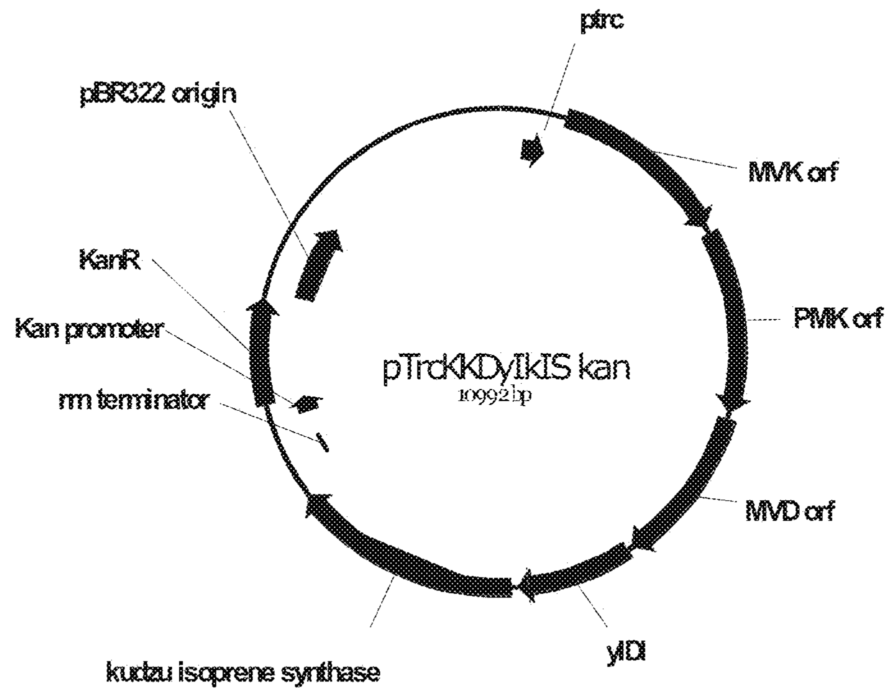

FIG. 24 is a map of pTrcKKDyIkIS kan.

FIGS. 25A-25D is a nucleotide sequence of pTrcKKDyIkIS kan (SEQ ID NO:33).

Figure 26:
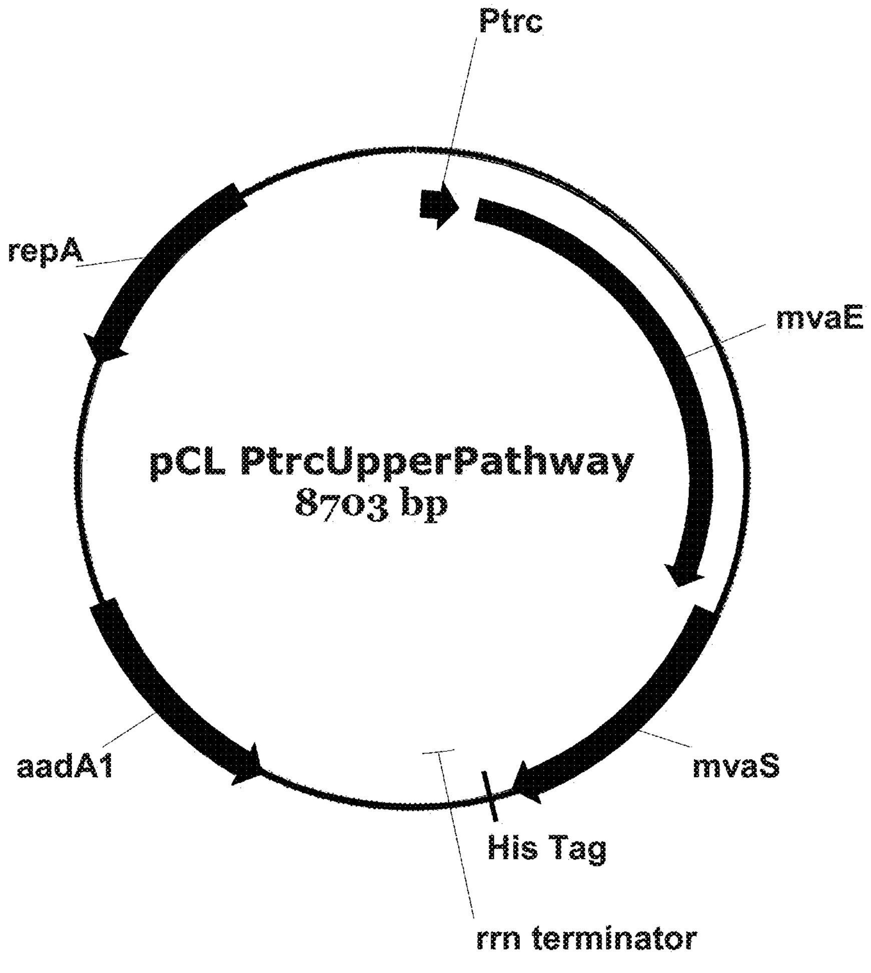

FIG. 26 is a map of pCL PtrcUpperPathway.

FIGS. 27A-27D is a nucleotide sequence of pCL PtrcUpperPathway (SEQ ID NO:46).

Figure 28:
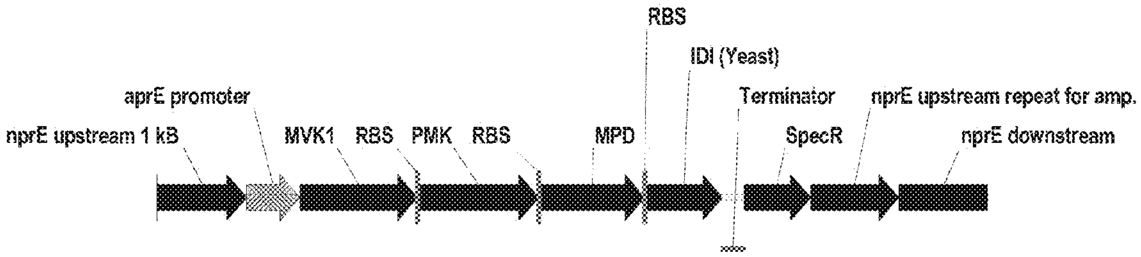

FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

FIGS. 29A-29D is a nucleotide sequence of cassette containing the lower MVA pathway and yeast idi for integration into the *B. subtilis* chromosome at the nprE locus (SEQ ID NO:47).

Figure 30:
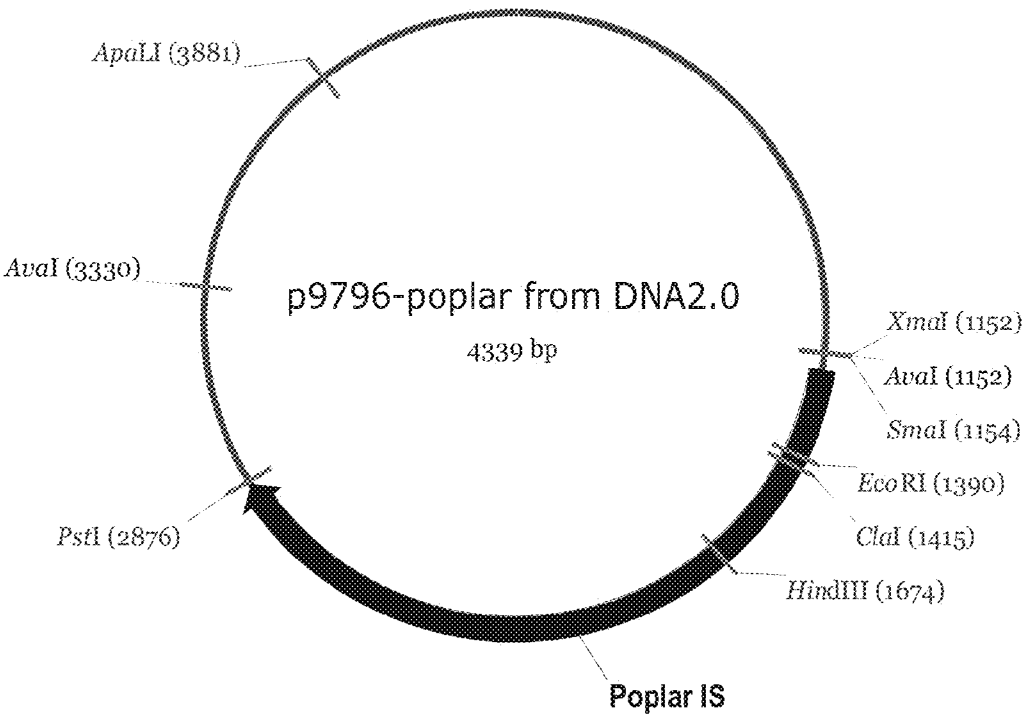

FIG. 30 is a map of p9796-poplar.

FIGS. 31A-31B is a nucleotide sequence of p9796-poplar (SEQ ID NO:48).

Figure 32:
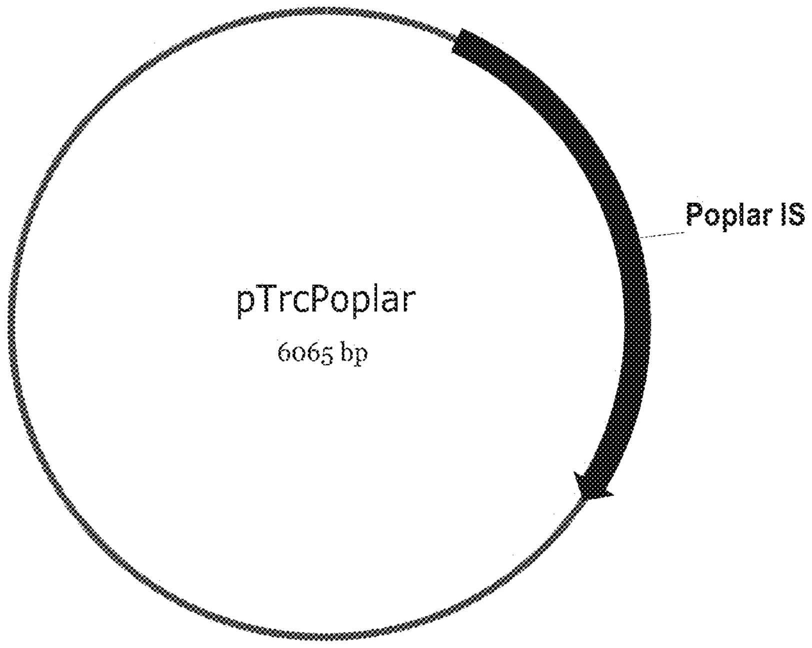

FIG. 32 is a map of pTrcPoplar.

FIGS. 33A-33C is a nucleotide sequence of pTrcPoplar (SEQ ID NO:49).

Figure 34:
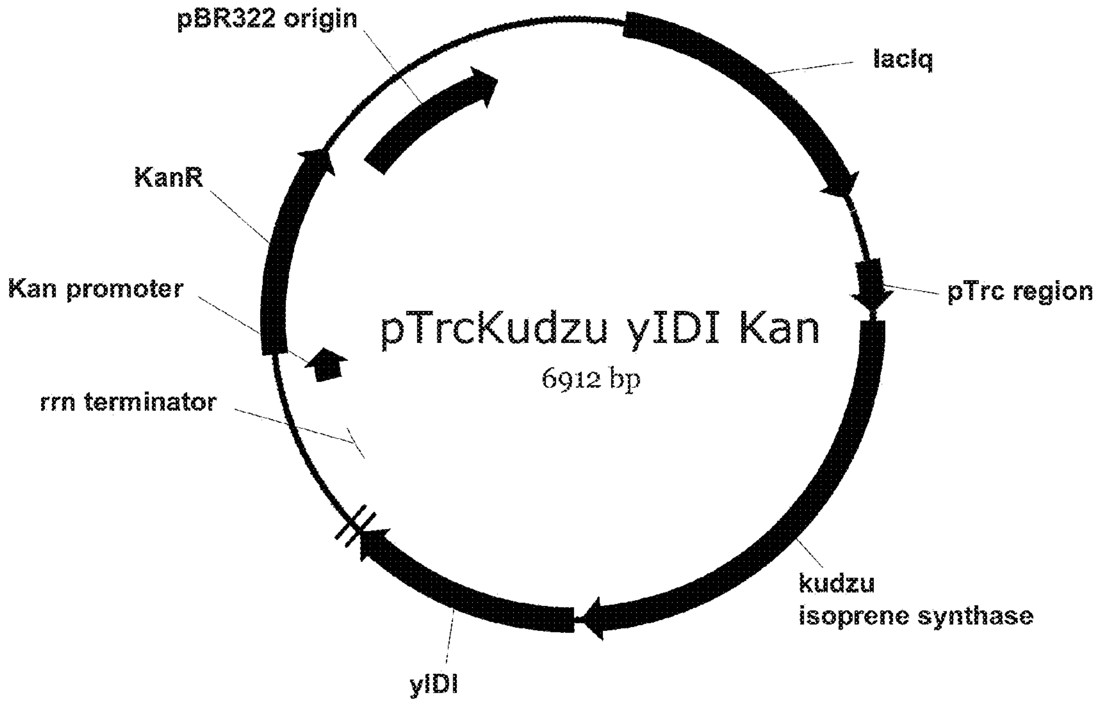

FIG. 34 is a map of pTrcKudzu yIDI Kan.

FIGS. 35A-35C is a nucleotide sequence of pTrcKudzu yIDI Kan (SEQ ID NO:50).

Figure 36:
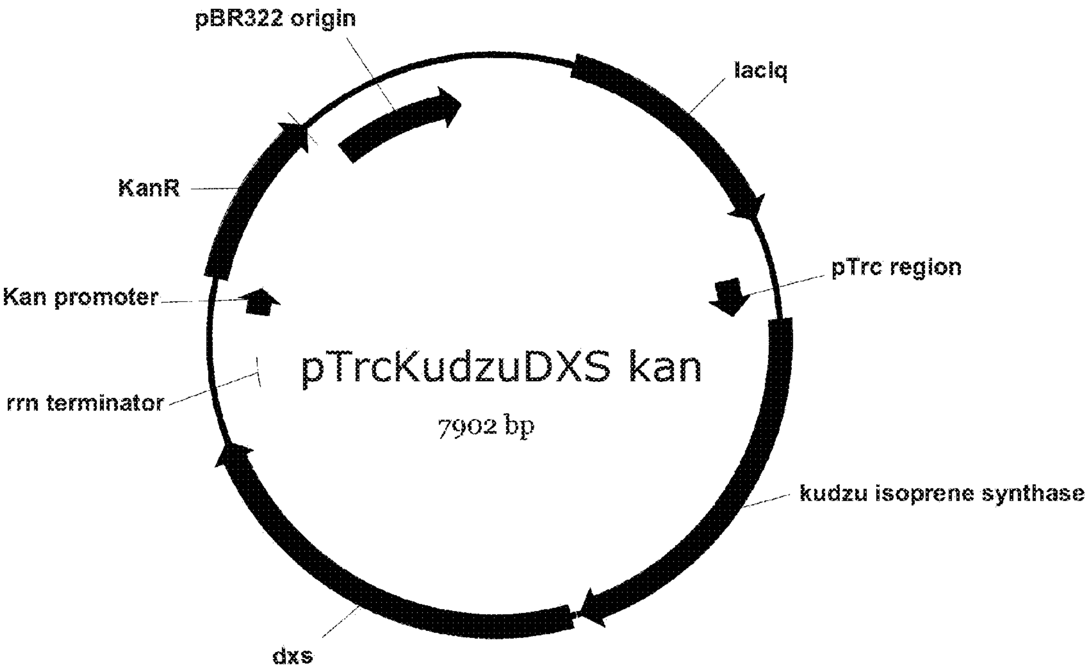

FIG. 36 is a map of pTrcKudzuDXS Kan.

FIGS. 37A-37C is a nucleotide sequence of pTrcKudzuDXS Kan (SEQ ID NO:51).

Figure 38:
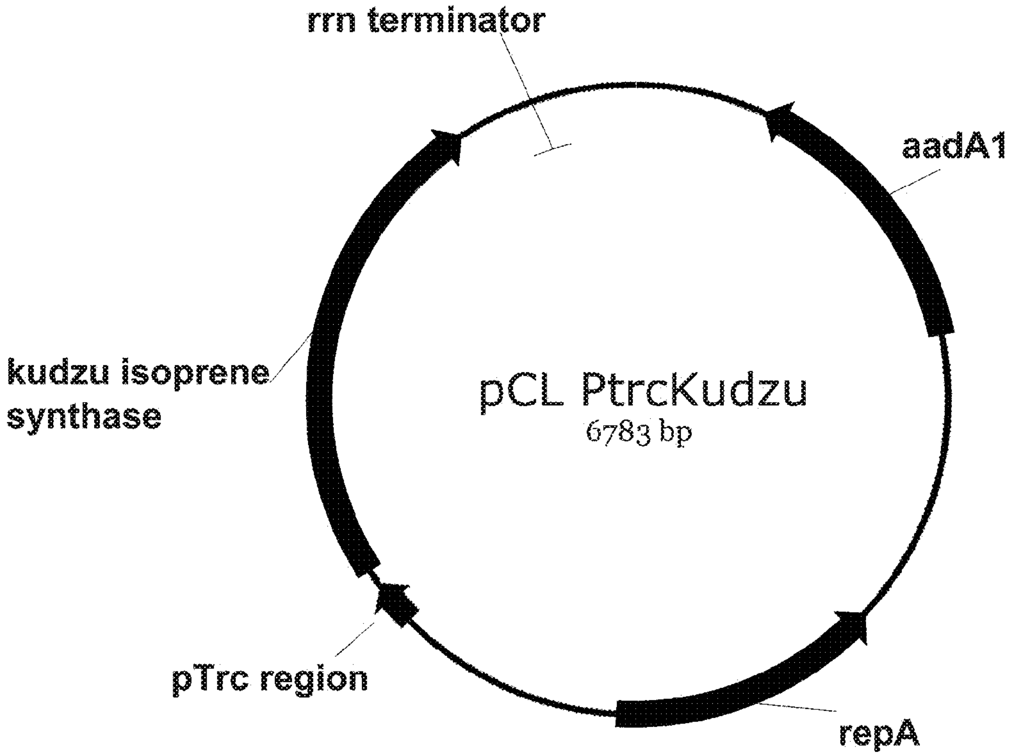

FIG. 38 is a map of pCL PtrcKudzu.

FIGS. 39A-39C is a nucleotide sequence of pCL PtrcKudzu (SEQ ID NO:52).

Figure 40:
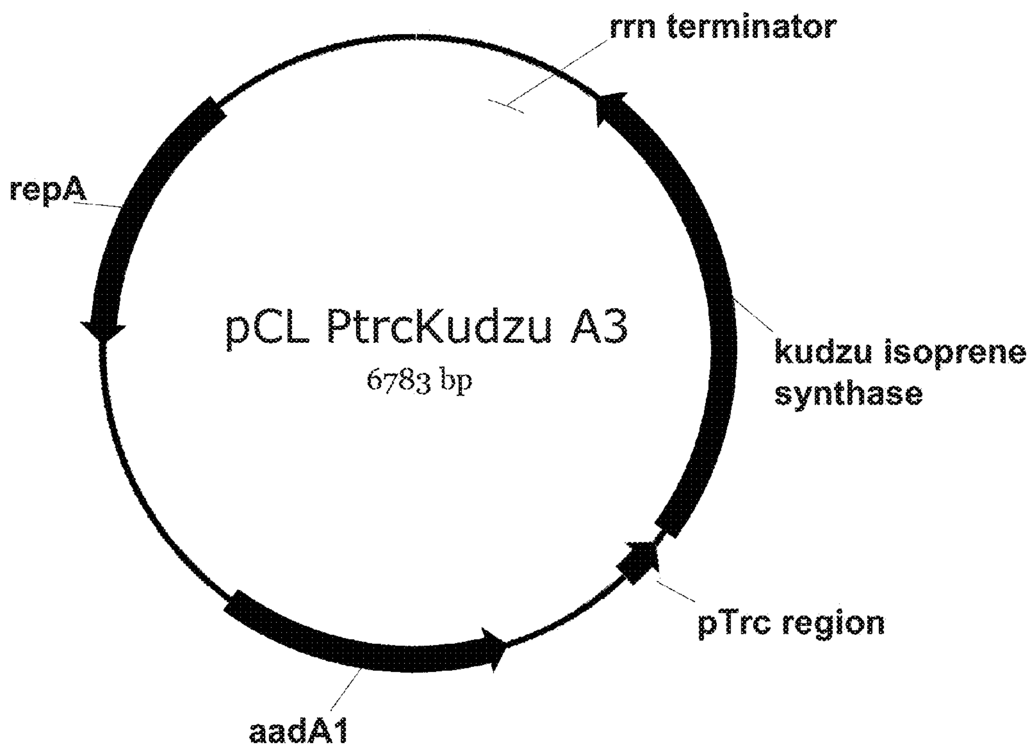

FIG. 40 is a map of pCL PtrcKudzu A3.

FIGS. 41A-41C is a nucleotide sequence of pCL PtrcKudzu A3 (SEQ ID NO:53).

Figure 42:
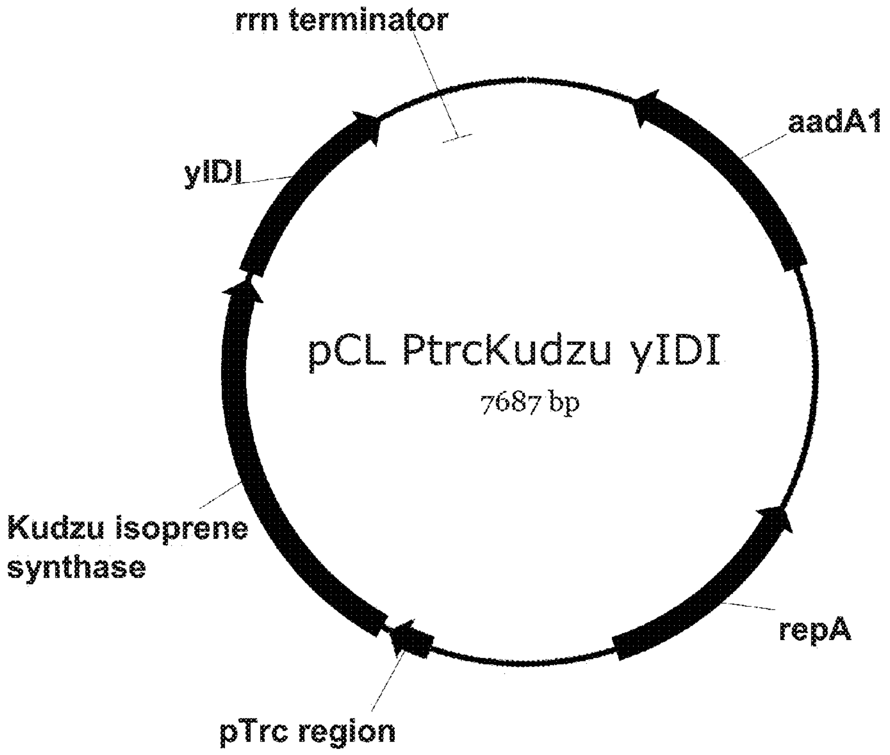

FIG. 42 is a map of pCL PtrcKudzu yIDI.

FIGS. 43A-43C is a nucleotide sequence of pCL PtrcKudzu yIDI (SEQ ID NO:54).

Figure 44:
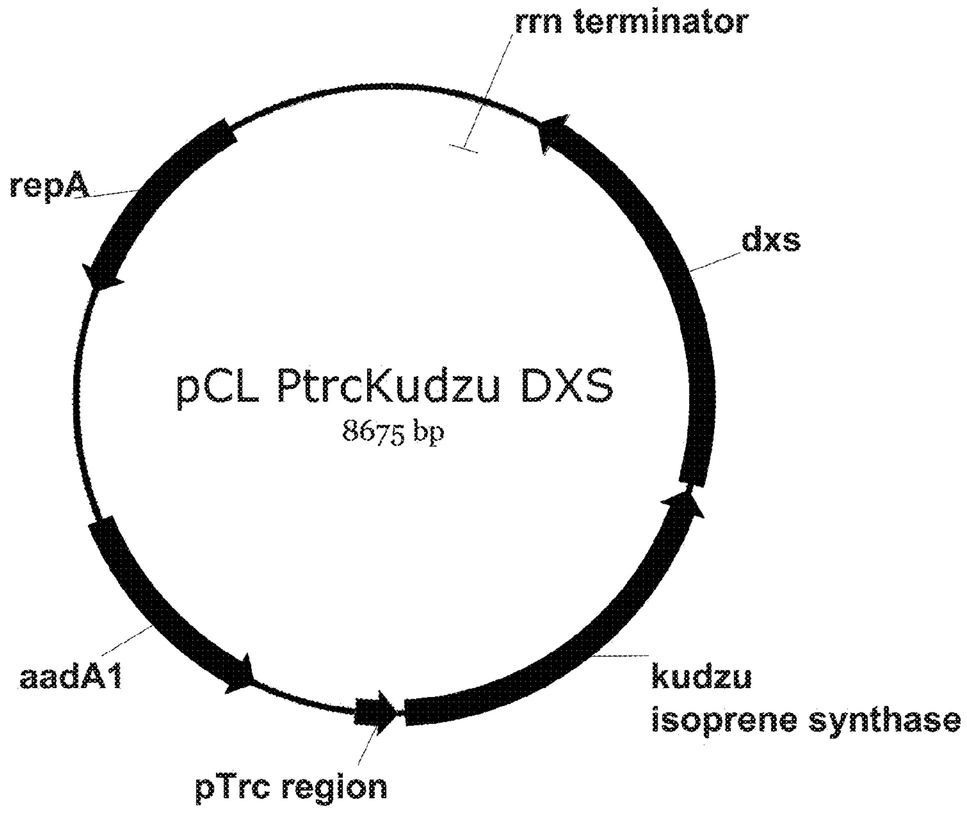
Figure 46A:
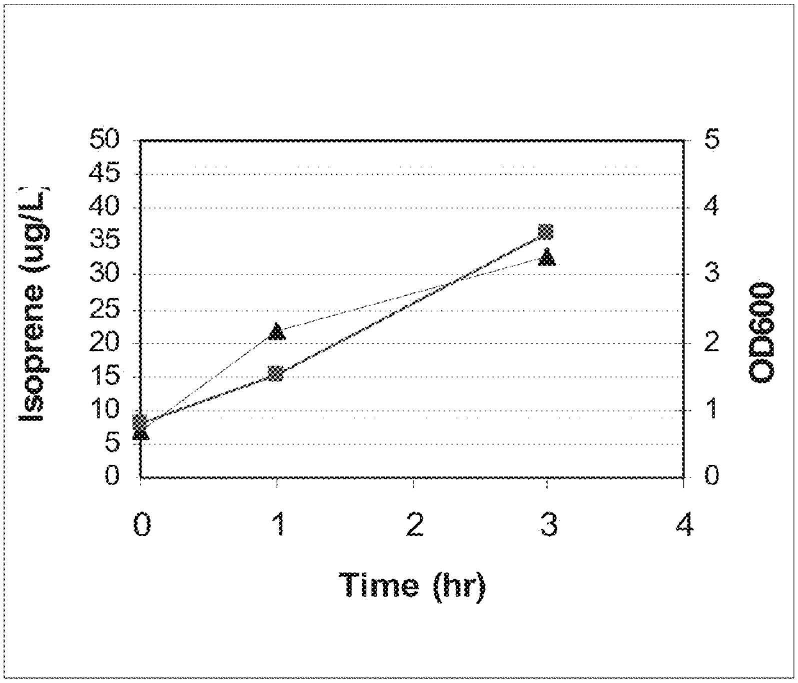
Figure 46B:
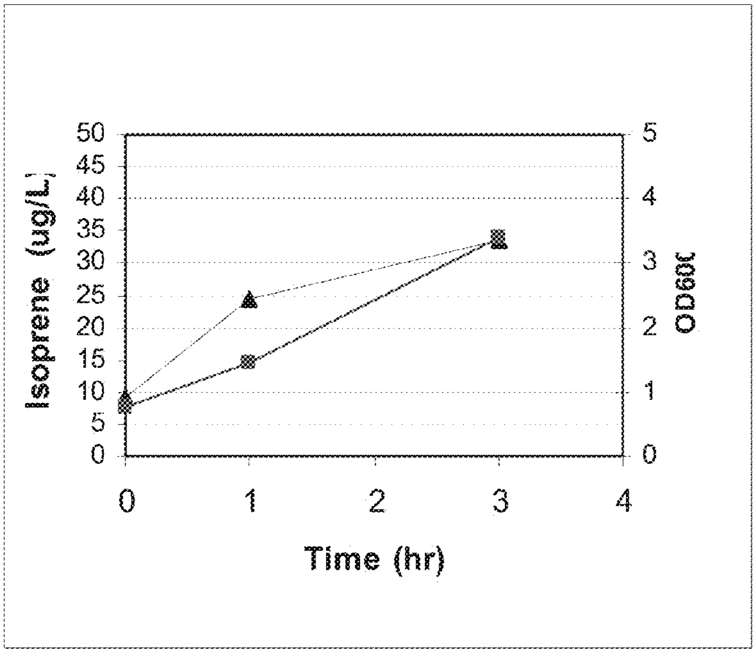
Figure 46C:
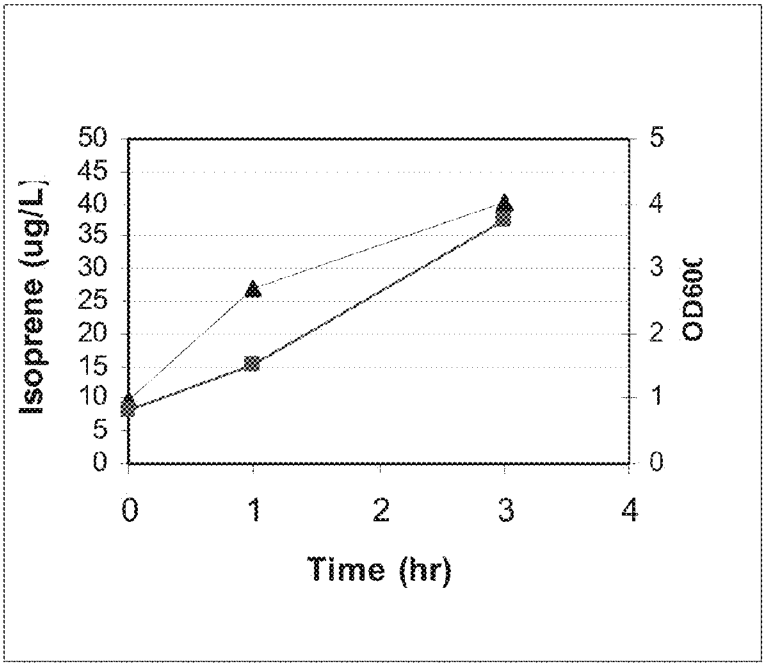
Figure 46D:
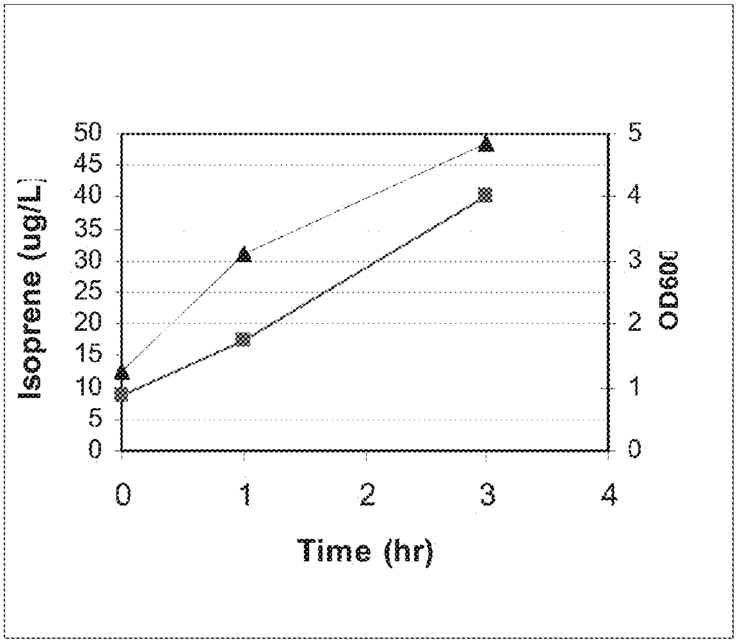
Figure 46E:
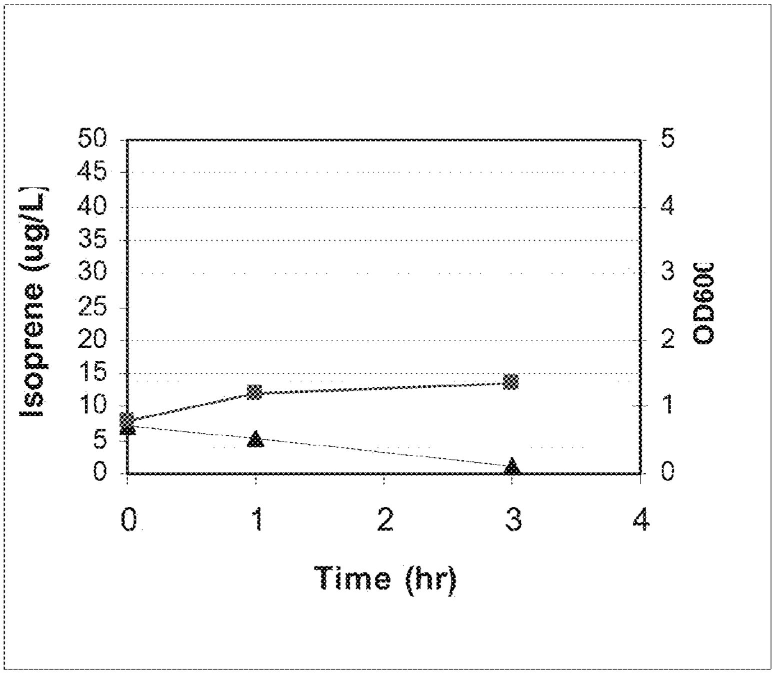

FIG. 44 is a map of pCL PtrcKudzu DXS.

FIGS. 45A-45D is a nucleotide sequence of pCL PtrcKudzu DXS (SEQ ID NO:55).

FIGS. 46A-46E shows graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent $OD_{600}$ measurements of the cultures at the indicated times post-inoculation and black triangles represent isoprene production at the indicated times post-inoculation.

Figure 47A:
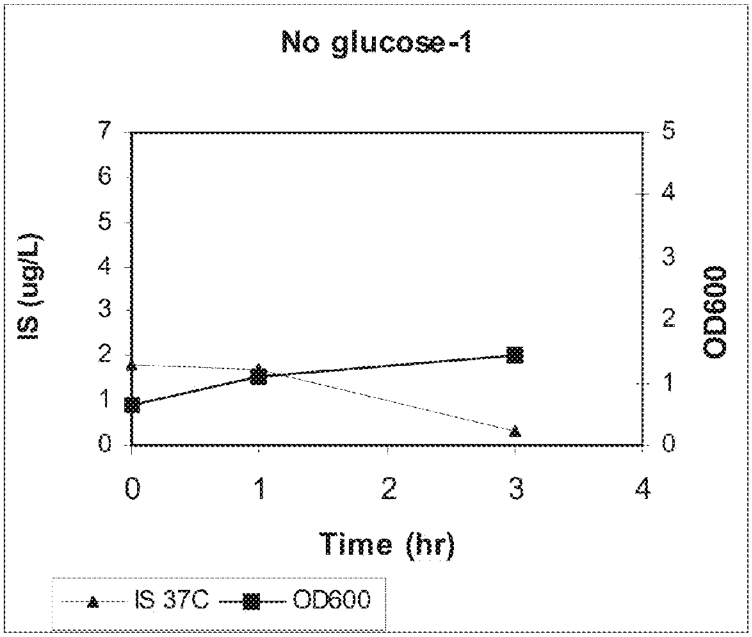

FIG. 47A shows a graph representing isoprene production by BL21 (λDE3) pTrcKudzu yIDI DXS (kan) in a culture with no glucose added. Squares represent $OD_{600}$, and triangles represent isoprene produced (μg/ml).

Figure 47B:
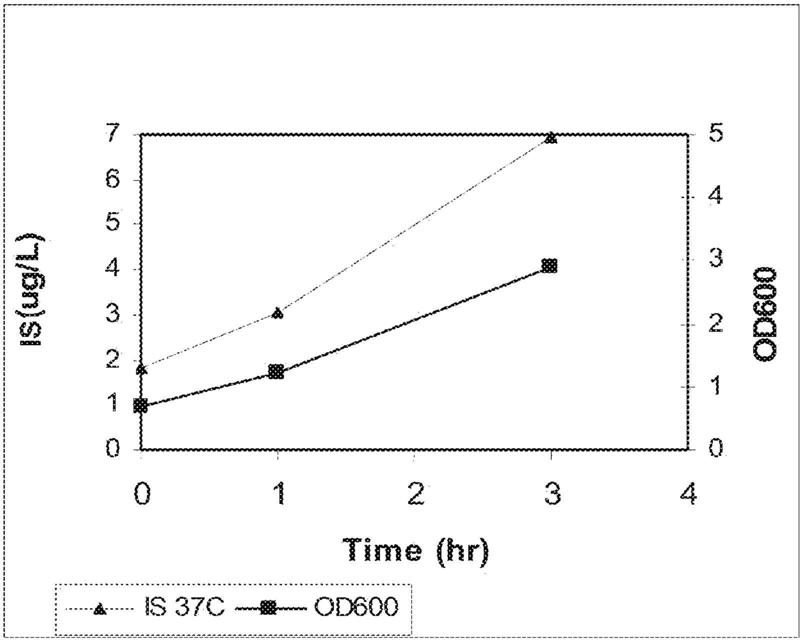

FIG. 47B shows a graph representing isoprene production from 1% glucose feedstock invert sugar by BL21 (λDE3) pTrcKudzu yIDI DXS (kan). Squares represent $OD_{600}$, and triangles represent isoprene produced (μg/ml).

Figure 47C:
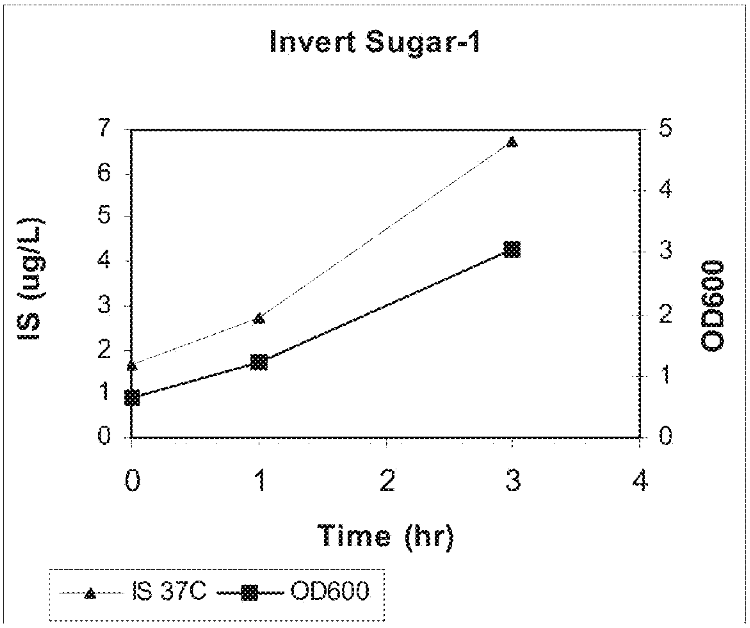

FIG. 47C shows a graph representing isoprene production from 1% invert sugar feedstock by BL21 (λDE3) pTrcKudzu yIDI DXS (kan). Squares represent $OD_{600}$, and triangles represent isoprene produced (μg/ml).

Figure 47D:
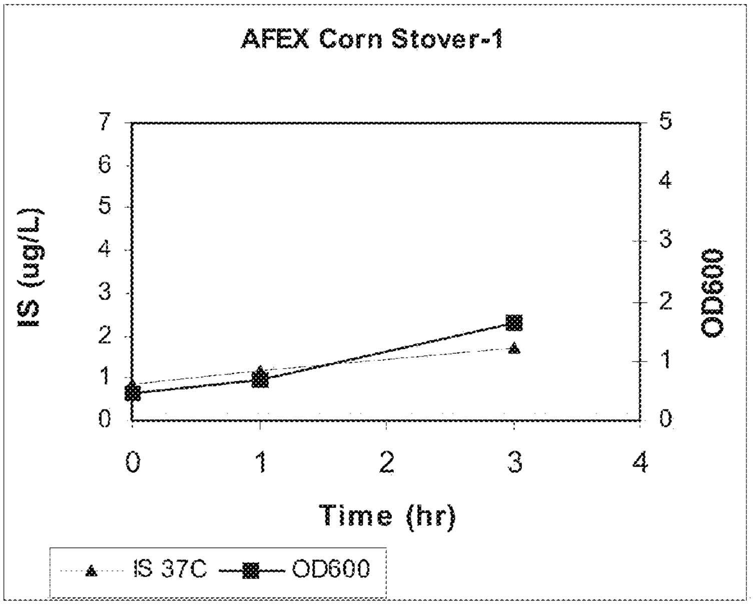

FIG. 47D shows a graph representing isoprene production from 1% AFEX corn stover feedstock by BL21 (λDE3) pTrcKudzu yIDI DXS (kan). Squares represent $OD_{600}$, and triangles represent isoprene produced (μg/ml).

Figure 48A:
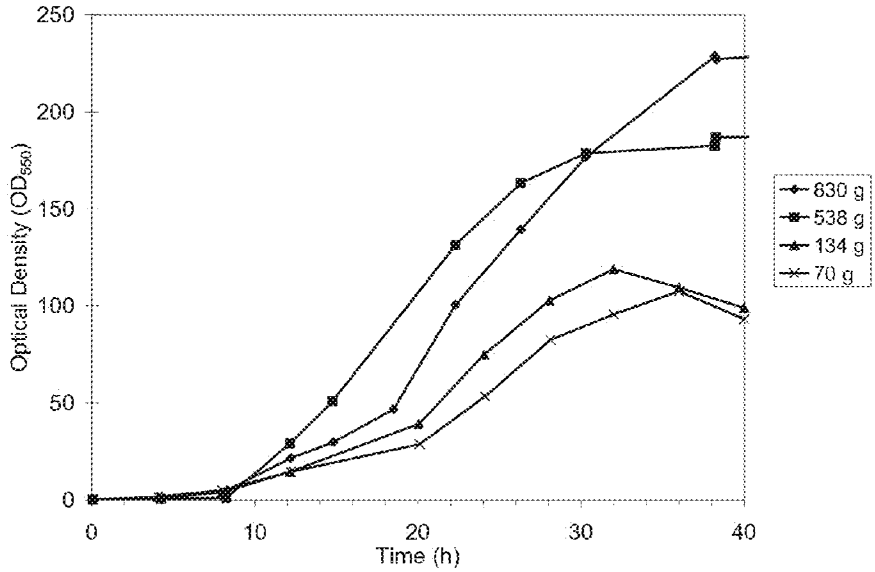
Figure 48B:
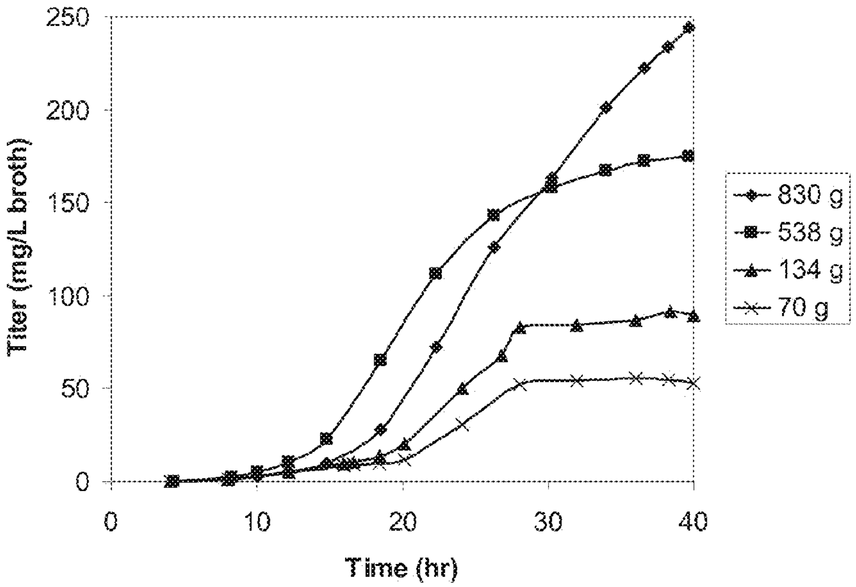
Figure 48C:
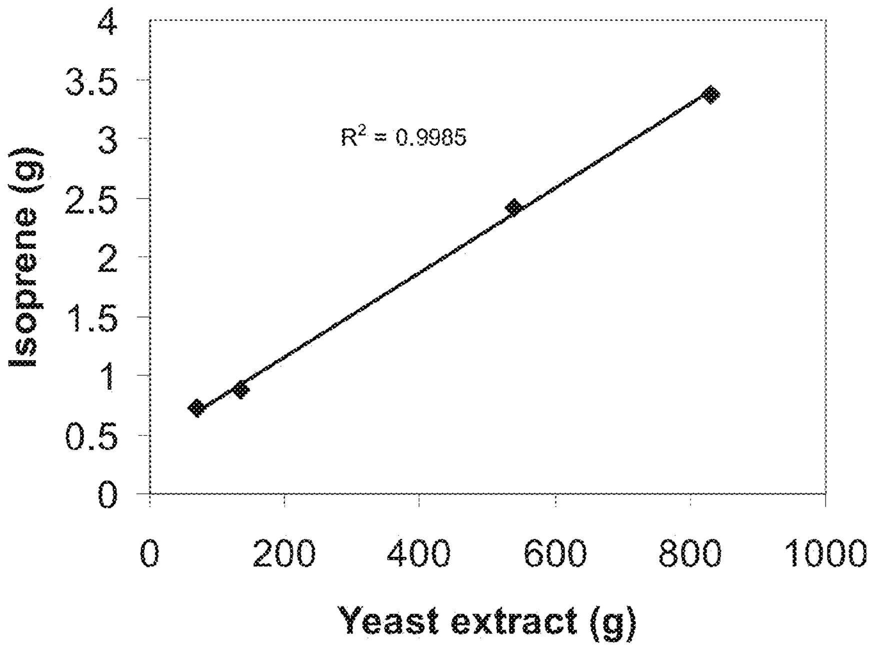

FIGS. 48A-48C shows graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.

Figure 49A:
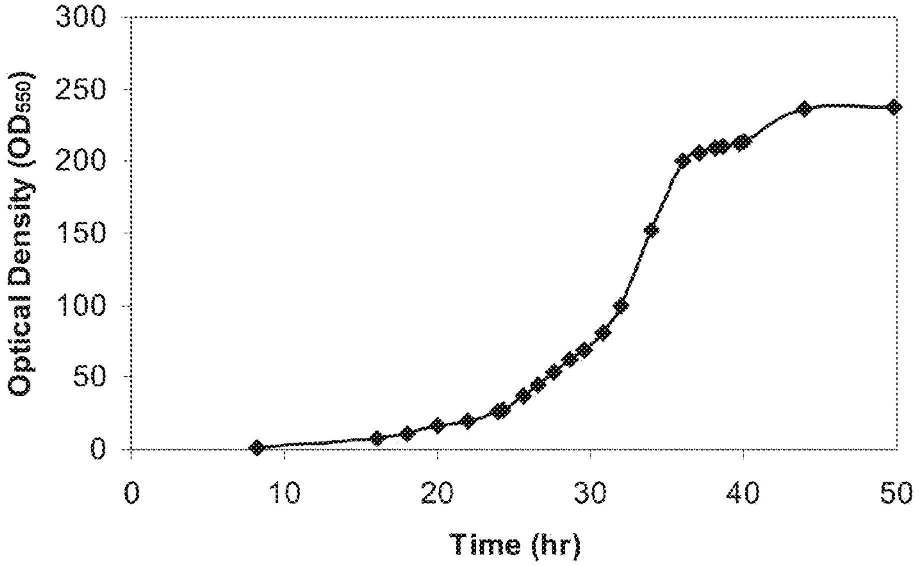
Figure 49B:
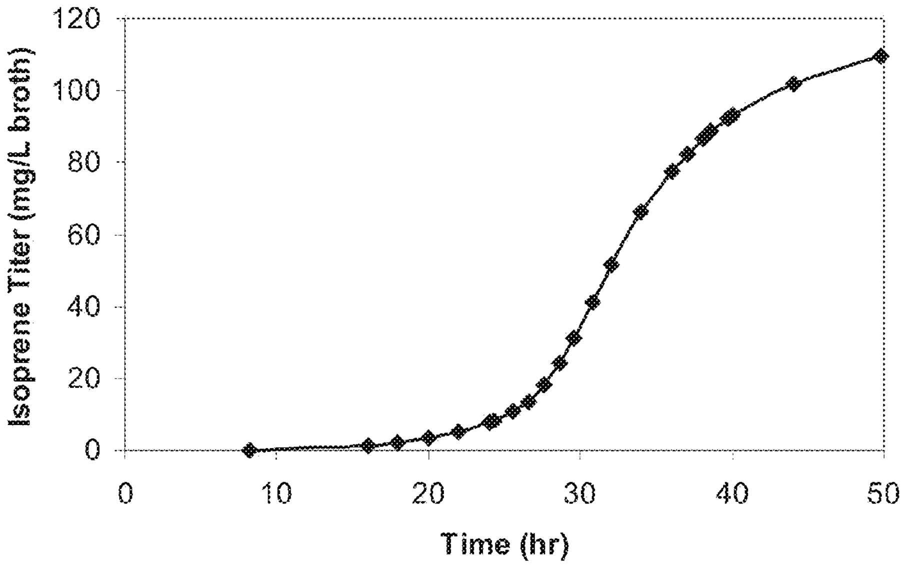
Figure 49C:
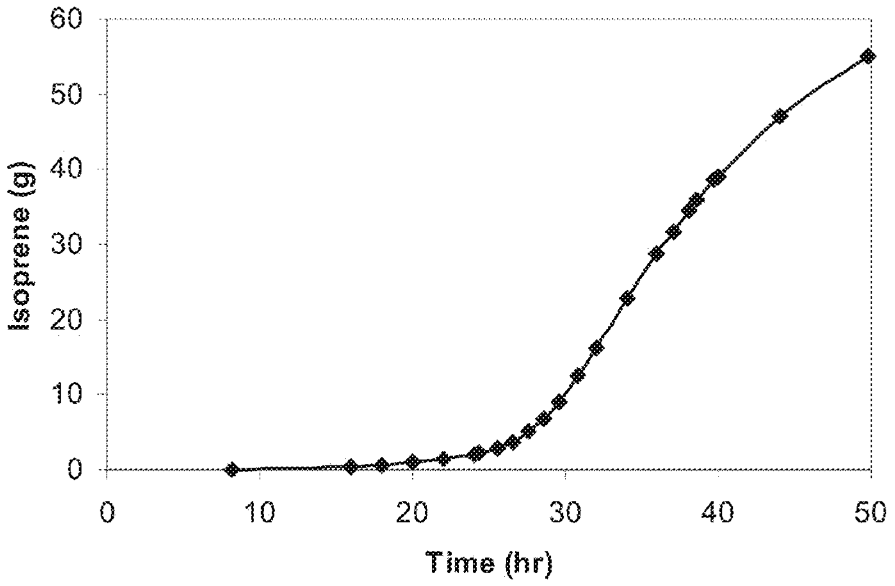

FIGS. 49A-49C shows graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.

Figure 50:
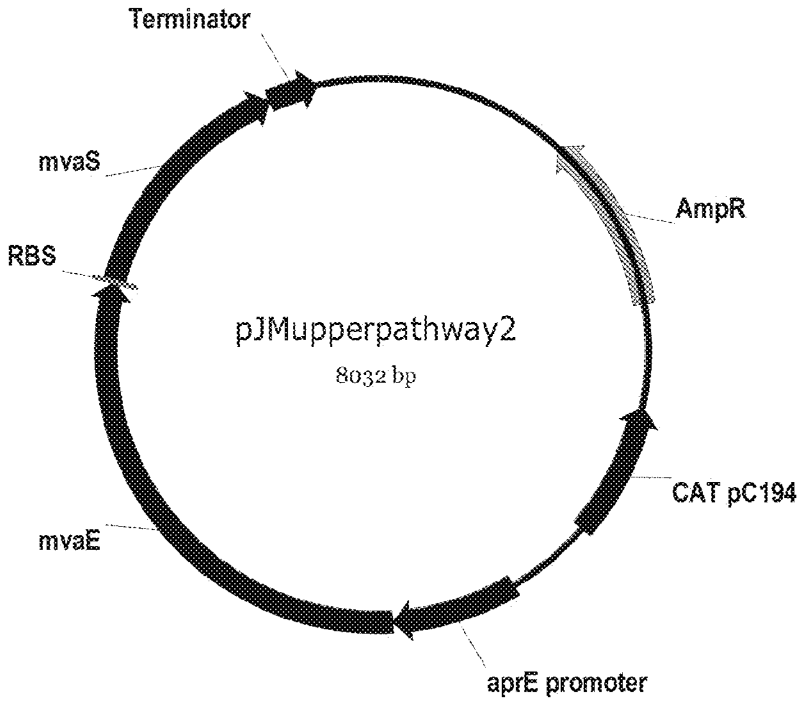

FIG. 50 is a map of pJMupperpathway2.

FIGS. 51A-51C is the nucleotide sequence of pJMupperpathway2 (SEQ ID NO:56).

Figure 52:
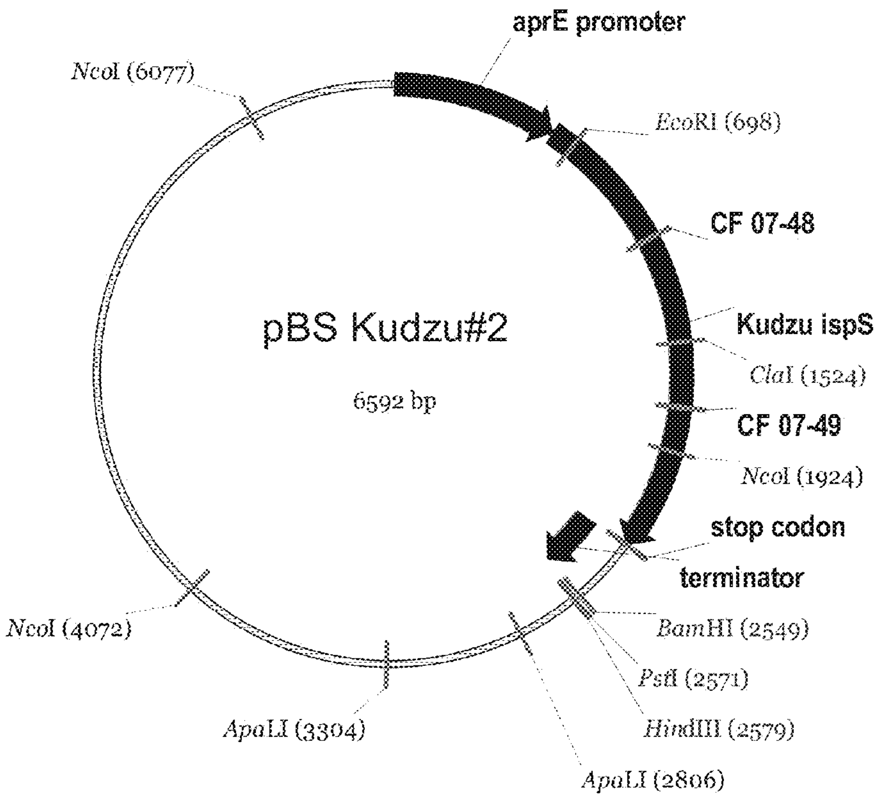

FIG. 52 is a map of pBS Kudzu #2.

Figure 53A:
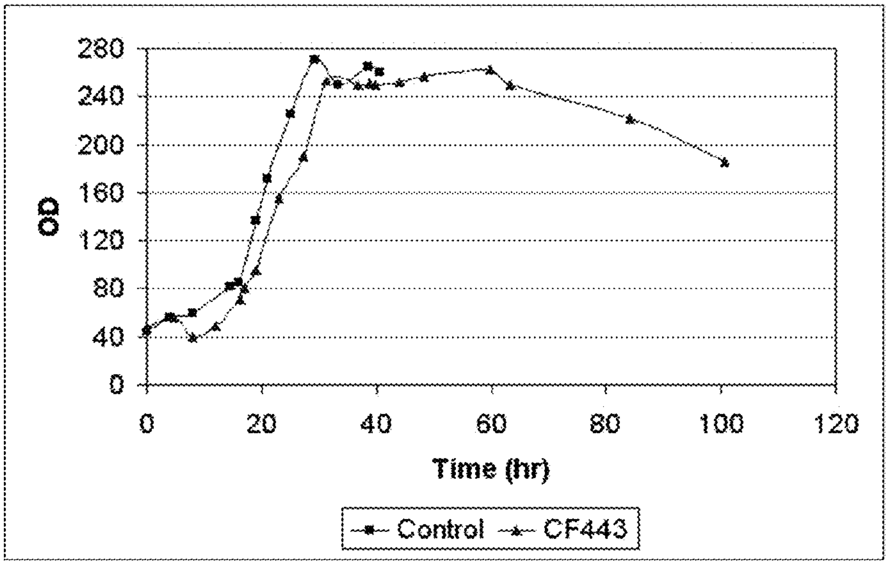

FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Figure 53B:
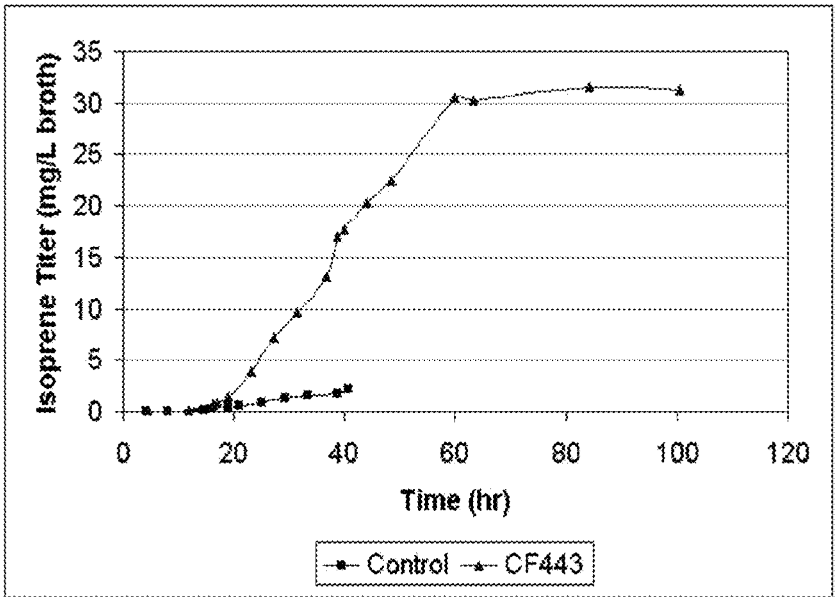

FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Figure 54:
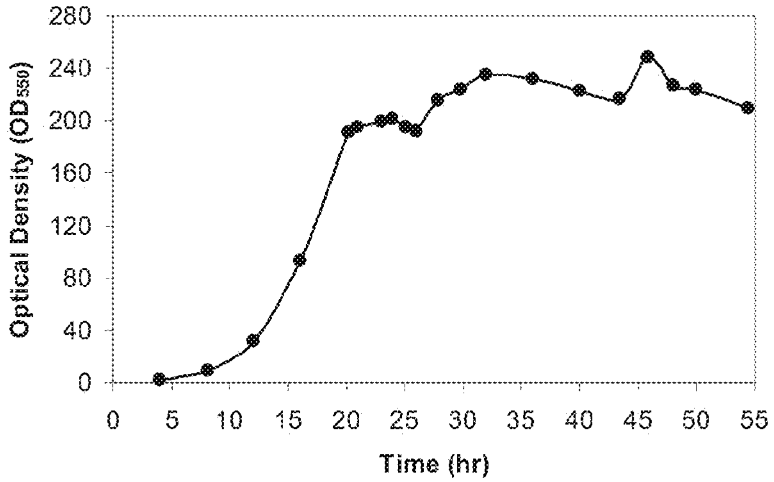

FIG. 54 is a time course of optical density within the 15-L bioreactor fed with glucose.

Figure 55:
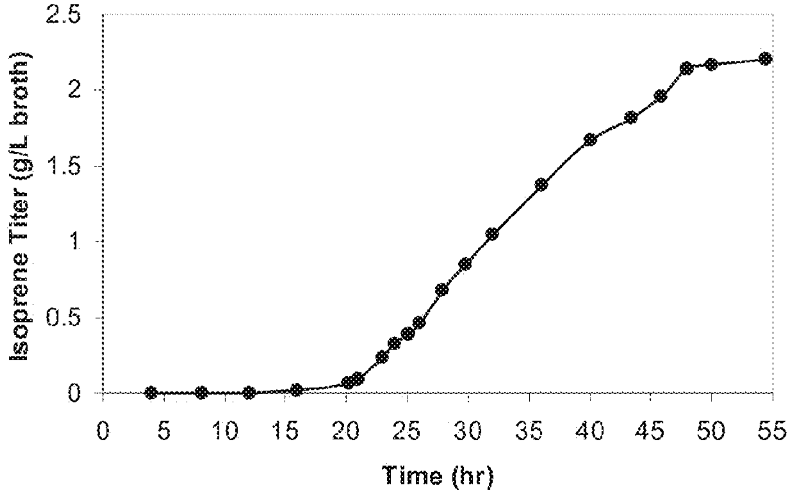

FIG. 55 is a time course of isoprene titer within the 15-L bioreactor fed with glucose. The titer is defined as the amount of isoprene produced per liter of fermentation broth.

Figure 56:
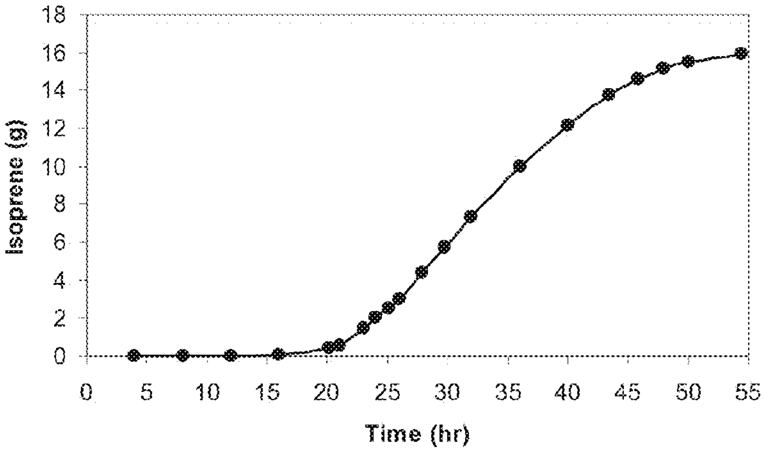

FIG. 56 is a time course of total isoprene produced from the 15-L bioreactor fed with glucose.

Figure 57:
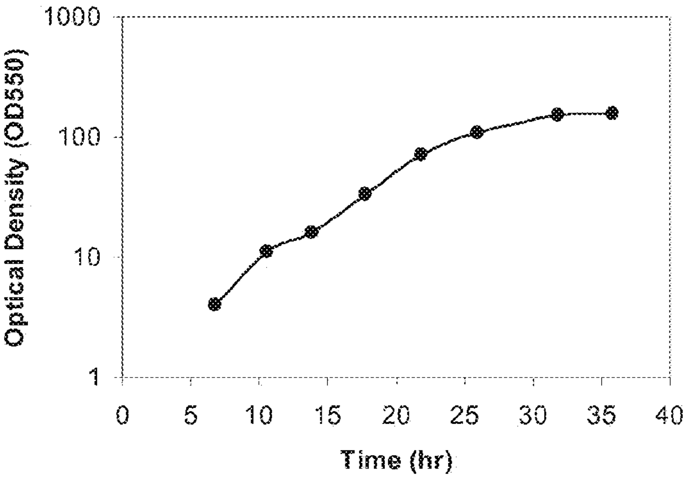

FIG. 57 is a time course of optical density within the 15-L bioreactor fed with glycerol.

Figure 58:
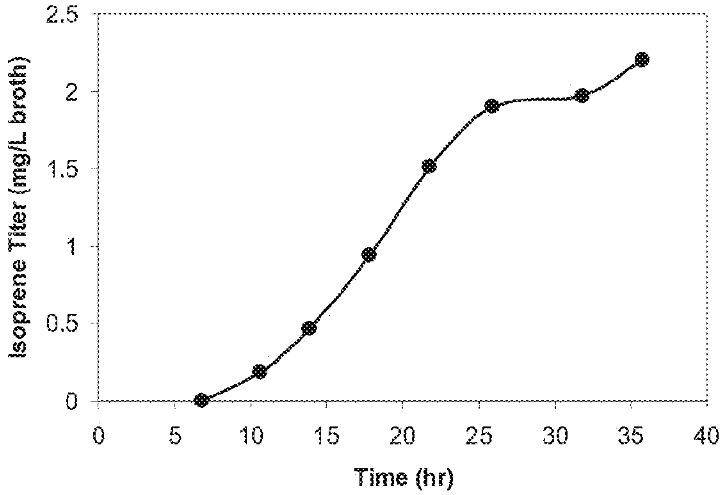

FIG. 58 is a time course of isoprene titer within the 15-L bioreactor fed with glycerol. The titer is defined as the amount of isoprene produced per liter of fermentation broth.

Figure 59:
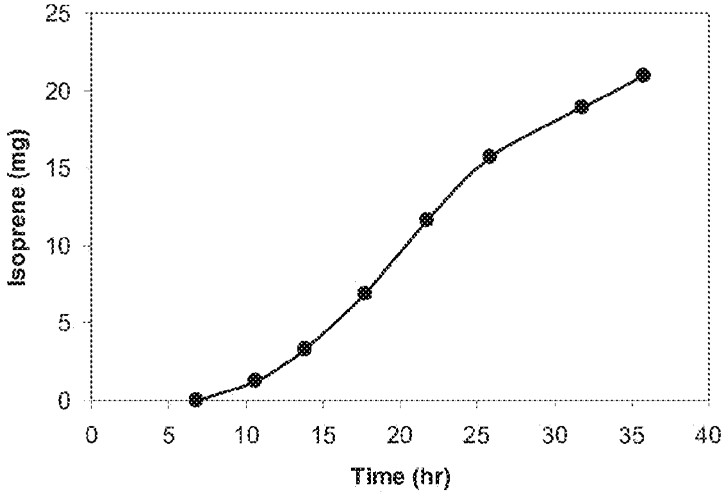

FIG. 59 is a time course of total isoprene produced from the 15-L bioreactor fed with glycerol.

Figure 60:
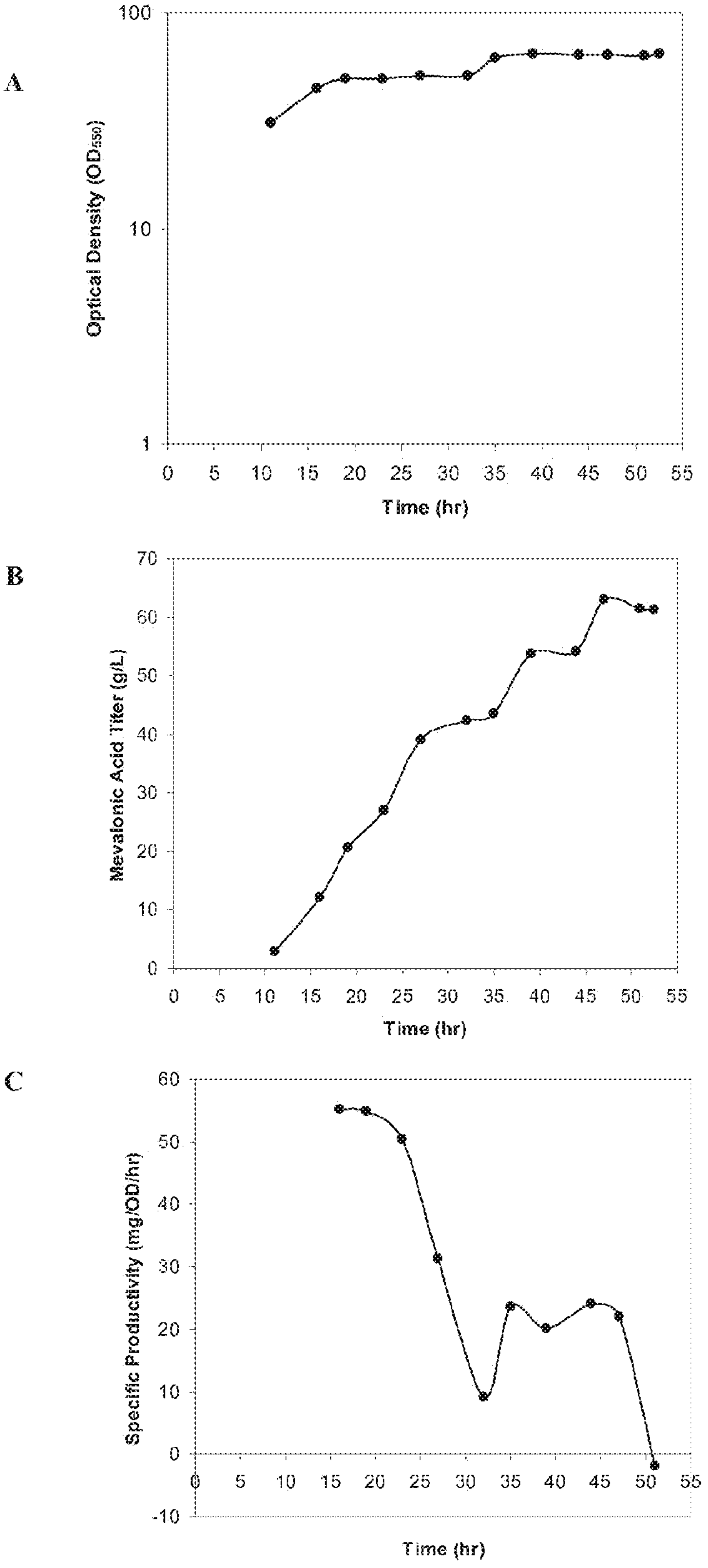

FIGS. 60A-60C are the time courses of optical density, mevalonic acid titer, and specific productivity within the 150-L bioreactor fed with glucose.

FIGS. 61A-61C are the time courses of optical density, mevalonic acid titer, and specific productivity within the 15-L bioreactor fed with glucose.

Figure 62:
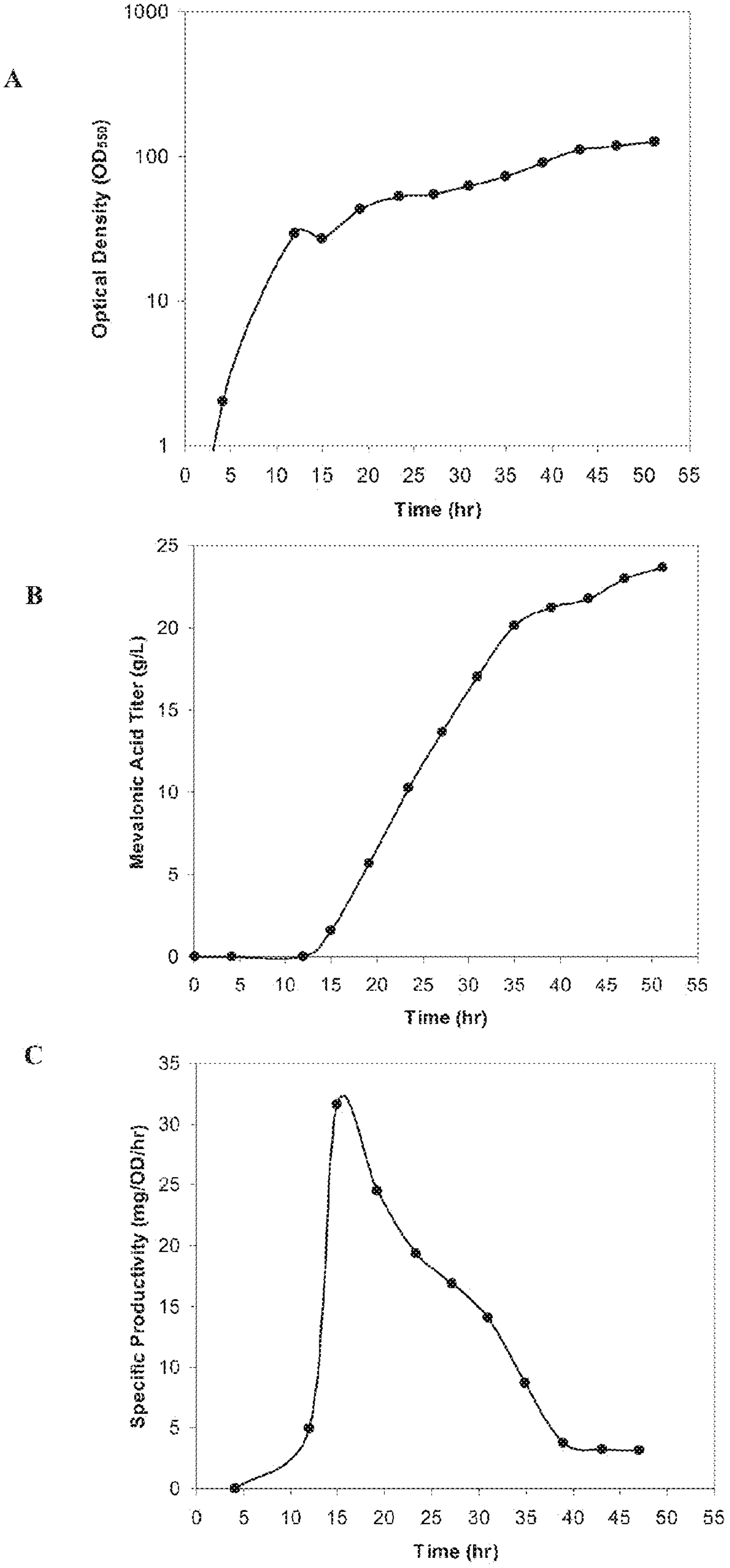

FIGS. 62A-62C are the time courses of optical density, mevalonic acid titer, and specific productivity within the 15-L bioreactor fed with glucose.

Figure 63:
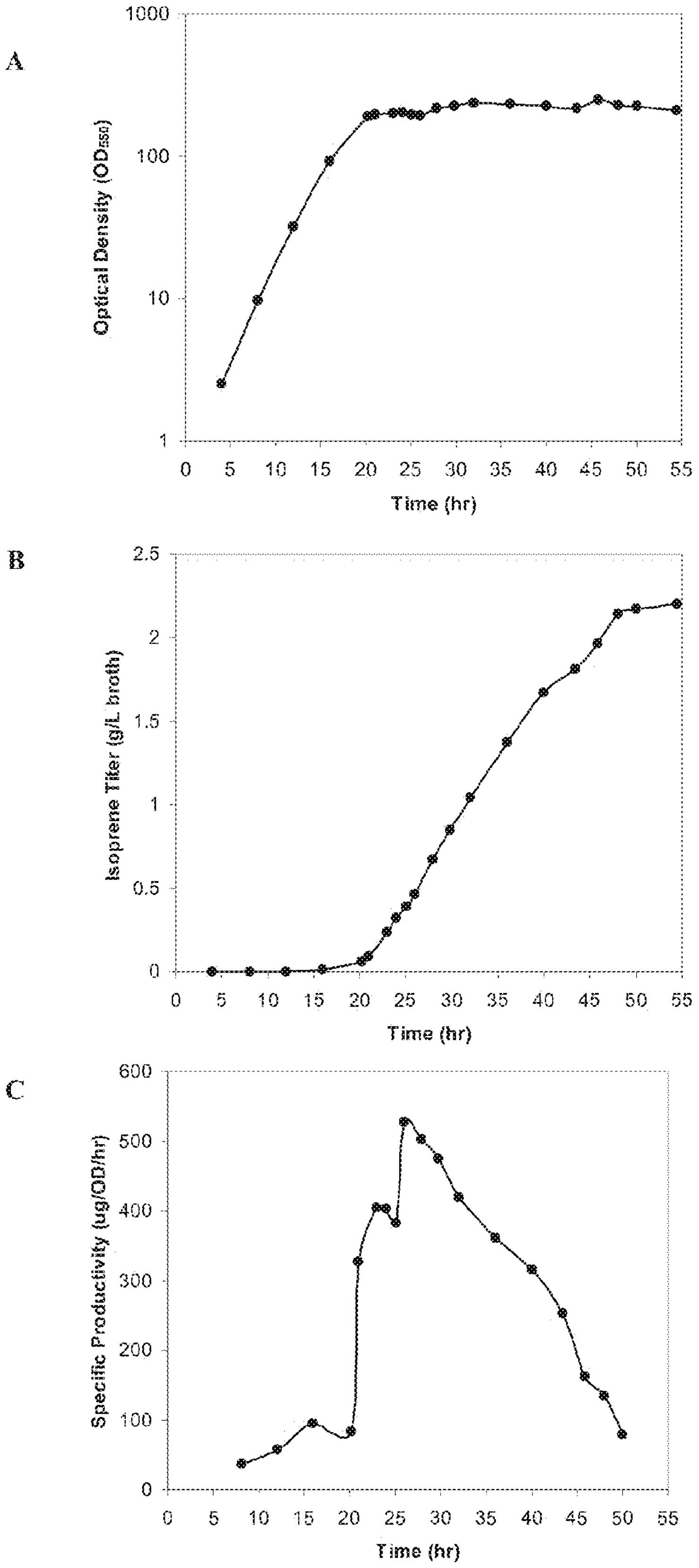

FIG. 63A-63C are the time courses of optical density, isoprene titer, and specific productivity within the 15-L bioreactor fed with glucose.

Figure 64:
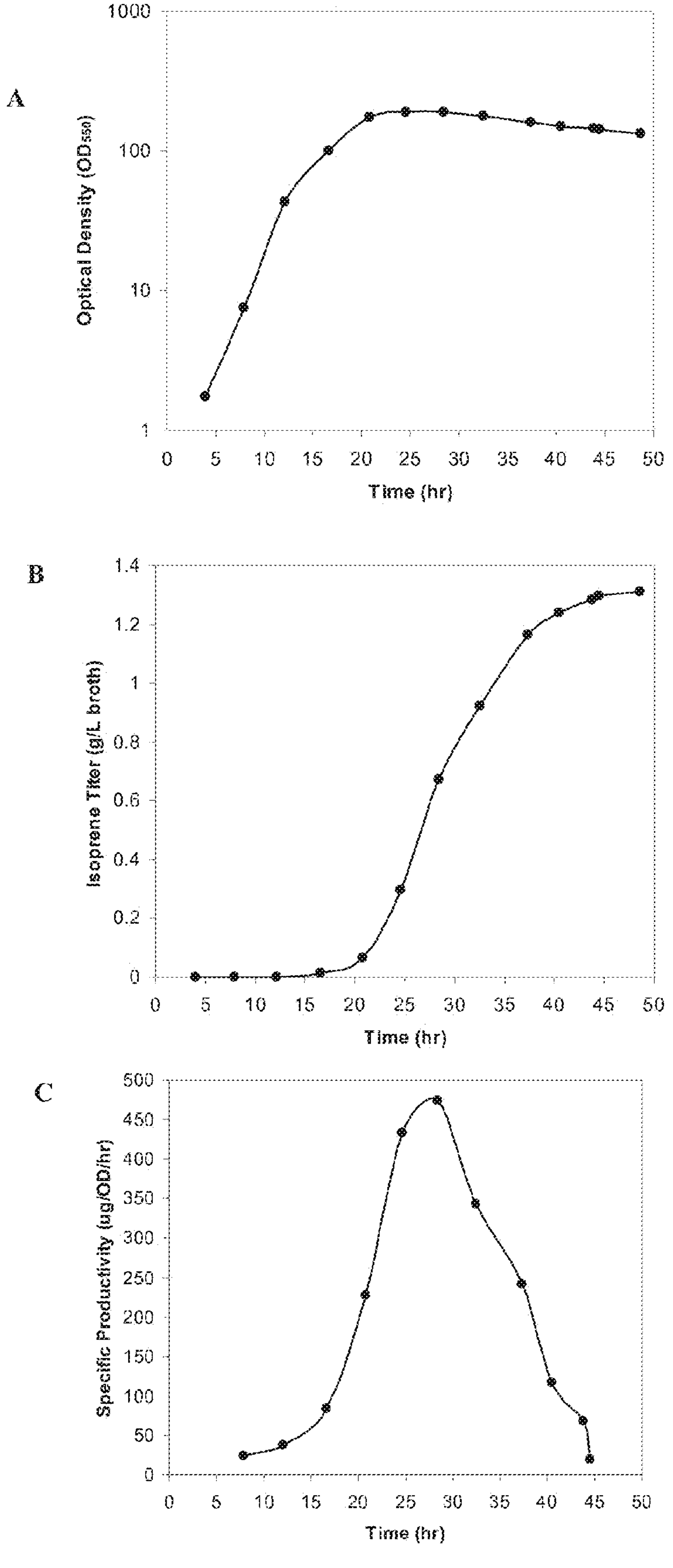

FIGS. 64A-64C are the time courses of optical density, isoprene titer, and specific productivity within the 15-L bioreactor fed with glucose.

Figure 65:
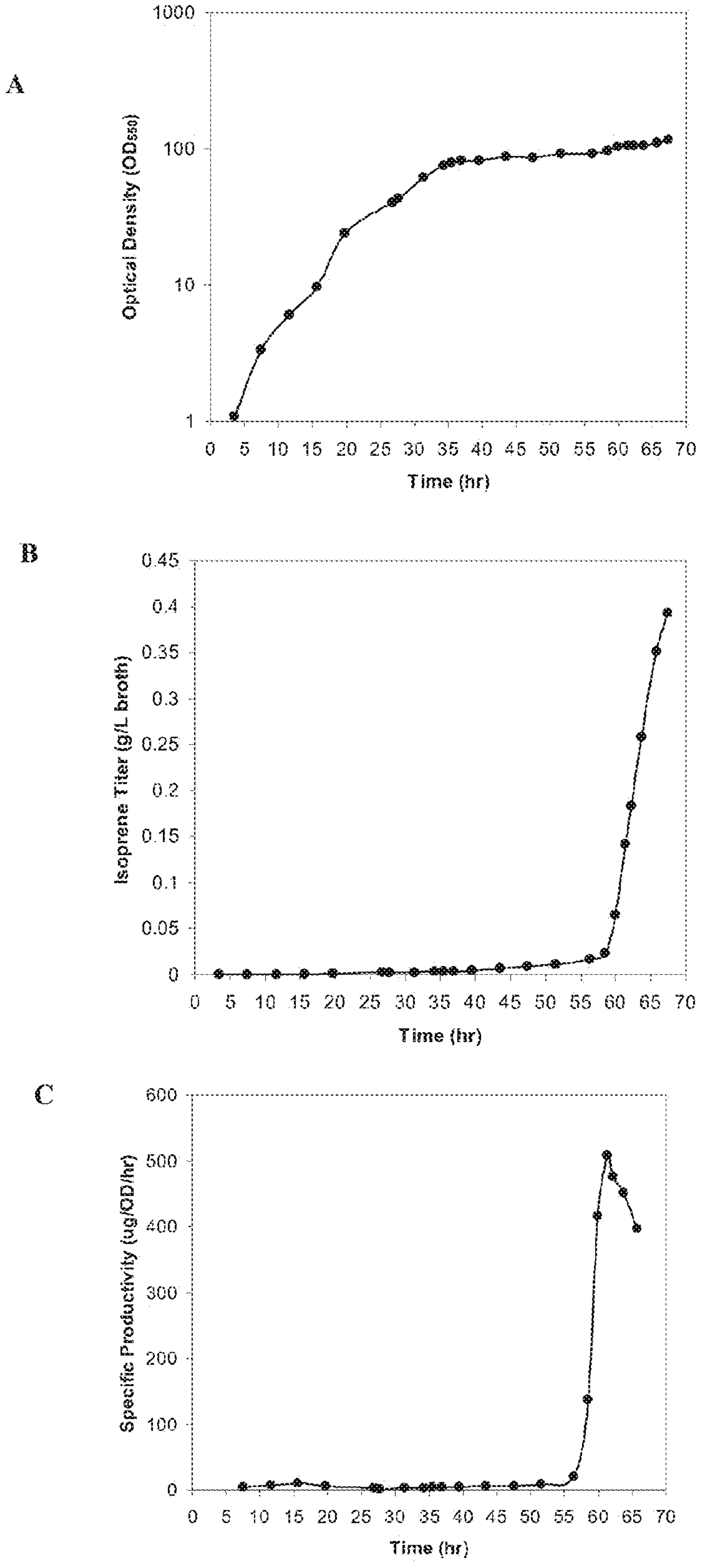

FIGS. 65A-65C are the time courses of optical density, isoprene titer, and specific productivity within the 15-L bioreactor fed with glucose.

Figure 66:
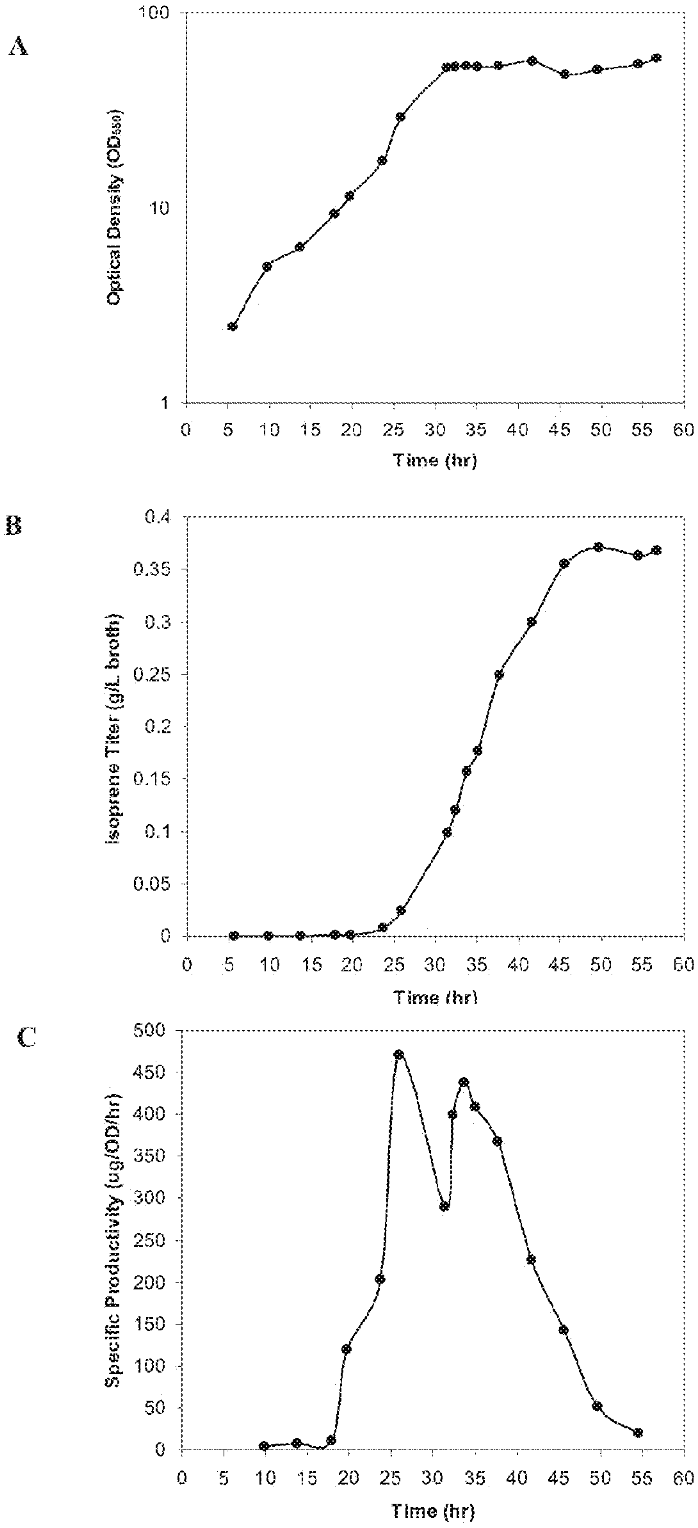

FIGS. 66A-66C are the time courses of optical density, isoprene titer, and specific productivity within the 15-L bioreactor fed with glucose.

Figure 67:
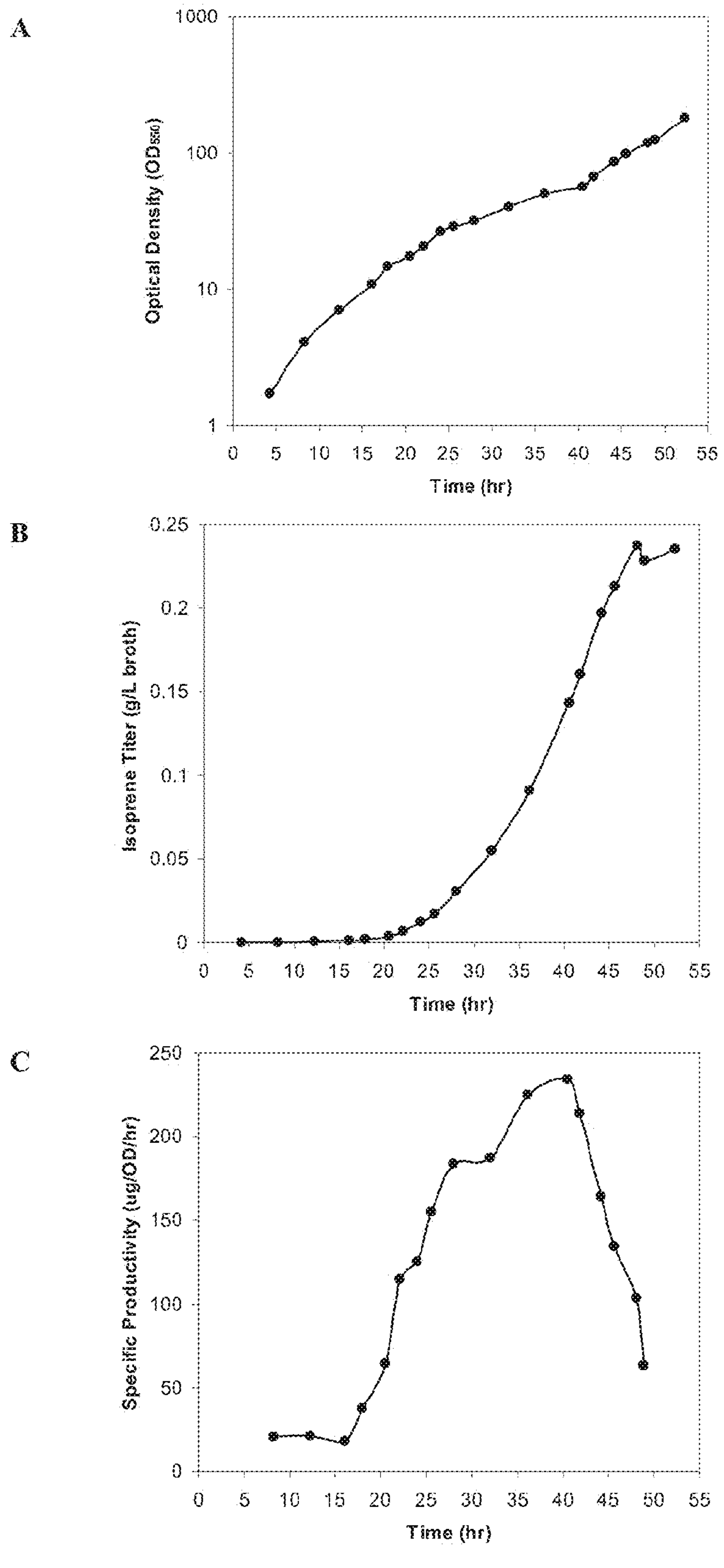

FIG. 67A-67C are the time courses of optical density, isoprene titer, and specific productivity within the 15-L bioreactor fed with glucose.

Figure 68:
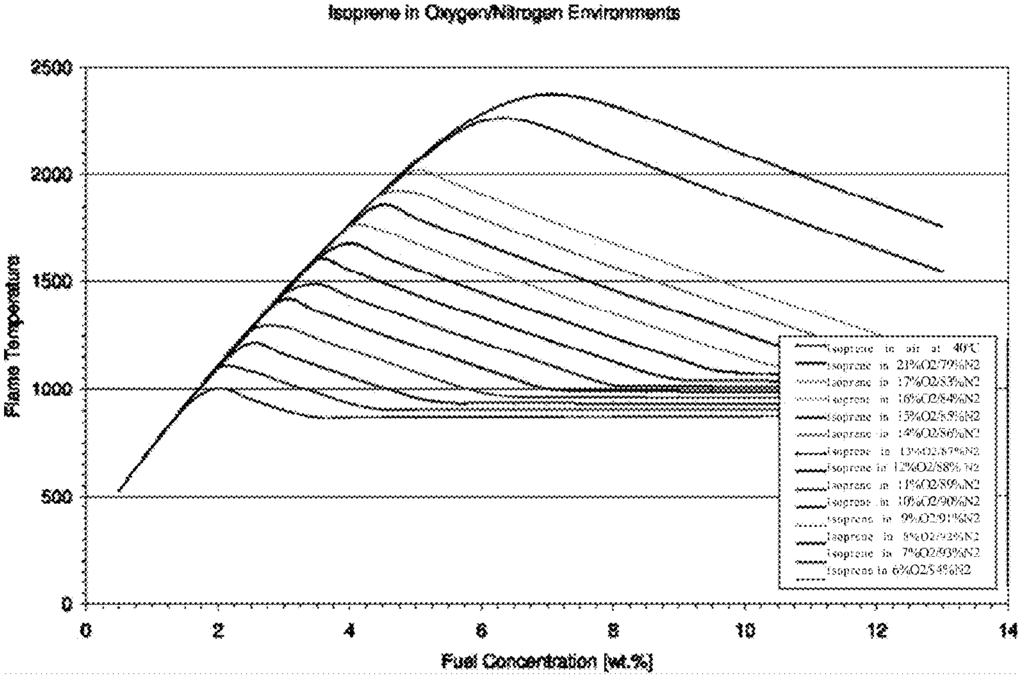

FIG. 68 is a graph of the calculated adiabatic flame temperatures for Series A as a function of fuel concentration for various oxygen levels. The figure legend lists the curves in the order in which they appear in the graph. For example, the first entry in the figure legend (isoprene in air at 40° C.) corresponds to the highest curve in the graph.

Figure 69:
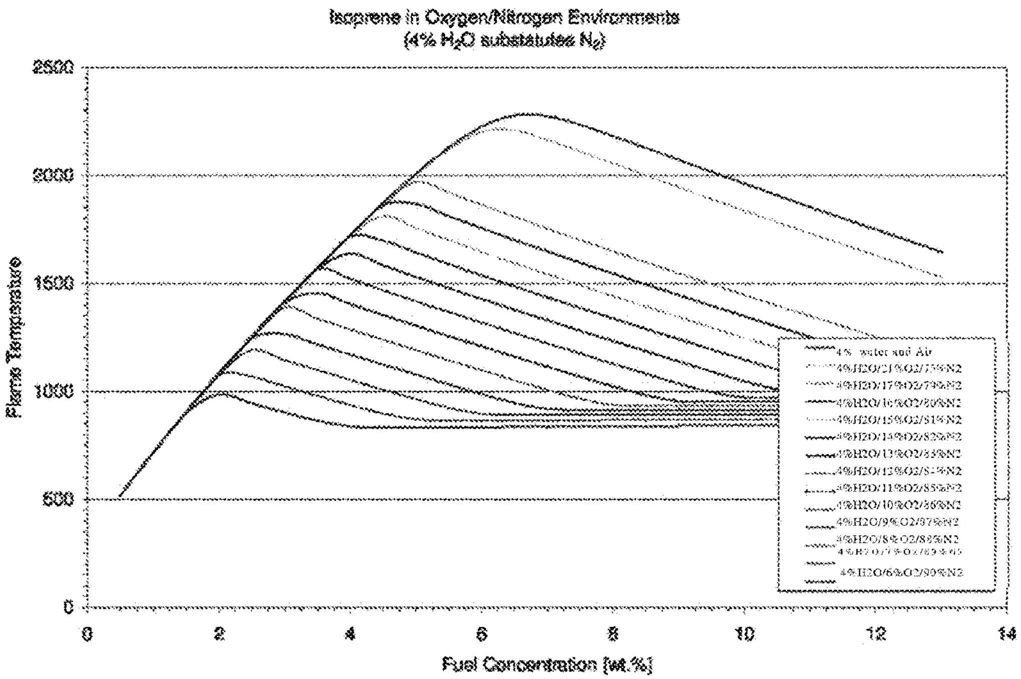

FIG. 69 is a graph of the calculated adiabatic flame temperatures for Series B as a function of fuel concentration for various oxygen levels with 4% water. The figure legend lists the curves in the order in which they appear in the graph.

Figure 70:
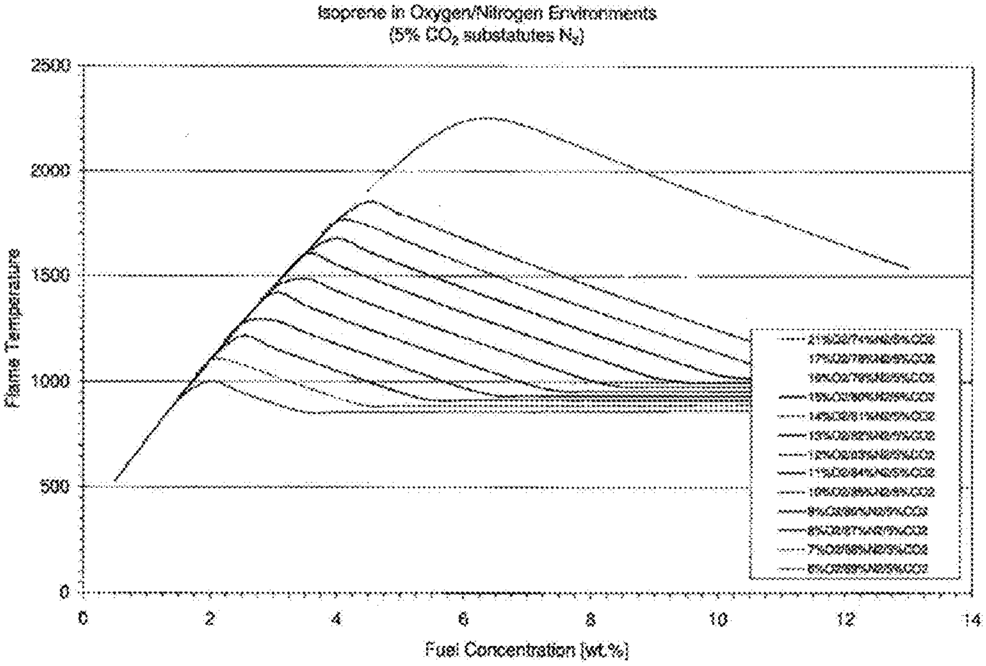

FIG. 70 is a graph of the calculated adiabatic flame temperatures for Series C as a function of fuel concentration for various oxygen levels with 5% $CO_2$. The figure legend lists the curves in the order in which they appear in the graph.

Figure 71:
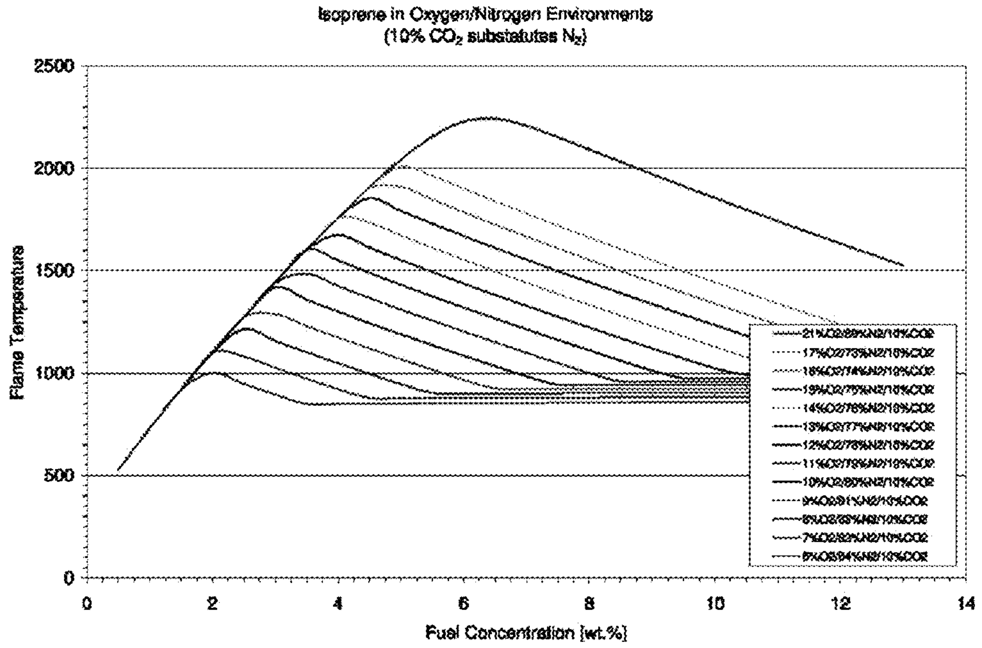

FIG. 71 is a graph of the calculated adiabatic flame temperatures for Series D as a function of fuel concentration for various oxygen levels with 10% $CO_2$. The figure legend lists the curves in the order in which they appear in the graph.

Figure 72:
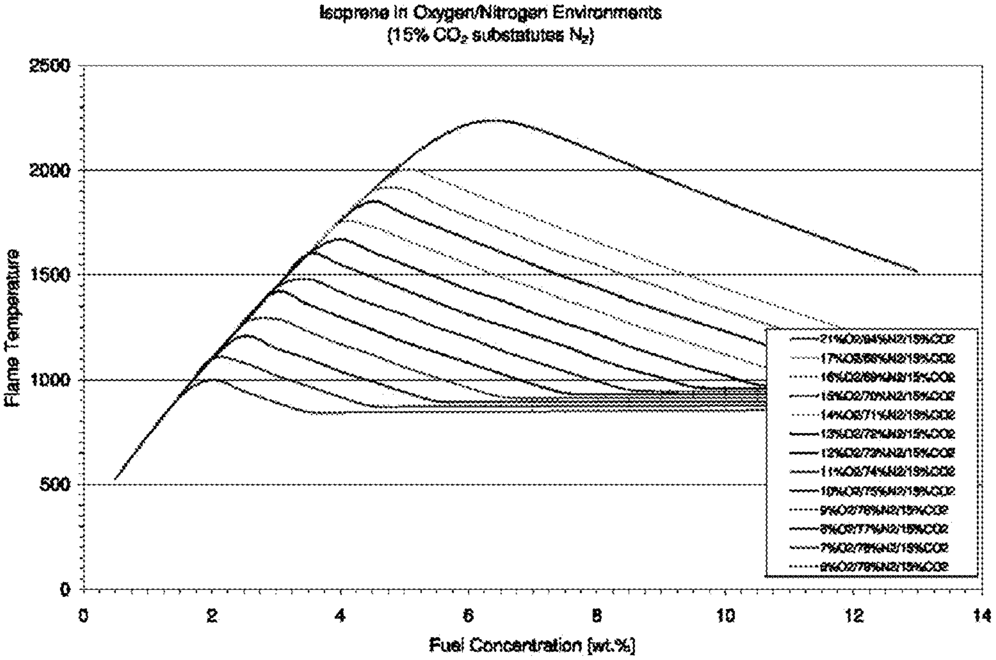

FIG. 72 is a graph of the calculated adiabatic flame temperatures for Series E as a function of fuel concentration for various oxygen levels with 15% $CO_2$. The figure legend lists the curves in the order in which they appear in the graph.

Figure 73:
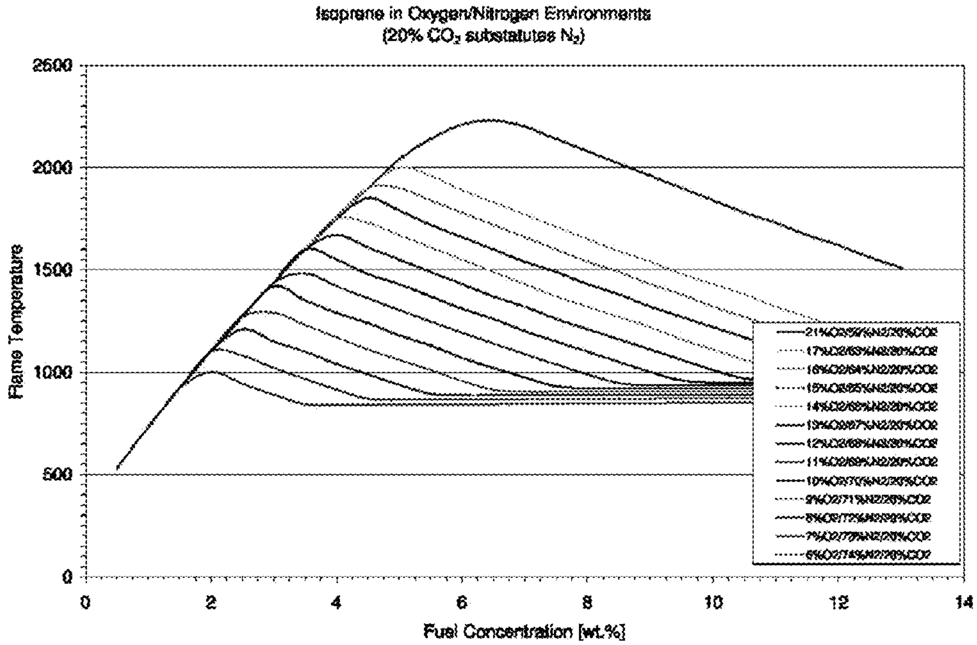

FIG. 73 is a graph of the calculated adiabatic flame temperatures for Series F as a function of fuel concentration for various oxygen levels with 20% $CO_2$. The figure legend lists the curves in the order in which they appear in the graph.

Figure 74:
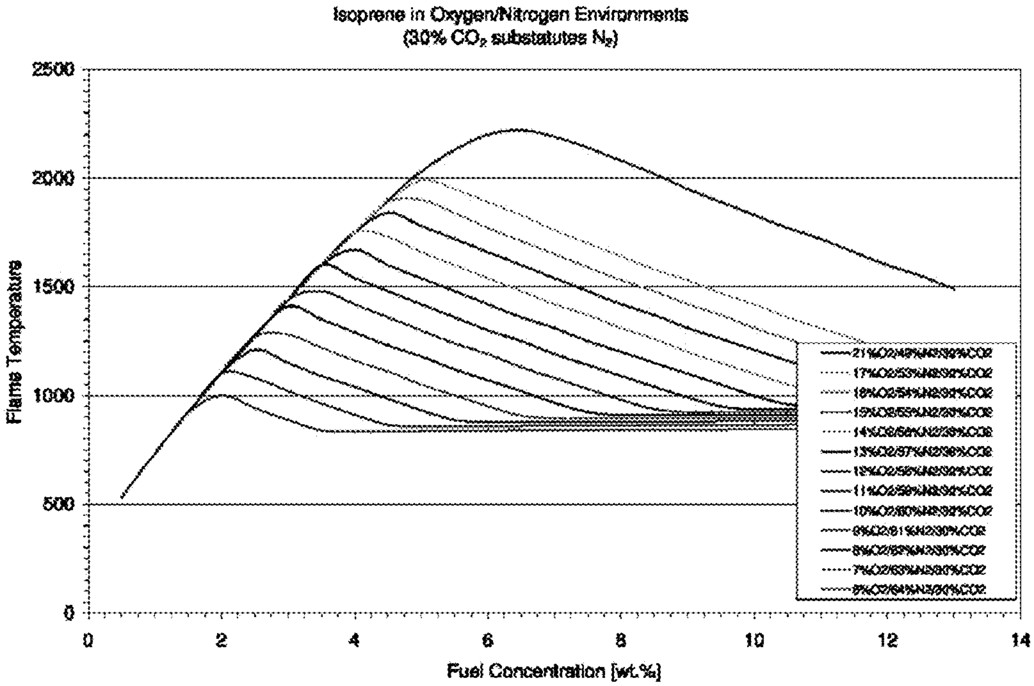

FIG. 74 is a graph of the calculated adiabatic flame temperatures for Series G as a function of fuel concentration for various oxygen levels with 30% $CO_2$. The figure legend lists the curves in the order in which they appear in the graph.

FIG. 75A is a table of the conversion of the CAFT Model results from weight percent to volume percent for series A.

Figure 75B:
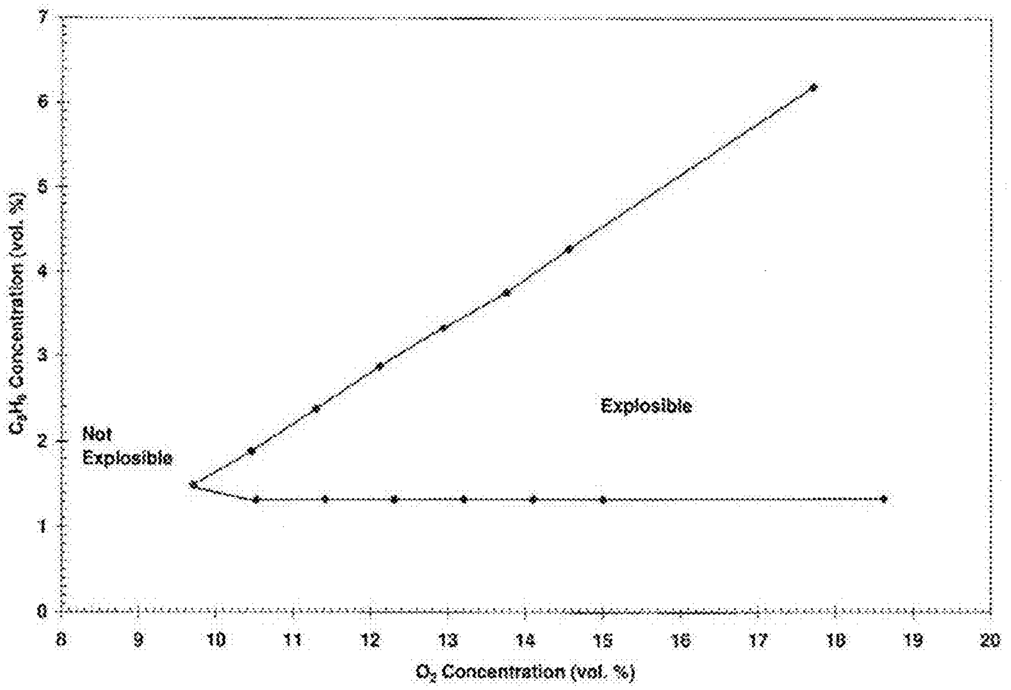

FIG. 75B is a graph of the flammability results from the CAFT model for Series A in FIG. 68 plotted as volume percent.

FIG. 76A is a table of the conversion of the CAFT Model results from weight percent to volume percent for series B.

Figure 76B:
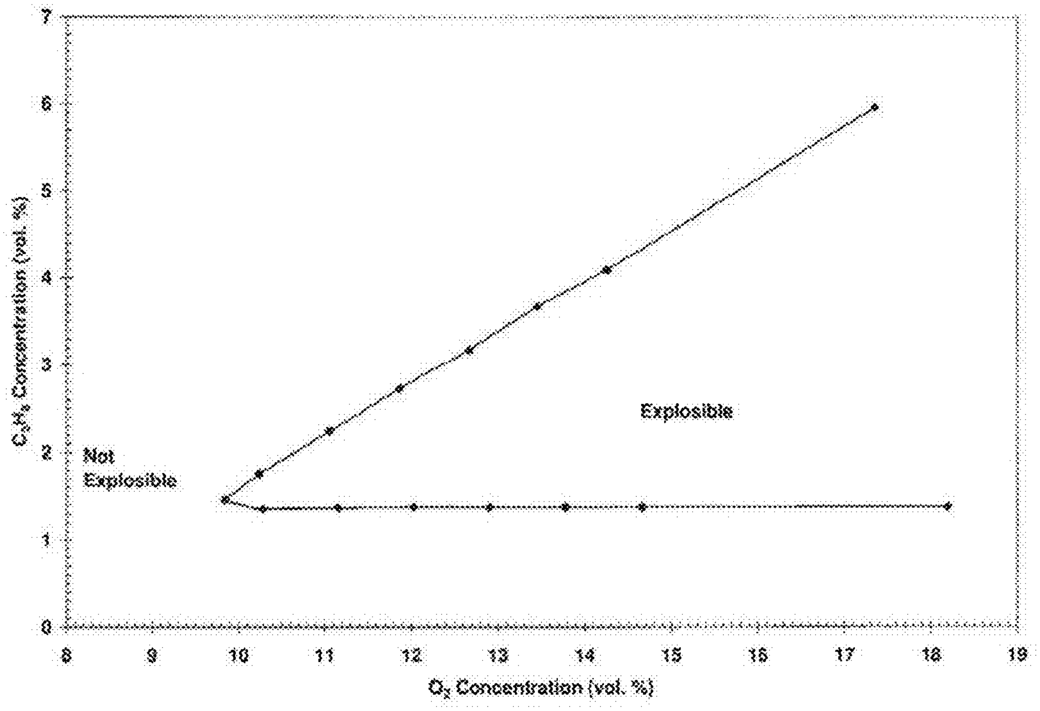

FIG. 76B is a graph of the flammability results from the CAFT model for Series B in FIG. 69 plotted as volume percent.

Figure 77:
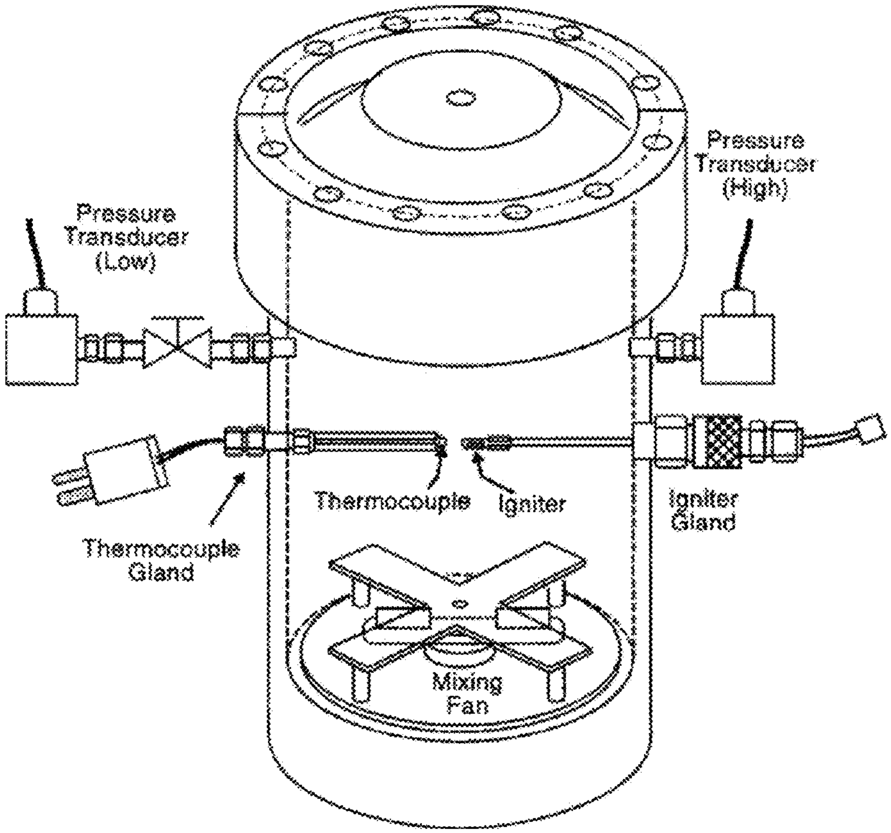

FIG. 77 is a figure of the flammability test vessel.

Figure 78A:
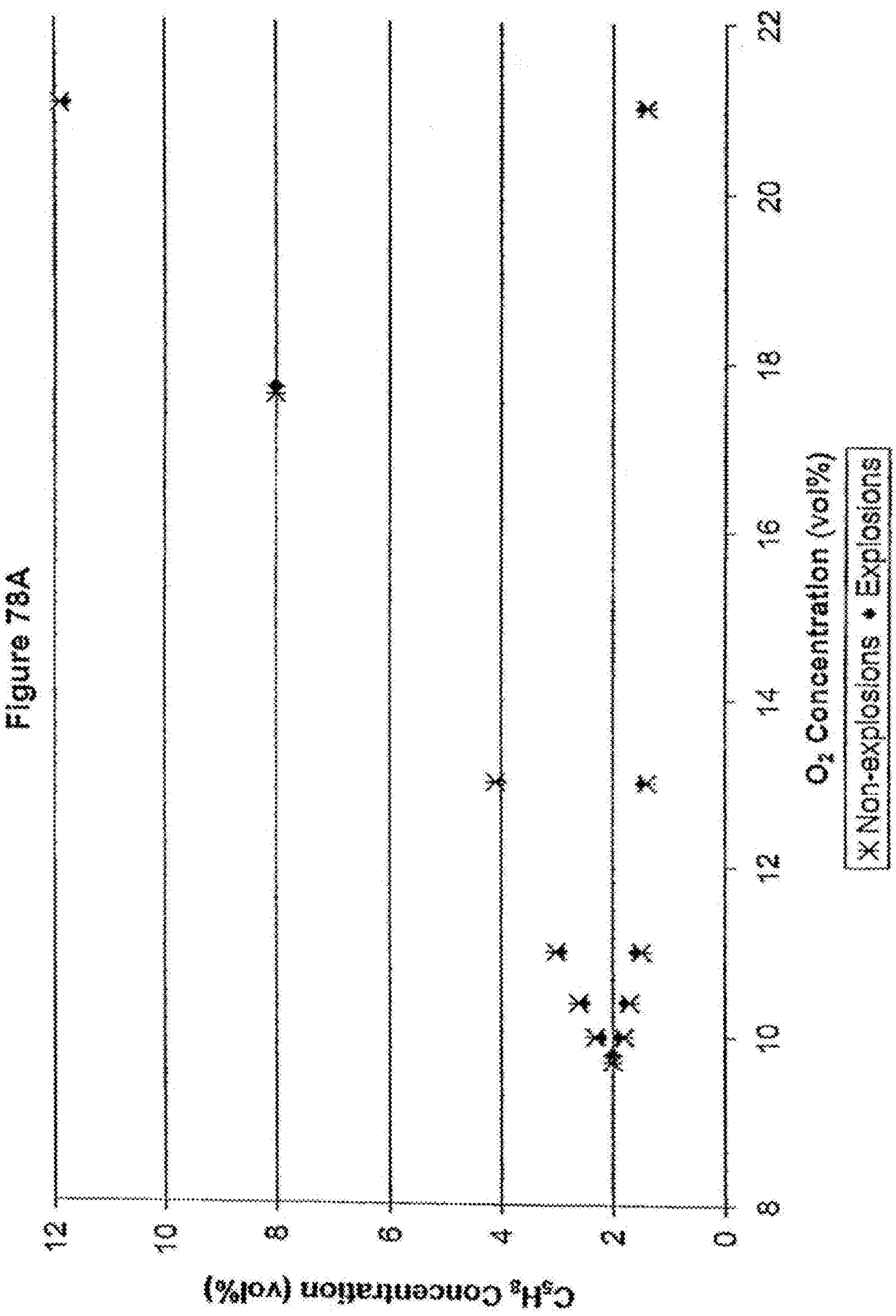

FIG. 78A is a graph of the flammability Curve for Test Series 1: 0% Steam, 0 psig, and 40° C.

FIG. 78B is a table summarizing the explosion and non-explosion data points for Test Series 1.

Figure 78C:
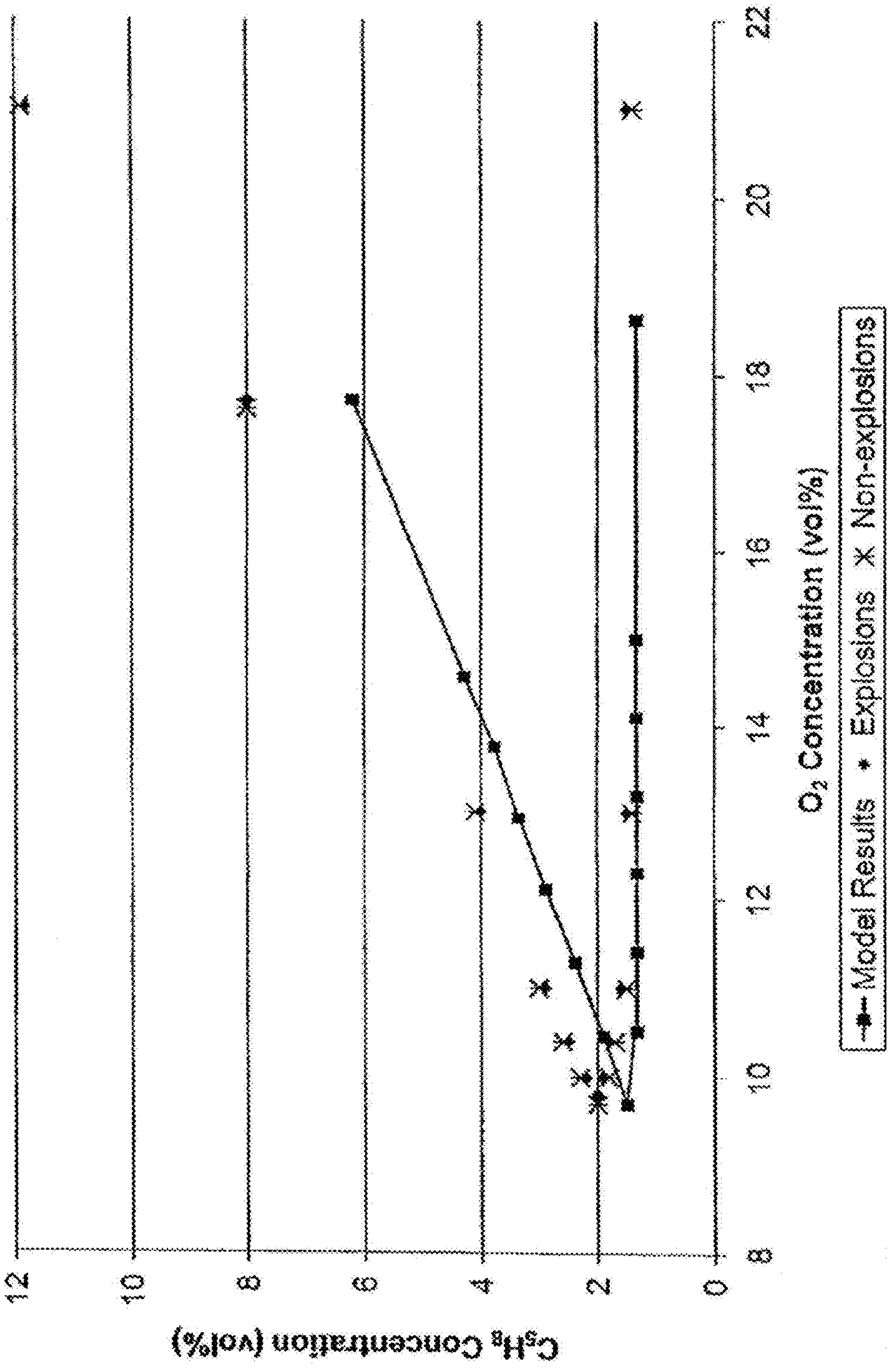

FIG. 78C is a graph of the flammability curve for Test Series 1 compared with the CAFT Model.

Figure 79A:
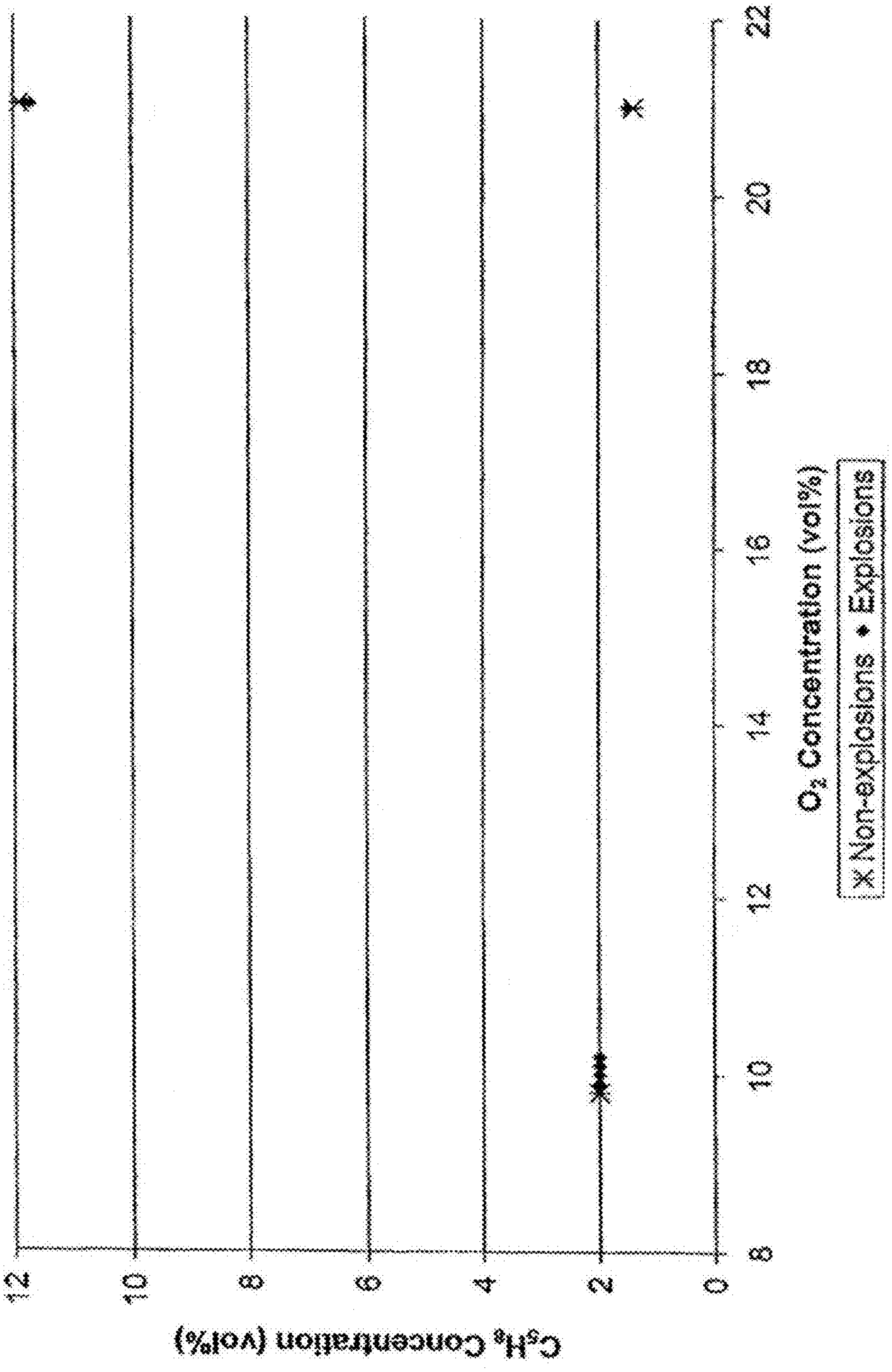

FIG. 79A is a graph of the flammability curve for Test Series 2: 4% Steam, 0 psig, and 40° C.

FIG. 79B is a table summarizing the explosion and non-explosion data points for Test Series 2.

Figure 79C:
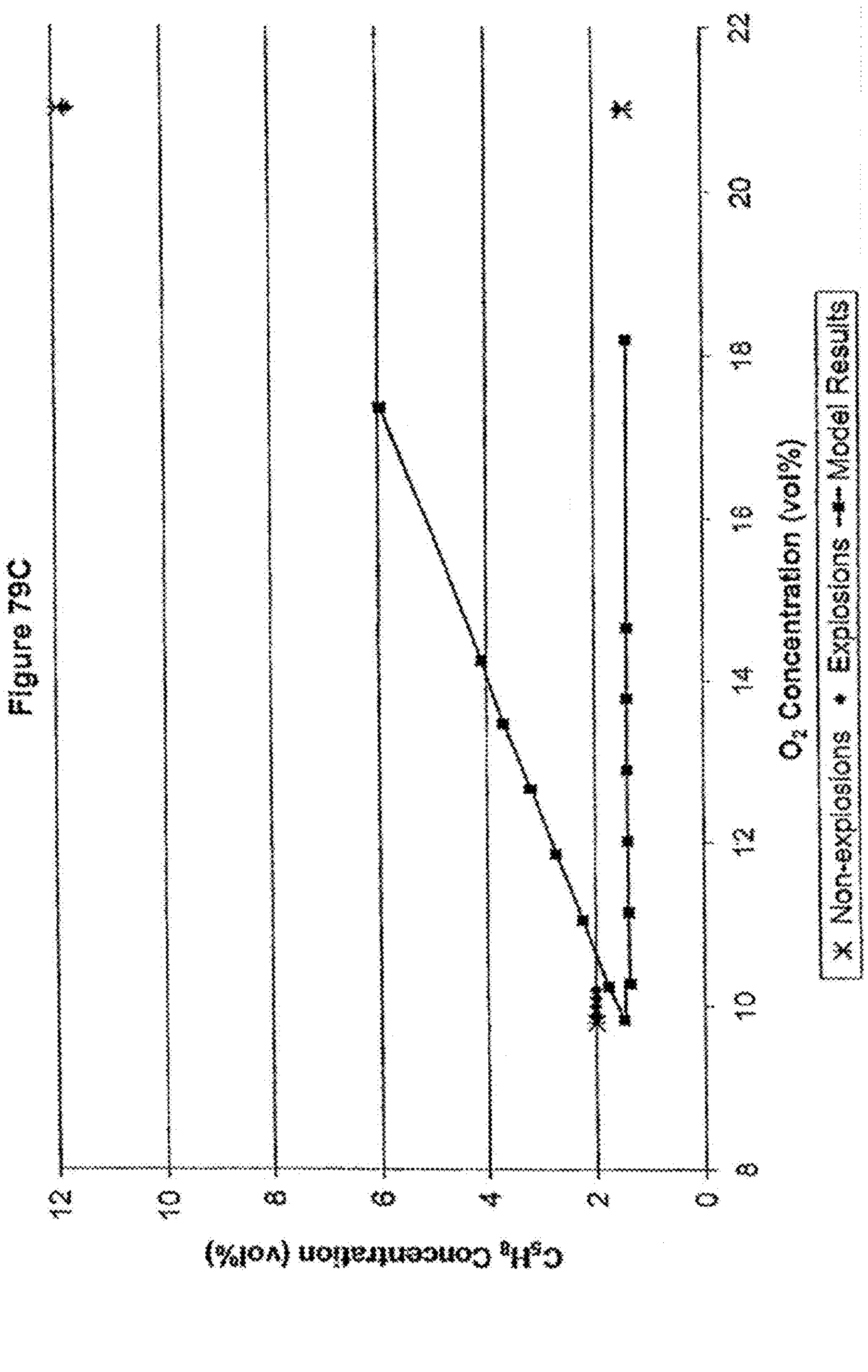

FIG. 79C is a graph of the flammability curve for Test Series 2 compared with the CAFT Model.

FIGS. 80A and 80B are a table of the detailed experimental conditions and results for Test Series 1.

FIG. 81 is a table of the detailed experimental conditions and results for Test Series 2.

Figure 82:
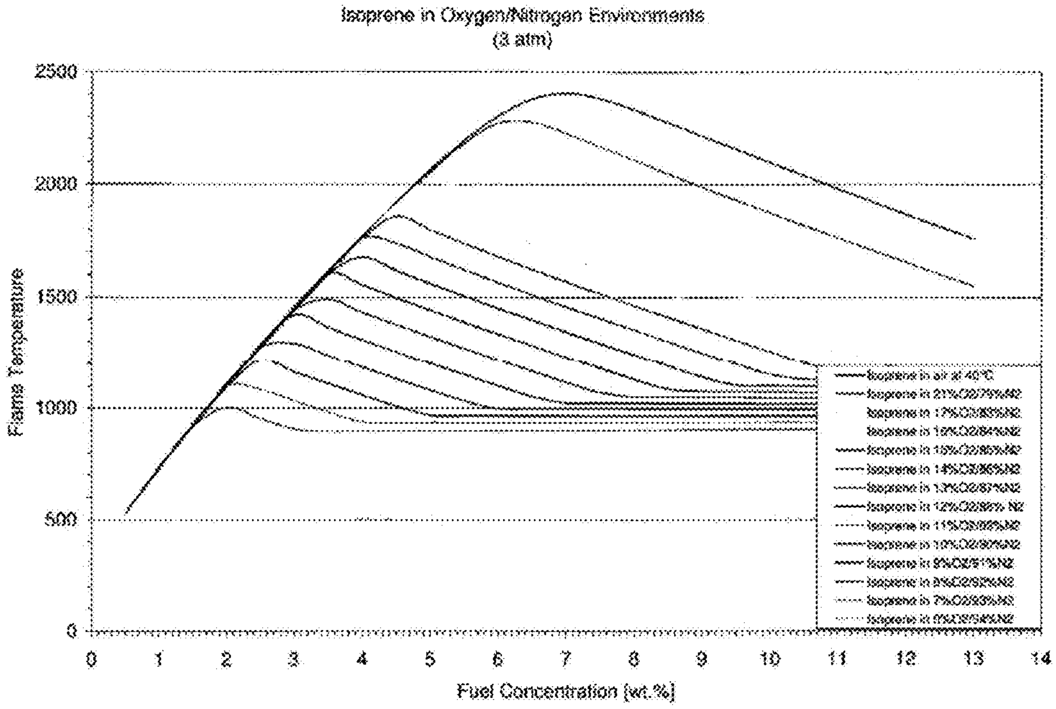

FIG. 82 is a graph of the calculated adiabatic flame temperature plotted as a function of fuel concentration for various nitrogen/oxygen ratios at 3 atmospheres of pressure.

Figure 83:
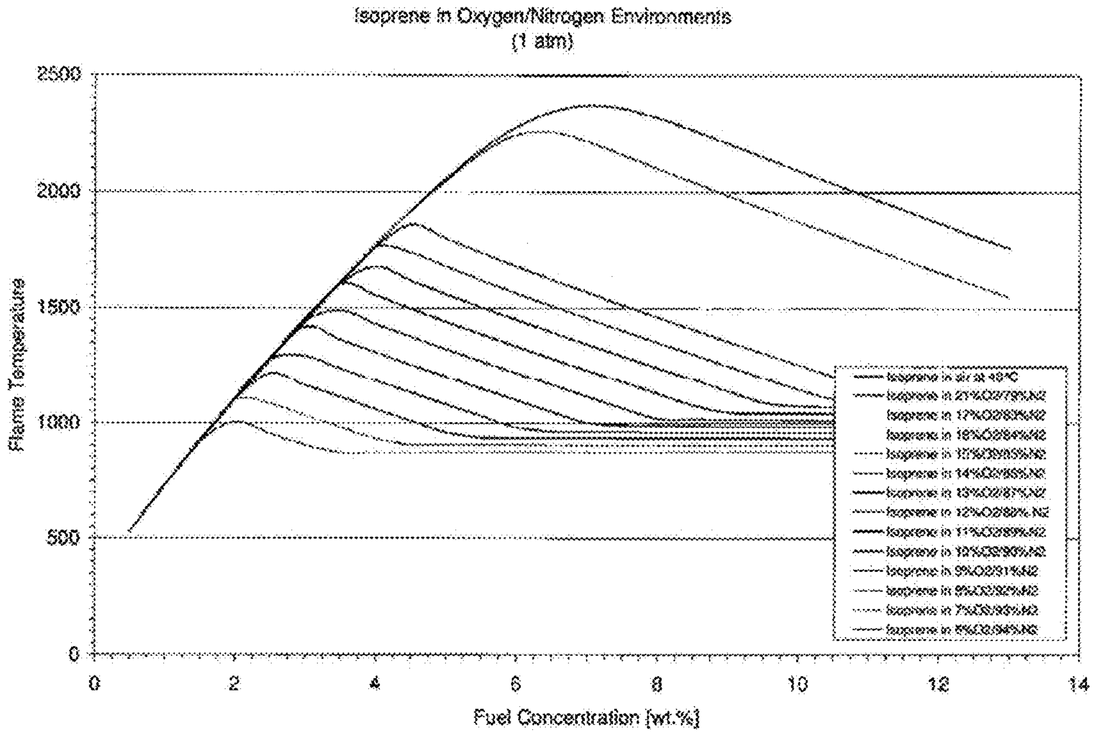

FIG. 83 is a graph of the calculated adiabatic flame temperature plotted as a function of fuel concentration for various nitrogen/oxygen ratios at 1 atmosphere of pressure.

Figure 84:
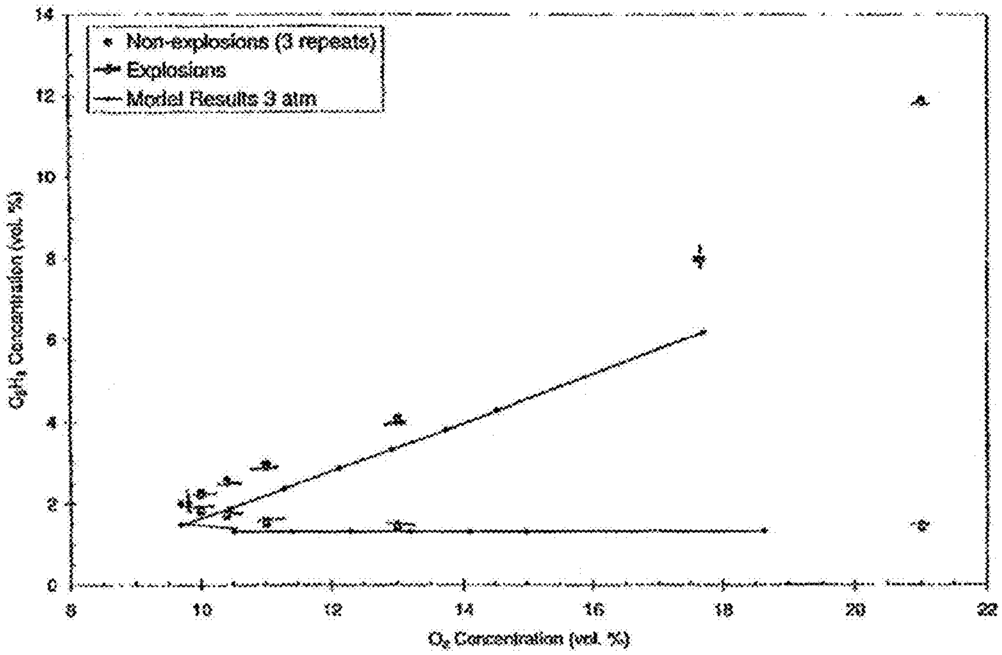

FIG. 84 is a graph of the flammability envelope constructed using data from FIG. 82 and following the methodology described in Example 13. The experimental data points (circles) are from tests described herein that were conducted at 1 atmosphere initial system pressure.

Figure 85:
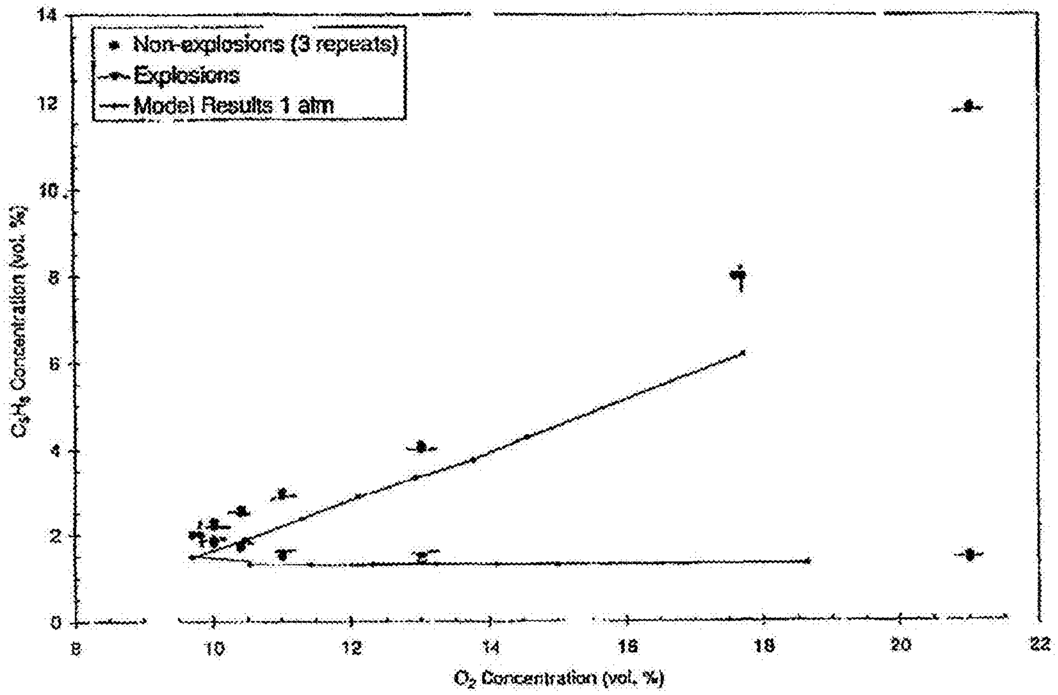

FIG. 85 is a graph of the flammability envelope constructed using data from FIG. 83 and following the methodology described in Example 13. The experimental data points (circles) are from tests described herein that were conducted at 1 atmosphere initial system pressure.

Figure 86A:
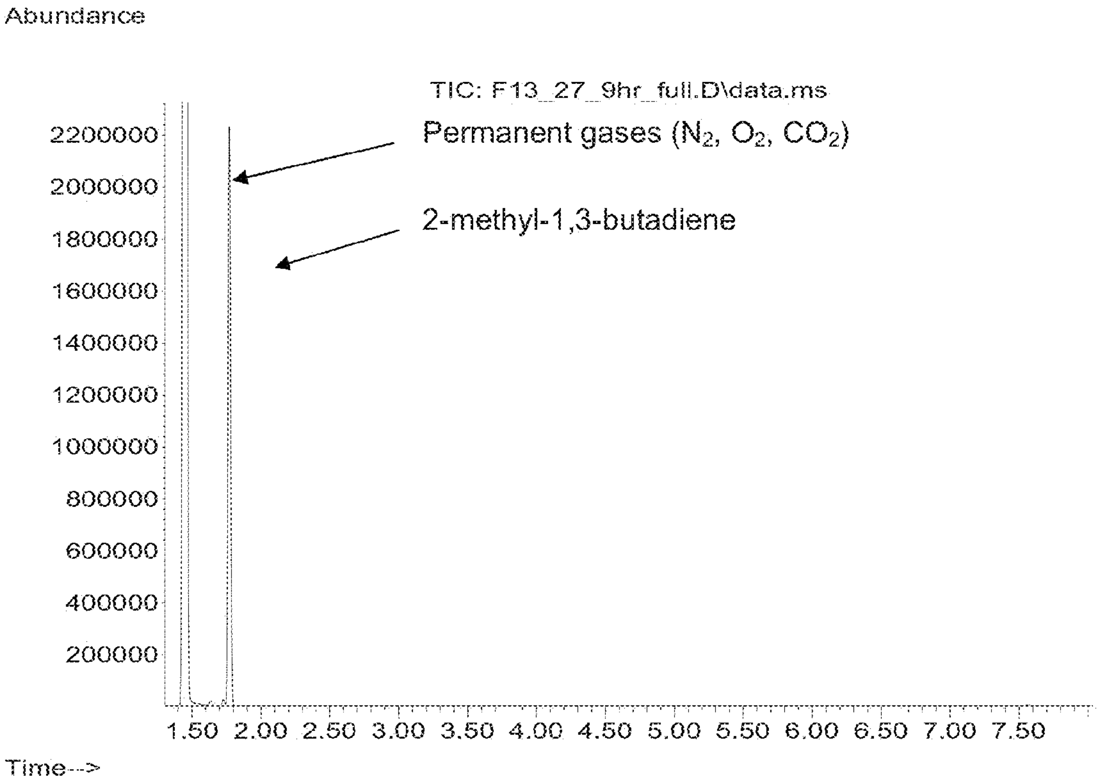

FIG. 86A is a GC/MS chromatogram of fermentation off-gas.

Figure 86B:
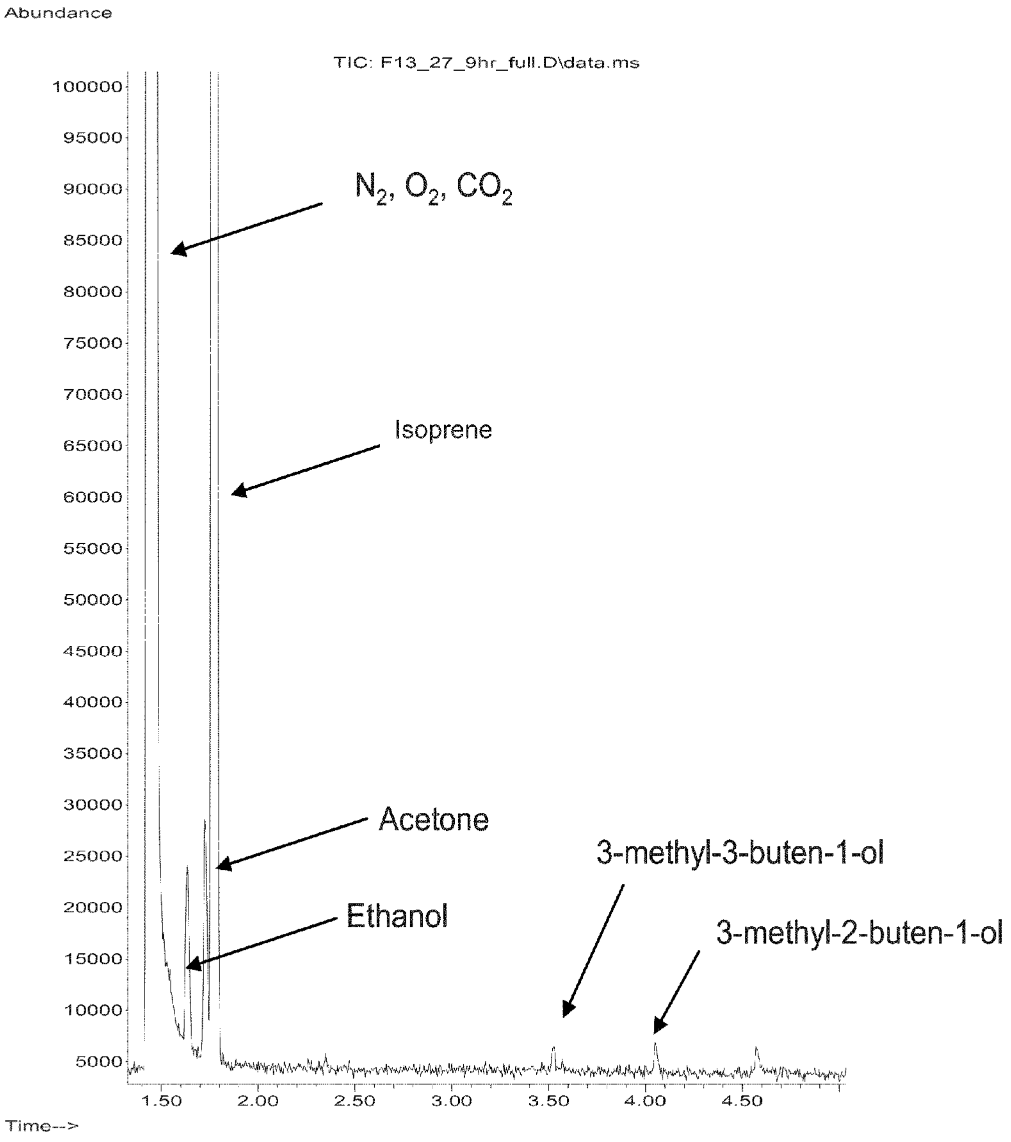

FIG. 86B is an expansion of FIG. 86A to show minor volatiles present in fermentation off-gas.

Figure 87A:
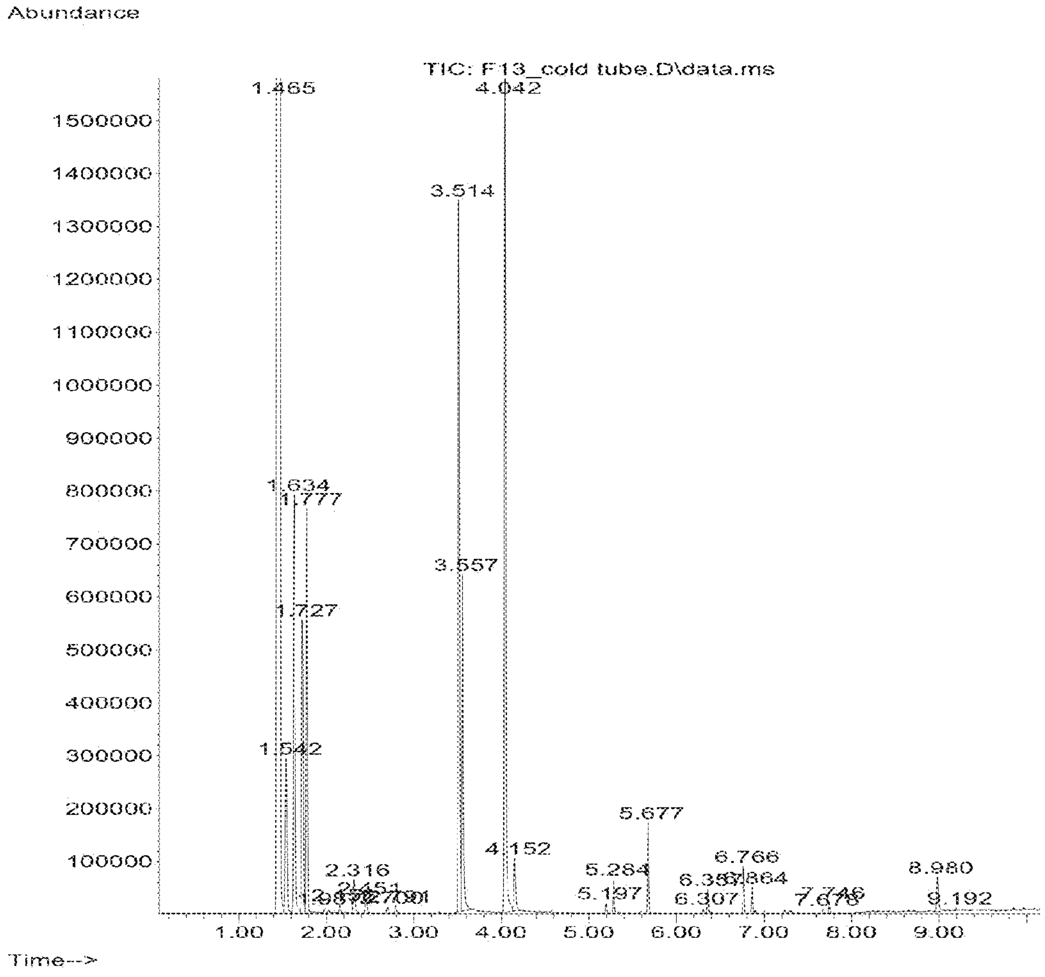

FIG. 87A is a GC/MS chromatogram of trace volatiles present in off-gas following cryo-trapping at −78° C.

Figure 87B:
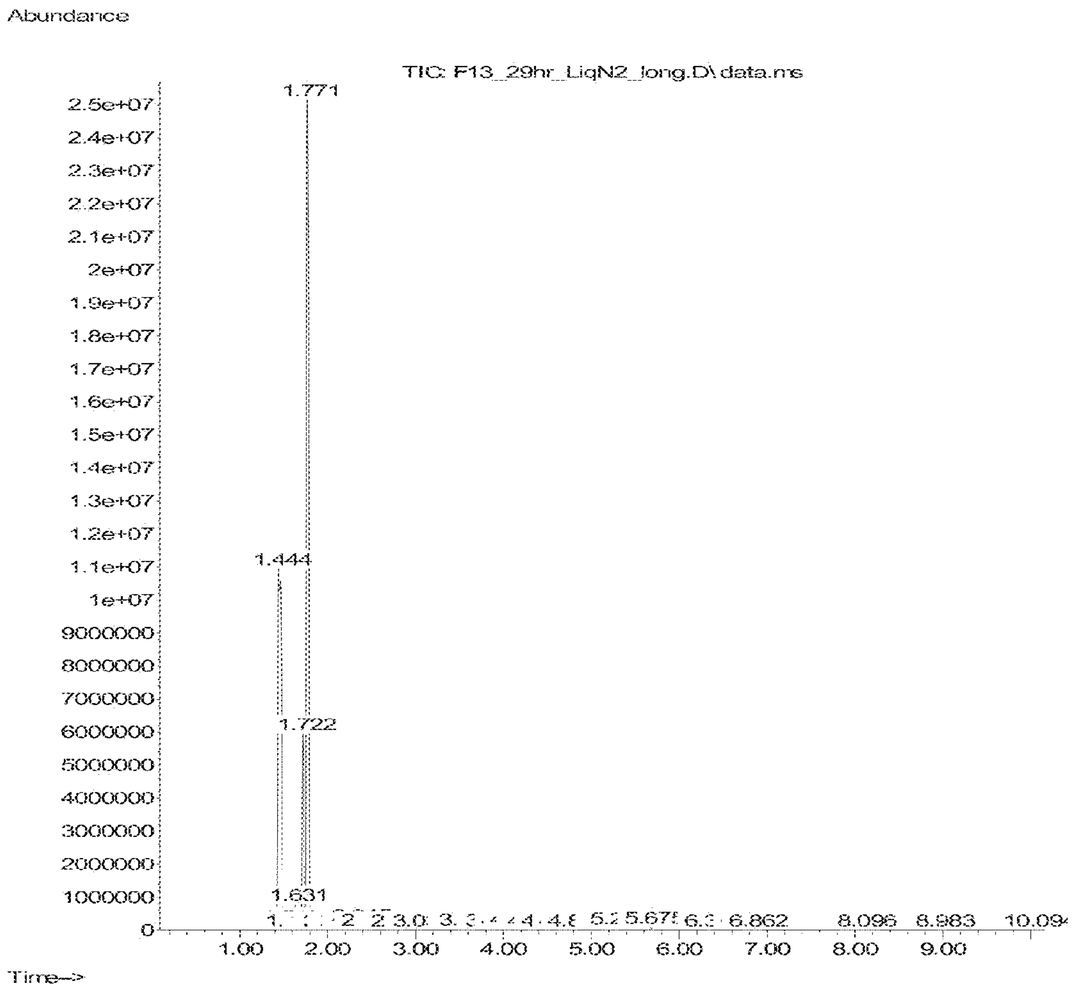

FIG. 87B is a GC/MS chromatogram of trace volatiles present in off-gas following cryo-trapping at −196° C.

Figure 87C:
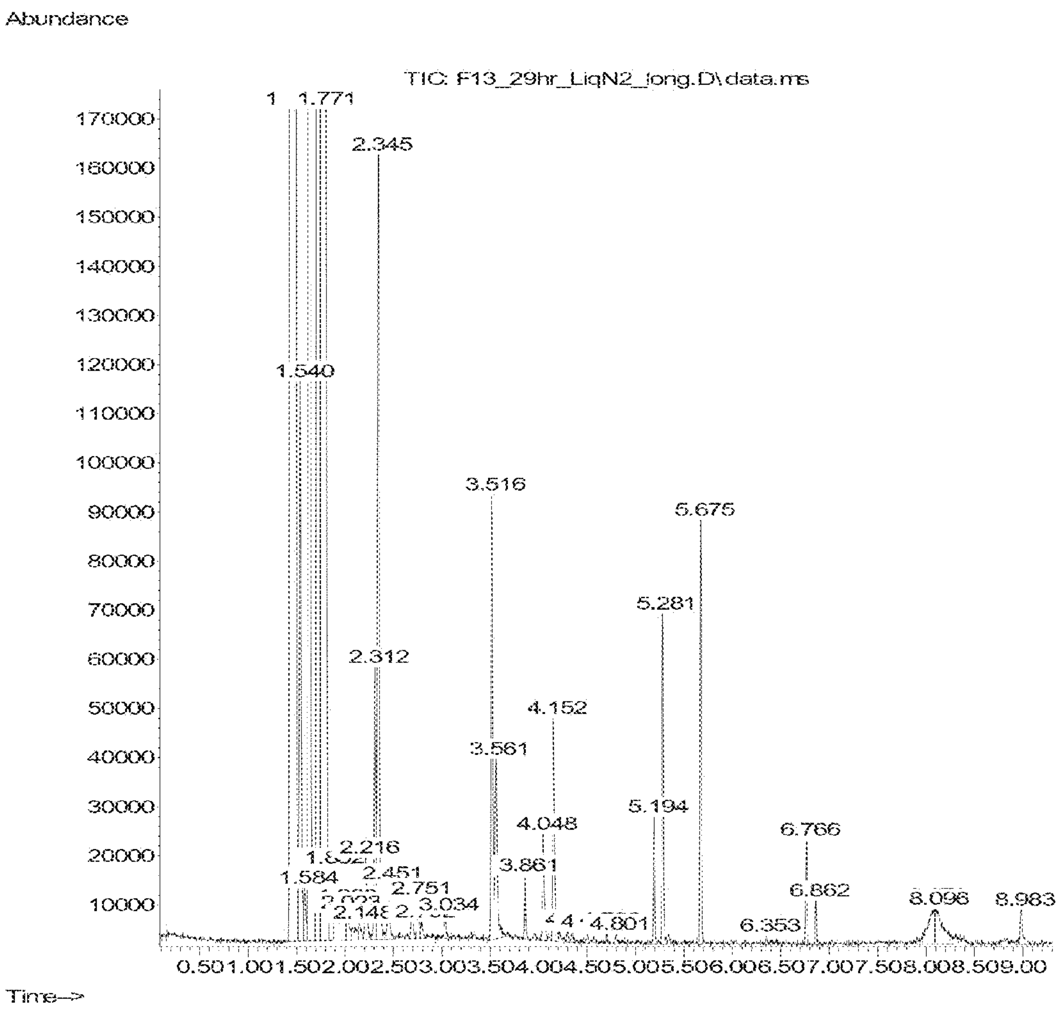

FIG. 87C is an expansion of FIG. 87B.

Figure 87D:
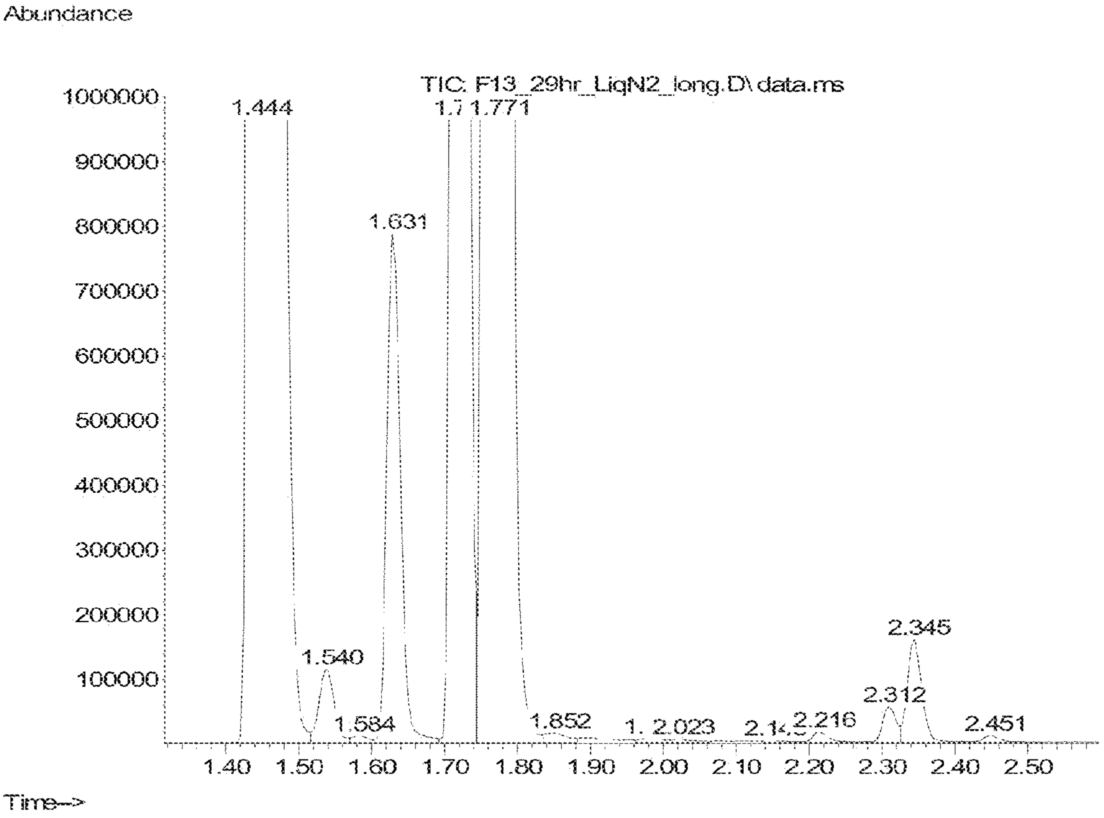

FIG. 87D is an expansion of FIG. 87C.

Figure 88A:
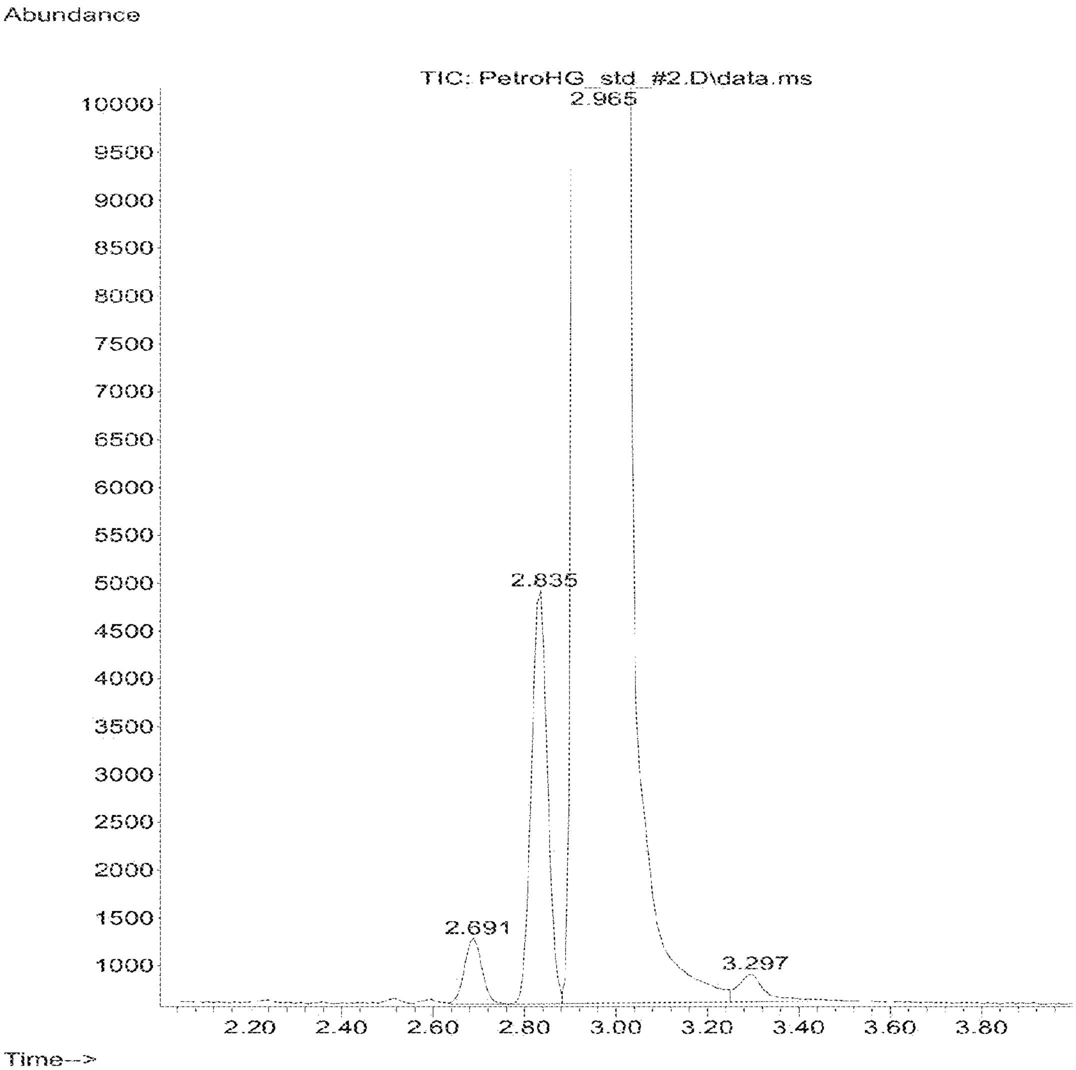
Figure 88B:
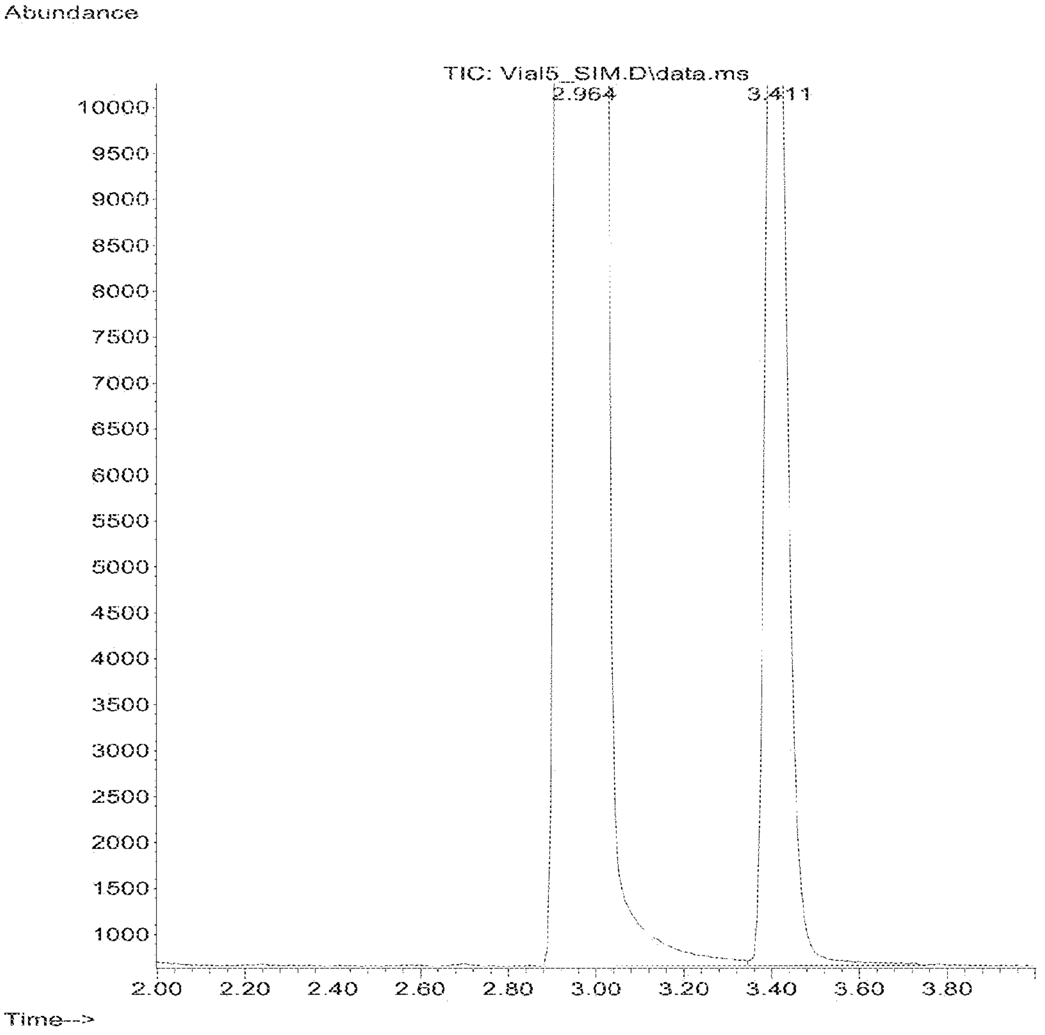

FIGS. 88A and 88B are GC/MS chromatogram comparing C5 hydrocarbons from petroleum-derived isoprene (FIG. 88A) and biologically produced isoprene (FIG. 88B). The standard contains three C5 hydrocarbon impurities eluting around the main isoprene peak (FIG. 88A). In contrast, biologically produced isoprene contains amounts of ethanol and acetone (run time of 3.41 minutes) (FIG. 88A).

Figure 89:
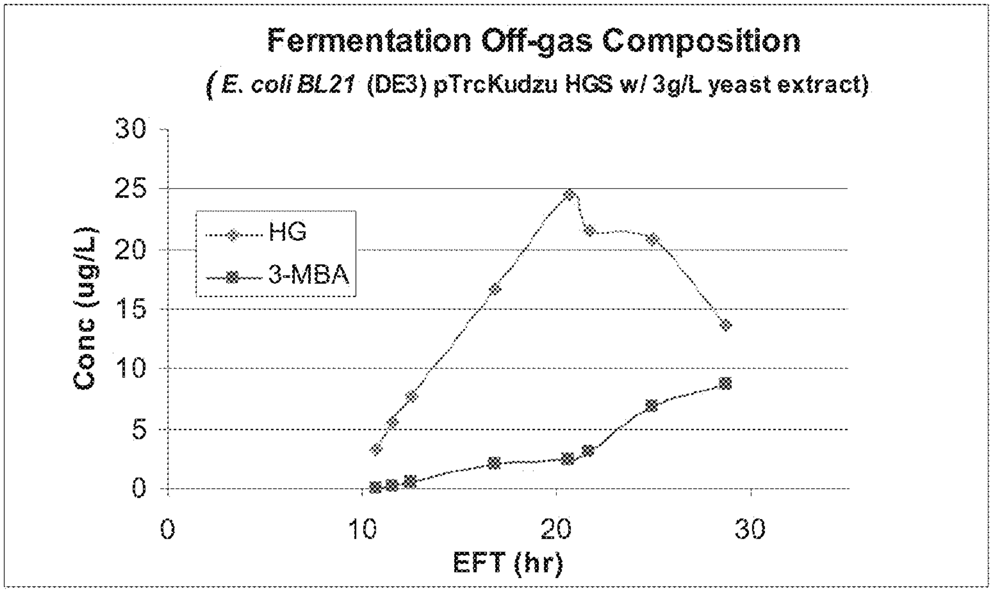

FIG. 89 is a graph of the analysis of fermentation off-gas of an *E. coli* BL21 (DE3) pTrcIS strain expressing a Kudzu isoprene synthase and fed glucose with 3 g/L yeast extract.

FIG. 90 shows the structures of several impurities that are structurally similar to isoprene and may also act as polymerization catalyst poisons.

Figure 91:
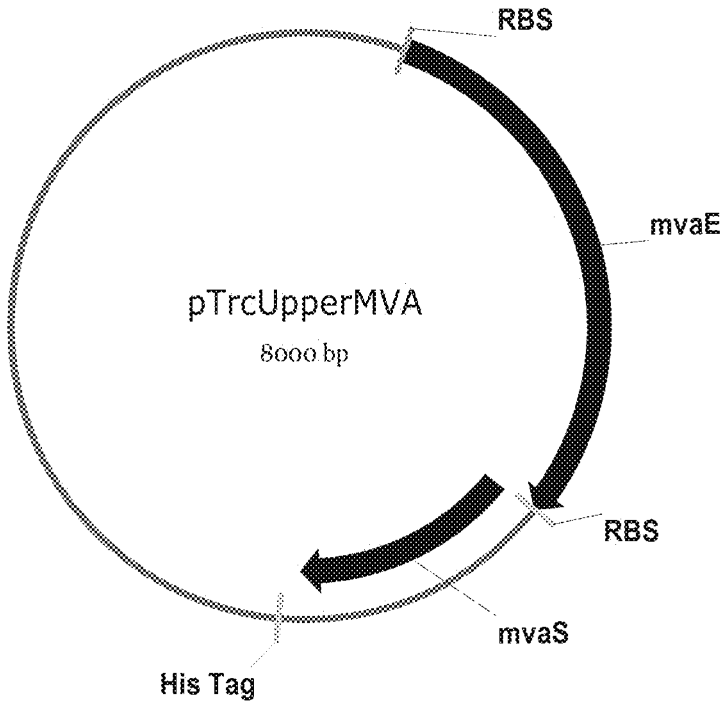

FIG. 91 is a map of pTrcHis2AUpperPathway (also called pTrcUpperMVA).

FIGS. 92A-92C are the nucleotide sequence of pTrcHis2AUpperPathway (also called pTrcUpperMVA) (SEQ ID NO:86).

Figure 93:
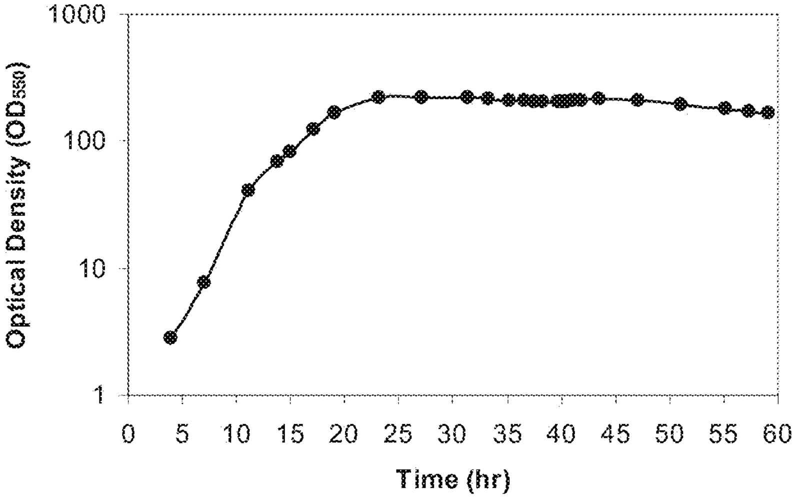

FIG. 93 is a time course of optical density within the 15-L bioreactor fed with glucose.

Figure 94:
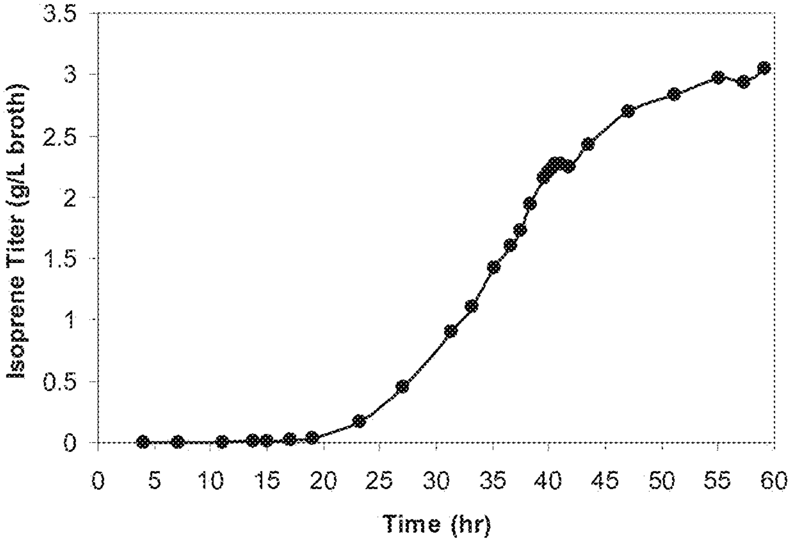

FIG. 94 is a time course of isoprene titer within the 15-L bioreactor fed with glucose. The titer is defined as the amount of isoprene produced per liter of fermentation broth.

Figure 95:
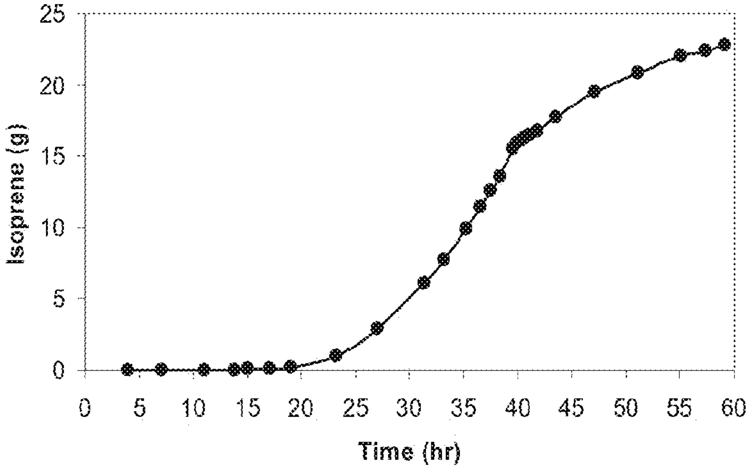

FIG. 95 is a time course of total isoprene produced from the 15-L bioreactor fed with glucose.

Figure 96:
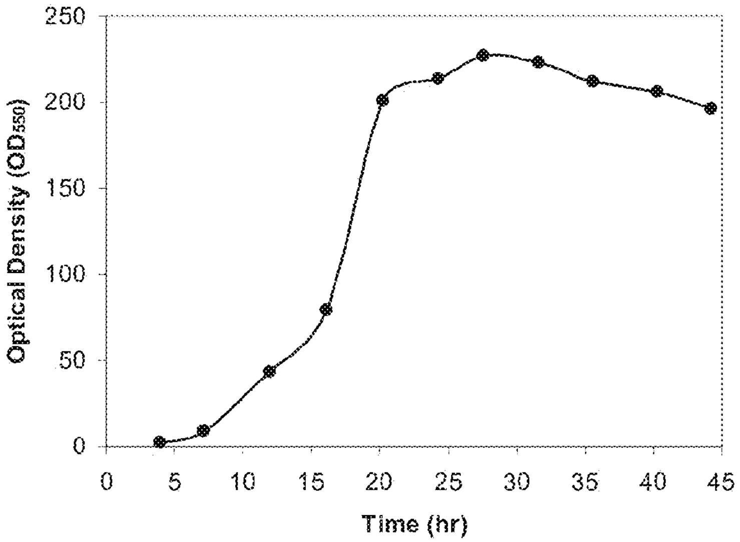

FIG. 96 is a time course of optical density within the 15-L bioreactor fed with invert sugar.

Figure 97:
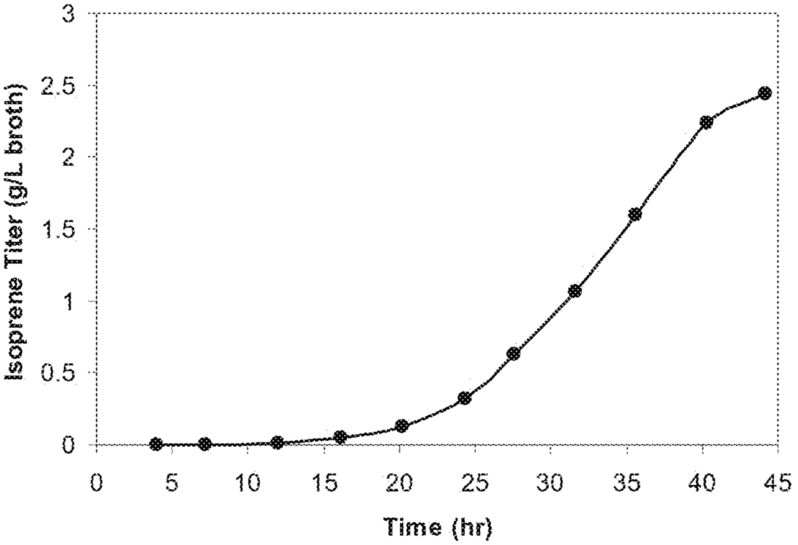

FIG. 97 is a time course of isoprene titer within the 15-L bioreactor fed with invert sugar. The titer is defined as the amount of isoprene produced per liter of fermentation broth.

Figure 98:
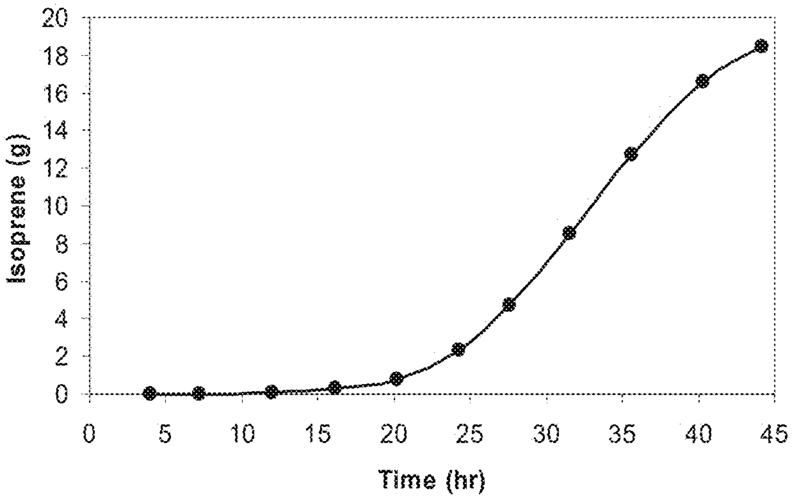

FIG. 98 is a time course of total isoprene produced from the 15-L bioreactor fed with invert sugar.

Figure 99:
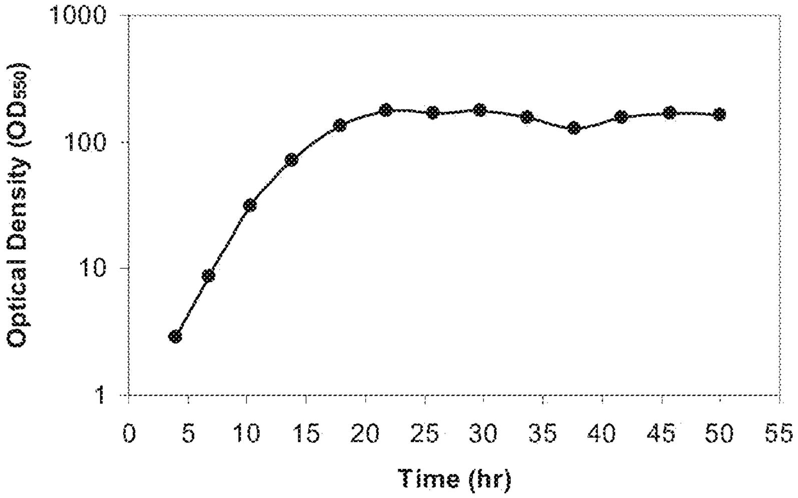

FIG. 99 is a time course of optical density within the 15-L bioreactor fed with glucose.

Figure 100:
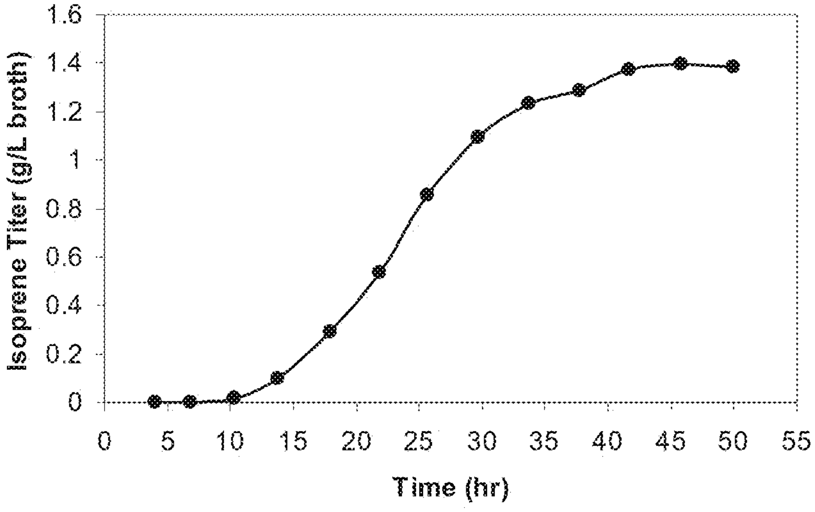

FIG. 100 is a time course of isoprene titer within the 15-L bioreactor fed with glucose. The titer is defined as the amount of isoprene produced per liter of fermentation broth.

Figure 101:
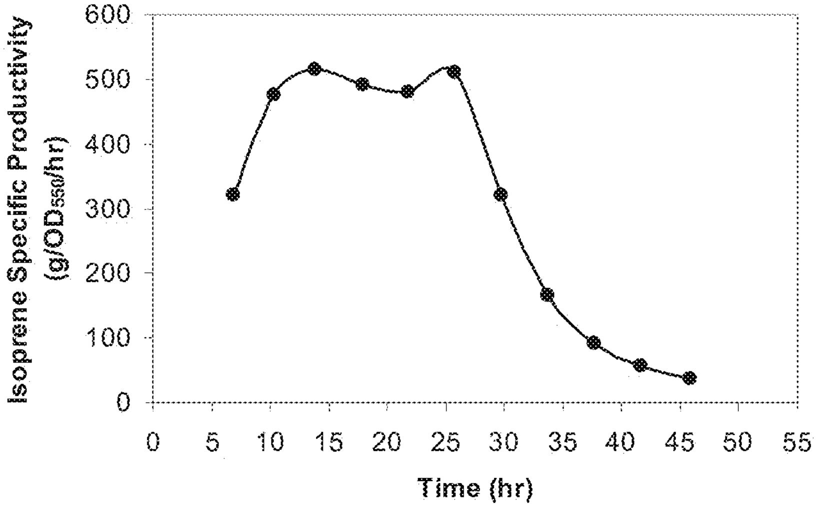

FIG. 101 is a time course of isoprene specific activity from the 15-L bioreactor fed with glucose.

Figure 102:
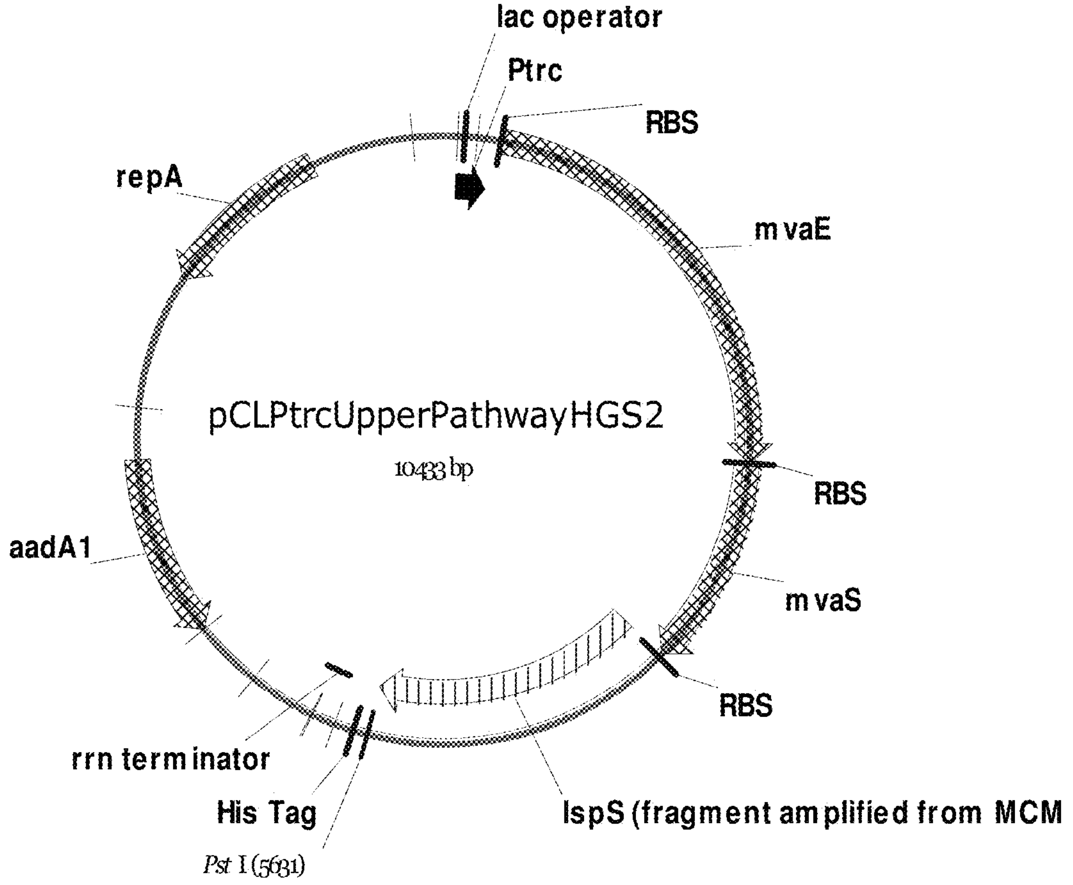

FIG. 102 is a map of pCLPtrcUpperPathwayHGS2.

FIGS. 103A-103C are the nucleotide sequence of pCLPtrcUpperPathwayHGS2 (SEQ ID NO:87).

Figure 104:
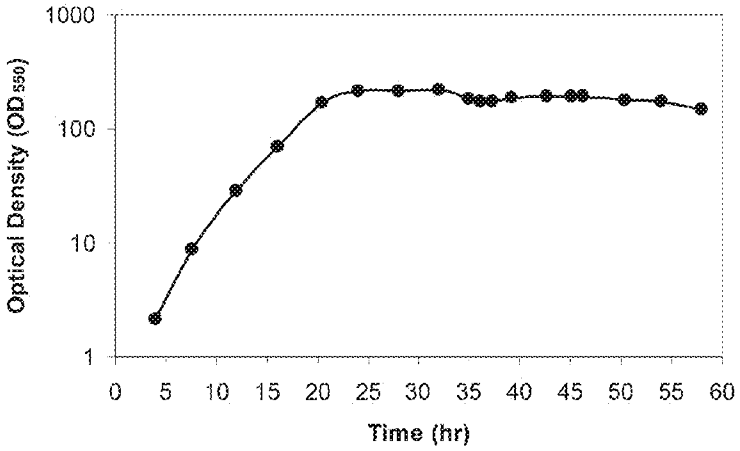

FIG. 104 is a time course of optical density within the 15-L bioreactor fed with glucose.

Figure 105:
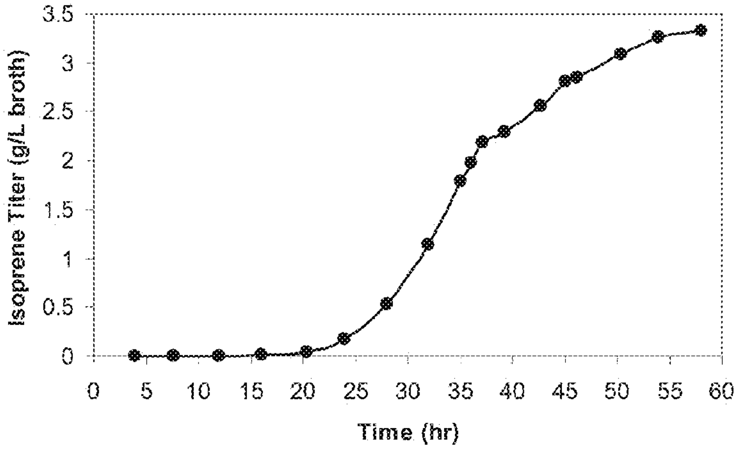

FIG. 105 is a time course of isoprene titer within the 15-L bioreactor fed with glucose. The titer is defined as the amount of isoprene produced per liter of fermentation broth.

Figure 106:
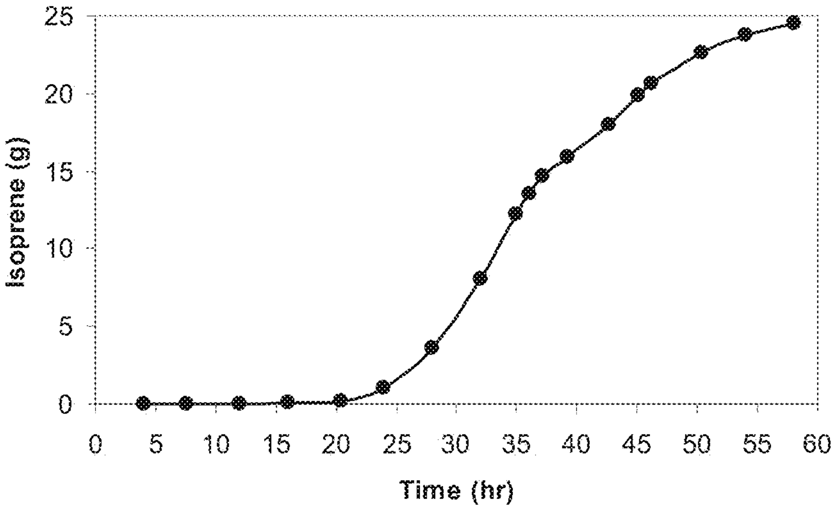

FIG. 106 is a time course of total isoprene produced from the 15-L bioreactor fed with glucose.

Figure 107:
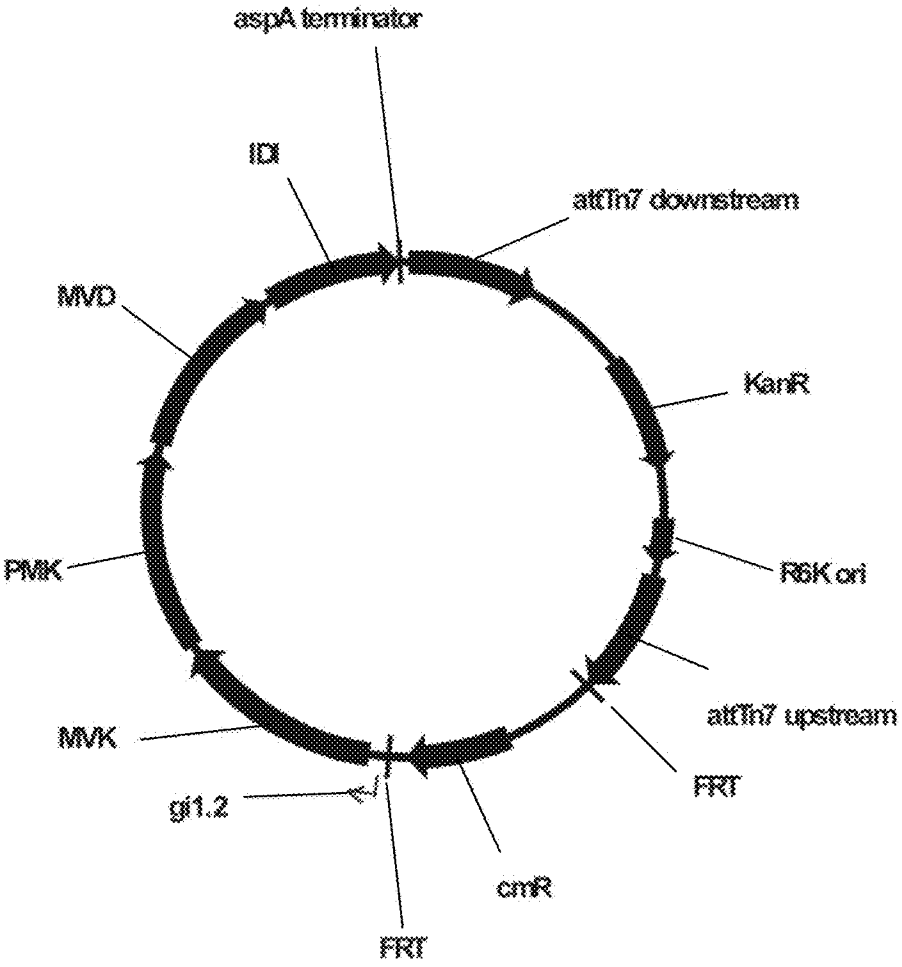

FIG. 107 is a map of plasmid MCM330.

FIGS. 108A-108C are the nucleotide sequence of plasmid MCM330 (SEQ ID NO:90).

Figure 109:
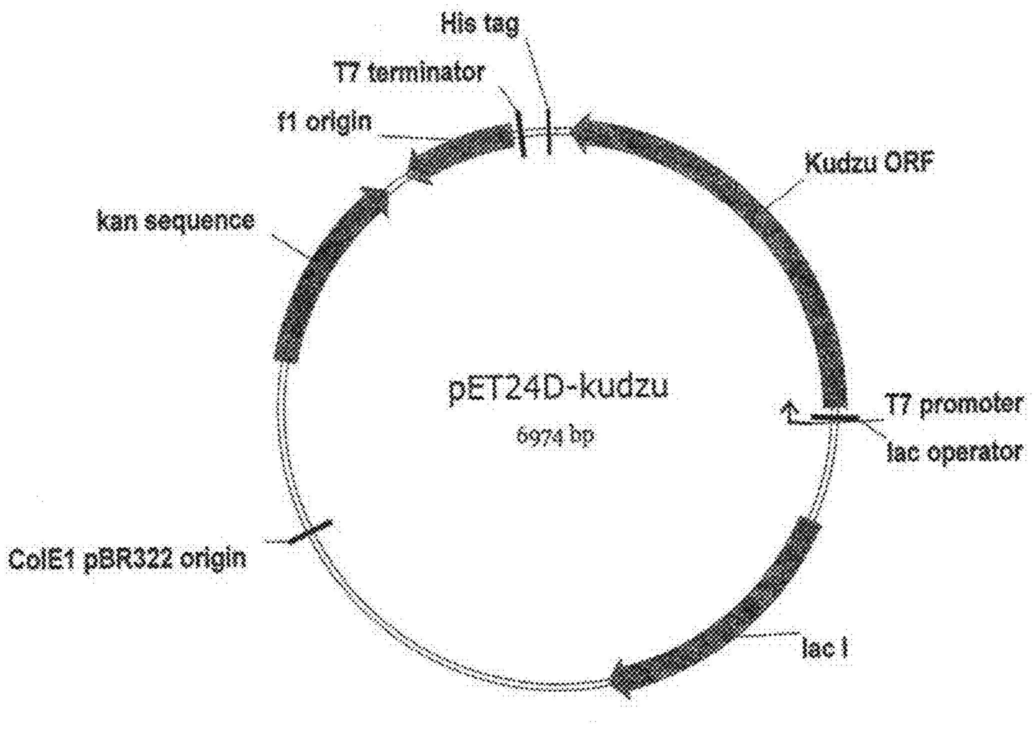

FIG. 109 is a map of pET24D-Kudzu.

FIGS. 110A and 110B are the nucleotide sequence of pET24D-Kudzu (SEQ ID NO:101).

Figure 111A:
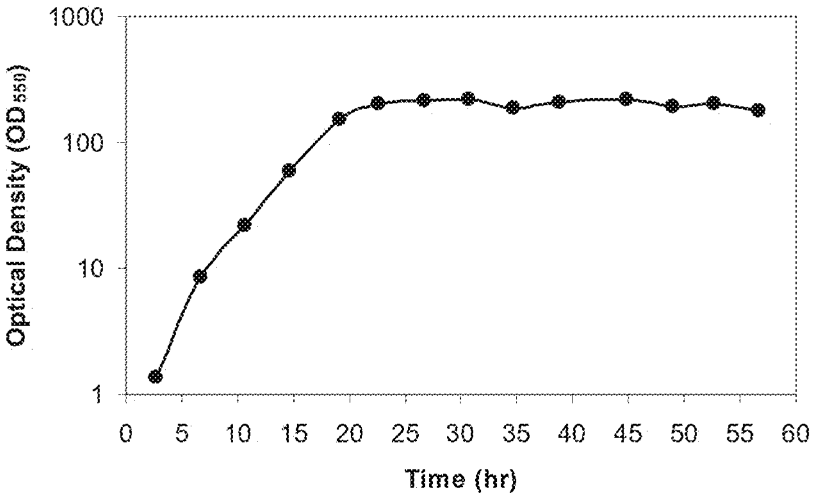

FIG. 111A is a time course of optical density within the 15-L bioreactor fed with glucose.

Figure 111B:
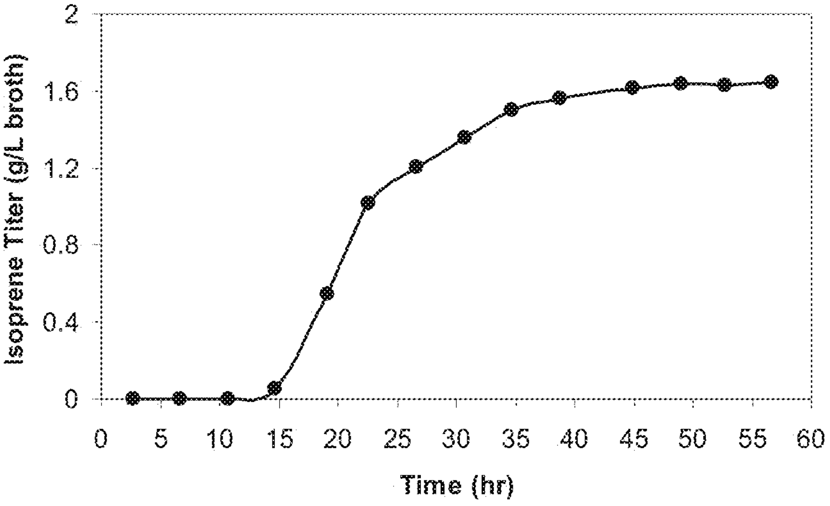

FIG. 111B is a time course of isoprene titer within the 15-L bioreactor fed with glucose. The titer is defined as the amount of isoprene produced per liter of fermentation broth.

Figure 111C:
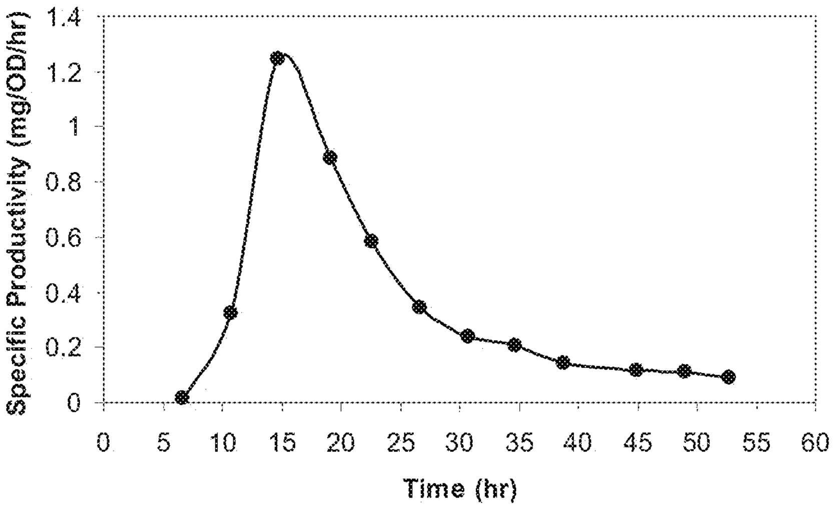

FIG. 111C is a time course of specific productivity of isoprene in the 15-L bioreactor fed with glucose.

DETAILED DESCRIPTION OF THE INVENTION

In one aspect, the invention features compositions and methods for the production of isoprene in increased amounts and/or purity. As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules.

The vast majority of isoprene is derived from petrochemical sources as an impure C5 hydrocarbon fraction which requires extensive purification before the material is suitable for polymerization. Several impurities are particularly problematic given their structural similarity to isoprene and the fact that they can act as polymerization catalyst poisons. Such compounds include 1,3-cyclopentadiene, cis- and trans-1,3-pentadiene, 1-pentyne, 2-pentyne, 3-methyl-1-butyne, trans-piperylene, cis-piperylene, pent-4-ene-1-yne, trans-pent-3-ene-1-yne, and cis-pent-3-ene-1-yne (FIG. 90). In some embodiments, the isoprene composition of the invention is substantially free of any contaminating unsaturated C5 hydrocarbons. As described further in Example 10, no detectable amount of unsaturated C5 hydrocarbons other than isoprene (such as 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) was found in isoprene compositions produced using the methods described herein. Some isoprene compositions produced using the methods described herein contain ethanol, acetone, and C5 prenyl alcohols as determined by GC/MS analysis. All of these components are far more readily removed from the isoprene stream than the isomeric C5 hydrocarbon fractions that are present in isoprene compositions derived from petrochemical sources. Accordingly, in some embodiments, the isoprene compositions of the invention require minimal treatment in order to be of polymerization grade.

In one aspect, compositions and methods of the invention increase the rate of isoprene production and increase the total amount of isoprene that is produced. For example, cell culture systems that generate $4.8\times10^4$ nmole/$g_{wcm}$/hr of isoprene have been produced (Table 1). The efficiency of these systems is demonstrated by the conversion of about 2.2% of the carbon that the cells consume from a cell culture medium into isoprene. As shown in the Examples and Table 2, approximately 3 g of isoprene per liter of broth was generated. If desired, even greater amounts of isoprene can be obtained using other conditions, such as those described herein. In some embodiments, a renewable carbon source is used for the production of isoprene. In some embodiments, the production of isoprene is decoupled from the growth of the cells. In some embodiments, the concentrations of isoprene and any oxidants are within the nonflammable ranges to reduce or eliminate the risk that a fire may occur during production or recovery of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) isoprene synthase polypeptide was expressed in a variety of host cells, such as *Escherichia coli, Panteoa citrea, Bacillus subtilis, Yarrowia lipolytica*, and *Trichoderma reesei*. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 300 mg of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention.

| Strain | Isoprene Production in a Headspace vial* Headspace concentration $\mu g/L_{gas}$ | Specific Rate $\mu g/L_{broth}$/hr/OD ($nmol/g_{wcm}$/hr) |
|---|---|---|
| *E. coli* BL21/pTrcKudzu IS | 1.40 | 53.2 (781.2) |
| *E. coli* BL21/pCL DXS yidi Kudzu IS | 7.61 | 289.1 ($4.25 \times 10^3$) |
| *E. coli* BL21/MCM127 with kudzu IS and entire MVA pathway | 23.0 | 874.1 ($12.8 \times 10^3$) |
| *E. coli* BL21/pET N-HisKudzu IS | 1.49 | 56.6 (831.1) |
| *Pantoea citrea*/pTrcKudzu IS | 0.66 | 25.1 (368.6) |
| *E. coli* w/Poplar IS [Miller (2001)] | — | 5.6 (82.2) |
| *Bacillis licheniformis* Fall US 5849970 | — | 4.2 (61.4) |
| *Yarrowia lipolytica* with kudzu isoprene synthase | ~0.05 μg/L | ~2 (~30) |
| *Trichoderma reesei* with kudzu isoprene synthase | ~0.05 μg/L | ~2 (~30) |
| *E. coli* BL21/pTrcKKD$_y$I$_k$IS with kudzu IS and lower MVA pathway | 85.9 | $3.2 \times 10^3$ ($4.8 \times 10^4$) |

*Normalized to 1 mL of 1 $OD_{600}$, cultured for 1 hour in a sealed headspace vial with a liquid to headspace volume ratio of 1:19.

The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

TABLE 2

Exemplary yields of isoprene in a fermentor using the cell cultures and methods of the invention.

| Strain | Isoprene Production in Fermentors Peak Headspace concentration** ($ug/L_{gas}$) | Titer ($mg/L_{broth}$) | Peak Specific rate $\mu g/L_{broth}$/hr/OD ($nmol/g_{wcm}$/hr) |
|---|---|---|---|
| *E. coli* BL21/pTrcKudzu with Kudzu IS | 52 | 41.2 | 37 (543.3) |
| *E. coli* FM5/pTrcKudzu IS | 3 | 3.5 | 21.4 (308.1) |
| *E. coli* BL21/triple strain (DXS, yidi, IS) | 285 | 300 | 240 ($3.52 \times 10^3$) |
| *E. coli* FM5/triple strain (DXS, yidi, IS) | 50.8 | 29 | 180.8 ($2.65 \times 10^3$) |
| *E. coli*/MCM127 with Kudzu IS and entire MVA pathway | 3815 | 3044 | 992.5 ($1.46 \times 10^4$) |
| *E. coli* BL21/pCLPtrc UpperPathway gi1.2 integrated lower pathway pTrcKudzu | 2418 | 1640 | 1248 ($1.83 \times 10^4$) |
| *E. coli* BL21/pCLPtrc UpperPathwayHGS2-pTrcKKDyIkIS | 3500 | 3300 | 1088 ($1.60 \times 10^4$) |

TABLE 2-continued

Exemplary yields of isoprene in a fermentor using the cell cultures and methods of the invention.

| Strain | Isoprene Production in Fermentors Peak Headspace concentration** ($ug/L_{gas}$) | Titer ($mg/L_{broth}$) | Peak Specific rate $\mu g/L_{broth}$/hr/OD ($nmol/g_{wcm}$/hr) |
|---|---|---|---|
| *Bacillus subtilis* wild-type | 1.5 | 2.5 | 0.8 (11.7) |
| *Bacillus* pBS Kudzu IS | 16.6 | ~30 (over 100 hrs) | 5 (73.4) |
| *Bacillus* Marburg 6051 [Wagner and Fall (1999)] | 2.04 | 0.61 | 24.5 (359.8) |
| *Bacillus* Marburg 6051 Fall US 5849970 | 0.7 | 0.15 | 6.8 (100) |

**Normalized to an off-gas flow rate of 1 vvm (1 volume off-gas per 1 $L_{broth}$ per minute).

The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

The encoded DXS and IDI polypeptides are part of the DXP pathway for the biosynthesis of isoprene (FIG. 19). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

For example, fermentation of *E. coli* cells with a kudzu isoprene synthase, *S. cerevisia* IDI, and *E. coli* DXS nucleic acids was used to produce isoprene. The levels of isoprene varied from 50 to 300 ⊠g/L over a time period of 15 hours (Example 7, part VII).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by *E. coli* cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

In some embodiments, the production of isoprene by cells by cells that contain a heterologous isoprene synthase nucleic acid is augmented by increasing the amount of a MVA polypeptide expressed by the cells (FIG. 19). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, *E. coli* cells containing a nucleic acid encoding a kudzu isoprene synthase polypeptide and nucleic acids encoding *Saccharomyces cerevisia* MVK, PMK, MVD, and IDI polypeptides generated isoprene at a rate of $6.67\times10^{-4}$ mol/$L_{broth}$/$OD_{600}$/hr (see Example 8). Additionally, a 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in *E. coli*. *E. coli* cells that contain nucleic acids for both the upper MVA pathway and the lower MVA pathway as well as a kudzu isoprene synthase (strain MCM 127) produced significantly more isoprene (874 ug/L) compared to *E. coli* cells with nucleic acids for only the lower MVA pathway and the kudzu isoprene synthase (strain MCM 131) (see Table 3 and Example 8, part VIII).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

As indicated in Example 7, part VI, the amount of isoprene produced can be further increased by adding yeast extract to the cell culture medium. In this example, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Both of these experiments used *E. coli* cells with kudzu isoprene synthase, *S. cerevisia* IDI, and *E. coli* DXS nucleic acids to produce isoprene. Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Isoprene production was also demonstrated using three types of hydrolyzed biomass (bagasse, corn stover, and soft wood pulp) as the carbon source (FIGS. 46A-C). *E. coli* cells with kudzu isoprene synthase, *S. cerevisia* IDI, and *E. coli* DXS nucleic acids produced as much isoprene from these hydrolyzed biomass carbon sources as from the equivalent amount of glucose (e.g., 1% glucose, w/v). If desired, any other biomass carbon source can be used in the compositions and methods of the invention. Biomass carbon sources are desirable because they are cheaper than many conventional cell mediums, thereby facilitating the economical production of isoprene.

Additionally, invert sugar was shown to function as a carbon source for the generation of isoprene (FIGS. 47C and 96-98). For example, 2.4 g/L of isoprene was produced from cells expressing MVA pathway polypeptides and a Kudzu isoprene synthase (Example 8, part XV). Glycerol was as also used as a carbon source for the generation of 2.2 mg/L of isoprene from cells expressing a Kudzu isoprene synthase (Example 8, part XIV). Expressing a DXS nucleic acid, an IDI nucleic acid, and/or one or more MVA pathway nucleic acids (such as nucleic acids encoding the entire MVA pathway) in addition to an isoprene synthase nucleic acid may increase the production of isoprene from glycerol.

In some embodiments, an oil is included in the cell medium. For example, *B. subtilis* cells containing a kudzu isoprene synthase nucleic acid produced isoprene when cultured in a cell medium containing an oil and a source of glucose (Example 4, part III). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

One of the major hurdles to commercial production of small molecules such as isoprene in cells (e.g., bacteria) is the decoupling of production of the molecule from growth of the cells. In some embodiments for the commercially viable production of isoprene, a significant amount of the carbon from the feedstock is converted to isoprene, rather than to the growth and maintenance of the cells ("carbon efficiency"). In various embodiments, the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In particular embodiments, a significant portion of the carbon from the feedstock that is converted to downstream products is converted to isoprene. As described further in Example 11, *E. coli* cells expressing MVA pathway and kudzu isoprene synthase nucleic acids exhibited decoupling of the production of isoprene or the intermediate mevalonic acid from growth, resulting in high carbon efficiency. In particular, mevalonic acid was formed from cells expressing the upper MVA pathway from *Enterococcus faecalis*. Isoprene was formed from cells expressing the upper MVA pathway from *Enterococcus faecalis*, the lower MVA pathway from *Saccharomyces cerevisiae*, and the isoprene synthase from *Pueraria montana* (Kudzu). This decoupling of isoprene or mevalonic acid production from growth was demonstrated in four different strains of *E. coli*: BL21(LDE3), BL21(LDE3) Tuner, FM5, and MG1655. The first two *E. coli* strains are B strains, and the latter two are K12 strains. Decoupling of production from growth was also demonstrated in a variant of MG1655 with ack and pta genes deleted. This variant also demonstrated less production of acetate.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides. In some embodiments, the fusion polypeptide includes part or all of a first polypeptide (e.g., an isoprene synthase, DXS, IDI, or MVA pathway polypeptide or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In various embodiments, a nucleic acid is a recombinant nucleic acid. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the world-wide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007, such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) is added to 25 μL of cell extract in a 20 ml Headspace vial with a metal screw cap and teflon coated silicon septum (Agilent Technologies) and cultured at 37° C. for 15 minutes with shaking. The reaction is quenched by adding 200 μL of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a naturally-occurring polypeptide or nucleic acid from *Pueraria montana* (kudzu) (Sharkey et al., Plant Physiology 137: 700-712, 2005), *Pueraria lobata*, poplar (such as *Populus alba*×*tremula* CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is not a naturally-occurring polypeptide or nucleic acid from poplar (such as *Populus alba*×*tremula* CAC35696).

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate polypeptides (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, 2nd ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (world-wide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, 2nd ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, ⊠ $P_L$, ⊠ $P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell. Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei cellobiohydrolase* 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell. Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, 2$^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2$^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 19). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, or *A. awamori*) (Ward et al., Appl. Microbiol. Biotechnol. 39: 7380743, 1993 and Goedegebuur et al., Genet. 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., *Sci.* 228: 21-26, 1985). The term "*Trichoderma*" or "*Trichoderma* sp." or "*Trichoderma* spp." refer to any fungal genus previously or currently classified as *Trichoderma.*

In some embodiments, the fungus is *A. nidulans, A. awamori, A. oryzae, A. aculeatus, A. niger, A. japonicus, T. reesei, T. viride, F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei.*

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, or strains of *Escherichia* such as *E. coli.*

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus.*

In some embodiments, the source organism is a gram-positive bacterium. Non-limiting examples include strains of *Streptomyces* (e.g., *S. lividans, S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus alba×tremula* CAC35696), aspen (such as *Populus tremuloides*), or *Quercus robur.*

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales, Pleurocapsales, Oscillatoriales, Nostocales*, or *Stigonematales.*

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.,* 53(2) 541-543, 1989, which is hereby incorporated by reference in its entirety, particularly with respect to carbon sources) and in bacteria (Hunter et. al., *Biochemistry,* 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd., [Int. Symp.],* $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell medias). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Methods for Decoupling Isoprene Production from Cell Growth

Desirably, carbon from the feedstock is converted to isoprene rather than to the growth and maintenance of the cells.

In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). For example, FIGS. 60A-67C illustrate that cells may continue to produce a substantial amount of mevalonic acid or isoprene after the cells reach an optical density such that they no longer divide or divide extremely slowly. In some cases, the optical density at 550 nm decreases over time (such as a decrease in the optical density after the cells are no longer in an exponential growth phase due to cell lysis, cessation of growth, lack of nutrients or other factors leading to lack of cell growth), and the cells continue to produce a substantial amount of mevalonic acid or isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000; 1,250; 1,500; 1,750; 2,000; 2,500; 3,000; 4,000; 5,000; 10,000; 20,000; 30,000; 40,000; 50,000; 100,000; 200,000; 300,000; 400,000; 500,000; 600,000; 700,000; 800,000; 900,000; 1,000,000 or more nmole of isoprene/gram of cells for the wet weight of the cells/hour (nmole/$g_{wcm}$/hr) during this time period. In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium) during this time period. In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

Production of Isoprene within Safe Operating Ranges

The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis

Test Suite 1:
isoprene: 0 wt %-14 wt %
$O_2$: 6 wt %-21 wt %
$N_2$: 79 wt %-94 wt %

Test Suite 2:
isoprene: 0 wt %-14 wt %
$O_2$: 6 wt %-21 wt %
$N_2$: 79 wt %-94 wt %
Saturated with $H_2O$ Test Suite 3:
isoprene: 0 wt %-14 wt %
$O_2$: 6 wt %-21 wt %
$N_2$: 79 wt %-94 wt %
$CO_2$: 5 wt %-30 wt %

(2) Experimental Testing for Final Determination of Flammability Limits

Test Suite 1:
isoprene: 0 wt %-14 wt %
$O_2$: 6 wt %-21 wt %
$N_2$: 79 wt %-94 wt %

Test Suite 2:
isoprene: 0 wt %-14 wt %
$O_2$: 6 wt %-21 wt %
$N_2$: 79 wt %-94 wt %
Saturated with $H_2O$ Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems,* 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 μm; 0.25 μm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

Carbon Yield=(moles carbon in isoprene produced)/(moles carbon in carbon source)*100 Equation 1%

For this calculation, yeast extract can be assumed to contain 50% w/w carbon. As an example, for the 500 liter described in Example 7, part VIII, the percent conversion of carbon into isoprene can be calculated as shown in Equation 2.

Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042% Equation 2%

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein. Example 11, part V describes the 1.53% conversion of carbon to isoprene using the methods described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate) Equation 3

1 nmol isoprene/$g_{wcm}$/hr=1 nmol isoprene/$L_{broth}$/hr/$OD_{600}$(This conversion assumes that one liter of broth with an $OD_{600}$ value of 1 has a wet cell weight of 1 gram.) Equation 4

1 nmol isoprene/$g_{wcm}$/hr=68.1 ng isoprene/$g_{wcm}$/hr (given the molecular weight of isoprene) Equation 5

1 nmol isoprene/$L_{gas}$ $O_2$/hr=90 nmol isoprene/$L_{broth}$/hr(at an $O_2$ flow rate of 90 L/hr per L of culture broth) Equation 6

1 ug isoprene/$L_{gas}$ isoprene in off-gas=60 ug isoprene/$L_{broth}$/hr at a flow rate of 60 $L_{gas}$ per $L_{broth}$(1 vvm) Equation 7

Units for Titer (Total and Specific)

1 nmol isoprene/mg cell protein=150 nmol isoprene/$L_{broth}$/$OD_{600}$(This conversion assumes that one liter of broth with an $OD_{600}$ value of 1 has a total cell protein of approximately 150 mg) (specific productivity) Equation 8

1 g isoprene/$L_{broth}$=14.7 mmol isoprene/$L_{broth}$(total titer) Equation 9

If desired, Equation 10 can be used to convert any of the units that include the wet weight of the cells into the corresponding units that include the dry weight of the cells.

Dry weight of cells=(wet weight of cells)/3.3 Equation 10

If desired, Equation 11 can be used to convert between units of ppm and ug/L. In particular, "ppm" means parts per million defined in terms of ug/g (w/w) or uL/L (vol/vol). Conversion of ug/L to ppm (e.g., ug of analyte per g of gas) can be performed by determining the mass per L of off-gas (i.e., the density of the gas). For example, a liter of air at STP has a density of approximately 1.2 g/L. Thus, a concentration of 1 ppm (ug/g) equals 0.83 ug/L at STP (equation 11). The conversion of ppm (ug/g) to ug/L is a function of both pressure, temperature, and overall composition of the off-gas.

1 ppm (ug/g) equals 0.83 ug/L at standard temperature and pressure (STP; 101.3 kPa (1 bar) and 273.15K). Equation 11

Conversion of ug/L to ppmv (e.g., uL of analyte per L of gas) can be performed using the Universal Gas Law (equation 12). For example, an off-gas concentration of 1000 ug/$L_{gas}$ corresponds to 14.7 umol/$L_{gas}$. The universal gas constant is 0.082057 L·atm $K^{-1}$ $mol^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

PV=nRT, where "P" is pressure, "V" is volume, "n" is moles of gas, "R" is the Universal gas constant, and "T" is temperature in Kelvin. Equation 12

The amount of impurities in isoprene compositions are typically measured herein on a weight per volume (w/v) basis in units such as ug/L. If desired, measurements in units of ug/L can be converted to units of mg/$m^3$ using equation 13.

1 ug/L=1 mg/$m^3$ Equation 13

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as 1-pentyne, 2-butyne, 2-methyl-1-butene-3-yne, and pent-4-ene-1-yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some embodiments, the isoprene composition includes ethanol, acetone, a C5 prenyl alcohol (such as 3-methyl-3-buten-1-ol or 3-methyl-2-buten-1-ol), or any two or more of the foregoing. In particular embodiments, the isoprene composition comprises greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In some embodiments, the isoprene composition comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 ug/L of ethanol, acetone, a C5 prenyl alcohol, or any two or more of the foregoing.

In some embodiments, the isoprene composition includes one or more of the following components: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-but-1-enyl acetate, 3-methyl-2-but-1-enyl acetate, (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). In various embodiments, the amount of one of these components relative to amount of isoprene in units of percentage by weight (i.e., weight of the component divided by the weight of isoprene times 100) is greater than or about 0.01, 0.02, 0.05, 0.1, 0.5, 1, 5, 10, 20, 30, 40, 50, 60, 70, 80, 90, 100, or 110% (w/w). In some embodiments, the relative detector response for the second compound compared to the detector response for isoprene is greater than or about 0.01, 0.02, 0.05, 0.1, 0.5, 1, 5, 10, 20, 30, 40, 50, 60, 70, 80, 90, 100, or 110%. In various embodiments, the amount of one of these components relative to amount of isoprene in units of percentage by weight (i.e., weight of the component divided by the weight of isoprene times 100) is between about 0.01 to about 105% (w/w), such as about 0.01 to about 90, about 0.01 to about 80, about 0.01 to about 50, about 0.01 to about 20, about 0.01 to about 10, about 0.02 to about 50, about 0.05 to about 50, about 0.1 to about 50, or 0.1 to about 20% (w/w).

In some embodiments, the isoprene composition includes one or more of the following: an alcohol, an aldehyde, or a ketone (such as any of the alcohols, aldehyes, or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone.

In some embodiments, the isoprene composition contains one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the isoprene composition contains 1 ppm or more of one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the concentration of more of one or more of the following: methanol, acetaldehyde, ethanol, methanethiol, 1-butanol, 3-methyl-1-propanol, acetone, acetic acid, 2-butanone, 2-methyl-1-butanol, or indole, is between about 1 to about 10,000 ppm in an isoprene composition (such as off-gas before it is purified). In some embodiments, the isoprene composition (such as off-gas after it has undergone one or more purification steps) includes one or more of the following: methanol, acetaldehyde, ethanol, methanethiol, 1-butanol, 3-methyl-1-propanol, acetone, acetic acid, 2-butanone, 2-methyl-1-butanol, or indole, at a concentration between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. Volatile organic compounds from cell cultures (such as volatile organic compounds in the headspace of cell cultures) can be analyzed using standard methods such as those described herein or other standard methods such as proton transfer reaction-mass spectrometry (see, for example, Bunge et al., *Applied and Environmental Microbiology,* 74(7):2179-2186, 2008 which is hereby incorporated by reference in its entirety, particular with respect to the analysis of volatile organic compounds).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

In some embodiments encompassed by the invention, a cell comprising one or more heterologous nucleic acids encoding an isoprene synthase polypeptide, DXS polypeptide, IDI polypeptide, and/or MVA pathway polypeptide produces an amount of an isoprenoid compound (such as a compound with 10 or more carbon atoms that is formed from the reaction of one or more IPP molecules with one or more DMAPP molecules) that is greater than or about 2-fold, 3-fold, 5-fold, 10-fold, 25-fold, 50-fold, 100-fold, 150-fold, 200-fold, 400-fold, or greater than the amount of the isoprenoid compound produced from a corresponding cell grown under essentially the same conditions without the one or more heterologous nucleic acids. In some embodiments encompassed by the invention, a cell comprising one or more heterologous nucleic acids encoding an isoprene synthase polypeptide, DXS polypeptide, IDI polypeptide, and/or MVA pathway polypeptide produces an amount of a C5 prenyl alcohol (such as 3-methyl-3-buten-1-ol or 3-methyl-2-buten-1-ol) that is greater than or about 2-fold, 3-fold, 5-fold, 10-fold, 25-fold, 50-fold, 100-fold, 150-fold, 200-fold, 400-fold, or greater than the amount of the C5 prenyl alcohol produced from a corresponding cell grown under essentially the same conditions without the one or more heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In particular, embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *E. Coli* Expressing Recombinant Kudzu Isoprene Synthase I. Construction of Vectors for Expression of the Kudzu Isoprene Synthase in *E. Coli*

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
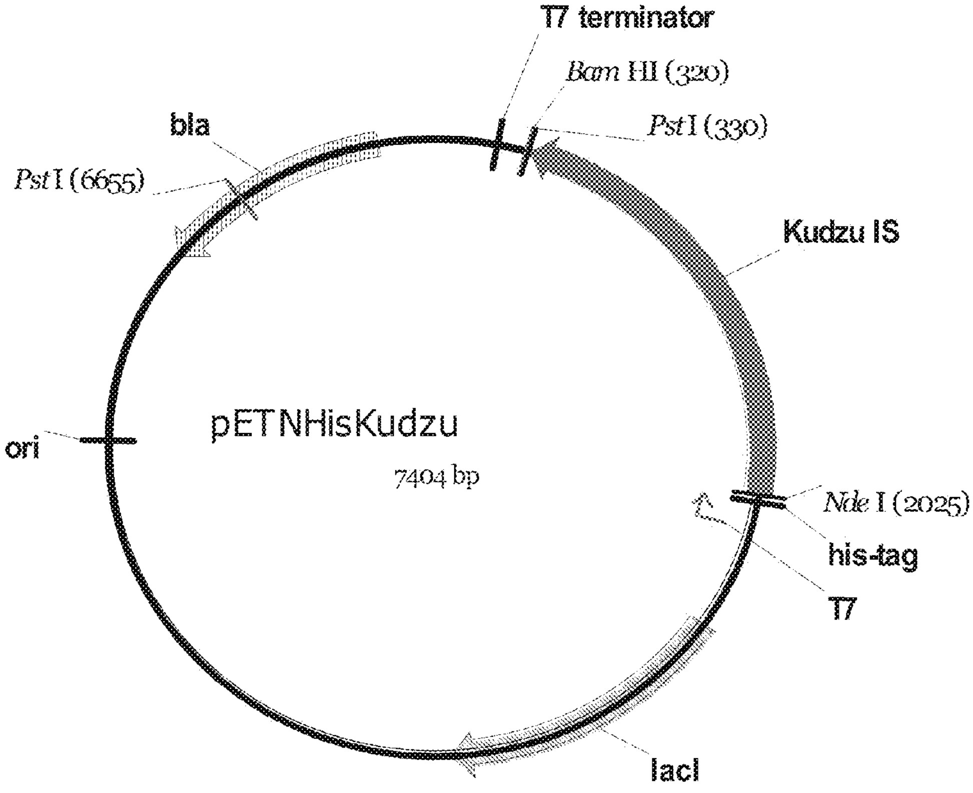
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGATCATATGTGTGCGACCTCTTCTCAATTTAC (SEQ ID NO:3) and pET-His-Kudzu-R: 5'-CGGTCGACGGATCCCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 µl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pET-NHisKudzu (FIGS. 4 and 5).

Figure 6:
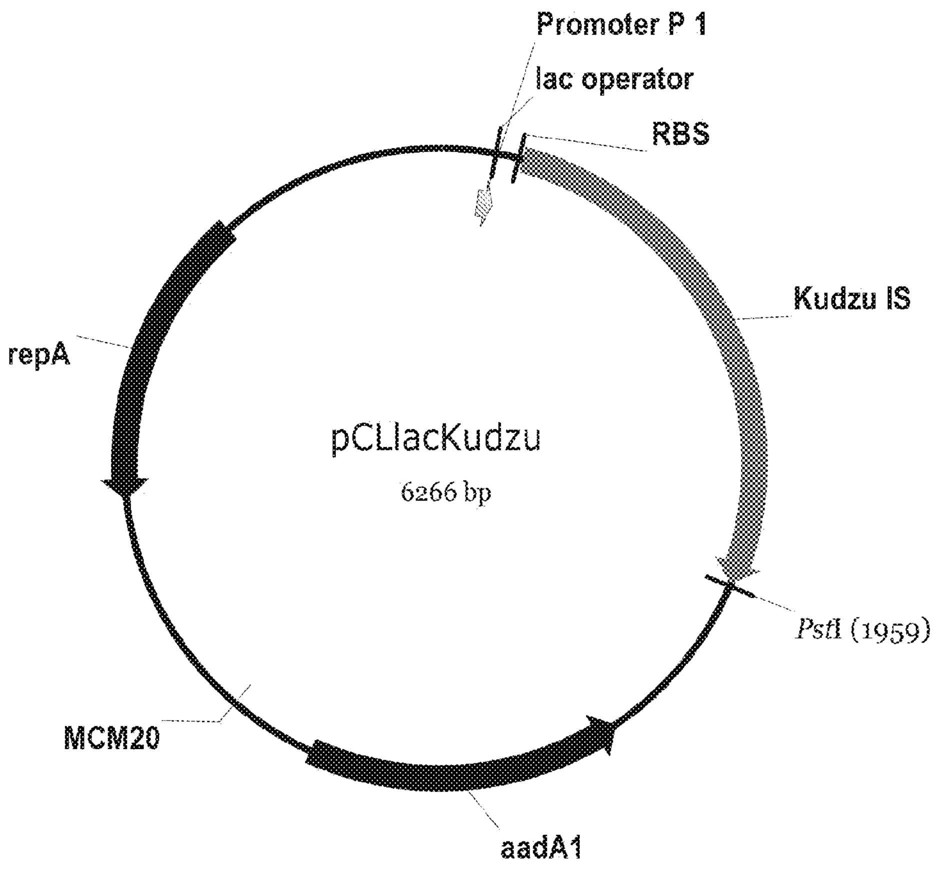
FIG. 6 is a map of pCL-lac-Kudzu.
Figure 8A:
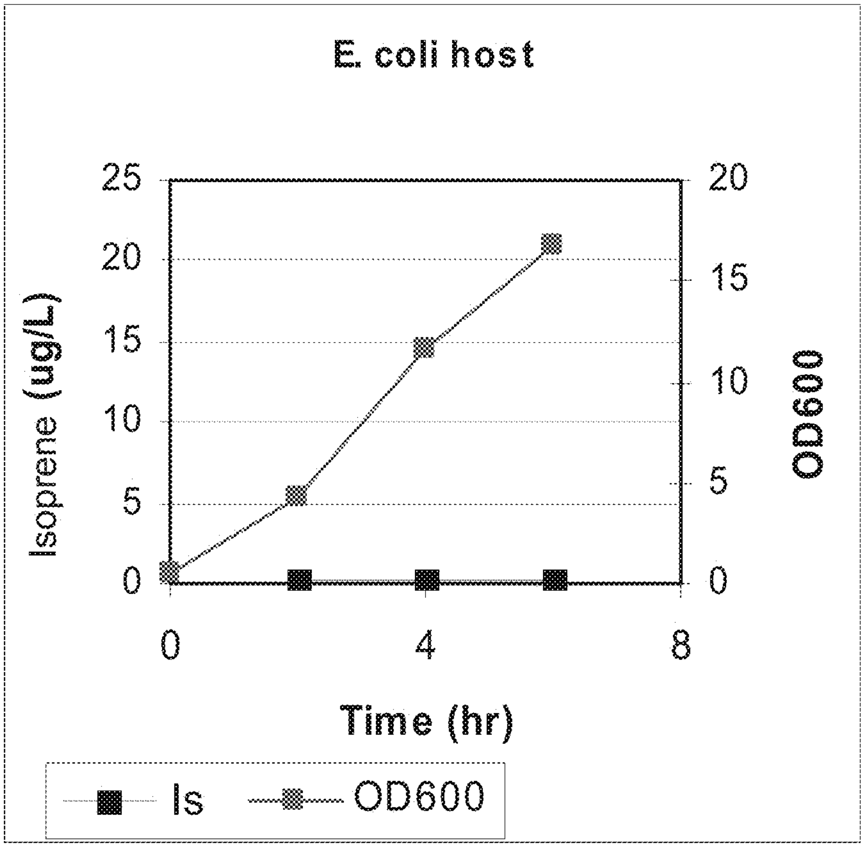
FIG. 8A is a graph showing the production of isoprene in *E. coli* BL21 cells with no vector.
Figure 8B:
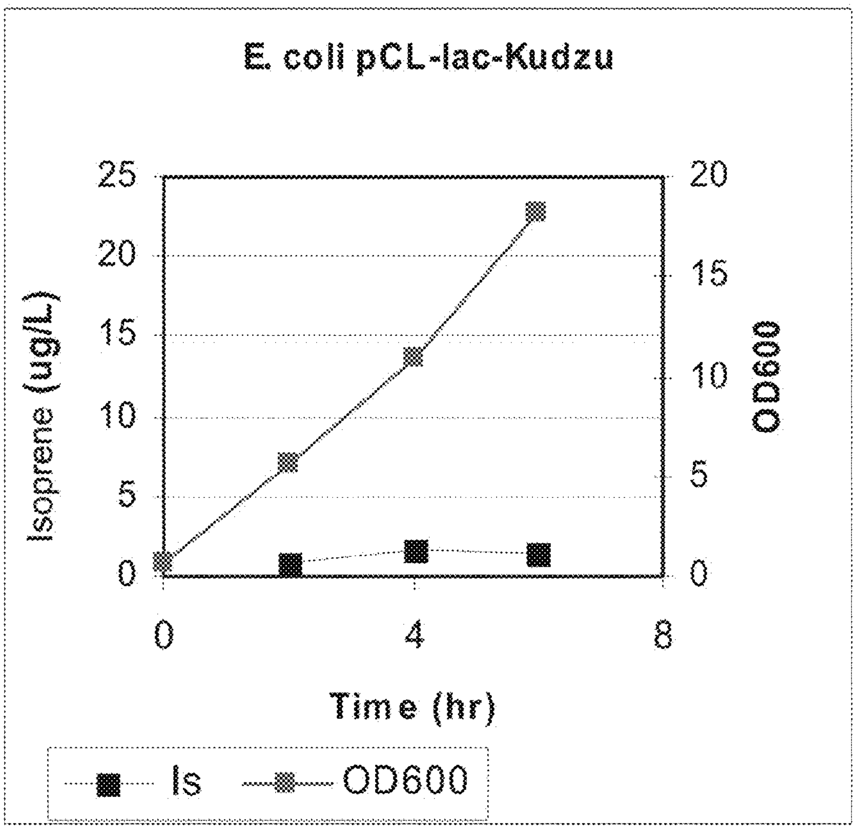
FIG. 8B is a graph showing the production of isoprene in *E. coli* BL21 cells with pCL-lac-Kudzu
Figure 8C:
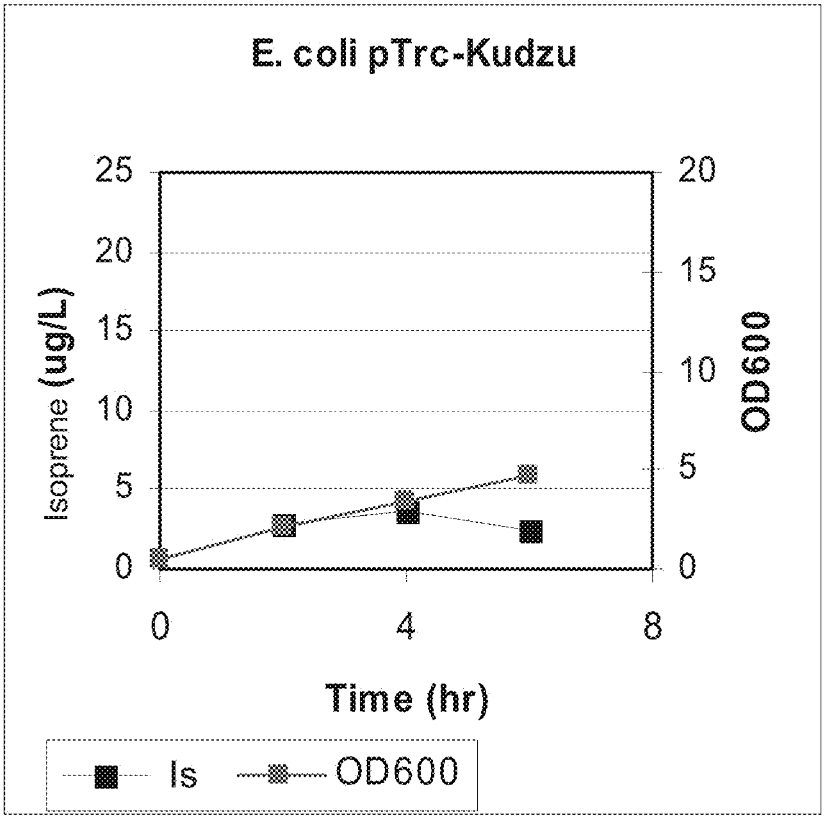
FIG. 8C is a graph showing the production of isoprene in *E. coli* BL21 cells with pTrcKudzu.
Figure 8D:
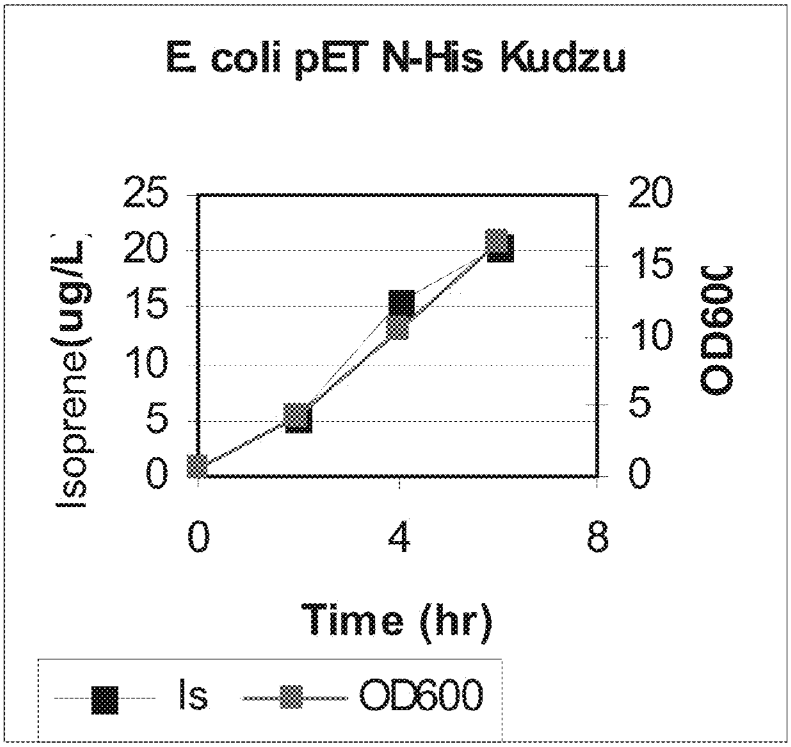
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATCGATTAAATAAGGAGGAATAAACC (SEQ ID NO:6) and BamH1-Kudzu R:

5'-CGGTCGACGGATCCCTGCAGTTAGACATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 2000 µg/L. The limit of detection was estimated to be 50 to 100 ng/L using this method.

III. Production of Isoprene in Shake Flasks Containing *E. Coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar)+carbenicillin (50 µg/ml) and incubated overnight at 37° C. Single colonies were inoculated into 250 ml baffled shake flasks containing 20 ml Luria Bertani broth (LB) and carbenicillin (100 µg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen)+carbenicillin (100 µg/ml) to an $OD_{600}$~0.05. The culture was incubated at 30° C. with shaking at 200 rpm. When the $OD_{600}$~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO4{*}7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and q.s. to volume. The final product was filter sterilized with 0.22µ filter (only, do not autoclave). The recipe for 1000× Modified Trace Metal Solution was as follows: Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in $diH_2O$, pH to 3.0 with HCl/NaOH, then q.s. to volume and filter sterilized with a 0.22μ filter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Production of Isoprene in *E. Coli* Expressing Recombinant Poplar Isoprene Synthase The protein sequence for the poplar (*Populus alba*×*Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), was verified by sequencing.

Example 3

Figure 10A:
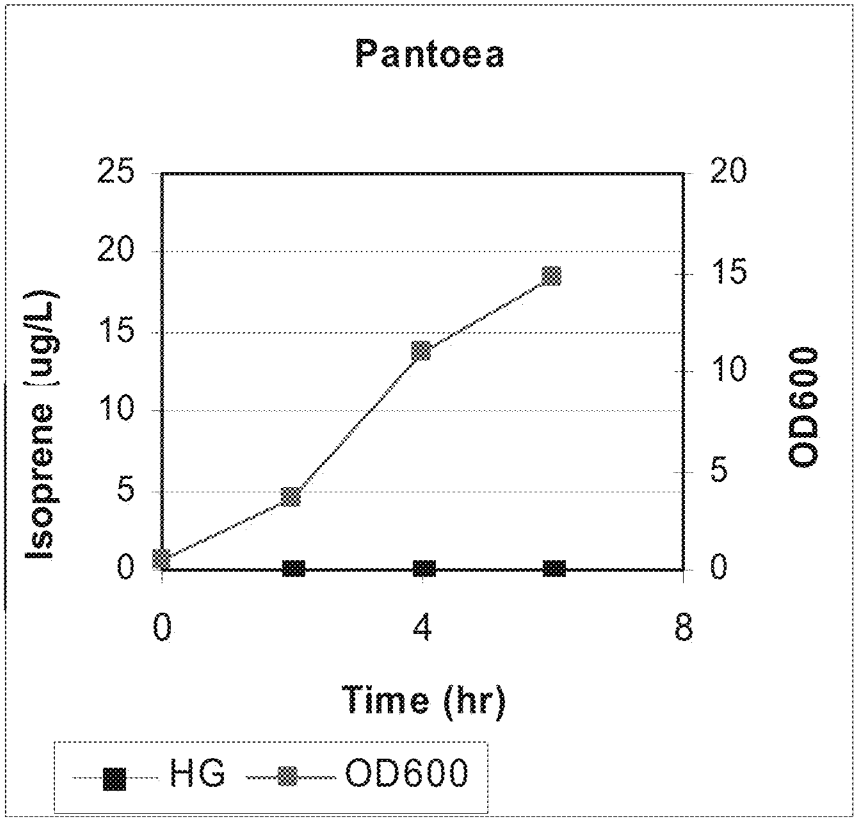
FIG. 10A is a graph showing the production of isoprene in *Panteoa citrea*. Control cells without recombinant kudzu isoprene synthase. Grey diamonds represent isoprene synthesis, black squares represent $OD_{600}$).
Figure 10B:
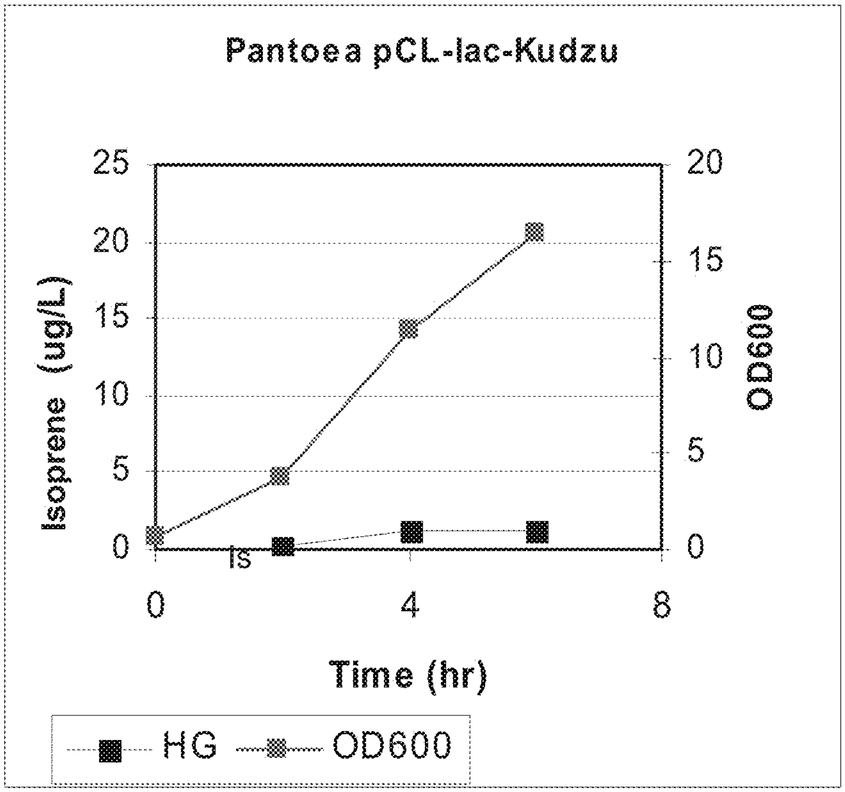
FIG. 10B is a graph showing the production of isoprene in *Panteoa citrea* expressing pCL-lac Kudzu. Grey diamonds represent isoprene synthesis, black squares represent $OD_{600}$.
Figure 10C:
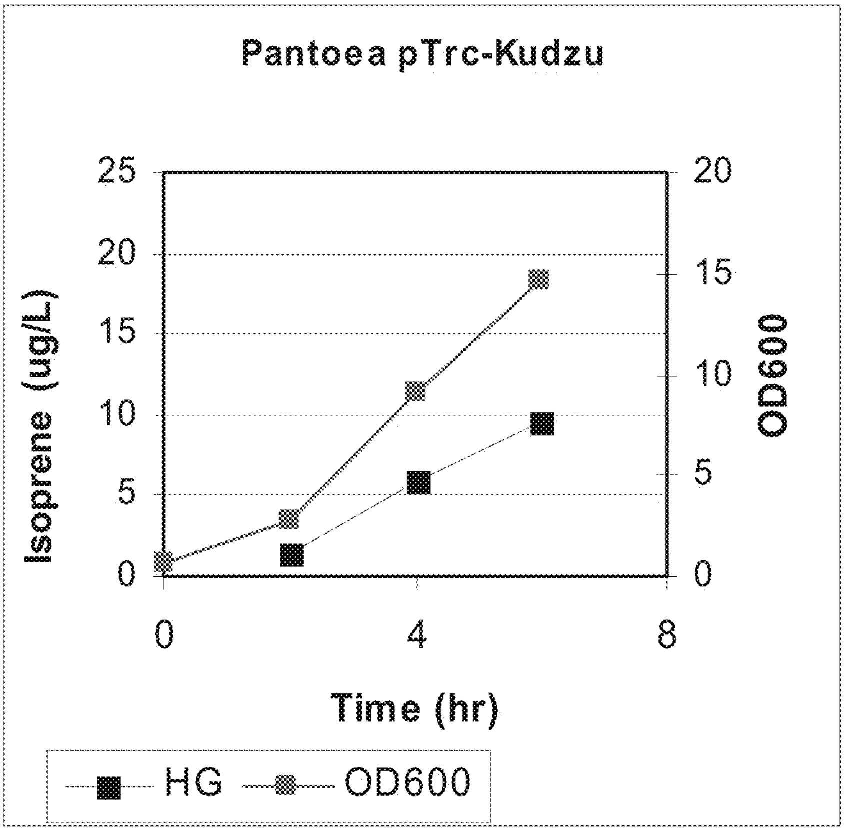
FIG. 10C is a graph showing the production of isoprene in *Panteoa citrea* expressing pTrcKudzu. Grey diamonds represent isoprene synthesis, black squares represent $OD_{600}$).

Production of Isoprene in *Panteoa citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Transformants were selected on LA containing carbenicillin (200 μg/ml) or spectinomycin (50 μg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. Subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis.* a) Amplification of the aprE Promoter

The aprE promoter was amplified from chromosomal DNA from *Bacillus subtilis* using the following primers:

```
CF 797 (+) Start aprE promoter MfeI
                                        (SEQ ID NO: 58)
5'-GACATCAATTGCTCCATTTTCTTCTGCTATC

CF 07-43 (-) Fuse aprE promoter to Kudzu ispS
                                        (SEQ ID NO: 59)
5'-ATTGAGAAGAGGTCGCACACACTCTTTACCCTCTCCTTTTA
```

b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+)
Fuse the aprE promoter to kudzu isoprene
synthase gene (GTG start codon)
                                        (SEQ ID NO: 60)
5'-TAAAAGGAGAGGGTAAAGAGTGTGTGCGACCTCTTCTCAAT

CF 07-45 (-) Fuse the 3' end of kudzu
isoprene synthase gene to the terminator
                                        (SEQ ID NO: 61)
5'-CCAAGGCCGGTTTTTTTTAGACATACATCAGCTGGTTAATC
```

c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu
isoprene synthase to the terminator
                                        (SEQ ID NO: 62)
5'-GATTAACCAGCTGATGTATGTCTAAAAAAAACCGGCCTTGG

CF 07-46 (-) End of
B. amyliquefaciens terminator (BamHI)
                                        (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                        (SEQ ID NO: 60)
5'-TAAAAGGAGAGGGTAAAGAGTGTGTGCGACCTCTTCTCAAT

CF 07-46 (-) End of B. amyliquefaciens
terminator (BamHI)
                                        (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                        (SEQ ID NO: 64)
5'-GACATCAATTGCTCCATTTTCTTCTGCTATC

CF 07-46 (-) End of B. amyliquefaciens
terminator (BamHI)
                                        (SEQ ID NO: 63)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA+50 carbenicillin plates. A total of six colonies were chosen and grown overnight in LB+50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                                    (SEQ ID NO: 65)
5'-GACATGAATTCCTCCATTTTCTTCTGC

CF 847 (+) Sequence in pXX 049 (end of aprE promoter)
                                                    (SEQ ID NO: 66)
5'-AGGAGAGGGTAAAGAGTGAG

CF 07-45 (-) Fuse the 3' end of kudzu isoprene synthase to the terminator
                                                    (SEQ ID NO: 61)
5'-CCAAGGCCGGTTTTTTTTAGACATACATCAGCTGGTTAATC

CF 07-48 (+) Sequencing primer for kudzu isoprene synthase
                                                    (SEQ ID NO: 67)
5'-CTTTTCCATCACCCACCTGAAG

CF 07-49 (+) Sequencing in kudzu isoprene synthase
                                                    (SEQ ID NO: 68)
5'-GGCGAAATGGTCCAACAACAAAATTATC
```

The plasmid designated pBS Kudzu #2 (FIGS. 52 and 12) was correct by sequencing and was transformed into BG 3594 comK, a *Bacillus subtilis* host strain. Selection was done on LA+5 chloramphenicol plates. A transformant was chosen and struck to single colonies on LA+5 chloramphenicol, then grown in LB+5 chloramphenicol until it reached an $OD_{600}$ of 1.5. It was stored frozen in a vial at −80° C. in the presence of glycerol. The resulting strain was designated CF 443.

Figure 11:
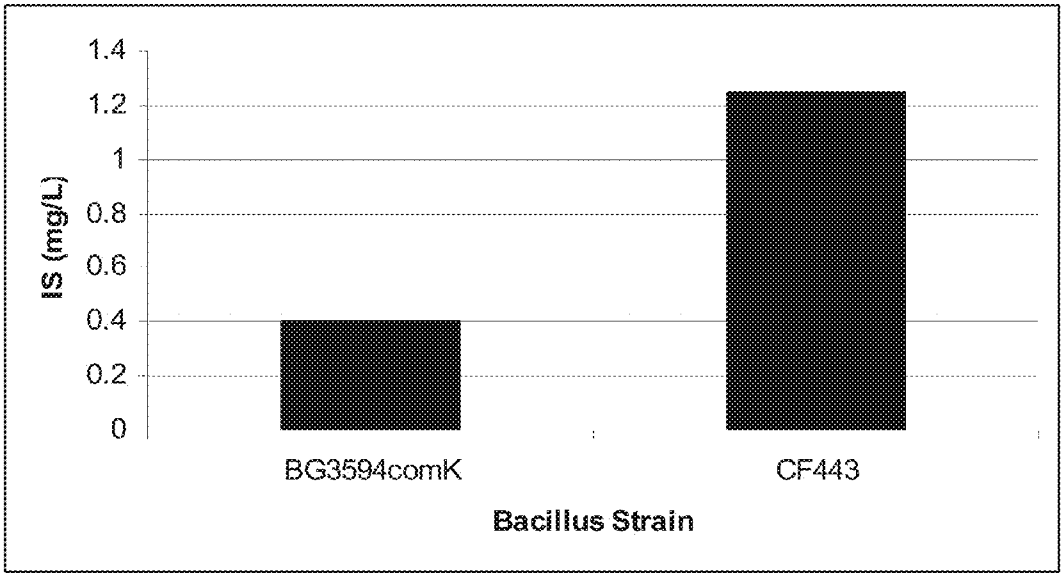
FIG. 11 is a graph showing the production of isoprene in *Bacillus subtilis* expressing recombinant isoprene synthase.

II. Production of Isoprene in Shake Flasks Containing *B. Subtilis* Cells Expressing Recombinant Isoprene Synthase Overnight cultures were inoculated with a single colony of CF 443 from a LA+Chloramphenicol (Cm, 25 μg/ml). Cultures were grown in LB+Cm at 37° C. with shaking at 200 rpm. These overnight cultures (1 ml) were used to inoculate 250 ml baffled shake flasks containing 25 ml Grants II media and chloramphenicol at a final concentration of 25 μg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2$*$2H_2O$, 0.4 g $FeSO_4$*$7H_20$, 0.1 g $MnSO_4$*$H_20$, 0.1 g $ZnSO_4$*$H_2O$, 0.05 g $CuCl_2$*$2H_2O$, 0.1 g $CoCl_2$*$6H_2O$, 0.1 g $Na_2MoO_4$*$2H_2O$, q.s. to 1 L with $H_2O$, Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. Subtilis.*

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 μl plasmid template (20 ng/ul), 1 μl Primer EL-945 (10 uM) 5'-GCTTATGGATCCTCTAGACTATTACACGTACATCAATTGG (SEQ ID NO:9), 1 μl Primer EL-965 (10 uM) 5'-CACCATGTGTGCAACCTCCTCCCAGTTTAC (SEQ ID NO:10), 1 μl dNTP (10 mM), 5 μl 10× PfuUltra II Fusion HS DNA Polymerase Buffer, 1 μl PfuUltra II Fusion HS DNA Polymerase, 40 μl water in a total reaction volume of 50 μl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 μl PCR reaction, 1 μl Salt solution, 1 μl TOPO pENTR/D-TOPO vector and 3 μl water in a total reaction volume of 6 μl. The reaction was incubated at room temperature for 5 minutes. One microliter of TOPO reaction was transformed into TOP10 chemically competent *E. coli* cells. The transformants were selected on LA+50 μg/ml kanamycin plates. Several colonies were picked and each was inoculated into a 5 ml tube containing LB+50 μg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3 g vector. Construction of pTrex3g is described in WO 2005/001036 A2. The reaction was performed following manufacturer's protocol for the Gateway LR Clonase II Enzyme Mix Kit (Invitrogen): 1 μl *Y. lipolytica* codon-optimized kudzu isoprene synthase gene pENTR/D-TOPO donor vector, 1 μl pTrex3g destination vector, 6 μl TE buffer, pH 8.0 in a total reaction volume of 8 μl. The reaction was incubated at room temperature for 1 hour and then 1 μl proteinase K solution was added and the incubation continued at 37° C. for 10 minutes. Then 1 μl of reaction was transformed into TOP10 chemically competent *E. coli* cells. The transformants were selected on LA+50 μg/ml carbenicillin plates. Several colonies were picked and each was inoculated into a 5 ml tube containing LB+50 μg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. Reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 μg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia*

I. Construction of Vectors for Expression of the Kudzu Isoprene Synthase in *Yarrowia lipolytica*.

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
                                        (SEQ ID NO: 69)
5'-GGTGAATTCAGTCTACTGGGGATTCCCAAATCTATATATACTGCAG

GTGAC

ICL1 5
                                        (SEQ ID NO: 70)
5'-GCAGGTGGGAAACTATGCACTCC

XPR 3
                                        (SEQ ID NO: 71)
5'-CCTGAATTCTGTTGGATTGGAGGATTGGATAGTGGG

XPR 5
                                        (SEQ ID NO: 72)
5'-GGTGTCGACGTACGGTCGAGCTTATTGACC

XPRT3
                                        (SEQ ID NO: 73)
5'-GGTGGGCCCGCATTTTGCCACCTACAAGCCAG

XPRT 5
                                        (SEQ ID NO: 74)
5'-GGTGAATTCTAGAGGATCCCAACGCTGTTGCCTACAACGG

Y18S3
                                        (SEQ ID NO: 75)
5'-GGTGCGGCCGCTGTCTGGACCTGGTGAGTTTCCCCG

Y18S 5
                                        (SEQ ID NO: 76)
5'-GGTGGGCCCATTAAATCAGTTATCGTTTATTTGATAG

YURA3
                                        (SEQ ID NO: 77)
5'-GGTGACCAGCAAGTCCATGGGTGGTTTGATCATGG

YURA 50
                                        (SEQ ID NO: 78)
5'-GGTGCGGCCGCCTTTGGAGTACGACTCCAACTATG

YURA 51
                                        (SEQ ID NO: 79)
5'-GCGGCCGCAGACTAAATTTATTTCAGTCTCC
```

For PCR amplification the PfuUltraII polymerase (Stratagene), supplier-provided buffer and dNTPs, 2.5 μM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba*×*Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. Lipolytica*.

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred μl aliquots of the cell suspension were mixed with linearized plasmid DNA solution (10-20 μg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 μg/L to 1 μg/L, FIG. 20). No isoprene was detected in the headspace of the control strains carrying phytase gene instead of an isoprene synthase gene.

Example 7

Production of Isoprene in *E. Coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the $kan^r$ gene which had been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 μg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 μg/ml kanamycin. Several transformants were isolated and sequenced and the resulting plasmid was called pTrcKudzu-yIDI(kan) (FIGS. 34 and 35).

iii) Construction of pTrcKudzu DXS Kan

Plasmid pTrcKudzuKan was digested with PstI, treated with SAP, heat killed and gel purified. It was ligated to a PCR product encoding dxs from *E. coli* with a synthetic RBS. The primers for PCR were MCM 13 5'-GATCATGCATTCGCCCTTAGGAGGTAAAAAAACAT-GAGTTTTGATATTGCCAAATACCC G (SEQ ID NO:18) and MCM14 5'-CATGCTGCAGTTATGCCAGCCAGGCCTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 μg/ml. Several transformants were isolated and sequenced and the resulting plasmid was called pTrcKudzu-DXS(kan) (FIGS. 36 and 37).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGGTAAAAAAACATGAGTTTTGATATTGCCAAATACCC G (SEQ ID NO:18) and MCM14 5'-CATGCTGCAGTTATGCCAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 μg/ml. Several clones were isolated and sequenced and two were selected. pCL PtrcKudzu and pCL PtrcKudzu (A3) have the insert in opposite orientations (FIGS. 38-41).

vi) Construction of pCL PtrcKudzu yIDI

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu yIDI (FIGS. 42 and 43).

vii) Construction of pCL PtrcKudzu DXS

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu DXS (FIGS. 44 and 45).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 μg/mL. Cultures of pCL PtrcKudzu (E), pCL PtrcKudzu, pCL PtrcKudzu-yIDI (F) and pCL PtrcKudzu-DXS (G) were grown in LB spectinomycin 50 μg/mL. Cultures were induced with 400 μM IPTG at time 0 ($OD_{600}$ approximately 0.5) and samples taken for isoprene headspace measurement (see Example 1). Results are shown in FIG. 23A-23G.

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 μg/ml) at 20° C. and used to inoculate shake flasks of TM3 (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_20$, and filter sterilized) containing 1% glucose. Flasks were incubated at 30° C. until an $OD_{600}$ of 0.8 was reached, and then induced with 400 μM IPTG. Samples were taken at various times after induction and the amount of isoprene in the head space was measured as described in Example 1. Results are shown in FIG. 23H.

III. Production of Isoprene from Biomass in *E. Coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L. and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 μg/ml). The culture was incubated overnight at 25° C. with shaking. The following day the overnight culture was diluted to an $OD_{600}$ of 0.05 in 25 ml of TM3+0.2% YE+1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. Coli*/pTrcKudzuIDIDXS

A single colony from a plate freshly transformed cells of BL21 (λDE3)/pTrcKudzu yIDI DXS (kan) was used to inoculate 5 mL of LB+kanamycin (50 μg/ml). The culture was incubated overnight at 25° C. with shaking. The following day the overnight culture was diluted to an $OD_{600}$ of 0.05 in 25 ml of TM3+0.2% YE+1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. Coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 μg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. Coli* Grown in Fed-Batch Culture Medium Recipe (Per Liter Fermentation Medium):

$K_2HPO_4$ 7.5 g, $MgSO_4$*$7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in di$H_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8

Production of Isoprene in *E. Coli* Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTACCGTTCTTAACTTCTGC, SEQ ID NO:21) and MVK-PstI-R (5'-ATGGCTGCAGGCCTATCGCAAATTAGCTTATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and TaqI restriction endonucleases and the fragment was gel purified and ligated into pTrcHis2B digested with SacI and BstBI. The resulting plasmid was named pTrcMVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCACCCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTGGAATTCGCCCTTCTGCAGC, SEQ ID NO:25) and NsiI-MVD 1 F (5'-GTAGATGCATGCAGAATTCGCCCTTAAGGAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATGCATCGCCCTTAGGAGGTAAAAAAAAATGAC, SEQ ID NO:28) to amplify the yIDI gene. In some cases the IPP isomerase gene, idi from *E. coli* was used. To amplify idi from *E. coli* chromosomal DNA, the following primer set was used: PstI-CIDI 1 R (5'-GTGTGATGGATATCTGCAGAATTCG, SEQ ID NO:29) and NsiI-CIDI 1 F (5'-CATCAATGCATCGCCCTTAGGAGGTAAAAAAACATG, SEQ ID NO:30). Template DNA was chromosomal DNA isolated by standard methods from *E. coli* FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into *E. coli* TOP10 cells and tranformants were grown at 37° C. overnight with selection on LA containing kanamycin (50 μg/ml). The transformants were verified by restriction enzyme digestion and one was frozen as a stock. The plasmid was designated pTrcKanKKDIy.

II. Cloning a Kudzu Isoprene Synthase Gene into pTrcKanKKDIy

The kudzu isoprene synthase gene was amplified by PCR from pTrcKudzu, described in Example 1, using primers MCM50 5'-GATCATGCATTCGCCCTTAGGAGGTAAAAAAACATGTGTGCGACCTCTTCTCAATTTAC T (SEQ ID NO:31) and MCM53 5'-CGGTCGACGGATCCCTGCAGTTAGACATACATCAGCTG (SEQ ID NO:32). The resulting PCR fragment was cloned into pCR2.1 and transformed into *E. coli* TOP10. This fragment contains the coding sequence for kudzu isoprene synthase and an upstream region containing a RBS from *E. coli*. Transformants were incubated overnight at 37° C. with selection on LA containing carbenicillin (50 μg/ml). The correct insertion of the fragment was verified by sequencing and this strain was designated MCM93.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into *E. coli* TOP10 cells and transformants were grown overnight at 37° C. with selection on LA containing Kanamycin at 50 μg/ml. The correct transformant was verified by restriction digestion and the plasmid was designated pTrcKKDyIkISKan (FIGS. 24 and 25). This plasmid was transformed into BL21(λDE3) cells (Invitrogen).

III. Isoprene Production from Mevalonate in *E. Coli* Expressing the Recombinant Lower Mevalonate Pathway and Isoprene Synthase from Kudzu.

Strain BL21/pTrcKKDyIkISKan was cultured in MOPS medium (Neidhardt et al., (1974) *J. Bacteriology* 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 μM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67\times10^{-4}$ mol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

```
CF 07-60 (+) Start of mvaE w/ RBS + ATG start
codon SacI
                                    (SEQ ID NO: 34)
5'-GAGACATGAGCTCAGGAGGTAAAAAAACATGAAAACAGTAGTTATT

ATTG

CF 07-62 (-) Fuse mvaE to mvaS with RBS in between
                                    (SEQ ID NO: 35)
5'-TTTATCAATCCCAATTGTCATGTTTTTTTACCTCCTTTATTGTTTT

CTTAAATC
```

The mvaS gene was amplified from *E. faecalis* genomic DNA (ATCC 700802D-5) with a RBS and spacer from *E. coli* in front using the following primers:

```
CF 07-61 (+) Fuse mvaE to mvaS with RBS in between
                                    (SEQ ID NO: 36)
5'-GATTTAAGAAAACAATAAAGGAGGTAAAAAAACATGACAATTGGG

ATTGATAAA

CF 07-102 (-) End of mvaS gene BglII
                                    (SEQ ID NO: 37)
5'-GACATGACATAGATCTTTAGTTTCGATAAGAACGAACGGT
```

The PCR fragments were fused together with PCR using the following primers:

```
CF 07-60 (+) Start of mvaE w/ RBS + ATG start
codon SacI
                                    (SEQ ID NO: 34)
5'-GAGACATGAGCTCAGGAGGTAAAAAAACATGAAAACAGTAGTTATT

ATTG

CF 07-102 (-) End of mvaS gene BglII
                                    (SEQ ID NO: 37)
5'-GACATGACATAGATCTTTAGTTTCGATAAGAACGAACGGT
```

The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA+50 μg/ml carbenicillin plates. A total of six colonies were chosen and grown overnight in LB+50 μg/ml carbenicillin and plasmids were isolated using a Qiagen kit. The plasmids were digested with SacI and BglII to check for inserts and one correct plasmid was sequenced with the following primers:

```
CF 07-58 (+) Start of mvaE gene
                                    (SEQ ID NO: 38)
5'-ATGAAAACAGTAGTTATTATTGATGC

CF 07-59 (-) End of mvaE gene
                                    (SEQ ID NO: 39)
5'-ATGTTATTGTTTTCTTAAATCATTTAAAATAGC

CF 07-82 (+) Start of mvaS gene
                                    (SEQ ID NO: 40)
5'-ATGACAATTGGGATTGATAAAATTAG

CF 07-83 (-) End of mvaS gene
                                    (SEQ ID NO: 41)
5'-TTAGTTTCGATAAGAACGAACGGT
```

-continued

```
CF 07-86 (+) Sequence in mvaE
                                (SEQ ID NO: 42)
5'-GAAATAGCCCCATTAGAAGTATC

CF 07-87 (+) Sequence in mvaE
                                (SEQ ID NO: 43)
5'-TTGCCAATCATATGATTGAAAATC

CF 07-88 (+) Sequence in mvaE
                                (SEQ ID NO: 44)
5'-GCTATGCTTCATTAGATCCTTATCG

CF 07-89 (+) Sequence mvaS
                                (SEQ ID NO: 45)
5'-GAAACCTACATCCAATCTTTTGCCC
```

The plasmid called pTrcHis2AUpperPathway#1 was correct by sequencing and was transformed into the commercially available *E. coli* strain BL21. Selection was done on LA+50 μg/ml carbenicillin. Two transformants were chosen and grown in LB+50 μg/mlcarbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 μg/ml). A correct colony was identified by screening for the presence of the insert by PCR. The plasmid was designated pCL PtrcUpperPathway (FIGS. 26 and 27A-27D).

VI. Strains Expressing the Combined Upper and Lower Mevalonic Acid Pathways

To obtain a strain with a complete mevalonic acid pathway plus kudzu isoprene synthase, plasmids pTrcKKDyIkISkan and pCLpTrcUpperPathway were both transformed into BL21(λDE3) competent cells (Invitrogen) and transformants were selected on LA containing kanamycin (50 μg/ml) and Spectinomycin (50 μg/ml). The transformants were checked by plasmid prep to ensure that both plasmids were retained in the host. The strain was designated MCM127.

VII. Production of Mevalonic Acid from Glucose in *E. Coli*/pUpperpathway

Single colonies of the BL21/pTrcHis2A-mvaE/mvaS or FM5/p pTrcHis2A-mvaE/mvaS are inoculated into LB+carbenicillin (100 μg/ml) and are grown overnight at 37° C. with shaking at 200 rpm. These cultures were diluted into 50 ml medium in 250 ml baffled flasks to an $OD_{600}$ of 0.1. The medium was TM3+1 or 2% glucose+carbenicillin (100 ug/ml) or TM3+1% glucose+hydrolyzed soy oil+carbenicillin (100 ug/ml) or TM3+biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 μM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli.*

VIII. Production of Isoprene from *E. Coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21(λDE3) and the transformations were done by standard methods. Transformants were selected on L agar containing kanamycin (50 μg/ml) or kanamycin plus spectinomycin (both at a concentration of 50 μg/ml). Plates were grown at 37° C. The resulting strains were designated as follows:

Grown on Kanamycin plus Spectinomycin (50 μg/ml each)

MCM127—pCL Upper MVA+pTrcKKDyIkIS (kan) in BL21(λDE3)

MCM131—pCL1920+pTrcKKDyIkIS (kan) in BL21 (λDE3)

MCM125—pCL Upper MVA+pTrcHis2B (kan) in BL21 (λDE3)

Grown on Kanamycin (50 μg/ml)

MCM64—pTrcKudzu yIDI DXS (kan) in BL21(λDE3)

MCM50—pTrcKudzu (kan) in BL21(λDE3)

MCM123—pTrcKudzu yIDI DXS DXR (kan) in BL21 (λDE3)

The above strains were streaked from freezer stocks to LA+appropriate antibiotic and grown overnight at 37° C. A single colony from each plate was used to inoculate shake flasks (25 ml LB+the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB+the appropriate antibiotic. The cultures were then diluted into 25 ml LB+1% glucose+ the appropriate antibiotic to an $OD_{600}$ of 0.1. Two flasks for each strain were set up, one set for induction with IPTG (800 μM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

| Production of isoprene in *E. coli* strains | |
|---|---|
| Strain | Isoprene (μg/liter/OD/hr |
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS#503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1$H NMR analysis. Samples for HPLC analysis were prepared by centrifugation at 14,000 rpm for 5 minutes to remove cells, followed by the addition of a 300 μl aliquot of supernatant to 900 μl of $H_2O$. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (R1) detection. Under these conditions mevalonic acid eluted as the lactone form at 18.5 minutes.

X. Production of Isoprene from *E. Coli* BL21 Containing the Upper MVA Pathway Plus Kudzu Isoprene Synthase A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 2.2 g/L of isoprene.

Medium Recipe (Per Liter Fermentation Medium):

The medium was generated using the following components per liter fermentation medium: $K_2HPO_4$ 7.5 g, $MgSO_4$*7$H_2O$ 2 g, citric acid monohydrate 2 g, ferric ammonium citrate 0.3 g, yeast extract 0.5 g, and 1000× modified trace metal solution 1 ml. All of the components were added together and dissolved in di$H_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4$*$H_2O$ 30 g, NaCl 10 g, $FeSO_4$*7$H_2O$ 1 g, $CoCl_2$*6$H_2O$ 1 g, ZnSO*7$H_2O$ 1 g, $CuSO_4$*5$H_2O$ 100 mg, $H_3BO_3$ 100 mg, and $NaMoO_4$*2$H_2O$ 100 mg. Each component was dissolved one at a time in di$H_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperPathway (FIG. 26) and pTrcKKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into soytone-yeast extract-glucose medium. After the inoculum grew to OD 1.0 when measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 54 hour fermentation was 3.7 kg. Induction was achieved by adding isopropyl-beta-D-1-thiogalactopyranoside (IPTG). The IPTG concentration was brought to 25 uM when the optical density at 550 nm ($OD_{550}$) reached a value of 10. The IPTG concentration was raised to 50 uM when $OD_{550}$ reached 190. IPTG concentration was raised to 100 uM at 38 hours of fermentation. The $OD_{550}$ profile within the bioreactor over time is shown in FIG. 54. The isoprene level in the off gas from the bioreactor was determined as described herein. The isoprene titer increased over the course of the fermentation to a final value of 2.2 g/L (FIG. 55). The total amount of isoprene produced during the 54 hour fermentation was 15.9 g, and the time course of production is shown in FIG. 56.

XI. Isoprene Fermentation from *E. Coli* Expressing Genes from the Mevalonic Acid Pathway and Grown in Fed-Batch Culture at the 15-L Scale A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 3.0 g/L of isoprene.

Medium Recipe (Per Liter Fermentation Medium):

The medium was generated using the following components per liter fermentation medium: $K_2HPO_4$ 7.5 g, $MgSO_4$*7$H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in di$H_2O$. This solution was autoclaved. The pH was adjusted to 7.0 with ammonium hydroxide (30%) and q.s. to volume. Glucose 10 g, thiamine*HC10.1 g, and antibiotics were added after sterilization and pH adjustment.

1000× Modified Trace Metal Solution:

The 1000× modified trace metal solution was generated using the following components: citric acids*$H_2O$ 40 g, $MnSO_{2t}$*$H_2O$ 30 g, NaCl 10 g, $FeSO_4$*7$H_2O$ 1 g, $CoCl_2$*6$H_2O$ 1 g, ZnSO*7$H_2O$ 1 g, $CuSO_4$*5$H_2O$ 100 mg, $H_3BO_3$ 100 mg, and $NaMoO_4$*2$H_2O$ 100 mg. Each component was dissolved one at a time in di$H_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 59 hour fermentation was 2.2 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 93. The isoprene level in the off gas from the bioreactor was determined as described herein. The isoprene titer increased over the course of the fermentation to a final value of 3.0 g/L (FIG. 94). The total amount of isoprene produced during the 59 hour fermentation was 22.8 g, and the time course of production is shown in FIG. 95. The molar yield of utilized carbon that went into producing isoprene during fermentation was 2.2%. The weight percent yield of isoprene from glucose was 1.0%.

XII. Isoprene Fermentation from *E. Coli* Expressing Genes from the Mevalonic Acid Pathway and Grown in Fed-Batch Culture at the 15-L Scale A 15-L scale fermentation of *E. coli* expressing mevalonic acid pathway polypeptides, *Pueraria lobata* isoprene synthase, and Kudzu isoprene synthase was used to produce isoprene from cells in fed-batch culture. This experiment demonstrates that growing cells under glucose limiting conditions resulted in the production of 3.3 g/L of isoprene.

i) Construction of pCLPtrcUpperPathwayHGS2

The gene encoding isoprene synthase from *Pueraria lobata* was PCR-amplified using primers NsiI-RBS-HGS F (CTTGATGCATCCTGCATTCGCCCTTAGGAGG, SEQ ID NO:88) and pTrcR(CCAGGCAAATTCTGTTTTATCAG, SEQ ID NO:89), and pTrcKKDyIkIS as a template. The PCR product thus obtained was restriction-digested with NsiI and PstI and gel-purified. The plasmid pCL PtrcUpperPathway was restriction-digested with PstI and dephosphorylated using rAPid alkaline phosphatase (Roche) according to manufacturer's instructions.

These DNA fragments were ligated together and the ligation reaction was transformed into *E. coli* Top10 chemically competent cells (Invitrogen), plated on L agar containing spectinomycin (50 ug/ml) and incubated overnight at 37° C. Plasmid DNA was prepared from 6 clones using the Qiaquick Spin Mini-prep kit. The plasmid DNA was digested with restriction enzymes EcoRV and MluI to identify a clone in which the insert had the right orientation (i.e., the gene oriented in the same way as the pTrc promoter).

The resulting correct plasmid was designated pCLPtrcUpperPathwayHGS2. This plasmid was assayed using the headspace assay described herein and found to produce isoprene in *E. coli* Top10, thus validating the functionality of the gene. The plasmid was transformed into BL21(LDE3) containing pTrcKKDyIkIS to yield the strain BL21/pCLPtrcUpperPathwayHGS2-pTrcKKDyIkIS. This strain has an extra copy of the isoprene synthase compared to the BL21/pCL PtrcUpperMVA and pTrc KKDyIkIS strain (Example 8, part XI). This strain also had increased expression and activity of HMGS compared to the BL21/pCL PtrcUpperMVA and pTrc KKDyIkIS strain used in Example 8, part XI.

ii) Isoprene Fermentation from *E. Coli* Expressing pCLPtrcUpperPathwayHGS2-pTrcKKDyIkIS and Grown in Fed-Batch Culture at the 15-L Scale Medium Recipe (Per Liter Fermentation Medium):

The medium was generated using the following components per liter fermentation medium: $K_2HPO_4$ 7.5 g, $MgSO_4$*$7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HC10.1 g, and antibiotics were added after sterilization and pH adjustment.

1000× Modified Trace Metal Solution:

The 1000× modified trace metal solution was generated using the following components: citric acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, $CuSO_4$*$5H_2O$ 100 mg, $H_3BO_3$ 100 mg, and $NaMoO_4$*$2H_2O$ 100 mg. Each component is dissolved one at a time in Di $H_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pCLPtrcUpperPathwayHGS2 and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0 measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 58 hour fermentation was 2.1 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 170. The $OD_{550}$ profile within the bioreactor over time is shown in FIG. 104. The isoprene level in the off gas from the bioreactor was determined as described herein. The isoprene titer increased over the course of the fermentation to a final value of 3.3 g/L (FIG. 105). The total amount of isoprene produced during the 58 hour fermentation was 24.5 g and the time course of production is shown in FIG. 106. The molar yield of utilized carbon that went into producing isoprene during fermentation was 2.5%. The weight percent yield of isoprene from glucose was 1.2%. Analysis showed that the activity of the isoprene synthase was increased by approximately 3-4 times that compared to BL21 expressing CL PtrcUpperMVA and pTrc KKDyIkIS plasmids (data not shown).

XIII Chromosomal Integration of the Lower Mevalonate Pathway in *E. coli.*

A synthetic operon containing mevalonate kinase, mevalonate phosphate kinase, mevalonate pyrophosphate decarboxylase, and the IPP isomerase was integerated into the chromosome of *E. coli*. If desired, expression may be altered by integrating different promoters 5' of the operon.

Table 9 lists primers used for this experiment.

TABLE 9

| Primers | | |
|---|---|---|
| MCM78 | attTn7 up rev for construct integration | gcatgctcgagcggccgcTTTTAATCAAACATCCTGCCAACTC (SEQ ID NO: 91) |

TABLE 9-continued

| Primers | | |
|---|---|---|
| MCM79 | attTn7 down rev for integration construct | gatcgaagggcgatcgTGTCACAGTCTGGCGAAACC G (SEQ ID NO: 92) |
| MCM88 | attTn7 up forw for integration construct | ctgaattctgcagatatcTGTTTTTCCACTCTTCGTTCA CTTT (SEQ ID NO: 93) |
| MCM89 | attTn7 down forw for integration construct | tctagagggcccAAGAAAAATGCCCCGCTTACG (SEQ ID NO: 94) |
| MCM104 | GI1.2 promoter - MVK | Gatcgcggccgcgcccttgacgatgccacatcctgagcaaataat tcaaccactaattgtgagcggataacacaaggaggaaacagctat gtcattaccgttcttaacttc (SEQ ID NO: 95) |
| MCM105 | aspA terminator - yIDI | Gatcgggccccaagaaaaaaggcacgtcatctgacgtgcctttttt atttgtagacgcgttgttatagcattcta (SEQ ID NO: 96) |
| MCM120 | Forward of attTn7: attTn7 homology, GB marker homology | aaagtagccgaagatgacggtttgtcacatggagttggcaggatgt ttgattaaaagcAATTAACCCTCACTAAAGGGCGG (SEQ ID NO: 97) |
| MCM127 | Rev complement of 1.2 GI: GB marker homology (extra long), promoter, RBS, ATG | AGAGTGTTCACCAAAAATAATAACCTTTCCCG GTGCAgaagttaagaacggtaatgacatagctgtttcctccttgt gttatccgctcacaattagtggttgaattatttgctcaggatgtggcatc gtcaagggcTAATACGACTCACTATAGGGCTCG (SEQ ID NO: 98) |

i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 uL reaction with luL 10 uM primers, 3 uL ddH2O, 45 uL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcKKDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM 120 and MCM 127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 uL PCR reactions containing 1 uL~10 ng/uL template, 1 uL each primer, 1.25 uL 10 mM dNTPs, 5 uL 10× buffer, 1 uL enzyme, and 39.75 uL ddH20. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 30° C. Transformant MCM330 was selected on LA with CMPS, Kan50 (FIGS. 107 and 108A-108C).

iii) Integration into *E. coli* Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 40 C. ddH2O before electroporation with 2 uL of DNA. Integrants were selected on L agar with containing chloramphenicol (5 ug/ml) and subsequently confirmed to not grow on L agar+Kanamycin (50 ug/ml). BL21 integrant MCM331 and MG1655 integrant MCM333 were frozen.

iv) Construction of pET24D-Kudzu Encoding Kudzu Isoprene Synthase

The kudzu isoprene synthase gene was subcloned into the pET24d vector (Novagen) from the pCR2.1 vector (Invitrogen). In particular, the kudzu isoprene synthase gene was amplified from the pTrcKudzu template DNA using primers MCM50 5'-GATCATGCAT TCGCCCTTAG GAGGTAAAAA AACATGTGTG CGACCTCTTC TCAATTTACT (SEQ ID NO:99) and MCM53 5'-CGGTCGACGG ATCCCTGCAG TTAGACATAC ATCAGCTG (SEQ ID NO:100). PCR reactions were carried out using Taq DNA Polymerase (Invitrogen), and the resulting PCR product was cloned into pCR2.1-TOPO TA cloning vector (Invitrogen), and transformed into *E. coli* Top10 chemically competent cells (Invitrogen). Transformants were plated on L agar containing carbenicillin (50 μg/ml) and incubated overnight at 37° C. Five ml Luria Broth cultures containing carbenicillin 50 μg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu isoprene synthase coding sequence in a pCR2.1 backbone.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu isoprene synthase fragment was ligated to the NcoI/BamH1 digested pET24d using the Rapid DNA Ligation Kit (Roche) at a 5:1 fragment to vector ratio in a total volume of 20 μl. A portion of the ligation mixture (5 μl) was transformed into *E. coli* Top 10 chemically competent cells and plated on L agar containing kanamycin (50 μg/ml). The correct transformant was confirmed by sequencing and transformed into chemically competent BL21(λDE3)pLysS cells (Novagen). A single colony was selected after overnight growth at 37° C. on L agar containing kanamycin (50 μg/ml). A map of the resulting plasmid designated as pET24D-Kudzu is shown in FIG. 109. The sequence of pET24D-Kudzu (SEQ ID NO:101) is shown in FIGS. 110A and 110B. Isoprene synthase activity was confirmed using a headspace assay.

v) Production Strains

Strains MCM331 and MCM333 were cotransformed with plasmids pCLPtrcupperpathway and either pTrcKudzu or pETKudzu, resulting in the strains shown in Table 10.

TABLE 10

Production Strains

| Background | Integrated Lower | Upper MVA plasmid | Isoprene synthase plasmid | Production Stain |
|---|---|---|---|---|
| BL21(DE3) | MCM331 | pCLPtrcUpper Pathway | pTrcKudzu | MCM343 |
| BL21(DE3) | MCM331 | pCLPtrcUpper Pathway | pET24D-Kudzu | MCM335 |
| MG1655 | MCM333 | pCLPtrcUpper Pathway | pTrcKudzu | MCM345 |

vi) Isoprene Fermentation from *E. Coli* Expressing Genes from the Mevalonic Acid Pathway and Grown in Fed-Batch Culture at the 15-L Scale.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HC10.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the gi1.2 integrated lower MVA pathway described above and the pCL PtrcUpperMVA and pTrcKudzu plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 57 hour fermentation was 3.9 kg. Induction was achieved by adding IPTG. The IPTG concentration was brought to 100 uM when the carbon dioxide evolution rate reached 100 mmol/L/hr. The $OD_{550}$ profile within the bioreactor over time is shown in FIG. 111A. The isoprene level in the off gas from the bioreactor was determined as described herein. The isoprene titer increased over the course of the fermentation to a final value of 1.6 g/L (FIG. 111B). The specific productivity of isoprene over the course of the fermentation is shown in FIG. 111C and peaked at 1.2 mg/OD/hr. The total amount of isoprene produced during the 57 hour fermentation was 16.2 g. The molar yield of utilized carbon that went into producing isoprene during fermentation was 0.9%. The weight percent yield of isoprene from glucose was 0.4%.

XIV. Production of Isoprene from *E. Coli* BL21 Containing the Kudzu Isoprene Synthase Using Glycerol as a Carbon Source A 15-L scale fermentation of *E. coli* expressing Kudzu isoprene synthase was used to produce isoprene from cells fed glycerol in fed-batch culture. This experiment demonstrates that growing cells in the presence of glycerol (without glucose) resulted in the production of 2.2 mg/L of isoprene.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glycerol 5.1 g, thiamine*HC10.1 g, and antibiotics were added after sterilization and pH adjustment.

1000× Modified Trace Metal Solution:

The medium was generated using the following components per liter fermentation medium: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the pTrcKudzu plasmid. This experiment was carried out to monitor isoprene formation from glycerol at the desired fermentation pH 7.0 and temperature 35° C. An inoculum of *E. coli* strain taken from a frozen vial was streaked onto an LA broth agar plate (with antibiotics) and incubated at 37° C. A single colony was inoculated into soytone-yeast extract-glucose medium and grown at 35° C. After the inoculum grew to OD 1.0, measured at 550 nm, 600 mL was used to inoculate a 7.5-L bioreactor.

Glycerol was fed at an exponential rate until cells reached an optical density at 550 nm ($OD_{550}$) of 153. The total amount of glycerol delivered to the bioreactor during the 36 hour fermentation was 1.7 kg. Other than the glucose in the inoculum, no glucose was added to the bioreactor. Induction was achieved by adding IPTG. The IPTG concentration was brought to 20 uM when the $OD_{550}$ reached a value of 50. The $OD_{550}$ profile within the bioreactor over time is shown in FIG. 57. The isoprene level in the off gas from the bioreactor was determined as described herein. The isoprene titer increased over the course of the fermentation to a final value of 2.2 mg/L (FIG. 58). The total amount of isoprene produced during the 54 hour fermentation was 20.9 mg, and the time course of production is shown in FIG. 59.

XV. Isoprene Fermentation from *E. Coli* Expressing Genes from the Mevalonic Acid Pathway and Grown in Fed-Batch Culture at the 15-L Scale Using Invert Sugar as a Carbon Source A 15-L scale fermentation of *E. coli* expressing mevalonic acid pathway polypeptides and Kudzu isoprene synthase was used to produce isoprene from cells fed invert sugar in fed-batch culture. This experiment demonstrates that growing cells in the presence of invert sugar resulted in the production of 2.4 g/L of isoprene.

Medium Recipe (Per Liter Fermentation Medium):

The medium was generated using the following components per liter fermentation medium: $K_2HPO_4$ 7.5 g, $MgSO_4$*7$H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in di$H_2O$. This solution was autoclaved. The pH was adjusted to 7.0 with ammonium hydroxide (30%) and q.s. to volume. Invert sugar 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4$*$H_2O$ 30 g, NaCl 10 g, $FeSO_4$*7$H_2O$ 1 g, $CoCl_2$*6$H_2O$ 1 g, ZnSO*7$H_2O$ 1 g, $CuSO_4$*5$H_2O$ 100 mg, $H_3BO_3$ 100 mg, and $NaMoO_4$*2$H_2O$ 100 mg. Each component is dissolved one at a time in Di H2O, pH to 3.0 with HCl/NaOH, then q.s. to volume and filter sterilized with 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from invert sugar at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Invert sugar was fed at an exponential rate until cells reached the stationary phase. After this time the invert sugar feed was decreased to meet metabolic demands. The total amount of invert sugar delivered to the bioreactor during the 44 hour fermentation was 2.4 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 200. The $OD_{550}$ profile within the bioreactor over time is shown in FIG. 96. The isoprene level in the off gas from the bioreactor was determined as described herein. The isoprene titer increased over the course of the fermentation to a final value of 2.4 g/L (FIG. 97). The total amount of isoprene produced during the 44 hour fermentation was 18.4 g and the time course of production is shown in FIG. 98. The molar yield of utilized carbon that went into producing isoprene during fermentation was 1.7%. The weight percent yield of isoprene from glucose was 0.8%.

Example 9

Construction of the Upper and Lower MVA Pathway for Integration into *Bacillus Subtilis*

I. Construction of the Upper MVA Pathway in *Bacillus subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allowed them to be fused together by a PCR reaction. PCR amplifications are carried out using Herculase polymerase according to manufacturer's instructions.

```
1. PaprE
CF 07-134 (+) Start of aprE promoter PstI
                                        (SEQ ID NO: 82)
5'-GACATCTGCAGCTCCATTTTCTTCTGC

CF 07-94 (-) Fuse PaprE to mvaE
                                        (SEQ ID NO: 83)
5'-CAATAATAACTACTGTTTTCACTCTTTACCCTCTCCTTTTAA
```

Template: *Bacillus subtilis* Chromosomal DNA

```
2. mvaE
CF 07-93 (+) fuse mvaE to the aprE promoter (GTG start codon)
                                                  (SEQ ID NO: 84)
5'-TTAAAAGGAGAGGGTAAAGAGTGAAAACAGTAGTTATTATTG

CF 07-62 (-) Fuse mvaE to mvaS with RBS in between
                                                  (SEQ ID NO: 35)
5'-TTTATCAATCCCAATTGTCATGTTTTTTTACCTCCTTTATTGTTTTCTTAAATC
```

Template: *Enterococcus faecalis* Chromosomal DNA (from ATCC)

```
3. mvaS
CF 07-61 (+) Fuse mvaE to mvaS with RBS in between
                                        (SEQ ID NO: 36)
5'-GATTTAAGAAAACAATAAAGGAGGTAAAAAAACATGACAATTGGGA

TTGATAAA

CF 07-124 (-) Fuse the end of mvaS to the
terminator
                                        (SEQ ID NO: 85)
5'-CGGGGCCAAGGCCGGTTTTTTTTAGTTTCGATAAGAACGAACGGT
```

Template: *Enterococcus faecalis* Chromosomal DNA

```
4. B. amyliquefaciens alkaline serine protease
terminator
CF 07-123 (+) Fuse the end of mvaS to the
terminator
                                    (SEQ ID NO: 102)
5'-ACCGTTCGTTCTTATCGAAACTAAAAAAAACCGGCCTTGGCCCCG

CF 07-46 (-) End of B. amyliquefaciens terminator
BamHI
                                     (SEQ ID NO: 63)
5'-GACATGACGGATCCGATTACGAATGCCGTCTC
```

Template: *Bacillus Amyliquefaciens* Chromosomal DNA

PCR Fusion Reactions

```
5. Fuse mvaE to mvaS
CF 07-93 (+) fuse mvaE to the aprE promoter (GTG start codon)
                                            (SEQ ID NO: 84)
5'-TTAAAAGGAGAGGGTAAAGAGTGAAAACAGTAGTTATTATTG

CF 07-124 (-) Fuse the end of mvaS to the terminator
                                            (SEQ ID NO: 85)
5'-CGGGGCCAAGGCCGGTTTTTTTTAGTTTCGATAAGAACGAACGGT
```

Template: #2 and 3 from Above

```
6. Fuse mvaE-mvaS to aprE promoter
CF 07-134 (+) Start of aprE promoter PstI
                                     (SEQ ID NO: 82)
5'-GACATCTGCAGCTCCATTTTCTTCTGC

CF 07-124 (-) Fuse the end of mvaS to the
terminator
                                     (SEQ ID NO: 85)
5'-CGGGGCCAAGGCCGGTTTTTTTTAGTTTCGATAAGAACGAACGGT
```

Template #1 and #4 from Above

```
7. Fuse PaprE-mvaE-mvaS to terminator
CF 07-134 (+) Start of aprE promoter PstI
                              (SEQ ID NO: 82)
5'-GACATCTGCAGCTCCATTTTCTTCTGC

CF 07-46 (-) End of B. amyliquefaciens
terminator BamHI
                              (SEQ ID NO: 63)
5'-GACATGACGGATCCGATTACGAATGCCGTCTC
```

Template: #4 and #6

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIGS. 50 and 51). Purified plasmid DNA is transformed into *Bacillus subtilis* aprEnprE Pxyl-comK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

```
Sequencing primers:
CF 07-134 (+) Start of aprE promoter PstI
                                    (SEQ ID NO: 82)
5'-GACATCTGCAGCTCCATTTTCTTCTGC

CF 07-58 (+) Start of mvaE gene
                                    (SEQ ID NO: 38)
5'-ATGAAAACAGTAGTTATTATTGATGC
```

-continued

```
CF 07-59 (-) End of mvaE gene
                                    (SEQ ID NO: 39)
5'-ATGTTATTGTTTTCTTAAATCATTTAAAATAGC

CF 07-82 (+) Start of mvaS gene
                                    (SEQ ID NO: 40)
5'-ATGACAATTGGGATTGATAAAATTAG

CF 07-83 (-) End of mvaS gene
                                    (SEQ ID NO: 41)
5'-TTAGTTTCGATAAGAACGAACGGT

CF 07-86 (+) Sequence in mvaE
                                    (SEQ ID NO: 42)
5'-GAAATAGCCCCATTAGAAGTATC

CF 07-87 (+) Sequence in mvaE
                                    (SEQ ID NO: 43)
5'-TTGCCAATCATATGATTGAAAATC

CF 07-88 (+) Sequence in mvaE
                                    (SEQ ID NO: 44)
5'-GCTATGCTTCATTAGATCCTTATCG

CF 07-89 (+) Sequence mvaS
                                    (SEQ ID NO: 45)
5'-GAAACCTACATCCAATCTTTTGCCC
```

Transformants are selected on LA containing chloramphenicol at a concentration of 5 μg/ml. One colony is confirmed to have the correct integration by sequencing and is plated on LA containing increasing concentrations of chloramphenicol over several days, to a final level of 25 μg/ml. This results in amplification of the cassette containing the genes of interest. The resulting strain is designated CF 455: pJMupperpathway#1 × *Bacillus subtilis* aprEnprE Pxyl comK (amplified to grow on LA containing chloramphenicol 25 μg/ml).

II. Construction of the Lower MVA Pathway in *Bacillus subtilis*

The lower MVA pathway, consisting of the genes mvkl, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10

Exemplary Isoprene Compositions and Methods of Making them

I. Compositional Analysis of Fermentation Off-Gas Containing Isoprene

A 14 L scale fermentation was performed with a recombinant *E. coli* BL21 (DE3) strain containing two plasmids (pCL upperMev; pTrcKKDyIkIS encoding the full mevalonate pathway for isoprenoid precursor biosynthesis, an isoprenyl pyrophosphate isomerase from yeast, and an isoprene synthase from Kudzu. Fermentation off-gas from the 14 L tank was collected into 20 mL headspace vials at around the time of peak isoprene productivity (27.9 hours elapsed fermentation time, "EFT") and analyzed by headspace GC/MS for volatile components.

Headspace analysis was performed with an Agilent 6890 GC/MS system fitted with an Agilent HP-5MS GC/MS column (30 m×250 μm; 0.25 μm film thickness). A combiPAL autoinjector was used for sampling 500 uL aliquots from 20 mL headspace vials. The GC/MS method utilized helium as the carrier gas at a flow of 1 mL/min. The injection port was held at 250° C. with a split ratio of 50:1. The oven temperature was held at 37° C. for an initial 2 minute period, followed an increase to 237° C. at a rate of 25° C./min for a total method time of 10 minutes. The Agilent 5793N mass selective detector scanned from m/z 29 to m/z 300. The limit of detection of this system is approximately 0.1 ug/$L_{gas}$ or approximately 0.1 ppm. If desired, more sensitive equipment with a lower limit of detection may be used.

The off-gas consisted of 99.925% (v/v) permanent gases ($N_2$, $CO_2$ and $O_2$), approximately 0.075% isoprene (2-methyl-1,3-butadiene) (~750 ppmv, 2100 μg/L) and minor amounts (<50 ppmv) of ethanol, acetone, and two C5 prenyl alcohols. The amount of water vapor was not determined but was estimated to be equal to the equilibrium vapor pressure at 0° C. The composition of the volatile organic fraction was determined by integration of the area under the peaks in the GC/MS chromatogram (FIGS. 86A and 86B) and is listed in Table 6. Calibration curves for ethanol and acetone standards enabled the conversion of GC area to gas phase concentration in units of ug/L using standard methods.

TABLE 6

Composition of volatile organic components in fermentation off-gas.

| Compound | RT (min) | GC area | Area % | Conc. (ug/L) |
|---|---|---|---|---|
| Ethanol | 1.669 | 239005 | 0.84 | 62 +/− 6 |
| Acetone | 1.703 | 288352 | 1.02 | 42 +/− 4 |
| Isoprene (2-methyl-1,3-butadiene) | 1.829 | 27764544 | 97.81 | 2000 +/− 200 |
| 3-methyl-3-buten-1-ol | 3.493 | 35060 | 0.12 | <10 |
| 3-methyl-2-buten-1-ol | 4.116 | 58153 | 0.20 | <10 |

The off-gas was analyzed at the 27.9 hour time point of a fermentation using an *E. coli* BL21 (DE3) strain expressing a heterologous mevalonate pathway, an isoprenyl pyrophosphate isomerase from yeast, and an isoprene synthase from Kudzu.

II. Measurement of Trace Volatile Organic Compounds (VOCs) Co-Produced with Isoprene During Fermentation of a Recombinant *E. Coli* Strain A 14 L scale fermentation was performed with a recombinant *E. coli* BL21 (DE3) strain containing two plasmids (pCL upperMev; pTrcKKDyIkIS) encoding the full mevalonate pathway for isoprenoid precursor biosynthesis, an isoprenyl pyrophosphate isomerase from yeast, and an isoprene synthase from Kudzu.

Fermentation off-gas was passed through cooled headspace vials in order to concentrate and identify trace volatile organic components. The off-gas from this fermentation was sampled at a rate of 1 L/min for 10 minutes through a 20 mL headspace vial packed with quartz wool (2 g) and cooled to −78° C. with dry ice. The vial was recapped with a fresh vial cap and analyzed by headspace GC/MS for trapped VOCs using the conditions described in Example 10, part I. The ratios of compounds observed in FIGS. 87A-87D are a combination of overall level in the fermentation off-gas, the relative vapor pressure at −78° C., and the detector response of the mass spectrometer. For example, the low level of isoprene relative to oxygenated volatiles (e.g., acetone and ethanol) is a function of the high volatility of this material such that it does not accumulate in the headspace vial at −78° C.

The presence of many of these compounds is unique to isoprene compositions derived from biological sources. The results are depicted in FIGS. 87A-87D and summarized in Tables 7A and 7B.

TABLE 7A

Trace volatiles present in off-gas produced by *E. coli* BL21 (DE3) (pCL upperMev; pTrcKKDyIkIS) following cryo-trapping at −78° C.

| Compound | RT (min) | GC Area[1] | Area %[2] | Ratio %[3] |
|---|---|---|---|---|
| Acetaldehyde | 1.542 | 4019861 | 4.841 | 40.14 |
| Ethanol | 1.634 | 10553620 | 12.708 | 105.39 |
| Acetone | 1.727 | 7236323 | 8.714 | 72.26 |
| 2-methyl-1,3-butadiene | 1.777 | 10013714 | 12.058 | 100.00 |
| 1-propanol | 1.987 | 163574 | 0.197 | 1.63 |
| Diacetyl | 2.156 | 221078 | 0.266 | 2.21 |
| 2-methyl-3-buten-2-ol | 2.316 | 902735 | 1.087 | 9.01 |
| 2-methyl-1-propanol | 2.451 | 446387 | 0.538 | 4.46 |
| 3-methyl-1-butanal | 2.7 | 165162 | 0.199 | 1.65 |
| 1-butanol | 2.791 | 231738 | 0.279 | 2.31 |
| 3-methyl-3-buten-1-ol | 3.514 | 14851860 | 17.884 | 148.32 |
| 3-methyl-1-butanol | 3.557 | 8458483 | 10.185 | 84.47 |
| 3-methyl-2-buten-1-ol | 4.042 | 18201341 | 21.917 | 181.76 |
| 3-methyl-2-butenal | 4.153 | 1837273 | 2.212 | 18.35 |
| 3-methylbutyl acetate | 5.197 | 196136 | 0.236 | 1.96 |
| 3-methyl-3-but-1-enyl acetate | 5.284 | 652132 | 0.785 | 6.51 |
| 2-heptanone | 5.348 | 67224 | 0.081 | 0.67 |
| 2,5-dimethylpyrazine | 5.591 | 58029 | 0.070 | 0.58 |
| 3-methyl-2-but-1-enyl acetate | 5.676 | 1686507 | 2.031 | 16.84 |
| 6-methyl-5-hepten-2-one | 6.307 | 101797 | 0.123 | 1.02 |
| 2,4,5-trimethylpyridine | 6.39 | 68477 | 0.082 | 0.68 |
| 2,3,5-trimethylpyrazine | 6.485 | 30420 | 0.037 | 0.30 |
| (E)-3,7-dimethyl-1,3,6-octatriene | 6.766 | 848928 | 1.022 | 8.48 |
| (Z)-3,7-dimethyl-1,3,6-octatriene | 6.864 | 448810 | 0.540 | 4.48 |
| 3-methyl-2-but-1-enyl butyrate | 7.294 | 105356 | 0.127 | 1.05 |
| Citronellal | 7.756 | 208092 | 0.251 | 2.08 |
| 2,3-cycloheptenolpyridine | 8.98 | 1119947 | 1.349 | 11.18 |

[1]GC area is the uncorrected area under the peak corresponding to the listed compound.
[2]Area % is the peak area expressed as a % relative to the total peak area of all compounds.
[3]Ratio % is the peak area expressed as a % relative to the peak area of 2-methyl-1,3-butadiene.

TABLE 7B

Trace volatiles present in off-gas produced by *E. coli* BL21 (DE3) (pCL upperMev; pTrcKKDyIkIS) following cryo-trapping at −196° C.

| Compound | RT (min) | GC Area[1] | Area %[2] | Ratio %[3] |
|---|---|---|---|---|
| Acetaldehyde | 1.54 | 1655710 | 0.276 | 0.33 |
| Methanethiol | 1.584 | 173620 | 0.029 | 0.03 |
| Ethanol | 1.631 | 10259680 | 1.707 | 2.03 |
| Acetone | 1.722 | 73089100 | 12.164 | 14.43 |
| 2-methyl-1,3-butadiene | 1.771 | 506349429 | 84.269 | 100.00 |
| methyl acetate | 1.852 | 320112 | 0.053 | 0.06 |
| 1-propanol | 1.983 | 156752 | 0.026 | 0.03 |
| Diacetyl | 2.148 | 67635 | 0.011 | 0.01 |
| 2-butanone | 2.216 | 254364 | 0.042 | 0.05 |
| 2-methyl-3-buten-2-ol | 2.312 | 684708 | 0.114 | 0.14 |
| ethyl acetate | 2.345 | 2226391 | 0.371 | 0.44 |
| 2-methyl-1-propanol | 2.451 | 187719 | 0.031 | 0.04 |
| 3-methyl-1-butanal | 2.696 | 115723 | 0.019 | 0.02 |
| 3-methyl-2-butanone | 2.751 | 116861 | 0.019 | 0.02 |
| 1-butanol | 2.792 | 54555 | 0.009 | 0.01 |
| 2-pentanone | 3.034 | 66520 | 0.011 | 0.01 |
| 3-methyl-3-buten-1-ol | 3.516 | 1123520 | 0.187 | 0.22 |
| 3-methyl-1-butanol | 3.561 | 572836 | 0.095 | 0.11 |
| ethyl isobutyrate | 3.861 | 142056 | 0.024 | 0.03 |
| 3-methyl-2-buten-1-ol | 4.048 | 302558 | 0.050 | 0.06 |
| 3-methyl-2-butenal | 4.152 | 585690 | 0.097 | 0.12 |
| butyl acetate | 4.502 | 29665 | 0.005 | 0.01 |
| 3-methylbutyl acetate | 5.194 | 271797 | 0.045 | 0.05 |
| 3-methyl-3-but-1-enyl acetate | 5.281 | 705366 | 0.117 | 0.14 |
| 3-methyl-2-but-1-enyl acetate | 5.675 | 815186 | 0.136 | 0.16 |
| (E)-3,7-dimethyl-1,3,6-octatriene | 6.766 | 207061 | 0.034 | 0.04 |
| (Z)-3,7-dimethyl-1,3,6-octatriene | 6.863 | 94294 | 0.016 | 0.02 |
| 2,3-cycloheptenolpyridine | 8.983 | 135104 | 0.022 | 0.03 |

[1]GC area is the uncorrected area under the peak corresponding to the listed compound.
[2]Area % is the peak area expressed as a % relative to the total peak area of all compounds.
[3]Ratio % is the peak area expressed as a % relative to the peak area of 2-methyl-1,3-butadiene.

III. Absence of C5 Hydrocarbon Isomers in Isoprene Derived from Fermentation.

Cryo-trapping of isoprene present in fermentation off-gas was performed using a 2 mL headspace vial cooled in liquid nitrogen. The off-gas (1 L/min) was first passed through a 20 mL vial containing sodium hydroxide pellets in order to minimize the accumulation of ice and solid $CO_2$ in the 2 mL vial (−196° C.). Approximately 10L of off-gas was passed through the vial, after which it was allowed to warm to −78° C. with venting, followed by resealing with a fresh vial cap and analysis by GC/MS.

GC/MS headspace analysis was performed with an Agilent 6890 GC/MS system using a 100 uL gas tight syringe in headspace mode. A Zebron ZB-624 GC/MS column (30 m×250 μm; 1.40 μm film thickness) was used for separation of analytes. The GC autoinjector was fitted with a gas-tight 100 uL syringe, and the needle height was adjusted to allow the injection of a 50 uL headspace sample from a 2 mL GC vial. The GC/MS method utilized helium as the carrier gas at a flow of 1 mL/min. The injection port was held at 200° C. with a split ratio of 20:1. The oven temperature was held at 37° C. for the 5 minute duration of the analysis. The Agilent 5793N mass selective detector was run in single ion monitoring (SIM) mode on m/z 55, 66, 67 and 70. Under these conditions, isoprene was observed to elute at 2.966 minutes (FIG. 88B). A standard of petroleum derived isoprene (Sigma-Aldrich) was also analyzed using this method and was found to contain additional C5 hydrocarbon isomers, which eluted shortly before or after the main peak and were quantified based on corrected GC area (FIG. 88A).

TABLE 8A

GC/MS analysis of petroleum-derived isoprene

| Compound | RT (min) | GC area | Area % of total C5 hydrocarbons |
|---|---|---|---|
| 2-methyl-1-butene | 2.689 | $18.2 \times 10^3$ | 0.017% |
| (Z)-2-pentene | 2.835 | $10.6 \times 10^4$ | 0.101% |
| Isoprene | 2.966 | $10.4 \times 10^7$ | 99.869% |
| 1,3-cyclopentadiene (CPD) | 3.297 | $12.8 \times 10^3$ | 0.012% |

TABLE 8B

GC/MS analysis of fermentation-derived isoprene (% total C5 hydrocarbons)

| Compound | RT (min) | Corrected GC Area | % of total C5 hydrocarbons |
|---|---|---|---|
| Isoprene | 2.966 | $8.1 \times 10^7$ | 100% |

In a separate experiment, a standard mixture of C5 hydrocarbons was analyzed to determine if the detector response was the same for each of the compounds. The compounds were 2-methyl-1-butene, 2-methyl-1,3-butadiene, (E)-2-pentene, (Z)-2-pentene and (E)-1,3-pentadiene. In this case, the analysis was performed on an Agilent DB-Petro column (100 m×0.25 mm, 0.50 um film thickness) held at 50° C. for 15 minutes. The GC/MS method utilized helium as the carrier gas at a flow of 1 mL/min. The injection port was held at 200° C. with a split ratio of 50:1. The Agilent 5793N mass selective detector was run in full scan mode from m/z 19 to m/z 250. Under these conditions, a 100 ug/L concentration of each standard produced the same detector response within experimental error.

IV. Compositions Comprising Isoprene Adsorbed to a Solid Phase.

Biologically-produced isoprene was adsorped to activated carbon resulting in a solid phase containing 50 to 99.9% carbon, 0.1% to 50% isoprene, 0.01% to 5% water, and minor amounts (<0.1%) of other volatile organic components.

Fermentation off-gas was run through a copper condensation coil held at 0° C., followed by a granulated silica desiccant filter in order to remove water vapor. The dehumidified off-gas was then run through carbon containing filters (Koby Jr, Koby Filters, MA) to the point at which breakthrough of isoprene was detected in the filter exhaust by GC/MS. The amount of isoprene adsorped to the cartridge can be determined indirectly by calculating the concentration in the off-gas, the overall flow rate and the percent breakthrough over the collection period. Alternately the adsorped isoprene can be recovered from the filters by thermal, vacuum, or solvent-mediated desorption.

V. Collection and Analysis of Condensed Isoprene.

Fermentation off-gas is dehumidified, and the $CO_2$ removed by filtration through a suitable adsorbant (e.g., ascarite). The resulting off-gas stream is then run through a liquid nitrogen-cooled condenser in order to condense the VOCs in the stream. The collection vessel contains t-butyl catechol to inhibit the resulting isoprene condensate. The condensate is analyzed by GC/MS and NMR in order to determine purity using standard methods, such as those described herein.

VI. Production of Prenyl Alcohols by Fermentation

Analysis of off-gas from an *E. coli* BL21 (DE3) strain expressing a Kudzu isoprene synthase revealed the presence of both isoprene and 3-methyl-3-buten-1-ol (isoprenol). The levels of the two compounds in the fermentation off-gas over the fermentation are shown in FIG. 89 as determined by headspace GC/MS. Levels of isoprenol (3-methyl-3-buten-1-ol, 3-MBA) attained was nearly 10 ug/$L_{offgas}$ in this experiment. Additional experiments produced levels of approximately 20 ug/$L_{offgas}$ in the fermentation off-gas.

Example 11

The De-Coupling of Growth and Production of Isoprene in *E. Coli* Expressing Genes from the Mevalonic Acid Pathway and Fermented in a Fed-Batch Culture Example 11 illustrates the de-coupling of cell growth from mevalonic acid and isoprene production.

I. Fermentation Conditions

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, ZnSO*$7H_2O$ 1 g, $CuSO_4*5H_2O$ 100 mg, $H_3BO_3$ 100 mg, and $NaMoO_4*2H_2O$ 100 mg. Each component was dissolved one at a time in Di $H_2O$, pH to 3.0 with HCl/NaOH, then q.s. to volume, and filter sterilized with a 0.22 micron filter.

Fermentation was performed with *E. coli* cells containing the pTrcHis2AUpperPathway (also called pTrcUpperMVA, FIGS. 91 and 92A-92C) (50 μg/ml carbenicillin) or the pCL PtrcUpperMVA (also called pCL PtrcUpperPathway (FIG. 26)) (50 μg/ml spectinomycin) plasmids. For experiments in which isoprene was produced, the *E. coli* cells also contained the pTrc KKDyIkIS (50 μg/mlkanamycin) plasmid. These experiments were carried out to monitor mevalonic acid or isoprene formation from glucose at the desired fermentation pH 7.0 and temperature 30° C. An inoculum of an *E. coli* strain taken from a frozen vial was streaked onto an LA broth agar plate (with antibiotics) and incubated at 37° C. A single colony was inoculated into tryptone-yeast extract medium. After the inoculum grew to optical density 1.0 when measured at 550 nm, it was used to inoculate the bioreactor.

Glucose was fed at an exponential rate until cells reached the stationary phase. After this time the glucose feed was decreased to meet metabolic demands. Induction was achieved by adding IPTG. The mevalonic acid concentration in fermentation broth was determined by applying perchloric acid (Sigma-Aldrich #244252) treated samples (0.3 M incubated at 4° C. for 5 minutes) to an organic acids HPLC column (BioRad #125-0140). The concentration was determined by comparing the broth mevalonic acid peak size to a calibration curve generated from mevalonolacetone (Sigma-Aldrich #M4667) treated with perchloric acid to form D,L-mevalonate. The isoprene level in the off gas from the bioreactor was determined as described herein. The isoprene titer is defined as the amount of isoprene produced per liter of fermentation broth.

II. Mevalonic Acid Production from *E. Coli* BL21 (DE3) Cells Expressing the pTrcUpperMVA Plasmid at a 150-L Scale BL21 (DE3) cells that were grown on a plate as explained above in Example 11, part I were inoculated into a flask containing 45 mL of tryptone-yeast extract medium and incubated at 30° C. with shaking at 170 rpm for 5 hours. This solution was transferred to a 5-L bioreactor of tryptone-yeast extract medium, and the cells were grown at 30° C. and 27.5 rpm until the culture reached an $OD_{550}$ of 1.0. The 5 L of inoculum was seeded into a 150-L bioreactor containing 45-kg of medium. The IPTG concentration was brought to 1.1 mM when the $OD_{550}$ reached a value of 10. The $OD_{550}$ profile within the bioreactor over time is shown in FIG. 60A. The mevalonic acid titer increased over the course of the fermentation to a final value of 61.3 g/L (FIG. 60B). The specific productivity profile throughout the fermentation is shown in FIG. 60C and a comparison to FIG. 60A illustrates the de-coupling of growth and mevalonic acid production. The total amount of mevalonic acid produced during the 52.5 hour fermentation was 4.0 kg from 14.1 kg of utilized glucose. The molar yield of utilized carbon that went into producing mevalonic acid during fermentation was 34.2%.

III. Mevalonic Acid Production from *E. Coli* BL21 (DE3) Cells Expressing the pTrcUpperMVA Plasmid at a 15-L Scale BL21 (DE3) cells that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 10. The $OD_{550}$ profile within the bioreactor over time is shown in FIG. 61A. The mevalonic acid titer increased over the course of the fermentation to a final value of 53.9 g/L (FIG. 61B). The specific productivity profile throughout the fermentation is shown in FIG. 61C and a comparison to FIG. 61A illustrates the de-coupling of growth and mevalonic acid production. The total amount of mevalonic acid produced during the 46.6 hour fermentation was 491 g from 2.1 kg of utilized glucose. The molar yield of utilized carbon that went into producing mevalonic acid during fermentation was 28.8%.

IV. Mevalonic Acid Production from *E. Coli* FM5 Cells Expressing the pTrcUpperMVA Plasmid at a 15-L Scale FM5 cells that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 30. The $OD_{550}$ profile within the bioreactor over time is shown in FIG. 62A. The mevalonic acid titer increased over the course of the fermentation to a final value of 23.7 g/L (FIG. 62B). The specific productivity profile throughout the fermentation is shown in FIG. 62C and a comparison to FIG. 62A illustrates the de-coupling of growth and mevalonic acid production. The total amount of mevalonic acid produced during the 51.2 hour fermentation was 140 g from 1.1 kg of utilized glucose. The molar yield of utilized carbon that went into producing mevalonic acid during fermentation was 15.2%.

V. Isoprene Production from *E. Coli* BL21 (DE3) Cells Expressing the pCL PtrcUpperMVA and pTrc KKDyIkIS Plasmids at a 15-L Scale BL21 (DE3) cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 25 μM when the $OD_{550}$ reached a value of 10. The IPTG concentration was raised to 50 uM when $OD_{550}$ reached 190. The IPTG concentration was raised to 100 uM at 38 hours of fermentation. The $OD_{550}$ profile within the bioreactor over time is shown in FIG. 63A. The isoprene titer increased over the course of the fermentation to a final value of 2.2 g/L broth (FIG. 63B). The specific productivity profile throughout the fermentation is shown in FIG. 63C and a comparison to FIG. 63A illustrates the de-coupling of growth and isoprene production. The total amount of isoprene produced during the 54.4 hour fermentation was 15.9 g from 2.3 kg of utilized glucose. The molar yield of utilized carbon that went into producing isoprene during fermentation was 1.53%.

VI. Isoprene Production from *E. Coli* BL21 (DE3) Tuner Cells Expressing the pCL PtrcUpperMVA and pTrc KKDyIkIS Plasmids at a 15-L Scale BL21 (DE3) tuner cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 26 μM when the $OD_{550}$ reached a value of 10. The IPTG concentration was raised to 50 uM when $OD_{550}$ reached 175. The $OD_{550}$ profile within the bioreactor over time is shown in FIG. 64A. The isoprene titer increased over the course of the fermentation to a final value of 1.3 g/L broth (FIG. 64B). The specific productivity profile throughout the fermentation is shown in FIG. 64C and a comparison to FIG. 64A illustrates the de-coupling of growth and isoprene production. The total amount of isoprene produced during the 48.6 hour fermentation was 9.9 g from 1.6 kg of utilized glucose. The molar yield of utilized carbon that went into producing isoprene during fermentation was 1.34%.

VII. Isoprene production from *E. coli* MG1655 cells expressing the pCL PtrcUpperMVA and pTrc KKDyIkIS plasmids at a 15-L scale MG1655 cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 24 μM when the $OD_{550}$ reached a value of 45. The $OD_{550}$ profile within the bioreactor over time is shown in FIG. 65A. The isoprene titer increased over the course of the fermentation to a final value of 393 mg/L broth (FIG. 65B). The specific productivity profile throughout the fermentation is shown in FIG. 65C and a comparison to FIG. 65A illustrates the de-coupling of growth and isoprene production. The total amount of isoprene produced during the 67.4 hour fermentation was 2.2 g from 520 g of utilized glucose. The molar yield of utilized carbon that went into producing isoprene during fermentation was 0.92%.

VIII. Isoprene Production from *E. Coli* MG1655Ack-Pta Cells Expressing the pCL PtrcUpperMVA and pTrc KKDyIkIS Plasmids at a 15-L Scale MG1655ack-pta cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 30 μM when the $OD_{550}$ reached a value of 10. The $OD_{550}$ profile within the bioreactor over time is shown in FIG. 66A. The isoprene titer increased over the course of the fermentation to a final value of 368 mg/L broth (FIG. 66B). The specific productivity profile throughout the fermentation is shown in FIG. 66C and a comparison to FIG. 66A illustrates the de-coupling of growth and isoprene production. The total amount of isoprene produced during the 56.7 hour fermentation was 1.8 g from 531 g of utilized glucose. The molar yield of utilized carbon that went into producing isoprene during fermentation was 0.73%.

IX. Isoprene Production from *E. Coli* FM5 Cells Expressing the pCL PtrcUpperMVA and pTrc KKDyIkIS Plasmids at a 15-L Scale FM5 cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 27 μM when the $OD_{550}$ reached a value of 15. The $OD_{550}$ profile within the bioreactor over time is shown in FIG. 67A. The isoprene titer increased over the course of the fermentation to a final value of 235 mg/L broth (FIG. 67B). The specific productivity profile throughout the fermentation is shown in FIG. 67C and a comparison to FIG. 67A illustrates the de-coupling of growth and isoprene production. The total amount of isoprene produced during the 52.3 hour fermentation was 1.4 g from 948 g of utilized glucose. The molar yield of utilized carbon that went into producing isoprene during fermentation was 0.32%.

Example 12

Production of Isoprene During the Exponential Growth Phase of *E. Coli* Expressing Genes from the Mevalonic Acid Pathway and Fermented in a Fed-Batch Culture Example 12 illustrates the production of isoprene during the exponential growth phase of cells.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in Di H2O, pH to 3.0 with HCl/NaOH, then q.s. to volume and filter sterilized with 0.22 micron filter.

Fermentation was performed in a 15-L bioreactor with ATCC11303 *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 50 hour fermentation was 2.0 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 99. The isoprene level in the off gas from the bioreactor was determined as described herein. The isoprene titer increased over the course of the fermentation to a final value of 1.4 g/L (FIG. 100). The total amount of isoprene produced during the 50 hour fermentation was 10.0 g. The profile of the isoprene specific productivity over time within the bioreactor is shown in FIG. 101. The molar yield of utilized carbon that contributed to producing isoprene during fermentation was 1.1%. The weight percent yield of isoprene from glucose was 0.5%.

Example 13

Flammability Modeling and Testing of Isoprene

I. Summary of Flammability Modeling and Testing of Isoprene

Flammability modeling and experiments were performed for various hydrocarbon/oxygen/nitrogen/water/carbon dioxide mixtures. This modeling and experimental tested was aimed at defining isoprene and oxygen/nitrogen flammability curves under specified steam and carbon monoxide concentrations at a fixed pressure and temperature. A matrix of the model conditions is shown in Table 4, and a matrix of the experiments performed is shown in Table 5.

TABLE 4

Summary of Modeled Isoprene Flammability

| Series | Temperature (° C.) | Pressure (psig) | Steam Concentration (wt %) | Carbon Dioxide Concentration (wt. %) | Isoprene Concentration (vol. %) | Oxygen Concentration (vol. %) |
|---|---|---|---|---|---|---|
| A | 40 | 0 | 0 | 0 | Varying | Varying |
| B | 40 | 0 | 4 | 0 | Varying | Varying |
| C | 40 | 0 | 0 | 5 | Varying | Varying |
| D | 40 | 0 | 0 | 10 | Varying | Varying |
| E | 40 | 0 | 0 | 15 | Varying | Varying |
| F | 40 | 0 | 0 | 20 | Varying | Varying |
| G | 40 | 0 | 0 | 30 | Varying | Varying |

TABLE 5

Summary of Isoprene Flammability Tests

| Series Number | Temperature (° C.) | Pressure (psig) | Steam Concentration (vol. %) | Isoprene Concentration (vol. %) | Oxygen Concentration (vol. %) |
|---|---|---|---|---|---|
| 1 | 40 | 0 | 0 | Varying | Varying |
| 2 | 40 | 0 | 4 | Varying | Varying |

II. Description of Calculated Adiabatic Flame Temperature (CAFT) Model

Calculated adiabatic flame temperatures (CAFT) along with a selected limit flame temperature for combustion propagation were used to determine the flammability envelope for isoprene. The computer program used in this study to calculate the flame temperatures is the NASA Glenn Research Center CEA (Chemical Equilibrium with Applications) software.

There are five steps involved in determining the flammability envelope using an adiabatic flame temperature model for a homogeneous combustion mechanism (where both the fuel and oxidant are in the gaseous state): selection of the desired reactants, selection of the test condition, selection of the limit flame temperature, modification of the reactants, and construction of a flammability envelope from calculations.

In this first step, selection of desired reactants, a decision must be made as to the reactant species that will be present in the system and the quantities of each. In many cases the computer programs used for the calculations have a list of reactant and product species. If any of the data for the species to be studied are not found in the program, they may be obtained from other sources such as the JANAF tables or from the internet. In this current model data for water, nitrogen, oxygen and carbon dioxide were present in the program database. The program database did not have isoprene as a species; therefore the thermodynamic properties were incorporated manually.

The next step is to decide whether the initial pressure and temperature conditions that the combustion process is taking place in. In this model the pressure was 1 atmosphere (absolute) and the temperature was 40° C., the boiling point of isoprene.

The limit flame temperature for combustion can be either selected based on theoretical principles or determined experimentally. Each method has its own limitations.

Based on prior studies, the limit flame temperatures of hydrocarbons fall in the range of 1000 K to 1500 K. For this model, the value of 1500 K was selected. This is the temperature at which the reaction of carbon monoxide to carbon dioxide (a highly exothermic reaction and constitutes a significant proportion of the flame energy) becomes self sustaining.

Once the limit flame temperature has been decided upon, model calculations are performed on the given reactant mixture (species concentrations) and the adiabatic flame temperature is determined. Flame propagation is considered to have occurred only if the temperature is greater than the limit flame temperature. The reactant mixture composition is then modified to create data sets for propagation and non-propagation mixtures.

This type of model shows good agreement with the experimentally determined flammability limits. Regions outside the derived envelope are nonflammable and regions within it are flammable. The shape of the envelope forms a nose. The nose of the envelope is related to the limiting oxygen concentration (LOC) for gaseous fuels.

III. Results from Calculated Adiabatic Flame Temperature (CAFT) Model

Plotted in FIGS. 68 through 74 are the CAFT model results for Series A to G, respectively. The figures plot the calculated adiabatic flame temperature (using the NASA CEA program) as a function of fuel concentration (by weight) for several oxygen/nitrogen ratios (by weight). The parts of the curve that are above 1500 K, the selected limit flame temperature, contain fuel levels sufficient for flame propagation. The results may be difficult to interpret in the form presented in FIGS. 68 through 74. Additionally, the current form is not conducive to comparison with experimental data which is generally presented in terms of volume percent.

Using Series A as an example the data in FIG. 68 can be plotted in the form of a traditional flammability envelope. Using FIG. 68 and reading across the 1500 K temperature line on the ordinate one can determine the fuel concentration for this limit flame temperature by dropping a tangent to the abscissa for each curve (oxygen to nitrogen ratio) that it intersects. These values can then be tabulated as weight percent of fuel for a given weight percent of oxidizer (FIG. 75A). Then knowing the composition of the fuel (100 wt. % isoprene) and the composition of the oxidizer (relative content of water, oxygen and nitrogen) molar quantities can be established.

From these molar quantities percentage volume concentrations can be calculated. The concentrations in terms of volume percent can then be plotted to generate a flammability envelope (FIG. 75B). The area bounded by the envelope is the explosible range and the area excluded is the non-explosible range. The “nose” of the envelope is the limiting oxygen concentration. FIGS. 76A and 76B contain the calculated volume concentrations for the flammability envelope for Series B generated from data presented in FIG. 69. A similar approach can be used on data presented in FIGS. 70-74.

IV. Flammability Testing Experimental Equipment and Procedure

Flammability testing was conducted in a 4 liter high pressure vessel. The vessel was cylindrical in shape with an inner diameter of 6" and an internal height of 8.625". The temperature of the vessel (and the gases inside) was maintained using external heaters that were controlled by a PID controller. To prevent heat losses, ceramic wool and reflective insulation were wrapped around the pressure vessel. Type K thermocouples were used the measure the temperature of the gas space as well as the temperature of the vessel itself. FIG. 77 illustrates the test vessel.

Before a test was ran, the vessel was evacuated and purged with nitrogen to ensure that any gases from previous tests were removed. A vacuum was then pulled on the vessel. The pressure after this had been done was typically around 0.06 bar(a). Due to the nitrogen purging, the gas responsible for this initial pressure was assumed to be nitrogen. Using partial pressures, water, isoprene, nitrogen, and oxygen were then added in the appropriate amounts to achieve the test conditions in question. A magnetically driven mixing fan within the vessel ensured mixing of the gaseous contents. The gases were allowed to mix for about 2 minutes with the fan being turned off approximately 1 minute prior to ignition.

The igniter was comprised of a 1.5 ohm nicrome coil and an AC voltage source on a timer circuit. Using an oscilloscope, it was determined that 34.4 VAC were delivered to the igniter for 3.2 seconds. A maximum current of 3.8 amps occurred approximately halfway into the ignition cycle. Thus, the maximum power was 131 W and the total energy provided over the ignition cycle was approximately 210 J.

Deflagration data was acquired using a variable reluctance Validyne DP215 pressure transducer connected to a data acquisition system. A gas mixture was considered to have deflagrated if the pressure rise was greater than or equal to 5%.

V. Results of Flammability Testing

The first experimental series (Series 1) was run at 40° C. and 0 psig with no steam. Running tests at varying concentrations of isoprene and oxygen produced the flammability curve shown in FIG. 78A. The data points shown in this curve are only those that border the curve. A detailed list of all the data points taken for this series is shown in FIGS. 80A and 80B.

FIG. 78B summarizes the explosibility data points shown in FIG. 78A. FIG. 78C is a comparison of the experimental data with the CAFT model predicted flammability envelope. The model agrees very well with the experimental data. Discrepancies may be due to the non-adiabatic nature of the test chamber and limitations of the model. The model looks at an infinite time horizon for the oxidation reaction and does not take into consideration any reaction kinetic limitation.

Additionally, the model is limited by the number of equilibrium chemical species that are in its database and thus may not properly predict pyrolytic species. Also, the flammability envelope developed by the model uses one value for a limit flame temperature (1500K). The limit flame temperature can be a range of values from 1,000K to 1,500K depending on the reacting chemical species. The complex nature of pyrolytic chemical species formed at fuel concentrations above the stoichiometric fuel/oxidizer level is one reason why the model may not accurately predict the upper flammable limit for this system.

The second experimental series (Series 2) was run at 40° C. and 0 psig with a fixed steam concentration of 4%. Running tests at varying concentrations of isoprene and oxygen produced the flammability curve shown in FIG. 79A. The data points shown in this curve are only those that border the curve. A detailed list of all the data points taken for this series is shown in FIG. 81. Due to the similarity between the data in Series 1 only the key points of lower flammable limit, limiting oxygen concentration, and upper flammable limits were tested. The addition of 4% steam to the test mixture did not significantly change the key limits of the flammability envelope. It should be noted that higher concentrations of steam/water and or other inertants may influence the flammability envelope.

FIG. 79B summarizes the explosibility data points shown in FIG. 79A. FIG. 79C is a comparison of the experimental data with the CAFT model predicted flammability envelope.

The model agrees very well with the experimental data. Discrepancies may be due to the same factors described in Series 1

V. Calculation of Flammability Limits of Isoprene in Air at 3 Atmospheres of Pressure The methods described in Example 13, parts I to IV were also used to calculate the flammability limits of isoprene at an absolute system pressure of 3 atmospheres and 40° C. These results were compared to those of Example 13, parts I to IV at an absolute system pressure of 1 atmosphere and 40° C. This higher pressure was tested because the flammability envelope expands or grows larger as the initial system pressure is increased. The upper flammability limit is affected the most, followed by the limiting oxygen composition. The lower flammability limit is the least affected (see, for example, "Bulletin 627—Flammability Characteristics of Combustible Gases and Vapors" written by Michael G. Zabetakis and published by the former US Bureau of Mines (1965), which is hereby incorporated by reference in its entirety, particular with respect to the calculation of flammability limits).

In FIG. 82, the calculated adiabatic flame temperature is plotted as a function of isoprene (fuel) concentration, expressed in weight percent of the total fuel/nitrogen/oxygen, where the system pressure was initially 3 atmospheres. The calculated flame temperatures are very similar to those determined initially in the 1 atmosphere system (FIG. 83). As a result, when flammability envelopes are generated using the calculated adiabatic flammability data, the curves are very similar (see FIGS. 84 and 85). Therefore, based on these theoretical calculations, a system pressure increase from 1 atmosphere to 3 atmosphere does not result in a significant increase/broadening of the flammability envelope. If desired, these model results may be validated using experimental testing (such as the experimental testing described herein at a pressure of 1 atmosphere).

VII. Summary of Flammability Studies

A calculated adiabatic temperature model was developed for the flammability envelope of the isoprene/oxygen/nitrogen/water/carbon dioxide system at 40° C. and 0 psig. The CAFT model that was developed agreed well with the experimental data generated by the tests conducted in this work. The experimental results from Series 1 and 2 validated the model results from Series A and B.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

APPENDIX 1

Exemplary 1-deoxy-D-xylulose-5-phosphate Synthase Nucleic Acids and Polypeptides ATH: AT3G21500(DXPS1) AT4G15560(CLA1) AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
XCC: XCC2434(dxs)
XCB: XC_1678

XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NGO0036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dxs)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735

SME: SMc00972(dxs)
ATU: Atu0745(dxs)
ATC: AGR_C__1351
RET: RHE_CH00913(dxs)
RLE: RL0973(dxs)
BME: BMEI1498
BMF: BAB1__0462(dxs)
BMS: BR0436(dxs)
BMB: BruAb1__0458(dxs)
BOV: BOV__0443(dxs)
BJA: bll2651(dxs)
BRA: BRADO2161(dxs)
BBT: BBta__2479(dxs)
RPA: RPA0952(dxs)
RPB: RPB__4460
RPC: RPC__1149
RPD: RPD__4305
RPE: RPE__1067
NWI: Nwi__0633
NHA: Nham__0778
BHE: BH04350(dxs)
BQU: BQ03540(dxs)
BBK: BARBAKC583__0400(dxs)
CCR: CC__2068
SIL: SPO0247(dxs)
SIT: TM1040__2920
RSP: RSP__0254(dxsA) RSP__1134(dxs)
JAN: Jann__0088 Jann__0170
RDE: RD1__0101(dxs) RD1__0548(dxs)
MMR: Mmar10__0849
HNE: HNE__1838(dxs)
ZMO: ZMO1234(dxs) ZMO1598(dxs)
NAR: Saro__0161
SAL: Sala__2354
ELI: ELI__12520
GOX: GOX0252
GBE: GbCGDNIH1__0221 GbCGDNIH1__2404
RRU: Rru_A0054 Rru_A2619
MAG: amb2904
MGM: Mmc1__1048
SUS: Acid__1783
BSU: BG11715(dxs)
BHA: BH2779
BAN: BA4400(dxs)
BAR: GBAA4400(dxs)
BAA: BA__4853
BAT: BAS4081
BCE: BC4176(dxs)
BCA: BCE__4249(dxs)
BCZ: BCZK3930(dxs)
BTK: BT9727__3919(dxs)
BTL: BALH__3785(dxs)
BLI: BL01523(dxs)
BLD: BLi02598(dxs)
BCL: ABC2462(dxs)
BAY: RBAM__022600
BPU: BPUM__2159
GKA: GK2392
GTN: GTNG__2322
LMO: lmo1365(tktB)
LMF: LMOf2365__1382(dxs)
LIN: lin1402(tktB)
LWE: lwe1380(tktB)
LLA: L108911(dxsA) L123365(dxsB)
LLC: LACR__1572 LACR__1843
LLM: llmg__0749(dxsB)
SAK: SAK__0263
LPL: lp__2610(dxs)
LJO: LJ0406
LAC: LBA0356
LSL: LSL__0209(dxs)
LGA: LGAS__0350
STH: STH1842
CAC: CAC2077 CA_P0106(dxs)
CPE: CPE1819
CPF: CPF__2073(dxs)
CPR: CPR__1787(dxs)
CTC: CTC01575
CNO: NT01CX__1983
CTH: Cthe__0828
CDF: CD1207(dxs)
CBO: CBO1881(dxs)
CBA: CLB__1818(dxs)
CBH: CLC__1825(dxs)
CBF: CLI__1945(dxs)
CKL: CKL__1231(dxs)
CHY: CHY__1985(dxs)
DSY: DSY2348
DRM: Dred__1078
PTH: PTH__1196(dxs)
SWO: Swol__0582
CSC: Csac__1853
TTE: TTE1298(dxs)
MTA: Moth__1511
MPE: MYPE730
MGA: MGA__1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV__3577(dxs)
MSM: MSMEG__2776(dxs)
MMC: Mmcs__2208
CGL: NCg11827(cg11902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM__1660(dxsA)
AAU: AAur__1790(dxs)
PAC: PPA1062
TFU: Tfu__1917
FRA: Francci3__1326
FAL: FRAAL2088(dxs)
ACE: Acel__1393
SEN: SACE__1815(dxs) SACE__4351
BLO: BL1132(dxs)
BAD: BAD__0513(dxs)
FNU: FN1208FN1464
RBA: RB2143(dxs)
CTR: CT331(dxs)
CTA: CTA__0359(dxs)
CMU: TC0608
CPN: CPn1060(tktB__2)
CPA: CP0790
CPJ: CPj1060(tktB__2)

CPT: CpB 1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary Acetyl-CoA-Acetyltransferase Nucleic Acids and Polypeptides

HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639 (MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)
AGO: AGOS_ADR165C
PIC: PICST_31707(ERG10)
CAL: CaO19.1591(erg10)
CGR: CAGL0L12364g
SPO: SPBC215.09c
MGR: MGG_01755 MGG_13499
ANI: ANI409.2
AFM: AFUA_6G14200 AFUA_8G04000
AOR: AO090103000012 AO090103000406
CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: S3052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO1881(atoB)
XOM: XOO_1778(XOO1778)
VCH: VCA0690
VCO: VC0395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925

PAU: PA14__38630(atoB)
PPU: PP__2051(atoB) PP__2215(fadAx) PP__3754 PP__4636
PPF: Pput__2009 Pput__2403 Pput__3523 Pput__4498
PST: PSPTO__0957(phbA-1) PSPTO__3164(phbA-2)
PSB: Psyr__0824 Psyr__3031
PSP: PSPPH__0850(phbA1) PSPPH__2209(phbA2)
PFL: PFL__1478(atoB-2) PFL__2321 PFL__3066 PFL__4330 (atoB-2) PFL__5283
PFO: Pfl__1269 Pfl__1739 Pfl__2074 Pfl__2868
PEN: PSEEN3197 PSEEN3547(fadAx) PSEEN4635(phbA)
PMY: Pmen__1138 Pmen__2036 Pmen__3597 Pmen__3662 Pmen__3820
PAR: Psyc__0252 Psyc__1169
PCR: Pcryo__0278 Pcryo__1236 Pcryo__1260
PRW: PsycPRwf__2011
ACI: ACIAD0694 ACIAD1612 ACIAD2516(atoB)
SON: SO__1677(atoB)
SDN: Sden__1943
SFR: Sfri__1338 Sfri__2063
SAZ: Sama__1375
SBL: Sbal__1495
SBM: Shew185__1489
SBN: Sba1195__1525
SLO: Shew__1667 Shew__2858
SPC: Sputcn32__1397
SSE: Ssed__1473 Ssed__3533
SPL: Spea__2783
SHE: Shewmr4__2597
SHM: Shewmr7__2664
SHN: Shewana3__2771
SHW: Sputw3181__2704
ILO: IL0872
CPS: CPS__1605 CPS__2626
PHA: PSHAa0908 PSHAa1454(atoB) PSHAa1586(atoB)
PAT: Patl__2923
SDE: Sde__3149
PIN: Ping__0659 Ping__2401
MAQ: Maqu__2117 Maqu__2489 Maqu__2696 Maqu__3162
CBU: CBU__0974
LPN: lpg1825(atoB)
LPF: lpl1789
LPP: lpp1788
NOC: Noc__1891
AEH: Mlg__0688 Mlg__2706
HHA: Hhal__1685
HCH: HCH__05299
CSA: Csal__0301 Csal__3068
ABO: ABO__0648(fadAx)
MMW: Mmwyl1__0073 Mmwyl1__3021 Mmwyl1__3053 Mmwyl1__3097 Mmwyl1__4182
AHA: AHA__2143(atoB)
CVI: CV__2088(atoB) CV__2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet__0106 Rmet__1357 Rmet__1362 Rmet__5156
BMA: BMA1316 BMA1321(phbA) BMA1436
BMV: BMASAVP1_A1805(bktB) BMASAVP1_A1810 (phbA)
BML: BMA10299_A0086(phbA) BMA10299_A0091
BMN: BMA10247__1076(bktB) BMA10247__1081(phbA)
BXE: Bxe_A2273 Bxe_A2335 Bxe_A2342 Bxe_A4255 Bxe_B0377 Bxe_B0739 Bxe_$CO_{332}$ Bxe_$CO_{574}$ Bxe_C0915
BVI: Bcep1808__0519 Bcep1808__1717 Bcep1808__2877 Bcep1808__3594 Bcep1808__4015 Bcep1808__5507 Bcep1808__5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen__1553 Bcen__1599 Bcen__2158 Bcen__2563 Bcen__2998 Bcen__6289
BCH: Bcen2424__0542 Bcen2424__1790 Bcen2424__2772 Bcen2424__5368 Bcen2424__6232 Bcen2424__6276
BAM: Bamb__0447 Bamb__1728 Bamb__2824 Bamb__4717 Bamb__5771 Bamb__5969
BPS: BPSL1426 BPSL1535(phbA) BPSL1540
BPM: BURPS1710b__2325(bktB) BURPS1710b__2330 (phbA) BURPS1710b__2453(atoB-2)
BPL: BURPS1106A__2197(bktB) BURPS1106A__2202 (phbA)
BPD: BURPS668__2160(bktB) BURPS668__2165(phbA)
BTE: BTH_I2144 BTH_I2256 BTH_I2261
PNU: Pnuc__0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer__0272 Rfer__1000 Rfer__1871 Rfer__2273 Rfer__2561 Rfer__2594 Rfer__3839
POL: Bpro__1577 Bpro__2140 Bpro__3113 Bpro__4187
PNA: Pnap__0060 Pnap__0458 Pnap__0867 Pnap__1159 Pnap__2136 Pnap__2804
AAV: Aave__0031 Aave__2478 Aave__3944 Aave__4368
AJS: Ajs__0014 Ajs__0124 Ajs__1931 Ajs__2073 Ajs__2317 Ajs__3548 Ajs__3738 Ajs__3776
VEI: Veis__1331 Veis__3818 Veis__4193
DAC: Daci__0025 Daci__0192 Daci__3601 Daci__5988
MPT: Mpe_A1536 Mpe_A1776 Mpe_A1869 Mpe_A3367
HAR: HEAR0577(phbA)
MMS: mma__0555
NEU: NE2262(bktB)
NET: Neut__0610
EBA: ebA5202 p2A409(tioL)
AZO: azo0464(fadA1) azo0469(fadA2) azo2172(thlA)
DAR: Daro__0098 Daro__3022
HPA: HPAG1__0675
HAC: Hac__0958(atoB)
GME: Gmet__1719 Gmet__2074 Gmet__2213 Gmet__2268 Gmet__3302
GUR: Gura__3043
BBA: Bd0404(atoB) Bd2095
DOL: Dole__0671 Dole__1778 Dole__2160 Dole__2187
ADE: Adeh__0062 Adeh__2365
AFW: Anae109__0064 Anae109__1504
MXA: MXAN__3791
SAT: SYN__02642
SFU: Sfum__2280 Sfum__3582
RPR: RP737
RCO: RC1134 RC1135
RFE: RF__0163(paaJ)
RBE: RBE__0139(paaJ)
RAK: AlC__05820
RBO: AlI__07215
RCM: AlE__04760

PUB: SAR11__0428(thlA)
MLO: mlr3847
MES: Meso__3374
PLA: Plav__1573 Plav__2783
SME: SMa1450 SMc03879(phbA)
SMD: Smed__0499 Smed__3117 Smed__5094 Smed__5096
ATU: Atu2769(atoB) Atu3475
ATC: AGR_C__5022(phbA) AGR_L__2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1__1783(phbA-1) BAB2__0790(phbA-2)
BMS: BR1772(phbA-1) BRA0448(phbA-2)
BMB: BruAb1__1756(phbA-1) BruAb2__0774(phbA-2)
BOV: BOV__1707(phbA-1)
OAN: Oant__1130 Oant__3107 Oant__3718 Oant__4020
BJA: bll0226(atoB) bll3949 bll7400 bll7819 blr3724(phbA)
BRA: BRADO0562(phbA) BRADO0983(pimB) BRADO3110 BRADO3134(atoB)
BBT: BBta__3558 BBta__3575(atoB) BBta__5147(pimB) BBta__7072(pimB) BBta__7614(phbA)
RPA: RPA0513(pcaF) RPA0531 RPA3715(pimB)
RPB: RPB__0509 RPB__0525 RPB__1748
RPC: RPC__0504 RPC__0636 RPC__0641 RPC__0832 RPC__1050 RPC__2005 RPC__2194 RPC__2228
RPD: RPD__0306 RPD__0320 RPD 3105 RPD__3306
RPE: RPE 0168 RPE__0248 RPE__3827
NWI: Nwi__3060
XAU: Xaut__3108 Xaut__4665
CCR: CC__0510 CC__0894 CC__3462
SIL: SPO0142(bktB) SPO0326(phbA) SPO0773 SPO3408
SIT: TM1040__0067 TM1040__2790 TM1040__3026 TM1040__3735
RSP: RSP__0745 RSP__1354 RSP 3184
RSH: Rsph17029__0022 Rsph17029__2401 Rsph17029__3179 Rsph17029__3921
RSQ: Rsph17025__0012 Rsph17025__2466 Rsph17025__2833
JAN: Jann__0262 Jann__0493 Jann__4050
RDE: RD1__0025 RD1__0201(bktB) RD1__3394(phbA)
PDE: Pden__2026 Pden__2663 Pden__2870 Pden__2907 Pden__4811 Pden__5022
DSH: Dshi__0074 Dshi__3066 Dshi__3331
MMR: Mmar10__0697
HNE: HNE__2706 HNE__3065 HNE 3133
NAR: Saro__0809 Saro__1069 Saro__1222 Saro__2306 Saro__2349
SAL: Sala__0781 Sala__1244 Sala__2896 Sala__3158
SWI: Swit__0632 Swit__0752 Swit__2893 Swit__3602 Swit__4887 Swit__5019 Swit__5309
ELI: ELI__01475 ELI__06705 ELI__12035
GBE: GbCGDNIH1__0447
ACR: Acry__1847 Acry__2256
RRU: Rru_A0274 Rru_A1380 Rru_A1469 Rru_A1946 Rru_A3387
MAG: amb0842
MGM: Mmc1__1165
ABA: Acid345__3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA__0445 BA__4172 BA__4700
BAT: BAS3418 BAS3932 BAS5193
BCE: BC3627 BC4023 BC5344
BCA: BCE__3646 BCE__4076 BCE__5475
BCZ: BCZK3329(mmgA) BCZK3780(thl) BCZK5044 (atoB)
BCY: Bcer98__2722 Bcer98__3865
BTK: BT9727__3379(mmgA) BT9727__3765(thl) BT9727__5028(atoB)
BTL: BALH__3262(mmgA) BALH__3642(fadA) BALH__4843(atoB)
BLI: BL03925(mmgA)
BLD: BLi03968(mmgA)
BCL: ABC0345 ABC2989 ABC3617 ABC3891(mmgA)
BAY: RBAM__022450
BPU: BPUM__2374(yhfS) BPUM__2941 BPUM__3373
OIH: OB0676 OB0689 OB2632 OB3013
GKA: GK1658 GK3397
SAU: SA0342 SA0534(vraB)
SAV: SAV0354 SAV0576(vraB)
SAM: MW0330 MW0531(vraB)
SAR: SAR0351(thl) SAR0581
SAS: SAS0330 SAS0534
SAC: SACOL0426 SACOL0622(atoB)
SAB: SAB0304(thl) SAB0526
SAA: SAUSA300__0355 SAUSA300__0560(vraB)
SAO: SAOUHSC__00336 SAOUHSC__00558
SAJ: SaurJH9__0402
SAH: SaurJH1__0412
SEP: SE0346 SE2384
SER: SERP0032 SERP0220
SHA: SH0510(mvaC) SH2417
SSP: SSP0325 SSP2145
LMO: lmo1414
LMF: LMOf2365__1433
LIN: lin1453
LWE: lwe1431
LLA: L11745(thiL) L25946(fadA)
LLC: LACR__1665 LACR__1956
LLM: llmg__0930(thiL)
SPY: SPy__0140 SPy__1637(atoB)
SPZ: M5005_Spy__0119 M5005_Spy__0432 M5005_Spy__1344(atoB)
SPM: spyM18__0136 spyM18__1645(atoB)
SPG: SpyM3__0108 SpyM3__1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK__0568
LJO: LJ1609
LAC: LBA0626(thiL)
LSA: LSA1486
LDB: Ldb0879
LBU: LBUL__0804
LBR: LVIS__2218
LCA: LSEI__1787
LGA: LGAS__1374
LRE: Lreu__0052
EFA: EF1364
OOE: OEOE__0529
STH: STH2913 STH725 STH804
CAC: CAC2873 CA_P0078(thiL)

CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CBO3200(thl)
CBE: Cbei_0411 Cbei_3630
CKL: CKL_3696(thlA1) CKL_3697(thlA2) CKL_3698 (thlA3)
AMT: Amet_4630
AOE: Clos_0084 Clos_0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred_1892
SWO: Swol_0308 Swol_0675 Swol_0789 Swol_1486 Swol_1934 Swol_2051
TTE: TTE0549(paaJ)
MTA: Moth_1260
MTU: Rv1135A Rv1323(fadA4) Rv3546(fadA5)
MTC: MT1365(phbA)
MBO: Mb1167 Mb1358(fadA4) Mb3576(fadA5) Mb3586c (fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCg12309(cg12392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF)
RHA1_ro03022 RHA1_ro03024 RHA1_ro03391 RHA1_ro03892 RHA1_ro04599 RHA1_ro05257 RHA1_ro08871
SCO: SCO5399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxy1_1582 Rxy1_1842 Rxy1_2389 Rxy1_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod_0314
PMO: Pmob_0515
HMA: rrnAC0896(acaB3) rrnAC2815(aca2) rrnAC3497 (yqeF) rrnB0240(aca1) rrnB0242(acaB2) rrnB0309 (acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(LOC578259)
DME: Dmel_CG4311(Hmgs)
CEL: F25B4.6
ATH: AT4G11820(BAP1)
OSA: 4331418 4347614
CME: CMM189C
SCE: YML126C(ERG13)

AGO: AGOS_ADL356C
PIC: PICST__83020
CAL: CaO19__7312(CaO19.7312)
CGR: CAGL0H04081g
SPO: SPAC4F8.14c(hcs)
MGR: MGG__01026
ANI: AN4923.2
AFM: AFUA__3G10660 AFUA__8G07210
AOR: AO090003000611 AO090010000487
CNE: CNCO5080 CNG02670
UMA: UM05362.1
ECU: ECU10__0510
DDI: DDBDRAFT__0217522 DDB__0219924(hgsA)
TET: TTHERM__00691190
TBR: Tb927.8.6110
YPE: YPO1457
YPK: y2712(pksG)
YPM: YP__1349(pksG)
YPA: YPA__0750
YPN: YPN__2521
YPP: YPDSF__1517
YPS: YPTB1475
CBD: COXBU7E912__1931
TCX: Tcr__1719
DNO: DNO__0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN__3948(tac) MXAN__4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300__2484
SAO: SAOUHSC__02860
SAJ: SaurJH9__2569
SAH: SaurJH1__2622
SEP: SE2110
SER: SERP2122
SHA: SH0508(mvaS)
SSP: SSP0324
LMO: lmo1415
LMF: LMOf2365__1434(mvaS)
LIN: lin1454
LWE: lwe1432(mvaS)
LLA: L13187(hmcM)
LLC: LACR__1666
LLM: llmg__0929(hmcM)
SPY: SPy__0881(mvaS.2)
SPZ: M5005_Spy__0687(mvaS.1)
SPM: spyM18__0942(mvaS2)
SPG: SpyM3__0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704

SPB: M28_Spy0667(mvaS.1)
SPN: SP__1727
SPR: spr1571(mvaS)
SPD: SPD__1537(mvaS)
SAG: SAG1316
SAN: gbs1386
SAK: SAK__1347
SMU: SMU.943c
STC: str0577(mvaS)
STL: stu0577(mvaS)
STE: STER__0621
SSA: SSA__0338(mvaS)
SSU: SSU05__1641
SSV: SSU98__1652
SGO: SGO__0244
LPL: lp__2067(mvaS)
LJO: LJ1607
LAC: LBA0628(hmcS)
LSA: LSA1484(mvaS)
LSL: LSL__0526
LDB: Ldb0881(mvaS)
LBU: LBUL__0806
LBR: LVIS__1363
LCA: LSEI__1785
LGA: LGAS__1372
LRE: Lreu__0676
PPE: PEPE__0868
EFA: EF1363
OOE: OEOE__0968
LME: LEUM__1184
NFA: nfa22120
SEN: SACE__4570(pksG)
BBU: BB0683
BGA: BG0706
BAF: BAPKO__0727
FJO: Fjoh__0678
HAL: VNG1615G(mvaB)
HMA: rrnAC1740(mvaS)
HWA: HQ2868A(mvaB)
NPH: NP2608A(mvaB__1) NP4836A(mvaB__2)

Exemplary Hydroxymethylglutaryl-CoA Reductase Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04__14 m24)
SPU: 373355(LOC373355)
DME: Dmel_CG10367 (Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2
AFM: AFUA__1G11230 AFUA__2G03700
AOR: AO090103000311 AO090120000217
CNE: CNF04830
UMA: UM03014.1
ECU: ECU10__1720
DDI: DDB__0191125(hmgA) DDB__0215357(hmgB)

TBR: Tb927.6.4540
TCR: 506831.40 509167.20
LMA: LmjF30.3190
VCH: VCA0723
VCO: VC0395__0662
VVU: VV2__0117
VVY: VVA0625
VPA: VPA0968
VFI: VFA0841
PAT: Patl__0427
CBU: CBU__0030 CBU__0610
CBD: COXBU7E912__0151 COXBU7E912__0622(hmgA)
TCX: Tcr__1717
DNO: DNO 0797
CVI: CV__1806
SUS: Acid__5728 Acid__6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR__1664
LLM: llmg__0931(mvaA)
SPY: SPy__0880(mvaS.1)
SPM: spyM18__0941(mvaS1)
SPG: SpyM3__0599(mvaS.1)
SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP__1726
SAG: SAG1317
SAN: gbs1387
STC: str0576(mvaA)
STL: stu0576(mvaA)
STE: STER__0620
SSA: SSA__0337(mvaA)
LPL: lp__0447(mvaA)
LJO: LJ1608
LSL: LSL__0224
LBR: LVIS__0450
LGA: LGAS__1373
EFA: EF1364
NFA: nfa22110
BGA: BG0708(mvaA)
SRU: SRU__2422
FPS: FP2341
MMP: MMP0087(hmgA)
MMQ: MmarC5__1589
MAC: MA3073(hmgA)
MBA: Mbar_A1972
MMA: MM__0335
MBU: Mbur__1098
MHU: Mhun__3004
MEM: Memar__2365
MBN: Mboo__0137
MTH: MTH562
MST: Msp__0584(hmgA)
MSI: Msm__0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA__2) NP2422A(mvaA__1)
TAC: Ta0406m
TVO: TVN1168
PTO: PTO1143
PAB: PAB2106(mvaA)
PFU: PF1848
TKO: TK0914
RCI: RCIX1027(hmgA) RCIX376(hmgA)
APE: APE__1869
IHO: Igni__0476
HBU: Hbut__1531
SSO: SSO0531
STO: ST1352
SAI: Saci__1359
PAI: PAE2182
PIS: Pisl__0814
PCL: Pcal__1085
PAS: Pars__0796

Exemplary Mevalonate Kinase Nucleic Acids and Polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(LOC585785)
DME: Dmel_CG33671
OSA: 4348331
SCE: YMR208W(ERG12)
AGO: AGOS_AER335W
PIC: PICST__40742(ERG12)
CGR: CAGL0F03861g
SPO: SPAC13G6.11c
MGR: MGG__06946
ANI: AN3869.2
AFM: AFUA__4G07780
AOR: AO090023000793
CNE: CNK01740
ECU: ECU09__1780
DDI: DDBDRAFT__0168621
TET: TTHERM__00637680
TBR: Tb927.4.4070
TCR: 436521.9 509237.10
LMA: LmjF31.0560
CBU: CBU__0608 CBU__0609
CBD: COXBU7E912__0620(mvk)
LPN: lpg2039
LPF: lpl12017
LPP: lpp2022
BBA: Bd1027(1 mbP) Bd1630(mvk)
MXA: MXAN__5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300__0572(mvk)
SAO: SAOUHSC__00577

SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(myk)
HMA: rrnAC0077(myk)
HWA: HQ2925A(mvk)
NPH: NP2850A(mvk)
PTO: PTO1352
PHO: PH1625
PAB: PAB0372(mvk)
PFU: PF1637(mvk)
TKO: TK1474
RCI: LRC399(mvk)
APE: APE_2439
HBU: Hbut_0877
SSO: SSO0383
STO: ST2185
SAI: Saci_2365(mvk)
MSE: Msed_1602
PAI: PAE3108
PIS: Pisl_0467
PCL: Pcal_1835

Exemplary Phosphomevalonate Kinase Nucleic Acids and Polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012

LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO 0241
LPL: lp_1733(mvaK2)
LJO: LJ1207
LAC: LBA1169
LSA: LSA0906(mvaK2)
LSL: LSL_0683
LDB: Ldb0997(mvaK)
LBU: LBUL_0904
LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978
SAI: Saci_1244

Exemplary Diphosphomevalonate Decarboxylase Nucleic Acids and Polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lpl2018
LPP: lpp2023
TCX: Tcr_1734
DNO: DNO_0504(mvaD)
BBA: Bd1629
MXA: MXAN_5018(mvaD)
OIH: OB0226
SAU: SA0548(mvaD)
SAV: SAV0591(mvaD)
SAM: MW0546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011
LWE: lwe0012(mvaD)
LLA: L9089(yeaH)
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvd1)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290

SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO 3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PTO0478 PTO1356
SSO: SSO2989
STO: ST0977
SAI: Saci_1245(mvd)
MSE: Msed_1576

Exemplary Isopentenyl-Diphosphate Delta-Isomerase (IDI) Nucleic Acids and Polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(LOC586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937
SSN: SSON_3042 SSON_3489(yhfK)
SBO: SBO_3103
SDY: SDY_3193
ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO 0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SPO0131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520

BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP0556
LMO: lmol383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO 0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni) MSMEG_2337(fni)
MUL: MUL_0380(idi2)
MVA: Mvan_1582 Mvan_2176
MGI: Mflv_1842 Mflv_4187
MMC: Mmcs_1954
MKM: Mkms_2000
MJL: Mjls_1934
CGL: NCgl2223(cgl2305)
CGB: cg2531(idi)
CEF: CE2207
CDI: DIP1730(idi)
NFA: nfa19790 nfa22100
RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean15570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxy1_0400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381

TTH: TT_P0067
TTJ: TTHB110
MJA: MJ0862
MMP: MMP0043
MMQ: MmarC5_1637
MMX: MmarC6 0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi) VNG6081G(crt_1) VNG6445G (crt_2) VNG7060 VNG7149
HMA: rrnAC3484(idi)
HWA: HQ2772A(idiA) HQ2847A(idiB)
NPH: NP0360A(idiB_1) NP4826A(idiA) NP5124A(idiB_2)
TAC: Ta0102
TVO: TVN0179
PTO: PTO0496
PHO: PH1202
PAB: PAB1662
PFU: PF0856
TKO: TK1470
RCI: LRC397(fni)
APE: APE_1765.1
SMR: Smar_0822
IHO: Igni_0804
HBU: Hbut_0539
SSO: SSO00063
STO: ST2059
SAI: Saci_0091
MSE: Msed_2136
PAI: PAE0801
PIS: Pisl_1093
PCL: Pcal_0017
PAS: Pars_0051
TPE: Tpen_0272

Exemplary Isoprene Synthase Nucleic Acids and Polypeptides

Genbank Accession Nos.
AY341431
AY316691
AY279379
AJ457070
AY182241

---

What is claimed is:

1. A biologically produced composition comprising:

(a) greater than 2 mg of isoprene and (b) one or more compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, (E)-3,7-dimethyl-1,3,6-octatriene, (Z)-3,7-dimethyl-1,3,6-octatriene, and 2,3-cycloheptenolpyridine, wherein the amount of the one of the one or more compounds relative to the amount of the isoprene is between about 0.01% to 105% (w/w).

2. The composition of claim 1, wherein at least a portion of the isoprene is in the gas phase.

3. The composition of claim 1, wherein the amount of one of the one or more compounds relative to the amount of the isoprene is between about 0.01% to about 90% (w/w), between about 0.01% to about 80% (w/w), between about 0.01% to about 50% (w/w), between about 0.01% to about 20% (w/w), between about 0.01% to about 10% (w/w), between about 0.02% to about 50% (w/w), between about 0.05% to about 50% (w/w), between about 0.1% to about 50% (w/w), or between about 0.1% to about 20% (w/w).

4. The composition of claim 3, wherein the amount of one of the one or more compounds relative to the amount of the isoprene is between about 0.01% to about 90% (w/w).

5. The composition of claim 3, wherein the amount of one of the one or more compounds relative to the amount of the isoprene is between about 0.01% to about 80% (w/w).

6. The composition of claim 3, wherein the amount of one of the one or more compounds relative to the amount of the isoprene is between about 0.01% to about 50% (w/w).

7. The composition of claim 3, wherein the amount of one of the one or more compounds relative to the amount of the isoprene is between about 0.01% to about 20% (w/w).

8. The composition of claim 3, wherein the amount of one of the one or more compounds relative to the amount of the isoprene is between about 0.01% to about 10% (w/w).

9. The composition of claim 3, wherein the amount of one of the one or more compounds relative to the amount of the isoprene is between about 0.02% to about 50% (w/w).

10. The composition of claim 3, wherein the amount of one of the one or more compounds relative to the amount of the isoprene is between about 0.05% to about 50% (w/w).

11. The composition of claim 3, wherein the amount of one of the one or more compounds relative to the amount of the isoprene is between about 0.1% to about 50% (w/w).

12. The composition of claim 3, wherein the amount of one of the one or more compounds relative to the amount of the isoprene is between about 0.1% to about 20% (w/w).

* * * * *